(12) United States Patent
Karpusas et al.

(10) Patent No.: US 7,910,099 B2
(45) Date of Patent: Mar. 22, 2011

(54) ANTIBODIES TO VLA-1

(75) Inventors: Michael Karpusas, Upper Darby, PA (US); Paul D. Lyne, Arlington, MA (US); Jose William Saldanha, Enfield (GB); Ellen A. Garber, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 12/727,965

(22) Filed: Mar. 19, 2010

(65) Prior Publication Data

US 2010/0272716 A1 Oct. 28, 2010

Related U.S. Application Data

(62) Division of application No. 12/015,213, filed on Jan. 16, 2008, now Pat. No. 7,723,073, which is a division of application No. 10/474,832, filed as application No. PCT/US02/11521 on Apr. 12, 2002, now Pat. No. 7,358,054.

(60) Provisional application No. 60/303,689, filed on Jul. 6, 2001, provisional application No. 60/283,794, filed on Apr. 13, 2001.

(51) Int. Cl.
*A61K 39/395* (2006.01)

(52) U.S. Cl. ............... 424/130.1; 424/133.1; 424/144.1

(58) Field of Classification Search .................. None
See application file for complete search history.

(56) References Cited

U.S. PATENT DOCUMENTS

| | | | |
|---|---|---|---|
| 5,391,481 A | 2/1995 | Chess et al. | 435/7.24 |
| 5,565,332 A | 10/1996 | Hoogenboom et al. | 435/69.1 |
| 5,648,260 A | 7/1997 | Winter et al. | 435/252.3 |
| 5,733,743 A | 3/1998 | Johnson et al. | 435/69.1 |
| 5,788,966 A | 8/1998 | Chess et al. | 424/144.1 |
| 5,789,650 A | 8/1998 | Lonberg et al. | 800/2 |
| 5,798,230 A | 8/1998 | Bornkamm et al. | 435/70.21 |
| 5,827,690 A | 10/1998 | Meade et al. | 435/69.6 |
| 5,855,888 A | 1/1999 | Nishida et al. | 424/156.1 |
| 5,859,205 A | 1/1999 | Adair et al. | |
| 6,001,961 A | 12/1999 | Jonczyk et al. | 530/317 |
| 6,016,159 A | 1/2000 | Faris | 348/57 |
| 6,075,181 A | 6/2000 | Kucherlapati et al. | 800/25 |
| 6,127,524 A | 10/2000 | Casipit et al. | 530/387.3 |
| 6,150,584 A | 11/2000 | Kucherlapati et al. | 800/18 |
| 6,162,963 A | 12/2000 | Kucherlapati et al. | 800/18 |
| 6,180,370 B1 | 1/2001 | Queen et al. | 435/69.6 |
| 6,291,650 B1 | 9/2001 | Winter et al. | 530/387.3 |
| 6,300,064 B1 | 10/2001 | Knappik et al. | 435/6 |
| 6,303,313 B1 | 10/2001 | Wigler et al. | 435/6 |
| 6,307,026 B1 | 10/2001 | King et al. | 530/387.3 |
| 6,326,403 B1 | 12/2001 | Hölzemann et al. | 514/563 |
| 6,632,927 B2 | 10/2003 | Adair et al. | |

FOREIGN PATENT DOCUMENTS

| | | |
|---|---|---|
| EP | 0 239 400 A2 | 9/1987 |
| EP | 0 843 961 A1 | 5/1998 |
| JP | 08-131185 | 5/1996 |
| JP | 08131185 | 5/1996 |
| WO | WO 90/07861 A1 | 7/1990 |
| WO | WO 99/61040 A2 | 12/1999 |
| WO | WO 99/61040 A3 | 12/1999 |
| WO | WO 00/20459 A1 | 4/2000 |
| WO | WO 00/72881 A1 | 12/2000 |
| WO | WO 01/73444 A2 | 10/2001 |
| WO | WO 01/96365 A1 | 12/2001 |

OTHER PUBLICATIONS

Padlan E.A., "Anatomy of the antibody molecule", Mol Immunol., Feb. 1994; 31(3):169-217.
Panka et al., "Variable region framework differences results in decreased or increased affinity of variant anti-digoxin antibodies", Proc Natl Acad Sci USA, May 1988; 85(9); 3080-4.
Portolano et al., "Lack of promiscuity in autoantigen-specific H and L chain combinations as revealed by human H and L chain "roulette"", J Immunol., Feb. 1, 1993; 150(3): 880-7.
E.T. Baldwin et al., "Cation Binding to the Integrin CD11b I Domain and Activation Model Assessment," *Structure*,6:923-935 (1998).
R. Briesewitz et al., "Expression of Native and Truncated Forms of the Human Integrin $\alpha_1$ Subunit," *J. Biol. Chem.*, 268:2989-2996 (1993).
P. Carter et al., "Humanization of an Anti-p185$^{HER2}$ Antibody for Human Cancer Therapy," *Proc. Natl. Acad. Sci. USA*, 89:4285-4289 (1992).
C. Chothia et al., "Conformations of Immunoglobulin Hypervariable Regions," *Nature*, 342:877-883 (1989).
M.S. Co et al., "Humanized Antibodies for Antiviral Therapy," *Proc. Nat. Acad. Sci. USA*, 88:2869-2873 (1991).
A.L. Corbi et al., "The Human Leukocyte Adhesion Glycoprotein Mac-1 (Complement Receptor Type 3, CD11b) $\alpha$ Subunit," *J. Biol. Chem.*, 263:12403-12411 (1988).
A.L. Corbi at al., "cDNA Cloning and Complete Primary Structure of the $\alpha$ Subunit of a Leukocyte Adhesion Glycoprotein, P150,95," *EMBO J.*, 6:4023-4028 (1987).
D. Cosgrove, et al., "Integrin $\alpha 1\beta 1$ and Transforming Growth Factor-$\beta 1$ Play Distinct Roles in Alport Glomerular Pathogenesis and Serve as Dual Targets for Metabolic Therapy," *Am. J. Path.*, 157:1649-1659 (2000).
D.R. Davies and G.H. Cohen, "Interactions of Protein Antigens with Antibodies," *Proc. Natl. Acad. Sci. USA*, 93:7-12 (1996).
A.R. de Fougerolles et al., "Global Expression Analysis of Extracellular Matrix-Integrin Interactions in Monocytes," *Immunity*, 13:749-758 (2000).
C.P. Edwards et al., "Identification of Amino Acids in the CD11a I-domain Important for Binding of the Leukocyte Function-associated Antigen-1 (LFA-1) to Intercellular Adhesion Molecule-1 (ICAM-1)", *J. Biol. Chem.*, 270, 12635-12640 (1995).
C. Eigenbrot et al., "X-ray Structures of the Antigen-binding Domains from Three Variants of Humanized anti-p185$^{HER2}$ Antibody 4D5 and Comparison with Molecular Modeling," *J. Mol. Biol.*, 229:969-995 (1993).

(Continued)

*Primary Examiner* — Maher M Haddad
(74) *Attorney, Agent, or Firm* — Lando & Anastasi, LLP

(57) ABSTRACT

Antibodies that specifically bind to VLA-1 integrin and methods of using these antibodies to treat immunological disorders in a subject. Also included are crystal structures of complexes formed by VLA-1 antibodies and their ligands, and VLA-1 antagonists and agonists identified by using the structure coordinates of these structures.

17 Claims, 131 Drawing Sheets

OTHER PUBLICATIONS

J. Emsley et al., "Structural Basis of Collagen Recognition by Integrin α2β1," *Cell*, 100:47-56 (2000).

J. Emsley et al., "Crystal Structure of the I Domain from Integrin α2β1," *J. Biol. Chem.*, 272:28512-28517 (1997).

J. Foote and G. Winter, "Antibody Framework Residues Affecting the Conformation of the Hypervariable Loops," *J. Mol. Biol.*, 224:487-499 (1992).

A.A. Gaspari and S.I. Katz, "Contact Hypersensitivity," *Current Protocols in Immunology*. J.E. Coligan, A.M. Kruisbeek, D.H. Margulies, E.M. Shevach, and W. Strober, editors. John Wiley & Sons, New York. Section 4.2.1-4.2.5 (1991).

P.J. Gotwals et al., "Divalent Cations Stabilize the α1β1 Integrin I Domain," *Biochemistry*, 38:8280-8288 (1999).

P.J. Gotwals et al., "The α1β1 Integrin Is Expressed during Neointima Formation in Rat Arteries and Mediates Collagen Matrix Reorganization," *J. Clin. Invest.*, 97:2469-2477 (1996).

M.H. Grayson et al., αdβ2 Integrin Is Expressed on Human Eosinophils and Functions as an Alternative Ligand for Vascular Cell Adhesion Molecule 1 (VCAM-1), *J. Exp. Med.*, 188:2187-2191 (1988).

L.L. Green et al., "Antigen-specific Human Monoclonal Antibodies From Mice Engineered With Human Ig Heavy and Light Chain YACs," *Nature Genetics*, 7:13-21 (1994).

M.E, Hemler et al., "Very Late Activation Antigens on Rheumatoid Synovial Fluid T Lymphocytes: Association with Stages of T Cell Activation," *J. Clin. Invest.*, 78:696-702 (1986).

M.E. Hemler et al., "VLA-1: A T Cell Surface Antigen which Defines a Novel Late Stage of Human T Cell Activation," *Eur. J. Immunol.*, 15:502-508 (1985).

C. Huang and B.D. Stollar, "A Majority of Ig H Chain cDNA of Normal Human Adult Blood Lymphocytes Resembles cDNA for Fetal Ig and Natural Autoantibodies," *J. Immunol.*, 151:5290-5300 (1993).

B. Hurtrel at al., "Different Time Course Patterns of Local Expression of Delayed-Type Hypersensitivity to Sheep Red Blood Cells in Mice," *Cell. Immunol.*, 142:252-263 (1992).

J.R. Huth et al., "NMR and Mutagenesis Evidence for an I Domain Allosteric Site that Regulates Lymphocyte Function-Associated Antigen 1 Ligand Binding," *Proc. Natl. Acad. Sci. U.S.A.*, 97:5231-5236 (2000).

M.J. Ignatius et al., "Molecular Cloning of the Rat Integrin $α_1$-Subunit: A Receptor for Laminin and Collagen," *J. Cell Biol.*, 111, 709-720 (1990).

S. Jones and J.M. Thornton, "Principles of Protein-Protein Interactions," *Proc. Natl. Acad. Sci. USA*, 93:13-20 (1996).

P.T. Jones et al., "Replacing the Complementarity-Determining Regions in a Human Antibody with Those from a Mouse," *Nature*, 321:522-525 (1986).

K. Kakimoto et al., "The Effect of Anti-adhesion Molecule Antibody on the Development of Collagen-Induced Arthritis," *Cell. Immunol.*, 142:326-337 (1992).

T. Kamata et al., "Critical Threonine and Aspartic Acid Residues within the I Domains of β2 Integrins for Interactions with Intercellular Adhesion Molecule 1 (ICAM-1) and C3bi," *J. Biol. Chem.*, 270:12531-12535 (1995).

P.J. Keely et al., "Alteration of Collagen-Dependent Adhesion, Motility, and Morphogenesis by the Expression of Antisense $α_2$ Integrin mRNA in Mammary Cells," *J. Cell Sci.*, 108:595-607 (1995).

A. Kern, et al., "The Role of the I Domain in Ligand Binding of the Human Integrin $α_1β_1$," *J. Biol. Chem.*, 269:22811-22816 (1994).

T. Kinashi and T.A. Springer, "Adhesion Molecules in Hematopoietic Cells," *Blood Cells*, 20:25-44 (1994).

S.L. King, at al., "Echovirus 1 Interaction with the Human Very Late Antigen-2 (Integrin α2β1) I Domain," *J. Biol. Chem.*, 272:28518-28522 (1997).

C.G. Knight et al., "The Collagen-binding A-domains of Integrins $α_1β_1$ and $α_2β_1$ Recognize the Same Specific Amino Acid Sequence, GFOGER, in Native (Triple-helical) Collagens," *J. Biol. Chem.*, 275:35-40 (2000).

F. Kolbinger et al., "Humanization of a Mouse Anti-human IgE Antibody: A Potential Therapeutic for IgE-mediated Allergies," *Protein Eng.*, 6:971-980 (1993).

O. Langholz et al., "Collagen and Collagenase Gene Expression in Three-dimensional Collagen Lattices Are Differentially Regulated by α1β1 and α2β1Integrins," *J. Cell Biol.*, 131:1903-1915 (1995).

R.S. Larson et al., "Primary Structure of the Leukocyte Function-associated Molecule-1 α Subunit: An Integrin with an Embedded Domain Defining a Protein Superfamily," *J. Cell Biol.*, 108:703-712 (1989).

J.-O. Lee et al., "Crystal Structure of the A Domain from the α Subunit of Integrin CR3 (CD11b/CD18)," *Cell*, 80:631-638 (1995).

J.-O. Lee et al., "Two Conformations of the Integrin A-domain (I-domain): A Pathway for Activation?" *Structure*, 3:1333-1340 (1995).

F. Mackay et al., "Lymphotoxin β Receptor Triggering Induces Activation of the Nuclear Factor κB Transcription Factor in Some Cell Types," *J. Biol. Chem.*, 271:24934-24938 (1996).

M.J. Mendez et al., "Functional Transplant of Megabase Human Immunoglobulin Loci Recapitulates Human Antibody Response in Mice," *Nature Genetics*, 15:146-156 (1997).

D.L. Mendrick et al., "Glomerular Epithelial and Mesangial Cells Differentially Modulate the Binding Specificities of VLA-1 and VLA-2," *Lab. Invest.*, 72:367-375 (1995).

D.L. Mendrick and D.M. Kelly, "Temporal Expression of VLA-2 and Modulation of its Ligand Specificity by Rat Glomerular Epithelial Cells in vitro," *Lab. Invest.*, 69:690-702 (1993).

Michishita et al., "A Novel Divalent Cation-Binding Site in the A Domain of the β2 Integrin CR3 (CD11b/CD18) is Essential for Ligand Binding," *Cell*, 72:857-867 (1993).

S. Miyake et al., "β1 Integrin-mediated Interaction with Extracellular Matrix Proteins Regulates Cytokine Gene Expression in Synovial Fluid Cells of Rheumatoid Arthritis Patients," *J. Exp. Med.*, 177:863-868 (1993).

K. Miyake et al., "Evidence for a Role of the Integrin VLA-4 in Lympho-hemopoiesis," *J. Exp. Med.*, 173:599-607 (1991).

P. Mombaerts et al., "RAG-1-Deficient Mice Have No Mature B and T Lymphocytes," *Cell*, 68:869-877 (1992).

L. Mori et al., "Attenuation of Collagen-Induced Arthritis in 55-kDa TNF Receptor Type 1 (TNFR1)-IgG1-Treated and TNFR1-Deficient Mice," *J. Immunol.*, 157:3178-3182 (1996).

Y.A. Muller et al., "VEGF and the Fab Fragment of a Humanized Neutralizing Antibody: Crystal Structure of the Complex at 2.4 Å Resolution and Mutational Analysis of the Interface," *Structure*, 6:1153-1167(1998).

Nolte et al., "Crystal Structure of the α1β1 Integrin I-Domain: Insights into Integrin I-Domain Function," *FEBS Lett.*, 452:379-385 (1999).

K. Noto et al., "Identification and Functional Characterization of Mouse CD29 with a mAb," *Int. Immunol.*, 7:835-842 (1995).

R. Orlandi at al., "Cloning Immunoglobulin Variable Domains for Expression by the Polymerase Chain Reaction," *Proc. Natl. Acad. Sci. USA*, 86:3833-3837 (1989).

D. Plows et al., "Mice Lacking Mature T and B Lymphocytes Develop Arthritic Lesions After Immunization with Type II Collagen," *J. Immunol.*, 162:1018-1023 (1999).

A. Qu and D.J. Leahy, "The Role of the Divalent Cation in the Structure of the I Domain from the CD11a/CD18 Integrin," *Structure*, 4:931-942 (1996).

A. Qu and D.J. Leahy, "Crystal Structure of the I-Domain from the CD11a/CD18 (LFA-1, $α_Lβ2$) Integrin," *Proc. Natl. Acad. Sci. USA*, 92:10277-10281 (1995).

R.L. Rich et al., "Trench-shaped Binding Sites Promote Multiple Glasses of Interactions between Collagen and the Adherence Receptors, $α_1β_1$ Integrin and *Staphylococcus aureus* Cna MSCRAMM," *J. Biol. Chem.*, 274:24906-24913 (1999).

L. Riechmann et al., "Reshaping Human Antibodies for Therapy," *Nature*, 332:323-327 (1988).

I. Riikonen et al., "Transforming Growth Factor-β Regulates Collagen Gel Contraction by Increasing α2β1 Integrin Expression in Osteogenic Cells," *J. Biol. Chem.*, 270:376-382 (1995).

A. Scheynius et al. "Reduced Contact Sensitivity Reactions in Mice Treated with Monoclonal Antibodies to Leukocyte Function-Associated Molecule-1 and Intercellular Adhesion Molecule-1," *J. Immunol.*, 150:655-663 (1993).

J.A. Schiro et al., "integrin α²β₁(VLA-2) Mediates Reorganization and Contraction of Collagen Matrices by Human Cells," *Cell*, 67:403-410 (1991).

D. Seiffge, "Protective Effects of Monoclonal Antibody to VLA-4 on Leukocyte Adhesion and Course of Disease in Adjuvant Arthritis in Rats," *J. Rheumatol.*, 23:2086-2091 (1996).

S.K. Shaw et al., "Molecular Cloning of the Human Mucosal Lymphocyte Integrin α$^E$ Subunit," *J. Biol Chem.*, 269:6016-6025 (1994).

A. Sonnenberg et al., "A Complex of Platelet Glycoproteins Ic and IIa Identified by a Rat Monoclonal Antibody," *J. Biol. Chem.*, 262:10376-10383 (1987).

T.A. Springer, "Adhesion Receptors of the Immune System," *Nature*, 346:425-434 (1990).

Y. Takada and M.E. Hemler, "The Primary Structure of the VLA-2/Collagen Receptor α² Subunit (Platelet GPIa): Homology to Other Integrins and the Presence of a Possible Collagen-binding Domain," *J. Cell Biol.*, 109:397-407 (1989).

P.C. Taylor et al., "Transfer of Type II Collagen-Induced Arthritis From DBA/1 to Severe Combined Immunodeficiency Mice Can Be Prevented by Blockage of Mac-1," *Immunology*, 88:315-321 (1996).

T.F. Tedder et al., "L-Selectin-deficient Mice Have Impaired Leukocyte Recruitment Into Inflammatory Sites," *J. Exp. Med.*, 181:2259-2264 (1995).

P.R. Tempest et al., "Reshaping a Human Monoclonal Antibody to Inhibit Human Respiratory Syncytial Virus Infection In vivo," *Bio/Technology*, 9:266-271 (1991).

M. Terashita et al., "Enhancement of Delayed-Type Hypersensitivity to Sheep Red Blood Cells in Mice by Granulocyte Colony-Stimulating Factor Administration at the Elicitation Phase," *J. Immunol.*, 156:4638-4643 (1996).

K. Terato et al., "Collagen-Induced Arthritis in Mice: Synergistic Effect of *E. coli* Lipopolysaccharide Bypasses Epitope Specificity in the Induction of Arthritis with Monoclonal Antibodies to Type II Collagen," *Autoimmunity*, 22:137-147 (1995).

K. Terato et al.,"Induction of Arthritis with Monoclonal Antibodies to Collagen," *J. Immunol.*, 148:2103-2108 (1992).

K. Tomizuka et al., "Functional Expression and Germline Transmission of a Human Chromosome Fragment in Chimaeric Mice," *Nature Genetics*, 16:133-143 (1997).

M. Verhoeyen et al., "Reshaping Human Antibodies: Grafting an Antilysozyme Activity," *Science*, 239:1534-1536 (1988).

E.S. Ward et al., "Binding Activities of a Repertoire of Single Immunoglobulin Variable Domains Secreted from *Escherichia coil*," *Nature*, 341:544-546 (1989).

M. Welschof et al., "Amino Acid Sequence based PCR Primers for Amplification of Rearranged Human Heavy and Light Chain Immunoglobulin Variable Region Genes," *J. Immunol. Meth.*, 179:203-214 (1995).

I. Bank et al., "Analysis of Recombinant Human α1 Integrin I-Domain with a Function-Blocking Monoclonal Antibody 1B3.1," *Isr. Med. Assoc. J.*, 2:19-20 (2000).

S.C.G. Brezinsky et al., "A Simple Method for Enriching Populations of Transfected CHO Cells for Cells of Higher Specific Productivity," *J. Immunol. Methods*, 277:141-155 (2003).

H. T. Cook et al., "Treatment with an Antibody to VLA-1 Integrin Reduces Glomerular and Tubulointerstitial Scarring in a Rat Model of Crescentic Glomerulonephritis," *Am. J. Pathol.*, 161:1265-1272 (2002).

T. O. Fischmann et al., "Crystallographic Refinement of the Three-Dimensional Structure of the FabD1.3-Lysozyme Complex at 2.5-Å Resolution," *J. Biol. Chem.*, 266:12915-12920 (1991).

M. A. Holmes et al., "Conformational Correction Mechanisms Aiding Antigen Recognition by a Humanized Antibody," *J. Exp. Med.*, 187:479-485 (1998).

A. Ianaro at al., "Anti-Very Late Antigen-1 Monoclonal Antibody Modulates the Development of Secondary Lesion and T-Cell Response in Experimental Arthritis," *Lab. Invest.*, 80:73-80 (2000).

Karpusas et al., "Crystal Structure of the α1β1 Integrin I Domain in Complex with an Antibody Fab Fragment," *J. Mol. Biol.*, 327:1031-1041 (2003).

Y. Li et al., "Three-Dimensional Structures of the Free and Antigen-Bound Fab from Monoclonal Antilysozyme Antibody HyHEL-63," *Biochemistry*, 39:6296-6309 (2000).

N. S. Sampson et al., "Global Gene Expression Analysis Reveals a Role for the α₁ Integrin in Renal Pathogenesis," *J. Biol. Chem.*, 276:34182-34188 (2001).

R. Briesewitz et al., "Expression of Native and Truncated Forms of the Human Integrin α₁ Subunit," *J. Bio. Chem.*, 268:2989-2996 (1993).

A. R. de Fougerolies at al., "Regulation of Inflammation by Collagen-Binding Integrins α1β1 and α2β1* in Models of Hypersensitivity and Arthritis," *J. Clin. Invest.*, 105:721-729 (2000).

M. Fabbri et al., "A Functional Monoclonal Antibody Recognizing the Human alpha1-Integrin I-Domain," *Tissue Antigens*, 48:47-51 (1996).

Shimoka,"Computational Design of an Integrin I Domain, etc.", Nature Structural Biology, vol. 7, No. 8 (Aug. 2000), pp. 674-678.

Bella Jordi,"Integrin-collagen complex:a metal glutamate handshake", Structure (London), vol. 8, No. 6 Jun. 15, 2000), pp. R121-R126.

Leibiger et al., "Variable domain-linked oligosaccharides of a human monoclonal IgG: structure and influence on antigen binding," *Biochem. J.* 338:529-238, 1999.

Shakin-Eshleman et al., "The Amino Acid at the *X* Position of an Asn-*X*-Ser Sequon is an Important Determinant of N-Linked Core-glycosylation Efficiency," *J. Biol. Chem.* 271:6363-6366, 1996.

Wright and Morrison, "Effect of Altered $C_H2$-associated Carbohydrate Structure on the Functional Properties and In Vivo Fate of Chimeric Mouse-Human Immunoglobulin G1," *J. Exp. Med.* 180:1087-1096, 1994.

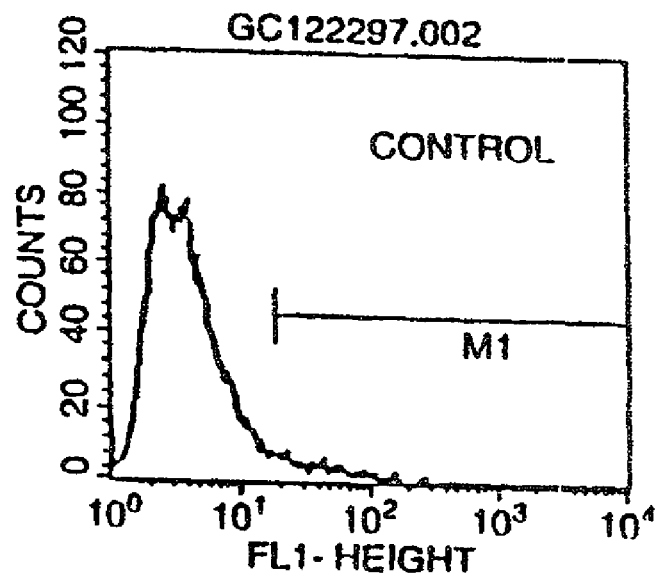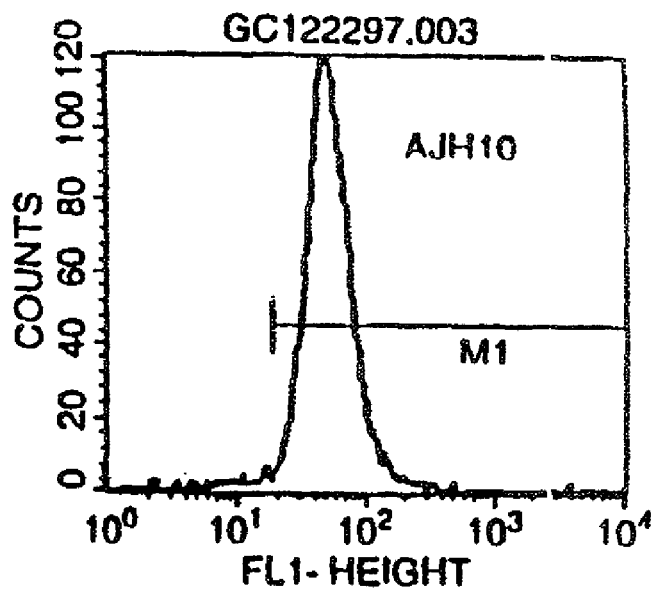
FIG. 14

Fig. 19: A-1

| | | | | | | | | | | | |
|---|---|---|---|---|---|---|---|---|---|---|---|
| ATOM | 1 | CB | THR | 145 | 131.250 | 52.244 | -9.297 | 1.00 | 82.68 | A | C |
| ATOM | 2 | OG1 | THR | 145 | 131.373 | 51.127 | -10.191 | 1.00 | 82.68 | A | O |
| ATOM | 3 | CG2 | THR | 145 | 132.601 | 52.936 | -9.145 | 1.00 | 82.68 | A | C |
| ATOM | 4 | C | THR | 145 | 129.280 | 51.301 | -8.080 | 1.00 | 146.54 | A | C |
| ATOM | 5 | O | THR | 145 | 128.489 | 51.352 | -7.134 | 1.00 | 146.94 | A | O |
| ATOM | 6 | N | THR | 145 | 131.576 | 50.663 | -7.360 | 1.00 | 144.92 | A | N |
| ATOM | 7 | CA | THR | 145 | 130.726 | 51.757 | -7.915 | 1.00 | 144.52 | A | C |
| ATOM | 8 | N | GLN | 146 | 128.941 | 50.856 | -9.288 | 1.00 | 36.14 | A | N |
| ATOM | 9 | CA | GLN | 146 | 127.592 | 50.397 | -9.569 | 1.00 | 34.29 | A | C |
| ATOM | 10 | CB | GLN | 146 | 127.046 | 51.086 | -10.823 | 1.00 | 99.89 | A | C |
| ATOM | 11 | CG | GLN | 146 | 127.887 | 50.902 | -12.065 | 1.00 | 99.89 | A | C |
| ATOM | 12 | CD | GLN | 146 | 127.274 | 51.575 | -13.279 | 1.00 | 99.89 | A | C |
| ATOM | 13 | OE1 | GLN | 146 | 127.787 | 51.454 | -14.392 | 1.00 | 99.89 | A | O |
| ATOM | 14 | NE2 | GLN | 146 | 126.170 | 52.290 | -13.070 | 1.00 | 99.89 | A | N |
| ATOM | 15 | C | GLN | 146 | 127.535 | 48.883 | -9.721 | 1.00 | 34.71 | A | C |
| ATOM | 16 | O | GLN | 146 | 128.084 | 48.314 | -10.667 | 1.00 | 36.57 | A | O |
| ATOM | 17 | N | LEU | 147 | 126.876 | 48.240 | -8.762 | 1.00 | 33.54 | A | N |
| ATOM | 18 | CA | LEU | 147 | 126.718 | 46.794 | -8.767 | 1.00 | 32.67 | A | C |
| ATOM | 19 | CB | LEU | 147 | 127.491 | 46.143 | -7.609 | 1.00 | 35.25 | A | C |
| ATOM | 20 | CG | LEU | 147 | 128.963 | 46.398 | -7.301 | 1.00 | 35.44 | A | C |
| ATOM | 21 | CD1 | LEU | 147 | 129.205 | 47.877 | -7.087 | 1.00 | 30.65 | A | C |
| ATOM | 22 | CD2 | LEU | 147 | 129.325 | 45.637 | -6.037 | 1.00 | 35.29 | A | C |
| ATOM | 23 | C | LEU | 147 | 125.247 | 46.451 | -8.575 | 1.00 | 31.65 | A | C |
| ATOM | 24 | O | LEU | 147 | 124.506 | 47.194 | -7.939 | 1.00 | 32.95 | A | O |
| ATOM | 25 | N | ASP | 148 | 124.832 | 45.325 | -9.142 | 1.00 | 25.19 | A | N |
| ATOM | 26 | CA | ASP | 148 | 123.477 | 44.817 | -8.976 | 1.00 | 22.65 | A | C |
| ATOM | 27 | CB | ASP | 148 | 122.907 | 44.329 | -10.302 | 1.00 | 27.55 | A | C |
| ATOM | 28 | CG | ASP | 148 | 122.330 | 45.446 | -11.125 | 1.00 | 27.17 | A | C |
| ATOM | 29 | OD1 | ASP | 148 | 121.787 | 45.158 | -12.208 | 1.00 | 26.28 | A | O |
| ATOM | 30 | OD2 | ASP | 148 | 122.413 | 46.612 | -10.686 | 1.00 | 25.35 | A | O |
| ATOM | 31 | C | ASP | 148 | 123.664 | 43.638 | -8.025 | 1.00 | 19.03 | A | C |
| ATOM | 32 | O | ASP | 148 | 124.119 | 42.567 | -8.422 | 1.00 | 18.33 | A | O |
| ATOM | 33 | N | ILE | 149 | 123.341 | 43.848 | -6.760 | 1.00 | 16.75 | A | N |
| ATOM | 34 | CA | ILE | 149 | 123.502 | 42.809 | -5.761 | 1.00 | 15.69 | A | C |
| ATOM | 35 | CB | ILE | 149 | 124.041 | 43.391 | -4.442 | 1.00 | 18.53 | A | C |
| ATOM | 36 | CG2 | ILE | 149 | 124.401 | 42.269 | -3.485 | 1.00 | 13.54 | A | C |
| ATOM | 37 | CG1 | ILE | 149 | 125.271 | 44.251 | -4.718 | 1.00 | 14.25 | A | C |
| ATOM | 38 | CD1 | ILE | 149 | 125.819 | 44.932 | -3.497 | 1.00 | 17.00 | A | C |
| ATOM | 39 | C | ILE | 149 | 122.185 | 42.129 | -5.456 | 1.00 | 17.34 | A | C |
| ATOM | 40 | O | ILE | 149 | 121.191 | 42.794 | -5.181 | 1.00 | 17.74 | A | O |
| ATOM | 41 | N | VAL | 150 | 122.175 | 40.805 | -5.526 | 1.00 | 11.00 | A | N |
| ATOM | 42 | CA | VAL | 150 | 120.987 | 40.036 | -5.193 | 1.00 | 12.56 | A | C |
| ATOM | 43 | CB | VAL | 150 | 120.571 | 39.089 | -6.336 | 1.00 | 16.85 | A | C |
| ATOM | 44 | CG1 | VAL | 150 | 119.409 | 38.210 | -5.885 | 1.00 | 19.04 | A | C |
| ATOM | 45 | CG2 | VAL | 150 | 120.164 | 39.894 | -7.555 | 1.00 | 18.66 | A | C |
| ATOM | 46 | C | VAL | 150 | 121.367 | 39.212 | -3.970 | 1.00 | 10.12 | A | C |
| ATOM | 47 | O | VAL | 150 | 122.387 | 38.526 | -3.973 | 1.00 | 8.27 | A | O |
| ATOM | 48 | N | ILE | 151 | 120.573 | 39.303 | -2.912 | 1.00 | 20.50 | A | N |
| ATOM | 49 | CA | ILE | 151 | 120.856 | 38.537 | -1.699 | 1.00 | 19.30 | A | C |
| ATOM | 50 | CB | ILE | 151 | 120.653 | 39.392 | -0.439 | 1.00 | 14.22 | A | C |
| ATOM | 51 | CG2 | ILE | 151 | 121.039 | 38.601 | 0.785 | 1.00 | 10.58 | A | C |
| ATOM | 52 | CG1 | ILE | 151 | 121.515 | 40.659 | -0.532 | 1.00 | 12.64 | A | C |
| ATOM | 53 | CD1 | ILE | 151 | 121.283 | 41.660 | 0.593 | 1.00 | 14.62 | A | C |
| ATOM | 54 | C | ILE | 151 | 119.931 | 37.329 | -1.646 | 1.00 | 17.42 | A | C |
| ATOM | 55 | O | ILE | 151 | 118.715 | 37.459 | -1.777 | 1.00 | 17.66 | A | O |
| ATOM | 56 | N | VAL | 152 | 120.511 | 36.150 | -1.470 | 1.00 | 17.56 | A | N |
| ATOM | 57 | CA | VAL | 152 | 119.741 | 34.915 | -1.428 | 1.00 | 18.41 | A | C |
| ATOM | 58 | CB | VAL | 152 | 120.395 | 33.849 | -2.309 | 1.00 | 11.45 | A | C |
| ATOM | 59 | CG1 | VAL | 152 | 119.470 | 32.664 | -2.460 | 1.00 | 10.58 | A | C |
| ATOM | 60 | CG2 | VAL | 152 | 120.758 | 34.458 | -3.667 | 1.00 | 7.89 | A | C |
| ATOM | 61 | C | VAL | 152 | 119.675 | 34.404 | -0.003 | 1.00 | 16.31 | A | C |
| ATOM | 62 | O | VAL | 152 | 120.602 | 33.755 | 0.469 | 1.00 | 9.91 | A | O |
| ATOM | 63 | N | LEU | 153 | 118.568 | 34.692 | 0.672 | 1.00 | 19.79 | A | N |
| ATOM | 64 | CA | LEU | 153 | 118.367 | 34.297 | 2.061 | 1.00 | 19.90 | A | C |
| ATOM | 65 | CB | LEU | 153 | 117.530 | 35.361 | 2.766 | 1.00 | 21.44 | A | C |
| ATOM | 66 | CG | LEU | 153 | 118.250 | 36.403 | 3.623 | 1.00 | 23.22 | A | C |
| ATOM | 67 | CD1 | LEU | 153 | 119.699 | 36.561 | 3.185 | 1.00 | 23.73 | A | C |
| ATOM | 68 | CD2 | LEU | 153 | 117.494 | 37.721 | 3.530 | 1.00 | 25.76 | A | C |
| ATOM | 69 | C | LEU | 153 | 117.732 | 32.929 | 2.300 | 1.00 | 20.96 | A | C |
| ATOM | 70 | O | LEU | 153 | 116.724 | 32.574 | 1.690 | 1.00 | 19.96 | A | O |
| ATOM | 71 | N | ASP | 154 | 118.336 | 32.165 | 3.200 | 1.00 | 19.89 | A | N |
| ATOM | 72 | CA | ASP | 154 | 117.820 | 30.854 | 3.554 | 1.00 | 19.37 | A | C |
| ATOM | 73 | CB | ASP | 154 | 118.952 | 29.983 | 4.129 | 1.00 | 22.72 | A | C |

Fig. 19: A-2

| | | | | | | | | | | | |
|---|---|---|---|---|---|---|---|---|---|---|---|
| ATOM | 74 | CG | ASP | 154 | 118.486 | 28.601 | 4.546 | 1.00 | 21.92 | A | C |
| ATOM | 75 | OD1 | ASP | 154 | 117.266 | 28.363 | 4.537 | 1.00 | 25.43 | A | O |
| ATOM | 76 | OD2 | ASP | 154 | 119.340 | 27.754 | 4.893 | 1.00 | 18.24 | A | O |
| ATOM | 77 | C | ASP | 154 | 116.770 | 31.153 | 4.623 | 1.00 | 22.71 | A | C |
| ATOM | 78 | O | ASP | 154 | 117.062 | 31.802 | 5.630 | 1.00 | 19.03 | A | O |
| ATOM | 79 | N | GLY | 155 | 115.540 | 30.718 | 4.393 | 1.00 | 3.06 | A | N |
| ATOM | 80 | CA | GLY | 155 | 114.491 | 30.948 | 5.370 | 1.00 | 5.13 | A | C |
| ATOM | 81 | C | GLY | 155 | 113.840 | 29.638 | 5.788 | 1.00 | 6.39 | A | C |
| ATOM | 82 | O | GLY | 155 | 112.751 | 29.633 | 6.368 | 1.00 | 8.88 | A | O |
| ATOM | 83 | N | SER | 156 | 114.512 | 28.521 | 5.494 | 1.00 | 19.70 | A | N |
| ATOM | 84 | CA | SER | 156 | 114.011 | 27.191 | 5.832 | 1.00 | 24.28 | A | C |
| ATOM | 85 | CB | SER | 156 | 114.994 | 26.111 | 5.353 | 1.00 | 33.45 | A | C |
| ATOM | 86 | OG | SER | 156 | 116.261 | 26.252 | 5.967 | 1.00 | 36.37 | A | O |
| ATOM | 87 | C | SER | 156 | 113.773 | 27.054 | 7.330 | 1.00 | 21.27 | A | C |
| ATOM | 88 | O | SER | 156 | 114.270 | 27.843 | 8.128 | 1.00 | 24.45 | A | O |
| ATOM | 89 | N | ASN | 157 | 113.008 | 26.037 | 7.700 | 1.00 | 21.98 | A | N |
| ATOM | 90 | CA | ASN | 157 | 112.686 | 25.802 | 9.091 | 1.00 | 19.06 | A | C |
| ATOM | 91 | CB | ASN | 157 | 112.027 | 24.435 | 9.247 | 1.00 | 21.82 | A | C |
| ATOM | 92 | CG | ASN | 157 | 110.586 | 24.434 | 8.785 | 1.00 | 23.31 | A | C |
| ATOM | 93 | OD1 | ASN | 157 | 109.944 | 23.385 | 8.706 | 1.00 | 20.38 | A | O |
| ATOM | 94 | ND2 | ASN | 157 | 110.066 | 25.612 | 8.479 | 1.00 | 20.59 | A | N |
| ATOM | 95 | C | ASN | 157 | 113.859 | 25.913 | 10.048 | 1.00 | 17.03 | A | C |
| ATOM | 96 | O | ASN | 157 | 113.720 | 26.498 | 11.132 | 1.00 | 15.01 | A | O |
| ATOM | 97 | N | SER | 158 | 115.006 | 25.367 | 9.653 | 1.00 | 15.99 | A | N |
| ATOM | 98 | CA | SER | 158 | 116.179 | 25.378 | 10.510 | 1.00 | 14.20 | A | C |
| ATOM | 99 | CB | SER | 158 | 117.327 | 24.603 | 9.864 | 1.00 | 26.18 | A | C |
| ATOM | 100 | OG | SER | 158 | 117.597 | 25.067 | 8.562 | 1.00 | 28.89 | A | O |
| ATOM | 101 | C | SER | 158 | 116.656 | 26.753 | 10.941 | 1.00 | 14.97 | A | C |
| ATOM | 102 | O | SER | 158 | 117.053 | 26.930 | 12.097 | 1.00 | 12.14 | A | O |
| ATOM | 103 | N | ILE | 159 | 116.623 | 27.730 | 10.039 | 1.00 | 8.33 | A | N |
| ATOM | 104 | CA | ILE | 159 | 117.050 | 29.083 | 10.379 | 1.00 | 12.93 | A | C |
| ATOM | 105 | CB | ILE | 159 | 116.801 | 30.035 | 9.193 | 1.00 | 9.66 | A | C |
| ATOM | 106 | CG2 | ILE | 159 | 117.138 | 31.479 | 9.592 | 1.00 | 9.57 | A | C |
| ATOM | 107 | CG1 | ILE | 159 | 117.650 | 29.609 | 8.000 | 1.00 | 14.44 | A | C |
| ATOM | 108 | CD1 | ILE | 159 | 119.134 | 29.804 | 8.204 | 1.00 | 19.60 | A | C |
| ATOM | 109 | C | ILE | 159 | 116.292 | 29.604 | 11.616 | 1.00 | 17.24 | A | C |
| ATOM | 110 | O | ILE | 159 | 115.059 | 29.575 | 11.659 | 1.00 | 16.65 | A | O |
| ATOM | 111 | N | TYR | 160 | 117.032 | 30.084 | 12.611 | 1.00 | 29.54 | A | N |
| ATOM | 112 | CA | TYR | 160 | 116.438 | 30.600 | 13.849 | 1.00 | 31.67 | A | C |
| ATOM | 113 | CB | TYR | 160 | 115.775 | 29.455 | 14.639 | 1.00 | 16.89 | A | C |
| ATOM | 114 | CG | TYR | 160 | 115.094 | 29.869 | 15.941 | 1.00 | 13.65 | A | C |
| ATOM | 115 | CD1 | TYR | 160 | 113.717 | 30.089 | 15.993 | 1.00 | 16.07 | A | C |
| ATOM | 116 | CE1 | TYR | 160 | 113.088 | 30.466 | 17.186 | 1.00 | 13.67 | A | C |
| ATOM | 117 | CD2 | TYR | 160 | 115.828 | 30.038 | 17.116 | 1.00 | 11.30 | A | C |
| ATOM | 118 | CE2 | TYR | 160 | 115.211 | 30.416 | 18.304 | 1.00 | 15.01 | A | C |
| ATOM | 119 | CZ | TYR | 160 | 113.841 | 30.627 | 18.338 | 1.00 | 14.36 | A | C |
| ATOM | 120 | OH | TYR | 160 | 113.227 | 30.987 | 19.522 | 1.00 | 19.36 | A | O |
| ATOM | 121 | C | TYR | 160 | 117.498 | 31.264 | 14.734 | 1.00 | 33.39 | A | C |
| ATOM | 122 | O | TYR | 160 | 118.567 | 30.703 | 14.970 | 1.00 | 39.31 | A | O |
| ATOM | 123 | N | PRO | 161 | 117.206 | 32.467 | 15.248 | 1.00 | 31.87 | A | N |
| ATOM | 124 | CD | PRO | 161 | 117.988 | 33.002 | 16.380 | 1.00 | 14.17 | A | C |
| ATOM | 125 | CA | PRO | 161 | 115.969 | 33.234 | 15.055 | 1.00 | 30.15 | A | C |
| ATOM | 126 | CB | PRO | 161 | 115.831 | 33.976 | 16.379 | 1.00 | 18.55 | A | C |
| ATOM | 127 | CG | PRO | 161 | 117.278 | 34.291 | 16.703 | 1.00 | 21.71 | A | C |
| ATOM | 128 | C | PRO | 161 | 116.038 | 34.183 | 13.852 | 1.00 | 28.81 | A | C |
| ATOM | 129 | O | PRO | 161 | 117.074 | 34.792 | 13.580 | 1.00 | 28.13 | A | O |
| ATOM | 130 | N | TRP | 162 | 114.919 | 34.320 | 13.149 | 1.00 | 29.23 | A | N |
| ATOM | 131 | CA | TRP | 162 | 114.839 | 35.170 | 11.967 | 1.00 | 30.30 | A | C |
| ATOM | 132 | CB | TRP | 162 | 113.388 | 35.250 | 11.493 | 1.00 | 29.17 | A | C |
| ATOM | 133 | CG | TRP | 162 | 113.214 | 35.826 | 10.120 | 1.00 | 29.69 | A | C |
| ATOM | 134 | CD2 | TRP | 162 | 113.838 | 35.375 | 8.912 | 1.00 | 24.53 | A | C |
| ATOM | 135 | CE2 | TRP | 162 | 113.338 | 36.175 | 7.859 | 1.00 | 28.08 | A | C |
| ATOM | 136 | CE3 | TRP | 162 | 114.768 | 34.373 | 8.615 | 1.00 | 23.94 | A | C |
| ATOM | 137 | CD1 | TRP | 162 | 112.387 | 36.854 | 9.758 | 1.00 | 28.88 | A | C |
| ATOM | 138 | NE1 | TRP | 162 | 112.455 | 37.071 | 8.403 | 1.00 | 30.75 | A | N |
| ATOM | 139 | CZ2 | TRP | 162 | 113.741 | 36.000 | 6.532 | 1.00 | 26.62 | A | C |
| ATOM | 140 | CZ3 | TRP | 162 | 115.167 | 34.202 | 7.288 | 1.00 | 22.27 | A | C |
| ATOM | 141 | CH2 | TRP | 162 | 114.652 | 35.012 | 6.268 | 1.00 | 27.18 | A | C |
| ATOM | 142 | C | TRP | 162 | 115.381 | 36.579 | 12.210 | 1.00 | 32.08 | A | C |
| ATOM | 143 | O | TRP | 162 | 116.074 | 37.133 | 11.352 | 1.00 | 31.23 | A | O |
| ATOM | 144 | N | GLU | 163 | 115.077 | 37.147 | 13.381 | 1.00 | 25.22 | A | N |
| ATOM | 145 | CA | GLU | 163 | 115.510 | 38.504 | 13.734 | 1.00 | 27.00 | A | C |
| ATOM | 146 | CB | GLU | 163 | 115.108 | 38.857 | 15.172 | 1.00 | 105.95 | A | C |

Fig. 19: A-3

```
ATOM    147  CG   GLU  163     115.906  38.145  16.248  1.00  112.26  A  C
ATOM    148  CD   GLU  163     115.816  38.833  17.603  1.00  114.40  A  C
ATOM    149  OE1  GLU  163     116.310  39.975  17.732  1.00  116.11  A  O
ATOM    150  OE2  GLU  163     115.253  38.232  18.541  1.00  113.36  A  O
ATOM    151  C    GLU  163     117.008  38.723  13.557  1.00   26.66  A  C
ATOM    152  O    GLU  163     117.448  39.799  13.136  1.00   22.83  A  O
ATOM    153  N    SER  164     117.800  37.709  13.865  1.00   20.71  A  N
ATOM    154  CA   SER  164     119.241  37.850  13.715  1.00   17.90  A  C
ATOM    155  CB   SER  164     119.955  36.647  14.335  1.00   27.61  A  C
ATOM    156  OG   SER  164     119.716  36.582  15.731  1.00   33.50  A  O
ATOM    157  C    SER  164     119.601  37.988  12.235  1.00   18.66  A  C
ATOM    158  O    SER  164     120.436  38.813  11.863  1.00   21.86  A  O
ATOM    159  N    VAL  165     118.956  37.179  11.398  1.00    9.03  A  N
ATOM    160  CA   VAL  165     119.189  37.213   9.961  1.00    8.42  A  C
ATOM    161  CB   VAL  165     118.303  36.166   9.226  1.00   21.53  A  C
ATOM    162  CG1  VAL  165     118.296  36.430   7.721  1.00   22.92  A  C
ATOM    163  CG2  VAL  165     118.826  34.760   9.505  1.00   24.53  A  C
ATOM    164  C    VAL  165     118.873  38.595   9.411  1.00    9.58  A  C
ATOM    165  O    VAL  165     119.610  39.131   8.574  1.00   11.40  A  O
ATOM    166  N    ILE  166     117.772  39.169   9.887  1.00   17.73  A  N
ATOM    167  CA   ILE  166     117.351  40.482   9.427  1.00   17.05  A  C
ATOM    168  CB   ILE  166     115.903  40.763   9.840  1.00   21.02  A  C
ATOM    169  CG2  ILE  166     115.489  42.162   9.413  1.00   20.23  A  C
ATOM    170  CG1  ILE  166     114.997  39.737   9.164  1.00   20.88  A  C
ATOM    171  CD1  ILE  166     113.538  39.919   9.499  1.00   17.28  A  C
ATOM    172  C    ILE  166     118.281  41.564   9.929  1.00   16.50  A  C
ATOM    173  O    ILE  166     118.560  42.520   9.206  1.00   18.25  A  O
ATOM    174  N    ALA  167     118.774  41.413  11.157  1.00   25.46  A  N
ATOM    175  CA   ALA  167     119.711  42.391  11.710  1.00   26.06  A  C
ATOM    176  CB   ALA  167     120.095  42.021  13.100  1.00    7.73  A  C
ATOM    177  C    ALA  167     120.941  42.371  10.823  1.00   27.27  A  C
ATOM    178  O    ALA  167     121.546  43.414  10.544  1.00   23.87  A  O
ATOM    179  N    PHE  168     121.303  41.167  10.383  1.00   18.13  A  N
ATOM    180  CA   PHE  168     122.442  40.989   9.498  1.00   16.65  A  C
ATOM    181  CB   PHE  168     122.626  39.513   9.158  1.00   32.51  A  C
ATOM    182  CG   PHE  168     123.514  39.273   7.970  1.00   31.01  A  C
ATOM    183  CD1  PHE  168     122.968  39.066   6.701  1.00   32.61  A  C
ATOM    184  CD2  PHE  168     124.894  39.290   8.106  1.00   29.32  A  C
ATOM    185  CE1  PHE  168     123.792  38.882   5.585  1.00   31.09  A  C
ATOM    186  CE2  PHE  168     125.724  39.109   7.000  1.00   31.14  A  C
ATOM    187  CZ   PHE  168     125.173  38.906   5.738  1.00   33.63  A  C
ATOM    188  C    PHE  168     122.222  41.796   8.227  1.00   17.51  A  C
ATOM    189  O    PHE  168     123.139  42.475   7.750  1.00   13.95  A  O
ATOM    190  N    LEU  169     121.007  41.719   7.680  1.00   16.88  A  N
ATOM    191  CA   LEU  169     120.677  42.467   6.471  1.00   19.47  A  C
ATOM    192  CB   LEU  169     119.262  42.140   6.000  1.00   14.12  A  C
ATOM    193  CG   LEU  169     119.041  40.860   5.213  1.00   13.28  A  C
ATOM    194  CD1  LEU  169     117.662  40.952   4.603  1.00    9.74  A  C
ATOM    195  CD2  LEU  169     120.100  40.694   4.127  1.00   10.14  A  C
ATOM    196  C    LEU  169     120.777  43.966   6.731  1.00   21.77  A  C
ATOM    197  O    LEU  169     121.409  44.694   5.968  1.00   23.20  A  O
ATOM    198  N    ASN  170     120.150  44.419   7.815  1.00   20.45  A  N
ATOM    199  CA   ASN  170     120.159  45.832   8.175  1.00   17.58  A  C
ATOM    200  CB   ASN  170     119.534  46.018   9.562  1.00   31.53  A  C
ATOM    201  CG   ASN  170     119.017  47.426   9.791  1.00   34.95  A  C
ATOM    202  OD1  ASN  170     119.740  48.282  10.284  1.00   30.48  A  O
ATOM    203  ND2  ASN  170     117.762  47.671   9.421  1.00   32.86  A  N
ATOM    204  C    ASN  170     121.587  46.341   8.151  1.00   17.59  A  C
ATOM    205  O    ASN  170     121.941  47.174   7.321  1.00   17.80  A  O
ATOM    206  N    ASP  171     122.412  45.812   9.040  1.00   11.82  A  N
ATOM    207  CA   ASP  171     123.816  46.218   9.120  1.00   13.94  A  C
ATOM    208  CB   ASP  171     124.588  45.282  10.048  1.00   56.27  A  C
ATOM    209  CG   ASP  171     124.405  45.627  11.508  1.00   63.92  A  C
ATOM    210  OD1  ASP  171     123.248  45.689  11.971  1.00   66.14  A  O
ATOM    211  OD2  ASP  171     125.427  45.834  12.196  1.00   65.78  A  O
ATOM    212  C    ASP  171     124.509  46.244   7.760  1.00   15.43  A  C
ATOM    213  O    ASP  171     125.223  47.194   7.435  1.00   14.15  A  O
ATOM    214  N    LEU  172     124.289  45.200   6.966  1.00   15.45  A  N
ATOM    215  CA   LEU  172     124.910  45.099   5.650  1.00   16.13  A  C
ATOM    216  CB   LEU  172     124.633  43.717   5.047  1.00   10.67  A  C
ATOM    217  CG   LEU  172     125.667  43.058   4.123  1.00   10.16  A  C
ATOM    218  CD1  LEU  172     124.905  42.379   2.979  1.00    7.76  A  C
ATOM    219  CD2  LEU  172     126.672  44.070   3.594  1.00    8.33  A  C
```

Fig. 19: A-4

| ATOM | 220 | C | LEU | 172 | 124.401 | 46.178 | 4.699 | 1.00 | 16.47 | A | C |
| --- | --- | --- | --- | --- | --- | --- | --- | --- | --- | --- | --- |
| ATOM | 221 | O | LEU | 172 | 125.182 | 46.951 | 4.156 | 1.00 | 16.46 | A | O |
| ATOM | 222 | N | LEU | 173 | 123.088 | 46.226 | 4.509 | 1.00 | 30.03 | A | N |
| ATOM | 223 | CA | LEU | 173 | 122.475 | 47.193 | 3.609 | 1.00 | 32.78 | A | C |
| ATOM | 224 | CB | LEU | 173 | 120.967 | 46.932 | 3.474 | 1.00 | 23.11 | A | C |
| ATOM | 225 | CG | LEU | 173 | 120.357 | 45.803 | 2.627 | 1.00 | 24.46 | A | C |
| ATOM | 226 | CD1 | LEU | 173 | 121.069 | 45.702 | 1.292 | 1.00 | 27.98 | A | C |
| ATOM | 227 | CD2 | LEU | 173 | 120.456 | 44.501 | 3.353 | 1.00 | 25.01 | A | C |
| ATOM | 228 | C | LEU | 173 | 122.675 | 48.663 | 3.984 | 1.00 | 34.21 | A | C |
| ATOM | 229 | O | LEU | 173 | 122.937 | 49.495 | 3.105 | 1.00 | 30.93 | A | O |
| ATOM | 230 | N | LYS | 174 | 122.558 | 48.989 | 5.271 | 1.00 | 33.34 | A | N |
| ATOM | 231 | CA | LYS | 174 | 122.684 | 50.379 | 5.693 | 1.00 | 33.56 | A | C |
| ATOM | 232 | CB | LYS | 174 | 122.428 | 50.508 | 7.193 | 1.00 | 32.34 | A | C |
| ATOM | 233 | CG | LYS | 174 | 123.590 | 50.195 | 8.102 | 1.00 | 32.67 | A | C |
| ATOM | 234 | CD | LYS | 174 | 123.170 | 50.471 | 9.551 | 1.00 | 31.92 | A | C |
| ATOM | 235 | CE | LYS | 174 | 124.365 | 50.601 | 10.504 | 1.00 | 27.17 | A | C |
| ATOM | 236 | NZ | LYS | 174 | 125.178 | 49.351 | 10.664 | 1.00 | 23.64 | A | N |
| ATOM | 237 | C | LYS | 174 | 124.004 | 51.046 | 5.317 | 1.00 | 31.92 | A | C |
| ATOM | 238 | O | LYS | 174 | 124.060 | 52.256 | 5.142 | 1.00 | 32.79 | A | O |
| ATOM | 239 | N | ARG | 175 | 125.059 | 50.255 | 5.176 | 1.00 | 34.34 | A | N |
| ATOM | 240 | CA | ARG | 175 | 126.385 | 50.759 | 4.797 | 1.00 | 36.57 | A | C |
| ATOM | 241 | CB | ARG | 175 | 127.468 | 49.712 | 5.125 | 1.00 | 50.56 | A | C |
| ATOM | 242 | CG | ARG | 175 | 127.708 | 49.400 | 6.606 | 1.00 | 57.49 | A | C |
| ATOM | 243 | CD | ARG | 175 | 128.550 | 48.120 | 6.760 | 1.00 | 61.77 | A | C |
| ATOM | 244 | NE | ARG | 175 | 129.398 | 48.107 | 7.957 | 1.00 | 66.67 | A | N |
| ATOM | 245 | CZ | ARG | 175 | 128.954 | 48.049 | 9.211 | 1.00 | 70.25 | A | C |
| ATOM | 246 | NH1 | ARG | 175 | 127.653 | 47.997 | 9.461 | 1.00 | 70.45 | A | N |
| ATOM | 247 | NH2 | ARG | 175 | 129.819 | 48.039 | 10.219 | 1.00 | 71.15 | A | N |
| ATOM | 248 | C | ARG | 175 | 126.461 | 51.051 | 3.288 | 1.00 | 34.10 | A | C |
| ATOM | 249 | O | ARG | 175 | 127.487 | 51.522 | 2.796 | 1.00 | 33.94 | A | O |
| ATOM | 250 | N | MET | 176 | 125.384 | 50.766 | 2.557 | 1.00 | 18.81 | A | N |
| ATOM | 251 | CA | MET | 176 | 125.371 | 50.959 | 1.104 | 1.00 | 15.29 | A | C |
| ATOM | 252 | CB | MET | 176 | 124.758 | 49.728 | 0.431 | 1.00 | 45.67 | A | C |
| ATOM | 253 | CG | MET | 176 | 125.646 | 48.505 | 0.474 | 1.00 | 42.57 | A | C |
| ATOM | 254 | SD | MET | 176 | 124.887 | 47.063 | -0.292 | 1.00 | 46.71 | A | S |
| ATOM | 255 | CE | MET | 176 | 124.633 | 46.046 | 1.139 | 1.00 | 40.22 | A | C |
| ATOM | 256 | C | MET | 176 | 124.679 | 52.199 | 0.546 | 1.00 | 18.80 | A | C |
| ATOM | 257 | O | MET | 176 | 123.797 | 52.768 | 1.176 | 1.00 | 18.87 | A | O |
| ATOM | 258 | N | ASP | 177 | 125.098 | 52.605 | -0.652 | 1.00 | 31.75 | A | N |
| ATOM | 259 | CA | ASP | 177 | 124.504 | 53.744 | -1.344 | 1.00 | 34.24 | A | C |
| ATOM | 260 | CB | ASP | 177 | 125.584 | 54.671 | -1.903 | 1.00 | 129.70 | A | C |
| ATOM | 261 | CG | ASP | 177 | 126.196 | 55.556 | -0.838 | 1.00 | 132.65 | A | C |
| ATOM | 262 | OD1 | ASP | 177 | 127.004 | 56.437 | -1.194 | 1.00 | 132.32 | A | O |
| ATOM | 263 | OD2 | ASP | 177 | 125.869 | 55.372 | 0.354 | 1.00 | 134.30 | A | O |
| ATOM | 264 | C | ASP | 177 | 123.638 | 53.207 | -2.480 | 1.00 | 34.16 | A | C |
| ATOM | 265 | O | ASP | 177 | 124.085 | 53.107 | -3.617 | 1.00 | 33.88 | A | O |
| ATOM | 266 | N | ILE | 178 | 122.402 | 52.848 | -2.153 | 1.00 | 22.62 | A | N |
| ATOM | 267 | CA | ILE | 178 | 121.464 | 52.307 | -3.122 | 1.00 | 22.76 | A | C |
| ATOM | 268 | CB | ILE | 178 | 120.326 | 51.524 | -2.407 | 1.00 | 26.30 | A | C |
| ATOM | 269 | CG2 | ILE | 178 | 119.208 | 51.207 | -3.390 | 1.00 | 24.58 | A | C |
| ATOM | 270 | CG1 | ILE | 178 | 120.866 | 50.222 | -1.803 | 1.00 | 27.36 | A | C |
| ATOM | 271 | CD1 | ILE | 178 | 121.188 | 50.292 | -0.325 | 1.00 | 29.20 | A | C |
| ATOM | 272 | C | ILE | 178 | 120.848 | 53.398 | -4.009 | 1.00 | 21.90 | A | C |
| ATOM | 273 | O | ILE | 178 | 120.532 | 54.501 | -3.539 | 1.00 | 23.89 | A | O |
| ATOM | 274 | N | GLY | 179 | 120.669 | 53.077 | -5.292 | 1.00 | 18.17 | A | N |
| ATOM | 275 | CA | GLY | 179 | 120.091 | 54.029 | -6.226 | 1.00 | 17.89 | A | C |
| ATOM | 276 | C | GLY | 179 | 120.123 | 53.536 | -7.658 | 1.00 | 18.65 | A | C |
| ATOM | 277 | O | GLY | 179 | 121.019 | 52.786 | -8.023 | 1.00 | 16.80 | A | O |
| ATOM | 278 | N | PRO | 180 | 119.150 | 53.937 | -8.498 | 1.00 | 18.34 | A | N |
| ATOM | 279 | CD | PRO | 180 | 117.980 | 54.770 | -8.159 | 1.00 | 16.60 | A | C |
| ATOM | 280 | CA | PRO | 180 | 119.094 | 53.512 | -9.901 | 1.00 | 19.40 | A | C |
| ATOM | 281 | CB | PRO | 180 | 118.044 | 54.442 | -10.498 | 1.00 | 15.44 | A | C |
| ATOM | 282 | CG | PRO | 180 | 117.074 | 54.573 | -9.365 | 1.00 | 17.83 | A | C |
| ATOM | 283 | C | PRO | 180 | 120.432 | 53.622 | -10.597 | 1.00 | 21.18 | A | C |
| ATOM | 284 | O | PRO | 180 | 120.706 | 52.877 | -11.529 | 1.00 | 21.82 | A | O |
| ATOM | 285 | N | LYS | 181 | 121.262 | 54.553 | -10.139 | 1.00 | 25.85 | A | N |
| ATOM | 286 | CA | LYS | 181 | 122.581 | 54.751 | -10.732 | 1.00 | 26.27 | A | C |
| ATOM | 287 | CB | LYS | 181 | 122.737 | 56.187 | -11.253 | 1.00 | 26.21 | A | C |
| ATOM | 288 | CG | LYS | 181 | 121.801 | 56.557 | -12.403 | 1.00 | 26.81 | A | C |
| ATOM | 289 | CD | LYS | 181 | 122.014 | 55.683 | -13.627 | 1.00 | 25.67 | A | C |
| ATOM | 290 | CE | LYS | 181 | 121.014 | 56.031 | -14.719 | 1.00 | 28.19 | A | C |
| ATOM | 291 | NZ | LYS | 181 | 121.097 | 55.146 | -15.923 | 1.00 | 27.76 | A | N |
| ATOM | 292 | C | LYS | 181 | 123.684 | 54.451 | -9.729 | 1.00 | 25.62 | A | C |

Fig. 19: A-5

```
ATOM    293  O    LYS   181     124.854   54.742   -9.975  1.00   23.94    A    O
ATOM    294  N    GLN   182     123.300   53.870   -8.599  1.00   34.95    A    N
ATOM    295  CA   GLN   182     124.246   53.513   -7.548  1.00   33.61    A    C
ATOM    296  CB   GLN   182     123.797   54.096   -6.207  1.00   89.66    A    C
ATOM    297  CG   GLN   182     123.331   55.528   -6.251  1.00   90.94    A    C
ATOM    298  CD   GLN   182     124.443   56.478   -6.597  1.00   92.56    A    C
ATOM    299  OE1  GLN   182     125.007   56.418   -7.686  1.00   93.40    A    O
ATOM    300  NE2  GLN   182     124.772   57.364   -5.667  1.00   93.92    A    N
ATOM    301  C    GLN   182     124.258   51.991   -7.439  1.00   32.52    A    C
ATOM    302  O    GLN   182     124.398   51.278   -8.429  1.00   36.85    A    O
ATOM    303  N    THR   183     124.096   51.507   -6.216  1.00   26.87    A    N
ATOM    304  CA   THR   183     124.052   50.083   -5.953  1.00   23.79    A    C
ATOM    305  CB   THR   183     124.642   49.767   -4.584  1.00   30.55    A    C
ATOM    306  OG1  THR   183     125.983   50.262   -4.526  1.00   27.00    A    O
ATOM    307  CG2  THR   183     124.629   48.274   -4.331  1.00   28.23    A    C
ATOM    308  C    THR   183     122.590   49.687   -5.944  1.00   23.45    A    C
ATOM    309  O    THR   183     121.752   50.380   -5.368  1.00   21.98    A    O
ATOM    310  N    GLN   184     122.269   48.592   -6.608  1.00   25.73    A    N
ATOM    311  CA   GLN   184     120.897   48.127   -6.612  1.00   21.38    A    C
ATOM    312  CB   GLN   184     120.399   47.898   -8.042  1.00   35.06    A    C
ATOM    313  CG   GLN   184     120.016   49.181   -8.770  1.00   34.81    A    C
ATOM    314  CD   GLN   184     118.982   48.942   -9.856  1.00   34.28    A    C
ATOM    315  OE1  GLN   184     119.215   48.164  -10.781  1.00   29.98    A    O
ATOM    316  NE2  GLN   184     117.834   49.604   -9.748  1.00   32.58    A    N
ATOM    317  C    GLN   184     120.862   46.839   -5.800  1.00   21.76    A    C
ATOM    318  O    GLN   184     121.832   46.087   -5.780  1.00   19.15    A    O
ATOM    319  N    VAL   185     119.753   46.599   -5.112  1.00   33.23    A    N
ATOM    320  CA   VAL   185     119.634   45.408   -4.298  1.00   31.60    A    C
ATOM    321  CB   VAL   185     119.868   45.742   -2.810  1.00   20.42    A    C
ATOM    322  CG1  VAL   185     119.572   44.535   -1.938  1.00   20.41    A    C
ATOM    323  CG2  VAL   185     121.294   46.148   -2.614  1.00    6.28    A    C
ATOM    324  C    VAL   185     118.297   44.701   -4.445  1.00   32.19    A    C
ATOM    325  O    VAL   185     117.237   45.322   -4.469  1.00   29.34    A    O
ATOM    326  N    GLY   186     118.369   43.382   -4.554  1.00   17.76    A    N
ATOM    327  CA   GLY   186     117.177   42.573   -4.672  1.00   19.39    A    C
ATOM    328  C    GLY   186     117.355   41.424   -3.711  1.00   17.37    A    C
ATOM    329  O    GLY   186     118.470   40.929   -3.543  1.00   22.73    A    O
ATOM    330  N    ILE   187     116.278   40.995   -3.073  1.00   15.41    A    N
ATOM    331  CA   ILE   187     116.395   39.906   -2.133  1.00   14.00    A    C
ATOM    332  CB   ILE   187     116.117   40.403   -0.675  1.00   10.12    A    C
ATOM    333  CG2  ILE   187     116.053   39.225    0.299  1.00    7.45    A    C
ATOM    334  CG1  ILE   187     117.232   41.364   -0.253  1.00   10.64    A    C
ATOM    335  CD1  ILE   187     117.156   41.817    1.176  1.00   11.69    A    C
ATOM    336  C    ILE   187     115.496   38.731   -2.485  1.00   13.29    A    C
ATOM    337  O    ILE   187     114.301   38.896   -2.768  1.00   12.19    A    O
ATOM    338  N    VAL   188     116.097   37.546   -2.473  1.00   16.67    A    N
ATOM    339  CA   VAL   188     115.403   36.303   -2.769  1.00   16.34    A    C
ATOM    340  CB   VAL   188     116.082   35.567   -3.951  1.00   11.96    A    C
ATOM    341  CG1  VAL   188     115.642   34.122   -3.993  1.00    7.23    A    C
ATOM    342  CG2  VAL   188     115.742   36.251   -5.248  1.00   12.38    A    C
ATOM    343  C    VAL   188     115.464   35.404   -1.536  1.00   14.88    A    C
ATOM    344  O    VAL   188     116.509   35.286   -0.895  1.00   14.29    A    O
ATOM    345  N    GLN   189     114.348   34.774   -1.194  1.00   30.23    A    N
ATOM    346  CA   GLN   189     114.335   33.873   -0.049  1.00   29.91    A    C
ATOM    347  CB   GLN   189     113.374   34.363    1.039  1.00   26.02    A    C
ATOM    348  CG   GLN   189     113.277   33.399    2.210  1.00   23.53    A    C
ATOM    349  CD   GLN   189     112.257   33.807    3.267  1.00   24.24    A    C
ATOM    350  OE1  GLN   189     111.891   32.998    4.125  1.00   25.46    A    O
ATOM    351  NE2  GLN   189     111.800   35.058    3.219  1.00   25.28    A    N
ATOM    352  C    GLN   189     113.911   32.490   -0.520  1.00   26.90    A    C
ATOM    353  O    GLN   189     113.056   32.366   -1.401  1.00   25.26    A    O
ATOM    354  N    TYR   190     114.516   31.455    0.063  1.00   12.87    A    N
ATOM    355  CA   TYR   190     114.196   30.084   -0.310  1.00   16.39    A    C
ATOM    356  CB   TYR   190     115.267   29.539   -1.257  1.00   17.86    A    C
ATOM    357  CG   TYR   190     116.599   29.241   -0.590  1.00   13.63    A    C
ATOM    358  CD1  TYR   190     116.887   27.963   -0.092  1.00   13.63    A    C
ATOM    359  CE1  TYR   190     118.104   27.687    0.517  1.00   13.63    A    C
ATOM    360  CD2  TYR   190     117.569   30.233   -0.453  1.00   13.63    A    C
ATOM    361  CE2  TYR   190     118.787   29.968    0.159  1.00   13.63    A    C
ATOM    362  CZ   TYR   190     119.053   28.698    0.640  1.00   13.63    A    C
ATOM    363  OH   TYR   190     120.278   28.442    1.228  1.00   13.63    A    O
ATOM    364  C    TYR   190     114.035   29.135    0.878  1.00   18.24    A    C
ATOM    365  O    TYR   190     114.456   29.424    2.003  1.00   18.32    A    O
```

Fig. 19: A-6

| | | | | | | | | | | | |
|---|---|---|---|---|---|---|---|---|---|---|---|
| ATOM | 366 | N | GLY | 191 | 113.417 | 27.994 | 0.588 | 1.00 | 15.40 | A | N |
| ATOM | 367 | CA | GLY | 191 | 113.171 | 26.954 | 1.572 | 1.00 | 13.15 | A | C |
| ATOM | 368 | C | GLY | 191 | 112.683 | 25.776 | 0.764 | 1.00 | 14.59 | A | C |
| ATOM | 369 | O | GLY | 191 | 113.482 | 25.084 | 0.139 | 1.00 | 17.97 | A | O |
| ATOM | 370 | N | GLU | 192 | 111.371 | 25.552 | 0.769 | 1.00 | 27.03 | A | N |
| ATOM | 371 | CA | GLU | 192 | 110.764 | 24.475 | -0.020 | 1.00 | 29.04 | A | C |
| ATOM | 372 | CB | GLU | 192 | 109.400 | 24.089 | 0.537 | 1.00 | 28.96 | A | C |
| ATOM | 373 | CG | GLU | 192 | 109.412 | 23.507 | 1.929 | 1.00 | 29.34 | A | C |
| ATOM | 374 | CD | GLU | 192 | 108.020 | 23.089 | 2.390 | 1.00 | 29.53 | A | C |
| ATOM | 375 | OE1 | GLU | 192 | 107.890 | 22.532 | 3.505 | 1.00 | 32.42 | A | O |
| ATOM | 376 | OE2 | GLU | 192 | 107.051 | 23.322 | 1.633 | 1.00 | 27.40 | A | O |
| ATOM | 377 | C | GLU | 192 | 110.562 | 25.062 | -1.410 | 1.00 | 28.85 | A | C |
| ATOM | 378 | O | GLU | 192 | 110.692 | 24.380 | -2.422 | 1.00 | 30.22 | A | O |
| ATOM | 379 | N | ASN | 193 | 110.236 | 26.350 | -1.433 | 1.00 | 34.68 | A | N |
| ATOM | 380 | CA | ASN | 193 | 110.019 | 27.088 | -2.668 | 1.00 | 35.89 | A | C |
| ATOM | 381 | CB | ASN | 193 | 108.566 | 27.527 | -2.769 | 1.00 | 60.91 | A | C |
| ATOM | 382 | CG | ASN | 193 | 107.606 | 26.388 | -2.564 | 1.00 | 64.08 | A | C |
| ATOM | 383 | OD1 | ASN | 193 | 107.545 | 25.804 | -1.488 | 1.00 | 68.19 | A | O |
| ATOM | 384 | ND2 | ASN | 193 | 106.849 | 26.058 | -3.601 | 1.00 | 66.19 | A | N |
| ATOM | 385 | C | ASN | 193 | 110.910 | 28.315 | -2.640 | 1.00 | 34.07 | A | C |
| ATOM | 386 | O | ASN | 193 | 111.759 | 28.459 | -1.760 | 1.00 | 35.07 | A | O |
| ATOM | 387 | N | VAL | 194 | 110.712 | 29.206 | -3.598 | 1.00 | 31.94 | A | N |
| ATOM | 388 | CA | VAL | 194 | 111.511 | 30.423 | -3.660 | 1.00 | 34.28 | A | C |
| ATOM | 389 | CB | VAL | 194 | 112.524 | 30.365 | -4.803 | 1.00 | 32.89 | A | C |
| ATOM | 390 | CG1 | VAL | 194 | 113.514 | 31.495 | -4.671 | 1.00 | 33.92 | A | C |
| ATOM | 391 | CG2 | VAL | 194 | 113.227 | 29.036 | -4.799 | 1.00 | 30.16 | A | C |
| ATOM | 392 | C | VAL | 194 | 110.601 | 31.608 | -3.914 | 1.00 | 32.05 | A | C |
| ATOM | 393 | O | VAL | 194 | 109.651 | 31.507 | -4.688 | 1.00 | 30.17 | A | O |
| ATOM | 394 | N | THR | 195 | 110.877 | 32.730 | -3.261 | 1.00 | 26.46 | A | N |
| ATOM | 395 | CA | THR | 195 | 110.058 | 33.915 | -3.474 | 1.00 | 27.64 | A | C |
| ATOM | 396 | CB | THR | 195 | 109.050 | 34.135 | -2.307 | 1.00 | 36.45 | A | C |
| ATOM | 397 | OG1 | THR | 195 | 109.728 | 34.654 | -1.163 | 1.00 | 40.46 | A | O |
| ATOM | 398 | CG2 | THR | 195 | 108.396 | 32.820 | -1.918 | 1.00 | 38.08 | A | C |
| ATOM | 399 | C | THR | 195 | 110.927 | 35.161 | -3.656 | 1.00 | 28.48 | A | C |
| ATOM | 400 | O | THR | 195 | 111.977 | 35.309 | -3.032 | 1.00 | 31.07 | A | O |
| ATOM | 401 | N | HIS | 196 | 110.492 | 36.040 | -4.545 | 1.00 | 36.83 | A | N |
| ATOM | 402 | CA | HIS | 196 | 111.196 | 37.281 | -4.819 | 1.00 | 36.93 | A | C |
| ATOM | 403 | CB | HIS | 196 | 110.843 | 37.772 | -6.225 | 1.00 | 33.18 | A | C |
| ATOM | 404 | CG | HIS | 196 | 111.434 | 36.951 | -7.326 | 1.00 | 29.68 | A | C |
| ATOM | 405 | CD2 | HIS | 196 | 110.933 | 35.910 | -8.032 | 1.00 | 30.31 | A | C |
| ATOM | 406 | ND1 | HIS | 196 | 112.707 | 37.169 | -7.813 | 1.00 | 28.33 | A | N |
| ATOM | 407 | CE1 | HIS | 196 | 112.965 | 36.296 | -8.772 | 1.00 | 25.05 | A | C |
| ATOM | 408 | NE2 | HIS | 196 | 111.905 | 35.521 | -8.924 | 1.00 | 23.26 | A | N |
| ATOM | 409 | C | HIS | 196 | 110.730 | 38.315 | -3.802 | 1.00 | 36.79 | A | C |
| ATOM | 410 | O | HIS | 196 | 109.687 | 38.933 | -3.997 | 1.00 | 35.45 | A | O |
| ATOM | 411 | N | GLU | 197 | 111.480 | 38.508 | -2.721 | 1.00 | 21.51 | A | N |
| ATOM | 412 | CA | GLU | 197 | 111.069 | 39.488 | -1.732 | 1.00 | 18.84 | A | C |
| ATOM | 413 | CB | GLU | 197 | 112.091 | 39.588 | -0.604 | 1.00 | 43.52 | A | C |
| ATOM | 414 | CG | GLU | 197 | 112.094 | 38.384 | 0.339 | 1.00 | 43.86 | A | C |
| ATOM | 415 | CD | GLU | 197 | 110.717 | 38.043 | 0.882 | 1.00 | 42.93 | A | C |
| ATOM | 416 | OE1 | GLU | 197 | 109.909 | 38.967 | 1.100 | 1.00 | 41.51 | A | O |
| ATOM | 417 | OE2 | GLU | 197 | 110.444 | 36.847 | 1.111 | 1.00 | 44.59 | A | O |
| ATOM | 418 | C | GLU | 197 | 110.882 | 40.832 | -2.442 | 1.00 | 16.31 | A | C |
| ATOM | 419 | O | GLU | 197 | 109.802 | 41.419 | -2.403 | 1.00 | 21.51 | A | O |
| ATOM | 420 | N | PHE | 198 | 111.921 | 41.325 | -3.098 | 1.00 | 11.53 | A | N |
| ATOM | 421 | CA | PHE | 198 | 111.786 | 42.562 | -3.845 | 1.00 | 13.33 | A | C |
| ATOM | 422 | CB | PHE | 198 | 111.803 | 43.785 | -2.901 | 1.00 | 15.90 | A | C |
| ATOM | 423 | CG | PHE | 198 | 113.092 | 44.003 | -2.153 | 1.00 | 14.15 | A | C |
| ATOM | 424 | CD1 | PHE | 198 | 114.262 | 44.390 | -2.823 | 1.00 | 20.29 | A | C |
| ATOM | 425 | CD2 | PHE | 198 | 113.115 | 43.912 | -0.756 | 1.00 | 10.34 | A | C |
| ATOM | 426 | CE1 | PHE | 198 | 115.427 | 44.685 | -2.113 | 1.00 | 16.32 | A | C |
| ATOM | 427 | CE2 | PHE | 198 | 114.274 | 44.208 | -0.039 | 1.00 | 14.80 | A | C |
| ATOM | 428 | CZ | PHE | 198 | 115.431 | 44.594 | -0.719 | 1.00 | 18.60 | A | C |
| ATOM | 429 | C | PHE | 198 | 112.829 | 42.652 | -4.956 | 1.00 | 16.01 | A | C |
| ATOM | 430 | O | PHE | 198 | 113.974 | 42.239 | -4.771 | 1.00 | 17.30 | A | O |
| ATOM | 431 | N | ASN | 199 | 112.418 | 43.152 | -6.123 | 1.00 | 19.42 | A | N |
| ATOM | 432 | CA | ASN | 199 | 113.321 | 43.265 | -7.276 | 1.00 | 19.71 | A | C |
| ATOM | 433 | CB | ASN | 199 | 112.540 | 43.562 | -8.548 | 1.00 | 30.06 | A | C |
| ATOM | 434 | CG | ASN | 199 | 111.465 | 42.548 | -8.824 | 1.00 | 31.32 | A | C |
| ATOM | 435 | OD1 | ASN | 199 | 111.726 | 41.350 | -8.934 | 1.00 | 32.85 | A | O |
| ATOM | 436 | ND2 | ASN | 199 | 110.236 | 43.029 | -8.948 | 1.00 | 30.20 | A | N |
| ATOM | 437 | C | ASN | 199 | 114.458 | 44.288 | -7.173 | 1.00 | 22.17 | A | C |
| ATOM | 438 | O | ASN | 199 | 114.430 | 45.215 | -6.351 | 1.00 | 19.98 | A | O |

Fig. 19: A-7

| | | | | | | | | | | | |
|---|---|---|---|---|---|---|---|---|---|---|---|
| ATOM | 439 | N | LEU | 200 | 115.445 | 44.107 | -8.044 | 1.00 | 18.99 | A | N |
| ATOM | 440 | CA | LEU | 200 | 116.619 | 44.958 | -8.078 | 1.00 | 20.95 | A | C |
| ATOM | 441 | CB | LEU | 200 | 117.556 | 44.524 | -9.212 | 1.00 | 24.87 | A | C |
| ATOM | 442 | CG | LEU | 200 | 118.631 | 43.490 | -8.869 | 1.00 | 22.72 | A | C |
| ATOM | 443 | CD1 | LEU | 200 | 119.348 | 43.048 | -10.130 | 1.00 | 27.84 | A | C |
| ATOM | 444 | CD2 | LEU | 200 | 119.617 | 44.089 | -7.869 | 1.00 | 23.89 | A | C |
| ATOM | 445 | C | LEU | 200 | 116.282 | 46.415 | -8.246 | 1.00 | 21.35 | A | C |
| ATOM | 446 | O | LEU | 200 | 116.960 | 47.274 | -7.688 | 1.00 | 22.37 | A | O |
| ATOM | 447 | N | ASN | 201 | 115.231 | 46.691 | -9.011 | 1.00 | 18.94 | A | N |
| ATOM | 448 | CA | ASN | 201 | 114.816 | 48.061 | -9.284 | 1.00 | 20.79 | A | C |
| ATOM | 449 | CB | ASN | 201 | 114.546 | 48.208 | -10.773 | 1.00 | 21.69 | A | C |
| ATOM | 450 | CG | ASN | 201 | 113.401 | 47.336 | -11.236 | 1.00 | 23.97 | A | C |
| ATOM | 451 | OD1 | ASN | 201 | 113.119 | 47.246 | -12.424 | 1.00 | 24.11 | A | O |
| ATOM | 452 | ND2 | ASN | 201 | 112.727 | 46.684 | -10.292 | 1.00 | 21.81 | A | N |
| ATOM | 453 | C | ASN | 201 | 113.572 | 48.510 | -8.509 | 1.00 | 20.84 | A | C |
| ATOM | 454 | O | ASN | 201 | 112.969 | 49.522 | -8.851 | 1.00 | 16.74 | A | O |
| ATOM | 455 | N | LYS | 202 | 113.182 | 47.770 | -7.477 | 1.00 | 23.30 | A | N |
| ATOM | 456 | CA | LYS | 202 | 111.998 | 48.137 | -6.710 | 1.00 | 23.42 | A | C |
| ATOM | 457 | CB | LYS | 202 | 111.621 | 47.022 | -5.741 | 1.00 | 34.18 | A | C |
| ATOM | 458 | CG | LYS | 202 | 110.337 | 47.265 | -4.944 | 1.00 | 35.72 | A | C |
| ATOM | 459 | CD | LYS | 202 | 109.099 | 47.092 | -5.803 | 1.00 | 37.63 | A | C |
| ATOM | 460 | CE | LYS | 202 | 109.162 | 45.813 | -6.678 | 1.00 | 43.38 | A | C |
| ATOM | 461 | NZ | LYS | 202 | 109.316 | 44.491 | -5.962 | 1.00 | 42.40 | A | N |
| ATOM | 462 | C | LYS | 202 | 112.188 | 49.428 | -5.930 | 1.00 | 22.29 | A | C |
| ATOM | 463 | O | LYS | 202 | 111.338 | 50.313 | -5.984 | 1.00 | 19.57 | A | O |
| ATOM | 464 | N | TYR | 203 | 113.292 | 49.538 | -5.203 | 1.00 | 24.72 | A | N |
| ATOM | 465 | CA | TYR | 203 | 113.538 | 50.731 | -4.407 | 1.00 | 24.40 | A | C |
| ATOM | 466 | CB | TYR | 203 | 113.769 | 50.348 | -2.942 | 1.00 | 32.57 | A | C |
| ATOM | 467 | CG | TYR | 203 | 112.679 | 49.461 | -2.396 | 1.00 | 31.24 | A | C |
| ATOM | 468 | CD1 | TYR | 203 | 112.869 | 48.086 | -2.282 | 1.00 | 31.85 | A | C |
| ATOM | 469 | CE1 | TYR | 203 | 111.842 | 47.251 | -1.844 | 1.00 | 28.32 | A | C |
| ATOM | 470 | CD2 | TYR | 203 | 111.427 | 49.986 | -2.050 | 1.00 | 34.13 | A | C |
| ATOM | 471 | CE2 | TYR | 203 | 110.393 | 49.161 | -1.611 | 1.00 | 36.88 | A | C |
| ATOM | 472 | CZ | TYR | 203 | 110.607 | 47.794 | -1.512 | 1.00 | 36.50 | A | C |
| ATOM | 473 | OH | TYR | 203 | 109.590 | 46.962 | -1.095 | 1.00 | 41.50 | A | O |
| ATOM | 474 | C | TYR | 203 | 114.713 | 51.541 | -4.938 | 1.00 | 25.04 | A | C |
| ATOM | 475 | O | TYR | 203 | 115.755 | 50.986 | -5.280 | 1.00 | 23.21 | A | O |
| ATOM | 476 | N | SER | 204 | 114.536 | 52.861 | -4.998 | 1.00 | 28.94 | A | N |
| ATOM | 477 | CA | SER | 204 | 115.557 | 53.764 | -5.513 | 1.00 | 30.79 | A | C |
| ATOM | 478 | CB | SER | 204 | 114.892 | 54.863 | -6.338 | 1.00 | 29.83 | A | C |
| ATOM | 479 | OG | SER | 204 | 113.945 | 55.577 | -5.558 | 1.00 | 31.66 | A | O |
| ATOM | 480 | C | SER | 204 | 116.372 | 54.402 | -4.412 | 1.00 | 33.37 | A | C |
| ATOM | 481 | O | SER | 204 | 117.247 | 55.214 | -4.680 | 1.00 | 33.88 | A | O |
| ATOM | 482 | N | SER | 205 | 116.089 | 54.027 | -3.173 | 1.00 | 27.33 | A | N |
| ATOM | 483 | CA | SER | 205 | 116.787 | 54.615 | -2.048 | 1.00 | 26.99 | A | C |
| ATOM | 484 | CB | SER | 205 | 115.874 | 55.628 | -1.378 | 1.00 | 50.70 | A | C |
| ATOM | 485 | OG | SER | 205 | 116.409 | 56.032 | -0.137 | 1.00 | 56.19 | A | O |
| ATOM | 486 | C | SER | 205 | 117.251 | 53.608 | -1.016 | 1.00 | 25.12 | A | C |
| ATOM | 487 | O | SER | 205 | 116.650 | 52.551 | -0.857 | 1.00 | 21.38 | A | O |
| ATOM | 488 | N | THR | 206 | 118.318 | 53.949 | -0.301 | 1.00 | 23.44 | A | N |
| ATOM | 489 | CA | THR | 206 | 118.854 | 53.075 | 0.735 | 1.00 | 24.79 | A | C |
| ATOM | 490 | CB | THR | 206 | 120.176 | 53.614 | 1.286 | 1.00 | 12.85 | A | C |
| ATOM | 491 | OG1 | THR | 206 | 121.137 | 53.683 | 0.227 | 1.00 | 11.66 | A | O |
| ATOM | 492 | CG2 | THR | 206 | 120.696 | 52.712 | 2.392 | 1.00 | 11.22 | A | C |
| ATOM | 493 | C | THR | 206 | 117.889 | 52.879 | 1.900 | 1.00 | 25.38 | A | C |
| ATOM | 494 | O | THR | 206 | 117.798 | 51.785 | 2.447 | 1.00 | 28.17 | A | O |
| ATOM | 495 | N | GLU | 207 | 117.173 | 53.926 | 2.299 | 1.00 | 23.18 | A | N |
| ATOM | 496 | CA | GLU | 207 | 116.238 | 53.746 | 3.394 | 1.00 | 22.34 | A | C |
| ATOM | 497 | CB | GLU | 207 | 115.800 | 55.083 | 3.986 | 1.00 | 114.79 | A | C |
| ATOM | 498 | CG | GLU | 207 | 115.317 | 56.095 | 2.992 | 1.00 | 115.51 | A | C |
| ATOM | 499 | CD | GLU | 207 | 114.757 | 57.325 | 3.675 | 1.00 | 116.92 | A | C |
| ATOM | 500 | OE1 | GLU | 207 | 115.428 | 57.857 | 4.587 | 1.00 | 116.15 | A | O |
| ATOM | 501 | OE2 | GLU | 207 | 113.648 | 57.761 | 3.302 | 1.00 | 115.82 | A | O |
| ATOM | 502 | C | GLU | 207 | 115.038 | 52.937 | 2.908 | 1.00 | 22.84 | A | C |
| ATOM | 503 | O | GLU | 207 | 114.515 | 52.094 | 3.640 | 1.00 | 22.79 | A | O |
| ATOM | 504 | N | GLU | 208 | 114.614 | 53.163 | 1.668 | 1.00 | 31.71 | A | N |
| ATOM | 505 | CA | GLU | 208 | 113.485 | 52.412 | 1.126 | 1.00 | 33.44 | A | C |
| ATOM | 506 | CB | GLU | 208 | 113.168 | 52.841 | -0.308 | 1.00 | 38.62 | A | C |
| ATOM | 507 | CG | GLU | 208 | 112.661 | 54.265 | -0.441 | 1.00 | 36.09 | A | C |
| ATOM | 508 | CD | GLU | 208 | 112.288 | 54.633 | -1.875 | 1.00 | 35.61 | A | C |
| ATOM | 509 | OE1 | GLU | 208 | 111.943 | 55.811 | -2.111 | 1.00 | 41.38 | A | O |
| ATOM | 510 | OE2 | GLU | 208 | 112.338 | 53.757 | -2.767 | 1.00 | 34.33 | A | O |
| ATOM | 511 | C | GLU | 208 | 113.808 | 50.920 | 1.148 | 1.00 | 34.14 | A | C |

Fig. 19: A-8

```
ATOM    512  O    GLU  208   112.942  50.093   1.426  1.00  35.14  A  O
ATOM    513  N    VAL  209   115.057  50.575   0.855  1.00  17.60  A  N
ATOM    514  CA   VAL  209   115.472  49.180   0.853  1.00  16.52  A  C
ATOM    515  CB   VAL  209   116.790  48.982   0.077  1.00  10.63  A  C
ATOM    516  CG1  VAL  209   117.501  47.719   0.538  1.00  10.96  A  C
ATOM    517  CG2  VAL  209   116.491  48.889  -1.398  1.00  11.65  A  C
ATOM    518  C    VAL  209   115.656  48.691   2.276  1.00  14.54  A  C
ATOM    519  O    VAL  209   115.278  47.558   2.596  1.00  13.50  A  O
ATOM    520  N    LEU  210   116.230  49.548   3.123  1.00  19.45  A  N
ATOM    521  CA   LEU  210   116.459  49.205   4.521  1.00  19.78  A  C
ATOM    522  CB   LEU  210   117.148  50.354   5.242  1.00  21.61  A  C
ATOM    523  CG   LEU  210   118.589  50.100   5.683  1.00  21.85  A  C
ATOM    524  CD1  LEU  210   119.093  51.347   6.358  1.00  18.40  A  C
ATOM    525  CD2  LEU  210   118.687  48.916   6.632  1.00  15.30  A  C
ATOM    526  C    LEU  210   115.148  48.894   5.223  1.00  18.04  A  C
ATOM    527  O    LEU  210   115.078  48.022   6.093  1.00  18.81  A  O
ATOM    528  N    VAL  211   114.107  49.618   4.839  1.00  25.49  A  N
ATOM    529  CA   VAL  211   112.798  49.443   5.432  1.00  25.25  A  C
ATOM    530  CB   VAL  211   111.916  50.685   5.175  1.00  19.83  A  C
ATOM    531  CG1  VAL  211   110.457  50.391   5.537  1.00  22.01  A  C
ATOM    532  CG2  VAL  211   112.446  51.859   5.989  1.00  20.44  A  C
ATOM    533  C    VAL  211   112.107  48.214   4.871  1.00  24.50  A  C
ATOM    534  O    VAL  211   111.437  47.483   5.593  1.00  25.18  A  O
ATOM    535  N    ALA  212   112.262  47.986   3.577  1.00  29.23  A  N
ATOM    536  CA   ALA  212   111.624  46.839   2.964  1.00  28.21  A  C
ATOM    537  CB   ALA  212   111.725  46.935   1.439  1.00   1.87  A  C
ATOM    538  C    ALA  212   112.275  45.559   3.465  1.00  26.02  A  C
ATOM    539  O    ALA  212   111.603  44.543   3.657  1.00  25.96  A  O
ATOM    540  N    ALA  213   113.587  45.618   3.680  1.00  33.07  A  N
ATOM    541  CA   ALA  213   114.339  44.464   4.147  1.00  34.24  A  C
ATOM    542  CB   ALA  213   115.803  44.787   4.176  1.00  20.72  A  C
ATOM    543  C    ALA  213   113.875  44.011   5.522  1.00  33.04  A  C
ATOM    544  O    ALA  213   113.659  42.824   5.746  1.00  30.67  A  O
ATOM    545  N    ASN  214   113.723  44.952   6.446  1.00  10.19  A  N
ATOM    546  CA   ASN  214   113.268  44.608   7.788  1.00  14.06  A  C
ATOM    547  CB   ASN  214   113.357  45.817   8.713  1.00  18.34  A  C
ATOM    548  CG   ASN  214   114.763  46.094   9.158  1.00  20.07  A  C
ATOM    549  OD1  ASN  214   115.597  46.563   8.377  1.00  22.00  A  O
ATOM    550  ND2  ASN  214   115.045  45.794  10.425  1.00  20.49  A  N
ATOM    551  C    ASN  214   111.847  44.081   7.828  1.00  16.45  A  C
ATOM    552  O    ASN  214   111.448  43.500   8.825  1.00  17.17  A  O
ATOM    553  N    LYS  215   111.080  44.289   6.764  1.00  16.88  A  N
ATOM    554  CA   LYS  215   109.705  43.817   6.744  1.00  17.32  A  C
ATOM    555  CB   LYS  215   108.804  44.772   5.926  1.00  20.45  A  C
ATOM    556  CG   LYS  215   108.670  46.176   6.531  1.00  28.03  A  C
ATOM    557  CD   LYS  215   107.387  46.902   6.115  1.00  31.57  A  C
ATOM    558  CE   LYS  215   107.304  47.155   4.607  1.00  35.03  A  C
ATOM    559  NZ   LYS  215   106.135  48.007   4.237  1.00  36.02  A  N
ATOM    560  C    LYS  215   109.617  42.399   6.193  1.00  15.45  A  C
ATOM    561  O    LYS  215   108.529  41.825   6.124  1.00  16.67  A  O
ATOM    562  N    ILE  216   110.757  41.824   5.812  1.00  28.84  A  N
ATOM    563  CA   ILE  216   110.754  40.475   5.262  1.00  25.65  A  C
ATOM    564  CB   ILE  216   112.088  40.123   4.594  1.00  13.08  A  C
ATOM    565  CG2  ILE  216   112.088  38.681   4.163  1.00   9.86  A  C
ATOM    566  CG1  ILE  216   112.298  41.002   3.362  1.00   9.76  A  C
ATOM    567  CD1  ILE  216   113.597  40.713   2.626  1.00   6.72  A  C
ATOM    568  C    ILE  216   110.459  39.445   6.333  1.00  24.10  A  C
ATOM    569  O    ILE  216   111.076  39.441   7.404  1.00  24.80  A  O
ATOM    570  N    VAL  217   109.503  38.574   6.017  1.00  14.68  A  N
ATOM    571  CA   VAL  217   109.065  37.511   6.904  1.00  16.45  A  C
ATOM    572  CB   VAL  217   107.535  37.425   6.901  1.00   9.81  A  C
ATOM    573  CG1  VAL  217   107.065  36.144   7.569  1.00   9.81  A  C
ATOM    574  CG2  VAL  217   106.967  38.647   7.626  1.00   9.81  A  C
ATOM    575  C    VAL  217   109.641  36.173   6.483  1.00  17.61  A  C
ATOM    576  O    VAL  217   109.794  35.895   5.298  1.00  17.07  A  O
ATOM    577  N    GLN  218   109.959  35.348   7.474  1.00  15.74  A  N
ATOM    578  CA   GLN  218   110.512  34.024   7.234  1.00  16.40  A  C
ATOM    579  CB   GLN  218   111.064  33.446   8.531  1.00  14.26  A  C
ATOM    580  CG   GLN  218   111.752  32.109   8.372  1.00  14.26  A  C
ATOM    581  CD   GLN  218   112.331  31.589   9.675  1.00  14.26  A  C
ATOM    582  OE1  GLN  218   113.166  30.685   9.668  1.00  14.26  A  O
ATOM    583  NE2  GLN  218   111.887  32.156  10.802  1.00  14.26  A  N
ATOM    584  C    GLN  218   109.392  33.151   6.719  1.00  15.85  A  C
```

Fig. 19: A-9

```
ATOM    585  O    GLN  218    108.335  33.103   7.328  1.00  19.60  A  O
ATOM    586  N    ARG  219    109.622  32.464   5.604  1.00  16.04  A  N
ATOM    587  CA   ARG  219    108.599  31.602   5.005  1.00  15.69  A  C
ATOM    588  CB   ARG  219    108.595  31.786   3.489  1.00  43.49  A  C
ATOM    589  CG   ARG  219    109.053  33.163   3.054  1.00  43.49  A  C
ATOM    590  CD   ARG  219    108.719  33.421   1.606  1.00  43.49  A  C
ATOM    591  NE   ARG  219    107.365  33.952   1.454  1.00  43.49  A  N
ATOM    592  CZ   ARG  219    107.042  35.232   1.606  1.00  43.49  A  C
ATOM    593  NH1  ARG  219    107.978  36.122   1.915  1.00  43.49  A  N
ATOM    594  NH2  ARG  219    105.786  35.621   1.443  1.00  43.49  A  N
ATOM    595  C    ARG  219    108.814  30.127   5.350  1.00  16.90  A  C
ATOM    596  O    ARG  219    108.073  29.253   4.886  1.00  16.91  A  O
ATOM    597  N    GLY  220    109.838  29.867   6.160  1.00   9.58  A  N
ATOM    598  CA   GLY  220    110.148  28.513   6.567  1.00   9.19  A  C
ATOM    599  C    GLY  220    110.442  27.562   5.422  1.00   8.86  A  C
ATOM    600  O    GLY  220    110.682  27.993   4.288  1.00   7.20  A  O
ATOM    601  N    GLY  221    110.435  26.266   5.730  1.00  16.50  A  N
ATOM    602  CA   GLY  221    110.682  25.265   4.718  1.00  15.07  A  C
ATOM    603  C    GLY  221    111.117  23.954   5.314  1.00  15.49  A  C
ATOM    604  O    GLY  221    112.038  23.928   6.124  1.00  12.29  A  O
ATOM    605  N    ARG  222    110.459  22.865   4.927  1.00  35.34  A  N
ATOM    606  CA   ARG  222    110.815  21.543   5.433  1.00  36.05  A  C
ATOM    607  CB   ARG  222    109.652  20.567   5.235  1.00  22.30  A  C
ATOM    608  CG   ARG  222    108.505  20.791   6.201  1.00  22.30  A  C
ATOM    609  CD   ARG  222    107.252  20.047   5.779  1.00  22.30  A  C
ATOM    610  NE   ARG  222    106.621  20.647   4.614  1.00  22.30  A  N
ATOM    611  CZ   ARG  222    105.459  20.247   4.103  1.00  22.30  A  C
ATOM    612  NH1  ARG  222    104.795  19.241   4.654  1.00  22.30  A  N
ATOM    613  NH2  ARG  222    104.951  20.857   3.042  1.00  22.30  A  N
ATOM    614  C    ARG  222    112.062  21.036   4.723  1.00  36.10  A  C
ATOM    615  O    ARG  222    112.626  20.017   5.107  1.00  36.87  A  O
ATOM    616  N    GLN  223    112.473  21.750   3.678  1.00  27.48  A  N
ATOM    617  CA   GLN  223    113.672  21.428   2.912  1.00  25.77  A  C
ATOM    618  CB   GLN  223    113.328  20.858   1.535  1.00  13.17  A  C
ATOM    619  CG   GLN  223    112.830  19.417   1.508  1.00  14.61  A  C
ATOM    620  CD   GLN  223    111.346  19.312   1.790  1.00  15.02  A  C
ATOM    621  OE1  GLN  223    110.533  20.016   1.190  1.00  15.42  A  O
ATOM    622  NE2  GLN  223    110.981  18.417   2.698  1.00  15.46  A  N
ATOM    623  C    GLN  223    114.498  22.706   2.724  1.00  26.51  A  C
ATOM    624  O    GLN  223    114.057  23.799   3.069  1.00  25.99  A  O
ATOM    625  N    THR  224    115.696  22.567   2.172  1.00  24.40  A  N
ATOM    626  CA   THR  224    116.581  23.704   1.948  1.00  22.28  A  C
ATOM    627  CB   THR  224    117.795  23.633   2.897  1.00  14.98  A  C
ATOM    628  OG1  THR  224    117.328  23.565   4.246  1.00  14.97  A  O
ATOM    629  CG2  THR  224    118.683  24.849   2.747  1.00  11.28  A  C
ATOM    630  C    THR  224    117.061  23.662   0.500  1.00  19.29  A  C
ATOM    631  O    THR  224    118.122  23.129   0.202  1.00  15.78  A  O
ATOM    632  N    MET  225    116.272  24.234  -0.395  1.00  14.15  A  N
ATOM    633  CA   MET  225    116.607  24.236  -1.810  1.00  15.04  A  C
ATOM    634  CB   MET  225    115.346  24.481  -2.636  1.00  22.98  A  C
ATOM    635  CG   MET  225    114.183  23.602  -2.267  1.00  20.41  A  C
ATOM    636  SD   MET  225    114.421  21.883  -2.704  1.00  28.15  A  S
ATOM    637  CE   MET  225    112.675  21.302  -2.554  1.00  24.73  A  C
ATOM    638  C    MET  225    117.653  25.275  -2.204  1.00  16.07  A  C
ATOM    639  O    MET  225    117.426  26.054  -3.136  1.00  17.53  A  O
ATOM    640  N    THR  226    118.791  25.297  -1.513  1.00  16.19  A  N
ATOM    641  CA   THR  226    119.841  26.259  -1.840  1.00  15.66  A  C
ATOM    642  CB   THR  226    121.155  25.905  -1.129  1.00  25.30  A  C
ATOM    643  OG1  THR  226    120.925  25.825   0.284  1.00  27.32  A  O
ATOM    644  CG2  THR  226    122.216  26.959  -1.414  1.00  23.02  A  C
ATOM    645  C    THR  226    120.100  26.337  -3.356  1.00  14.26  A  C
ATOM    646  O    THR  226    120.229  27.418  -3.917  1.00   8.95  A  O
ATOM    647  N    ALA  227    120.158  25.190  -4.019  1.00   9.41  A  N
ATOM    648  CA   ALA  227    120.408  25.162  -5.448  1.00   8.35  A  C
ATOM    649  CB   ALA  227    120.422  23.738  -5.939  1.00  23.80  A  C
ATOM    650  C    ALA  227    119.342  25.951  -6.188  1.00   9.01  A  C
ATOM    651  O    ALA  227    119.644  26.759  -7.067  1.00   9.81  A  O
ATOM    652  N    LEU  228    118.085  25.711  -5.842  1.00  28.18  A  N
ATOM    653  CA   LEU  228    116.985  26.410  -6.489  1.00  26.62  A  C
ATOM    654  CB   LEU  228    115.649  25.860  -5.988  1.00  14.81  A  C
ATOM    655  CG   LEU  228    114.372  26.485  -6.557  1.00  22.70  A  C
ATOM    656  CD1  LEU  228    114.356  26.363  -8.080  1.00  20.29  A  C
ATOM    657  CD2  LEU  228    113.163  25.801  -5.947  1.00  19.75  A  C
```

Fig. 19: A-10

```
ATOM    658  C   LEU 228     117.067  27.909  -6.221  1.00  25.80  A  C
ATOM    659  O   LEU 228     116.885  28.719  -7.129  1.00  28.78  A  O
ATOM    660  N   GLY 229     117.341  28.274  -4.971  1.00  23.50  A  N
ATOM    661  CA  GLY 229     117.449  29.679  -4.624  1.00  25.86  A  C
ATOM    662  C   GLY 229     118.464  30.407  -5.495  1.00  28.42  A  C
ATOM    663  O   GLY 229     118.149  31.428  -6.108  1.00  29.01  A  O
ATOM    664  N   ILE 230     119.682  29.876  -5.562  1.00  20.49  A  N
ATOM    665  CA  ILE 230     120.736  30.498  -6.354  1.00  21.82  A  C
ATOM    666  CB  ILE 230     122.096  29.779  -6.195  1.00   2.66  A  C
ATOM    667  CG2 ILE 230     123.168  30.546  -6.953  1.00   2.66  A  C
ATOM    668  CG1 ILE 230     122.486  29.692  -4.720  1.00   2.66  A  C
ATOM    669  CD1 ILE 230     123.773  28.920  -4.474  1.00   2.66  A  C
ATOM    670  C   ILE 230     120.386  30.508  -7.830  1.00  22.08  A  C
ATOM    671  O   ILE 230     120.614  31.498  -8.511  1.00  20.01  A  O
ATOM    672  N   ASP 231     119.841  29.409  -8.333  1.00  32.19  A  N
ATOM    673  CA  ASP 231     119.473  29.352  -9.743  1.00  30.59  A  C
ATOM    674  CB  ASP 231     118.959  27.958 -10.103  1.00  35.41  A  C
ATOM    675  CG  ASP 231     118.860  27.739 -11.604  1.00  42.41  A  C
ATOM    676  OD1 ASP 231     119.910  27.778 -12.281  1.00  41.17  A  O
ATOM    677  OD2 ASP 231     117.735  27.525 -12.103  1.00  45.95  A  O
ATOM    678  C   ASP 231     118.392  30.395 -10.048  1.00  31.57  A  C
ATOM    679  O   ASP 231     118.429  31.048 -11.090  1.00  28.79  A  O
ATOM    680  N   THR 232     117.443  30.554  -9.126  1.00  18.29  A  N
ATOM    681  CA  THR 232     116.347  31.510  -9.296  1.00  17.08  A  C
ATOM    682  CB  THR 232     115.287  31.347  -8.194  1.00  20.70  A  C
ATOM    683  OG1 THR 232     114.714  30.041  -8.279  1.00  19.21  A  O
ATOM    684  CG2 THR 232     114.191  32.370  -8.358  1.00  14.24  A  C
ATOM    685  C   THR 232     116.859  32.937  -9.264  1.00  17.71  A  C
ATOM    686  O   THR 232     116.390  33.801 -10.010  1.00  17.88  A  O
ATOM    687  N   ALA 233     117.815  33.187  -8.379  1.00  19.66  A  N
ATOM    688  CA  ALA 233     118.395  34.517  -8.270  1.00  22.31  A  C
ATOM    689  CB  ALA 233     119.364  34.580  -7.099  1.00  15.15  A  C
ATOM    690  C   ALA 233     119.125  34.796  -9.575  1.00  24.62  A  C
ATOM    691  O   ALA 233     119.187  35.929 -10.031  1.00  26.53  A  O
ATOM    692  N   ARG 234     119.666  33.746 -10.180  1.00  30.19  A  N
ATOM    693  CA  ARG 234     120.390  33.879 -11.434  1.00  33.29  A  C
ATOM    694  CB  ARG 234     121.241  32.637 -11.693  1.00  15.32  A  C
ATOM    695  CG  ARG 234     122.345  32.875 -12.693  1.00  15.32  A  C
ATOM    696  CD  ARG 234     122.760  31.617 -13.460  1.00  15.32  A  C
ATOM    697  NE  ARG 234     121.839  31.311 -14.554  1.00  15.32  A  N
ATOM    698  CZ  ARG 234     120.875  30.405 -14.481  1.00  15.32  A  C
ATOM    699  NH1 ARG 234     120.708  29.713 -13.368  1.00  15.32  A  N
ATOM    700  NH2 ARG 234     120.078  30.188 -15.511  1.00  15.32  A  N
ATOM    701  C   ARG 234     119.446  34.083 -12.619  1.00  35.42  A  C
ATOM    702  O   ARG 234     119.409  35.153 -13.215  1.00  35.47  A  O
ATOM    703  N   LYS 235     118.666  33.057 -12.941  1.00  67.48  A  N
ATOM    704  CA  LYS 235     117.767  33.124 -14.085  1.00  67.43  A  C
ATOM    705  CB  LYS 235     117.204  31.730 -14.397  1.00  53.18  A  C
ATOM    706  CG  LYS 235     115.965  31.308 -13.615  1.00  54.33  A  C
ATOM    707  CD  LYS 235     115.583  29.867 -13.970  1.00  54.15  A  C
ATOM    708  CE  LYS 235     114.146  29.517 -13.590  1.00  54.95  A  C
ATOM    709  NZ  LYS 235     113.873  29.660 -12.135  1.00  55.71  A  N
ATOM    710  C   LYS 235     116.628  34.134 -14.017  1.00  67.57  A  C
ATOM    711  O   LYS 235     116.074  34.500 -15.054  1.00  67.91  A  O
ATOM    712  N   GLU 236     116.277  34.596 -12.822  1.00  98.68  A  N
ATOM    713  CA  GLU 236     115.186  35.558 -12.693  1.00 100.30  A  C
ATOM    714  CB  GLU 236     114.087  34.999 -11.781  1.00  50.64  A  C
ATOM    715  CG  GLU 236     113.008  34.192 -12.510  1.00  53.41  A  C
ATOM    716  CD  GLU 236     112.199  33.276 -11.582  1.00  55.89  A  C
ATOM    717  OE1 GLU 236     111.660  33.760 -10.565  1.00  55.98  A  O
ATOM    718  OE2 GLU 236     112.098  32.065 -11.875  1.00  55.73  A  O
ATOM    719  C   GLU 236     115.627  36.917 -12.174  1.00  98.85  A  C
ATOM    720  O   GLU 236     115.638  37.900 -12.912  1.00 100.28  A  O
ATOM    721  N   ALA 237     115.991  36.969 -10.899  1.00  71.25  A  N
ATOM    722  CA  ALA 237     116.405  38.218 -10.276  1.00  68.72  A  C
ATOM    723  CB  ALA 237     117.046  37.934  -8.932  1.00  56.85  A  C
ATOM    724  C   ALA 237     117.349  39.046 -11.139  1.00  67.56  A  C
ATOM    725  O   ALA 237     117.225  40.267 -11.200  1.00  65.98  A  O
ATOM    726  N   PHE 238     118.283  38.385 -11.812  1.00  41.81  A  N
ATOM    727  CA  PHE 238     119.256  39.080 -12.651  1.00  41.24  A  C
ATOM    728  CB  PHE 238     120.606  38.369 -12.591  1.00  47.57  A  C
ATOM    729  CG  PHE 238     121.413  38.696 -11.378  1.00  46.60  A  C
ATOM    730  CD1 PHE 238     121.686  37.725 -10.419  1.00  47.83  A  C
```

Fig. 19: A-11

| ATOM | 731 | CD2 | PHE | 238 | 121.931 | 39.970 | -11.208 | 1.00 | 44.20 | A | C |
|---|---|---|---|---|---|---|---|---|---|---|---|
| ATOM | 732 | CE1 | PHE | 238 | 122.476 | 38.023 | -9.298 | 1.00 | 45.63 | A | C |
| ATOM | 733 | CE2 | PHE | 238 | 122.719 | 40.282 | -10.094 | 1.00 | 50.51 | A | C |
| ATOM | 734 | CZ | PHE | 238 | 122.993 | 39.305 | -9.137 | 1.00 | 51.93 | A | C |
| ATOM | 735 | C | PHE | 238 | 118.861 | 39.252 | -14.116 | 1.00 | 43.09 | A | C |
| ATOM | 736 | O | PHE | 238 | 119.699 | 39.129 | -15.017 | 1.00 | 43.19 | A | O |
| ATOM | 737 | N | THR | 239 | 117.586 | 39.520 | -14.362 | 1.00 | 28.84 | A | N |
| ATOM | 738 | CA | THR | 239 | 117.117 | 39.744 | -15.724 | 1.00 | 32.78 | A | C |
| ATOM | 739 | CB | THR | 239 | 115.952 | 38.821 | -16.086 | 1.00 | 22.29 | A | C |
| ATOM | 740 | OG1 | THR | 239 | 114.866 | 39.059 | -15.191 | 1.00 | 20.25 | A | O |
| ATOM | 741 | CG2 | THR | 239 | 116.363 | 37.382 | -15.988 | 1.00 | 25.20 | A | C |
| ATOM | 742 | C | THR | 239 | 116.655 | 41.202 | -15.798 | 1.00 | 33.04 | A | C |
| ATOM | 743 | O | THR | 239 | 115.955 | 41.695 | -14.902 | 1.00 | 33.54 | A | O |
| ATOM | 744 | N | GLU | 240 | 117.067 | 41.881 | -16.868 | 1.00 | 73.11 | A | N |
| ATOM | 745 | CA | GLU | 240 | 116.755 | 43.291 | -17.085 | 1.00 | 73.36 | A | C |
| ATOM | 746 | CB | GLU | 240 | 116.995 | 43.654 | -18.549 | 1.00 | 97.49 | A | C |
| ATOM | 747 | CG | GLU | 240 | 117.147 | 45.141 | -18.793 | 1.00 | 102.13 | A | C |
| ATOM | 748 | CD | GLU | 240 | 117.738 | 45.441 | -20.152 | 1.00 | 105.04 | A | C |
| ATOM | 749 | OE1 | GLU | 240 | 118.794 | 44.858 | -20.483 | 1.00 | 105.14 | A | O |
| ATOM | 750 | OE2 | GLU | 240 | 117.151 | 46.263 | -20.885 | 1.00 | 105.11 | A | O |
| ATOM | 751 | C | GLU | 240 | 115.336 | 43.665 | -16.689 | 1.00 | 74.71 | A | C |
| ATOM | 752 | O | GLU | 240 | 115.083 | 44.772 | -16.210 | 1.00 | 75.92 | A | O |
| ATOM | 753 | N | ALA | 241 | 114.417 | 42.730 | -16.885 | 1.00 | 32.59 | A | N |
| ATOM | 754 | CA | ALA | 241 | 113.016 | 42.952 | -16.552 | 1.00 | 33.44 | A | C |
| ATOM | 755 | CB | ALA | 241 | 112.170 | 41.769 | -17.051 | 1.00 | 4.05 | A | C |
| ATOM | 756 | C | ALA | 241 | 112.802 | 43.165 | -15.044 | 1.00 | 32.91 | A | C |
| ATOM | 757 | O | ALA | 241 | 111.809 | 43.759 | -14.622 | 1.00 | 34.37 | A | O |
| ATOM | 758 | N | ARG | 242 | 113.725 | 42.678 | -14.223 | 1.00 | 31.60 | A | N |
| ATOM | 759 | CA | ARG | 242 | 113.585 | 42.851 | -12.786 | 1.00 | 31.34 | A | C |
| ATOM | 760 | CB | ARG | 242 | 113.757 | 41.500 | -12.079 | 1.00 | 27.81 | A | C |
| ATOM | 761 | CG | ARG | 242 | 112.489 | 40.658 | -12.052 | 1.00 | 28.01 | A | C |
| ATOM | 762 | CD | ARG | 242 | 112.669 | 39.440 | -11.160 | 1.00 | 28.87 | A | C |
| ATOM | 763 | NE | ARG | 242 | 111.425 | 39.010 | -10.515 | 1.00 | 30.07 | A | N |
| ATOM | 764 | CZ | ARG | 242 | 110.582 | 38.106 | -11.011 | 1.00 | 29.27 | A | C |
| ATOM | 765 | NH1 | ARG | 242 | 110.846 | 37.525 | -12.176 | 1.00 | 28.32 | A | N |
| ATOM | 766 | NH2 | ARG | 242 | 109.485 | 37.769 | -10.334 | 1.00 | 31.29 | A | N |
| ATOM | 767 | C | ARG | 242 | 114.557 | 43.898 | -12.231 | 1.00 | 32.54 | A | C |
| ATOM | 768 | O | ARG | 242 | 114.824 | 43.954 | -11.026 | 1.00 | 35.55 | A | O |
| ATOM | 769 | N | GLY | 243 | 115.080 | 44.733 | -13.122 | 1.00 | 38.70 | A | N |
| ATOM | 770 | CA | GLY | 243 | 115.996 | 45.775 | -12.706 | 1.00 | 36.85 | A | C |
| ATOM | 771 | C | GLY | 243 | 117.468 | 45.462 | -12.890 | 1.00 | 35.13 | A | C |
| ATOM | 772 | O | GLY | 243 | 118.318 | 46.139 | -12.308 | 1.00 | 34.75 | A | O |
| ATOM | 773 | N | ALA | 244 | 117.792 | 44.447 | -13.683 | 1.00 | 32.25 | A | N |
| ATOM | 774 | CA | ALA | 244 | 119.190 | 44.119 | -13.896 | 1.00 | 30.25 | A | C |
| ATOM | 775 | CB | ALA | 244 | 119.326 | 42.709 | -14.442 | 1.00 | 67.28 | A | C |
| ATOM | 776 | C | ALA | 244 | 119.750 | 45.130 | -14.886 | 1.00 | 32.13 | A | C |
| ATOM | 777 | O | ALA | 244 | 119.437 | 45.088 | -16.068 | 1.00 | 31.59 | A | O |
| ATOM | 778 | N | ARG | 245 | 120.566 | 46.054 | -14.401 | 1.00 | 18.96 | A | N |
| ATOM | 779 | CA | ARG | 245 | 121.154 | 47.074 | -15.258 | 1.00 | 19.79 | A | C |
| ATOM | 780 | CB | ARG | 245 | 121.853 | 48.130 | -14.399 | 1.00 | 36.60 | A | C |
| ATOM | 781 | CG | ARG | 245 | 120.888 | 49.043 | -13.655 | 1.00 | 39.07 | A | C |
| ATOM | 782 | CD | ARG | 245 | 121.614 | 49.991 | -12.741 | 1.00 | 39.28 | A | C |
| ATOM | 783 | NE | ARG | 245 | 122.309 | 49.254 | -11.701 | 1.00 | 33.70 | A | N |
| ATOM | 784 | CZ | ARG | 245 | 122.997 | 49.824 | -10.726 | 1.00 | 33.52 | A | C |
| ATOM | 785 | NH1 | ARG | 245 | 123.084 | 51.145 | -10.662 | 1.00 | 32.72 | A | N |
| ATOM | 786 | NH2 | ARG | 245 | 123.590 | 49.075 | -9.810 | 1.00 | 30.81 | A | N |
| ATOM | 787 | C | ARG | 245 | 122.131 | 46.493 | -16.266 | 1.00 | 18.16 | A | C |
| ATOM | 788 | O | ARG | 245 | 123.003 | 45.710 | -15.911 | 1.00 | 14.27 | A | O |
| ATOM | 789 | N | ARG | 246 | 121.985 | 46.896 | -17.525 | 1.00 | 55.16 | A | N |
| ATOM | 790 | CA | ARG | 246 | 122.848 | 46.429 | -18.607 | 1.00 | 57.95 | A | C |
| ATOM | 791 | CB | ARG | 246 | 122.447 | 47.078 | -19.928 | 1.00 | 115.62 | A | C |
| ATOM | 792 | CG | ARG | 246 | 123.405 | 46.764 | -21.067 | 1.00 | 120.98 | A | C |
| ATOM | 793 | CD | ARG | 246 | 123.057 | 47.546 | -22.318 | 1.00 | 126.90 | A | C |
| ATOM | 794 | NE | ARG | 246 | 121.637 | 47.444 | -22.641 | 1.00 | 129.81 | A | N |
| ATOM | 795 | CZ | ARG | 246 | 120.981 | 46.298 | -22.804 | 1.00 | 132.92 | A | C |
| ATOM | 796 | NH1 | ARG | 246 | 121.615 | 45.138 | -22.676 | 1.00 | 132.61 | A | N |
| ATOM | 797 | NH2 | ARG | 246 | 119.685 | 46.314 | -23.094 | 1.00 | 133.70 | A | N |
| ATOM | 798 | C | ARG | 246 | 124.313 | 46.736 | -18.364 | 1.00 | 55.77 | A | C |
| ATOM | 799 | O | ARG | 246 | 124.671 | 47.879 | -18.092 | 1.00 | 58.40 | A | O |
| ATOM | 800 | N | GLY | 247 | 125.151 | 45.711 | -18.475 | 1.00 | 47.75 | A | N |
| ATOM | 801 | CA | GLY | 247 | 126.587 | 45.878 | -18.302 | 1.00 | 50.33 | A | C |
| ATOM | 802 | C | GLY | 247 | 127.097 | 46.294 | -16.934 | 1.00 | 50.40 | A | C |
| ATOM | 803 | O | GLY | 247 | 128.129 | 46.958 | -16.824 | 1.00 | 53.36 | A | O |

Fig. 19: A-12

| | | | | | | | | | | |
|---|---|---|---|---|---|---|---|---|---|---|
| ATOM | 804 | N | VAL | 248 | 126.382 | 45.911 | -15.887 | 1.00 | 40.38 | A N |
| ATOM | 805 | CA | VAL | 248 | 126.790 | 46.248 | -14.535 | 1.00 | 38.39 | A C |
| ATOM | 806 | CB | VAL | 248 | 125.653 | 46.928 | -13.780 | 1.00 | 41.70 | A C |
| ATOM | 807 | CG1 | VAL | 248 | 126.049 | 47.136 | -12.331 | 1.00 | 39.35 | A C |
| ATOM | 808 | CG2 | VAL | 248 | 125.331 | 48.250 | -14.436 | 1.00 | 33.47 | A C |
| ATOM | 809 | C | VAL | 248 | 127.173 | 44.970 | -13.807 | 1.00 | 41.41 | A C |
| ATOM | 810 | O | VAL | 248 | 126.530 | 43.936 | -13.993 | 1.00 | 45.46 | A O |
| ATOM | 811 | N | LYS | 249 | 128.208 | 45.036 | -12.975 | 1.00 | 30.45 | A N |
| ATOM | 812 | CA | LYS | 249 | 128.645 | 43.852 | -12.250 | 1.00 | 31.36 | A C |
| ATOM | 813 | CB | LYS | 249 | 129.799 | 44.186 | -11.299 | 1.00 | 85.59 | A C |
| ATOM | 814 | CG | LYS | 249 | 130.426 | 42.940 | -10.690 | 1.00 | 91.11 | A C |
| ATOM | 815 | CD | LYS | 249 | 130.844 | 41.943 | -11.782 | 1.00 | 92.18 | A C |
| ATOM | 816 | CE | LYS | 249 | 131.040 | 40.539 | -11.224 | 1.00 | 94.54 | A C |
| ATOM | 817 | NZ | LYS | 249 | 131.548 | 39.546 | -12.218 | 1.00 | 97.36 | A N |
| ATOM | 818 | C | LYS | 249 | 127.503 | 43.190 | -11.473 | 1.00 | 30.02 | A C |
| ATOM | 819 | O | LYS | 249 | 126.706 | 43.862 | -10.815 | 1.00 | 29.84 | A O |
| ATOM | 820 | N | LYS | 250 | 127.432 | 41.864 | -11.559 | 1.00 | 29.51 | A N |
| ATOM | 821 | CA | LYS | 250 | 126.396 | 41.110 | -10.879 | 1.00 | 29.16 | A C |
| ATOM | 822 | CB | LYS | 250 | 125.763 | 40.134 | -11.871 | 1.00 | 45.59 | A C |
| ATOM | 823 | CG | LYS | 250 | 125.050 | 40.864 | -12.996 | 1.00 | 44.19 | A C |
| ATOM | 824 | CD | LYS | 250 | 124.892 | 40.022 | -14.263 | 1.00 | 45.74 | A C |
| ATOM | 825 | CE | LYS | 250 | 123.827 | 38.928 | -14.135 | 1.00 | 44.90 | A C |
| ATOM | 826 | NZ | LYS | 250 | 123.513 | 38.274 | -15.453 | 1.00 | 46.72 | A N |
| ATOM | 827 | C | LYS | 250 | 126.979 | 40.391 | -9.663 | 1.00 | 28.51 | A C |
| ATOM | 828 | O | LYS | 250 | 127.849 | 39.541 | -9.804 | 1.00 | 28.19 | A O |
| ATOM | 829 | N | VAL | 251 | 126.493 | 40.754 | -8.474 | 1.00 | 23.05 | A N |
| ATOM | 830 | CA | VAL | 251 | 126.954 | 40.173 | -7.219 | 1.00 | 22.96 | A C |
| ATOM | 831 | CB | VAL | 251 | 127.504 | 41.263 | -6.307 | 1.00 | 28.85 | A C |
| ATOM | 832 | CG1 | VAL | 251 | 127.901 | 40.676 | -4.959 | 1.00 | 27.00 | A C |
| ATOM | 833 | CG2 | VAL | 251 | 128.678 | 41.928 | -6.974 | 1.00 | 30.06 | A C |
| ATOM | 834 | C | VAL | 251 | 125.863 | 39.421 | -6.451 | 1.00 | 21.44 | A C |
| ATOM | 835 | O | VAL | 251 | 124.778 | 39.945 | -6.232 | 1.00 | 17.44 | A O |
| ATOM | 836 | N | MET | 252 | 126.168 | 38.199 | -6.023 | 1.00 | 19.32 | A N |
| ATOM | 837 | CA | MET | 252 | 125.212 | 37.383 | -5.278 | 1.00 | 20.30 | A C |
| ATOM | 838 | CB | MET | 252 | 124.949 | 36.073 | -6.024 | 1.00 | 19.49 | A C |
| ATOM | 839 | CG | MET | 252 | 123.850 | 35.212 | -5.425 | 1.00 | 18.18 | A C |
| ATOM | 840 | SD | MET | 252 | 123.556 | 33.701 | -6.379 | 1.00 | 22.23 | A S |
| ATOM | 841 | CE | MET | 252 | 123.009 | 34.366 | -7.960 | 1.00 | 13.54 | A C |
| ATOM | 842 | C | MET | 252 | 125.730 | 37.072 | -3.875 | 1.00 | 19.32 | A C |
| ATOM | 843 | O | MET | 252 | 126.880 | 36.675 | -3.704 | 1.00 | 21.69 | A O |
| ATOM | 844 | N | VAL | 253 | 124.886 | 37.261 | -2.869 | 1.00 | 11.70 | A N |
| ATOM | 845 | CA | VAL | 253 | 125.286 | 36.971 | -1.505 | 1.00 | 12.85 | A C |
| ATOM | 846 | CB | VAL | 253 | 125.173 | 38.221 | -0.593 | 1.00 | 5.67 | A C |
| ATOM | 847 | CG1 | VAL | 253 | 125.508 | 37.856 | 0.842 | 1.00 | 7.09 | A C |
| ATOM | 848 | CG2 | VAL | 253 | 126.118 | 39.310 | -1.079 | 1.00 | 5.31 | A C |
| ATOM | 849 | C | VAL | 253 | 124.370 | 35.881 | -0.974 | 1.00 | 12.42 | A C |
| ATOM | 850 | O | VAL | 253 | 123.166 | 36.093 | -0.870 | 1.00 | 10.86 | A O |
| ATOM | 851 | N | ILE | 254 | 124.936 | 34.716 | -0.649 | 1.00 | 26.88 | A N |
| ATOM | 852 | CA | ILE | 254 | 124.142 | 33.597 | -0.126 | 1.00 | 23.78 | A C |
| ATOM | 853 | CB | ILE | 254 | 124.457 | 32.266 | -0.847 | 1.00 | 10.72 | A C |
| ATOM | 854 | CG2 | ILE | 254 | 123.584 | 31.171 | -0.294 | 1.00 | 7.19 | A C |
| ATOM | 855 | CG1 | ILE | 254 | 124.220 | 32.397 | -2.352 | 1.00 | 9.30 | A C |
| ATOM | 856 | CD1 | ILE | 254 | 125.307 | 33.140 | -3.078 | 1.00 | 8.93 | A C |
| ATOM | 857 | C | ILE | 254 | 124.379 | 33.370 | 1.359 | 1.00 | 21.87 | A C |
| ATOM | 858 | O | ILE | 254 | 125.508 | 33.431 | 1.833 | 1.00 | 23.74 | A O |
| ATOM | 859 | N | VAL | 255 | 123.300 | 33.105 | 2.084 | 1.00 | 38.19 | A N |
| ATOM | 860 | CA | VAL | 255 | 123.379 | 32.858 | 3.516 | 1.00 | 36.93 | A C |
| ATOM | 861 | CB | VAL | 255 | 122.733 | 33.994 | 4.328 | 1.00 | 13.80 | A C |
| ATOM | 862 | CG1 | VAL | 255 | 123.224 | 33.949 | 5.753 | 1.00 | 12.25 | A C |
| ATOM | 863 | CG2 | VAL | 255 | 123.056 | 35.325 | 3.713 | 1.00 | 14.44 | A C |
| ATOM | 864 | C | VAL | 255 | 122.592 | 31.594 | 3.798 | 1.00 | 34.68 | A C |
| ATOM | 865 | O | VAL | 255 | 121.431 | 31.491 | 3.403 | 1.00 | 36.68 | A O |
| ATOM | 866 | N | THR | 256 | 123.210 | 30.632 | 4.474 | 1.00 | 19.22 | A N |
| ATOM | 867 | CA | THR | 256 | 122.514 | 29.387 | 4.798 | 1.00 | 20.04 | A C |
| ATOM | 868 | CB | THR | 256 | 122.477 | 28.457 | 3.566 | 1.00 | 10.08 | A C |
| ATOM | 869 | OG1 | THR | 256 | 122.032 | 27.147 | 3.952 | 1.00 | 6.12 | A O |
| ATOM | 870 | CG2 | THR | 256 | 123.851 | 28.387 | 2.926 | 1.00 | 8.93 | A C |
| ATOM | 871 | C | THR | 256 | 123.128 | 28.650 | 5.995 | 1.00 | 23.52 | A C |
| ATOM | 872 | O | THR | 256 | 124.303 | 28.831 | 6.310 | 1.00 | 19.68 | A O |
| ATOM | 873 | N | ASP | 257 | 122.323 | 27.829 | 6.663 | 1.00 | 46.58 | A N |
| ATOM | 874 | CA | ASP | 257 | 122.794 | 27.097 | 7.830 | 1.00 | 46.96 | A C |
| ATOM | 875 | CB | ASP | 257 | 122.069 | 27.585 | 9.091 | 1.00 | 21.89 | A C |
| ATOM | 876 | CG | ASP | 257 | 120.655 | 27.009 | 9.225 | 1.00 | 27.25 | A C |

Fig. 19: A-13

```
ATOM    877  OD1 ASP   257     120.089   26.573    8.191  1.00   27.72    A  O
ATOM    878  OD2 ASP   257     120.110   27.006   10.362  1.00   32.52    A  O
ATOM    879  C   ASP   257     122.599   25.596    7.693  1.00   43.55    A  C
ATOM    880  O   ASP   257     122.525   24.883    8.695  1.00   42.79    A  O
ATOM    881  N   GLY   258     122.510   25.106    6.461  1.00   42.38    A  N
ATOM    882  CA  GLY   258     122.330   23.678    6.283  1.00   44.80    A  C
ATOM    883  C   GLY   258     122.618   23.150    4.896  1.00   48.62    A  C
ATOM    884  O   GLY   258     122.523   23.871    3.903  1.00   44.34    A  O
ATOM    885  N   GLU   259     122.984   21.876    4.832  1.00   88.78    A  N
ATOM    886  CA  GLU   259     123.265   21.230    3.562  1.00   90.66    A  C
ATOM    887  CB  GLU   259     123.650   19.770    3.782  1.00   87.02    A  C
ATOM    888  CG  GLU   259     124.983   19.588    4.461  1.00   94.80    A  C
ATOM    889  CD  GLU   259     125.130   18.214    5.070  1.00   98.61    A  C
ATOM    890  OE1 GLU   259     126.256   17.861    5.481  1.00  105.36    A  O
ATOM    891  OE2 GLU   259     124.115   17.490    5.147  1.00   98.63    A  O
ATOM    892  C   GLU   259     122.004   21.298    2.727  1.00   89.52    A  C
ATOM    893  O   GLU   259     120.927   20.906    3.174  1.00   86.69    A  O
ATOM    894  N   SER   260     122.140   21.815    1.517  1.00   31.72    A  N
ATOM    895  CA  SER   260     121.007   21.922    0.615  1.00   34.88    A  C
ATOM    896  CB  SER   260     121.435   22.606   -0.685  1.00  104.64    A  C
ATOM    897  OG  SER   260     122.467   21.872   -1.325  1.00  105.15    A  O
ATOM    898  C   SER   260     120.489   20.526    0.304  1.00   34.78    A  C
ATOM    899  O   SER   260     121.257   19.571    0.315  1.00   30.81    A  O
ATOM    900  N   HIS   261     119.192   20.409    0.039  1.00  119.42    A  N
ATOM    901  CA  HIS   261     118.609   19.114   -0.284  1.00  123.77    A  C
ATOM    902  CB  HIS   261     117.107   19.116    0.020  1.00   89.56    A  C
ATOM    903  CG  HIS   261     116.789   19.030    1.482  1.00   92.76    A  C
ATOM    904  CD2 HIS   261     116.610   19.997    2.413  1.00   91.87    A  C
ATOM    905  ND1 HIS   261     116.648   17.830    2.147  1.00   94.24    A  N
ATOM    906  CE1 HIS   261     116.393   18.065    3.422  1.00   94.31    A  C
ATOM    907  NE2 HIS   261     116.365   19.372    3.610  1.00   91.58    A  N
ATOM    908  C   HIS   261     118.866   18.815   -1.754  1.00  124.83    A  C
ATOM    909  O   HIS   261     118.732   17.676   -2.203  1.00  122.05    A  O
ATOM    910  N   ASP   262     119.251   19.850   -2.495  1.00   94.20    A  N
ATOM    911  CA  ASP   262     119.556   19.709   -3.913  1.00   99.17    A  C
ATOM    912  CB  ASP   262     118.838   20.798   -4.732  1.00   77.35    A  C
ATOM    913  CG  ASP   262     118.558   22.065   -3.929  1.00   77.35    A  C
ATOM    914  OD1 ASP   262     119.382   22.429   -3.067  1.00   77.35    A  O
ATOM    915  OD2 ASP   262     117.515   22.708   -4.179  1.00   77.35    A  O
ATOM    916  C   ASP   262     121.065   19.758   -4.191  1.00   99.22    A  C
ATOM    917  O   ASP   262     121.510   20.456   -5.104  1.00   99.08    A  O
ATOM    918  N   ASN   263     121.842   19.009   -3.406  1.00   48.33    A  N
ATOM    919  CA  ASN   263     123.300   18.956   -3.558  1.00   49.50    A  C
ATOM    920  CB  ASN   263     123.896   17.820   -2.719  1.00   78.20    A  C
ATOM    921  CG  ASN   263     123.359   17.781   -1.303  1.00   82.57    A  C
ATOM    922  OD1 ASN   263     123.578   18.703   -0.511  1.00   84.07    A  O
ATOM    923  ND2 ASN   263     122.651   16.702   -0.974  1.00   77.07    A  N
ATOM    924  C   ASN   263     123.657   18.684   -5.012  1.00   50.14    A  C
ATOM    925  O   ASN   263     124.574   19.286   -5.572  1.00   49.04    A  O
ATOM    926  N   TYR   264     122.915   17.754   -5.601  1.00   83.05    A  N
ATOM    927  CA  TYR   264     123.112   17.330   -6.976  1.00   80.90    A  C
ATOM    928  CB  TYR   264     121.905   16.512   -7.431  1.00  165.37    A  C
ATOM    929  CG  TYR   264     121.684   15.297   -6.568  1.00  165.37    A  C
ATOM    930  CD1 TYR   264     121.294   15.427   -5.234  1.00  165.37    A  C
ATOM    931  CE1 TYR   264     121.137   14.312   -4.419  1.00  165.37    A  C
ATOM    932  CD2 TYR   264     121.909   14.016   -7.067  1.00  165.37    A  C
ATOM    933  CE2 TYR   264     121.753   12.892   -6.262  1.00  165.37    A  C
ATOM    934  CZ  TYR   264     121.369   13.048   -4.939  1.00  165.37    A  C
ATOM    935  OH  TYR   264     121.224   11.940   -4.139  1.00  165.37    A  O
ATOM    936  C   TYR   264     123.396   18.439   -7.977  1.00   79.55    A  C
ATOM    937  O   TYR   264     124.509   18.536   -8.498  1.00   76.68    A  O
ATOM    938  N   ARG   265     122.406   19.283   -8.245  1.00   83.26    A  N
ATOM    939  CA  ARG   265     122.605   20.340   -9.224  1.00   82.16    A  C
ATOM    940  CB  ARG   265     121.297   20.636   -9.957  1.00   36.62    A  C
ATOM    941  CG  ARG   265     120.182   21.225   -9.142  1.00   37.07    A  C
ATOM    942  CD  ARG   265     119.267   21.953  -10.110  1.00   38.90    A  C
ATOM    943  NE  ARG   265     118.140   22.620   -9.464  1.00   44.29    A  N
ATOM    944  CZ  ARG   265     117.562   23.714   -9.947  1.00   44.46    A  C
ATOM    945  NH1 ARG   265     118.016   24.257  -11.071  1.00   49.09    A  N
ATOM    946  NH2 ARG   265     116.528   24.258   -9.321  1.00   48.43    A  N
ATOM    947  C   ARG   265     123.211   21.644   -8.720  1.00   81.41    A  C
ATOM    948  O   ARG   265     123.137   22.668   -9.396  1.00   82.72    A  O
ATOM    949  N   LEU   266     123.819   21.614   -7.543  1.00   27.19    A  N
```

Fig. 19: A-14

| | | | | | | | | | | |
|---|---|---|---|---|---|---|---|---|---|---|
| ATOM | 950 | CA | LEU | 266 | 124.435 | 22.815 | -7.003 | 1.00 | 28.76 | A | C |
| ATOM | 951 | CB | LEU | 266 | 124.798 | 22.601 | -5.539 | 1.00 | 4.24 | A | C |
| ATOM | 952 | CG | LEU | 266 | 125.336 | 23.820 | -4.797 | 1.00 | 3.45 | A | C |
| ATOM | 953 | CD1 | LEU | 266 | 124.393 | 24.999 | -4.976 | 1.00 | 5.79 | A | C |
| ATOM | 954 | CD2 | LEU | 266 | 125.502 | 23.466 | -3.320 | 1.00 | 1.87 | A | C |
| ATOM | 955 | C | LEU | 266 | 125.684 | 23.084 | -7.828 | 1.00 | 31.58 | A | C |
| ATOM | 956 | O | LEU | 266 | 126.086 | 24.226 | -8.022 | 1.00 | 31.46 | A | O |
| ATOM | 957 | N | LYS | 267 | 126.286 | 22.007 | -8.317 | 1.00 | 45.65 | A | N |
| ATOM | 958 | CA | LYS | 267 | 127.479 | 22.088 | -9.149 | 1.00 | 47.96 | A | C |
| ATOM | 959 | CB | LYS | 267 | 127.949 | 20.673 | -9.497 | 1.00 | 72.30 | A | C |
| ATOM | 960 | CG | LYS | 267 | 129.239 | 20.583 | -10.298 | 1.00 | 72.30 | A | C |
| ATOM | 961 | CD | LYS | 267 | 130.428 | 20.277 | -9.403 | 1.00 | 72.30 | A | C |
| ATOM | 962 | CE | LYS | 267 | 131.649 | 19.894 | -10.230 | 1.00 | 72.30 | A | C |
| ATOM | 963 | NZ | LYS | 267 | 132.793 | 19.452 | -9.381 | 1.00 | 72.30 | A | N |
| ATOM | 964 | C | LYS | 267 | 127.103 | 22.842 | -10.427 | 1.00 | 47.45 | A | C |
| ATOM | 965 | O | LYS | 267 | 127.763 | 23.810 | -10.809 | 1.00 | 46.97 | A | O |
| ATOM | 966 | N | GLN | 268 | 126.032 | 22.389 | -11.074 | 1.00 | 32.65 | A | N |
| ATOM | 967 | CA | GLN | 268 | 125.553 | 22.999 | -12.303 | 1.00 | 31.62 | A | C |
| ATOM | 968 | CB | GLN | 268 | 124.292 | 22.295 | -12.798 | 1.00 | 88.56 | A | C |
| ATOM | 969 | CG | GLN | 268 | 124.449 | 20.845 | -13.182 | 1.00 | 88.56 | A | C |
| ATOM | 970 | CD | GLN | 268 | 123.119 | 20.227 | -13.576 | 1.00 | 88.56 | A | C |
| ATOM | 971 | OE1 | GLN | 268 | 123.059 | 19.078 | -14.010 | 1.00 | 88.56 | A | O |
| ATOM | 972 | NE2 | GLN | 268 | 122.041 | 20.992 | -13.423 | 1.00 | 88.56 | A | N |
| ATOM | 973 | C | GLN | 268 | 125.221 | 24.474 | -12.100 | 1.00 | 27.37 | A | C |
| ATOM | 974 | O | GLN | 268 | 125.678 | 25.332 | -12.851 | 1.00 | 28.55 | A | O |
| ATOM | 975 | N | VAL | 269 | 124.410 | 24.767 | -11.089 | 1.00 | 11.19 | A | N |
| ATOM | 976 | CA | VAL | 269 | 124.007 | 26.140 | -10.830 | 1.00 | 8.94 | A | C |
| ATOM | 977 | CB | VAL | 269 | 123.088 | 26.223 | -9.598 | 1.00 | 22.95 | A | C |
| ATOM | 978 | CG1 | VAL | 269 | 122.650 | 27.667 | -9.374 | 1.00 | 18.60 | A | C |
| ATOM | 979 | CG2 | VAL | 269 | 121.872 | 25.334 | -9.801 | 1.00 | 20.81 | A | C |
| ATOM | 980 | C | VAL | 269 | 125.198 | 27.076 | -10.649 | 1.00 | 8.53 | A | C |
| ATOM | 981 | O | VAL | 269 | 125.286 | 28.093 | -11.318 | 1.00 | 11.37 | A | O |
| ATOM | 982 | N | ILE | 270 | 126.114 | 26.744 | -9.746 | 1.00 | 5.57 | A | N |
| ATOM | 983 | CA | ILE | 270 | 127.291 | 27.585 | -9.535 | 1.00 | 6.19 | A | C |
| ATOM | 984 | CB | ILE | 270 | 128.281 | 26.944 | -8.533 | 1.00 | 12.81 | A | C |
| ATOM | 985 | CG2 | ILE | 270 | 129.592 | 27.731 | -8.504 | 1.00 | 7.43 | A | C |
| ATOM | 986 | CG1 | ILE | 270 | 127.671 | 26.926 | -7.135 | 1.00 | 10.37 | A | C |
| ATOM | 987 | CD1 | ILE | 270 | 127.367 | 28.317 | -6.591 | 1.00 | 11.49 | A | C |
| ATOM | 988 | C | ILE | 270 | 128.001 | 27.775 | -10.870 | 1.00 | 10.06 | A | C |
| ATOM | 989 | O | ILE | 270 | 128.549 | 28.838 | -11.140 | 1.00 | 8.84 | A | O |
| ATOM | 990 | N | GLN | 271 | 127.981 | 26.729 | -11.696 | 1.00 | 7.96 | A | N |
| ATOM | 991 | CA | GLN | 271 | 128.605 | 26.751 | -13.011 | 1.00 | 10.02 | A | C |
| ATOM | 992 | CB | GLN | 271 | 128.434 | 25.394 | -13.698 | 1.00 | 84.89 | A | C |
| ATOM | 993 | CG | GLN | 271 | 129.267 | 25.214 | -14.947 | 1.00 | 86.79 | A | C |
| ATOM | 994 | CD | GLN | 271 | 130.744 | 25.366 | -14.665 | 1.00 | 89.29 | A | C |
| ATOM | 995 | OE1 | GLN | 271 | 131.244 | 26.477 | -14.506 | 1.00 | 89.62 | A | O |
| ATOM | 996 | NE2 | GLN | 271 | 131.451 | 24.243 | -14.583 | 1.00 | 90.86 | A | N |
| ATOM | 997 | C | GLN | 271 | 127.962 | 27.842 | -13.860 | 1.00 | 12.48 | A | C |
| ATOM | 998 | O | GLN | 271 | 128.644 | 28.733 | -14.348 | 1.00 | 15.17 | A | O |
| ATOM | 999 | N | ASP | 272 | 126.648 | 27.770 | -14.031 | 1.00 | 33.57 | A | N |
| ATOM | 1000 | CA | ASP | 272 | 125.929 | 28.758 | -14.818 | 1.00 | 34.85 | A | C |
| ATOM | 1001 | CB | ASP | 272 | 124.430 | 28.459 | -14.786 | 1.00 | 74.39 | A | C |
| ATOM | 1002 | CG | ASP | 272 | 124.084 | 27.142 | -15.454 | 1.00 | 76.01 | A | C |
| ATOM | 1003 | OD1 | ASP | 272 | 123.000 | 26.589 | -15.163 | 1.00 | 78.08 | A | O |
| ATOM | 1004 | OD2 | ASP | 272 | 124.893 | 26.665 | -16.278 | 1.00 | 82.27 | A | O |
| ATOM | 1005 | C | ASP | 272 | 126.194 | 30.163 | -14.283 | 1.00 | 35.65 | A | C |
| ATOM | 1006 | O | ASP | 272 | 126.190 | 31.131 | -15.042 | 1.00 | 33.10 | A | O |
| ATOM | 1007 | N | CYS | 273 | 126.426 | 30.280 | -12.978 | 1.00 | 42.88 | A | N |
| ATOM | 1008 | CA | CYS | 273 | 126.698 | 31.582 | -12.387 | 1.00 | 41.31 | A | C |
| ATOM | 1009 | CB | CYS | 273 | 126.630 | 31.516 | -10.862 | 1.00 | 24.14 | A | C |
| ATOM | 1010 | SG | CYS | 273 | 124.940 | 31.489 | -10.191 | 1.00 | 22.24 | A | S |
| ATOM | 1011 | C | CYS | 273 | 128.059 | 32.090 | -12.826 | 1.00 | 41.68 | A | C |
| ATOM | 1012 | O | CYS | 273 | 128.244 | 33.288 | -13.008 | 1.00 | 35.99 | A | O |
| ATOM | 1013 | N | GLU | 274 | 129.010 | 31.178 | -12.994 | 1.00 | 20.07 | A | N |
| ATOM | 1014 | CA | GLU | 274 | 130.364 | 31.531 | -13.440 | 1.00 | 22.87 | A | C |
| ATOM | 1015 | CB | GLU | 274 | 131.317 | 30.338 | -13.298 | 1.00 | 39.18 | A | C |
| ATOM | 1016 | CG | GLU | 274 | 132.090 | 30.309 | -11.989 | 1.00 | 44.30 | A | C |
| ATOM | 1017 | CD | GLU | 274 | 133.041 | 31.490 | -11.836 | 1.00 | 49.41 | A | C |
| ATOM | 1018 | OE1 | GLU | 274 | 133.622 | 31.659 | -10.740 | 1.00 | 51.28 | A | O |
| ATOM | 1019 | OE2 | GLU | 274 | 133.212 | 32.251 | -12.812 | 1.00 | 53.97 | A | O |
| ATOM | 1020 | C | GLU | 274 | 130.345 | 31.984 | -14.893 | 1.00 | 25.29 | A | C |
| ATOM | 1021 | O | GLU | 274 | 131.031 | 32.931 | -15.266 | 1.00 | 27.49 | A | O |
| ATOM | 1022 | N | ASP | 275 | 129.550 | 31.298 | -15.707 | 1.00 | 41.03 | A | N |

Fig. 19: A-15

```
ATOM   1023  CA   ASP  275    129.421  31.625  -17.119  1.00  39.77  A  C
ATOM   1024  CB   ASP  275    128.538  30.594  -17.822  1.00  63.42  A  C
ATOM   1025  CG   ASP  275    129.106  29.203  -17.757  1.00  64.69  A  C
ATOM   1026  OD1  ASP  275    129.987  28.959  -16.906  1.00  68.39  A  O
ATOM   1027  OD2  ASP  275    128.657  28.352  -18.551  1.00  66.35  A  O
ATOM   1028  C    ASP  275    128.789  32.996  -17.295  1.00  38.76  A  C
ATOM   1029  O    ASP  275    128.883  33.595  -18.367  1.00  34.31  A  O
ATOM   1030  N    GLU  276    128.137  33.485  -16.247  1.00  28.36  A  N
ATOM   1031  CA   GLU  276    127.479  34.771  -16.328  1.00  28.01  A  C
ATOM   1032  CB   GLU  276    126.019  34.617  -15.913  1.00  53.33  A  C
ATOM   1033  CG   GLU  276    125.310  33.520  -16.700  1.00  53.20  A  C
ATOM   1034  CD   GLU  276    123.807  33.493  -16.487  1.00  54.30  A  C
ATOM   1035  OE1  GLU  276    123.150  32.629  -17.102  1.00  55.01  A  O
ATOM   1036  OE2  GLU  276    123.280  34.330  -15.717  1.00  51.24  A  O
ATOM   1037  C    GLU  276    128.172  35.841  -15.504  1.00  26.84  A  C
ATOM   1038  O    GLU  276    127.621  36.919  -15.288  1.00  27.95  A  O
ATOM   1039  N    ASN  277    129.382  35.535  -15.050  1.00  28.50  A  N
ATOM   1040  CA   ASN  277    130.185  36.472  -14.268  1.00  28.47  A  C
ATOM   1041  CB   ASN  277    130.607  37.655  -15.140  1.00  86.35  A  C
ATOM   1042  CG   ASN  277    131.230  37.218  -16.439  1.00  91.27  A  C
ATOM   1043  OD1  ASN  277    132.263  36.548  -16.451  1.00  91.09  A  O
ATOM   1044  ND2  ASN  277    130.601  37.589  -17.550  1.00  90.23  A  N
ATOM   1045  C    ASN  277    129.493  37.014  -13.018  1.00  24.82  A  C
ATOM   1046  O    ASN  277    129.476  38.226  -12.790  1.00  25.80  A  O
ATOM   1047  N    ILE  278    128.925  36.127  -12.207  1.00  15.37  A  N
ATOM   1048  CA   ILE  278    128.261  36.560  -10.989  1.00  15.82  A  C
ATOM   1049  CB   ILE  278    126.963  35.773  -10.747  1.00  17.43  A  C
ATOM   1050  CG2  ILE  278    126.304  36.243   -9.454  1.00  18.82  A  C
ATOM   1051  CG1  ILE  278    126.016  35.949  -11.932  1.00  14.88  A  C
ATOM   1052  CD1  ILE  278    124.742  35.153  -11.796  1.00  17.16  A  C
ATOM   1053  C    ILE  278    129.168  36.345   -9.780  1.00  16.42  A  C
ATOM   1054  O    ILE  278    129.363  35.212   -9.354  1.00  16.76  A  O
ATOM   1055  N    GLN  279    129.737  37.426   -9.244  1.00  26.25  A  N
ATOM   1056  CA   GLN  279    130.578  37.335   -8.053  1.00  25.85  A  C
ATOM   1057  CB   GLN  279    131.035  38.716   -7.605  1.00  41.76  A  C
ATOM   1058  CG   GLN  279    131.959  39.382   -8.574  1.00  47.54  A  C
ATOM   1059  CD   GLN  279    133.158  38.524   -8.894  1.00  51.46  A  C
ATOM   1060  OE1  GLN  279    133.992  38.255   -8.023  1.00  45.70  A  O
ATOM   1061  NE2  GLN  279    133.252  38.078  -10.146  1.00  51.05  A  N
ATOM   1062  C    GLN  279    129.716  36.736   -6.958  1.00  23.72  A  C
ATOM   1063  O    GLN  279    128.609  37.216   -6.692  1.00  20.64  A  O
ATOM   1064  N    ARG  280    130.214  35.697   -6.310  1.00  16.06  A  N
ATOM   1065  CA   ARG  280    129.440  35.054   -5.258  1.00  17.58  A  C
ATOM   1066  CB   ARG  280    129.107  33.620   -5.661  1.00  19.51  A  C
ATOM   1067  CG   ARG  280    128.413  33.488   -6.997  1.00  18.14  A  C
ATOM   1068  CD   ARG  280    128.274  32.021   -7.371  1.00  17.81  A  C
ATOM   1069  NE   ARG  280    129.576  31.365   -7.441  1.00  14.86  A  N
ATOM   1070  CZ   ARG  280    130.427  31.489   -8.452  1.00  18.77  A  C
ATOM   1071  NH1  ARG  280    130.131  32.241   -9.493  1.00  21.69  A  N
ATOM   1072  NH2  ARG  280    131.579  30.846   -8.422  1.00  23.71  A  N
ATOM   1073  C    ARG  280    130.123  35.037   -3.892  1.00  17.24  A  C
ATOM   1074  O    ARG  280    131.269  34.592   -3.750  1.00  16.97  A  O
ATOM   1075  N    PHE  281    129.406  35.539   -2.894  1.00  21.33  A  N
ATOM   1076  CA   PHE  281    129.889  35.538   -1.527  1.00  23.32  A  C
ATOM   1077  CB   PHE  281    129.848  36.933   -0.924  1.00  12.67  A  C
ATOM   1078  CG   PHE  281    130.754  37.900   -1.603  1.00  15.70  A  C
ATOM   1079  CD1  PHE  281    130.419  38.434   -2.837  1.00  19.55  A  C
ATOM   1080  CD2  PHE  281    131.968  38.250   -1.024  1.00  17.43  A  C
ATOM   1081  CE1  PHE  281    131.281  39.305   -3.487  1.00  19.61  A  C
ATOM   1082  CE2  PHE  281    132.842  39.120   -1.665  1.00  15.16  A  C
ATOM   1083  CZ   PHE  281    132.498  39.650   -2.900  1.00  16.59  A  C
ATOM   1084  C    PHE  281    128.925  34.646   -0.785  1.00  24.03  A  C
ATOM   1085  O    PHE  281    127.710  34.867   -0.821  1.00  26.40  A  O
ATOM   1086  N    SER  282    129.449  33.613   -0.141  1.00  13.47  A  N
ATOM   1087  CA   SER  282    128.594  32.705    0.602  1.00  15.32  A  C
ATOM   1088  CB   SER  282    128.746  31.272    0.084  1.00  11.38  A  C
ATOM   1089  OG   SER  282    130.081  30.816    0.216  1.00   7.93  A  O
ATOM   1090  C    SER  282    128.947  32.782    2.069  1.00  17.20  A  C
ATOM   1091  O    SER  282    130.066  33.135    2.435  1.00  21.06  A  O
ATOM   1092  N    ILE  283    127.969  32.477    2.908  1.00  24.08  A  N
ATOM   1093  CA   ILE  283    128.164  32.504    4.343  1.00  22.00  A  C
ATOM   1094  CB   ILE  283    127.517  33.733    4.968  1.00  17.91  A  C
ATOM   1095  CG2  ILE  283    127.843  33.791    6.442  1.00  18.72  A  C
```

Fig. 19: A-16

| | | | | | | | | | | |
|---|---|---|---|---|---|---|---|---|---|---|
| ATOM | 1096 | CG1 | ILE | 283 | 128.045 | 34.986 | 4.281 | 1.00 | 14.38 | A C |
| ATOM | 1097 | CD1 | ILE | 283 | 127.103 | 36.171 | 4.383 | 1.00 | 17.94 | A C |
| ATOM | 1098 | C | ILE | 283 | 127.510 | 31.273 | 4.912 | 1.00 | 21.07 | A C |
| ATOM | 1099 | O | ILE | 283 | 126.394 | 30.917 | 4.536 | 1.00 | 20.93 | A O |
| ATOM | 1100 | N | ALA | 284 | 128.204 | 30.618 | 5.823 | 1.00 | 29.93 | A N |
| ATOM | 1101 | CA | ALA | 284 | 127.663 | 29.421 | 6.412 | 1.00 | 29.95 | A C |
| ATOM | 1102 | CB | ALA | 284 | 128.548 | 28.253 | 6.070 | 1.00 | 1.87 | A C |
| ATOM | 1103 | C | ALA | 284 | 127.507 | 29.536 | 7.920 | 1.00 | 28.08 | A C |
| ATOM | 1104 | O | ALA | 284 | 128.482 | 29.740 | 8.641 | 1.00 | 26.74 | A O |
| ATOM | 1105 | N | ILE | 285 | 126.270 | 29.422 | 8.389 | 1.00 | 31.23 | A N |
| ATOM | 1106 | CA | ILE | 285 | 125.997 | 29.457 | 9.817 | 1.00 | 25.43 | A C |
| ATOM | 1107 | CB | ILE | 285 | 124.529 | 29.859 | 10.107 | 1.00 | 43.54 | A C |
| ATOM | 1108 | CG2 | ILE | 285 | 124.187 | 29.569 | 11.555 | 1.00 | 38.36 | A C |
| ATOM | 1109 | CG1 | ILE | 285 | 124.306 | 31.344 | 9.791 | 1.00 | 38.87 | A C |
| ATOM | 1110 | CD1 | ILE | 285 | 124.206 | 31.670 | 8.315 | 1.00 | 40.01 | A C |
| ATOM | 1111 | C | ILE | 285 | 126.227 | 28.022 | 10.296 | 1.00 | 28.75 | A C |
| ATOM | 1112 | O | ILE | 285 | 125.523 | 27.106 | 9.872 | 1.00 | 30.49 | A O |
| ATOM | 1113 | N | LEU | 286 | 127.205 | 27.818 | 11.169 | 1.00 | 38.23 | A N |
| ATOM | 1114 | CA | LEU | 286 | 127.497 | 26.471 | 11.649 | 1.00 | 38.71 | A C |
| ATOM | 1115 | CB | LEU | 286 | 128.999 | 26.313 | 11.876 | 1.00 | 50.51 | A C |
| ATOM | 1116 | CG | LEU | 286 | 129.917 | 26.722 | 10.727 | 1.00 | 53.33 | A C |
| ATOM | 1117 | CD1 | LEU | 286 | 131.340 | 26.363 | 11.105 | 1.00 | 55.89 | A C |
| ATOM | 1118 | CD2 | LEU | 286 | 129.513 | 26.019 | 9.441 | 1.00 | 55.00 | A C |
| ATOM | 1119 | C | LEU | 286 | 126.760 | 26.069 | 12.923 | 1.00 | 39.16 | A C |
| ATOM | 1120 | O | LEU | 286 | 127.068 | 25.036 | 13.517 | 1.00 | 40.00 | A O |
| ATOM | 1121 | N | GLY | 287 | 125.789 | 26.875 | 13.339 | 1.00 | 72.80 | A N |
| ATOM | 1122 | CA | GLY | 287 | 125.042 | 26.579 | 14.551 | 1.00 | 71.58 | A C |
| ATOM | 1123 | C | GLY | 287 | 124.586 | 25.139 | 14.700 | 1.00 | 69.16 | A C |
| ATOM | 1124 | O | GLY | 287 | 125.056 | 24.419 | 15.583 | 1.00 | 73.26 | A O |
| ATOM | 1125 | N | THR | 296 | 131.112 | 19.210 | 10.542 | 1.00 | 87.02 | A N |
| ATOM | 1126 | CA | THR | 296 | 130.609 | 20.333 | 9.766 | 1.00 | 87.06 | A C |
| ATOM | 1127 | CB | THR | 296 | 130.702 | 21.652 | 10.554 | 1.00 | 100.17 | A C |
| ATOM | 1128 | OG1 | THR | 296 | 132.071 | 21.903 | 10.895 | 1.00 | 105.23 | A O |
| ATOM | 1129 | CG2 | THR | 296 | 129.861 | 21.592 | 11.817 | 1.00 | 100.04 | A C |
| ATOM | 1130 | C | THR | 296 | 131.387 | 20.535 | 8.479 | 1.00 | 88.04 | A C |
| ATOM | 1131 | O | THR | 296 | 130.985 | 21.331 | 7.631 | 1.00 | 86.85 | A O |
| ATOM | 1132 | N | GLU | 297 | 132.497 | 19.825 | 8.322 | 1.00 | 78.34 | A N |
| ATOM | 1133 | CA | GLU | 297 | 133.304 | 20.020 | 7.128 | 1.00 | 81.80 | A C |
| ATOM | 1134 | CB | GLU | 297 | 134.577 | 19.171 | 7.169 | 1.00 | 125.47 | A C |
| ATOM | 1135 | CG | GLU | 297 | 134.403 | 17.709 | 6.851 | 1.00 | 132.50 | A C |
| ATOM | 1136 | CD | GLU | 297 | 135.690 | 17.103 | 6.342 | 1.00 | 133.75 | A C |
| ATOM | 1137 | OE1 | GLU | 297 | 135.709 | 15.886 | 6.067 | 1.00 | 135.24 | A O |
| ATOM | 1138 | OE2 | GLU | 297 | 136.682 | 17.853 | 6.212 | 1.00 | 137.19 | A O |
| ATOM | 1139 | C | GLU | 297 | 132.550 | 19.770 | 5.832 | 1.00 | 79.84 | A C |
| ATOM | 1140 | O | GLU | 297 | 132.581 | 20.609 | 4.931 | 1.00 | 79.34 | A O |
| ATOM | 1141 | N | LYS | 298 | 131.865 | 18.638 | 5.728 | 1.00 | 42.69 | A N |
| ATOM | 1142 | CA | LYS | 298 | 131.125 | 18.352 | 4.505 | 1.00 | 42.69 | A C |
| ATOM | 1143 | CB | LYS | 298 | 130.281 | 17.087 | 4.678 | 1.00 | 102.63 | A C |
| ATOM | 1144 | CG | LYS | 298 | 129.695 | 16.562 | 3.376 | 1.00 | 111.34 | A C |
| ATOM | 1145 | CD | LYS | 298 | 129.117 | 15.166 | 3.545 | 1.00 | 113.06 | A C |
| ATOM | 1146 | CE | LYS | 298 | 130.167 | 14.187 | 4.057 | 1.00 | 116.88 | A C |
| ATOM | 1147 | NZ | LYS | 298 | 131.378 | 14.159 | 3.195 | 1.00 | 121.20 | A N |
| ATOM | 1148 | C | LYS | 298 | 130.228 | 19.547 | 4.143 | 1.00 | 40.29 | A C |
| ATOM | 1149 | O | LYS | 298 | 130.032 | 19.853 | 2.964 | 1.00 | 41.17 | A O |
| ATOM | 1150 | N | PHE | 299 | 129.700 | 20.218 | 5.167 | 1.00 | 38.43 | A N |
| ATOM | 1151 | CA | PHE | 299 | 128.839 | 21.380 | 4.978 | 1.00 | 36.67 | A C |
| ATOM | 1152 | CB | PHE | 299 | 128.100 | 21.712 | 6.283 | 1.00 | 55.97 | A C |
| ATOM | 1153 | CG | PHE | 299 | 127.256 | 22.967 | 6.209 | 1.00 | 48.41 | A C |
| ATOM | 1154 | CD1 | PHE | 299 | 126.319 | 23.146 | 5.186 | 1.00 | 44.86 | A C |
| ATOM | 1155 | CD2 | PHE | 299 | 127.400 | 23.970 | 7.160 | 1.00 | 46.14 | A C |
| ATOM | 1156 | CE1 | PHE | 299 | 125.545 | 24.307 | 5.117 | 1.00 | 44.27 | A C |
| ATOM | 1157 | CE2 | PHE | 299 | 126.627 | 25.132 | 7.095 | 1.00 | 40.55 | A C |
| ATOM | 1158 | CZ | PHE | 299 | 125.701 | 25.299 | 6.073 | 1.00 | 39.06 | A C |
| ATOM | 1159 | C | PHE | 299 | 129.684 | 22.573 | 4.544 | 1.00 | 37.02 | A C |
| ATOM | 1160 | O | PHE | 299 | 129.439 | 23.190 | 3.504 | 1.00 | 32.83 | A O |
| ATOM | 1161 | N | VAL | 300 | 130.682 | 22.896 | 5.352 | 1.00 | 13.94 | A N |
| ATOM | 1162 | CA | VAL | 300 | 131.551 | 24.010 | 5.034 | 1.00 | 18.89 | A C |
| ATOM | 1163 | CB | VAL | 300 | 132.752 | 24.068 | 5.993 | 1.00 | 40.51 | A C |
| ATOM | 1164 | CG1 | VAL | 300 | 133.769 | 25.076 | 5.493 | 1.00 | 44.08 | A C |
| ATOM | 1165 | CG2 | VAL | 300 | 132.282 | 24.451 | 7.382 | 1.00 | 44.52 | A C |
| ATOM | 1166 | C | VAL | 300 | 132.061 | 23.893 | 3.607 | 1.00 | 17.53 | A C |
| ATOM | 1167 | O | VAL | 300 | 132.177 | 24.889 | 2.906 | 1.00 | 18.03 | A O |
| ATOM | 1168 | N | GLU | 301 | 132.365 | 22.679 | 3.164 | 1.00 | 18.30 | A N |

Fig. 19: A-17

| ATOM | 1169 | CA | GLU | 301 | 132.866 | 22.513 | 1.808 | 1.00 | 18.96 | A | C |
|------|------|-----|-----|-----|---------|--------|--------|------|-------|---|---|
| ATOM | 1170 | CB | GLU | 301 | 133.407 | 21.094 | 1.605 | 1.00 | 40.16 | A | C |
| ATOM | 1171 | CG | GLU | 301 | 134.058 | 20.854 | 0.243 | 1.00 | 42.43 | A | C |
| ATOM | 1172 | CD | GLU | 301 | 135.049 | 21.943 | -0.155 | 1.00 | 48.24 | A | C |
| ATOM | 1173 | OE1 | GLU | 301 | 135.956 | 22.267 | 0.645 | 1.00 | 47.79 | A | O |
| ATOM | 1174 | OE2 | GLU | 301 | 134.918 | 22.469 | -1.282 | 1.00 | 50.51 | A | O |
| ATOM | 1175 | C | GLU | 301 | 131.770 | 22.832 | 0.791 | 1.00 | 17.53 | A | C |
| ATOM | 1176 | O | GLU | 301 | 132.034 | 23.458 | -0.242 | 1.00 | 15.61 | A | O |
| ATOM | 1177 | N | GLU | 302 | 130.541 | 22.420 | 1.097 | 1.00 | 32.12 | A | N |
| ATOM | 1178 | CA | GLU | 302 | 129.412 | 22.667 | 0.210 | 1.00 | 31.93 | A | C |
| ATOM | 1179 | CB | GLU | 302 | 128.127 | 22.084 | 0.801 | 1.00 | 76.04 | A | C |
| ATOM | 1180 | CG | GLU | 302 | 126.894 | 22.274 | -0.071 | 1.00 | 75.79 | A | C |
| ATOM | 1181 | CD | GLU | 302 | 125.659 | 21.594 | 0.501 | 1.00 | 72.72 | A | C |
| ATOM | 1182 | OE1 | GLU | 302 | 125.651 | 20.349 | 0.584 | 1.00 | 72.70 | A | O |
| ATOM | 1183 | OE2 | GLU | 302 | 124.698 | 22.302 | 0.872 | 1.00 | 77.14 | A | O |
| ATOM | 1184 | C | GLU | 302 | 129.237 | 24.158 | -0.033 | 1.00 | 35.00 | A | C |
| ATOM | 1185 | O | GLU | 302 | 129.040 | 24.580 | -1.170 | 1.00 | 34.26 | A | O |
| ATOM | 1186 | N | ILE | 303 | 129.334 | 24.953 | 1.031 | 1.00 | 23.69 | A | N |
| ATOM | 1187 | CA | ILE | 303 | 129.171 | 26.405 | 0.936 | 1.00 | 23.74 | A | C |
| ATOM | 1188 | CB | ILE | 303 | 128.933 | 27.019 | 2.326 | 1.00 | 28.42 | A | C |
| ATOM | 1189 | CG2 | ILE | 303 | 128.556 | 28.480 | 2.199 | 1.00 | 23.60 | A | C |
| ATOM | 1190 | CG1 | ILE | 303 | 127.823 | 26.245 | 3.046 | 1.00 | 26.02 | A | C |
| ATOM | 1191 | CD1 | ILE | 303 | 126.599 | 25.926 | 2.183 | 1.00 | 22.48 | A | C |
| ATOM | 1192 | C | ILE | 303 | 130.340 | 27.129 | 0.267 | 1.00 | 25.77 | A | C |
| ATOM | 1193 | O | ILE | 303 | 130.133 | 28.036 | -0.553 | 1.00 | 28.26 | A | O |
| ATOM | 1194 | N | LYS | 304 | 131.564 | 26.740 | 0.612 | 1.00 | 28.18 | A | N |
| ATOM | 1195 | CA | LYS | 304 | 132.733 | 27.363 | 0.003 | 1.00 | 28.98 | A | C |
| ATOM | 1196 | CB | LYS | 304 | 134.018 | 26.713 | 0.501 | 1.00 | 31.11 | A | C |
| ATOM | 1197 | CG | LYS | 304 | 134.415 | 27.051 | 1.915 | 1.00 | 37.78 | A | C |
| ATOM | 1198 | CD | LYS | 304 | 135.810 | 26.502 | 2.190 | 1.00 | 39.31 | A | C |
| ATOM | 1199 | CE | LYS | 304 | 136.298 | 26.803 | 3.599 | 1.00 | 42.04 | A | C |
| ATOM | 1200 | NZ | LYS | 304 | 137.673 | 26.262 | 3.857 | 1.00 | 44.22 | A | N |
| ATOM | 1201 | C | LYS | 304 | 132.665 | 27.210 | -1.512 | 1.00 | 25.07 | A | C |
| ATOM | 1202 | O | LYS | 304 | 133.033 | 28.118 | -2.252 | 1.00 | 29.15 | A | O |
| ATOM | 1203 | N | SER | 305 | 132.195 | 26.054 | -1.965 | 1.00 | 30.32 | A | N |
| ATOM | 1204 | CA | SER | 305 | 132.100 | 25.785 | -3.386 | 1.00 | 27.48 | A | C |
| ATOM | 1205 | CB | SER | 305 | 131.702 | 24.329 | -3.635 | 1.00 | 18.09 | A | C |
| ATOM | 1206 | OG | SER | 305 | 130.352 | 24.088 | -3.293 | 1.00 | 14.77 | A | O |
| ATOM | 1207 | C | SER | 305 | 131.094 | 26.709 | -4.044 | 1.00 | 28.00 | A | C |
| ATOM | 1208 | O | SER | 305 | 131.137 | 26.917 | -5.263 | 1.00 | 30.57 | A | O |
| ATOM | 1209 | N | ILE | 306 | 130.181 | 27.258 | -3.247 | 1.00 | 37.08 | A | N |
| ATOM | 1210 | CA | ILE | 306 | 129.180 | 28.176 | -3.783 | 1.00 | 33.83 | A | C |
| ATOM | 1211 | CB | ILE | 306 | 127.990 | 28.319 | -2.831 | 1.00 | 15.00 | A | C |
| ATOM | 1212 | CG2 | ILE | 306 | 127.190 | 29.565 | -3.167 | 1.00 | 15.73 | A | C |
| ATOM | 1213 | CG1 | ILE | 306 | 127.118 | 27.069 | -2.929 | 1.00 | 17.63 | A | C |
| ATOM | 1214 | CD1 | ILE | 306 | 125.993 | 27.029 | -1.916 | 1.00 | 15.34 | A | C |
| ATOM | 1215 | C | ILE | 306 | 129.812 | 29.544 | -4.008 | 1.00 | 31.59 | A | C |
| ATOM | 1216 | O | ILE | 306 | 129.361 | 30.333 | -4.851 | 1.00 | 32.12 | A | O |
| ATOM | 1217 | N | ALA | 307 | 130.874 | 29.805 | -3.251 | 1.00 | 20.26 | A | N |
| ATOM | 1218 | CA | ALA | 307 | 131.584 | 31.062 | -3.349 | 1.00 | 22.45 | A | C |
| ATOM | 1219 | CB | ALA | 307 | 132.444 | 31.260 | -2.118 | 1.00 | 5.65 | A | C |
| ATOM | 1220 | C | ALA | 307 | 132.441 | 31.113 | -4.611 | 1.00 | 22.11 | A | C |
| ATOM | 1221 | O | ALA | 307 | 132.622 | 30.103 | -5.302 | 1.00 | 21.10 | A | O |
| ATOM | 1222 | N | SER | 308 | 132.953 | 32.307 | -4.906 | 1.00 | 24.29 | A | N |
| ATOM | 1223 | CA | SER | 308 | 133.796 | 32.533 | -6.072 | 1.00 | 27.22 | A | C |
| ATOM | 1224 | CB | SER | 308 | 133.489 | 33.899 | -6.700 | 1.00 | 15.61 | A | C |
| ATOM | 1225 | OG | SER | 308 | 132.299 | 33.860 | -7.460 | 1.00 | 19.00 | A | O |
| ATOM | 1226 | C | SER | 308 | 135.264 | 32.482 | -5.690 | 1.00 | 30.87 | A | C |
| ATOM | 1227 | O | SER | 308 | 135.625 | 32.797 | -4.555 | 1.00 | 28.21 | A | O |
| ATOM | 1228 | N | GLU | 309 | 136.103 | 32.069 | -6.640 | 1.00 | 26.43 | A | N |
| ATOM | 1229 | CA | GLU | 309 | 137.542 | 32.008 | -6.418 | 1.00 | 29.92 | A | C |
| ATOM | 1230 | CB | GLU | 309 | 138.224 | 31.266 | -7.569 | 1.00 | 73.14 | A | C |
| ATOM | 1231 | CG | GLU | 309 | 137.811 | 29.809 | -7.737 | 1.00 | 78.51 | A | C |
| ATOM | 1232 | CD | GLU | 309 | 138.181 | 28.950 | -6.541 | 1.00 | 81.27 | A | C |
| ATOM | 1233 | OE1 | GLU | 309 | 138.103 | 27.708 | -6.651 | 1.00 | 83.60 | A | O |
| ATOM | 1234 | OE2 | GLU | 309 | 138.544 | 29.514 | -5.487 | 1.00 | 85.42 | A | O |
| ATOM | 1235 | C | GLU | 309 | 138.009 | 33.461 | -6.396 | 1.00 | 30.67 | A | C |
| ATOM | 1236 | O | GLU | 309 | 137.580 | 34.257 | -7.230 | 1.00 | 32.32 | A | O |
| ATOM | 1237 | N | PRO | 310 | 138.882 | 33.834 | -5.442 | 1.00 | 19.51 | A | N |
| ATOM | 1238 | CD | PRO | 310 | 139.395 | 35.217 | -5.381 | 1.00 | 49.07 | A | C |
| ATOM | 1239 | CA | PRO | 310 | 139.483 | 33.029 | -4.377 | 1.00 | 19.70 | A | C |
| ATOM | 1240 | CB | PRO | 310 | 140.703 | 33.851 | -3.982 | 1.00 | 50.90 | A | C |
| ATOM | 1241 | CG | PRO | 310 | 140.182 | 35.231 | -4.065 | 1.00 | 50.46 | A | C |

Fig. 19: A-18

| ATOM | 1242 | C   | PRO | 310 | 138.569 | 32.751 | -3.178 | 1.00 | 20.19  | A | C |
|------|------|-----|-----|-----|---------|--------|--------|------|--------|---|---|
| ATOM | 1243 | O   | PRO | 310 | 138.229 | 33.654 | -2.394 | 1.00 | 16.98  | A | O |
| ATOM | 1244 | N   | THR | 311 | 138.197 | 31.483 | -3.043 | 1.00 | 25.93  | A | N |
| ATOM | 1245 | CA  | THR | 311 | 137.352 | 31.013 | -1.957 | 1.00 | 26.80  | A | C |
| ATOM | 1246 | CB  | THR | 311 | 137.618 | 29.521 | -1.695 | 1.00 | 73.61  | A | C |
| ATOM | 1247 | OG1 | THR | 311 | 137.053 | 29.145 | -0.434 | 1.00 | 77.77  | A | O |
| ATOM | 1248 | CG2 | THR | 311 | 139.118 | 29.244 | -1.696 | 1.00 | 76.69  | A | C |
| ATOM | 1249 | C   | THR | 311 | 137.521 | 31.781 | -0.643 | 1.00 | 28.67  | A | C |
| ATOM | 1250 | O   | THR | 311 | 136.535 | 32.173 | -0.025 | 1.00 | 29.84  | A | O |
| ATOM | 1251 | N   | GLU | 312 | 138.759 | 32.009 | -0.223 | 1.00 | 47.89  | A | N |
| ATOM | 1252 | CA  | GLU | 312 | 139.007 | 32.713 | 1.029  | 1.00 | 46.51  | A | C |
| ATOM | 1253 | CB  | GLU | 312 | 140.506 | 32.751 | 1.340  | 1.00 | 98.24  | A | C |
| ATOM | 1254 | CG  | GLU | 312 | 141.354 | 33.411 | 0.268  | 1.00 | 100.00 | A | C |
| ATOM | 1255 | CD  | GLU | 312 | 142.621 | 34.031 | 0.825  | 1.00 | 99.11  | A | C |
| ATOM | 1256 | OE1 | GLU | 312 | 143.491 | 34.431 | 0.024  | 1.00 | 102.46 | A | O |
| ATOM | 1257 | OE2 | GLU | 312 | 142.742 | 34.130 | 2.065  | 1.00 | 99.98  | A | O |
| ATOM | 1258 | C   | GLU | 312 | 138.453 | 34.134 | 1.092  | 1.00 | 45.13  | A | C |
| ATOM | 1259 | O   | GLU | 312 | 137.997 | 34.576 | 2.147  | 1.00 | 45.09  | A | O |
| ATOM | 1260 | N   | LYS | 313 | 138.490 | 34.856 | -0.021 | 1.00 | 49.11  | A | N |
| ATOM | 1261 | CA  | LYS | 313 | 137.990 | 36.226 | -0.024 | 1.00 | 48.31  | A | C |
| ATOM | 1262 | CB  | LYS | 313 | 138.797 | 37.091 | -1.000 | 1.00 | 91.02  | A | C |
| ATOM | 1263 | CG  | LYS | 313 | 140.171 | 37.508 | -0.486 | 1.00 | 90.90  | A | C |
| ATOM | 1264 | CD  | LYS | 313 | 140.081 | 38.565 | 0.620  | 1.00 | 87.20  | A | C |
| ATOM | 1265 | CE  | LYS | 313 | 139.966 | 39.982 | 0.066  | 1.00 | 89.24  | A | C |
| ATOM | 1266 | NZ  | LYS | 313 | 138.804 | 40.159 | -0.842 | 1.00 | 93.72  | A | N |
| ATOM | 1267 | C   | LYS | 313 | 136.511 | 36.307 | -0.374 | 1.00 | 49.46  | A | C |
| ATOM | 1268 | O   | LYS | 313 | 135.973 | 37.397 | -0.580 | 1.00 | 51.78  | A | O |
| ATOM | 1269 | N   | HIS | 314 | 135.849 | 35.159 | -0.427 | 1.00 | 27.67  | A | N |
| ATOM | 1270 | CA  | HIS | 314 | 134.437 | 35.137 | -0.775 | 1.00 | 28.52  | A | C |
| ATOM | 1271 | CB  | HIS | 314 | 134.274 | 34.652 | -2.212 | 1.00 | 32.51  | A | C |
| ATOM | 1272 | CG  | HIS | 314 | 134.872 | 35.574 | -3.224 | 1.00 | 29.37  | A | C |
| ATOM | 1273 | CD2 | HIS | 314 | 136.073 | 35.552 | -3.849 | 1.00 | 28.84  | A | C |
| ATOM | 1274 | ND1 | HIS | 314 | 134.220 | 36.697 | -3.683 | 1.00 | 28.95  | A | N |
| ATOM | 1275 | CE1 | HIS | 314 | 134.992 | 37.326 | -4.551 | 1.00 | 28.24  | A | C |
| ATOM | 1276 | NE2 | HIS | 314 | 136.122 | 36.652 | -4.669 | 1.00 | 28.63  | A | N |
| ATOM | 1277 | C   | HIS | 314 | 133.587 | 34.277 | 0.141  | 1.00 | 28.65  | A | C |
| ATOM | 1278 | O   | HIS | 314 | 132.366 | 34.238 | -0.008 | 1.00 | 32.05  | A | O |
| ATOM | 1279 | N   | PHE | 315 | 134.230 | 33.591 | 1.081  | 1.00 | 32.99  | A | N |
| ATOM | 1280 | CA  | PHE | 315 | 133.519 | 32.723 | 2.013  | 1.00 | 32.79  | A | C |
| ATOM | 1281 | CB  | PHE | 315 | 134.045 | 31.294 | 1.878  | 1.00 | 35.38  | A | C |
| ATOM | 1282 | CG  | PHE | 315 | 133.476 | 30.339 | 2.884  | 1.00 | 30.36  | A | C |
| ATOM | 1283 | CD1 | PHE | 315 | 132.123 | 30.026 | 2.877  | 1.00 | 32.20  | A | C |
| ATOM | 1284 | CD2 | PHE | 315 | 134.298 | 29.749 | 3.839  | 1.00 | 28.44  | A | C |
| ATOM | 1285 | CE1 | PHE | 315 | 131.592 | 29.144 | 3.800  | 1.00 | 27.15  | A | C |
| ATOM | 1286 | CE2 | PHE | 315 | 133.783 | 28.866 | 4.769  | 1.00 | 29.14  | A | C |
| ATOM | 1287 | CZ  | PHE | 315 | 132.421 | 28.560 | 4.749  | 1.00 | 30.81  | A | C |
| ATOM | 1288 | C   | PHE | 315 | 133.640 | 33.198 | 3.466  | 1.00 | 33.51  | A | C |
| ATOM | 1289 | O   | PHE | 315 | 134.706 | 33.643 | 3.896  | 1.00 | 34.91  | A | O |
| ATOM | 1290 | N   | PHE | 316 | 132.539 | 33.104 | 4.210  | 1.00 | 26.09  | A | N |
| ATOM | 1291 | CA  | PHE | 316 | 132.513 | 33.516 | 5.610  | 1.00 | 23.14  | A | C |
| ATOM | 1292 | CB  | PHE | 316 | 131.707 | 34.803 | 5.780  | 1.00 | 27.51  | A | C |
| ATOM | 1293 | CG  | PHE | 316 | 132.343 | 36.008 | 5.155  | 1.00 | 31.13  | A | C |
| ATOM | 1294 | CD1 | PHE | 316 | 132.125 | 36.312 | 3.822  | 1.00 | 26.72  | A | C |
| ATOM | 1295 | CD2 | PHE | 316 | 133.182 | 36.827 | 5.903  | 1.00 | 27.98  | A | C |
| ATOM | 1296 | CE1 | PHE | 316 | 132.737 | 37.420 | 3.237  | 1.00 | 29.29  | A | C |
| ATOM | 1297 | CE2 | PHE | 316 | 133.799 | 37.931 | 5.334  | 1.00 | 31.09  | A | C |
| ATOM | 1298 | CZ  | PHE | 316 | 133.577 | 38.230 | 3.998  | 1.00 | 31.32  | A | C |
| ATOM | 1299 | C   | PHE | 316 | 131.909 | 32.434 | 6.497  | 1.00 | 21.07  | A | C |
| ATOM | 1300 | O   | PHE | 316 | 130.901 | 31.831 | 6.153  | 1.00 | 20.31  | A | O |
| ATOM | 1301 | N   | ASN | 317 | 132.533 | 32.220 | 7.647  | 1.00 | 37.16  | A | N |
| ATOM | 1302 | CA  | ASN | 317 | 132.093 | 31.214 | 8.599  | 1.00 | 38.38  | A | C |
| ATOM | 1303 | CB  | ASN | 317 | 133.288 | 30.385 | 9.047  | 1.00 | 74.28  | A | C |
| ATOM | 1304 | CG  | ASN | 317 | 133.055 | 28.919 | 8.888  | 1.00 | 77.27  | A | C |
| ATOM | 1305 | OD1 | ASN | 317 | 131.954 | 28.433 | 9.138  | 1.00 | 79.20  | A | O |
| ATOM | 1306 | ND2 | ASN | 317 | 134.088 | 28.190 | 8.478  | 1.00 | 75.53  | A | N |
| ATOM | 1307 | C   | ASN | 317 | 131.487 | 31.893 | 9.817  | 1.00 | 39.34  | A | C |
| ATOM | 1308 | O   | ASN | 317 | 132.001 | 32.902 | 10.285 | 1.00 | 40.20  | A | O |
| ATOM | 1309 | N   | VAL | 318 | 130.398 | 31.348 | 10.336 | 1.00 | 30.64  | A | N |
| ATOM | 1310 | CA  | VAL | 318 | 129.763 | 31.924 | 11.521 | 1.00 | 29.27  | A | C |
| ATOM | 1311 | CB  | VAL | 318 | 128.531 | 32.778 | 11.144 | 1.00 | 70.89  | A | C |
| ATOM | 1312 | CG1 | VAL | 318 | 127.896 | 33.349 | 12.386 | 1.00 | 71.02  | A | C |
| ATOM | 1313 | CG2 | VAL | 318 | 128.942 | 33.899 | 10.223 | 1.00 | 70.87  | A | C |
| ATOM | 1314 | C   | VAL | 318 | 129.331 | 30.808 | 12.482 | 1.00 | 24.42  | A | C |

Fig. 19: A-19

| | | | | | | | | | | | |
|---|---|---|---|---|---|---|---|---|---|---|---|
| ATOM | 1315 | O | VAL | 318 | 128.872 | 29.744 | 12.053 | 1.00 | 25.09 | A | O |
| ATOM | 1316 | N | SER | 319 | 129.482 | 31.045 | 13.779 | 1.00 | 32.47 | A | N |
| ATOM | 1317 | CA | SER | 319 | 129.108 | 30.035 | 14.752 | 1.00 | 31.73 | A | C |
| ATOM | 1318 | CB | SER | 319 | 129.669 | 30.384 | 16.134 | 1.00 | 29.19 | A | C |
| ATOM | 1319 | OG | SER | 319 | 129.289 | 31.687 | 16.538 | 1.00 | 41.14 | A | O |
| ATOM | 1320 | C | SER | 319 | 127.600 | 29.840 | 14.831 | 1.00 | 30.33 | A | C |
| ATOM | 1321 | O | SER | 319 | 127.132 | 28.716 | 14.963 | 1.00 | 28.40 | A | O |
| ATOM | 1322 | N | ASP | 320 | 126.839 | 30.926 | 14.741 | 1.00 | 32.33 | A | N |
| ATOM | 1323 | CA | ASP | 320 | 125.382 | 30.846 | 14.816 | 1.00 | 32.31 | A | C |
| ATOM | 1324 | CB | ASP | 320 | 124.934 | 30.632 | 16.275 | 1.00 | 63.91 | A | C |
| ATOM | 1325 | CG | ASP | 320 | 125.369 | 31.760 | 17.209 | 1.00 | 62.36 | A | C |
| ATOM | 1326 | OD1 | ASP | 320 | 126.586 | 31.992 | 17.364 | 1.00 | 61.04 | A | O |
| ATOM | 1327 | OD2 | ASP | 320 | 124.486 | 32.412 | 17.801 | 1.00 | 62.91 | A | O |
| ATOM | 1328 | C | ASP | 320 | 124.698 | 32.088 | 14.237 | 1.00 | 30.68 | A | C |
| ATOM | 1329 | O | ASP | 320 | 125.367 | 33.072 | 13.905 | 1.00 | 30.46 | A | O |
| ATOM | 1330 | N | GLU | 321 | 123.371 | 32.042 | 14.110 | 1.00 | 35.58 | A | N |
| ATOM | 1331 | CA | GLU | 321 | 122.614 | 33.173 | 13.569 | 1.00 | 36.56 | A | C |
| ATOM | 1332 | CB | GLU | 321 | 121.126 | 33.029 | 13.889 | 1.00 | 84.00 | A | C |
| ATOM | 1333 | CG | GLU | 321 | 120.285 | 32.398 | 12.796 | 1.00 | 77.84 | A | C |
| ATOM | 1334 | CD | GLU | 321 | 120.602 | 30.938 | 12.569 | 1.00 | 77.59 | A | C |
| ATOM | 1335 | OE1 | GLU | 321 | 120.595 | 30.164 | 13.549 | 1.00 | 79.02 | A | O |
| ATOM | 1336 | OE2 | GLU | 321 | 120.849 | 30.565 | 11.404 | 1.00 | 81.63 | A | O |
| ATOM | 1337 | C | GLU | 321 | 123.101 | 34.500 | 14.134 | 1.00 | 40.55 | A | C |
| ATOM | 1338 | O | GLU | 321 | 123.278 | 35.475 | 13.397 | 1.00 | 37.31 | A | O |
| ATOM | 1339 | N | LEU | 322 | 123.323 | 34.519 | 15.447 | 1.00 | 25.97 | A | N |
| ATOM | 1340 | CA | LEU | 322 | 123.769 | 35.717 | 16.155 | 1.00 | 28.66 | A | C |
| ATOM | 1341 | CB | LEU | 322 | 123.925 | 35.407 | 17.648 | 1.00 | 49.06 | A | C |
| ATOM | 1342 | CG | LEU | 322 | 122.646 | 35.281 | 18.477 | 1.00 | 47.69 | A | C |
| ATOM | 1343 | CD1 | LEU | 322 | 121.935 | 36.625 | 18.486 | 1.00 | 49.43 | A | C |
| ATOM | 1344 | CD2 | LEU | 322 | 121.745 | 34.194 | 17.917 | 1.00 | 52.74 | A | C |
| ATOM | 1345 | C | LEU | 322 | 125.052 | 36.368 | 15.644 | 1.00 | 30.25 | A | C |
| ATOM | 1346 | O | LEU | 322 | 125.106 | 37.580 | 15.459 | 1.00 | 33.60 | A | O |
| ATOM | 1347 | N | ALA | 323 | 126.080 | 35.558 | 15.424 | 1.00 | 27.12 | A | N |
| ATOM | 1348 | CA | ALA | 323 | 127.358 | 36.071 | 14.965 | 1.00 | 27.55 | A | C |
| ATOM | 1349 | CB | ALA | 323 | 128.420 | 34.994 | 15.112 | 1.00 | 20.92 | A | C |
| ATOM | 1350 | C | ALA | 323 | 127.368 | 36.631 | 13.539 | 1.00 | 27.96 | A | C |
| ATOM | 1351 | O | ALA | 323 | 128.363 | 37.227 | 13.120 | 1.00 | 27.98 | A | O |
| ATOM | 1352 | N | LEU | 324 | 126.280 | 36.451 | 12.794 | 1.00 | 44.60 | A | N |
| ATOM | 1353 | CA | LEU | 324 | 126.231 | 36.961 | 11.427 | 1.00 | 43.08 | A | C |
| ATOM | 1354 | CB | LEU | 324 | 124.807 | 36.875 | 10.867 | 1.00 | 12.96 | A | C |
| ATOM | 1355 | CG | LEU | 324 | 124.398 | 35.546 | 10.215 | 1.00 | 11.69 | A | C |
| ATOM | 1356 | CD1 | LEU | 324 | 122.900 | 35.547 | 9.935 | 1.00 | 10.83 | A | C |
| ATOM | 1357 | CD2 | LEU | 324 | 125.197 | 35.331 | 8.938 | 1.00 | 9.62 | A | C |
| ATOM | 1358 | C | LEU | 324 | 126.734 | 38.400 | 11.346 | 1.00 | 46.61 | A | C |
| ATOM | 1359 | O | LEU | 324 | 127.545 | 38.735 | 10.484 | 1.00 | 43.15 | A | O |
| ATOM | 1360 | N | VAL | 325 | 126.257 | 39.244 | 12.252 | 1.00 | 37.14 | A | N |
| ATOM | 1361 | CA | VAL | 325 | 126.657 | 40.645 | 12.297 | 1.00 | 40.67 | A | C |
| ATOM | 1362 | CB | VAL | 325 | 126.111 | 41.328 | 13.549 | 1.00 | 15.02 | A | C |
| ATOM | 1363 | CG1 | VAL | 325 | 124.613 | 41.517 | 13.425 | 1.00 | 15.13 | A | C |
| ATOM | 1364 | CG2 | VAL | 325 | 126.453 | 40.503 | 14.773 | 1.00 | 18.41 | A | C |
| ATOM | 1365 | C | VAL | 325 | 128.168 | 40.840 | 12.304 | 1.00 | 43.49 | A | C |
| ATOM | 1366 | O | VAL | 325 | 128.706 | 41.663 | 11.560 | 1.00 | 45.55 | A | O |
| ATOM | 1367 | N | THR | 326 | 128.844 | 40.088 | 13.161 | 1.00 | 37.74 | A | N |
| ATOM | 1368 | CA | THR | 326 | 130.289 | 40.164 | 13.286 | 1.00 | 39.15 | A | C |
| ATOM | 1369 | CB | THR | 326 | 130.768 | 39.218 | 14.391 | 1.00 | 28.63 | A | C |
| ATOM | 1370 | OG1 | THR | 326 | 130.648 | 37.863 | 13.944 | 1.00 | 30.54 | A | O |
| ATOM | 1371 | CG2 | THR | 326 | 129.911 | 39.398 | 15.643 | 1.00 | 31.00 | A | C |
| ATOM | 1372 | C | THR | 326 | 130.996 | 39.790 | 11.985 | 1.00 | 39.16 | A | C |
| ATOM | 1373 | O | THR | 326 | 132.105 | 39.268 | 12.005 | 1.00 | 37.98 | A | O |
| ATOM | 1374 | N | ILE | 327 | 130.358 | 40.065 | 10.854 | 1.00 | 29.50 | A | N |
| ATOM | 1375 | CA | ILE | 327 | 130.922 | 39.739 | 9.552 | 1.00 | 29.69 | A | C |
| ATOM | 1376 | CB | ILE | 327 | 130.407 | 38.343 | 9.098 | 1.00 | 36.77 | A | C |
| ATOM | 1377 | CG2 | ILE | 327 | 129.867 | 38.372 | 7.679 | 1.00 | 37.54 | A | C |
| ATOM | 1378 | CG1 | ILE | 327 | 131.539 | 37.335 | 9.199 | 1.00 | 37.13 | A | C |
| ATOM | 1379 | CD1 | ILE | 327 | 131.100 | 35.928 | 8.903 | 1.00 | 36.80 | A | C |
| ATOM | 1380 | C | ILE | 327 | 130.572 | 40.816 | 8.520 | 1.00 | 30.20 | A | C |
| ATOM | 1381 | O | ILE | 327 | 131.284 | 41.008 | 7.530 | 1.00 | 30.45 | A | O |
| ATOM | 1382 | N | VAL | 328 | 129.478 | 41.527 | 8.766 | 1.00 | 25.26 | A | N |
| ATOM | 1383 | CA | VAL | 328 | 129.040 | 42.565 | 7.851 | 1.00 | 27.40 | A | C |
| ATOM | 1384 | CB | VAL | 328 | 127.851 | 43.363 | 8.436 | 1.00 | 56.37 | A | C |
| ATOM | 1385 | CG1 | VAL | 328 | 126.752 | 42.408 | 8.838 | 1.00 | 58.32 | A | C |
| ATOM | 1386 | CG2 | VAL | 328 | 128.301 | 44.197 | 9.626 | 1.00 | 57.64 | A | C |
| ATOM | 1387 | C | VAL | 328 | 130.159 | 43.539 | 7.485 | 1.00 | 27.32 | A | C |

Fig. 19: A-20

| ATOM | 1388 | O | VAL | 328 | 130.220 | 44.017 | 6.355 | 1.00 | 26.60 | A | O |
| ATOM | 1389 | N | LYS | 329 | 131.047 | 43.837 | 8.426 | 1.00 | 32.39 | A | N |
| ATOM | 1390 | CA | LYS | 329 | 132.121 | 44.773 | 8.124 | 1.00 | 31.60 | A | C |
| ATOM | 1391 | CB | LYS | 329 | 132.949 | 45.076 | 9.378 | 1.00 | 67.11 | A | C |
| ATOM | 1392 | CG | LYS | 329 | 133.861 | 46.291 | 9.242 | 1.00 | 68.66 | A | C |
| ATOM | 1393 | CD | LYS | 329 | 134.737 | 46.454 | 10.474 | 1.00 | 70.98 | A | C |
| ATOM | 1394 | CE | LYS | 329 | 135.540 | 47.746 | 10.437 | 1.00 | 74.02 | A | C |
| ATOM | 1395 | NZ | LYS | 329 | 134.660 | 48.952 | 10.496 | 1.00 | 77.70 | A | N |
| ATOM | 1396 | C | LYS | 329 | 133.014 | 44.194 | 7.036 | 1.00 | 29.77 | A | C |
| ATOM | 1397 | O | LYS | 329 | 133.205 | 44.802 | 5.978 | 1.00 | 30.98 | A | O |
| ATOM | 1398 | N | ALA | 330 | 133.551 | 43.008 | 7.293 | 1.00 | 29.12 | A | N |
| ATOM | 1399 | CA | ALA | 330 | 134.425 | 42.365 | 6.331 | 1.00 | 29.15 | A | C |
| ATOM | 1400 | CB | ALA | 330 | 134.997 | 41.091 | 6.922 | 1.00 | 30.19 | A | C |
| ATOM | 1401 | C | ALA | 330 | 133.681 | 42.056 | 5.043 | 1.00 | 30.30 | A | C |
| ATOM | 1402 | O | ALA | 330 | 134.207 | 42.269 | 3.955 | 1.00 | 30.20 | A | O |
| ATOM | 1403 | N | LEU | 331 | 132.457 | 41.551 | 5.168 | 1.00 | 22.22 | A | N |
| ATOM | 1404 | CA | LEU | 331 | 131.661 | 41.206 | 3.994 | 1.00 | 19.86 | A | C |
| ATOM | 1405 | CB | LEU | 331 | 130.284 | 40.667 | 4.403 | 1.00 | 36.97 | A | C |
| ATOM | 1406 | CG | LEU | 331 | 129.567 | 39.761 | 3.389 | 1.00 | 33.39 | A | C |
| ATOM | 1407 | CD1 | LEU | 331 | 128.110 | 39.600 | 3.787 | 1.00 | 35.02 | A | C |
| ATOM | 1408 | CD2 | LEU | 331 | 129.658 | 40.343 | 1.996 | 1.00 | 29.08 | A | C |
| ATOM | 1409 | C | LEU | 331 | 131.483 | 42.467 | 3.162 | 1.00 | 19.89 | A | C |
| ATOM | 1410 | O | LEU | 331 | 131.741 | 42.468 | 1.961 | 1.00 | 19.24 | A | O |
| ATOM | 1411 | N | GLY | 332 | 131.045 | 43.535 | 3.830 | 1.00 | 15.82 | A | N |
| ATOM | 1412 | CA | GLY | 332 | 130.824 | 44.811 | 3.179 | 1.00 | 16.92 | A | C |
| ATOM | 1413 | C | GLY | 332 | 132.024 | 45.309 | 2.402 | 1.00 | 17.18 | A | C |
| ATOM | 1414 | O | GLY | 332 | 131.911 | 45.651 | 1.224 | 1.00 | 21.05 | A | O |
| ATOM | 1415 | N | GLU | 333 | 133.185 | 45.347 | 3.045 | 1.00 | 34.74 | A | N |
| ATOM | 1416 | CA | GLU | 333 | 134.369 | 45.831 | 2.362 | 1.00 | 32.80 | A | C |
| ATOM | 1417 | CB | GLU | 333 | 135.472 | 46.165 | 3.371 | 1.00 | 75.29 | A | C |
| ATOM | 1418 | CG | GLU | 333 | 136.139 | 44.968 | 4.005 | 1.00 | 73.66 | A | C |
| ATOM | 1419 | CD | GLU | 333 | 137.251 | 45.363 | 4.959 | 1.00 | 73.68 | A | C |
| ATOM | 1420 | OE1 | GLU | 333 | 137.953 | 44.459 | 5.456 | 1.00 | 75.73 | A | O |
| ATOM | 1421 | OE2 | GLU | 333 | 137.421 | 46.575 | 5.215 | 1.00 | 67.80 | A | O |
| ATOM | 1422 | C | GLU | 333 | 134.888 | 44.841 | 1.322 | 1.00 | 31.78 | A | C |
| ATOM | 1423 | O | GLU | 333 | 135.370 | 45.236 | 0.261 | 1.00 | 31.40 | A | O |
| ATOM | 1424 | N | ARG | 334 | 134.781 | 43.552 | 1.610 | 1.00 | 50.02 | A | N |
| ATOM | 1425 | CA | ARG | 334 | 135.275 | 42.563 | 0.669 | 1.00 | 53.40 | A | C |
| ATOM | 1426 | CB | ARG | 334 | 135.064 | 41.152 | 1.215 | 1.00 | 83.27 | A | C |
| ATOM | 1427 | CG | ARG | 334 | 136.000 | 40.123 | 0.607 | 1.00 | 82.56 | A | C |
| ATOM | 1428 | CD | ARG | 334 | 136.564 | 39.198 | 1.677 | 1.00 | 81.32 | A | C |
| ATOM | 1429 | NE | ARG | 334 | 137.441 | 39.901 | 2.612 | 1.00 | 76.87 | A | N |
| ATOM | 1430 | CZ | ARG | 334 | 137.888 | 39.383 | 3.753 | 1.00 | 80.96 | A | C |
| ATOM | 1431 | NH1 | ARG | 334 | 137.537 | 38.148 | 4.108 | 1.00 | 77.70 | A | N |
| ATOM | 1432 | NH2 | ARG | 334 | 138.686 | 40.097 | 4.539 | 1.00 | 87.10 | A | N |
| ATOM | 1433 | C | ARG | 334 | 134.556 | 42.757 | -0.654 | 1.00 | 54.70 | A | C |
| ATOM | 1434 | O | ARG | 334 | 135.170 | 42.716 | -1.716 | 1.00 | 51.62 | A | O |
| ATOM | 1435 | N | ILE | 335 | 133.253 | 42.988 | -0.591 | 1.00 | 36.48 | A | N |
| ATOM | 1436 | CA | ILE | 335 | 132.473 | 43.214 | -1.803 | 1.00 | 36.41 | A | C |
| ATOM | 1437 | CB | ILE | 335 | 130.940 | 42.967 | -1.539 | 1.00 | 33.09 | A | C |
| ATOM | 1438 | CG2 | ILE | 335 | 130.524 | 43.522 | -0.203 | 1.00 | 35.87 | A | C |
| ATOM | 1439 | CG1 | ILE | 335 | 130.094 | 43.611 | -2.630 | 1.00 | 34.31 | A | C |
| ATOM | 1440 | CD1 | ILE | 335 | 128.612 | 43.520 | -2.368 | 1.00 | 37.10 | A | C |
| ATOM | 1441 | C | ILE | 335 | 132.742 | 44.663 | -2.215 | 1.00 | 34.70 | A | C |
| ATOM | 1442 | O | ILE | 335 | 132.421 | 45.092 | -3.326 | 1.00 | 37.30 | A | O |
| ATOM | 1443 | N | PHE | 336 | 133.392 | 45.377 | -1.299 | 1.00 | 108.43 | A | N |
| ATOM | 1444 | CA | PHE | 336 | 133.744 | 46.789 | -1.419 | 1.00 | 108.06 | A | C |
| ATOM | 1445 | CB | PHE | 336 | 135.092 | 46.989 | -2.157 | 1.00 | 57.00 | A | C |
| ATOM | 1446 | CG | PHE | 336 | 135.114 | 46.540 | -3.601 | 1.00 | 53.32 | A | C |
| ATOM | 1447 | CD1 | PHE | 336 | 134.135 | 46.941 | -4.508 | 1.00 | 52.74 | A | C |
| ATOM | 1448 | CD2 | PHE | 336 | 136.178 | 45.779 | -4.073 | 1.00 | 51.27 | A | C |
| ATOM | 1449 | CE1 | PHE | 336 | 134.219 | 46.589 | -5.868 | 1.00 | 43.07 | A | C |
| ATOM | 1450 | CE2 | PHE | 336 | 136.271 | 45.426 | -5.422 | 1.00 | 45.63 | A | C |
| ATOM | 1451 | CZ | PHE | 336 | 135.292 | 45.832 | -6.319 | 1.00 | 46.09 | A | C |
| ATOM | 1452 | C | PHE | 336 | 132.662 | 47.670 | -2.020 | 1.00 | 108.09 | A | C |
| ATOM | 1453 | O | PHE | 336 | 131.623 | 47.131 | -2.453 | 1.00 | 87.71 | A | O |
| ATOM | 1454 | OXT | PHE | 336 | 132.864 | 48.902 | -2.024 | 1.00 | 40.49 | A | O |
| ATOM | 1455 | CB | GLU | 1 | 119.537 | 12.185 | 27.786 | 1.00 | 88.08 | H | C |
| ATOM | 1456 | CG | GLU | 1 | 118.650 | 11.120 | 28.419 | 1.00 | 88.08 | H | C |
| ATOM | 1457 | CD | GLU | 1 | 119.399 | 10.237 | 29.409 | 1.00 | 88.08 | H | C |
| ATOM | 1458 | OE1 | GLU | 1 | 120.127 | 10.777 | 30.271 | 1.00 | 88.08 | H | O |
| ATOM | 1459 | OE2 | GLU | 1 | 119.251 | 8.998 | 29.324 | 1.00 | 88.08 | H | O |
| ATOM | 1460 | C | GLU | 1 | 118.366 | 14.360 | 28.176 | 1.00 | 62.78 | H | C |

Fig. 19: A-21

| ATOM | 1461 | O   | GLU | 1  | 117.763 | 15.033 | 29.012 | 1.00 | 62.78  | H | O |
|------|------|-----|-----|----|---------|--------|--------|------|--------|---|---|
| ATOM | 1462 | N   | GLU | 1  | 119.687 | 13.262 | 30.016 | 1.00 | 62.78  | H | N |
| ATOM | 1463 | CA  | GLU | 1  | 119.580 | 13.515 | 28.553 | 1.00 | 62.78  | H | C |
| ATOM | 1464 | N   | VAL | 2  | 118.019 | 14.312 | 26.896 | 1.00 | 44.26  | H | N |
| ATOM | 1465 | CA  | VAL | 2  | 116.896 | 15.064 | 26.359 | 1.00 | 44.26  | H | C |
| ATOM | 1466 | CB  | VAL | 2  | 117.154 | 15.460 | 24.909 | 1.00 | 15.14  | H | C |
| ATOM | 1467 | CG1 | VAL | 2  | 118.610 | 15.840 | 24.732 | 1.00 | 15.14  | H | C |
| ATOM | 1468 | CG2 | VAL | 2  | 116.807 | 14.309 | 23.997 | 1.00 | 15.14  | H | C |
| ATOM | 1469 | C   | VAL | 2  | 115.677 | 14.174 | 26.353 | 1.00 | 44.26  | H | C |
| ATOM | 1470 | O   | VAL | 2  | 115.803 | 12.951 | 26.347 | 1.00 | 44.26  | H | O |
| ATOM | 1471 | N   | GLN | 3  | 114.497 | 14.780 | 26.340 | 1.00 | 25.45  | H | N |
| ATOM | 1472 | CA  | GLN | 3  | 113.280 | 13.984 | 26.288 | 1.00 | 25.45  | H | C |
| ATOM | 1473 | CB  | GLN | 3  | 113.191 | 13.046 | 27.494 | 1.00 | 105.15 | H | C |
| ATOM | 1474 | CG  | GLN | 3  | 113.307 | 13.707 | 28.841 | 1.00 | 105.15 | H | C |
| ATOM | 1475 | CD  | GLN | 3  | 113.015 | 12.733 | 29.961 | 1.00 | 105.15 | H | C |
| ATOM | 1476 | OE1 | GLN | 3  | 113.554 | 11.623 | 29.990 | 1.00 | 105.15 | H | O |
| ATOM | 1477 | NE2 | GLN | 3  | 112.157 | 13.139 | 30.892 | 1.00 | 105.15 | H | N |
| ATOM | 1478 | C   | GLN | 3  | 111.961 | 14.708 | 26.119 | 1.00 | 25.45  | H | C |
| ATOM | 1479 | O   | GLN | 3  | 111.809 | 15.887 | 26.438 | 1.00 | 25.45  | H | O |
| ATOM | 1480 | N   | LEU | 4  | 111.009 | 13.959 | 25.588 | 1.00 | 27.88  | H | N |
| ATOM | 1481 | CA  | LEU | 4  | 109.668 | 14.446 | 25.339 | 1.00 | 27.88  | H | C |
| ATOM | 1482 | CB  | LEU | 4  | 109.347 | 14.369 | 23.842 | 1.00 | 33.14  | H | C |
| ATOM | 1483 | CG  | LEU | 4  | 110.367 | 14.924 | 22.847 | 1.00 | 33.14  | H | C |
| ATOM | 1484 | CD1 | LEU | 4  | 109.821 | 14.772 | 21.438 | 1.00 | 33.14  | H | C |
| ATOM | 1485 | CD2 | LEU | 4  | 110.646 | 16.385 | 23.155 | 1.00 | 33.14  | H | C |
| ATOM | 1486 | C   | LEU | 4  | 108.755 | 13.507 | 26.095 | 1.00 | 27.88  | H | C |
| ATOM | 1487 | O   | LEU | 4  | 108.871 | 12.282 | 25.960 | 1.00 | 27.88  | H | O |
| ATOM | 1488 | N   | VAL | 5  | 107.858 | 14.061 | 26.901 | 1.00 | 26.47  | H | N |
| ATOM | 1489 | CA  | VAL | 5  | 106.942 | 13.215 | 27.656 | 1.00 | 26.47  | H | C |
| ATOM | 1490 | CB  | VAL | 5  | 107.176 | 13.329 | 29.197 | 1.00 | 25.39  | H | C |
| ATOM | 1491 | CG1 | VAL | 5  | 107.281 | 14.772 | 29.606 | 1.00 | 25.39  | H | C |
| ATOM | 1492 | CG2 | VAL | 5  | 106.046 | 12.654 | 29.947 | 1.00 | 25.39  | H | C |
| ATOM | 1493 | C   | VAL | 5  | 105.520 | 13.578 | 27.297 | 1.00 | 26.47  | H | C |
| ATOM | 1494 | O   | VAL | 5  | 105.031 | 14.664 | 27.635 | 1.00 | 26.47  | H | O |
| ATOM | 1495 | N   | GLU | 6  | 104.868 | 12.650 | 26.601 | 1.00 | 23.78  | H | N |
| ATOM | 1496 | CA  | GLU | 6  | 103.495 | 12.835 | 26.133 | 1.00 | 23.78  | H | C |
| ATOM | 1497 | CB  | GLU | 6  | 103.258 | 11.995 | 24.885 | 1.00 | 29.58  | H | C |
| ATOM | 1498 | CG  | GLU | 6  | 104.409 | 12.017 | 23.933 | 1.00 | 29.58  | H | C |
| ATOM | 1499 | CD  | GLU | 6  | 104.188 | 11.109 | 22.756 | 1.00 | 29.58  | H | C |
| ATOM | 1500 | OE1 | GLU | 6  | 105.194 | 10.664 | 22.168 | 1.00 | 29.58  | H | O |
| ATOM | 1501 | OE2 | GLU | 6  | 103.013 | 10.846 | 22.413 | 1.00 | 29.58  | H | O |
| ATOM | 1502 | C   | GLU | 6  | 102.429 | 12.485 | 27.155 | 1.00 | 23.78  | H | C |
| ATOM | 1503 | O   | GLU | 6  | 102.680 | 11.740 | 28.101 | 1.00 | 23.78  | H | O |
| ATOM | 1504 | N   | SER | 7  | 101.242 | 13.047 | 26.937 | 1.00 | 26.30  | H | N |
| ATOM | 1505 | CA  | SER | 7  | 100.061 | 12.823 | 27.766 | 1.00 | 26.30  | H | C |
| ATOM | 1506 | CB  | SER | 7  | 100.177 | 13.535 | 29.102 | 1.00 | 32.56  | H | C |
| ATOM | 1507 | OG  | SER | 7  | 100.574 | 14.871 | 28.906 | 1.00 | 32.56  | H | O |
| ATOM | 1508 | C   | SER | 7  | 98.886  | 13.381 | 26.998 | 1.00 | 26.30  | H | C |
| ATOM | 1509 | O   | SER | 7  | 99.060  | 14.248 | 26.136 | 1.00 | 26.30  | H | O |
| ATOM | 1510 | N   | GLY | 8  | 97.693  | 12.872 | 27.287 | 1.00 | 41.74  | H | N |
| ATOM | 1511 | CA  | GLY | 8  | 96.514  | 13.360 | 26.598 | 1.00 | 41.74  | H | C |
| ATOM | 1512 | C   | GLY | 8  | 95.807  | 12.321 | 25.752 | 1.00 | 41.74  | H | C |
| ATOM | 1513 | O   | GLY | 8  | 94.745  | 12.603 | 25.201 | 1.00 | 41.74  | H | O |
| ATOM | 1514 | N   | GLY | 9  | 96.383  | 11.127 | 25.637 | 1.00 | 47.50  | H | N |
| ATOM | 1515 | CA  | GLY | 9  | 95.751  | 10.079 | 24.851 | 1.00 | 47.50  | H | C |
| ATOM | 1516 | C   | GLY | 9  | 94.431  | 9.601  | 25.446 | 1.00 | 47.50  | H | C |
| ATOM | 1517 | O   | GLY | 9  | 94.038  | 10.020 | 26.536 | 1.00 | 47.50  | H | O |
| ATOM | 1518 | N   | GLY | 10 | 93.732  | 8.723  | 24.735 | 1.00 | 16.50  | H | N |
| ATOM | 1519 | CA  | GLY | 10 | 92.469  | 8.225  | 25.244 | 1.00 | 16.50  | H | C |
| ATOM | 1520 | C   | GLY | 10 | 91.485  | 7.806  | 24.169 | 1.00 | 16.50  | H | C |
| ATOM | 1521 | O   | GLY | 10 | 91.830  | 7.701  | 22.990 | 1.00 | 16.50  | H | O |
| ATOM | 1522 | N   | LEU | 11 | 90.251  | 7.559  | 24.595 | 1.00 | 37.61  | H | N |
| ATOM | 1523 | CA  | LEU | 11 | 89.175  | 7.137  | 23.710 | 1.00 | 37.61  | H | C |
| ATOM | 1524 | CB  | LEU | 11 | 88.388  | 6.003  | 24.365 | 1.00 | 18.32  | H | C |
| ATOM | 1525 | CG  | LEU | 11 | 86.959  | 5.715  | 23.885 | 1.00 | 18.32  | H | C |
| ATOM | 1526 | CD1 | LEU | 11 | 86.962  | 5.148  | 22.463 | 1.00 | 18.32  | H | C |
| ATOM | 1527 | CD2 | LEU | 11 | 86.313  | 4.729  | 24.856 | 1.00 | 18.32  | H | C |
| ATOM | 1528 | C   | LEU | 11 | 88.235  | 8.292  | 23.436 | 1.00 | 37.61  | H | C |
| ATOM | 1529 | O   | LEU | 11 | 87.769  | 8.943  | 24.365 | 1.00 | 37.61  | H | O |
| ATOM | 1530 | N   | VAL | 12 | 87.961  | 8.550  | 22.165 | 1.00 | 31.23  | H | N |
| ATOM | 1531 | CA  | VAL | 12 | 87.048  | 9.624  | 21.792 | 1.00 | 31.23  | H | C |
| ATOM | 1532 | CB  | VAL | 12 | 87.794  | 10.800 | 21.144 | 1.00 | 52.64  | H | C |
| ATOM | 1533 | CG1 | VAL | 12 | 88.609  | 11.532 | 22.192 | 1.00 | 52.64  | H | C |

Fig. 19: A-22

```
ATOM   1534  CG2 VAL    12      88.699  10.290  20.039  1.00  52.64      H  C
ATOM   1535  C   VAL    12      86.062   9.045  20.794  1.00  31.23      H  C
ATOM   1536  O   VAL    12      86.365   8.057  20.138  1.00  31.23      H  O
ATOM   1537  N   GLN    13      84.882   9.640  20.681  1.00  27.32      H  N
ATOM   1538  CA  GLN    13      83.894   9.126  19.741  1.00  27.32      H  C
ATOM   1539  CB  GLN    13      82.493   9.391  20.270  1.00  92.40      H  C
ATOM   1540  CG  GLN    13      82.206   8.652  21.553  1.00  92.40      H  C
ATOM   1541  CD  GLN    13      80.808   8.906  22.056  1.00  92.40      H  C
ATOM   1542  OE1 GLN    13      79.836   8.766  21.310  1.00  92.40      H  O
ATOM   1543  NE2 GLN    13      80.693   9.276  23.329  1.00  92.40      H  N
ATOM   1544  C   GLN    13      84.063   9.747  18.356  1.00  27.32      H  C
ATOM   1545  O   GLN    13      84.400  10.924  18.227  1.00  27.32      H  O
ATOM   1546  N   PRO    14      83.834   8.955  17.298  1.00  39.48      H  N
ATOM   1547  CD  PRO    14      83.418   7.539  17.302  1.00  31.44      H  C
ATOM   1548  CA  PRO    14      83.971   9.452  15.929  1.00  39.48      H  C
ATOM   1549  CB  PRO    14      83.219   8.406  15.118  1.00  31.44      H  C
ATOM   1550  CG  PRO    14      83.584   7.145  15.837  1.00  31.44      H  C
ATOM   1551  C   PRO    14      83.401  10.849  15.766  1.00  39.48      H  C
ATOM   1552  O   PRO    14      82.235  11.076  16.053  1.00  39.48      H  O
ATOM   1553  N   GLY    15      84.233  11.784  15.319  1.00  28.44      H  N
ATOM   1554  CA  GLY    15      83.788  13.154  15.130  1.00  28.44      H  C
ATOM   1555  C   GLY    15      84.048  14.065  16.323  1.00  28.44      H  C
ATOM   1556  O   GLY    15      83.759  15.265  16.269  1.00  28.44      H  O
ATOM   1557  N   GLY    16      84.588  13.496  17.401  1.00  22.09      H  N
ATOM   1558  CA  GLY    16      84.880  14.266  18.601  1.00  22.09      H  C
ATOM   1559  C   GLY    16      86.286  14.826  18.571  1.00  22.09      H  C
ATOM   1560  O   GLY    16      86.900  14.912  17.507  1.00  22.09      H  O
ATOM   1561  N   SER    17      86.819  15.202  19.726  1.00  31.69      H  N
ATOM   1562  CA  SER    17      88.161  15.762  19.749  1.00  31.69      H  C
ATOM   1563  CB  SER    17      88.085  17.272  19.592  1.00  54.23      H  C
ATOM   1564  OG  SER    17      87.308  17.829  20.625  1.00  54.23      H  O
ATOM   1565  C   SER    17      88.953  15.416  21.000  1.00  31.69      H  C
ATOM   1566  O   SER    17      88.427  14.824  21.944  1.00  31.69      H  O
ATOM   1567  N   LEU    18      90.227  15.794  20.995  1.00  31.76      H  N
ATOM   1568  CA  LEU    18      91.132  15.515  22.105  1.00  31.76      H  C
ATOM   1569  CB  LEU    18      91.452  14.019  22.124  1.00  63.56      H  C
ATOM   1570  CG  LEU    18      92.462  13.465  23.124  1.00  63.56      H  C
ATOM   1571  CD1 LEU    18      92.121  13.932  24.536  1.00  63.56      H  C
ATOM   1572  CD2 LEU    18      92.462  11.942  23.017  1.00  63.56      H  C
ATOM   1573  C   LEU    18      92.407  16.334  21.899  1.00  31.76      H  C
ATOM   1574  O   LEU    18      92.622  16.884  20.815  1.00  31.76      H  O
ATOM   1575  N   ARG    19      93.243  16.443  22.928  1.00  39.26      H  N
ATOM   1576  CA  ARG    19      94.475  17.207  22.781  1.00  39.26      H  C
ATOM   1577  CB  ARG    19      94.303  18.650  23.258  1.00  32.50      H  C
ATOM   1578  CG  ARG    19      95.571  19.474  23.063  1.00  32.50      H  C
ATOM   1579  CD  ARG    19      95.481  20.862  23.667  1.00  32.50      H  C
ATOM   1580  NE  ARG    19      95.387  20.846  25.125  1.00  32.50      H  N
ATOM   1581  CZ  ARG    19      95.262  21.936  25.879  1.00  32.50      H  C
ATOM   1582  NH1 ARG    19      95.220  23.138  25.322  1.00  32.50      H  N
ATOM   1583  NH2 ARG    19      95.162  21.824  27.193  1.00  32.50      H  N
ATOM   1584  C   ARG    19      95.668  16.606  23.500  1.00  39.26      H  C
ATOM   1585  O   ARG    19      95.687  16.469  24.732  1.00  39.26      H  O
ATOM   1586  N   LEU    20      96.677  16.266  22.709  1.00  36.74      H  N
ATOM   1587  CA  LEU    20      97.896  15.695  23.241  1.00  36.74      H  C
ATOM   1588  CB  LEU    20      98.534  14.737  22.222  1.00  31.69      H  C
ATOM   1589  CG  LEU    20      97.601  13.846  21.390  1.00  31.69      H  C
ATOM   1590  CD1 LEU    20      98.426  12.870  20.555  1.00  31.69      H  C
ATOM   1591  CD2 LEU    20      96.659  13.093  22.292  1.00  31.69      H  C
ATOM   1592  C   LEU    20      98.854  16.838  23.533  1.00  36.74      H  C
ATOM   1593  O   LEU    20      98.866  17.856  22.840  1.00  36.74      H  O
ATOM   1594  N   SER    21      99.638  16.664  24.584  1.00  25.68      H  N
ATOM   1595  CA  SER    21     100.635  17.640  24.974  1.00  25.68      H  C
ATOM   1596  CB  SER    21     100.273  18.278  26.307  1.00  13.03      H  C
ATOM   1597  OG  SER    21      99.718  17.320  27.175  1.00  13.03      H  O
ATOM   1598  C   SER    21     101.901  16.838  25.099  1.00  25.68      H  C
ATOM   1599  O   SER    21     101.851  15.635  25.336  1.00  25.68      H  O
ATOM   1600  N   CYS    22     103.036  17.498  24.931  1.00  22.18      H  N
ATOM   1601  CA  CYS    22     104.321  16.822  25.008  1.00  22.18      H  C
ATOM   1602  C   CYS    22     105.255  17.765  25.713  1.00  22.18      H  C
ATOM   1603  O   CYS    22     105.491  18.863  25.229  1.00  22.18      H  O
ATOM   1604  CB  CYS    22     104.804  16.543  23.603  1.00  57.35      H  C
ATOM   1605  SG  CYS    22     106.473  15.867  23.383  1.00  57.35      H  S
ATOM   1606  N   ALA    23     105.769  17.349  26.867  1.00  26.87      H  N
```

Fig. 19: A-23

| ATOM | 1607 | CA | ALA | 23 | 106.669 | 18.191 | 27.654 | 1.00 | 26.87 | H | C |
| --- | --- | --- | --- | --- | --- | --- | --- | --- | --- | --- | --- |
| ATOM | 1608 | CB | ALA | 23 | 106.470 | 17.937 | 29.141 | 1.00 | 9.84 | H | C |
| ATOM | 1609 | C | ALA | 23 | 108.125 | 17.989 | 27.284 | 1.00 | 26.87 | H | C |
| ATOM | 1610 | O | ALA | 23 | 108.683 | 16.899 | 27.437 | 1.00 | 26.87 | H | O |
| ATOM | 1611 | N | ALA | 24 | 108.738 | 19.058 | 26.800 | 1.00 | 13.29 | H | N |
| ATOM | 1612 | CA | ALA | 24 | 110.124 | 18.988 | 26.409 | 1.00 | 13.29 | H | C |
| ATOM | 1613 | CB | ALA | 24 | 110.357 | 19.851 | 25.183 | 1.00 | 45.62 | H | C |
| ATOM | 1614 | C | ALA | 24 | 111.023 | 19.432 | 27.552 | 1.00 | 13.29 | H | C |
| ATOM | 1615 | O | ALA | 24 | 110.664 | 20.304 | 28.356 | 1.00 | 13.29 | H | O |
| ATOM | 1616 | N | SER | 25 | 112.194 | 18.819 | 27.617 | 1.00 | 22.11 | H | N |
| ATOM | 1617 | CA | SER | 25 | 113.168 | 19.152 | 28.634 | 1.00 | 22.11 | H | C |
| ATOM | 1618 | CB | SER | 25 | 112.731 | 18.582 | 29.982 | 1.00 | 51.20 | H | C |
| ATOM | 1619 | OG | SER | 25 | 112.401 | 17.214 | 29.862 | 1.00 | 51.20 | H | O |
| ATOM | 1620 | C | SER | 25 | 114.526 | 18.591 | 28.232 | 1.00 | 22.11 | H | C |
| ATOM | 1621 | O | SER | 25 | 114.614 | 17.539 | 27.590 | 1.00 | 22.11 | H | O |
| ATOM | 1622 | N | GLY | 26 | 115.582 | 19.306 | 28.591 | 1.00 | 10.76 | H | N |
| ATOM | 1623 | CA | GLY | 26 | 116.914 | 18.844 | 28.263 | 1.00 | 10.76 | H | C |
| ATOM | 1624 | C | GLY | 26 | 117.553 | 19.585 | 27.107 | 1.00 | 10.76 | H | C |
| ATOM | 1625 | O | GLY | 26 | 118.728 | 19.367 | 26.809 | 1.00 | 10.76 | H | O |
| ATOM | 1626 | N | PHE | 27 | 116.794 | 20.458 | 26.448 | 1.00 | 18.08 | H | N |
| ATOM | 1627 | CA | PHE | 27 | 117.325 | 21.207 | 25.318 | 1.00 | 18.08 | H | C |
| ATOM | 1628 | CB | PHE | 27 | 117.241 | 20.373 | 24.031 | 1.00 | 16.53 | H | C |
| ATOM | 1629 | CG | PHE | 27 | 115.842 | 19.974 | 23.651 | 1.00 | 16.53 | H | C |
| ATOM | 1630 | CD1 | PHE | 27 | 115.089 | 19.140 | 24.476 | 1.00 | 16.53 | H | C |
| ATOM | 1631 | CD2 | PHE | 27 | 115.269 | 20.448 | 22.476 | 1.00 | 16.53 | H | C |
| ATOM | 1632 | CE1 | PHE | 27 | 113.770 | 18.782 | 24.137 | 1.00 | 16.53 | H | C |
| ATOM | 1633 | CE2 | PHE | 27 | 113.958 | 20.101 | 22.125 | 1.00 | 16.53 | H | C |
| ATOM | 1634 | CZ | PHE | 27 | 113.203 | 19.268 | 22.954 | 1.00 | 16.53 | H | C |
| ATOM | 1635 | C | PHE | 27 | 116.592 | 22.528 | 25.135 | 1.00 | 18.08 | H | C |
| ATOM | 1636 | O | PHE | 27 | 115.566 | 22.780 | 25.763 | 1.00 | 18.08 | H | O |
| ATOM | 1637 | N | THR | 28 | 117.139 | 23.377 | 24.276 | 1.00 | 42.88 | H | N |
| ATOM | 1638 | CA | THR | 28 | 116.544 | 24.672 | 24.017 | 1.00 | 42.88 | H | C |
| ATOM | 1639 | CB | THR | 28 | 117.575 | 25.604 | 23.381 | 1.00 | 53.65 | H | C |
| ATOM | 1640 | OG1 | THR | 28 | 118.841 | 25.399 | 24.018 | 1.00 | 53.65 | H | O |
| ATOM | 1641 | CG2 | THR | 28 | 117.168 | 27.056 | 23.561 | 1.00 | 53.65 | H | C |
| ATOM | 1642 | C | THR | 28 | 115.369 | 24.463 | 23.074 | 1.00 | 42.88 | H | C |
| ATOM | 1643 | O | THR | 28 | 115.484 | 24.666 | 21.868 | 1.00 | 42.88 | H | O |
| ATOM | 1644 | N | PHE | 29 | 114.239 | 24.051 | 23.644 | 1.00 | 29.92 | H | N |
| ATOM | 1645 | CA | PHE | 29 | 113.004 | 23.772 | 22.901 | 1.00 | 29.92 | H | C |
| ATOM | 1646 | CB | PHE | 29 | 111.855 | 23.614 | 23.906 | 1.00 | 3.95 | H | C |
| ATOM | 1647 | CG | PHE | 29 | 110.503 | 23.347 | 23.276 | 1.00 | 3.95 | H | C |
| ATOM | 1648 | CD1 | PHE | 29 | 110.208 | 22.102 | 22.696 | 1.00 | 3.95 | H | C |
| ATOM | 1649 | CD2 | PHE | 29 | 109.504 | 24.336 | 23.283 | 1.00 | 3.95 | H | C |
| ATOM | 1650 | CE1 | PHE | 29 | 108.939 | 21.852 | 22.139 | 1.00 | 3.95 | H | C |
| ATOM | 1651 | CE2 | PHE | 29 | 108.234 | 24.092 | 22.727 | 1.00 | 3.95 | H | C |
| ATOM | 1652 | CZ | PHE | 29 | 107.953 | 22.860 | 22.160 | 1.00 | 3.95 | H | C |
| ATOM | 1653 | C | PHE | 29 | 112.611 | 24.777 | 21.797 | 1.00 | 29.92 | H | C |
| ATOM | 1654 | O | PHE | 29 | 112.390 | 24.389 | 20.647 | 1.00 | 29.92 | H | O |
| ATOM | 1655 | N | SER | 30 | 112.539 | 26.058 | 22.144 | 1.00 | 32.50 | H | N |
| ATOM | 1656 | CA | SER | 30 | 112.139 | 27.105 | 21.199 | 1.00 | 32.50 | H | C |
| ATOM | 1657 | CB | SER | 30 | 112.335 | 28.473 | 21.852 | 1.00 | 67.50 | H | C |
| ATOM | 1658 | OG | SER | 30 | 113.644 | 28.591 | 22.372 | 1.00 | 67.50 | H | O |
| ATOM | 1659 | C | SER | 30 | 112.799 | 27.107 | 19.812 | 1.00 | 32.50 | H | C |
| ATOM | 1660 | O | SER | 30 | 112.191 | 27.504 | 18.816 | 1.00 | 32.50 | H | O |
| ATOM | 1661 | N | ARG | 31 | 114.037 | 26.649 | 19.751 | 1.00 | 18.89 | H | N |
| ATOM | 1662 | CA | ARG | 31 | 114.801 | 26.636 | 18.515 | 1.00 | 18.89 | H | C |
| ATOM | 1663 | CB | ARG | 31 | 116.292 | 26.604 | 18.886 | 1.00 | 48.17 | H | C |
| ATOM | 1664 | CG | ARG | 31 | 117.217 | 25.955 | 17.887 | 1.00 | 48.17 | H | C |
| ATOM | 1665 | CD | ARG | 31 | 118.650 | 26.425 | 18.112 | 1.00 | 48.17 | H | C |
| ATOM | 1666 | NE | ARG | 31 | 119.135 | 26.203 | 19.476 | 1.00 | 48.17 | H | N |
| ATOM | 1667 | CZ | ARG | 31 | 120.228 | 26.777 | 19.980 | 1.00 | 48.17 | H | C |
| ATOM | 1668 | NH1 | ARG | 31 | 120.950 | 27.608 | 19.238 | 1.00 | 48.17 | H | N |
| ATOM | 1669 | NH2 | ARG | 31 | 120.604 | 26.524 | 21.226 | 1.00 | 48.17 | H | N |
| ATOM | 1670 | C | ARG | 31 | 114.463 | 25.523 | 17.521 | 1.00 | 18.89 | H | C |
| ATOM | 1671 | O | ARG | 31 | 114.520 | 25.723 | 16.313 | 1.00 | 18.89 | H | O |
| ATOM | 1672 | N | TYR | 32 | 114.095 | 24.353 | 18.027 | 1.00 | 15.47 | H | N |
| ATOM | 1673 | CA | TYR | 32 | 113.791 | 23.200 | 17.179 | 1.00 | 15.47 | H | C |
| ATOM | 1674 | CB | TYR | 32 | 113.949 | 21.922 | 17.996 | 1.00 | 6.03 | H | C |
| ATOM | 1675 | CG | TYR | 32 | 115.367 | 21.653 | 18.426 | 1.00 | 6.03 | H | C |
| ATOM | 1676 | CD1 | TYR | 32 | 115.934 | 22.336 | 19.500 | 1.00 | 6.03 | H | C |
| ATOM | 1677 | CE1 | TYR | 32 | 117.249 | 22.097 | 19.889 | 1.00 | 6.03 | H | C |
| ATOM | 1678 | CD2 | TYR | 32 | 116.153 | 20.722 | 17.747 | 1.00 | 6.03 | H | C |
| ATOM | 1679 | CE2 | TYR | 32 | 117.467 | 20.477 | 18.122 | 1.00 | 6.03 | H | C |

Fig. 19: A-24

| | | | | | | | | | | |
|---|---|---|---|---|---|---|---|---|---|---|
| ATOM | 1680 | CZ | TYR | 32 | 118.013 | 21.165 | 19.198 | 1.00 | 6.03 | H | C |
| ATOM | 1681 | OH | TYR | 32 | 119.317 | 20.907 | 19.597 | 1.00 | 6.03 | H | O |
| ATOM | 1682 | C | TYR | 32 | 112.426 | 23.184 | 16.534 | 1.00 | 15.47 | H | C |
| ATOM | 1683 | O | TYR | 32 | 111.480 | 23.748 | 17.058 | 1.00 | 15.47 | H | O |
| ATOM | 1684 | N | THR | 33 | 112.309 | 22.545 | 15.382 | 1.00 | 10.91 | H | N |
| ATOM | 1685 | CA | THR | 33 | 110.988 | 22.451 | 14.792 | 1.00 | 10.91 | H | C |
| ATOM | 1686 | CB | THR | 33 | 111.032 | 22.556 | 13.230 | 1.00 | 11.96 | H | C |
| ATOM | 1687 | OG1 | THR | 33 | 111.079 | 21.259 | 12.639 | 1.00 | 11.96 | H | O |
| ATOM | 1688 | CG2 | THR | 33 | 112.251 | 23.338 | 12.786 | 1.00 | 11.96 | H | C |
| ATOM | 1689 | C | THR | 33 | 110.501 | 21.082 | 15.303 | 1.00 | 10.91 | H | C |
| ATOM | 1690 | O | THR | 33 | 111.188 | 20.061 | 15.157 | 1.00 | 10.91 | H | O |
| ATOM | 1691 | N | MET | 34 | 109.348 | 21.070 | 15.960 | 1.00 | 21.14 | H | N |
| ATOM | 1692 | CA | MET | 34 | 108.815 | 19.835 | 16.518 | 1.00 | 21.14 | H | C |
| ATOM | 1693 | CB | MET | 34 | 108.188 | 20.094 | 17.888 | 1.00 | 16.88 | H | C |
| ATOM | 1694 | CG | MET | 34 | 109.035 | 20.899 | 18.847 | 1.00 | 16.88 | H | C |
| ATOM | 1695 | SD | MET | 34 | 110.603 | 20.131 | 19.122 | 1.00 | 16.88 | H | S |
| ATOM | 1696 | CE | MET | 34 | 110.155 | 18.770 | 20.240 | 1.00 | 16.88 | H | C |
| ATOM | 1697 | C | MET | 34 | 107.760 | 19.218 | 15.614 | 1.00 | 21.14 | H | C |
| ATOM | 1698 | O | MET | 34 | 107.160 | 19.905 | 14.781 | 1.00 | 21.14 | H | O |
| ATOM | 1699 | N | SER | 35 | 107.519 | 17.925 | 15.802 | 1.00 | 15.88 | H | N |
| ATOM | 1700 | CA | SER | 35 | 106.533 | 17.232 | 14.997 | 1.00 | 15.88 | H | C |
| ATOM | 1701 | CB | SER | 35 | 107.205 | 16.581 | 13.794 | 1.00 | 13.53 | H | C |
| ATOM | 1702 | OG | SER | 35 | 107.895 | 17.550 | 13.034 | 1.00 | 13.53 | H | O |
| ATOM | 1703 | C | SER | 35 | 105.767 | 16.168 | 15.763 | 1.00 | 15.88 | H | C |
| ATOM | 1704 | O | SER | 35 | 106.058 | 15.867 | 16.926 | 1.00 | 15.88 | H | O |
| ATOM | 1705 | N | TRP | 36 | 104.765 | 15.617 | 15.087 | 1.00 | 13.73 | H | N |
| ATOM | 1706 | CA | TRP | 36 | 103.948 | 14.556 | 15.626 | 1.00 | 13.73 | H | C |
| ATOM | 1707 | CB | TRP | 36 | 102.510 | 15.023 | 15.849 | 1.00 | 20.04 | H | C |
| ATOM | 1708 | CG | TRP | 36 | 102.337 | 15.903 | 17.039 | 1.00 | 20.04 | H | C |
| ATOM | 1709 | CD2 | TRP | 36 | 102.259 | 15.489 | 18.406 | 1.00 | 20.04 | H | C |
| ATOM | 1710 | CE2 | TRP | 36 | 102.112 | 16.654 | 19.186 | 1.00 | 20.04 | H | C |
| ATOM | 1711 | CE3 | TRP | 36 | 102.301 | 14.248 | 19.046 | 1.00 | 20.04 | H | C |
| ATOM | 1712 | CD1 | TRP | 36 | 102.236 | 17.255 | 17.045 | 1.00 | 20.04 | H | C |
| ATOM | 1713 | NE1 | TRP | 36 | 102.100 | 17.716 | 18.329 | 1.00 | 20.04 | H | N |
| ATOM | 1714 | CZ2 | TRP | 36 | 102.004 | 16.622 | 20.576 | 1.00 | 20.04 | H | C |
| ATOM | 1715 | CZ3 | TRP | 36 | 102.192 | 14.211 | 20.442 | 1.00 | 20.04 | H | C |
| ATOM | 1716 | CH2 | TRP | 36 | 102.044 | 15.396 | 21.190 | 1.00 | 20.04 | H | C |
| ATOM | 1717 | C | TRP | 36 | 103.978 | 13.470 | 14.565 | 1.00 | 13.73 | H | C |
| ATOM | 1718 | O | TRP | 36 | 103.879 | 13.769 | 13.373 | 1.00 | 13.73 | H | O |
| ATOM | 1719 | N | VAL | 37 | 104.138 | 12.221 | 15.006 | 1.00 | 21.09 | H | N |
| ATOM | 1720 | CA | VAL | 37 | 104.179 | 11.054 | 14.125 | 1.00 | 21.09 | H | C |
| ATOM | 1721 | CB | VAL | 37 | 105.622 | 10.464 | 14.053 | 1.00 | 6.36 | H | C |
| ATOM | 1722 | CG1 | VAL | 37 | 105.591 | 9.017 | 13.642 | 1.00 | 6.36 | H | C |
| ATOM | 1723 | CG2 | VAL | 37 | 106.461 | 11.253 | 13.057 | 1.00 | 6.36 | H | C |
| ATOM | 1724 | C | VAL | 37 | 103.229 | 10.041 | 14.748 | 1.00 | 21.09 | H | C |
| ATOM | 1725 | O | VAL | 37 | 103.144 | 9.940 | 15.963 | 1.00 | 21.09 | H | O |
| ATOM | 1726 | N | ARG | 38 | 102.508 | 9.294 | 13.929 | 1.00 | 17.98 | H | N |
| ATOM | 1727 | CA | ARG | 38 | 101.562 | 8.309 | 14.454 | 1.00 | 17.98 | H | C |
| ATOM | 1728 | CB | ARG | 38 | 100.133 | 8.697 | 14.058 | 1.00 | 13.99 | H | C |
| ATOM | 1729 | CG | ARG | 38 | 100.106 | 9.210 | 12.633 | 1.00 | 13.99 | H | C |
| ATOM | 1730 | CD | ARG | 38 | 98.899 | 8.817 | 11.839 | 1.00 | 13.99 | H | C |
| ATOM | 1731 | NE | ARG | 38 | 97.664 | 9.434 | 12.289 | 1.00 | 13.99 | H | N |
| ATOM | 1732 | CZ | ARG | 38 | 96.652 | 9.707 | 11.470 | 1.00 | 13.99 | H | C |
| ATOM | 1733 | NH1 | ARG | 38 | 96.744 | 9.432 | 10.171 | 1.00 | 13.99 | H | N |
| ATOM | 1734 | NH2 | ARG | 38 | 95.533 | 10.224 | 11.960 | 1.00 | 13.99 | H | N |
| ATOM | 1735 | C | ARG | 38 | 101.856 | 6.925 | 13.895 | 1.00 | 17.98 | H | C |
| ATOM | 1736 | O | ARG | 38 | 102.468 | 6.785 | 12.840 | 1.00 | 17.98 | H | O |
| ATOM | 1737 | N | GLN | 39 | 101.386 | 5.909 | 14.604 | 1.00 | 17.63 | H | N |
| ATOM | 1738 | CA | GLN | 39 | 101.560 | 4.521 | 14.200 | 1.00 | 17.63 | H | C |
| ATOM | 1739 | CB | GLN | 39 | 102.659 | 3.866 | 15.051 | 1.00 | 12.11 | H | C |
| ATOM | 1740 | CG | GLN | 39 | 102.976 | 2.424 | 14.712 | 1.00 | 12.11 | H | C |
| ATOM | 1741 | CD | GLN | 39 | 104.396 | 2.025 | 15.134 | 1.00 | 12.11 | H | C |
| ATOM | 1742 | OE1 | GLN | 39 | 104.811 | 2.262 | 16.272 | 1.00 | 12.11 | H | O |
| ATOM | 1743 | NE2 | GLN | 39 | 105.143 | 1.414 | 14.212 | 1.00 | 12.11 | H | N |
| ATOM | 1744 | C | GLN | 39 | 100.206 | 3.847 | 14.429 | 1.00 | 17.63 | H | C |
| ATOM | 1745 | O | GLN | 39 | 99.712 | 3.770 | 15.562 | 1.00 | 17.63 | H | O |
| ATOM | 1746 | N | ALA | 40 | 99.590 | 3.399 | 13.344 | 1.00 | 55.11 | H | N |
| ATOM | 1747 | CA | ALA | 40 | 98.300 | 2.737 | 13.436 | 1.00 | 55.11 | H | C |
| ATOM | 1748 | CB | ALA | 40 | 97.605 | 2.754 | 12.088 | 1.00 | 43.12 | H | C |
| ATOM | 1749 | C | ALA | 40 | 98.536 | 1.302 | 13.881 | 1.00 | 55.11 | H | C |
| ATOM | 1750 | O | ALA | 40 | 99.626 | 0.762 | 13.687 | 1.00 | 55.11 | H | O |
| ATOM | 1751 | N | PRO | 41 | 97.517 | 0.670 | 14.491 | 1.00 | 55.83 | H | N |
| ATOM | 1752 | CD | PRO | 41 | 96.189 | 1.237 | 14.782 | 1.00 | 86.02 | H | C |

Fig. 19: A-25

| | | | | | | | | | | |
|---|---|---|---|---|---|---|---|---|---|---|
| ATOM | 1753 | CA | PRO | 41 | 97.600 | -0.712 | 14.969 | 1.00 | 55.83 | H C |
| ATOM | 1754 | CB | PRO | 41 | 96.169 | -1.009 | 15.400 | 1.00 | 86.02 | H C |
| ATOM | 1755 | CG | PRO | 41 | 95.681 | 0.315 | 15.859 | 1.00 | 86.02 | H C |
| ATOM | 1756 | C | PRO | 41 | 98.057 | -1.624 | 13.838 | 1.00 | 55.83 | H C |
| ATOM | 1757 | O | PRO | 41 | 97.423 | -1.670 | 12.781 | 1.00 | 55.83 | H O |
| ATOM | 1758 | N | GLY | 42 | 99.160 | -2.335 | 14.061 | 1.00 | 43.01 | H N |
| ATOM | 1759 | CA | GLY | 42 | 99.684 | -3.227 | 13.042 | 1.00 | 43.01 | H C |
| ATOM | 1760 | C | GLY | 42 | 100.227 | -2.529 | 11.800 | 1.00 | 43.01 | H C |
| ATOM | 1761 | O | GLY | 42 | 100.480 | -3.175 | 10.775 | 1.00 | 43.01 | H O |
| ATOM | 1762 | N | LYS | 43 | 100.415 | -1.212 | 11.882 | 1.00 | 46.16 | H N |
| ATOM | 1763 | CA | LYS | 43 | 100.922 | -0.446 | 10.750 | 1.00 | 46.16 | H C |
| ATOM | 1764 | CB | LYS | 43 | 99.896 | 0.612 | 10.334 | 1.00 | 59.60 | H C |
| ATOM | 1765 | CG | LYS | 43 | 98.800 | 0.081 | 9.421 | 1.00 | 59.60 | H C |
| ATOM | 1766 | CD | LYS | 43 | 98.003 | -1.023 | 10.079 | 1.00 | 59.60 | H C |
| ATOM | 1767 | CE | LYS | 43 | 97.230 | -1.831 | 9.047 | 1.00 | 59.60 | H C |
| ATOM | 1768 | NZ | LYS | 43 | 98.125 | -2.590 | 8.124 | 1.00 | 59.60 | H N |
| ATOM | 1769 | C | LYS | 43 | 102.278 | 0.215 | 10.994 | 1.00 | 46.16 | H C |
| ATOM | 1770 | O | LYS | 43 | 102.889 | 0.060 | 12.063 | 1.00 | 46.16 | H O |
| ATOM | 1771 | N | GLY | 44 | 102.742 | 0.942 | 9.976 | 1.00 | 50.42 | H N |
| ATOM | 1772 | CA | GLY | 44 | 104.016 | 1.631 | 10.054 | 1.00 | 50.42 | H C |
| ATOM | 1773 | C | GLY | 44 | 103.916 | 3.004 | 10.691 | 1.00 | 50.42 | H C |
| ATOM | 1774 | O | GLY | 44 | 103.001 | 3.281 | 11.462 | 1.00 | 50.42 | H O |
| ATOM | 1775 | N | LEU | 45 | 104.862 | 3.870 | 10.347 | 1.00 | 25.59 | H N |
| ATOM | 1776 | CA | LEU | 45 | 104.933 | 5.229 | 10.883 | 1.00 | 25.59 | H C |
| ATOM | 1777 | CB | LEU | 45 | 106.387 | 5.544 | 11.224 | 1.00 | 8.94 | H C |
| ATOM | 1778 | CG | LEU | 45 | 107.011 | 4.480 | 12.118 | 1.00 | 8.94 | H C |
| ATOM | 1779 | CD1 | LEU | 45 | 108.520 | 4.578 | 12.054 | 1.00 | 8.94 | H C |
| ATOM | 1780 | CD2 | LEU | 45 | 106.481 | 4.638 | 13.541 | 1.00 | 8.94 | H C |
| ATOM | 1781 | C | LEU | 45 | 104.394 | 6.259 | 9.893 | 1.00 | 25.59 | H C |
| ATOM | 1782 | O | LEU | 45 | 104.613 | 6.142 | 8.684 | 1.00 | 25.59 | H O |
| ATOM | 1783 | N | GLU | 46 | 103.698 | 7.268 | 10.411 | 1.00 | 28.67 | H N |
| ATOM | 1784 | CA | GLU | 46 | 103.111 | 8.308 | 9.569 | 1.00 | 28.67 | H C |
| ATOM | 1785 | CB | GLU | 46 | 101.617 | 8.045 | 9.370 | 1.00 | 21.38 | H C |
| ATOM | 1786 | CG | GLU | 46 | 100.977 | 8.902 | 8.304 | 1.00 | 21.38 | H C |
| ATOM | 1787 | CD | GLU | 46 | 99.555 | 8.471 | 7.972 | 1.00 | 21.38 | H C |
| ATOM | 1788 | OE1 | GLU | 46 | 98.711 | 8.399 | 8.903 | 1.00 | 21.38 | H O |
| ATOM | 1789 | OE2 | GLU | 46 | 99.283 | 8.214 | 6.776 | 1.00 | 21.38 | H O |
| ATOM | 1790 | C | GLU | 46 | 103.304 | 9.698 | 10.152 | 1.00 | 28.67 | H C |
| ATOM | 1791 | O | GLU | 46 | 102.942 | 9.962 | 11.301 | 1.00 | 28.67 | H O |
| ATOM | 1792 | N | TRP | 47 | 103.887 | 10.579 | 9.347 | 1.00 | 2.61 | H N |
| ATOM | 1793 | CA | TRP | 47 | 104.132 | 11.944 | 9.758 | 1.00 | 2.61 | H C |
| ATOM | 1794 | CB | TRP | 47 | 105.055 | 12.618 | 8.757 | 1.00 | 14.19 | H C |
| ATOM | 1795 | CG | TRP | 47 | 105.068 | 14.095 | 8.904 | 1.00 | 14.19 | H C |
| ATOM | 1796 | CD2 | TRP | 47 | 104.446 | 15.035 | 8.036 | 1.00 | 14.19 | H C |
| ATOM | 1797 | CE2 | TRP | 47 | 104.681 | 16.323 | 8.578 | 1.00 | 14.19 | H C |
| ATOM | 1798 | CE3 | TRP | 47 | 103.709 | 14.919 | 6.852 | 1.00 | 14.19 | H C |
| ATOM | 1799 | CD1 | TRP | 47 | 105.644 | 14.824 | 9.914 | 1.00 | 14.19 | H C |
| ATOM | 1800 | NE1 | TRP | 47 | 105.418 | 16.161 | 9.723 | 1.00 | 14.19 | H N |
| ATOM | 1801 | CZ2 | TRP | 47 | 104.201 | 17.490 | 7.969 | 1.00 | 14.19 | H C |
| ATOM | 1802 | CZ3 | TRP | 47 | 103.233 | 16.074 | 6.248 | 1.00 | 14.19 | H C |
| ATOM | 1803 | CH2 | TRP | 47 | 103.480 | 17.344 | 6.808 | 1.00 | 14.19 | H C |
| ATOM | 1804 | C | TRP | 47 | 102.791 | 12.673 | 9.802 | 1.00 | 2.61 | H C |
| ATOM | 1805 | O | TRP | 47 | 102.083 | 12.752 | 8.796 | 1.00 | 2.61 | H O |
| ATOM | 1806 | N | VAL | 48 | 102.443 | 13.215 | 10.962 | 1.00 | 34.26 | H N |
| ATOM | 1807 | CA | VAL | 48 | 101.165 | 13.895 | 11.114 | 1.00 | 34.26 | H C |
| ATOM | 1808 | CB | VAL | 48 | 100.576 | 13.639 | 12.523 | 1.00 | 16.29 | H C |
| ATOM | 1809 | CG1 | VAL | 48 | 99.137 | 14.148 | 12.623 | 1.00 | 16.29 | H C |
| ATOM | 1810 | CG2 | VAL | 48 | 100.624 | 12.187 | 12.812 | 1.00 | 16.29 | H C |
| ATOM | 1811 | C | VAL | 48 | 101.246 | 15.393 | 10.884 | 1.00 | 34.26 | H C |
| ATOM | 1812 | O | VAL | 48 | 100.563 | 15.932 | 10.015 | 1.00 | 34.26 | H O |
| ATOM | 1813 | N | ALA | 49 | 102.078 | 16.068 | 11.665 | 1.00 | 19.79 | H N |
| ATOM | 1814 | CA | ALA | 49 | 102.198 | 17.505 | 11.533 | 1.00 | 19.79 | H C |
| ATOM | 1815 | CB | ALA | 49 | 101.052 | 18.193 | 12.288 | 1.00 | 1.87 | H C |
| ATOM | 1816 | C | ALA | 49 | 103.542 | 17.994 | 12.041 | 1.00 | 19.79 | H C |
| ATOM | 1817 | O | ALA | 49 | 104.295 | 17.244 | 12.645 | 1.00 | 19.79 | H O |
| ATOM | 1818 | N | THR | 50 | 103.816 | 19.271 | 11.795 | 1.00 | 29.76 | H N |
| ATOM | 1819 | CA | THR | 50 | 105.067 | 19.906 | 12.184 | 1.00 | 29.76 | H C |
| ATOM | 1820 | CB | THR | 50 | 106.142 | 19.637 | 11.127 | 1.00 | 20.69 | H C |
| ATOM | 1821 | OG1 | THR | 50 | 106.390 | 18.232 | 11.065 | 1.00 | 20.69 | H O |
| ATOM | 1822 | CG2 | THR | 50 | 107.422 | 20.357 | 11.460 | 1.00 | 20.69 | H C |
| ATOM | 1823 | C | THR | 50 | 104.897 | 21.416 | 12.327 | 1.00 | 29.76 | H C |
| ATOM | 1824 | O | THR | 50 | 104.113 | 22.035 | 11.616 | 1.00 | 29.76 | H O |
| ATOM | 1825 | N | ILE | 51 | 105.649 | 21.994 | 13.258 | 1.00 | 20.54 | H N |

Fig. 19: A-26

| ATOM | 1826 | CA | ILE | 51 | 105.626 | 23.424 | 13.530 | 1.00 | 20.54 | H | C |
|---|---|---|---|---|---|---|---|---|---|---|---|
| ATOM | 1827 | CB | ILE | 51 | 104.824 | 23.714 | 14.816 | 1.00 | 27.11 | H | C |
| ATOM | 1828 | CG2 | ILE | 51 | 105.430 | 22.955 | 15.975 | 1.00 | 27.11 | H | C |
| ATOM | 1829 | CG1 | ILE | 51 | 104.805 | 25.217 | 15.108 | 1.00 | 27.11 | H | C |
| ATOM | 1830 | CD1 | ILE | 51 | 104.073 | 25.593 | 16.389 | 1.00 | 27.11 | H | C |
| ATOM | 1831 | C | ILE | 51 | 107.090 | 23.813 | 13.723 | 1.00 | 20.54 | H | C |
| ATOM | 1832 | O | ILE | 51 | 107.781 | 23.208 | 14.533 | 1.00 | 20.54 | H | O |
| ATOM | 1833 | N | SER | 52 | 107.565 | 24.803 | 12.970 | 1.00 | 28.49 | H | N |
| ATOM | 1834 | CA | SER | 52 | 108.962 | 25.234 | 13.047 | 1.00 | 28.49 | H | C |
| ATOM | 1835 | CB | SER | 52 | 109.356 | 26.018 | 11.797 | 1.00 | 35.37 | H | C |
| ATOM | 1836 | OG | SER | 52 | 108.819 | 27.332 | 11.832 | 1.00 | 35.37 | H | O |
| ATOM | 1837 | C | SER | 52 | 109.236 | 26.105 | 14.256 | 1.00 | 28.49 | H | C |
| ATOM | 1838 | O | SER | 52 | 108.316 | 26.461 | 14.994 | 1.00 | 28.49 | H | O |
| ATOM | 1839 | N | GLY | 53 | 110.509 | 26.452 | 14.451 | 1.00 | 16.74 | H | N |
| ATOM | 1840 | CA | GLY | 53 | 110.864 | 27.295 | 15.568 | 1.00 | 16.74 | H | C |
| ATOM | 1841 | C | GLY | 53 | 110.203 | 28.651 | 15.410 | 1.00 | 16.74 | H | C |
| ATOM | 1842 | O | GLY | 53 | 110.093 | 29.412 | 16.369 | 1.00 | 16.74 | H | O |
| ATOM | 1843 | N | GLY | 54 | 109.746 | 28.939 | 14.192 | 1.00 | 26.55 | H | N |
| ATOM | 1844 | CA | GLY | 54 | 109.120 | 30.218 | 13.907 | 1.00 | 26.55 | H | C |
| ATOM | 1845 | C | GLY | 54 | 107.605 | 30.253 | 13.815 | 1.00 | 26.55 | H | C |
| ATOM | 1846 | O | GLY | 54 | 107.020 | 31.317 | 13.607 | 1.00 | 26.55 | H | O |
| ATOM | 1847 | N | GLY | 55 | 106.953 | 29.105 | 13.948 | 1.00 | 34.83 | H | N |
| ATOM | 1848 | CA | GLY | 55 | 105.505 | 29.105 | 13.889 | 1.00 | 34.83 | H | C |
| ATOM | 1849 | C | GLY | 55 | 104.878 | 28.610 | 12.604 | 1.00 | 34.83 | H | C |
| ATOM | 1850 | O | GLY | 55 | 103.657 | 28.663 | 12.458 | 1.00 | 34.83 | H | O |
| ATOM | 1851 | N | HIS | 56 | 105.683 | 28.149 | 11.655 | 1.00 | 20.17 | H | N |
| ATOM | 1852 | CA | HIS | 56 | 105.091 | 27.643 | 10.426 | 1.00 | 20.17 | H | C |
| ATOM | 1853 | CB | HIS | 56 | 106.117 | 27.522 | 9.302 | 1.00 | 75.35 | H | C |
| ATOM | 1854 | CG | HIS | 56 | 106.829 | 28.797 | 8.996 | 1.00 | 75.35 | H | C |
| ATOM | 1855 | CD2 | HIS | 56 | 106.561 | 29.773 | 8.096 | 1.00 | 75.35 | H | C |
| ATOM | 1856 | ND1 | HIS | 56 | 107.959 | 29.201 | 9.677 | 1.00 | 75.35 | H | N |
| ATOM | 1857 | CE1 | HIS | 56 | 108.356 | 30.370 | 9.209 | 1.00 | 75.35 | H | C |
| ATOM | 1858 | NE2 | HIS | 56 | 107.525 | 30.739 | 8.250 | 1.00 | 75.35 | H | N |
| ATOM | 1859 | C | HIS | 56 | 104.585 | 26.266 | 10.774 | 1.00 | 20.17 | H | C |
| ATOM | 1860 | O | HIS | 56 | 105.309 | 25.465 | 11.350 | 1.00 | 20.17 | H | O |
| ATOM | 1861 | N | THR | 57 | 103.331 | 25.994 | 10.458 | 1.00 | 9.30 | H | N |
| ATOM | 1862 | CA | THR | 57 | 102.793 | 24.676 | 10.728 | 1.00 | 9.30 | H | C |
| ATOM | 1863 | CB | THR | 57 | 101.437 | 24.766 | 11.475 | 1.00 | 25.93 | H | C |
| ATOM | 1864 | OG1 | THR | 57 | 100.483 | 25.493 | 10.691 | 1.00 | 25.93 | H | O |
| ATOM | 1865 | CG2 | THR | 57 | 101.624 | 25.460 | 12.821 | 1.00 | 25.93 | H | C |
| ATOM | 1866 | C | THR | 57 | 102.657 | 23.911 | 9.403 | 1.00 | 9.30 | H | C |
| ATOM | 1867 | O | THR | 57 | 102.437 | 24.503 | 8.348 | 1.00 | 9.30 | H | O |
| ATOM | 1868 | N | TYR | 58 | 102.849 | 22.598 | 9.463 | 1.00 | 10.35 | H | N |
| ATOM | 1869 | CA | TYR | 58 | 102.739 | 21.729 | 8.293 | 1.00 | 10.35 | H | C |
| ATOM | 1870 | CB | TYR | 58 | 104.115 | 21.217 | 7.912 | 1.00 | 22.31 | H | C |
| ATOM | 1871 | CG | TYR | 58 | 105.023 | 22.324 | 7.485 | 1.00 | 22.31 | H | C |
| ATOM | 1872 | CD1 | TYR | 58 | 105.051 | 22.744 | 6.167 | 1.00 | 22.31 | H | C |
| ATOM | 1873 | CE1 | TYR | 58 | 105.871 | 23.765 | 5.768 | 1.00 | 22.31 | H | C |
| ATOM | 1874 | CD2 | TYR | 58 | 105.843 | 22.967 | 8.399 | 1.00 | 22.31 | H | C |
| ATOM | 1875 | CE2 | TYR | 58 | 106.667 | 23.997 | 8.007 | 1.00 | 22.31 | H | C |
| ATOM | 1876 | CZ | TYR | 58 | 106.674 | 24.388 | 6.689 | 1.00 | 22.31 | H | C |
| ATOM | 1877 | OH | TYR | 58 | 107.478 | 25.419 | 6.279 | 1.00 | 22.31 | H | O |
| ATOM | 1878 | C | TYR | 58 | 101.812 | 20.565 | 8.635 | 1.00 | 10.35 | H | C |
| ATOM | 1879 | O | TYR | 58 | 101.699 | 20.164 | 9.801 | 1.00 | 10.35 | H | O |
| ATOM | 1880 | N | TYR | 59 | 101.147 | 20.007 | 7.634 | 1.00 | 15.64 | H | N |
| ATOM | 1881 | CA | TYR | 59 | 100.219 | 18.936 | 7.931 | 1.00 | 15.64 | H | C |
| ATOM | 1882 | CB | TYR | 59 | 98.843 | 19.542 | 8.203 | 1.00 | 11.32 | H | C |
| ATOM | 1883 | CG | TYR | 59 | 98.803 | 20.511 | 9.360 | 1.00 | 11.32 | H | C |
| ATOM | 1884 | CD1 | TYR | 59 | 98.625 | 20.058 | 10.661 | 1.00 | 11.32 | H | C |
| ATOM | 1885 | CE1 | TYR | 59 | 98.540 | 20.942 | 11.731 | 1.00 | 11.32 | H | C |
| ATOM | 1886 | CD2 | TYR | 59 | 98.912 | 21.886 | 9.148 | 1.00 | 11.32 | H | C |
| ATOM | 1887 | CE2 | TYR | 59 | 98.835 | 22.783 | 10.208 | 1.00 | 11.32 | H | C |
| ATOM | 1888 | CZ | TYR | 59 | 98.640 | 22.302 | 11.502 | 1.00 | 11.32 | H | C |
| ATOM | 1889 | OH | TYR | 59 | 98.498 | 23.177 | 12.557 | 1.00 | 11.32 | H | O |
| ATOM | 1890 | C | TYR | 59 | 100.071 | 17.883 | 6.856 | 1.00 | 15.64 | H | C |
| ATOM | 1891 | O | TYR | 59 | 100.150 | 18.182 | 5.666 | 1.00 | 15.64 | H | O |
| ATOM | 1892 | N | LEU | 60 | 99.854 | 16.644 | 7.286 | 1.00 | 33.81 | H | N |
| ATOM | 1893 | CA | LEU | 60 | 99.616 | 15.539 | 6.366 | 1.00 | 33.81 | H | C |
| ATOM | 1894 | CB | LEU | 60 | 99.625 | 14.217 | 7.135 | 1.00 | 13.27 | H | C |
| ATOM | 1895 | CG | LEU | 60 | 99.371 | 12.896 | 6.406 | 1.00 | 13.27 | H | C |
| ATOM | 1896 | CD1 | LEU | 60 | 100.681 | 12.371 | 5.800 | 1.00 | 13.27 | H | C |
| ATOM | 1897 | CD2 | LEU | 60 | 98.804 | 11.882 | 7.397 | 1.00 | 13.27 | H | C |
| ATOM | 1898 | C | LEU | 60 | 98.198 | 15.861 | 5.869 | 1.00 | 33.81 | H | C |

Fig. 19: A-27

| | | | | | | | | | | | |
|---|---|---|---|---|---|---|---|---|---|---|---|
| ATOM | 1899 | O | LEU | 60 | 97.329 | 16.255 | 6.659 | 1.00 | 33.81 | H | O |
| ATOM | 1900 | N | ASP | 61 | 97.962 | 15.710 | 4.573 | 1.00 | 24.56 | H | N |
| ATOM | 1901 | CA | ASP | 61 | 96.659 | 16.028 | 3.991 | 1.00 | 24.56 | H | C |
| ATOM | 1902 | CB | ASP | 61 | 96.639 | 15.579 | 2.530 | 1.00 | 55.35 | H | C |
| ATOM | 1903 | CG | ASP | 61 | 97.719 | 16.260 | 1.708 | 1.00 | 55.35 | H | C |
| ATOM | 1904 | OD1 | ASP | 61 | 98.919 | 16.083 | 2.023 | 1.00 | 55.35 | H | O |
| ATOM | 1905 | OD2 | ASP | 61 | 97.374 | 16.981 | 0.754 | 1.00 | 55.35 | H | O |
| ATOM | 1906 | C | ASP | 61 | 95.436 | 15.495 | 4.731 | 1.00 | 24.56 | H | C |
| ATOM | 1907 | O | ASP | 61 | 94.515 | 16.254 | 5.043 | 1.00 | 24.56 | H | O |
| ATOM | 1908 | N | SER | 62 | 95.432 | 14.198 | 5.024 | 1.00 | 20.78 | H | N |
| ATOM | 1909 | CA | SER | 62 | 94.317 | 13.567 | 5.717 | 1.00 | 20.78 | H | C |
| ATOM | 1910 | CB | SER | 62 | 94.630 | 12.085 | 5.955 | 1.00 | 31.68 | H | C |
| ATOM | 1911 | OG | SER | 62 | 95.820 | 11.902 | 6.708 | 1.00 | 31.68 | H | O |
| ATOM | 1912 | C | SER | 62 | 93.882 | 14.216 | 7.044 | 1.00 | 20.78 | H | C |
| ATOM | 1913 | O | SER | 62 | 92.732 | 14.053 | 7.475 | 1.00 | 20.78 | H | O |
| ATOM | 1914 | N | VAL | 63 | 94.779 | 14.949 | 7.695 | 1.00 | 24.27 | H | N |
| ATOM | 1915 | CA | VAL | 63 | 94.439 | 15.567 | 8.968 | 1.00 | 24.27 | H | C |
| ATOM | 1916 | CB | VAL | 63 | 95.478 | 15.202 | 10.049 | 1.00 | 45.54 | H | C |
| ATOM | 1917 | CG1 | VAL | 63 | 95.642 | 13.698 | 10.110 | 1.00 | 45.54 | H | C |
| ATOM | 1918 | CG2 | VAL | 63 | 96.812 | 15.873 | 9.752 | 1.00 | 45.54 | H | C |
| ATOM | 1919 | C | VAL | 63 | 94.374 | 17.083 | 8.839 | 1.00 | 24.27 | H | C |
| ATOM | 1920 | O | VAL | 63 | 94.112 | 17.812 | 9.823 | 1.00 | 24.27 | H | O |
| ATOM | 1921 | N | LYS | 64 | 94.611 | 17.556 | 7.618 | 1.00 | 38.99 | H | N |
| ATOM | 1922 | CA | LYS | 64 | 94.611 | 18.985 | 7.348 | 1.00 | 38.99 | H | C |
| ATOM | 1923 | CB | LYS | 64 | 94.983 | 19.235 | 5.889 | 1.00 | 39.16 | H | C |
| ATOM | 1924 | CG | LYS | 64 | 95.736 | 20.528 | 5.671 | 1.00 | 39.16 | H | C |
| ATOM | 1925 | CD | LYS | 64 | 96.417 | 20.521 | 4.309 | 1.00 | 39.16 | H | C |
| ATOM | 1926 | CE | LYS | 64 | 97.432 | 19.380 | 4.176 | 1.00 | 39.16 | H | C |
| ATOM | 1927 | NZ | LYS | 64 | 98.011 | 19.296 | 2.803 | 1.00 | 39.16 | H | N |
| ATOM | 1928 | C | LYS | 64 | 93.262 | 19.607 | 7.667 | 1.00 | 38.99 | H | C |
| ATOM | 1929 | O | LYS | 64 | 92.240 | 19.212 | 7.121 | 1.00 | 38.99 | H | O |
| ATOM | 1930 | N | GLY | 65 | 93.263 | 20.577 | 8.567 | 1.00 | 28.42 | H | N |
| ATOM | 1931 | CA | GLY | 65 | 92.019 | 21.219 | 8.918 | 1.00 | 28.42 | H | C |
| ATOM | 1932 | C | GLY | 65 | 91.277 | 20.501 | 10.021 | 1.00 | 28.42 | H | C |
| ATOM | 1933 | O | GLY | 65 | 90.271 | 21.005 | 10.509 | 1.00 | 28.42 | H | O |
| ATOM | 1934 | N | ARG | 66 | 91.751 | 19.324 | 10.414 | 1.00 | 48.07 | H | N |
| ATOM | 1935 | CA | ARG | 66 | 91.098 | 18.588 | 11.488 | 1.00 | 48.07 | H | C |
| ATOM | 1936 | CB | ARG | 66 | 90.783 | 17.154 | 11.064 | 1.00 | 36.61 | H | C |
| ATOM | 1937 | CG | ARG | 66 | 89.845 | 17.052 | 9.887 | 1.00 | 36.61 | H | C |
| ATOM | 1938 | CD | ARG | 66 | 89.484 | 15.608 | 9.571 | 1.00 | 36.61 | H | C |
| ATOM | 1939 | NE | ARG | 66 | 90.654 | 14.750 | 9.346 | 1.00 | 36.61 | H | N |
| ATOM | 1940 | CZ | ARG | 66 | 91.133 | 13.877 | 10.236 | 1.00 | 36.61 | H | C |
| ATOM | 1941 | NH1 | ARG | 66 | 90.545 | 13.739 | 11.421 | 1.00 | 36.61 | H | N |
| ATOM | 1942 | NH2 | ARG | 66 | 92.203 | 13.144 | 9.944 | 1.00 | 36.61 | H | N |
| ATOM | 1943 | C | ARG | 66 | 92.018 | 18.568 | 12.687 | 1.00 | 48.07 | H | C |
| ATOM | 1944 | O | ARG | 66 | 91.584 | 18.312 | 13.808 | 1.00 | 48.07 | H | O |
| ATOM | 1945 | N | PHE | 67 | 93.296 | 18.839 | 12.438 | 1.00 | 31.81 | H | N |
| ATOM | 1946 | CA | PHE | 67 | 94.304 | 18.854 | 13.490 | 1.00 | 31.81 | H | C |
| ATOM | 1947 | CB | PHE | 67 | 95.372 | 17.802 | 13.211 | 1.00 | 34.94 | H | C |
| ATOM | 1948 | CG | PHE | 67 | 94.937 | 16.394 | 13.444 | 1.00 | 34.94 | H | C |
| ATOM | 1949 | CD1 | PHE | 67 | 93.763 | 15.907 | 12.902 | 1.00 | 34.94 | H | C |
| ATOM | 1950 | CD2 | PHE | 67 | 95.748 | 15.530 | 14.158 | 1.00 | 34.94 | H | C |
| ATOM | 1951 | CE1 | PHE | 67 | 93.400 | 14.564 | 13.063 | 1.00 | 34.94 | H | C |
| ATOM | 1952 | CE2 | PHE | 67 | 95.400 | 14.192 | 14.326 | 1.00 | 34.94 | H | C |
| ATOM | 1953 | CZ | PHE | 67 | 94.222 | 13.706 | 13.777 | 1.00 | 34.94 | H | C |
| ATOM | 1954 | C | PHE | 67 | 94.989 | 20.209 | 13.520 | 1.00 | 31.81 | H | C |
| ATOM | 1955 | O | PHE | 67 | 95.054 | 20.899 | 12.501 | 1.00 | 31.81 | H | O |
| ATOM | 1956 | N | THR | 68 | 95.511 | 20.587 | 14.683 | 1.00 | 27.20 | H | N |
| ATOM | 1957 | CA | THR | 68 | 96.233 | 21.851 | 14.804 | 1.00 | 27.20 | H | C |
| ATOM | 1958 | CB | THR | 68 | 95.344 | 22.998 | 15.384 | 1.00 | 14.56 | H | C |
| ATOM | 1959 | OG1 | THR | 68 | 94.400 | 23.434 | 14.399 | 1.00 | 14.56 | H | O |
| ATOM | 1960 | CG2 | THR | 68 | 96.196 | 24.192 | 15.758 | 1.00 | 14.56 | H | C |
| ATOM | 1961 | C | THR | 68 | 97.466 | 21.680 | 15.689 | 1.00 | 27.20 | H | C |
| ATOM | 1962 | O | THR | 68 | 97.355 | 21.393 | 16.882 | 1.00 | 27.20 | H | O |
| ATOM | 1963 | N | ILE | 69 | 98.643 | 21.847 | 15.099 | 1.00 | 22.74 | H | N |
| ATOM | 1964 | CA | ILE | 69 | 99.869 | 21.718 | 15.861 | 1.00 | 22.74 | H | C |
| ATOM | 1965 | CB | ILE | 69 | 100.991 | 21.084 | 15.020 | 1.00 | 13.28 | H | C |
| ATOM | 1966 | CG2 | ILE | 69 | 101.417 | 22.022 | 13.933 | 1.00 | 13.28 | H | C |
| ATOM | 1967 | CG1 | ILE | 69 | 102.188 | 20.736 | 15.908 | 1.00 | 13.28 | H | C |
| ATOM | 1968 | CD1 | ILE | 69 | 103.226 | 19.848 | 15.206 | 1.00 | 13.28 | H | C |
| ATOM | 1969 | C | ILE | 69 | 100.287 | 23.096 | 16.336 | 1.00 | 22.74 | H | C |
| ATOM | 1970 | O | ILE | 69 | 100.282 | 24.065 | 15.578 | 1.00 | 22.74 | H | O |
| ATOM | 1971 | N | SER | 70 | 100.632 | 23.188 | 17.608 | 1.00 | 15.22 | H | N |

Fig. 19: A-28

```
ATOM   1972  CA   SER  70   101.032  24.460  18.183  1.00  15.22  H  C
ATOM   1973  CB   SER  70    99.834  25.147  18.851  1.00   3.12  H  C
ATOM   1974  OG   SER  70    99.588  24.606  20.144  1.00   3.12  H  O
ATOM   1975  C    SER  70   102.088  24.203  19.235  1.00  15.22  H  C
ATOM   1976  O    SER  70   102.392  23.053  19.557  1.00  15.22  H  O
ATOM   1977  N    ARG  71   102.636  25.281  19.780  1.00  42.13  H  N
ATOM   1978  CA   ARG  71   103.640  25.158  20.813  1.00  42.13  H  C
ATOM   1979  CB   ARG  71   105.039  25.089  20.210  1.00  12.52  H  C
ATOM   1980  CG   ARG  71   105.417  26.296  19.388  1.00  12.52  H  C
ATOM   1981  CD   ARG  71   106.906  26.507  19.436  1.00  12.52  H  C
ATOM   1982  NE   ARG  71   107.644  25.627  18.540  1.00  12.52  H  N
ATOM   1983  CZ   ARG  71   108.844  25.114  18.816  1.00  12.52  H  C
ATOM   1984  NH1  ARG  71   109.444  25.380  19.970  1.00  12.52  H  N
ATOM   1985  NH2  ARG  71   109.456  24.354  17.924  1.00  12.52  H  N
ATOM   1986  C    ARG  71   103.568  26.341  21.739  1.00  42.13  H  C
ATOM   1987  O    ARG  71   103.115  27.416  21.352  1.00  42.13  H  O
ATOM   1988  N    ASP  72   104.003  26.131  22.973  1.00  26.38  H  N
ATOM   1989  CA   ASP  72   104.034  27.197  23.954  1.00  26.38  H  C
ATOM   1990  CB   ASP  72   102.949  27.026  25.007  1.00  47.03  H  C
ATOM   1991  CG   ASP  72   103.003  28.108  26.050  1.00  47.03  H  C
ATOM   1992  OD1  ASP  72   102.157  28.112  26.964  1.00  47.03  H  O
ATOM   1993  OD2  ASP  72   103.907  28.959  25.953  1.00  47.03  H  O
ATOM   1994  C    ASP  72   105.402  27.159  24.607  1.00  26.38  H  C
ATOM   1995  O    ASP  72   105.618  26.508  25.633  1.00  26.38  H  O
ATOM   1996  N    ASN  73   106.325  27.868  23.979  1.00  50.64  H  N
ATOM   1997  CA   ASN  73   107.692  27.939  24.441  1.00  50.64  H  C
ATOM   1998  CB   ASN  73   108.522  28.747  23.446  1.00  30.24  H  C
ATOM   1999  CG   ASN  73   108.584  28.091  22.086  1.00  30.24  H  C
ATOM   2000  OD1  ASN  73   109.170  28.625  21.149  1.00  30.24  H  O
ATOM   2001  ND2  ASN  73   107.984  26.917  21.974  1.00  30.24  H  N
ATOM   2002  C    ASN  73   107.827  28.516  25.841  1.00  50.64  H  C
ATOM   2003  O    ASN  73   108.898  28.436  26.438  1.00  50.64  H  O
ATOM   2004  N    SER  74   106.758  29.097  26.376  1.00  33.75  H  N
ATOM   2005  CA   SER  74   106.848  29.644  27.723  1.00  33.75  H  C
ATOM   2006  CB   SER  74   105.593  30.429  28.093  1.00  48.57  H  C
ATOM   2007  OG   SER  74   104.534  29.556  28.444  1.00  48.57  H  O
ATOM   2008  C    SER  74   106.979  28.456  28.653  1.00  33.75  H  C
ATOM   2009  O    SER  74   107.681  28.530  29.660  1.00  33.75  H  O
ATOM   2010  N    LYS  75   106.312  27.354  28.302  1.00  39.57  H  N
ATOM   2011  CA   LYS  75   106.352  26.142  29.119  1.00  39.57  H  C
ATOM   2012  CB   LYS  75   104.973  25.889  29.732  1.00  42.48  H  C
ATOM   2013  CG   LYS  75   103.842  25.924  28.731  1.00  42.48  H  C
ATOM   2014  CD   LYS  75   102.482  25.985  29.418  1.00  42.48  H  C
ATOM   2015  CE   LYS  75   102.156  27.393  29.918  1.00  42.48  H  C
ATOM   2016  NZ   LYS  75   103.090  27.928  30.963  1.00  42.48  H  N
ATOM   2017  C    LYS  75   106.843  24.894  28.380  1.00  39.57  H  C
ATOM   2018  O    LYS  75   106.497  23.767  28.744  1.00  39.57  H  O
ATOM   2019  N    ASN  76   107.660  25.110  27.353  1.00  44.84  H  N
ATOM   2020  CA   ASN  76   108.245  24.043  26.539  1.00  44.84  H  C
ATOM   2021  CB   ASN  76   109.572  23.608  27.139  1.00  31.30  H  C
ATOM   2022  CG   ASN  76   110.528  24.766  27.312  1.00  31.30  H  C
ATOM   2023  OD1  ASN  76   111.666  24.593  27.739  1.00  31.30  H  O
ATOM   2024  ND2  ASN  76   110.067  25.965  26.979  1.00  31.30  H  N
ATOM   2025  C    ASN  76   107.362  22.827  26.322  1.00  44.84  H  C
ATOM   2026  O    ASN  76   107.793  21.681  26.479  1.00  44.84  H  O
ATOM   2027  N    THR  77   106.121  23.090  25.941  1.00  30.42  H  N
ATOM   2028  CA   THR  77   105.181  22.032  25.686  1.00  30.42  H  C
ATOM   2029  CB   THR  77   103.989  22.131  26.628  1.00  46.49  H  C
ATOM   2030  OG1  THR  77   104.446  21.977  27.974  1.00  46.49  H  O
ATOM   2031  CG2  THR  77   102.975  21.045  26.319  1.00  46.49  H  C
ATOM   2032  C    THR  77   104.708  22.182  24.254  1.00  30.42  H  C
ATOM   2033  O    THR  77   104.488  23.291  23.786  1.00  30.42  H  O
ATOM   2034  N    LEU  78   104.583  21.056  23.563  1.00  20.66  H  N
ATOM   2035  CA   LEU  78   104.135  21.017  22.185  1.00  20.66  H  C
ATOM   2036  CB   LEU  78   104.978  20.024  21.394  1.00  19.59  H  C
ATOM   2037  CG   LEU  78   104.550  19.758  19.953  1.00  19.59  H  C
ATOM   2038  CD1  LEU  78   104.575  21.055  19.166  1.00  19.59  H  C
ATOM   2039  CD2  LEU  78   105.470  18.731  19.320  1.00  19.59  H  C
ATOM   2040  C    LEU  78   102.716  20.520  22.298  1.00  20.66  H  C
ATOM   2041  O    LEU  78   102.368  19.921  23.312  1.00  20.66  H  O
ATOM   2042  N    TYR  79   101.902  20.753  21.271  1.00  30.75  H  N
ATOM   2043  CA   TYR  79   100.498  20.333  21.294  1.00  30.75  H  C
ATOM   2044  CB   TYR  79    99.591  21.494  21.728  1.00  47.95  H  C
```

Fig. 19: A-29

```
ATOM   2045  CG   TYR  79      99.809  22.008  23.119  1.00  47.95      H  C
ATOM   2046  CD1  TYR  79      99.166  21.430  24.205  1.00  47.95      H  C
ATOM   2047  CE1  TYR  79      99.357  21.916  25.491  1.00  47.95      H  C
ATOM   2048  CD2  TYR  79     100.655  23.085  23.349  1.00  47.95      H  C
ATOM   2049  CE2  TYR  79     100.857  23.579  24.628  1.00  47.95      H  C
ATOM   2050  CZ   TYR  79     100.204  22.991  25.695  1.00  47.95      H  C
ATOM   2051  OH   TYR  79     100.404  23.493  26.958  1.00  47.95      H  O
ATOM   2052  C    TYR  79      99.966  19.863  19.950  1.00  30.75      H  C
ATOM   2053  O    TYR  79     100.418  20.316  18.898  1.00  30.75      H  O
ATOM   2054  N    LEU  80      98.981  18.969  20.003  1.00  19.83      H  N
ATOM   2055  CA   LEU  80      98.308  18.472  18.811  1.00  19.83      H  C
ATOM   2056  CB   LEU  80      98.776  17.070  18.397  1.00   5.08      H  C
ATOM   2057  CG   LEU  80      98.132  16.598  17.076  1.00   5.08      H  C
ATOM   2058  CD1  LEU  80      98.706  17.386  15.914  1.00   5.08      H  C
ATOM   2059  CD2  LEU  80      98.352  15.111  16.874  1.00   5.08      H  C
ATOM   2060  C    LEU  80      96.838  18.411  19.182  1.00  19.83      H  C
ATOM   2061  O    LEU  80      96.398  17.503  19.879  1.00  19.83      H  O
ATOM   2062  N    GLN  81      96.091  19.412  18.742  1.00  24.43      H  N
ATOM   2063  CA   GLN  81      94.671  19.463  19.004  1.00  24.43      H  C
ATOM   2064  CB   GLN  81      94.169  20.911  18.966  1.00  60.73      H  C
ATOM   2065  CG   GLN  81      92.710  21.093  19.399  1.00  60.73      H  C
ATOM   2066  CD   GLN  81      92.505  20.974  20.911  1.00  60.73      H  C
ATOM   2067  OE1  GLN  81      92.981  21.810  21.691  1.00  60.73      H  O
ATOM   2068  NE2  GLN  81      91.787  19.935  21.328  1.00  60.73      H  N
ATOM   2069  C    GLN  81      94.064  18.672  17.867  1.00  24.43      H  C
ATOM   2070  O    GLN  81      94.376  18.921  16.698  1.00  24.43      H  O
ATOM   2071  N    MET  82      93.205  17.718  18.210  1.00  35.69      H  N
ATOM   2072  CA   MET  82      92.559  16.878  17.211  1.00  35.69      H  C
ATOM   2073  CB   MET  82      92.989  15.424  17.383  1.00  24.95      H  C
ATOM   2074  CG   MET  82      94.481  15.209  17.363  1.00  24.95      H  C
ATOM   2075  SD   MET  82      94.896  13.491  17.609  1.00  24.95      H  S
ATOM   2076  CE   MET  82      94.985  13.427  19.373  1.00  24.95      H  C
ATOM   2077  C    MET  82      91.051  16.957  17.316  1.00  35.69      H  C
ATOM   2078  O    MET  82      90.479  16.599  18.338  1.00  35.69      H  O
ATOM   2079  N    ASN  83      90.414  17.416  16.247  1.00  28.29      H  N
ATOM   2080  CA   ASN  83      88.968  17.536  16.204  1.00  28.29      H  C
ATOM   2081  CB   ASN  83      88.550  18.989  15.985  1.00  66.28      H  C
ATOM   2082  CG   ASN  83      89.274  19.943  16.899  1.00  66.28      H  C
ATOM   2083  OD1  ASN  83      89.213  19.819  18.121  1.00  66.28      H  O
ATOM   2084  ND2  ASN  83      89.970  20.910  16.309  1.00  66.28      H  N
ATOM   2085  C    ASN  83      88.502  16.728  15.025  1.00  28.29      H  C
ATOM   2086  O    ASN  83      89.306  16.348  14.185  1.00  28.29      H  O
ATOM   2087  N    SER  84      87.199  16.486  14.954  1.00  57.41      H  N
ATOM   2088  CA   SER  84      86.618  15.739  13.847  1.00  57.41      H  C
ATOM   2089  CB   SER  84      86.648  16.584  12.574  1.00  29.12      H  C
ATOM   2090  OG   SER  84      86.027  17.836  12.786  1.00  29.12      H  O
ATOM   2091  C    SER  84      87.374  14.450  13.603  1.00  57.41      H  C
ATOM   2092  O    SER  84      87.642  14.085  12.456  1.00  57.41      H  O
ATOM   2093  N    LEU  85      87.725  13.769  14.687  1.00  32.34      H  N
ATOM   2094  CA   LEU  85      88.452  12.513  14.595  1.00  32.34      H  C
ATOM   2095  CB   LEU  85      88.818  12.009  15.990  1.00  15.22      H  C
ATOM   2096  CG   LEU  85      89.913  12.880  16.600  1.00  15.22      H  C
ATOM   2097  CD1  LEU  85      90.082  12.594  18.078  1.00  15.22      H  C
ATOM   2098  CD2  LEU  85      91.204  12.636  15.828  1.00  15.22      H  C
ATOM   2099  C    LEU  85      87.641  11.460  13.877  1.00  32.34      H  C
ATOM   2100  O    LEU  85      86.434  11.369  14.050  1.00  32.34      H  O
ATOM   2101  N    ARG  86      88.319  10.680  13.049  1.00  24.27      H  N
ATOM   2102  CA   ARG  86      87.686   9.604  12.316  1.00  24.27      H  C
ATOM   2103  CB   ARG  86      87.858   9.801  10.815  1.00  51.87      H  C
ATOM   2104  CG   ARG  86      87.146  11.026  10.286  1.00  51.87      H  C
ATOM   2105  CD   ARG  86      86.864  10.887   8.808  1.00  51.87      H  C
ATOM   2106  NE   ARG  86      87.237  12.088   8.076  1.00  51.87      H  N
ATOM   2107  CZ   ARG  86      88.470  12.581   8.043  1.00  51.87      H  C
ATOM   2108  NH1  ARG  86      89.444  11.967   8.707  1.00  51.87      H  N
ATOM   2109  NH2  ARG  86      88.733  13.676   7.334  1.00  51.87      H  N
ATOM   2110  C    ARG  86      88.387   8.343  12.769  1.00  24.27      H  C
ATOM   2111  O    ARG  86      89.367   8.416  13.514  1.00  24.27      H  O
ATOM   2112  N    ALA  87      87.894   7.191  12.335  1.00  40.98      H  N
ATOM   2113  CA   ALA  87      88.499   5.928  12.733  1.00  40.98      H  C
ATOM   2114  CB   ALA  87      87.678   4.763  12.196  1.00  28.01      H  C
ATOM   2115  C    ALA  87      89.937   5.833  12.242  1.00  40.98      H  C
ATOM   2116  O    ALA  87      90.824   5.425  12.989  1.00  40.98      H  O
ATOM   2117  N    GLU  88      90.169   6.222  10.993  1.00  32.24      H  N
```

Fig. 19: A-30

| | | | | | | | | | | |
|---|---|---|---|---|---|---|---|---|---|---|
| ATOM | 2118 | CA | GLU | 88 | 91.511 | 6.157 | 10.433 | 1.00 | 32.24 | H C |
| ATOM | 2119 | CB | GLU | 88 | 91.583 | 6.890 | 9.094 | 1.00 | 72.38 | H C |
| ATOM | 2120 | CG | GLU | 88 | 90.432 | 6.614 | 8.169 | 1.00 | 72.38 | H C |
| ATOM | 2121 | CD | GLU | 88 | 89.327 | 7.623 | 8.336 | 1.00 | 72.38 | H C |
| ATOM | 2122 | OE1 | GLU | 88 | 89.529 | 8.792 | 7.937 | 1.00 | 72.38 | H O |
| ATOM | 2123 | OE2 | GLU | 88 | 88.265 | 7.246 | 8.874 | 1.00 | 72.38 | H O |
| ATOM | 2124 | C | GLU | 88 | 92.529 | 6.780 | 11.372 | 1.00 | 32.24 | H C |
| ATOM | 2125 | O | GLU | 88 | 93.691 | 6.370 | 11.417 | 1.00 | 32.24 | H O |
| ATOM | 2126 | N | ASP | 89 | 92.080 | 7.772 | 12.128 | 1.00 | 18.63 | H N |
| ATOM | 2127 | CA | ASP | 89 | 92.935 | 8.497 | 13.054 | 1.00 | 18.63 | H C |
| ATOM | 2128 | CB | ASP | 89 | 92.212 | 9.764 | 13.507 | 1.00 | 29.25 | H C |
| ATOM | 2129 | CG | ASP | 89 | 92.073 | 10.775 | 12.392 | 1.00 | 29.25 | H C |
| ATOM | 2130 | OD1 | ASP | 89 | 91.297 | 11.732 | 12.553 | 1.00 | 29.25 | H O |
| ATOM | 2131 | OD2 | ASP | 89 | 92.748 | 10.622 | 11.355 | 1.00 | 29.25 | H O |
| ATOM | 2132 | C | ASP | 89 | 93.434 | 7.724 | 14.268 | 1.00 | 18.63 | H C |
| ATOM | 2133 | O | ASP | 89 | 94.391 | 8.149 | 14.922 | 1.00 | 18.63 | H O |
| ATOM | 2134 | N | THR | 90 | 92.817 | 6.588 | 14.575 | 1.00 | 29.66 | H N |
| ATOM | 2135 | CA | THR | 90 | 93.261 | 5.845 | 15.749 | 1.00 | 29.66 | H C |
| ATOM | 2136 | CB | THR | 90 | 92.303 | 4.668 | 16.113 | 1.00 | 30.61 | H C |
| ATOM | 2137 | OG1 | THR | 90 | 92.601 | 3.537 | 15.293 | 1.00 | 30.61 | H O |
| ATOM | 2138 | CG2 | THR | 90 | 90.828 | 5.072 | 15.903 | 1.00 | 30.61 | H C |
| ATOM | 2139 | C | THR | 90 | 94.664 | 5.311 | 15.527 | 1.00 | 29.66 | H C |
| ATOM | 2140 | O | THR | 90 | 94.961 | 4.727 | 14.492 | 1.00 | 29.66 | H O |
| ATOM | 2141 | N | ALA | 91 | 95.532 | 5.553 | 16.499 | 1.00 | 11.25 | H N |
| ATOM | 2142 | CA | ALA | 91 | 96.918 | 5.094 | 16.451 | 1.00 | 11.25 | H C |
| ATOM | 2143 | CB | ALA | 91 | 97.629 | 5.690 | 15.259 | 1.00 | 1.87 | H C |
| ATOM | 2144 | C | ALA | 91 | 97.611 | 5.536 | 17.729 | 1.00 | 11.25 | H C |
| ATOM | 2145 | O | ALA | 91 | 96.972 | 6.044 | 18.646 | 1.00 | 11.25 | H O |
| ATOM | 2146 | N | VAL | 92 | 98.915 | 5.312 | 17.797 | 1.00 | 22.44 | H N |
| ATOM | 2147 | CA | VAL | 92 | 99.694 | 5.755 | 18.947 | 1.00 | 22.44 | H C |
| ATOM | 2148 | CB | VAL | 92 | 100.654 | 4.665 | 19.465 | 1.00 | 21.44 | H C |
| ATOM | 2149 | CG1 | VAL | 92 | 101.306 | 3.966 | 18.298 | 1.00 | 21.44 | H C |
| ATOM | 2150 | CG2 | VAL | 92 | 101.716 | 5.284 | 20.346 | 1.00 | 21.44 | H C |
| ATOM | 2151 | C | VAL | 92 | 100.482 | 6.913 | 18.363 | 1.00 | 22.44 | H C |
| ATOM | 2152 | O | VAL | 92 | 101.107 | 6.771 | 17.310 | 1.00 | 22.44 | H O |
| ATOM | 2153 | N | TYR | 93 | 100.413 | 8.066 | 19.019 | 1.00 | 21.58 | H N |
| ATOM | 2154 | CA | TYR | 93 | 101.105 | 9.261 | 18.538 | 1.00 | 21.58 | H C |
| ATOM | 2155 | CB | TYR | 93 | 100.161 | 10.470 | 18.585 | 1.00 | 12.38 | H C |
| ATOM | 2156 | CG | TYR | 93 | 99.000 | 10.385 | 17.624 | 1.00 | 12.38 | H C |
| ATOM | 2157 | CD1 | TYR | 93 | 98.023 | 9.399 | 17.759 | 1.00 | 12.38 | H C |
| ATOM | 2158 | CE1 | TYR | 93 | 96.975 | 9.287 | 16.836 | 1.00 | 12.38 | H C |
| ATOM | 2159 | CD2 | TYR | 93 | 98.899 | 11.264 | 16.553 | 1.00 | 12.38 | H C |
| ATOM | 2160 | CE2 | TYR | 93 | 97.863 | 11.165 | 15.634 | 1.00 | 12.38 | H C |
| ATOM | 2161 | CZ | TYR | 93 | 96.908 | 10.173 | 15.773 | 1.00 | 12.38 | H C |
| ATOM | 2162 | OH | TYR | 93 | 95.915 | 10.043 | 14.827 | 1.00 | 12.38 | H O |
| ATOM | 2163 | C | TYR | 93 | 102.384 | 9.577 | 19.312 | 1.00 | 21.58 | H C |
| ATOM | 2164 | O | TYR | 93 | 102.466 | 9.401 | 20.531 | 1.00 | 21.58 | H O |
| ATOM | 2165 | N | TYR | 94 | 103.381 | 10.049 | 18.579 | 1.00 | 19.04 | H N |
| ATOM | 2166 | CA | TYR | 94 | 104.668 | 10.409 | 19.151 | 1.00 | 19.04 | H C |
| ATOM | 2167 | CB | TYR | 94 | 105.789 | 9.576 | 18.533 | 1.00 | 29.80 | H C |
| ATOM | 2168 | CG | TYR | 94 | 105.548 | 8.101 | 18.431 | 1.00 | 29.80 | H C |
| ATOM | 2169 | CD1 | TYR | 94 | 105.948 | 7.237 | 19.454 | 1.00 | 29.80 | H C |
| ATOM | 2170 | CE1 | TYR | 94 | 105.768 | 5.876 | 19.345 | 1.00 | 29.80 | H C |
| ATOM | 2171 | CD2 | TYR | 94 | 104.958 | 7.563 | 17.298 | 1.00 | 29.80 | H C |
| ATOM | 2172 | CE2 | TYR | 94 | 104.773 | 6.204 | 17.177 | 1.00 | 29.80 | H C |
| ATOM | 2173 | CZ | TYR | 94 | 105.179 | 5.363 | 18.202 | 1.00 | 29.80 | H C |
| ATOM | 2174 | OH | TYR | 94 | 104.996 | 4.007 | 18.071 | 1.00 | 29.80 | H O |
| ATOM | 2175 | C | TYR | 94 | 104.991 | 11.853 | 18.805 | 1.00 | 19.04 | H C |
| ATOM | 2176 | O | TYR | 94 | 104.867 | 12.244 | 17.642 | 1.00 | 19.04 | H O |
| ATOM | 2177 | N | CYS | 95 | 105.383 | 12.654 | 19.791 | 1.00 | 25.07 | H N |
| ATOM | 2178 | CA | CYS | 95 | 105.806 | 14.000 | 19.466 | 1.00 | 25.07 | H C |
| ATOM | 2179 | C | CYS | 95 | 107.228 | 13.689 | 19.096 | 1.00 | 25.07 | H C |
| ATOM | 2180 | O | CYS | 95 | 107.716 | 12.584 | 19.342 | 1.00 | 25.07 | H O |
| ATOM | 2181 | CB | CYS | 95 | 105.784 | 14.942 | 20.647 | 1.00 | 46.53 | H C |
| ATOM | 2182 | SG | CYS | 95 | 106.112 | 14.206 | 22.267 | 1.00 | 46.53 | H S |
| ATOM | 2183 | N | THR | 96 | 107.931 | 14.657 | 18.549 | 1.00 | 31.61 | H N |
| ATOM | 2184 | CA | THR | 96 | 109.253 | 14.331 | 18.115 | 1.00 | 31.61 | H C |
| ATOM | 2185 | CB | THR | 96 | 109.088 | 13.445 | 16.861 | 1.00 | 32.15 | H C |
| ATOM | 2186 | OG1 | THR | 96 | 110.331 | 12.862 | 16.494 | 1.00 | 32.15 | H O |
| ATOM | 2187 | CG2 | THR | 96 | 108.554 | 14.260 | 15.708 | 1.00 | 32.15 | H C |
| ATOM | 2188 | C | THR | 96 | 110.045 | 15.577 | 17.830 | 1.00 | 31.61 | H C |
| ATOM | 2189 | O | THR | 96 | 109.530 | 16.548 | 17.260 | 1.00 | 31.61 | H O |
| ATOM | 2190 | N | ARG | 97 | 111.292 | 15.610 | 18.270 | 1.00 | 26.02 | H N |

Fig. 19: A-31

```
ATOM   2191  CA   ARG   97    112.135  16.759  17.996  1.00   26.02   H  C
ATOM   2192  CB   ARG   97    113.220  16.959  19.053  1.00   22.53   H  C
ATOM   2193  CG   ARG   97    114.076  18.184  18.766  1.00   22.53   H  C
ATOM   2194  CD   ARG   97    115.204  18.345  19.764  1.00   22.53   H  C
ATOM   2195  NE   ARG   97    116.357  17.532  19.411  1.00   22.53   H  N
ATOM   2196  CZ   ARG   97    117.494  17.509  20.099  1.00   22.53   H  C
ATOM   2197  NH1  ARG   97    117.635  18.257  21.183  1.00   22.53   H  N
ATOM   2198  NH2  ARG   97    118.494  16.739  19.704  1.00   22.53   H  N
ATOM   2199  C    ARG   97    112.799  16.473  16.665  1.00   26.02   H  C
ATOM   2200  O    ARG   97    113.145  15.322  16.357  1.00   26.02   H  O
ATOM   2201  N    GLY   98    112.980  17.528  15.882  1.00   13.43   H  N
ATOM   2202  CA   GLY   98    113.586  17.367  14.582  1.00   13.43   H  C
ATOM   2203  C    GLY   98    114.947  17.995  14.496  1.00   13.43   H  C
ATOM   2204  O    GLY   98    115.308  18.850  15.281  1.00   13.43   H  O
ATOM   2205  N    PHE   99    115.719  17.537  13.534  1.00   20.13   H  N
ATOM   2206  CA   PHE   99    117.038  18.065  13.315  1.00   20.13   H  C
ATOM   2207  CB   PHE   99    118.018  16.902  13.211  1.00   25.23   H  C
ATOM   2208  CG   PHE   99    119.338  17.271  12.628  1.00   25.23   H  C
ATOM   2209  CD1  PHE   99    119.587  17.079  11.279  1.00   25.23   H  C
ATOM   2210  CD2  PHE   99    120.326  17.828  13.420  1.00   25.23   H  C
ATOM   2211  CE1  PHE   99    120.804  17.437  10.721  1.00   25.23   H  C
ATOM   2212  CE2  PHE   99    121.543  18.191  12.875  1.00   25.23   H  C
ATOM   2213  CZ   PHE   99    121.784  17.994  11.517  1.00   25.23   H  C
ATOM   2214  C    PHE   99    116.887  18.819  11.996  1.00   20.13   H  C
ATOM   2215  O    PHE   99    115.950  18.551  11.241  1.00   20.13   H  O
ATOM   2216  N    GLY  100    117.768  19.774  11.719  1.00   15.08   H  N
ATOM   2217  CA   GLY  100    117.655  20.513  10.469  1.00   15.08   H  C
ATOM   2218  C    GLY  100    116.285  21.139  10.274  1.00   15.08   H  C
ATOM   2219  O    GLY  100    115.682  21.636  11.216  1.00   15.08   H  O
ATOM   2220  N    ASP  101    115.779  21.128   9.050  1.00    7.89   H  N
ATOM   2221  CA   ASP  101    114.462  21.692   8.812  1.00    7.89   H  C
ATOM   2222  CB   ASP  101    114.195  21.848   7.302  1.00   13.13   H  C
ATOM   2223  CG   ASP  101    115.328  22.587   6.564  1.00   13.13   H  C
ATOM   2224  OD1  ASP  101    115.921  23.558   7.105  1.00   13.13   H  O
ATOM   2225  OD2  ASP  101    115.616  22.190   5.417  1.00   13.13   H  O
ATOM   2226  C    ASP  101    113.406  20.785   9.460  1.00    7.89   H  C
ATOM   2227  O    ASP  101    112.222  20.844   9.124  1.00    7.89   H  O
ATOM   2228  N    GLY  102    113.854  19.924  10.374  1.00   22.31   H  N
ATOM   2229  CA   GLY  102    112.952  19.043  11.100  1.00   22.31   H  C
ATOM   2230  C    GLY  102    112.588  17.674  10.562  1.00   22.31   H  C
ATOM   2231  O    GLY  102    111.927  16.915  11.263  1.00   22.31   H  O
ATOM   2232  N    GLY  103    113.001  17.347   9.343  1.00   25.09   H  N
ATOM   2233  CA   GLY  103    112.662  16.054   8.772  1.00   25.09   H  C
ATOM   2234  C    GLY  103    113.342  14.844   9.403  1.00   25.09   H  C
ATOM   2235  O    GLY  103    112.948  13.703   9.156  1.00   25.09   H  O
ATOM   2236  N    TYR  104    114.376  15.071  10.202  1.00   22.52   H  N
ATOM   2237  CA   TYR  104    115.070  13.961  10.844  1.00   22.52   H  C
ATOM   2238  CB   TYR  104    116.578  14.114  10.715  1.00   15.87   H  C
ATOM   2239  CG   TYR  104    117.342  13.175  11.599  1.00   15.87   H  C
ATOM   2240  CD1  TYR  104    118.507  13.600  12.233  1.00   15.87   H  C
ATOM   2241  CE1  TYR  104    119.198  12.776  13.100  1.00   15.87   H  C
ATOM   2242  CD2  TYR  104    116.884  11.880  11.844  1.00   15.87   H  C
ATOM   2243  CE2  TYR  104    117.575  11.034  12.713  1.00   15.87   H  C
ATOM   2244  CZ   TYR  104    118.734  11.498  13.343  1.00   15.87   H  C
ATOM   2245  OH   TYR  104    119.417  10.713  14.239  1.00   15.87   H  O
ATOM   2246  C    TYR  104    114.665  13.991  12.296  1.00   22.52   H  C
ATOM   2247  O    TYR  104    114.933  14.956  13.001  1.00   22.52   H  O
ATOM   2248  N    PHE  105    114.036  12.909  12.733  1.00   16.00   H  N
ATOM   2249  CA   PHE  105    113.501  12.806  14.073  1.00   16.00   H  C
ATOM   2250  CB   PHE  105    112.292  11.890  14.031  1.00   16.01   H  C
ATOM   2251  CG   PHE  105    111.269  12.327  13.020  1.00   16.01   H  C
ATOM   2252  CD1  PHE  105    110.782  13.627  13.038  1.00   16.01   H  C
ATOM   2253  CD2  PHE  105    110.827  11.459  12.023  1.00   16.01   H  C
ATOM   2254  CE1  PHE  105    109.880  14.059  12.091  1.00   16.01   H  C
ATOM   2255  CE2  PHE  105    109.918  11.885  11.067  1.00   16.01   H  C
ATOM   2256  CZ   PHE  105    109.443  13.190  11.101  1.00   16.01   H  C
ATOM   2257  C    PHE  105    114.442  12.433  15.179  1.00   16.00   H  C
ATOM   2258  O    PHE  105    114.543  11.283  15.595  1.00   16.00   H  O
ATOM   2259  N    ASP  106    115.105  13.481  15.642  1.00   29.40   H  N
ATOM   2260  CA   ASP  106    116.089  13.519  16.714  1.00   29.40   H  C
ATOM   2261  CB   ASP  106    116.251  14.976  17.117  1.00   39.43   H  C
ATOM   2262  CG   ASP  106    117.656  15.400  17.133  1.00   39.43   H  C
ATOM   2263  OD1  ASP  106    118.492  14.528  17.433  1.00   39.43   H  O
```

Fig. 19: A-32

| ATOM | 2264 | OD2 | ASP | 106 | 117.922 | 16.591 | 16.859 | 1.00 | 39.43 | H | O |
|------|------|-----|-----|-----|---------|--------|--------|------|-------|---|---|
| ATOM | 2265 | C | ASP | 106 | 115.797 | 12.728 | 17.993 | 1.00 | 29.40 | H | C |
| ATOM | 2266 | O | ASP | 106 | 116.567 | 11.861 | 18.396 | 1.00 | 29.40 | H | O |
| ATOM | 2267 | N | VAL | 107 | 114.687 | 13.094 | 18.635 | 1.00 | 7.69 | H | N |
| ATOM | 2268 | CA | VAL | 107 | 114.248 | 12.533 | 19.906 | 1.00 | 7.69 | H | C |
| ATOM | 2269 | CB | VAL | 107 | 114.402 | 13.600 | 21.026 | 1.00 | 10.61 | H | C |
| ATOM | 2270 | CG1 | VAL | 107 | 113.985 | 13.045 | 22.374 | 1.00 | 10.61 | H | C |
| ATOM | 2271 | CG2 | VAL | 107 | 115.838 | 14.116 | 21.048 | 1.00 | 10.61 | H | C |
| ATOM | 2272 | C | VAL | 107 | 112.778 | 12.199 | 19.765 | 1.00 | 7.69 | H | C |
| ATOM | 2273 | O | VAL | 107 | 112.107 | 12.835 | 18.970 | 1.00 | 7.69 | H | O |
| ATOM | 2274 | N | TRP | 108 | 112.285 | 11.224 | 20.540 | 1.00 | 26.84 | H | N |
| ATOM | 2275 | CA | TRP | 108 | 110.871 | 10.795 | 20.510 | 1.00 | 26.84 | H | C |
| ATOM | 2276 | CB | TRP | 108 | 110.729 | 9.405 | 19.868 | 1.00 | 1.87 | H | C |
| ATOM | 2277 | CG | TRP | 108 | 111.201 | 9.329 | 18.468 | 1.00 | 1.87 | H | C |
| ATOM | 2278 | CD2 | TRP | 108 | 110.431 | 8.950 | 17.328 | 1.00 | 1.87 | H | C |
| ATOM | 2279 | CE2 | TRP | 108 | 111.287 | 9.020 | 16.201 | 1.00 | 1.87 | H | C |
| ATOM | 2280 | CE3 | TRP | 108 | 109.102 | 8.557 | 17.142 | 1.00 | 1.87 | H | C |
| ATOM | 2281 | CD1 | TRP | 108 | 112.460 | 9.606 | 18.008 | 1.00 | 1.87 | H | C |
| ATOM | 2282 | NE1 | TRP | 108 | 112.520 | 9.422 | 16.648 | 1.00 | 1.87 | H | N |
| ATOM | 2283 | CZ2 | TRP | 108 | 110.854 | 8.710 | 14.904 | 1.00 | 1.87 | H | C |
| ATOM | 2284 | CZ3 | TRP | 108 | 108.667 | 8.244 | 15.836 | 1.00 | 1.87 | H | C |
| ATOM | 2285 | CH2 | TRP | 108 | 109.547 | 8.325 | 14.742 | 1.00 | 1.87 | H | C |
| ATOM | 2286 | C | TRP | 108 | 110.204 | 10.724 | 21.881 | 1.00 | 26.84 | H | C |
| ATOM | 2287 | O | TRP | 108 | 110.859 | 10.503 | 22.899 | 1.00 | 26.84 | H | O |
| ATOM | 2288 | N | GLY | 109 | 108.889 | 10.907 | 21.889 | 1.00 | 15.55 | H | N |
| ATOM | 2289 | CA | GLY | 109 | 108.134 | 10.811 | 23.125 | 1.00 | 15.55 | H | C |
| ATOM | 2290 | C | GLY | 109 | 107.896 | 9.331 | 23.386 | 1.00 | 15.55 | H | C |
| ATOM | 2291 | O | GLY | 109 | 108.170 | 8.502 | 22.511 | 1.00 | 15.55 | H | O |
| ATOM | 2292 | N | GLN | 110 | 107.393 | 8.971 | 24.563 | 1.00 | 21.92 | H | N |
| ATOM | 2293 | CA | GLN | 110 | 107.161 | 7.554 | 24.852 | 1.00 | 21.92 | H | C |
| ATOM | 2294 | CB | GLN | 110 | 106.800 | 7.338 | 26.325 | 1.00 | 44.26 | H | C |
| ATOM | 2295 | CG | GLN | 110 | 105.404 | 7.798 | 26.703 | 1.00 | 44.26 | H | C |
| ATOM | 2296 | CD | GLN | 110 | 105.321 | 9.283 | 26.957 | 1.00 | 44.26 | H | C |
| ATOM | 2297 | OE1 | GLN | 110 | 105.573 | 10.102 | 26.071 | 1.00 | 44.26 | H | O |
| ATOM | 2298 | NE2 | GLN | 110 | 104.967 | 9.642 | 28.181 | 1.00 | 44.26 | H | N |
| ATOM | 2299 | C | GLN | 110 | 106.051 | 6.979 | 23.973 | 1.00 | 21.92 | H | C |
| ATOM | 2300 | O | GLN | 110 | 106.054 | 5.798 | 23.651 | 1.00 | 21.92 | H | O |
| ATOM | 2301 | N | GLY | 111 | 105.114 | 7.824 | 23.574 | 1.00 | 22.63 | H | N |
| ATOM | 2302 | CA | GLY | 111 | 104.014 | 7.361 | 22.761 | 1.00 | 22.63 | H | C |
| ATOM | 2303 | C | GLY | 111 | 102.758 | 7.463 | 23.597 | 1.00 | 22.63 | H | C |
| ATOM | 2304 | O | GLY | 111 | 102.834 | 7.414 | 24.827 | 1.00 | 22.63 | H | O |
| ATOM | 2305 | N | THR | 112 | 101.611 | 7.619 | 22.938 | 1.00 | 17.52 | H | N |
| ATOM | 2306 | CA | THR | 112 | 100.333 | 7.740 | 23.630 | 1.00 | 17.52 | H | C |
| ATOM | 2307 | CB | THR | 112 | 100.058 | 9.211 | 24.030 | 1.00 | 34.98 | H | C |
| ATOM | 2308 | OG1 | THR | 112 | 98.958 | 9.261 | 24.939 | 1.00 | 34.98 | H | O |
| ATOM | 2309 | CG2 | THR | 112 | 99.734 | 10.055 | 22.809 | 1.00 | 34.98 | H | C |
| ATOM | 2310 | C | THR | 112 | 99.228 | 7.203 | 22.717 | 1.00 | 17.52 | H | C |
| ATOM | 2311 | O | THR | 112 | 99.133 | 7.559 | 21.533 | 1.00 | 17.52 | H | O |
| ATOM | 2312 | N | LEU | 113 | 98.396 | 6.340 | 23.292 | 1.00 | 32.82 | H | N |
| ATOM | 2313 | CA | LEU | 113 | 97.318 | 5.668 | 22.576 | 1.00 | 32.82 | H | C |
| ATOM | 2314 | CB | LEU | 113 | 96.953 | 4.374 | 23.328 | 1.00 | 26.98 | H | C |
| ATOM | 2315 | CG | LEU | 113 | 95.842 | 3.431 | 22.856 | 1.00 | 26.98 | H | C |
| ATOM | 2316 | CD1 | LEU | 113 | 94.455 | 4.057 | 23.105 | 1.00 | 26.98 | H | C |
| ATOM | 2317 | CD2 | LEU | 113 | 96.055 | 3.115 | 21.392 | 1.00 | 26.98 | H | C |
| ATOM | 2318 | C | LEU | 113 | 96.073 | 6.498 | 22.354 | 1.00 | 32.82 | H | C |
| ATOM | 2319 | O | LEU | 113 | 95.448 | 6.964 | 23.299 | 1.00 | 32.82 | H | O |
| ATOM | 2320 | N | VAL | 114 | 95.708 | 6.671 | 21.094 | 1.00 | 38.48 | H | N |
| ATOM | 2321 | CA | VAL | 114 | 94.506 | 7.419 | 20.767 | 1.00 | 38.48 | H | C |
| ATOM | 2322 | CB | VAL | 114 | 94.809 | 8.658 | 19.870 | 1.00 | 53.69 | H | C |
| ATOM | 2323 | CG1 | VAL | 114 | 93.518 | 9.420 | 19.571 | 1.00 | 53.69 | H | C |
| ATOM | 2324 | CG2 | VAL | 114 | 95.798 | 9.575 | 20.562 | 1.00 | 53.69 | H | C |
| ATOM | 2325 | C | VAL | 114 | 93.557 | 6.484 | 20.022 | 1.00 | 38.48 | H | C |
| ATOM | 2326 | O | VAL | 114 | 93.859 | 6.003 | 18.928 | 1.00 | 38.48 | H | O |
| ATOM | 2327 | N | THR | 115 | 92.411 | 6.216 | 20.629 | 1.00 | 29.76 | H | N |
| ATOM | 2328 | CA | THR | 115 | 91.414 | 5.356 | 20.012 | 1.00 | 29.76 | H | C |
| ATOM | 2329 | CB | THR | 115 | 91.081 | 4.125 | 20.916 | 1.00 | 30.84 | H | C |
| ATOM | 2330 | OG1 | THR | 115 | 92.292 | 3.453 | 21.300 | 1.00 | 30.84 | H | O |
| ATOM | 2331 | CG2 | THR | 115 | 90.180 | 3.151 | 20.170 | 1.00 | 30.84 | H | C |
| ATOM | 2332 | C | THR | 115 | 90.133 | 6.164 | 19.803 | 1.00 | 29.76 | H | C |
| ATOM | 2333 | O | THR | 115 | 89.700 | 6.905 | 20.694 | 1.00 | 29.76 | H | O |
| ATOM | 2334 | N | VAL | 116 | 89.543 | 6.056 | 18.619 | 1.00 | 38.29 | H | N |
| ATOM | 2335 | CA | VAL | 116 | 88.289 | 6.747 | 18.371 | 1.00 | 38.29 | H | C |
| ATOM | 2336 | CB | VAL | 116 | 88.395 | 7.822 | 17.240 | 1.00 | 10.28 | H | C |

Fig. 19: A-33

```
ATOM   2337  CG1 VAL  116      89.861    8.088   16.922  1.00   10.28      H   C
ATOM   2338  CG2 VAL  116      87.575    7.415   15.994  1.00   10.28      H   C
ATOM   2339  C   VAL  116      87.303    5.656   17.996  1.00   38.29      H   C
ATOM   2340  O   VAL  116      87.545    4.888   17.063  1.00   38.29      H   O
ATOM   2341  N   SER  117      86.207    5.579   18.746  1.00   41.53      H   N
ATOM   2342  CA  SER  117      85.193    4.565   18.517  1.00   41.53      H   C
ATOM   2343  CB  SER  117      85.768    3.182   18.851  1.00   61.62      H   C
ATOM   2344  OG  SER  117      84.788    2.165   18.751  1.00   61.62      H   O
ATOM   2345  C   SER  117      83.959    4.815   19.366  1.00   41.53      H   C
ATOM   2346  O   SER  117      84.049    5.336   20.482  1.00   41.53      H   O
ATOM   2347  N   SER  118      82.808    4.431   18.828  1.00   36.79      H   N
ATOM   2348  CA  SER  118      81.538    4.581   19.525  1.00   36.79      H   C
ATOM   2349  CB  SER  118      80.401    4.226   18.579  1.00   49.30      H   C
ATOM   2350  OG  SER  118      80.598    2.919   18.069  1.00   49.30      H   O
ATOM   2351  C   SER  118      81.510    3.649   20.740  1.00   36.79      H   C
ATOM   2352  O   SER  118      80.753    3.853   21.685  1.00   35.84      H   O
ATOM   2353  N   ALA  119      82.339    2.616   20.707  1.00   26.31      H   N
ATOM   2354  CA  ALA  119      82.412    1.679   21.815  1.00   26.31      H   C
ATOM   2355  CB  ALA  119      83.569    0.707   21.617  1.00   20.55      H   C
ATOM   2356  C   ALA  119      82.611    2.461   23.100  1.00   26.31      H   C
ATOM   2357  O   ALA  119      83.319    3.477   23.124  1.00   26.31      H   O
ATOM   2358  N   SER  120      81.988    1.975   24.166  1.00   39.08      H   N
ATOM   2359  CA  SER  120      82.074    2.621   25.462  1.00   39.08      H   C
ATOM   2360  CB  SER  120      80.711    2.597   26.151  1.00   57.76      H   C
ATOM   2361  OG  SER  120      79.720    3.179   25.329  1.00   57.76      H   O
ATOM   2362  C   SER  120      83.086    1.938   26.353  1.00   39.08      H   C
ATOM   2363  O   SER  120      83.194    0.715   26.362  1.00   39.08      H   O
ATOM   2364  N   THR  121      83.837    2.734   27.100  1.00   26.62      H   N
ATOM   2365  CA  THR  121      84.813    2.188   28.023  1.00   25.63      H   C
ATOM   2366  CB  THR  121      85.274    3.267   29.002  1.00   27.79      H   C
ATOM   2367  OG1 THR  121      85.860    4.353   28.268  1.00   32.58      H   O
ATOM   2368  CG2 THR  121      86.273    2.691   30.007  1.00   25.52      H   C
ATOM   2369  C   THR  121      84.108    1.078   28.801  1.00   26.35      H   C
ATOM   2370  O   THR  121      82.919    1.189   29.098  1.00   29.95      H   O
ATOM   2371  N   LYS  122      84.828    0.007   29.116  1.00   53.26      H   N
ATOM   2372  CA  LYS  122      84.243   -1.102   29.864  1.00   50.64      H   C
ATOM   2373  CB  LYS  122      83.333   -1.930   28.947  1.00   42.70      H   C
ATOM   2374  CG  LYS  122      83.009   -3.347   29.437  1.00   44.07      H   C
ATOM   2375  CD  LYS  122      82.469   -3.373   30.864  1.00   47.16      H   C
ATOM   2376  CE  LYS  122      82.216   -4.805   31.337  1.00   51.36      H   C
ATOM   2377  NZ  LYS  122      81.986   -4.880   32.809  1.00   50.23      H   N
ATOM   2378  C   LYS  122      85.301   -1.991   30.496  1.00   52.40      H   C
ATOM   2379  O   LYS  122      86.154   -2.548   29.809  1.00   54.02      H   O
ATOM   2380  N   GLY  123      85.240   -2.114   31.817  1.00   42.56      H   N
ATOM   2381  CA  GLY  123      86.188   -2.952   32.530  1.00   42.89      H   C
ATOM   2382  C   GLY  123      86.213   -4.396   32.035  1.00   44.35      H   C
ATOM   2383  O   GLY  123      85.222   -4.907   31.503  1.00   40.33      H   O
ATOM   2384  N   PRO  124      87.346   -5.090   32.198  1.00   44.81      H   N
ATOM   2385  CD  PRO  124      88.680   -4.632   32.633  1.00   21.78      H   C
ATOM   2386  CA  PRO  124      87.397   -6.472   31.731  1.00   46.19      H   C
ATOM   2387  CB  PRO  124      88.868   -6.668   31.439  1.00   22.93      H   C
ATOM   2388  CG  PRO  124      89.504   -5.905   32.561  1.00   22.69      H   C
ATOM   2389  C   PRO  124      86.899   -7.461   32.764  1.00   45.69      H   C
ATOM   2390  O   PRO  124      86.854   -7.170   33.961  1.00   46.94      H   O
ATOM   2391  N   SER  125      86.507   -8.631   32.287  1.00   43.49      H   N
ATOM   2392  CA  SER  125      86.053   -9.678   33.176  1.00   38.23      H   C
ATOM   2393  CB  SER  125      84.858  -10.416   32.579  1.00   23.34      H   C
ATOM   2394  OG  SER  125      83.756   -9.544   32.402  1.00   25.34      H   O
ATOM   2395  C   SER  125      87.262  -10.587   33.200  1.00   33.52      H   C
ATOM   2396  O   SER  125      87.738  -10.972   32.139  1.00   32.91      H   O
ATOM   2397  N   VAL  126      87.787  -10.873   34.386  1.00   23.96      H   N
ATOM   2398  CA  VAL  126      88.962  -11.727   34.452  1.00   20.86      H   C
ATOM   2399  CB  VAL  126      90.135  -11.003   35.174  1.00   22.19      H   C
ATOM   2400  CG1 VAL  126      89.894   -9.504   35.113  1.00   17.46      H   C
ATOM   2401  CG2 VAL  126      90.331  -11.507   36.597  1.00   22.90      H   C
ATOM   2402  C   VAL  126      88.666  -13.091   35.065  1.00   20.51      H   C
ATOM   2403  O   VAL  126      88.382  -13.227   36.256  1.00   24.79      H   O
ATOM   2404  N   PHE  127      88.713  -14.105   34.213  1.00   27.15      H   N
ATOM   2405  CA  PHE  127      88.443  -15.464   34.625  1.00   29.56      H   C
ATOM   2406  CB  PHE  127      87.628  -16.167   33.544  1.00   16.06      H   C
ATOM   2407  CG  PHE  127      86.392  -15.419   33.141  1.00   12.41      H   C
ATOM   2408  CD1 PHE  127      85.380  -15.167   34.071  1.00   11.21      H   C
ATOM   2409  CD2 PHE  127      86.255  -14.922   31.840  1.00   10.06      H   C
```

Fig. 19: A-34

```
ATOM   2410  CE1 PHE 127      84.254 -14.428  33.721  1.00  12.93      H  C
ATOM   2411  CE2 PHE 127      85.126 -14.174  31.470  1.00   6.89      H  C
ATOM   2412  CZ  PHE 127      84.125 -13.925  32.413  1.00   6.94      H  C
ATOM   2413  C   PHE 127      89.763 -16.183  34.825  1.00  31.37      H  C
ATOM   2414  O   PHE 127      90.806 -15.733  34.351  1.00  34.05      H  O
ATOM   2415  N   PRO 128      89.743 -17.310  35.540  1.00  21.35      H  N
ATOM   2416  CD  PRO 128      88.681 -17.812  36.434  1.00  32.37      H  C
ATOM   2417  CA  PRO 128      90.996 -18.039  35.752  1.00  22.25      H  C
ATOM   2418  CB  PRO 128      90.823 -18.577  37.161  1.00  34.03      H  C
ATOM   2419  CG  PRO 128      89.358 -18.983  37.130  1.00  33.18      H  C
ATOM   2420  C   PRO 128      91.198 -19.176  34.739  1.00  21.65      H  C
ATOM   2421  O   PRO 128      90.235 -19.770  34.244  1.00  21.29      H  O
ATOM   2422  N   LEU 129      92.457 -19.457  34.432  1.00  17.17      H  N
ATOM   2423  CA  LEU 129      92.811 -20.557  33.545  1.00  19.61      H  C
ATOM   2424  CB  LEU 129      93.683 -20.061  32.396  1.00  18.81      H  C
ATOM   2425  CG  LEU 129      93.086 -18.872  31.635  1.00  18.17      H  C
ATOM   2426  CD1 LEU 129      94.115 -18.254  30.696  1.00  16.12      H  C
ATOM   2427  CD2 LEU 129      91.886 -19.341  30.870  1.00  11.94      H  C
ATOM   2428  C   LEU 129      93.601 -21.457  34.497  1.00  23.45      H  C
ATOM   2429  O   LEU 129      94.824 -21.481  34.499  1.00  25.82      H  O
ATOM   2430  N   ALA 130      92.870 -22.179  35.332  1.00  16.93      H  N
ATOM   2431  CA  ALA 130      93.455 -23.046  36.341  1.00  18.97      H  C
ATOM   2432  CB  ALA 130      92.363 -23.561  37.256  1.00  49.82      H  C
ATOM   2433  C   ALA 130      94.280 -24.219  35.846  1.00  18.88      H  C
ATOM   2434  O   ALA 130      93.928 -24.876  34.869  1.00  20.61      H  O
ATOM   2435  N   PRO 131      95.401 -24.490  36.534  1.00  29.98      H  N
ATOM   2436  CD  PRO 131      95.929 -23.703  37.665  1.00  16.68      H  C
ATOM   2437  CA  PRO 131      96.301 -25.595  36.198  1.00  27.20      H  C
ATOM   2438  CB  PRO 131      97.453 -25.424  37.196  1.00  12.88      H  C
ATOM   2439  CG  PRO 131      96.815 -24.691  38.354  1.00  15.86      H  C
ATOM   2440  C   PRO 131      95.534 -26.897  36.405  1.00  26.68      H  C
ATOM   2441  O   PRO 131      94.666 -26.978  37.274  1.00  27.16      H  O
ATOM   2442  N   SER 132      95.838 -27.912  35.607  1.00  64.88      H  N
ATOM   2443  CA  SER 132      95.138 -29.187  35.720  1.00  67.56      H  C
ATOM   2444  CB  SER 132      93.745 -29.075  35.086  1.00  44.77      H  C
ATOM   2445  OG  SER 132      93.824 -28.747  33.704  1.00  46.53      H  O
ATOM   2446  C   SER 132      95.918 -30.284  35.020  1.00  69.15      H  C
ATOM   2447  O   SER 132      97.107 -30.139  34.757  1.00  69.80      H  O
ATOM   2448  N   SER 133      95.247 -31.391  34.732  1.00  58.75      H  N
ATOM   2449  CA  SER 133      95.894 -32.483  34.024  1.00  61.13      H  C
ATOM   2450  CB  SER 133      95.007 -33.738  34.068  1.00  91.14      H  C
ATOM   2451  OG  SER 133      93.668 -33.456  33.684  1.00 100.88      H  O
ATOM   2452  C   SER 133      96.121 -32.017  32.576  1.00  60.76      H  C
ATOM   2453  O   SER 133      97.091 -32.413  31.927  1.00  61.01      H  O
ATOM   2454  N   LYS 134      95.220 -31.156  32.095  1.00 101.65      H  N
ATOM   2455  CA  LYS 134      95.285 -30.605  30.739  1.00 102.79      H  C
ATOM   2456  CB  LYS 134      93.951 -29.962  30.341  1.00  44.82      H  C
ATOM   2457  CG  LYS 134      92.703 -30.784  30.609  1.00  52.94      H  C
ATOM   2458  CD  LYS 134      92.058 -30.452  31.959  1.00  55.86      H  C
ATOM   2459  CE  LYS 134      90.686 -31.127  32.091  1.00  53.71      H  C
ATOM   2460  NZ  LYS 134      89.988 -30.792  33.367  1.00  52.28      H  N
ATOM   2461  C   LYS 134      96.364 -29.531  30.655  1.00 102.96      H  C
ATOM   2462  O   LYS 134      96.932 -29.284  29.589  1.00 104.03      H  O
ATOM   2463  N   SER 135      96.619 -28.885  31.791  1.00  77.03      H  N
ATOM   2464  CA  SER 135      97.611 -27.818  31.896  1.00  76.76      H  C
ATOM   2465  CB  SER 135      97.069 -26.698  32.784  1.00  81.66      H  C
ATOM   2466  OG  SER 135      95.726 -26.390  32.443  1.00  81.07      H  O
ATOM   2467  C   SER 135      98.911 -28.358  32.488  1.00  71.98      H  C
ATOM   2468  O   SER 135      99.733 -27.601  33.006  1.00  72.29      H  O
ATOM   2469  N   THR 136      99.075 -29.676  32.418  1.00  86.02      H  N
ATOM   2470  CA  THR 136     100.262 -30.351  32.932  1.00  86.44      H  C
ATOM   2471  CB  THR 136      99.897 -31.391  34.036  1.00  47.16      H  C
ATOM   2472  OG1 THR 136      99.491 -30.715  35.237  1.00  47.25      H  O
ATOM   2473  CG2 THR 136     101.096 -32.281  34.354  1.00  50.70      H  C
ATOM   2474  C   THR 136     100.977 -31.072  31.788  1.00  86.90      H  C
ATOM   2475  O   THR 136     100.334 -31.615  30.885  1.00  85.81      H  O
ATOM   2476  N   SER 137     102.309 -31.059  31.836  1.00  82.54      H  N
ATOM   2477  CA  SER 137     103.164 -31.700  30.834  1.00  82.34      H  C
ATOM   2478  CB  SER 137     103.113 -30.942  29.495  1.00  65.40      H  C
ATOM   2479  OG  SER 137     101.863 -31.097  28.841  1.00  66.87      H  O
ATOM   2480  C   SER 137     104.600 -31.715  31.352  1.00  82.68      H  C
ATOM   2481  O   SER 137     105.321 -30.722  31.244  1.00  84.11      H  O
ATOM   2482  N   GLY 138     105.016 -32.845  31.911  1.00  62.73      H  N
```

Fig. 19: A-35

```
ATOM   2483  CA  GLY   138     106.361 -32.941  32.438  1.00  62.79      H  C
ATOM   2484  C   GLY   138     106.394 -32.371  33.840  1.00  65.01      H  C
ATOM   2485  O   GLY   138     105.392 -32.410  34.555  1.00  65.52      H  O
ATOM   2486  N   GLY   139     107.537 -31.827  34.237  1.00  45.62      H  N
ATOM   2487  CA  GLY   139     107.645 -31.267  35.570  1.00  45.97      H  C
ATOM   2488  C   GLY   139     107.037 -29.884  35.680  1.00  46.52      H  C
ATOM   2489  O   GLY   139     107.020 -29.297  36.762  1.00  50.66      H  O
ATOM   2490  N   THR   140     106.527 -29.365  34.568  1.00  41.37      H  N
ATOM   2491  CA  THR   140     105.941 -28.030  34.571  1.00  35.80      H  C
ATOM   2492  CB  THR   140     106.626 -27.108  33.533  1.00  32.97      H  C
ATOM   2493  OG1 THR   140     105.886 -27.138  32.311  1.00  30.01      H  O
ATOM   2494  CG2 THR   140     108.052 -27.574  33.250  1.00  33.92      H  C
ATOM   2495  C   THR   140     104.434 -27.993  34.299  1.00  32.68      H  C
ATOM   2496  O   THR   140     103.884 -28.820  33.560  1.00  31.27      H  O
ATOM   2497  N   ALA   141     103.777 -27.013  34.914  1.00  23.19      H  N
ATOM   2498  CA  ALA   141     102.350 -26.817  34.752  1.00  23.90      H  C
ATOM   2499  CB  ALA   141     101.647 -26.823  36.087  1.00  31.87      H  C
ATOM   2500  C   ALA   141     102.121 -25.408  34.206  1.00  24.06      H  C
ATOM   2501  O   ALA   141     102.930 -24.498  34.415  1.00  28.34      H  O
ATOM   2502  N   ALA   142     101.022 -25.239  33.487  1.00  36.28      H  N
ATOM   2503  CA  ALA   142     100.685 -23.948  32.924  1.00  31.12      H  C
ATOM   2504  CB  ALA   142     100.507 -24.062  31.419  1.00   1.87      H  C
ATOM   2505  C   ALA   142      99.389 -23.519  33.588  1.00  29.11      H  C
ATOM   2506  O   ALA   142      98.565 -24.359  33.961  1.00  33.50      H  O
ATOM   2507  N   LEU   143      99.233 -22.211  33.751  1.00  27.06      H  N
ATOM   2508  CA  LEU   143      98.054 -21.611  34.372  1.00  31.22      H  C
ATOM   2509  CB  LEU   143      98.154 -21.670  35.900  1.00  28.24      H  C
ATOM   2510  CG  LEU   143      99.269 -20.865  36.582  1.00  30.55      H  C
ATOM   2511  CD1 LEU   143      98.702 -19.526  36.991  1.00  23.14      H  C
ATOM   2512  CD2 LEU   143      99.817 -21.596  37.809  1.00  37.29      H  C
ATOM   2513  C   LEU   143      98.068 -20.169  33.913  1.00  34.46      H  C
ATOM   2514  O   LEU   143      99.069 -19.700  33.364  1.00  32.14      H  O
ATOM   2515  N   GLY   144      96.970 -19.458  34.128  1.00  25.78      H  N
ATOM   2516  CA  GLY   144      96.922 -18.074  33.694  1.00  28.57      H  C
ATOM   2517  C   GLY   144      95.578 -17.425  33.896  1.00  31.81      H  C
ATOM   2518  O   GLY   144      94.693 -17.985  34.543  1.00  35.57      H  O
ATOM   2519  N   CYS   145      95.420 -16.235  33.335  1.00  24.76      H  N
ATOM   2520  CA  CYS   145      94.177 -15.501  33.471  1.00  23.67      H  C
ATOM   2521  C   CYS   145      93.665 -15.071  32.122  1.00  21.65      H  C
ATOM   2522  O   CYS   145      94.437 -14.868  31.188  1.00  22.23      H  O
ATOM   2523  CB  CYS   145      94.385 -14.273  34.363  1.00  28.67      H  C
ATOM   2524  SG  CYS   145      94.354 -14.658  36.141  1.00  36.96      H  S
ATOM   2525  N   LEU   146      92.351 -14.940  32.024  1.00  43.52      H  N
ATOM   2526  CA  LEU   146      91.712 -14.512  30.792  1.00  43.76      H  C
ATOM   2527  CB  LEU   146      90.715 -15.580  30.314  1.00  38.89      H  C
ATOM   2528  CG  LEU   146      89.754 -15.245  29.164  1.00  28.77      H  C
ATOM   2529  CD1 LEU   146      90.519 -14.669  27.982  1.00  25.69      H  C
ATOM   2530  CD2 LEU   146      88.989 -16.489  28.755  1.00  35.84      H  C
ATOM   2531  C   LEU   146      90.997 -13.188  31.055  1.00  45.61      H  C
ATOM   2532  O   LEU   146      89.943 -13.160  31.690  1.00  45.79      H  O
ATOM   2533  N   VAL   147      91.609 -12.098  30.593  1.00  12.91      H  N
ATOM   2534  CA  VAL   147      91.069 -10.732  30.716  1.00  12.94      H  C
ATOM   2535  CB  VAL   147      92.231  -9.696  30.638  1.00  24.21      H  C
ATOM   2536  CG1 VAL   147      91.703  -8.291  30.722  1.00  25.32      H  C
ATOM   2537  CG2 VAL   147      93.212  -9.947  31.778  1.00  13.52      H  C
ATOM   2538  C   VAL   147      90.101 -10.563  29.532  1.00  18.31      H  C
ATOM   2539  O   VAL   147      90.532 -10.460  28.381  1.00  18.59      H  O
ATOM   2540  N   LYS   148      88.798 -10.519  29.806  1.00  25.16      H  N
ATOM   2541  CA  LYS   148      87.835 -10.467  28.709  1.00  29.22      H  C
ATOM   2542  CB  LYS   148      87.140 -11.827  28.609  1.00  15.56      H  C
ATOM   2543  CG  LYS   148      86.353 -12.032  27.348  1.00  22.92      H  C
ATOM   2544  CD  LYS   148      85.731 -13.405  27.355  1.00  22.16      H  C
ATOM   2545  CE  LYS   148      84.795 -13.570  26.190  1.00  24.54      H  C
ATOM   2546  NZ  LYS   148      85.514 -13.308  24.928  1.00  22.92      H  N
ATOM   2547  C   LYS   148      86.777  -9.372  28.646  1.00  32.79      H  C
ATOM   2548  O   LYS   148      86.332  -8.844  29.664  1.00  33.18      H  O
ATOM   2549  N   ASP   149      86.387  -9.069  27.409  1.00  55.13      H  N
ATOM   2550  CA  ASP   149      85.381  -8.070  27.078  1.00  53.92      H  C
ATOM   2551  CB  ASP   149      83.993  -8.595  27.429  1.00  38.49      H  C
ATOM   2552  CG  ASP   149      83.635  -9.853  26.661  1.00  42.52      H  C
ATOM   2553  OD1 ASP   149      83.797  -9.882  25.421  1.00  46.52      H  O
ATOM   2554  OD2 ASP   149      83.181 -10.817  27.305  1.00  41.08      H  O
ATOM   2555  C   ASP   149      85.585  -6.690  27.698  1.00  56.06      H  C
```

Fig. 19: A-36

| ATOM | 2556 | O | ASP | 149 | 84.720 | -6.175 | 28.415 | 1.00 | 57.30 | H | O |
|---|---|---|---|---|---|---|---|---|---|---|---|
| ATOM | 2557 | N | TYR | 150 | 86.734 | -6.091 | 27.399 | 1.00 | 33.00 | H | N |
| ATOM | 2558 | CA | TYR | 150 | 87.072 | -4.770 | 27.897 | 1.00 | 33.34 | H | C |
| ATOM | 2559 | CB | TYR | 150 | 88.306 | -4.844 | 28.797 | 1.00 | 39.19 | H | C |
| ATOM | 2560 | CG | TYR | 150 | 89.622 | -5.155 | 28.097 | 1.00 | 44.75 | H | C |
| ATOM | 2561 | CD1 | TYR | 150 | 90.405 | -4.137 | 27.556 | 1.00 | 44.06 | H | C |
| ATOM | 2562 | CE1 | TYR | 150 | 91.653 | -4.401 | 26.994 | 1.00 | 46.40 | H | C |
| ATOM | 2563 | CD2 | TYR | 150 | 90.121 | -6.457 | 28.046 | 1.00 | 44.23 | H | C |
| ATOM | 2564 | CE2 | TYR | 150 | 91.369 | -6.730 | 27.483 | 1.00 | 43.19 | H | C |
| ATOM | 2565 | CZ | TYR | 150 | 92.130 | -5.694 | 26.963 | 1.00 | 45.07 | H | C |
| ATOM | 2566 | OH | TYR | 150 | 93.376 | -5.942 | 26.431 | 1.00 | 42.66 | H | O |
| ATOM | 2567 | C | TYR | 150 | 87.331 | -3.838 | 26.723 | 1.00 | 34.19 | H | C |
| ATOM | 2568 | O | TYR | 150 | 87.420 | -4.275 | 25.569 | 1.00 | 36.79 | H | O |
| ATOM | 2569 | N | PHE | 151 | 87.450 | -2.549 | 27.034 | 1.00 | 53.36 | H | N |
| ATOM | 2570 | CA | PHE | 151 | 87.686 | -1.522 | 26.034 | 1.00 | 51.06 | H | C |
| ATOM | 2571 | CB | PHE | 151 | 86.520 | -1.506 | 25.038 | 1.00 | 22.52 | H | C |
| ATOM | 2572 | CG | PHE | 151 | 86.663 | -0.500 | 23.923 | 1.00 | 22.34 | H | C |
| ATOM | 2573 | CD1 | PHE | 151 | 86.509 | 0.865 | 24.164 | 1.00 | 21.58 | H | C |
| ATOM | 2574 | CD2 | PHE | 151 | 86.896 | -0.923 | 22.616 | 1.00 | 24.08 | H | C |
| ATOM | 2575 | CE1 | PHE | 151 | 86.576 | 1.789 | 23.117 | 1.00 | 22.62 | H | C |
| ATOM | 2576 | CE2 | PHE | 151 | 86.968 | -0.003 | 21.558 | 1.00 | 25.39 | H | C |
| ATOM | 2577 | CZ | PHE | 151 | 86.805 | 1.351 | 21.809 | 1.00 | 25.56 | H | C |
| ATOM | 2578 | C | PHE | 151 | 87.819 | -0.175 | 26.734 | 1.00 | 48.17 | H | C |
| ATOM | 2579 | O | PHE | 151 | 87.161 | 0.084 | 27.737 | 1.00 | 47.45 | H | O |
| ATOM | 2580 | N | PRO | 152 | 88.712 | 0.685 | 26.232 | 1.00 | 46.09 | H | N |
| ATOM | 2581 | CD | PRO | 152 | 88.959 | 2.055 | 26.730 | 1.00 | 7.14 | H | C |
| ATOM | 2582 | CA | PRO | 152 | 89.554 | 0.388 | 25.065 | 1.00 | 47.66 | H | C |
| ATOM | 2583 | CB | PRO | 152 | 89.773 | 1.765 | 24.464 | 1.00 | 12.39 | H | C |
| ATOM | 2584 | CG | PRO | 152 | 90.017 | 2.594 | 25.730 | 1.00 | 9.55 | H | C |
| ATOM | 2585 | C | PRO | 152 | 90.835 | -0.199 | 25.636 | 1.00 | 47.42 | H | C |
| ATOM | 2586 | O | PRO | 152 | 90.826 | -0.716 | 26.748 | 1.00 | 49.63 | H | O |
| ATOM | 2587 | N | GLU | 153 | 91.933 | -0.128 | 24.894 | 1.00 | 48.37 | H | N |
| ATOM | 2588 | CA | GLU | 153 | 93.200 | -0.620 | 25.422 | 1.00 | 45.01 | H | C |
| ATOM | 2589 | CB | GLU | 153 | 94.232 | -0.788 | 24.308 | 1.00 | 35.76 | H | C |
| ATOM | 2590 | CG | GLU | 153 | 93.983 | -1.951 | 23.370 | 1.00 | 41.71 | H | C |
| ATOM | 2591 | CD | GLU | 153 | 94.465 | -3.279 | 23.920 | 1.00 | 49.73 | H | C |
| ATOM | 2592 | OE1 | GLU | 153 | 94.329 | -4.276 | 23.191 | 1.00 | 53.96 | H | O |
| ATOM | 2593 | OE2 | GLU | 153 | 94.979 | -3.337 | 25.062 | 1.00 | 49.06 | H | O |
| ATOM | 2594 | C | GLU | 153 | 93.667 | 0.487 | 26.355 | 1.00 | 40.62 | H | C |
| ATOM | 2595 | O | GLU | 153 | 93.160 | 1.611 | 26.288 | 1.00 | 43.09 | H | O |
| ATOM | 2596 | N | PRO | 154 | 94.626 | 0.193 | 27.242 | 1.00 | 31.67 | H | N |
| ATOM | 2597 | CD | PRO | 154 | 95.605 | 1.250 | 27.562 | 1.00 | 24.24 | H | C |
| ATOM | 2598 | CA | PRO | 154 | 95.266 | -1.107 | 27.404 | 1.00 | 32.01 | H | C |
| ATOM | 2599 | CB | PRO | 154 | 96.707 | -0.803 | 27.072 | 1.00 | 23.56 | H | C |
| ATOM | 2600 | CG | PRO | 154 | 96.899 | 0.447 | 27.855 | 1.00 | 23.31 | H | C |
| ATOM | 2601 | C | PRO | 154 | 95.127 | -1.577 | 28.846 | 1.00 | 37.33 | H | C |
| ATOM | 2602 | O | PRO | 154 | 94.929 | -0.788 | 29.770 | 1.00 | 40.93 | H | O |
| ATOM | 2603 | N | VAL | 155 | 95.270 | -2.874 | 29.029 | 1.00 | 27.89 | H | N |
| ATOM | 2604 | CA | VAL | 155 | 95.171 | -3.468 | 30.339 | 1.00 | 28.93 | H | C |
| ATOM | 2605 | CB | VAL | 155 | 94.167 | -4.647 | 30.309 | 1.00 | 32.63 | H | C |
| ATOM | 2606 | CG1 | VAL | 155 | 94.624 | -5.699 | 29.306 | 1.00 | 39.44 | H | C |
| ATOM | 2607 | CG2 | VAL | 155 | 94.030 | -5.243 | 31.690 | 1.00 | 38.09 | H | C |
| ATOM | 2608 | C | VAL | 155 | 96.561 | -3.969 | 30.715 | 1.00 | 29.75 | H | C |
| ATOM | 2609 | O | VAL | 155 | 97.319 | -4.427 | 29.856 | 1.00 | 34.58 | H | O |
| ATOM | 2610 | N | THR | 156 | 96.898 | -3.864 | 31.995 | 1.00 | 30.47 | H | N |
| ATOM | 2611 | CA | THR | 156 | 98.195 | -4.322 | 32.482 | 1.00 | 30.67 | H | C |
| ATOM | 2612 | CB | THR | 156 | 98.855 | -3.316 | 33.458 | 1.00 | 37.06 | H | C |
| ATOM | 2613 | OG1 | THR | 156 | 98.554 | -3.699 | 34.810 | 1.00 | 41.96 | H | O |
| ATOM | 2614 | CG2 | THR | 156 | 98.346 | -1.895 | 33.213 | 1.00 | 35.30 | H | C |
| ATOM | 2615 | C | THR | 156 | 97.956 | -5.589 | 33.276 | 1.00 | 28.26 | H | C |
| ATOM | 2616 | O | THR | 156 | 96.915 | -5.736 | 33.906 | 1.00 | 24.33 | H | O |
| ATOM | 2617 | N | VAL | 157 | 98.914 | -6.501 | 33.250 | 1.00 | 20.40 | H | N |
| ATOM | 2618 | CA | VAL | 157 | 98.784 | -7.731 | 34.014 | 1.00 | 23.86 | H | C |
| ATOM | 2619 | CB | VAL | 157 | 98.263 | -8.918 | 33.149 | 1.00 | 6.55 | H | C |
| ATOM | 2620 | CG1 | VAL | 157 | 98.307 | -10.191 | 33.970 | 1.00 | 2.70 | H | C |
| ATOM | 2621 | CG2 | VAL | 157 | 96.817 | -8.649 | 32.662 | 1.00 | 8.40 | H | C |
| ATOM | 2622 | C | VAL | 157 | 100.122 | -8.142 | 34.618 | 1.00 | 25.91 | H | C |
| ATOM | 2623 | O | VAL | 157 | 101.130 | -8.220 | 33.918 | 1.00 | 28.24 | H | O |
| ATOM | 2624 | N | SER | 158 | 100.127 | -8.401 | 35.918 | 1.00 | 37.92 | H | N |
| ATOM | 2625 | CA | SER | 158 | 101.333 | -8.840 | 36.606 | 1.00 | 38.42 | H | C |
| ATOM | 2626 | CB | SER | 158 | 101.852 | -7.738 | 37.521 | 1.00 | 26.79 | H | C |
| ATOM | 2627 | OG | SER | 158 | 101.008 | -7.591 | 38.648 | 1.00 | 29.78 | H | O |
| ATOM | 2628 | C | SER | 158 | 100.947 | -10.064 | 37.439 | 1.00 | 37.35 | H | C |

Fig. 19: A-37

| | | | | | | | | | | |
|---|---|---|---|---|---|---|---|---|---|---|
| ATOM | 2629 | O | SER | 158 | 99.765 | -10.366 | 37.583 | 1.00 | 35.45 | H | O |
| ATOM | 2630 | N | TRP | 159 | 101.926 | -10.772 | 37.989 | 1.00 | 38.23 | H | N |
| ATOM | 2631 | CA | TRP | 159 | 101.604 | -11.945 | 38.790 | 1.00 | 38.96 | H | C |
| ATOM | 2632 | CB | TRP | 159 | 102.060 | -13.224 | 38.074 | 1.00 | 33.06 | H | C |
| ATOM | 2633 | CG | TRP | 159 | 101.197 | -13.555 | 36.899 | 1.00 | 30.80 | H | C |
| ATOM | 2634 | CD2 | TRP | 159 | 100.089 | -14.463 | 36.879 | 1.00 | 31.04 | H | C |
| ATOM | 2635 | CE2 | TRP | 159 | 99.540 | -14.423 | 35.577 | 1.00 | 29.21 | H | C |
| ATOM | 2636 | CE3 | TRP | 159 | 99.507 | -15.307 | 37.836 | 1.00 | 31.84 | H | C |
| ATOM | 2637 | CD1 | TRP | 159 | 101.271 | -13.015 | 35.649 | 1.00 | 26.46 | H | C |
| ATOM | 2638 | NE1 | TRP | 159 | 100.280 | -13.531 | 34.848 | 1.00 | 30.17 | H | N |
| ATOM | 2639 | CZ2 | TRP | 159 | 98.439 | -15.196 | 35.204 | 1.00 | 33.73 | H | C |
| ATOM | 2640 | CZ3 | TRP | 159 | 98.407 | -16.079 | 37.465 | 1.00 | 33.56 | H | C |
| ATOM | 2641 | CH2 | TRP | 159 | 97.887 | -16.018 | 36.158 | 1.00 | 34.95 | H | C |
| ATOM | 2642 | C | TRP | 159 | 102.166 | -11.908 | 40.203 | 1.00 | 41.53 | H | C |
| ATOM | 2643 | O | TRP | 159 | 103.355 | -11.670 | 40.412 | 1.00 | 40.45 | H | O |
| ATOM | 2644 | N | ASN | 160 | 101.295 | -12.163 | 41.170 | 1.00 | 50.63 | H | N |
| ATOM | 2645 | CA | ASN | 160 | 101.699 | -12.153 | 42.557 | 1.00 | 51.18 | H | C |
| ATOM | 2646 | CB | ASN | 160 | 102.753 | -13.230 | 42.814 | 1.00 | 31.23 | H | C |
| ATOM | 2647 | CG | ASN | 160 | 102.145 | -14.619 | 42.946 | 1.00 | 28.65 | H | C |
| ATOM | 2648 | OD1 | ASN | 160 | 100.924 | -14.784 | 42.911 | 1.00 | 22.55 | H | O |
| ATOM | 2649 | ND2 | ASN | 160 | 103.000 | -15.630 | 43.107 | 1.00 | 28.71 | H | N |
| ATOM | 2650 | C | ASN | 160 | 102.245 | -10.777 | 42.891 | 1.00 | 53.56 | H | C |
| ATOM | 2651 | O | ASN | 160 | 103.277 | -10.637 | 43.554 | 1.00 | 51.84 | H | O |
| ATOM | 2652 | N | SER | 161 | 101.548 | -9.758 | 42.397 | 1.00 | 57.36 | H | N |
| ATOM | 2653 | CA | SER | 161 | 101.915 | -8.372 | 42.651 | 1.00 | 58.07 | H | C |
| ATOM | 2654 | CB | SER | 161 | 101.833 | -8.106 | 44.161 | 1.00 | 44.49 | H | C |
| ATOM | 2655 | OG | SER | 161 | 100.611 | -8.586 | 44.713 | 1.00 | 48.26 | H | O |
| ATOM | 2656 | C | SER | 161 | 103.305 | -7.997 | 42.118 | 1.00 | 57.98 | H | C |
| ATOM | 2657 | O | SER | 161 | 103.779 | -6.883 | 42.329 | 1.00 | 58.91 | H | O |
| ATOM | 2658 | N | GLY | 162 | 103.957 | -8.927 | 41.431 | 1.00 | 43.40 | H | N |
| ATOM | 2659 | CA | GLY | 162 | 105.271 | -8.641 | 40.886 | 1.00 | 41.61 | H | C |
| ATOM | 2660 | C | GLY | 162 | 106.343 | -9.670 | 41.195 | 1.00 | 41.13 | H | C |
| ATOM | 2661 | O | GLY | 162 | 107.340 | -9.756 | 40.475 | 1.00 | 41.89 | H | O |
| ATOM | 2662 | N | ALA | 163 | 106.144 | -10.460 | 42.248 | 1.00 | 32.79 | H | N |
| ATOM | 2663 | CA | ALA | 163 | 107.135 | -11.462 | 42.644 | 1.00 | 33.15 | H | C |
| ATOM | 2664 | CB | ALA | 163 | 106.845 | -11.956 | 44.065 | 1.00 | 7.75 | H | C |
| ATOM | 2665 | C | ALA | 163 | 107.265 | -12.651 | 41.702 | 1.00 | 33.69 | H | C |
| ATOM | 2666 | O | ALA | 163 | 108.154 | -13.473 | 41.868 | 1.00 | 36.52 | H | O |
| ATOM | 2667 | N | LEU | 164 | 106.378 | -12.750 | 40.722 | 1.00 | 33.04 | H | N |
| ATOM | 2668 | CA | LEU | 164 | 106.412 | -13.847 | 39.755 | 1.00 | 28.09 | H | C |
| ATOM | 2669 | CB | LEU | 164 | 105.146 | -14.701 | 39.869 | 1.00 | 29.67 | H | C |
| ATOM | 2670 | CG | LEU | 164 | 105.008 | -15.851 | 38.870 | 1.00 | 27.43 | H | C |
| ATOM | 2671 | CD1 | LEU | 164 | 105.976 | -16.963 | 39.215 | 1.00 | 24.01 | H | C |
| ATOM | 2672 | CD2 | LEU | 164 | 103.605 | -16.370 | 38.903 | 1.00 | 22.28 | H | C |
| ATOM | 2673 | C | LEU | 164 | 106.483 | -13.227 | 38.370 | 1.00 | 26.00 | H | C |
| ATOM | 2674 | O | LEU | 164 | 105.492 | -12.663 | 37.893 | 1.00 | 20.06 | H | O |
| ATOM | 2675 | N | THR | 165 | 107.656 | -13.326 | 37.740 | 1.00 | 28.49 | H | N |
| ATOM | 2676 | CA | THR | 165 | 107.893 | -12.758 | 36.410 | 1.00 | 32.54 | H | C |
| ATOM | 2677 | CB | THR | 165 | 108.927 | -11.613 | 36.462 | 1.00 | 18.33 | H | C |
| ATOM | 2678 | OG1 | THR | 165 | 110.114 | -12.057 | 37.139 | 1.00 | 21.15 | H | O |
| ATOM | 2679 | CG2 | THR | 165 | 108.348 | -10.419 | 37.184 | 1.00 | 20.86 | H | C |
| ATOM | 2680 | C | THR | 165 | 108.394 | -13.770 | 35.397 | 1.00 | 33.42 | H | C |
| ATOM | 2681 | O | THR | 165 | 108.028 | -13.717 | 34.227 | 1.00 | 34.44 | H | O |
| ATOM | 2682 | N | SER | 166 | 109.244 | -14.683 | 35.849 | 1.00 | 63.46 | H | N |
| ATOM | 2683 | CA | SER | 166 | 109.804 | -15.702 | 34.973 | 1.00 | 62.93 | H | C |
| ATOM | 2684 | CB | SER | 166 | 110.901 | -16.472 | 35.710 | 1.00 | 37.10 | H | C |
| ATOM | 2685 | OG | SER | 166 | 111.503 | -17.442 | 34.870 | 1.00 | 42.11 | H | O |
| ATOM | 2686 | C | SER | 166 | 108.748 | -16.678 | 34.458 | 1.00 | 60.85 | H | C |
| ATOM | 2687 | O | SER | 166 | 107.955 | -17.226 | 35.227 | 1.00 | 60.31 | H | O |
| ATOM | 2688 | N | GLY | 167 | 108.744 | -16.895 | 33.148 | 1.00 | 58.61 | H | N |
| ATOM | 2689 | CA | GLY | 167 | 107.784 | -17.812 | 32.566 | 1.00 | 55.44 | H | C |
| ATOM | 2690 | C | GLY | 167 | 106.425 | -17.181 | 32.332 | 1.00 | 49.55 | H | C |
| ATOM | 2691 | O | GLY | 167 | 105.462 | -17.878 | 32.010 | 1.00 | 51.52 | H | O |
| ATOM | 2692 | N | VAL | 168 | 106.340 | -15.864 | 32.491 | 1.00 | 12.32 | H | N |
| ATOM | 2693 | CA | VAL | 168 | 105.081 | -15.183 | 32.280 | 1.00 | 12.04 | H | C |
| ATOM | 2694 | CB | VAL | 168 | 104.933 | -13.970 | 33.190 | 1.00 | 2.74 | H | C |
| ATOM | 2695 | CG1 | VAL | 168 | 103.590 | -13.273 | 32.906 | 1.00 | 2.74 | H | C |
| ATOM | 2696 | CG2 | VAL | 168 | 105.070 | -14.398 | 34.630 | 1.00 | 2.83 | H | C |
| ATOM | 2697 | C | VAL | 168 | 104.965 | -14.687 | 30.852 | 1.00 | 11.82 | H | C |
| ATOM | 2698 | O | VAL | 168 | 105.894 | -14.087 | 30.319 | 1.00 | 11.28 | H | O |
| ATOM | 2699 | N | HIS | 169 | 103.807 | -14.931 | 30.253 | 1.00 | 28.24 | H | N |
| ATOM | 2700 | CA | HIS | 169 | 103.518 | -14.512 | 28.891 | 1.00 | 24.96 | H | C |
| ATOM | 2701 | CB | HIS | 169 | 103.566 | -15.695 | 27.924 | 1.00 | 1.87 | H | C |

Fig. 19: A-38

| ATOM | 2702 | CG | HIS | 169 | 104.935 | -16.209 | 27.634 | 1.00 | 1.87 | H | C |
| --- | --- | --- | --- | --- | --- | --- | --- | --- | --- | --- | --- |
| ATOM | 2703 | CD2 | HIS | 169 | 105.456 | -17.452 | 27.739 | 1.00 | 10.72 | H | C |
| ATOM | 2704 | ND1 | HIS | 169 | 105.935 | -15.415 | 27.114 | 1.00 | 4.04 | H | N |
| ATOM | 2705 | CE1 | HIS | 169 | 107.015 | -16.147 | 26.912 | 1.00 | 11.56 | H | C |
| ATOM | 2706 | NE2 | HIS | 169 | 106.750 | -17.387 | 27.282 | 1.00 | 3.03 | H | N |
| ATOM | 2707 | C | HIS | 169 | 102.106 | -13.934 | 28.818 | 1.00 | 26.88 | H | C |
| ATOM | 2708 | O | HIS | 169 | 101.143 | -14.679 | 28.610 | 1.00 | 27.44 | H | O |
| ATOM | 2709 | N | THR | 170 | 101.960 | -12.628 | 28.995 | 1.00 | 15.52 | H | N |
| ATOM | 2710 | CA | THR | 170 | 100.637 | -12.030 | 28.885 | 1.00 | 14.61 | H | C |
| ATOM | 2711 | CB | THR | 170 | 100.472 | -10.872 | 29.894 | 1.00 | 20.19 | H | C |
| ATOM | 2712 | OG1 | THR | 170 | 99.403 | -10.021 | 29.470 | 1.00 | 14.32 | H | O |
| ATOM | 2713 | CG2 | THR | 170 | 101.760 | -10.096 | 30.042 | 1.00 | 25.14 | H | C |
| ATOM | 2714 | C | THR | 170 | 100.487 | -11.553 | 27.433 | 1.00 | 15.32 | H | C |
| ATOM | 2715 | O | THR | 170 | 101.023 | -10.532 | 27.053 | 1.00 | 11.65 | H | O |
| ATOM | 2716 | N | PHE | 171 | 99.762 | -12.324 | 26.630 | 1.00 | 23.28 | H | N |
| ATOM | 2717 | CA | PHE | 171 | 99.587 | -12.046 | 25.206 | 1.00 | 17.85 | H | C |
| ATOM | 2718 | CB | PHE | 171 | 98.695 | -13.110 | 24.554 | 1.00 | 15.23 | H | C |
| ATOM | 2719 | CG | PHE | 171 | 99.138 | -14.521 | 24.806 | 1.00 | 7.97 | H | C |
| ATOM | 2720 | CD1 | PHE | 171 | 98.731 | -15.195 | 25.955 | 1.00 | 8.65 | H | C |
| ATOM | 2721 | CD2 | PHE | 171 | 99.978 | -15.174 | 23.903 | 1.00 | 7.84 | H | C |
| ATOM | 2722 | CE1 | PHE | 171 | 99.153 | -16.492 | 26.202 | 1.00 | 17.36 | H | C |
| ATOM | 2723 | CE2 | PHE | 171 | 100.407 | -16.473 | 24.144 | 1.00 | 15.22 | H | C |
| ATOM | 2724 | CZ | PHE | 171 | 99.993 | -17.133 | 25.295 | 1.00 | 16.34 | H | C |
| ATOM | 2725 | C | PHE | 171 | 99.032 | -10.692 | 24.793 | 1.00 | 18.20 | H | C |
| ATOM | 2726 | O | PHE | 171 | 98.344 | -10.015 | 25.552 | 1.00 | 23.73 | H | O |
| ATOM | 2727 | N | PRO | 172 | 99.341 | -10.278 | 23.557 | 1.00 | 21.77 | H | N |
| ATOM | 2728 | CD | PRO | 172 | 100.227 | -10.890 | 22.550 | 1.00 | 20.32 | H | C |
| ATOM | 2729 | CA | PRO | 172 | 98.827 | -8.999 | 23.088 | 1.00 | 23.20 | H | C |
| ATOM | 2730 | CB | PRO | 172 | 99.595 | -8.775 | 21.782 | 1.00 | 20.71 | H | C |
| ATOM | 2731 | CG | PRO | 172 | 99.834 | -10.148 | 21.287 | 1.00 | 18.82 | H | C |
| ATOM | 2732 | C | PRO | 172 | 97.339 | -9.235 | 22.876 | 1.00 | 25.11 | H | C |
| ATOM | 2733 | O | PRO | 172 | 96.916 | -10.364 | 22.645 | 1.00 | 23.46 | H | O |
| ATOM | 2734 | N | ALA | 173 | 96.551 | -8.172 | 22.960 | 1.00 | 24.67 | H | N |
| ATOM | 2735 | CA | ALA | 173 | 95.104 | -8.267 | 22.815 | 1.00 | 27.18 | H | C |
| ATOM | 2736 | CB | ALA | 173 | 94.439 | -7.079 | 23.498 | 1.00 | 1.87 | H | C |
| ATOM | 2737 | C | ALA | 173 | 94.604 | -8.379 | 21.391 | 1.00 | 30.18 | H | C |
| ATOM | 2738 | O | ALA | 173 | 95.304 | -8.080 | 20.426 | 1.00 | 32.13 | H | O |
| ATOM | 2739 | N | VAL | 174 | 93.365 | -8.820 | 21.277 | 1.00 | 21.72 | H | N |
| ATOM | 2740 | CA | VAL | 174 | 92.753 | -8.964 | 19.984 | 1.00 | 23.16 | H | C |
| ATOM | 2741 | CB | VAL | 174 | 92.841 | -10.406 | 19.511 | 1.00 | 28.95 | H | C |
| ATOM | 2742 | CG1 | VAL | 174 | 92.103 | -10.566 | 18.201 | 1.00 | 32.21 | H | C |
| ATOM | 2743 | CG2 | VAL | 174 | 94.305 | -10.797 | 19.356 | 1.00 | 26.32 | H | C |
| ATOM | 2744 | C | VAL | 174 | 91.302 | -8.508 | 20.058 | 1.00 | 25.36 | H | C |
| ATOM | 2745 | O | VAL | 174 | 90.611 | -8.718 | 21.069 | 1.00 | 25.35 | H | O |
| ATOM | 2746 | N | LEU | 175 | 90.860 | -7.856 | 18.987 | 1.00 | 41.55 | H | N |
| ATOM | 2747 | CA | LEU | 175 | 89.504 | -7.338 | 18.890 | 1.00 | 40.23 | H | C |
| ATOM | 2748 | CB | LEU | 175 | 89.443 | -6.276 | 17.787 | 1.00 | 23.29 | H | C |
| ATOM | 2749 | CG | LEU | 175 | 88.728 | -4.928 | 17.990 | 1.00 | 20.94 | H | C |
| ATOM | 2750 | CD1 | LEU | 175 | 88.634 | -4.511 | 19.463 | 1.00 | 21.45 | H | C |
| ATOM | 2751 | CD2 | LEU | 175 | 89.518 | -3.900 | 17.186 | 1.00 | 22.78 | H | C |
| ATOM | 2752 | C | LEU | 175 | 88.539 | -8.474 | 18.588 | 1.00 | 42.85 | H | C |
| ATOM | 2753 | O | LEU | 175 | 88.738 | -9.233 | 17.638 | 1.00 | 45.50 | H | O |
| ATOM | 2754 | N | GLN | 176 | 87.500 | -8.592 | 19.407 | 1.00 | 41.11 | H | N |
| ATOM | 2755 | CA | GLN | 176 | 86.514 | -9.645 | 19.228 | 1.00 | 42.33 | H | C |
| ATOM | 2756 | CB | GLN | 176 | 85.852 | -9.990 | 20.564 | 1.00 | 38.15 | H | C |
| ATOM | 2757 | CG | GLN | 176 | 86.817 | -10.276 | 21.703 | 1.00 | 37.93 | H | C |
| ATOM | 2758 | CD | GLN | 176 | 86.109 | -10.801 | 22.939 | 1.00 | 36.82 | H | C |
| ATOM | 2759 | OE1 | GLN | 176 | 85.562 | -11.899 | 22.923 | 1.00 | 36.67 | H | O |
| ATOM | 2760 | NE2 | GLN | 176 | 86.108 | -10.014 | 24.011 | 1.00 | 33.13 | H | N |
| ATOM | 2761 | C | GLN | 176 | 85.439 | -9.207 | 18.245 | 1.00 | 44.39 | H | C |
| ATOM | 2762 | O | GLN | 176 | 85.274 | -8.018 | 17.969 | 1.00 | 34.09 | H | O |
| ATOM | 2763 | N | SER | 177 | 84.708 | -10.182 | 17.718 | 1.00 | 59.83 | H | N |
| ATOM | 2764 | CA | SER | 177 | 83.624 | -9.902 | 16.790 | 1.00 | 58.61 | H | C |
| ATOM | 2765 | CB | SER | 177 | 82.804 | -11.177 | 16.558 | 1.00 | 104.21 | H | C |
| ATOM | 2766 | OG | SER | 177 | 81.708 | -10.945 | 15.689 | 1.00 | 104.01 | H | O |
| ATOM | 2767 | C | SER | 177 | 82.759 | -8.832 | 17.448 | 1.00 | 60.09 | H | C |
| ATOM | 2768 | O | SER | 177 | 82.169 | -7.985 | 16.778 | 1.00 | 62.26 | H | O |
| ATOM | 2769 | N | SER | 178 | 82.722 | -8.877 | 18.778 | 1.00 | 34.26 | H | N |
| ATOM | 2770 | CA | SER | 178 | 81.942 | -7.952 | 19.596 | 1.00 | 32.97 | H | C |
| ATOM | 2771 | CB | SER | 178 | 81.798 | -8.510 | 21.019 | 1.00 | 67.89 | H | C |
| ATOM | 2772 | OG | SER | 178 | 83.057 | -8.636 | 21.663 | 1.00 | 66.22 | H | O |
| ATOM | 2773 | C | SER | 178 | 82.538 | -6.554 | 19.671 | 1.00 | 32.95 | H | C |
| ATOM | 2774 | O | SER | 178 | 81.921 | -5.640 | 20.210 | 1.00 | 35.05 | H | O |

Fig. 19: A-39

```
ATOM   2775  N    GLY   179      83.738   -6.382   19.135  1.00  43.45      H  N
ATOM   2776  CA   GLY   179      84.357   -5.072   19.191  1.00  46.81      H  C
ATOM   2777  C    GLY   179      84.972   -4.821   20.552  1.00  50.21      H  C
ATOM   2778  O    GLY   179      85.380   -3.707   20.869  1.00  50.30      H  O
ATOM   2779  N    LEU   180      85.020   -5.862   21.369  1.00  30.24      H  N
ATOM   2780  CA   LEU   180      85.620   -5.749   22.686  1.00  32.27      H  C
ATOM   2781  CB   LEU   180      84.706   -6.380   23.730  1.00  33.41      H  C
ATOM   2782  CG   LEU   180      83.485   -5.524   24.054  1.00  32.78      H  C
ATOM   2783  CD1  LEU   180      82.513   -6.292   24.902  1.00  27.00      H  C
ATOM   2784  CD2  LEU   180      83.943   -4.278   24.781  1.00  32.58      H  C
ATOM   2785  C    LEU   180      86.974   -6.442   22.672  1.00  32.86      H  C
ATOM   2786  O    LEU   180      87.135   -7.488   22.054  1.00  36.18      H  O
ATOM   2787  N    TYR   181      87.952   -5.843   23.336  1.00  31.41      H  N
ATOM   2788  CA   TYR   181      89.293   -6.409   23.387  1.00  32.68      H  C
ATOM   2789  CB   TYR   181      90.297   -5.323   23.792  1.00  57.58      H  C
ATOM   2790  CG   TYR   181      90.773   -4.445   22.651  1.00  56.39      H  C
ATOM   2791  CD1  TYR   181      91.591   -4.961   21.647  1.00  57.58      H  C
ATOM   2792  CE1  TYR   181      92.063   -4.155   20.605  1.00  57.08      H  C
ATOM   2793  CD2  TYR   181      90.430   -3.092   22.585  1.00  56.67      H  C
ATOM   2794  CE2  TYR   181      90.899   -2.273   21.543  1.00  57.48      H  C
ATOM   2795  CZ   TYR   181      91.717   -2.816   20.559  1.00  58.33      H  C
ATOM   2796  OH   TYR   181      92.202   -2.033   19.533  1.00  62.35      H  O
ATOM   2797  C    TYR   181      89.361   -7.573   24.375  1.00  31.73      H  C
ATOM   2798  O    TYR   181      88.581   -7.512   25.324  1.00  32.08      H  O
ATOM   2799  N    SER   182      90.287   -8.499   24.149  1.00  35.13      H  N
ATOM   2800  CA   SER   182      90.446   -9.642   25.045  1.00  32.04      H  C
ATOM   2801  CB   SER   182      89.439  -10.741   24.700  1.00  65.40      H  C
ATOM   2802  OG   SER   182      89.612  -11.868   25.543  1.00  59.63      H  O
ATOM   2803  C    SER   182      91.860  -10.209   24.970  1.00  33.65      H  C
ATOM   2804  O    SER   182      92.494  -10.187   23.906  1.00  37.13      H  O
ATOM   2805  N    LEU   183      92.351  -10.713   26.101  1.00  28.98      H  N
ATOM   2806  CA   LEU   183      93.689  -11.290   26.152  1.00  24.91      H  C
ATOM   2807  CB   LEU   183      94.753  -10.179   26.189  1.00  31.36      H  C
ATOM   2808  CG   LEU   183      94.913   -9.263   27.414  1.00  23.12      H  C
ATOM   2809  CD1  LEU   183      95.475  -10.014   28.625  1.00  27.02      H  C
ATOM   2810  CD2  LEU   183      95.849   -8.148   27.036  1.00  19.84      H  C
ATOM   2811  C    LEU   183      93.898  -12.209   27.342  1.00  24.58      H  C
ATOM   2812  O    LEU   183      93.179  -12.135   28.326  1.00  18.76      H  O
ATOM   2813  N    SER   184      94.894  -13.077   27.250  1.00  26.13      H  N
ATOM   2814  CA   SER   184      95.205  -13.967   28.357  1.00  26.65      H  C
ATOM   2815  CB   SER   184      95.000  -15.445   27.968  1.00  16.60      H  C
ATOM   2816  OG   SER   184      93.638  -15.750   27.710  1.00  22.49      H  O
ATOM   2817  C    SER   184      96.660  -13.752   28.784  1.00  22.47      H  C
ATOM   2818  O    SER   184      97.546  -13.511   27.953  1.00  21.27      H  O
ATOM   2819  N    SER   185      96.896  -13.786   30.087  1.00  27.49      H  N
ATOM   2820  CA   SER   185      98.251  -13.670   30.575  1.00  25.55      H  C
ATOM   2821  CB   SER   185      98.389  -12.634   31.678  1.00  27.24      H  C
ATOM   2822  OG   SER   185      99.760  -12.516   32.031  1.00  25.68      H  O
ATOM   2823  C    SER   185      98.460  -15.060   31.123  1.00  23.97      H  C
ATOM   2824  O    SER   185      97.652  -15.551   31.912  1.00  25.28      H  O
ATOM   2825  N    VAL   186      99.533  -15.699   30.679  1.00  29.81      H  N
ATOM   2826  CA   VAL   186      99.830  -17.060   31.064  1.00  29.28      H  C
ATOM   2827  CB   VAL   186      99.717  -17.966   29.831  1.00  20.56      H  C
ATOM   2828  CG1  VAL   186     100.305  -19.306   30.112  1.00  20.80      H  C
ATOM   2829  CG2  VAL   186      98.253  -18.121   29.446  1.00  19.74      H  C
ATOM   2830  C    VAL   186     101.204  -17.193   31.664  1.00  30.42      H  C
ATOM   2831  O    VAL   186     102.097  -16.416   31.357  1.00  31.20      H  O
ATOM   2832  N    VAL   187     101.359  -18.179   32.540  1.00  29.47      H  N
ATOM   2833  CA   VAL   187     102.645  -18.457   33.178  1.00  26.42      H  C
ATOM   2834  CB   VAL   187     102.739  -17.797   34.586  1.00  27.93      H  C
ATOM   2835  CG1  VAL   187     101.681  -18.385   35.507  1.00  26.86      H  C
ATOM   2836  CG2  VAL   187     104.134  -17.994   35.180  1.00  26.29      H  C
ATOM   2837  C    VAL   187     102.842  -19.975   33.309  1.00  20.75      H  C
ATOM   2838  O    VAL   187     101.882  -20.743   33.316  1.00  22.47      H  O
ATOM   2839  N    THR   188     104.098  -20.397   33.377  1.00   5.29      H  N
ATOM   2840  CA   THR   188     104.441  -21.807   33.539  1.00   7.86      H  C
ATOM   2841  CB   THR   188     105.280  -22.327   32.366  1.00  35.20      H  C
ATOM   2842  OG1  THR   188     106.425  -21.487   32.194  1.00  33.26      H  O
ATOM   2843  CG2  THR   188     104.453  -22.337   31.078  1.00  39.96      H  C
ATOM   2844  C    THR   188     105.270  -21.870   34.802  1.00  13.86      H  C
ATOM   2845  O    THR   188     106.194  -21.077   34.975  1.00  18.45      H  O
ATOM   2846  N    VAL   189     104.921  -22.799   35.688  1.00  28.00      H  N
ATOM   2847  CA   VAL   189     105.613  -22.963   36.965  1.00  25.42      H  C
```

Fig. 19: A-40

```
ATOM   2848  CB   VAL  189    104.755  -22.412  38.137  1.00  24.28  H  C
ATOM   2849  CG1  VAL  189    104.399  -20.951  37.904  1.00  17.23  H  C
ATOM   2850  CG2  VAL  189    103.478  -23.234  38.270  1.00  17.84  H  C
ATOM   2851  C    VAL  189    105.875  -24.439  37.242  1.00  32.15  H  C
ATOM   2852  O    VAL  189    105.386  -25.309  36.523  1.00  35.18  H  O
ATOM   2853  N    PRO  190    106.671  -24.738  38.280  1.00  50.39  H  N
ATOM   2854  CD   PRO  190    107.545  -23.823  39.036  1.00  32.03  H  C
ATOM   2855  CA   PRO  190    106.962  -26.133  38.624  1.00  50.40  H  C
ATOM   2856  CB   PRO  190    107.911  -26.001  39.814  1.00  29.50  H  C
ATOM   2857  CG   PRO  190    108.651  -24.746  39.514  1.00  29.72  H  C
ATOM   2858  C    PRO  190    105.650  -26.801  39.018  1.00  50.46  H  C
ATOM   2859  O    PRO  190    104.899  -26.267  39.834  1.00  48.43  H  O
ATOM   2860  N    SER  191    105.357  -27.953  38.436  1.00  54.29  H  N
ATOM   2861  CA   SER  191    104.122  -28.638  38.774  1.00  60.79  H  C
ATOM   2862  CB   SER  191    104.111  -30.036  38.157  1.00  30.49  H  C
ATOM   2863  OG   SER  191    104.076  -29.980  36.740  1.00  31.07  H  O
ATOM   2864  C    SER  191    104.009  -28.730  40.297  1.00  63.91  H  C
ATOM   2865  O    SER  191    102.986  -28.361  40.882  1.00  66.82  H  O
ATOM   2866  N    SER  192    105.084  -29.201  40.924  1.00  39.50  H  N
ATOM   2867  CA   SER  192    105.177  -29.374  42.376  1.00  40.99  H  C
ATOM   2868  CB   SER  192    106.602  -29.776  42.739  1.00  41.75  H  C
ATOM   2869  OG   SER  192    107.475  -28.675  42.565  1.00  41.65  H  O
ATOM   2870  C    SER  192    104.795  -28.150  43.220  1.00  42.26  H  C
ATOM   2871  O    SER  192    104.403  -28.286  44.381  1.00  48.17  H  O
ATOM   2872  N    SER  193    104.923  -26.960  42.645  1.00  20.64  H  N
ATOM   2873  CA   SER  193    104.601  -25.733  43.365  1.00  22.36  H  C
ATOM   2874  CB   SER  193    105.396  -24.567  42.771  1.00  39.90  H  C
ATOM   2875  OG   SER  193    104.973  -24.284  41.447  1.00  36.65  H  O
ATOM   2876  C    SER  193    103.097  -25.380  43.392  1.00  22.92  H  C
ATOM   2877  O    SER  193    102.697  -24.363  43.963  1.00  25.84  H  O
ATOM   2878  N    LEU  194    102.268  -26.218  42.776  1.00  41.78  H  N
ATOM   2879  CA   LEU  194    100.827  -25.974  42.741  1.00  45.87  H  C
ATOM   2880  CB   LEU  194    100.172  -26.850  41.677  1.00  23.80  H  C
ATOM   2881  CG   LEU  194    100.533  -26.605  40.216  1.00  21.31  H  C
ATOM   2882  CD1  LEU  194     99.975  -27.739  39.377  1.00  19.27  H  C
ATOM   2883  CD2  LEU  194     99.973  -25.246  39.757  1.00  15.31  H  C
ATOM   2884  C    LEU  194    100.177  -26.276  44.080  1.00  49.01  H  C
ATOM   2885  O    LEU  194     99.209  -25.623  44.478  1.00  48.38  H  O
ATOM   2886  N    GLY  195    100.718  -27.272  44.770  1.00  65.65  H  N
ATOM   2887  CA   GLY  195    100.160  -27.676  46.043  1.00  68.76  H  C
ATOM   2888  C    GLY  195    100.625  -26.877  47.235  1.00  66.22  H  C
ATOM   2889  O    GLY  195    100.051  -26.992  48.314  1.00  68.30  H  O
ATOM   2890  N    THR  196    101.659  -26.067  47.053  1.00  33.26  H  N
ATOM   2891  CA   THR  196    102.175  -25.265  48.155  1.00  32.73  H  C
ATOM   2892  CB   THR  196    103.575  -25.763  48.585  1.00  30.77  H  C
ATOM   2893  OG1  THR  196    104.489  -25.676  47.478  1.00  28.63  H  O
ATOM   2894  CG2  THR  196    103.488  -27.213  49.071  1.00  27.23  H  C
ATOM   2895  C    THR  196    102.251  -23.786  47.813  1.00  35.97  H  C
ATOM   2896  O    THR  196    102.179  -22.933  48.695  1.00  36.72  H  O
ATOM   2897  N    GLN  197    102.389  -23.488  46.527  1.00  53.90  H  N
ATOM   2898  CA   GLN  197    102.478  -22.110  46.060  1.00  54.25  H  C
ATOM   2899  CB   GLN  197    103.480  -22.031  44.906  1.00  42.12  H  C
ATOM   2900  CG   GLN  197    104.561  -20.975  45.045  1.00  45.66  H  C
ATOM   2901  CD   GLN  197    104.051  -19.587  44.765  1.00  49.49  H  C
ATOM   2902  OE1  GLN  197    103.257  -19.032  45.528  1.00  50.05  H  O
ATOM   2903  NE2  GLN  197    104.500  -19.013  43.656  1.00  49.01  H  N
ATOM   2904  C    GLN  197    101.105  -21.617  45.604  1.00  52.98  H  C
ATOM   2905  O    GLN  197    100.314  -22.382  45.050  1.00  55.53  H  O
ATOM   2906  N    THR  198    100.829  -20.338  45.847  1.00  30.38  H  N
ATOM   2907  CA   THR  198     99.559  -19.719  45.470  1.00  29.29  H  C
ATOM   2908  CB   THR  198     98.922  -18.970  46.677  1.00  45.77  H  C
ATOM   2909  OG1  THR  198     97.546  -18.682  46.404  1.00  43.55  H  O
ATOM   2910  CG2  THR  198     99.643  -17.644  46.929  1.00  47.95  H  C
ATOM   2911  C    THR  198     99.811  -18.719  44.338  1.00  27.94  H  C
ATOM   2912  O    THR  198    100.722  -17.891  44.413  1.00  31.22  H  O
ATOM   2913  N    TYR  199     99.008  -18.789  43.285  1.00  40.84  H  N
ATOM   2914  CA   TYR  199     99.191  -17.874  42.168  1.00  31.26  H  C
ATOM   2915  CB   TYR  199     99.402  -18.681  40.880  1.00  39.46  H  C
ATOM   2916  CG   TYR  199    100.677  -19.496  40.904  1.00  33.83  H  C
ATOM   2917  CD1  TYR  199    101.911  -18.901  40.630  1.00  31.63  H  C
ATOM   2918  CE1  TYR  199    103.107  -19.626  40.735  1.00  31.28  H  C
ATOM   2919  CD2  TYR  199    100.662  -20.847  41.282  1.00  32.94  H  C
ATOM   2920  CE2  TYR  199    101.850  -21.590  41.392  1.00  33.91  H  C
```

Fig. 19: A-41

| ATOM | 2921 | CZ | TYR | 199 | 103.069 | -20.972 | 41.118 | 1.00 | 33.40 | H | C |
|---|---|---|---|---|---|---|---|---|---|---|---|
| ATOM | 2922 | OH | TYR | 199 | 104.244 | -21.685 | 41.223 | 1.00 | 37.29 | H | O |
| ATOM | 2923 | C | TYR | 199 | 98.029 | -16.897 | 42.014 | 1.00 | 31.50 | H | C |
| ATOM | 2924 | O | TYR | 199 | 96.876 | -17.302 | 41.913 | 1.00 | 32.18 | H | O |
| ATOM | 2925 | N | ILE | 200 | 98.342 | -15.605 | 42.026 | 1.00 | 38.61 | H | N |
| ATOM | 2926 | CA | ILE | 200 | 97.329 | -14.566 | 41.858 | 1.00 | 39.11 | H | C |
| ATOM | 2927 | CB | ILE | 200 | 97.265 | -13.574 | 43.051 | 1.00 | 27.10 | H | C |
| ATOM | 2928 | CG2 | ILE | 200 | 96.185 | -12.540 | 42.793 | 1.00 | 26.36 | H | C |
| ATOM | 2929 | CG1 | ILE | 200 | 96.978 | -14.301 | 44.363 | 1.00 | 30.59 | H | C |
| ATOM | 2930 | CD1 | ILE | 200 | 98.119 | -15.184 | 44.842 | 1.00 | 36.15 | H | C |
| ATOM | 2931 | C | ILE | 200 | 97.730 | -13.736 | 40.649 | 1.00 | 41.59 | H | C |
| ATOM | 2932 | O | ILE | 200 | 98.916 | -13.517 | 40.415 | 1.00 | 45.01 | H | O |
| ATOM | 2933 | N | CYS | 201 | 96.758 | -13.283 | 39.867 | 1.00 | 30.01 | H | N |
| ATOM | 2934 | CA | CYS | 201 | 97.092 | -12.434 | 38.735 | 1.00 | 27.23 | H | C |
| ATOM | 2935 | C | CYS | 201 | 96.476 | -11.075 | 39.011 | 1.00 | 24.60 | H | C |
| ATOM | 2936 | O | CYS | 201 | 95.307 | -10.967 | 39.386 | 1.00 | 22.36 | H | O |
| ATOM | 2937 | CB | CYS | 201 | 96.577 | -12.997 | 37.394 | 1.00 | 42.80 | H | C |
| ATOM | 2938 | SG | CYS | 201 | 94.784 | -12.909 | 37.090 | 1.00 | 39.16 | H | S |
| ATOM | 2939 | N | ASN | 202 | 97.282 | -10.035 | 38.849 | 1.00 | 26.40 | H | N |
| ATOM | 2940 | CA | ASN | 202 | 96.819 | -8.683 | 39.080 | 1.00 | 32.39 | H | C |
| ATOM | 2941 | CB | ASN | 202 | 97.884 | -7.902 | 39.846 | 1.00 | 36.85 | H | C |
| ATOM | 2942 | CG | ASN | 202 | 98.507 | -8.720 | 40.954 | 1.00 | 39.80 | H | C |
| ATOM | 2943 | OD1 | ASN | 202 | 99.570 | -9.314 | 40.779 | 1.00 | 38.11 | H | O |
| ATOM | 2944 | ND2 | ASN | 202 | 97.837 | -8.776 | 42.097 | 1.00 | 41.02 | H | N |
| ATOM | 2945 | C | ASN | 202 | 96.530 | -8.025 | 37.743 | 1.00 | 36.08 | H | C |
| ATOM | 2946 | O | ASN | 202 | 97.419 | -7.867 | 36.911 | 1.00 | 40.34 | H | O |
| ATOM | 2947 | N | VAL | 203 | 95.273 | -7.668 | 37.533 | 1.00 | 28.99 | H | N |
| ATOM | 2948 | CA | VAL | 203 | 94.868 | -7.017 | 36.295 | 1.00 | 29.18 | H | C |
| ATOM | 2949 | CB | VAL | 203 | 93.691 | -7.781 | 35.624 | 1.00 | 21.70 | H | C |
| ATOM | 2950 | CG1 | VAL | 203 | 93.321 | -7.134 | 34.274 | 1.00 | 17.35 | H | C |
| ATOM | 2951 | CG2 | VAL | 203 | 94.067 | -9.236 | 35.450 | 1.00 | 25.16 | H | C |
| ATOM | 2952 | C | VAL | 203 | 94.443 | -5.580 | 36.615 | 1.00 | 32.31 | H | C |
| ATOM | 2953 | O | VAL | 203 | 93.808 | -5.320 | 37.643 | 1.00 | 27.84 | H | O |
| ATOM | 2954 | N | ASN | 204 | 94.799 | -4.648 | 35.741 | 1.00 | 45.86 | H | N |
| ATOM | 2955 | CA | ASN | 204 | 94.442 | -3.266 | 35.979 | 1.00 | 50.50 | H | C |
| ATOM | 2956 | CB | ASN | 204 | 95.565 | -2.570 | 36.739 | 1.00 | 59.79 | H | C |
| ATOM | 2957 | CG | ASN | 204 | 95.186 | -1.176 | 37.164 | 1.00 | 65.34 | H | C |
| ATOM | 2958 | OD1 | ASN | 204 | 94.801 | -0.347 | 36.338 | 1.00 | 69.10 | H | O |
| ATOM | 2959 | ND2 | ASN | 204 | 95.287 | -0.906 | 38.459 | 1.00 | 65.59 | H | N |
| ATOM | 2960 | C | ASN | 204 | 94.109 | -2.486 | 34.709 | 1.00 | 51.54 | H | C |
| ATOM | 2961 | O | ASN | 204 | 94.985 | -2.164 | 33.905 | 1.00 | 51.77 | H | O |
| ATOM | 2962 | N | HIS | 205 | 92.828 | -2.176 | 34.550 | 1.00 | 30.40 | H | N |
| ATOM | 2963 | CA | HIS | 205 | 92.338 | -1.431 | 33.396 | 1.00 | 29.10 | H | C |
| ATOM | 2964 | CB | HIS | 205 | 90.994 | -1.998 | 32.957 | 1.00 | 20.87 | H | C |
| ATOM | 2965 | CG | HIS | 205 | 90.444 | -1.371 | 31.718 | 1.00 | 25.68 | H | C |
| ATOM | 2966 | CD2 | HIS | 205 | 89.209 | -0.889 | 31.437 | 1.00 | 28.69 | H | C |
| ATOM | 2967 | ND1 | HIS | 205 | 91.165 | -1.282 | 30.548 | 1.00 | 23.44 | H | N |
| ATOM | 2968 | CE1 | HIS | 205 | 90.396 | -0.780 | 29.597 | 1.00 | 25.19 | H | C |
| ATOM | 2969 | NE2 | HIS | 205 | 89.203 | -0.534 | 30.110 | 1.00 | 28.16 | H | N |
| ATOM | 2970 | C | HIS | 205 | 92.157 | 0.022 | 33.793 | 1.00 | 30.12 | H | C |
| ATOM | 2971 | O | HIS | 205 | 91.057 | 0.429 | 34.173 | 1.00 | 28.02 | H | O |
| ATOM | 2972 | N | LYS | 206 | 93.228 | 0.805 | 33.714 | 1.00 | 50.94 | H | N |
| ATOM | 2973 | CA | LYS | 206 | 93.138 | 2.209 | 34.084 | 1.00 | 49.11 | H | C |
| ATOM | 2974 | CB | LYS | 206 | 94.486 | 2.906 | 33.867 | 1.00 | 50.82 | H | C |
| ATOM | 2975 | CG | LYS | 206 | 95.536 | 2.476 | 34.895 | 1.00 | 57.82 | H | C |
| ATOM | 2976 | CD | LYS | 206 | 96.809 | 3.325 | 34.857 | 1.00 | 61.64 | H | C |
| ATOM | 2977 | CE | LYS | 206 | 97.793 | 2.906 | 35.959 | 1.00 | 63.00 | H | C |
| ATOM | 2978 | NZ | LYS | 206 | 99.049 | 3.715 | 35.960 | 1.00 | 66.30 | H | N |
| ATOM | 2979 | C | LYS | 206 | 92.017 | 2.949 | 33.353 | 1.00 | 47.68 | H | C |
| ATOM | 2980 | O | LYS | 206 | 91.318 | 3.765 | 33.955 | 1.00 | 46.73 | H | O |
| ATOM | 2981 | N | PRO | 207 | 91.810 | 2.650 | 32.057 | 1.00 | 33.42 | H | N |
| ATOM | 2982 | CD | PRO | 207 | 92.613 | 1.722 | 31.239 | 1.00 | 21.52 | H | C |
| ATOM | 2983 | CA | PRO | 207 | 90.770 | 3.285 | 31.241 | 1.00 | 34.06 | H | C |
| ATOM | 2984 | CB | PRO | 207 | 90.831 | 2.501 | 29.936 | 1.00 | 21.18 | H | C |
| ATOM | 2985 | CG | PRO | 207 | 92.286 | 2.156 | 29.831 | 1.00 | 24.69 | H | C |
| ATOM | 2986 | C | PRO | 207 | 89.366 | 3.280 | 31.846 | 1.00 | 34.36 | H | C |
| ATOM | 2987 | O | PRO | 207 | 88.452 | 3.927 | 31.311 | 1.00 | 32.31 | H | O |
| ATOM | 2988 | N | SER | 208 | 89.190 | 2.545 | 32.944 | 1.00 | 25.18 | H | N |
| ATOM | 2989 | CA | SER | 208 | 87.893 | 2.481 | 33.628 | 1.00 | 28.11 | H | C |
| ATOM | 2990 | CB | SER | 208 | 87.055 | 1.320 | 33.094 | 1.00 | 29.27 | H | C |
| ATOM | 2991 | OG | SER | 208 | 87.724 | 0.096 | 33.315 | 1.00 | 27.44 | H | O |
| ATOM | 2992 | C | SER | 208 | 88.120 | 2.314 | 35.126 | 1.00 | 31.08 | H | C |
| ATOM | 2993 | O | SER | 208 | 87.266 | 1.789 | 35.846 | 1.00 | 34.78 | H | O |

Fig. 19: A-42

| ATOM | 2994 | N | ASN | 209 | 89.284 | 2.777 | 35.573 | 1.00 | 68.02 | H | N |
|---|---|---|---|---|---|---|---|---|---|---|---|
| ATOM | 2995 | CA | ASN | 209 | 89.678 | 2.701 | 36.970 | 1.00 | 70.18 | H | C |
| ATOM | 2996 | CB | ASN | 209 | 89.073 | 3.879 | 37.741 | 1.00 | 49.77 | H | C |
| ATOM | 2997 | CG | ASN | 209 | 89.673 | 4.044 | 39.125 | 1.00 | 56.50 | H | C |
| ATOM | 2998 | OD1 | ASN | 209 | 90.885 | 3.963 | 39.301 | 1.00 | 62.08 | H | O |
| ATOM | 2999 | ND2 | ASN | 209 | 88.824 | 4.290 | 40.114 | 1.00 | 57.03 | H | N |
| ATOM | 3000 | C | ASN | 209 | 89.267 | 1.360 | 37.593 | 1.00 | 68.80 | H | C |
| ATOM | 3001 | O | ASN | 209 | 88.708 | 1.304 | 38.690 | 1.00 | 68.05 | H | O |
| ATOM | 3002 | N | THR | 210 | 89.555 | 0.282 | 36.871 | 1.00 | 35.45 | H | N |
| ATOM | 3003 | CA | THR | 210 | 89.246 | -1.061 | 37.322 | 1.00 | 37.08 | H | C |
| ATOM | 3004 | CB | THR | 210 | 88.640 | -1.883 | 36.201 | 1.00 | 55.80 | H | C |
| ATOM | 3005 | OG1 | THR | 210 | 87.416 | -1.273 | 35.787 | 1.00 | 56.14 | H | O |
| ATOM | 3006 | CG2 | THR | 210 | 88.367 | -3.303 | 36.668 | 1.00 | 57.05 | H | C |
| ATOM | 3007 | C | THR | 210 | 90.538 | -1.719 | 37.762 | 1.00 | 36.35 | H | C |
| ATOM | 3008 | O | THR | 210 | 91.613 | -1.388 | 37.266 | 1.00 | 34.79 | H | O |
| ATOM | 3009 | N | LYS | 211 | 90.426 | -2.655 | 38.692 | 1.00 | 33.96 | H | N |
| ATOM | 3010 | CA | LYS | 211 | 91.588 | -3.352 | 39.207 | 1.00 | 34.09 | H | C |
| ATOM | 3011 | CB | LYS | 211 | 92.366 | -2.422 | 40.154 | 1.00 | 52.60 | H | C |
| ATOM | 3012 | CG | LYS | 211 | 93.360 | -3.095 | 41.117 | 1.00 | 57.40 | H | C |
| ATOM | 3013 | CD | LYS | 211 | 94.338 | -4.040 | 40.416 | 1.00 | 62.07 | H | C |
| ATOM | 3014 | CE | LYS | 211 | 95.636 | -4.228 | 41.216 | 1.00 | 64.56 | H | C |
| ATOM | 3015 | NZ | LYS | 211 | 95.432 | -4.548 | 42.660 | 1.00 | 65.70 | H | N |
| ATOM | 3016 | C | LYS | 211 | 91.147 | -4.609 | 39.935 | 1.00 | 32.12 | H | C |
| ATOM | 3017 | O | LYS | 211 | 90.611 | -4.525 | 41.036 | 1.00 | 32.03 | H | O |
| ATOM | 3018 | N | VAL | 212 | 91.357 | -5.772 | 39.322 | 1.00 | 43.02 | H | N |
| ATOM | 3019 | CA | VAL | 212 | 90.971 | -7.017 | 39.973 | 1.00 | 37.80 | H | C |
| ATOM | 3020 | CB | VAL | 212 | 89.728 | -7.685 | 39.308 | 1.00 | 28.95 | H | C |
| ATOM | 3021 | CG1 | VAL | 212 | 88.671 | -6.639 | 39.021 | 1.00 | 26.33 | H | C |
| ATOM | 3022 | CG2 | VAL | 212 | 90.125 | -8.431 | 38.059 | 1.00 | 26.83 | H | C |
| ATOM | 3023 | C | VAL | 212 | 92.086 | -8.042 | 40.020 | 1.00 | 39.84 | H | C |
| ATOM | 3024 | O | VAL | 212 | 92.832 | -8.224 | 39.057 | 1.00 | 39.92 | H | O |
| ATOM | 3025 | N | ASP | 213 | 92.184 | -8.709 | 41.162 | 1.00 | 52.39 | H | N |
| ATOM | 3026 | CA | ASP | 213 | 93.177 | -9.743 | 41.376 | 1.00 | 49.02 | H | C |
| ATOM | 3027 | CB | ASP | 213 | 93.900 | -9.493 | 42.692 | 1.00 | 46.86 | H | C |
| ATOM | 3028 | CG | ASP | 213 | 94.548 | -8.128 | 42.740 | 1.00 | 52.80 | H | C |
| ATOM | 3029 | OD1 | ASP | 213 | 95.420 | -7.852 | 41.887 | 1.00 | 56.11 | H | O |
| ATOM | 3030 | OD2 | ASP | 213 | 94.182 | -7.329 | 43.626 | 1.00 | 57.38 | H | O |
| ATOM | 3031 | C | ASP | 213 | 92.433 | -11.067 | 41.423 | 1.00 | 46.03 | H | C |
| ATOM | 3032 | O | ASP | 213 | 91.537 | -11.248 | 42.236 | 1.00 | 45.16 | H | O |
| ATOM | 3033 | N | LYS | 214 | 92.796 | -11.993 | 40.548 | 1.00 | 33.42 | H | N |
| ATOM | 3034 | CA | LYS | 214 | 92.124 | -13.282 | 40.502 | 1.00 | 29.46 | H | C |
| ATOM | 3035 | CB | LYS | 214 | 91.732 | -13.602 | 39.055 | 0.00 | 52.86 | H | C |
| ATOM | 3036 | CG | LYS | 214 | 90.422 | -14.370 | 38.875 | 0.00 | 47.62 | H | C |
| ATOM | 3037 | CD | LYS | 214 | 90.398 | -15.699 | 39.614 | 0.00 | 43.68 | H | C |
| ATOM | 3038 | CE | LYS | 214 | 89.852 | -15.541 | 41.024 | 0.00 | 41.24 | H | C |
| ATOM | 3039 | NZ | LYS | 214 | 88.452 | -15.037 | 41.021 | 0.00 | 39.27 | H | N |
| ATOM | 3040 | C | LYS | 214 | 93.027 | -14.377 | 41.047 | 1.00 | 29.66 | H | C |
| ATOM | 3041 | O | LYS | 214 | 94.160 | -14.549 | 40.585 | 1.00 | 27.06 | H | O |
| ATOM | 3042 | N | LYS | 215 | 92.533 | -15.103 | 42.045 | 1.00 | 38.49 | H | N |
| ATOM | 3043 | CA | LYS | 215 | 93.289 | -16.207 | 42.617 | 1.00 | 34.59 | H | C |
| ATOM | 3044 | CB | LYS | 215 | 92.788 | -16.531 | 44.032 | 0.00 | 48.10 | H | C |
| ATOM | 3045 | CG | LYS | 215 | 92.812 | -15.343 | 44.987 | 0.00 | 42.43 | H | C |
| ATOM | 3046 | CD | LYS | 215 | 92.403 | -15.737 | 46.401 | 0.00 | 38.17 | H | C |
| ATOM | 3047 | CE | LYS | 215 | 93.458 | -16.597 | 47.089 | 0.00 | 35.48 | H | C |
| ATOM | 3048 | NZ | LYS | 215 | 93.695 | -17.895 | 46.397 | 0.00 | 33.32 | H | N |
| ATOM | 3049 | C | LYS | 215 | 93.042 | -17.391 | 41.675 | 1.00 | 36.50 | H | C |
| ATOM | 3050 | O | LYS | 215 | 91.901 | -17.770 | 41.413 | 1.00 | 38.63 | H | O |
| ATOM | 3051 | N | VAL | 216 | 94.113 | -17.939 | 41.122 | 1.00 | 32.15 | H | N |
| ATOM | 3052 | CA | VAL | 216 | 93.996 | -19.081 | 40.224 | 1.00 | 32.08 | H | C |
| ATOM | 3053 | CB | VAL | 216 | 94.801 | -18.850 | 38.923 | 1.00 | 21.03 | H | C |
| ATOM | 3054 | CG1 | VAL | 216 | 94.435 | -19.912 | 37.880 | 1.00 | 20.14 | H | C |
| ATOM | 3055 | CG2 | VAL | 216 | 94.482 | -17.480 | 38.375 | 1.00 | 18.92 | H | C |
| ATOM | 3056 | C | VAL | 216 | 94.504 | -20.334 | 40.948 | 1.00 | 33.21 | H | C |
| ATOM | 3057 | O | VAL | 216 | 95.696 | -20.441 | 41.248 | 1.00 | 33.32 | H | O |
| ATOM | 3058 | N | GLU | 217 | 93.586 | -21.269 | 41.219 | 1.00 | 45.06 | H | N |
| ATOM | 3059 | CA | GLU | 217 | 93.871 | -22.508 | 41.949 | 1.00 | 48.19 | H | C |
| ATOM | 3060 | CB | GLU | 217 | 93.065 | -22.532 | 43.250 | 1.00 | 91.11 | H | C |
| ATOM | 3061 | CG | GLU | 217 | 93.114 | -21.248 | 44.065 | 1.00 | 95.99 | H | C |
| ATOM | 3062 | CD | GLU | 217 | 91.872 | -21.005 | 44.901 | 1.00 | 101.94 | H | C |
| ATOM | 3063 | OE1 | GLU | 217 | 90.757 | -21.353 | 44.453 | 1.00 | 105.02 | H | O |
| ATOM | 3064 | OE2 | GLU | 217 | 92.013 | -20.475 | 46.029 | 1.00 | 105.37 | H | O |
| ATOM | 3065 | C | GLU | 217 | 93.426 | -23.720 | 41.109 | 1.00 | 48.96 | H | C |
| ATOM | 3066 | O | GLU | 217 | 92.500 | -23.643 | 40.332 | 1.00 | 51.24 | H | O |

Fig. 19: A-43

| ATOM | 3067 | N | PRO | 218 | 94.078 | -24.870 | 41.265 | 1.00 | 42.53 | H | N |
|------|------|-----|-----|-----|--------|---------|--------|------|--------|---|---|
| ATOM | 3068 | CD | PRO | 218 | 95.339 | -25.074 | 41.993 | 1.00 | 48.02 | H | C |
| ATOM | 3069 | CA | PRO | 218 | 93.711 | -26.079 | 40.509 | 1.00 | 40.69 | H | C |
| ATOM | 3070 | CB | PRO | 218 | 94.962 | -26.924 | 40.609 | 1.00 | 42.70 | H | C |
| ATOM | 3071 | CG | PRO | 218 | 95.482 | -26.557 | 41.957 | 1.00 | 44.19 | H | C |
| ATOM | 3072 | C | PRO | 218 | 92.544 | -26.782 | 41.183 | 1.00 | 41.85 | H | C |
| ATOM | 3073 | O | PRO | 218 | 92.513 | -26.844 | 42.403 | 1.00 | 45.36 | H | O |
| ATOM | 3074 | N | LYS | 219 | 91.638 | -27.354 | 40.396 | 1.00 | 112.06 | H | N |
| ATOM | 3075 | CA | LYS | 219 | 90.475 | -28.045 | 40.934 | 1.00 | 111.92 | H | C |
| ATOM | 3076 | CB | LYS | 219 | 89.635 | -28.618 | 39.794 | 0.00 | 52.93 | H | C |
| ATOM | 3077 | CG | LYS | 219 | 89.522 | -27.658 | 38.654 | 0.00 | 47.21 | H | C |
| ATOM | 3078 | CD | LYS | 219 | 88.205 | -27.801 | 37.948 | 0.00 | 42.71 | H | C |
| ATOM | 3079 | CE | LYS | 219 | 88.174 | -26.793 | 36.845 | 0.00 | 39.84 | H | C |
| ATOM | 3080 | NZ | LYS | 219 | 86.847 | -26.599 | 36.249 | 0.00 | 37.57 | H | N |
| ATOM | 3081 | C | LYS | 219 | 90.867 | -29.169 | 41.892 | 1.00 | 116.73 | H | C |
| ATOM | 3082 | O | LYS | 219 | 90.330 | -29.223 | 43.021 | 1.00 | 116.18 | H | O |
| ATOM | 3083 | OXT | LYS | 219 | 91.705 | -30.007 | 41.503 | 1.00 | 36.39 | H | O |
| ATOM | 3084 | CB | ILE | 2 | 109.298 | 10.543 | -2.157 | 1.00 | 31.85 | L | C |
| ATOM | 3085 | CG2 | ILE | 2 | 110.285 | 9.382 | -2.130 | 1.00 | 31.85 | L | C |
| ATOM | 3086 | CG1 | ILE | 2 | 109.803 | 11.664 | -3.069 | 1.00 | 31.85 | L | C |
| ATOM | 3087 | CD1 | ILE | 2 | 111.143 | 12.240 | -2.656 | 1.00 | 31.85 | L | C |
| ATOM | 3088 | C | ILE | 2 | 107.518 | 8.858 | -1.778 | 1.00 | 41.66 | L | C |
| ATOM | 3089 | O | ILE | 2 | 107.155 | 9.019 | -0.613 | 1.00 | 41.66 | L | O |
| ATOM | 3090 | N | ILE | 2 | 106.898 | 11.133 | -2.646 | 1.00 | 41.66 | L | N |
| ATOM | 3091 | CA | ILE | 2 | 107.922 | 10.043 | -2.648 | 1.00 | 41.66 | L | C |
| ATOM | 3092 | N | GLN | 3 | 107.597 | 7.665 | -2.361 | 1.00 | 28.81 | L | N |
| ATOM | 3093 | CA | GLN | 3 | 107.244 | 6.433 | -1.669 | 1.00 | 28.81 | L | C |
| ATOM | 3094 | CB | GLN | 3 | 106.206 | 5.677 | -2.484 | 1.00 | 56.92 | L | C |
| ATOM | 3095 | CG | GLN | 3 | 105.708 | 4.412 | -1.837 | 1.00 | 56.92 | L | C |
| ATOM | 3096 | CD | GLN | 3 | 104.579 | 3.778 | -2.622 | 1.00 | 56.92 | L | C |
| ATOM | 3097 | OE1 | GLN | 3 | 104.124 | 2.681 | -2.298 | 1.00 | 56.92 | L | O |
| ATOM | 3098 | NE2 | GLN | 3 | 104.116 | 4.469 | -3.661 | 1.00 | 56.92 | L | N |
| ATOM | 3099 | C | GLN | 3 | 108.482 | 5.557 | -1.428 | 1.00 | 28.81 | L | C |
| ATOM | 3100 | O | GLN | 3 | 109.297 | 5.322 | -2.327 | 1.00 | 28.81 | L | O |
| ATOM | 3101 | N | LEU | 4 | 108.615 | 5.088 | -0.195 | 1.00 | 39.62 | L | N |
| ATOM | 3102 | CA | LEU | 4 | 109.744 | 4.260 | 0.198 | 1.00 | 39.62 | L | C |
| ATOM | 3103 | CB | LEU | 4 | 110.377 | 4.820 | 1.469 | 1.00 | 19.64 | L | C |
| ATOM | 3104 | CG | LEU | 4 | 111.546 | 5.792 | 1.348 | 1.00 | 19.64 | L | C |
| ATOM | 3105 | CD1 | LEU | 4 | 111.407 | 6.643 | 0.092 | 1.00 | 19.64 | L | C |
| ATOM | 3106 | CD2 | LEU | 4 | 111.614 | 6.640 | 2.617 | 1.00 | 19.64 | L | C |
| ATOM | 3107 | C | LEU | 4 | 109.323 | 2.823 | 0.445 | 1.00 | 39.62 | L | C |
| ATOM | 3108 | O | LEU | 4 | 108.470 | 2.548 | 1.289 | 1.00 | 39.62 | L | O |
| ATOM | 3109 | N | THR | 5 | 109.935 | 1.903 | -0.289 | 1.00 | 16.92 | L | N |
| ATOM | 3110 | CA | THR | 5 | 109.634 | 0.485 | -0.152 | 1.00 | 16.92 | L | C |
| ATOM | 3111 | CB | THR | 5 | 108.945 | -0.038 | -1.437 | 1.00 | 21.45 | L | C |
| ATOM | 3112 | OG1 | THR | 5 | 109.307 | -1.402 | -1.651 | 1.00 | 21.45 | L | O |
| ATOM | 3113 | CG2 | THR | 5 | 109.324 | 0.802 | -2.641 | 1.00 | 21.45 | L | C |
| ATOM | 3114 | C | THR | 5 | 110.908 | -0.312 | 0.186 | 1.00 | 16.92 | L | C |
| ATOM | 3115 | O | THR | 5 | 111.849 | -0.382 | -0.601 | 1.00 | 16.92 | L | O |
| ATOM | 3116 | N | GLN | 6 | 110.919 | -0.880 | 1.391 | 1.00 | 17.69 | L | N |
| ATOM | 3117 | CA | GLN | 6 | 112.040 | -1.661 | 1.933 | 1.00 | 17.69 | L | C |
| ATOM | 3118 | CB | GLN | 6 | 112.078 | -1.544 | 3.468 | 1.00 | 15.96 | L | C |
| ATOM | 3119 | CG | GLN | 6 | 111.898 | -0.138 | 4.014 | 1.00 | 15.96 | L | C |
| ATOM | 3120 | CD | GLN | 6 | 112.007 | -0.060 | 5.535 | 1.00 | 15.96 | L | C |
| ATOM | 3121 | OE1 | GLN | 6 | 111.626 | 0.944 | 6.139 | 1.00 | 15.96 | L | O |
| ATOM | 3122 | NE2 | GLN | 6 | 112.541 | -1.115 | 6.158 | 1.00 | 15.96 | L | N |
| ATOM | 3123 | C | GLN | 6 | 111.962 | -3.143 | 1.588 | 1.00 | 17.69 | L | C |
| ATOM | 3124 | O | GLN | 6 | 110.882 | -3.675 | 1.352 | 1.00 | 17.69 | L | O |
| ATOM | 3125 | N | SER | 7 | 113.107 | -3.814 | 1.595 | 1.00 | 44.56 | L | N |
| ATOM | 3126 | CA | SER | 7 | 113.148 | -5.238 | 1.293 | 1.00 | 44.56 | L | C |
| ATOM | 3127 | CB | SER | 7 | 113.109 | -5.470 | -0.214 | 1.00 | 33.18 | L | C |
| ATOM | 3128 | OG | SER | 7 | 114.194 | -4.813 | -0.837 | 1.00 | 33.18 | L | O |
| ATOM | 3129 | C | SER | 7 | 114.394 | -5.898 | 1.855 | 1.00 | 44.56 | L | C |
| ATOM | 3130 | O | SER | 7 | 115.480 | -5.328 | 1.811 | 1.00 | 44.56 | L | O |
| ATOM | 3131 | N | PRO | 8 | 114.246 | -7.107 | 2.415 | 1.00 | 19.10 | L | N |
| ATOM | 3132 | CD | PRO | 8 | 115.292 | -7.921 | 3.063 | 1.00 | 16.76 | L | C |
| ATOM | 3133 | CA | PRO | 8 | 112.945 | -7.771 | 2.494 | 1.00 | 19.10 | L | C |
| ATOM | 3134 | CB | PRO | 8 | 113.303 | -9.161 | 3.004 | 1.00 | 16.76 | L | C |
| ATOM | 3135 | CG | PRO | 8 | 114.481 | -8.882 | 3.905 | 1.00 | 16.76 | L | C |
| ATOM | 3136 | C | PRO | 8 | 112.068 | -7.023 | 3.479 | 1.00 | 19.10 | L | C |
| ATOM | 3137 | O | PRO | 8 | 112.517 | -6.069 | 4.125 | 1.00 | 19.10 | L | O |
| ATOM | 3138 | N | SER | 9 | 110.822 | -7.460 | 3.589 | 1.00 | 12.41 | L | N |
| ATOM | 3139 | CA | SER | 9 | 109.885 | -6.851 | 4.516 | 1.00 | 12.41 | L | C |

Fig. 19: A-44

| ATOM | 3140 | CB | SER | 9 | 108.466 | -7.059 | 4.023 | 1.00 | 25.43 | L | C |
| ATOM | 3141 | OG | SER | 9 | 108.345 | -6.555 | 2.707 | 1.00 | 25.43 | L | O |
| ATOM | 3142 | C | SER | 9 | 110.083 | -7.558 | 5.837 | 1.00 | 12.41 | L | C |
| ATOM | 3143 | O | SER | 9 | 109.904 | -6.983 | 6.904 | 1.00 | 12.41 | L | O |
| ATOM | 3144 | N | SER | 10 | 110.492 | -8.817 | 5.745 | 1.00 | 33.63 | L | N |
| ATOM | 3145 | CA | SER | 10 | 110.720 | -9.645 | 6.910 | 1.00 | 33.63 | L | C |
| ATOM | 3146 | CB | SER | 10 | 109.490 | -10.517 | 7.144 | 1.00 | 43.13 | L | C |
| ATOM | 3147 | OG | SER | 10 | 109.614 | -11.248 | 8.338 | 1.00 | 43.13 | L | O |
| ATOM | 3148 | C | SER | 10 | 111.942 | -10.504 | 6.624 | 1.00 | 33.63 | L | C |
| ATOM | 3149 | O | SER | 10 | 112.226 | -10.814 | 5.470 | 1.00 | 33.63 | L | O |
| ATOM | 3150 | N | LEU | 11 | 112.677 | -10.880 | 7.666 | 1.00 | 38.19 | L | N |
| ATOM | 3151 | CA | LEU | 11 | 113.867 | -11.709 | 7.484 | 1.00 | 38.19 | L | C |
| ATOM | 3152 | CB | LEU | 11 | 115.020 | -10.880 | 6.894 | 1.00 | 33.64 | L | C |
| ATOM | 3153 | CG | LEU | 11 | 115.721 | -9.849 | 7.793 | 1.00 | 33.64 | L | C |
| ATOM | 3154 | CD1 | LEU | 11 | 116.757 | -10.532 | 8.667 | 1.00 | 33.64 | L | C |
| ATOM | 3155 | CD2 | LEU | 11 | 116.401 | -8.807 | 6.927 | 1.00 | 33.64 | L | C |
| ATOM | 3156 | C | LEU | 11 | 114.319 | -12.335 | 8.792 | 1.00 | 38.19 | L | C |
| ATOM | 3157 | O | LEU | 11 | 114.365 | -11.672 | 9.829 | 1.00 | 38.19 | L | O |
| ATOM | 3158 | N | SER | 12 | 114.661 | -13.616 | 8.736 | 1.00 | 42.98 | L | N |
| ATOM | 3159 | CA | SER | 12 | 115.128 | -14.320 | 9.916 | 1.00 | 42.98 | L | C |
| ATOM | 3160 | CB | SER | 12 | 114.334 | -15.612 | 10.103 | 1.00 | 67.78 | L | C |
| ATOM | 3161 | OG | SER | 12 | 114.474 | -16.092 | 11.426 | 1.00 | 67.78 | L | O |
| ATOM | 3162 | C | SER | 12 | 116.611 | -14.628 | 9.738 | 1.00 | 42.98 | L | C |
| ATOM | 3163 | O | SER | 12 | 117.031 | -15.118 | 8.697 | 1.00 | 42.98 | L | O |
| ATOM | 3164 | N | ALA | 13 | 117.407 | -14.320 | 10.749 | 1.00 | 25.03 | L | N |
| ATOM | 3165 | CA | ALA | 13 | 118.836 | -14.575 | 10.667 | 1.00 | 25.03 | L | C |
| ATOM | 3166 | CB | ALA | 13 | 119.556 | -13.340 | 10.124 | 1.00 | 41.64 | L | C |
| ATOM | 3167 | C | ALA | 13 | 119.390 | -14.952 | 12.037 | 1.00 | 25.03 | L | C |
| ATOM | 3168 | O | ALA | 13 | 118.829 | -14.571 | 13.067 | 1.00 | 25.03 | L | O |
| ATOM | 3169 | N | SER | 14 | 120.493 | -15.701 | 12.045 | 1.00 | 32.48 | L | N |
| ATOM | 3170 | CA | SER | 14 | 121.111 | -16.132 | 13.294 | 1.00 | 32.48 | L | C |
| ATOM | 3171 | CB | SER | 14 | 121.594 | -17.569 | 13.160 | 1.00 | 77.12 | L | C |
| ATOM | 3172 | OG | SER | 14 | 122.348 | -17.721 | 11.975 | 1.00 | 77.12 | L | O |
| ATOM | 3173 | C | SER | 14 | 122.269 | -15.231 | 13.691 | 1.00 | 32.48 | L | C |
| ATOM | 3174 | O | SER | 14 | 122.893 | -14.595 | 12.841 | 1.00 | 32.48 | L | O |
| ATOM | 3175 | N | VAL | 15 | 122.545 | -15.166 | 14.988 | 1.00 | 47.29 | L | N |
| ATOM | 3176 | CA | VAL | 15 | 123.637 | -14.336 | 15.470 | 1.00 | 47.29 | L | C |
| ATOM | 3177 | CB | VAL | 15 | 123.996 | -14.657 | 16.937 | 1.00 | 53.16 | L | C |
| ATOM | 3178 | CG1 | VAL | 15 | 123.121 | -13.847 | 17.881 | 1.00 | 53.16 | L | C |
| ATOM | 3179 | CG2 | VAL | 15 | 123.808 | -16.148 | 17.198 | 1.00 | 53.16 | L | C |
| ATOM | 3180 | C | VAL | 15 | 124.858 | -14.575 | 14.606 | 1.00 | 47.29 | L | C |
| ATOM | 3181 | O | VAL | 15 | 125.164 | -15.712 | 14.250 | 1.00 | 47.29 | L | O |
| ATOM | 3182 | N | GLY | 16 | 125.537 | -13.495 | 14.247 | 1.00 | 32.44 | L | N |
| ATOM | 3183 | CA | GLY | 16 | 126.728 | -13.615 | 13.431 | 1.00 | 32.44 | L | C |
| ATOM | 3184 | C | GLY | 16 | 126.506 | -13.463 | 11.945 | 1.00 | 32.44 | L | C |
| ATOM | 3185 | O | GLY | 16 | 127.467 | -13.306 | 11.191 | 1.00 | 32.44 | L | O |
| ATOM | 3186 | N | ASP | 17 | 125.255 | -13.524 | 11.510 | 1.00 | 32.03 | L | N |
| ATOM | 3187 | CA | ASP | 17 | 124.959 | -13.367 | 10.092 | 1.00 | 32.03 | L | C |
| ATOM | 3188 | CB | ASP | 17 | 123.533 | -13.814 | 9.788 | 1.00 | 55.01 | L | C |
| ATOM | 3189 | CG | ASP | 17 | 123.344 | -15.291 | 9.961 | 1.00 | 55.01 | L | C |
| ATOM | 3190 | OD1 | ASP | 17 | 122.211 | -15.771 | 9.739 | 1.00 | 55.01 | L | O |
| ATOM | 3191 | OD2 | ASP | 17 | 124.331 | -15.965 | 10.320 | 1.00 | 55.01 | L | O |
| ATOM | 3192 | C | ASP | 17 | 125.109 | -11.905 | 9.677 | 1.00 | 32.03 | L | C |
| ATOM | 3193 | O | ASP | 17 | 125.041 | -10.997 | 10.517 | 1.00 | 32.03 | L | O |
| ATOM | 3194 | N | ARG | 18 | 125.324 | -11.680 | 8.385 | 1.00 | 40.86 | L | N |
| ATOM | 3195 | CA | ARG | 18 | 125.447 | -10.325 | 7.875 | 1.00 | 40.86 | L | C |
| ATOM | 3196 | CB | ARG | 18 | 126.587 | -10.231 | 6.865 | 1.00 | 78.37 | L | C |
| ATOM | 3197 | CG | ARG | 18 | 126.790 | -8.842 | 6.293 | 1.00 | 78.37 | L | C |
| ATOM | 3198 | CD | ARG | 18 | 128.223 | -8.662 | 5.812 | 1.00 | 78.37 | L | C |
| ATOM | 3199 | NE | ARG | 18 | 128.413 | -7.408 | 5.087 | 1.00 | 78.37 | L | N |
| ATOM | 3200 | CZ | ARG | 18 | 127.841 | -7.131 | 3.918 | 1.00 | 78.37 | L | C |
| ATOM | 3201 | NH1 | ARG | 18 | 127.042 | -8.021 | 3.336 | 1.00 | 78.37 | L | N |
| ATOM | 3202 | NH2 | ARG | 18 | 128.064 | -5.960 | 3.334 | 1.00 | 78.37 | L | N |
| ATOM | 3203 | C | ARG | 18 | 124.116 | -9.986 | 7.220 | 1.00 | 40.86 | L | C |
| ATOM | 3204 | O | ARG | 18 | 123.690 | -10.656 | 6.284 | 1.00 | 40.86 | L | O |
| ATOM | 3205 | N | VAL | 19 | 123.455 | -8.948 | 7.721 | 1.00 | 26.42 | L | N |
| ATOM | 3206 | CA | VAL | 19 | 122.157 | -8.549 | 7.193 | 1.00 | 26.42 | L | C |
| ATOM | 3207 | CB | VAL | 19 | 121.154 | -8.426 | 8.335 | 1.00 | 32.94 | L | C |
| ATOM | 3208 | CG1 | VAL | 19 | 119.768 | -8.214 | 7.783 | 1.00 | 32.94 | L | C |
| ATOM | 3209 | CG2 | VAL | 19 | 121.204 | -9.678 | 9.194 | 1.00 | 32.94 | L | C |
| ATOM | 3210 | C | VAL | 19 | 122.200 | -7.235 | 6.420 | 1.00 | 26.42 | L | C |
| ATOM | 3211 | O | VAL | 19 | 122.902 | -6.306 | 6.798 | 1.00 | 26.42 | L | O |
| ATOM | 3212 | N | THR | 20 | 121.443 | -7.160 | 5.333 | 1.00 | 42.24 | L | N |

Fig. 19: A-45

| ATOM | 3213 | CA | THR | 20 | 121.408 | -5.950 | 4.519 | 1.00 | 42.24 | L | C |
|---|---|---|---|---|---|---|---|---|---|---|---|
| ATOM | 3214 | CB | THR | 20 | 122.310 | -6.097 | 3.289 | 1.00 | 29.90 | L | C |
| ATOM | 3215 | OG1 | THR | 20 | 123.680 | -6.127 | 3.714 | 1.00 | 29.90 | L | O |
| ATOM | 3216 | CG2 | THR | 20 | 122.099 | -4.944 | 2.326 | 1.00 | 29.90 | L | C |
| ATOM | 3217 | C | THR | 20 | 120.008 | -5.582 | 4.050 | 1.00 | 42.24 | L | C |
| ATOM | 3218 | O | THR | 20 | 119.477 | -6.202 | 3.127 | 1.00 | 42.24 | L | O |
| ATOM | 3219 | N | ILE | 21 | 119.418 | -4.568 | 4.683 | 1.00 | 13.95 | L | N |
| ATOM | 3220 | CA | ILE | 21 | 118.077 | -4.114 | 4.326 | 1.00 | 13.95 | L | C |
| ATOM | 3221 | CB | ILE | 21 | 117.349 | -3.486 | 5.541 | 1.00 | 24.11 | L | C |
| ATOM | 3222 | CG2 | ILE | 21 | 115.892 | -3.176 | 5.186 | 1.00 | 24.11 | L | C |
| ATOM | 3223 | CG1 | ILE | 21 | 117.390 | -4.457 | 6.720 | 1.00 | 24.11 | L | C |
| ATOM | 3224 | CD1 | ILE | 21 | 116.709 | -3.936 | 7.960 | 1.00 | 24.11 | L | C |
| ATOM | 3225 | C | ILE | 21 | 118.180 | -3.081 | 3.217 | 1.00 | 13.95 | L | C |
| ATOM | 3226 | O | ILE | 21 | 119.036 | -2.208 | 3.251 | 1.00 | 13.95 | L | O |
| ATOM | 3227 | N | THR | 22 | 117.305 | -3.190 | 2.230 | 1.00 | 27.07 | L | N |
| ATOM | 3228 | CA | THR | 22 | 117.304 | -2.266 | 1.107 | 1.00 | 27.07 | L | C |
| ATOM | 3229 | CB | THR | 22 | 117.335 | -3.022 | -0.239 | 1.00 | 29.03 | L | C |
| ATOM | 3230 | OG1 | THR | 22 | 118.613 | -3.642 | -0.404 | 1.00 | 29.03 | L | O |
| ATOM | 3231 | CG2 | THR | 22 | 117.084 | -2.084 | -1.391 | 1.00 | 29.03 | L | C |
| ATOM | 3232 | C | THR | 22 | 116.067 | -1.385 | 1.123 | 1.00 | 27.07 | L | C |
| ATOM | 3233 | O | THR | 22 | 114.951 | -1.871 | 1.313 | 1.00 | 27.07 | L | O |
| ATOM | 3234 | N | CYS | 23 | 116.281 | -0.089 | 0.916 | 1.00 | 32.83 | L | N |
| ATOM | 3235 | CA | CYS | 23 | 115.203 | 0.896 | 0.882 | 1.00 | 32.83 | L | C |
| ATOM | 3236 | C | CYS | 23 | 115.259 | 1.546 | -0.489 | 1.00 | 32.83 | L | C |
| ATOM | 3237 | O | CYS | 23 | 116.250 | 2.187 | -0.837 | 1.00 | 32.83 | L | O |
| ATOM | 3238 | CB | CYS | 23 | 115.424 | 1.947 | 1.973 | 1.00 | 18.66 | L | C |
| ATOM | 3239 | SG | CYS | 23 | 114.216 | 3.310 | 2.141 | 1.00 | 18.66 | L | S |
| ATOM | 3240 | N | SER | 24 | 114.199 | 1.355 | -1.268 | 1.00 | 11.34 | L | N |
| ATOM | 3241 | CA | SER | 24 | 114.110 | 1.924 | -2.612 | 1.00 | 11.34 | L | C |
| ATOM | 3242 | CB | SER | 24 | 113.696 | 0.853 | -3.614 | 1.00 | 28.67 | L | C |
| ATOM | 3243 | OG | SER | 24 | 114.642 | -0.190 | -3.632 | 1.00 | 28.67 | L | O |
| ATOM | 3244 | C | SER | 24 | 113.096 | 3.058 | -2.641 | 1.00 | 11.34 | L | C |
| ATOM | 3245 | O | SER | 24 | 111.971 | 2.910 | -2.154 | 1.00 | 11.34 | L | O |
| ATOM | 3246 | N | ALA | 25 | 113.496 | 4.186 | -3.217 | 1.00 | 32.05 | L | N |
| ATOM | 3247 | CA | ALA | 25 | 112.617 | 5.343 | -3.286 | 1.00 | 32.05 | L | C |
| ATOM | 3248 | CB | ALA | 25 | 113.312 | 6.567 | -2.707 | 1.00 | 44.86 | L | C |
| ATOM | 3249 | C | ALA | 25 | 112.139 | 5.633 | -4.699 | 1.00 | 32.05 | L | C |
| ATOM | 3250 | O | ALA | 25 | 112.918 | 5.619 | -5.658 | 1.00 | 32.05 | L | O |
| ATOM | 3251 | N | SER | 26 | 110.839 | 5.901 | -4.803 | 1.00 | 26.80 | L | N |
| ATOM | 3252 | CA | SER | 26 | 110.179 | 6.204 | -6.070 | 1.00 | 26.80 | L | C |
| ATOM | 3253 | CB | SER | 26 | 108.717 | 6.572 | -5.814 | 1.00 | 23.33 | L | C |
| ATOM | 3254 | OG | SER | 26 | 108.617 | 7.713 | -4.984 | 1.00 | 23.33 | L | O |
| ATOM | 3255 | C | SER | 26 | 110.866 | 7.338 | -6.813 | 1.00 | 26.80 | L | C |
| ATOM | 3256 | O | SER | 26 | 110.814 | 7.404 | -8.032 | 1.00 | 26.80 | L | O |
| ATOM | 3257 | N | SER | 27 | 111.496 | 8.234 | -6.066 | 1.00 | 22.71 | L | N |
| ATOM | 3258 | CA | SER | 27 | 112.210 | 9.363 | -6.644 | 1.00 | 22.71 | L | C |
| ATOM | 3259 | CB | SER | 27 | 111.439 | 10.661 | -6.406 | 1.00 | 47.74 | L | C |
| ATOM | 3260 | OG | SER | 27 | 110.105 | 10.552 | -6.862 | 1.00 | 47.74 | L | O |
| ATOM | 3261 | C | SER | 27 | 113.547 | 9.438 | -5.934 | 1.00 | 22.71 | L | C |
| ATOM | 3262 | O | SER | 27 | 113.666 | 8.982 | -4.805 | 1.00 | 22.71 | L | O |
| ATOM | 3263 | N | SER | 28 | 114.555 | 10.004 | -6.586 | 1.00 | 37.73 | L | N |
| ATOM | 3264 | CA | SER | 28 | 115.874 | 10.121 | -5.972 | 1.00 | 37.73 | L | C |
| ATOM | 3265 | CB | SER | 28 | 116.890 | 10.583 | -7.010 | 1.00 | 36.75 | L | C |
| ATOM | 3266 | OG | SER | 28 | 116.486 | 11.818 | -7.573 | 1.00 | 36.75 | L | O |
| ATOM | 3267 | C | SER | 28 | 115.846 | 11.106 | -4.804 | 1.00 | 37.73 | L | C |
| ATOM | 3268 | O | SER | 28 | 115.043 | 12.038 | -4.775 | 1.00 | 37.73 | L | O |
| ATOM | 3269 | N | VAL | 29 | 116.726 | 10.890 | -3.838 | 1.00 | 35.34 | L | N |
| ATOM | 3270 | CA | VAL | 29 | 116.807 | 11.753 | -2.669 | 1.00 | 35.34 | L | C |
| ATOM | 3271 | CB | VAL | 29 | 116.002 | 11.154 | -1.484 | 1.00 | 39.96 | L | C |
| ATOM | 3272 | CG1 | VAL | 29 | 114.521 | 11.097 | -1.842 | 1.00 | 39.96 | L | C |
| ATOM | 3273 | CG2 | VAL | 29 | 116.506 | 9.755 | -1.147 | 1.00 | 39.96 | L | C |
| ATOM | 3274 | C | VAL | 29 | 118.277 | 11.895 | -2.289 | 1.00 | 35.34 | L | C |
| ATOM | 3275 | O | VAL | 29 | 119.076 | 11.001 | -2.571 | 1.00 | 35.34 | L | O |
| ATOM | 3276 | N | ASN | 30 | 118.641 | 13.007 | -1.658 | 1.00 | 55.44 | L | N |
| ATOM | 3277 | CA | ASN | 30 | 120.033 | 13.236 | -1.278 | 1.00 | 55.44 | L | C |
| ATOM | 3278 | CB | ASN | 30 | 120.252 | 14.722 | -0.974 | 1.00 | 66.75 | L | C |
| ATOM | 3279 | CG | ASN | 30 | 119.176 | 15.292 | -0.071 | 1.00 | 66.75 | L | C |
| ATOM | 3280 | OD1 | ASN | 30 | 118.006 | 15.359 | -0.453 | 1.00 | 66.75 | L | O |
| ATOM | 3281 | ND2 | ASN | 30 | 119.561 | 15.694 | 1.138 | 1.00 | 66.75 | L | N |
| ATOM | 3282 | C | ASN | 30 | 120.510 | 12.386 | -0.095 | 1.00 | 55.44 | L | C |
| ATOM | 3283 | O | ASN | 30 | 121.705 | 12.099 | 0.033 | 1.00 | 55.44 | L | O |
| ATOM | 3284 | N | HIS | 31 | 119.586 | 11.985 | 0.770 | 1.00 | 34.66 | L | N |
| ATOM | 3285 | CA | HIS | 31 | 119.947 | 11.172 | 1.923 | 1.00 | 34.66 | L | C |

Fig. 19: A-46

| | | | | | | | | | | |
|---|---|---|---|---|---|---|---|---|---|---|
| ATOM | 3286 | CB | HIS | 31 | 120.290 | 12.049 | 3.132 | 1.00 | 51.96 | L C |
| ATOM | 3287 | CG | HIS | 31 | 121.623 | 12.725 | 3.042 | 1.00 | 51.96 | L C |
| ATOM | 3288 | CD2 | HIS | 31 | 122.763 | 12.534 | 3.744 | 1.00 | 51.96 | L C |
| ATOM | 3289 | ND1 | HIS | 31 | 121.879 | 13.763 | 2.172 | 1.00 | 51.96 | L N |
| ATOM | 3290 | CE1 | HIS | 31 | 123.118 | 14.186 | 2.345 | 1.00 | 51.96 | L C |
| ATOM | 3291 | NE2 | HIS | 31 | 123.676 | 13.457 | 3.294 | 1.00 | 51.96 | L N |
| ATOM | 3292 | C | HIS | 31 | 118.811 | 10.241 | 2.316 | 1.00 | 34.66 | L C |
| ATOM | 3293 | O | HIS | 31 | 117.736 | 10.267 | 1.707 | 1.00 | 34.66 | L O |
| ATOM | 3294 | N | MET | 32 | 119.070 | 9.415 | 3.332 | 1.00 | 24.85 | L N |
| ATOM | 3295 | CA | MET | 32 | 118.081 | 8.489 | 3.864 | 1.00 | 24.85 | L C |
| ATOM | 3296 | CB | MET | 32 | 118.189 | 7.126 | 3.187 | 1.00 | 22.87 | L C |
| ATOM | 3297 | CG | MET | 32 | 116.961 | 6.226 | 3.394 | 1.00 | 22.87 | L C |
| ATOM | 3298 | SD | MET | 32 | 115.381 | 6.922 | 2.757 | 1.00 | 22.87 | L S |
| ATOM | 3299 | CE | MET | 32 | 115.727 | 7.028 | 1.012 | 1.00 | 22.87 | L C |
| ATOM | 3300 | C | MET | 32 | 118.316 | 8.340 | 5.360 | 1.00 | 24.85 | L C |
| ATOM | 3301 | O | MET | 32 | 119.454 | 8.377 | 5.831 | 1.00 | 24.85 | L O |
| ATOM | 3302 | N | PHE | 33 | 117.244 | 8.180 | 6.118 | 1.00 | 7.47 | L N |
| ATOM | 3303 | CA | PHE | 33 | 117.391 | 8.029 | 7.554 | 1.00 | 7.47 | L C |
| ATOM | 3304 | CB | PHE | 33 | 116.693 | 9.171 | 8.285 | 1.00 | 11.22 | L C |
| ATOM | 3305 | CG | PHE | 33 | 117.205 | 10.533 | 7.901 | 1.00 | 11.22 | L C |
| ATOM | 3306 | CD1 | PHE | 33 | 116.901 | 11.078 | 6.652 | 1.00 | 11.22 | L C |
| ATOM | 3307 | CD2 | PHE | 33 | 118.017 | 11.259 | 8.776 | 1.00 | 11.22 | L C |
| ATOM | 3308 | CE1 | PHE | 33 | 117.399 | 12.325 | 6.275 | 1.00 | 11.22 | L C |
| ATOM | 3309 | CE2 | PHE | 33 | 118.519 | 12.501 | 8.407 | 1.00 | 11.22 | L C |
| ATOM | 3310 | CZ | PHE | 33 | 118.207 | 13.035 | 7.149 | 1.00 | 11.22 | L C |
| ATOM | 3311 | C | PHE | 33 | 116.817 | 6.702 | 7.994 | 1.00 | 7.47 | L C |
| ATOM | 3312 | O | PHE | 33 | 115.959 | 6.150 | 7.320 | 1.00 | 7.47 | L O |
| ATOM | 3313 | N | TRP | 34 | 117.301 | 6.186 | 9.118 | 1.00 | 15.67 | L N |
| ATOM | 3314 | CA | TRP | 34 | 116.815 | 4.912 | 9.618 | 1.00 | 15.67 | L C |
| ATOM | 3315 | CB | TRP | 34 | 117.859 | 3.818 | 9.414 | 1.00 | 16.49 | L C |
| ATOM | 3316 | CG | TRP | 34 | 118.217 | 3.590 | 7.992 | 1.00 | 16.49 | L C |
| ATOM | 3317 | CD2 | TRP | 34 | 117.671 | 2.592 | 7.123 | 1.00 | 16.49 | L C |
| ATOM | 3318 | CE2 | TRP | 34 | 118.315 | 2.732 | 5.872 | 1.00 | 16.49 | L C |
| ATOM | 3319 | CE3 | TRP | 34 | 116.702 | 1.596 | 7.279 | 1.00 | 16.49 | L C |
| ATOM | 3320 | CD1 | TRP | 34 | 119.137 | 4.278 | 7.259 | 1.00 | 16.49 | L C |
| ATOM | 3321 | NE1 | TRP | 34 | 119.205 | 3.767 | 5.984 | 1.00 | 16.49 | L N |
| ATOM | 3322 | CZ2 | TRP | 34 | 118.024 | 1.914 | 4.782 | 1.00 | 16.49 | L C |
| ATOM | 3323 | CZ3 | TRP | 34 | 116.409 | 0.780 | 6.194 | 1.00 | 16.49 | L C |
| ATOM | 3324 | CH2 | TRP | 34 | 117.069 | 0.945 | 4.960 | 1.00 | 16.49 | L C |
| ATOM | 3325 | C | TRP | 34 | 116.459 | 4.960 | 11.086 | 1.00 | 15.67 | L C |
| ATOM | 3326 | O | TRP | 34 | 117.149 | 5.593 | 11.882 | 1.00 | 15.67 | L O |
| ATOM | 3327 | N | TYR | 35 | 115.370 | 4.288 | 11.437 | 1.00 | 19.71 | L N |
| ATOM | 3328 | CA | TYR | 35 | 114.939 | 4.229 | 12.820 | 1.00 | 19.71 | L C |
| ATOM | 3329 | CB | TYR | 35 | 113.591 | 4.922 | 13.007 | 1.00 | 25.75 | L C |
| ATOM | 3330 | CG | TYR | 35 | 113.623 | 6.381 | 12.621 | 1.00 | 25.75 | L C |
| ATOM | 3331 | CD1 | TYR | 35 | 113.255 | 6.790 | 11.344 | 1.00 | 25.75 | L C |
| ATOM | 3332 | CE1 | TYR | 35 | 113.310 | 8.124 | 10.980 | 1.00 | 25.75 | L C |
| ATOM | 3333 | CD2 | TYR | 35 | 114.052 | 7.353 | 13.527 | 1.00 | 25.75 | L C |
| ATOM | 3334 | CE2 | TYR | 35 | 114.110 | 8.685 | 13.173 | 1.00 | 25.75 | L C |
| ATOM | 3335 | CZ | TYR | 35 | 113.737 | 9.064 | 11.899 | 1.00 | 25.75 | L C |
| ATOM | 3336 | OH | TYR | 35 | 113.776 | 10.384 | 11.540 | 1.00 | 25.75 | L O |
| ATOM | 3337 | C | TYR | 35 | 114.821 | 2.781 | 13.207 | 1.00 | 19.71 | L C |
| ATOM | 3338 | O | TYR | 35 | 114.508 | 1.937 | 12.373 | 1.00 | 19.71 | L O |
| ATOM | 3339 | N | GLN | 36 | 115.100 | 2.491 | 14.468 | 1.00 | 30.18 | L N |
| ATOM | 3340 | CA | GLN | 36 | 114.987 | 1.136 | 14.964 | 1.00 | 30.18 | L C |
| ATOM | 3341 | CB | GLN | 36 | 116.292 | 0.659 | 15.597 | 1.00 | 33.56 | L C |
| ATOM | 3342 | CG | GLN | 36 | 116.109 | -0.625 | 16.387 | 1.00 | 33.56 | L C |
| ATOM | 3343 | CD | GLN | 36 | 117.154 | -0.806 | 17.464 | 1.00 | 33.56 | L C |
| ATOM | 3344 | OE1 | GLN | 36 | 118.296 | -1.161 | 17.179 | 1.00 | 33.56 | L O |
| ATOM | 3345 | NE2 | GLN | 36 | 116.770 | -0.550 | 18.716 | 1.00 | 33.56 | L N |
| ATOM | 3346 | C | GLN | 36 | 113.902 | 1.124 | 16.017 | 1.00 | 30.18 | L C |
| ATOM | 3347 | O | GLN | 36 | 113.986 | 1.852 | 17.008 | 1.00 | 30.18 | L O |
| ATOM | 3348 | N | GLN | 37 | 112.877 | 0.311 | 15.803 | 1.00 | 31.84 | L N |
| ATOM | 3349 | CA | GLN | 37 | 111.811 | 0.209 | 16.778 | 1.00 | 31.84 | L C |
| ATOM | 3350 | CB | GLN | 37 | 110.467 | 0.599 | 16.162 | 1.00 | 26.28 | L C |
| ATOM | 3351 | CG | GLN | 37 | 109.335 | 0.494 | 17.165 | 1.00 | 26.28 | L C |
| ATOM | 3352 | CD | GLN | 37 | 108.003 | 0.979 | 16.632 | 1.00 | 26.28 | L C |
| ATOM | 3353 | OE1 | GLN | 37 | 107.573 | 0.597 | 15.537 | 1.00 | 26.28 | L O |
| ATOM | 3354 | NE2 | GLN | 37 | 107.328 | 1.819 | 17.417 | 1.00 | 26.28 | L N |
| ATOM | 3355 | C | GLN | 37 | 111.729 | -1.201 | 17.360 | 1.00 | 31.84 | L C |
| ATOM | 3356 | O | GLN | 37 | 111.571 | -2.189 | 16.637 | 1.00 | 31.84 | L O |
| ATOM | 3357 | N | LYS | 38 | 111.861 | -1.285 | 18.676 | 1.00 | 33.78 | L N |
| ATOM | 3358 | CA | LYS | 38 | 111.776 | -2.561 | 19.366 | 1.00 | 33.78 | L C |

Fig. 19: A-47

| ATOM | 3359 | CB  | LYS | 38 | 112.784 | -2.618 | 20.519 | 1.00 | 38.31 | L | C |
| ATOM | 3360 | CG  | LYS | 38 | 114.209 | -2.306 | 20.094 | 1.00 | 38.31 | L | C |
| ATOM | 3361 | CD  | LYS | 38 | 115.224 | -2.552 | 21.207 | 1.00 | 38.31 | L | C |
| ATOM | 3362 | CE  | LYS | 38 | 115.494 | -4.034 | 21.402 | 1.00 | 38.31 | L | C |
| ATOM | 3363 | NZ  | LYS | 38 | 115.954 | -4.720 | 20.154 | 1.00 | 38.31 | L | N |
| ATOM | 3364 | C   | LYS | 38 | 110.346 | -2.671 | 19.889 | 1.00 | 33.78 | L | C |
| ATOM | 3365 | O   | LYS | 38 | 109.770 | -1.690 | 20.354 | 1.00 | 33.78 | L | O |
| ATOM | 3366 | N   | PRO | 39 | 109.757 | -3.873 | 19.818 | 1.00 | 36.51 | L | N |
| ATOM | 3367 | CD  | PRO | 39 | 110.419 | -5.128 | 19.422 | 1.00 | 56.09 | L | C |
| ATOM | 3368 | CA  | PRO | 39 | 108.389 | -4.139 | 20.271 | 1.00 | 36.51 | L | C |
| ATOM | 3369 | CB  | PRO | 39 | 108.376 | -5.652 | 20.409 | 1.00 | 56.09 | L | C |
| ATOM | 3370 | CG  | PRO | 39 | 109.254 | -6.072 | 19.283 | 1.00 | 56.09 | L | C |
| ATOM | 3371 | C   | PRO | 39 | 107.976 | -3.434 | 21.559 | 1.00 | 36.51 | L | C |
| ATOM | 3372 | O   | PRO | 39 | 108.664 | -3.523 | 22.573 | 1.00 | 36.51 | L | O |
| ATOM | 3373 | N   | GLY | 40 | 106.846 | -2.735 | 21.503 | 1.00 | 29.94 | L | N |
| ATOM | 3374 | CA  | GLY | 40 | 106.330 | -2.036 | 22.667 | 1.00 | 29.94 | L | C |
| ATOM | 3375 | C   | GLY | 40 | 107.025 | -0.738 | 23.034 | 1.00 | 29.94 | L | C |
| ATOM | 3376 | O   | GLY | 40 | 106.669 | -0.119 | 24.037 | 1.00 | 29.94 | L | O |
| ATOM | 3377 | N   | LYS | 41 | 108.019 | -0.332 | 22.243 | 1.00 | 32.57 | L | N |
| ATOM | 3378 | CA  | LYS | 41 | 108.754 |  0.903 | 22.503 | 1.00 | 32.57 | L | C |
| ATOM | 3379 | CB  | LYS | 41 | 110.231 |  0.611 | 22.804 | 1.00 | 82.45 | L | C |
| ATOM | 3380 | CG  | LYS | 41 | 110.466 | -0.251 | 24.040 | 1.00 | 82.45 | L | C |
| ATOM | 3381 | CD  | LYS | 41 | 111.905 | -0.157 | 24.579 | 1.00 | 82.45 | L | C |
| ATOM | 3382 | CE  | LYS | 41 | 112.977 | -0.603 | 23.575 | 1.00 | 82.45 | L | C |
| ATOM | 3383 | NZ  | LYS | 41 | 113.257 |  0.396 | 22.496 | 1.00 | 82.45 | L | N |
| ATOM | 3384 | C   | LYS | 41 | 108.656 |  1.860 | 21.319 | 1.00 | 32.57 | L | C |
| ATOM | 3385 | O   | LYS | 41 | 108.243 |  1.480 | 20.227 | 1.00 | 32.57 | L | O |
| ATOM | 3386 | N   | ALA | 42 | 109.029 |  3.112 | 21.547 | 1.00 | 30.66 | L | N |
| ATOM | 3387 | CA  | ALA | 42 | 108.990 |  4.126 | 20.502 | 1.00 | 30.66 | L | C |
| ATOM | 3388 | CB  | ALA | 42 | 108.980 |  5.513 | 21.129 | 1.00 | 32.87 | L | C |
| ATOM | 3389 | C   | ALA | 42 | 110.209 |  3.973 | 19.606 | 1.00 | 30.66 | L | C |
| ATOM | 3390 | O   | ALA | 42 | 111.235 |  3.436 | 20.028 | 1.00 | 30.66 | L | O |
| ATOM | 3391 | N   | PRO | 43 | 110.112 |  4.435 | 18.351 | 1.00 | 23.79 | L | N |
| ATOM | 3392 | CD  | PRO | 43 | 108.939 |  4.976 | 17.647 | 1.00 |  7.10 | L | C |
| ATOM | 3393 | CA  | PRO | 43 | 111.248 |  4.323 | 17.440 | 1.00 | 23.79 | L | C |
| ATOM | 3394 | CB  | PRO | 43 | 110.727 |  4.980 | 16.170 | 1.00 |  7.10 | L | C |
| ATOM | 3395 | CG  | PRO | 43 | 109.275 |  4.677 | 16.212 | 1.00 |  7.10 | L | C |
| ATOM | 3396 | C   | PRO | 43 | 112.476 |  5.042 | 18.007 | 1.00 | 23.79 | L | C |
| ATOM | 3397 | O   | PRO | 43 | 112.359 |  5.903 | 18.877 | 1.00 | 23.79 | L | O |
| ATOM | 3398 | N   | LYS | 44 | 113.652 |  4.678 | 17.514 | 1.00 | 26.42 | L | N |
| ATOM | 3399 | CA  | LYS | 44 | 114.888 |  5.283 | 17.972 | 1.00 | 26.42 | L | C |
| ATOM | 3400 | CB  | LYS | 44 | 115.656 |  4.289 | 18.843 | 1.00 | 45.11 | L | C |
| ATOM | 3401 | CG  | LYS | 44 | 115.840 |  4.724 | 20.288 | 1.00 | 45.11 | L | C |
| ATOM | 3402 | CD  | LYS | 44 | 116.535 |  3.651 | 21.131 | 1.00 | 45.11 | L | C |
| ATOM | 3403 | CE  | LYS | 44 | 115.656 |  2.400 | 21.338 | 1.00 | 45.11 | L | C |
| ATOM | 3404 | NZ  | LYS | 44 | 115.359 |  1.613 | 20.087 | 1.00 | 45.11 | L | N |
| ATOM | 3405 | C   | LYS | 44 | 115.741 |  5.673 | 16.767 | 1.00 | 26.42 | L | C |
| ATOM | 3406 | O   | LYS | 44 | 115.898 |  4.888 | 15.829 | 1.00 | 26.42 | L | O |
| ATOM | 3407 | N   | PRO | 45 | 116.287 |  6.902 | 16.764 | 1.00 | 19.50 | L | N |
| ATOM | 3408 | CD  | PRO | 45 | 116.146 |  7.943 | 17.794 | 1.00 |  7.61 | L | C |
| ATOM | 3409 | CA  | PRO | 45 | 117.132 |  7.362 | 15.649 | 1.00 | 19.50 | L | C |
| ATOM | 3410 | CB  | PRO | 45 | 117.638 |  8.720 | 16.120 | 1.00 |  7.61 | L | C |
| ATOM | 3411 | CG  | PRO | 45 | 116.547 |  9.180 | 17.041 | 1.00 |  7.61 | L | C |
| ATOM | 3412 | C   | PRO | 45 | 118.273 |  6.367 | 15.542 | 1.00 | 19.50 | L | C |
| ATOM | 3413 | O   | PRO | 45 | 118.925 |  6.082 | 16.549 | 1.00 | 19.50 | L | O |
| ATOM | 3414 | N   | TRP | 46 | 118.521 |  5.848 | 14.342 | 1.00 | 23.41 | L | N |
| ATOM | 3415 | CA  | TRP | 46 | 119.581 |  4.861 | 14.158 | 1.00 | 23.41 | L | C |
| ATOM | 3416 | CB  | TRP | 46 | 118.980 |  3.559 | 13.643 | 1.00 | 20.77 | L | C |
| ATOM | 3417 | CG  | TRP | 46 | 119.662 |  2.382 | 14.178 | 1.00 | 20.77 | L | C |
| ATOM | 3418 | CD2 | TRP | 46 | 119.738 |  2.007 | 15.554 | 1.00 | 20.77 | L | C |
| ATOM | 3419 | CE2 | TRP | 46 | 120.509 |  0.829 | 15.624 | 1.00 | 20.77 | L | C |
| ATOM | 3420 | CE3 | TRP | 46 | 119.229 |  2.554 | 16.737 | 1.00 | 20.77 | L | C |
| ATOM | 3421 | CD1 | TRP | 46 | 120.365 |  1.446 | 13.481 | 1.00 | 20.77 | L | C |
| ATOM | 3422 | NE1 | TRP | 46 | 120.879 |  0.504 | 14.345 | 1.00 | 20.77 | L | N |
| ATOM | 3423 | CZ2 | TRP | 46 | 120.786 |  0.191 | 16.834 | 1.00 | 20.77 | L | C |
| ATOM | 3424 | CZ3 | TRP | 46 | 119.505 |  1.918 | 17.938 | 1.00 | 20.77 | L | C |
| ATOM | 3425 | CH2 | TRP | 46 | 120.276 |  0.750 | 17.977 | 1.00 | 20.77 | L | C |
| ATOM | 3426 | C   | TRP | 46 | 120.691 |  5.302 | 13.209 | 1.00 | 23.41 | L | C |
| ATOM | 3427 | O   | TRP | 46 | 121.871 |  5.174 | 13.507 | 1.00 | 23.41 | L | O |
| ATOM | 3428 | N   | ILE | 47 | 120.306 |  5.806 | 12.048 | 1.00 | 21.62 | L | N |
| ATOM | 3429 | CA  | ILE | 47 | 121.275 |  6.248 | 11.073 | 1.00 | 21.62 | L | C |
| ATOM | 3430 | CB  | ILE | 47 | 121.515 |  5.160 | 10.008 | 1.00 | 12.16 | L | C |
| ATOM | 3431 | CG2 | ILE | 47 | 122.473 |  5.668 |  8.929 | 1.00 | 12.16 | L | C |

Fig. 19: A-48

| ATOM | 3432 | CG1 | ILE | 47 | 122.067 | 3.902 | 10.670 | 1.00 | 12.16 | L | C |
|---|---|---|---|---|---|---|---|---|---|---|---|
| ATOM | 3433 | CD1 | ILE | 47 | 122.301 | 2.746 | 9.686 | 1.00 | 12.16 | L | C |
| ATOM | 3434 | C | ILE | 47 | 120.694 | 7.482 | 10.408 | 1.00 | 21.62 | L | C |
| ATOM | 3435 | O | ILE | 47 | 119.600 | 7.424 | 9.840 | 1.00 | 21.62 | L | O |
| ATOM | 3436 | N | TYR | 48 | 121.408 | 8.603 | 10.510 | 1.00 | 27.63 | L | N |
| ATOM | 3437 | CA | TYR | 48 | 120.961 | 9.842 | 9.887 | 1.00 | 27.63 | L | C |
| ATOM | 3438 | CB | TYR | 48 | 120.899 | 10.992 | 10.892 | 1.00 | 47.89 | L | C |
| ATOM | 3439 | CG | TYR | 48 | 122.206 | 11.318 | 11.564 | 1.00 | 47.89 | L | C |
| ATOM | 3440 | CD1 | TYR | 48 | 122.762 | 10.454 | 12.502 | 1.00 | 47.89 | L | C |
| ATOM | 3441 | CE1 | TYR | 48 | 123.961 | 10.766 | 13.143 | 1.00 | 47.89 | L | C |
| ATOM | 3442 | CD2 | TYR | 48 | 122.881 | 12.503 | 11.277 | 1.00 | 47.89 | L | C |
| ATOM | 3443 | CE2 | TYR | 48 | 124.078 | 12.827 | 11.907 | 1.00 | 47.89 | L | C |
| ATOM | 3444 | CZ | TYR | 48 | 124.617 | 11.957 | 12.843 | 1.00 | 47.89 | L | C |
| ATOM | 3445 | OH | TYR | 48 | 125.803 | 12.269 | 13.483 | 1.00 | 47.89 | L | O |
| ATOM | 3446 | C | TYR | 48 | 121.922 | 10.181 | 8.766 | 1.00 | 27.63 | L | C |
| ATOM | 3447 | O | TYR | 48 | 122.992 | 9.575 | 8.646 | 1.00 | 27.63 | L | O |
| ATOM | 3448 | N | LEU | 49 | 121.535 | 11.150 | 7.948 | 1.00 | 28.95 | L | N |
| ATOM | 3449 | CA | LEU | 49 | 122.344 | 11.550 | 6.811 | 1.00 | 28.95 | L | C |
| ATOM | 3450 | CB | LEU | 49 | 123.421 | 12.568 | 7.232 | 1.00 | 11.18 | L | C |
| ATOM | 3451 | CG | LEU | 49 | 123.051 | 14.040 | 7.473 | 1.00 | 11.18 | L | C |
| ATOM | 3452 | CD1 | LEU | 49 | 122.174 | 14.552 | 6.344 | 1.00 | 11.18 | L | C |
| ATOM | 3453 | CD2 | LEU | 49 | 122.333 | 14.178 | 8.780 | 1.00 | 11.18 | L | C |
| ATOM | 3454 | C | LEU | 49 | 122.997 | 10.350 | 6.117 | 1.00 | 28.95 | L | C |
| ATOM | 3455 | O | LEU | 49 | 124.204 | 10.323 | 5.920 | 1.00 | 28.95 | L | O |
| ATOM | 3456 | N | THR | 50 | 122.192 | 9.351 | 5.777 | 1.00 | 29.56 | L | N |
| ATOM | 3457 | CA | THR | 50 | 122.666 | 8.165 | 5.072 | 1.00 | 29.56 | L | C |
| ATOM | 3458 | CB | THR | 50 | 123.352 | 8.566 | 3.770 | 1.00 | 23.05 | L | C |
| ATOM | 3459 | OG1 | THR | 50 | 122.490 | 9.434 | 3.040 | 1.00 | 23.05 | L | O |
| ATOM | 3460 | CG2 | THR | 50 | 123.647 | 7.335 | 2.923 | 1.00 | 23.05 | L | C |
| ATOM | 3461 | C | THR | 50 | 123.582 | 7.152 | 5.767 | 1.00 | 29.56 | L | C |
| ATOM | 3462 | O | THR | 50 | 123.229 | 5.976 | 5.888 | 1.00 | 29.56 | L | O |
| ATOM | 3463 | N | SER | 51 | 124.757 | 7.586 | 6.203 | 1.00 | 25.90 | L | N |
| ATOM | 3464 | CA | SER | 51 | 125.697 | 6.670 | 6.839 | 1.00 | 25.90 | L | C |
| ATOM | 3465 | CB | SER | 51 | 126.976 | 6.594 | 6.003 | 1.00 | 41.07 | L | C |
| ATOM | 3466 | OG | SER | 51 | 127.467 | 7.893 | 5.715 | 1.00 | 41.07 | L | O |
| ATOM | 3467 | C | SER | 51 | 126.049 | 6.998 | 8.287 | 1.00 | 25.90 | L | C |
| ATOM | 3468 | O | SER | 51 | 126.578 | 6.160 | 9.015 | 1.00 | 25.90 | L | O |
| ATOM | 3469 | N | ASN | 52 | 125.749 | 8.211 | 8.712 | 1.00 | 36.32 | L | N |
| ATOM | 3470 | CA | ASN | 52 | 126.050 | 8.615 | 10.075 | 1.00 | 36.32 | L | C |
| ATOM | 3471 | CB | ASN | 52 | 125.741 | 10.092 | 10.247 | 1.00 | 35.00 | L | C |
| ATOM | 3472 | CG | ASN | 52 | 126.708 | 10.954 | 9.499 | 1.00 | 35.00 | L | C |
| ATOM | 3473 | OD1 | ASN | 52 | 127.881 | 11.022 | 9.857 | 1.00 | 35.00 | L | O |
| ATOM | 3474 | ND2 | ASN | 52 | 126.236 | 11.608 | 8.439 | 1.00 | 35.00 | L | N |
| ATOM | 3475 | C | ASN | 52 | 125.288 | 7.815 | 11.109 | 1.00 | 36.32 | L | C |
| ATOM | 3476 | O | ASN | 52 | 124.059 | 7.766 | 11.078 | 1.00 | 36.32 | L | O |
| ATOM | 3477 | N | LEU | 53 | 126.018 | 7.190 | 12.027 | 1.00 | 27.25 | L | N |
| ATOM | 3478 | CA | LEU | 53 | 125.387 | 6.408 | 13.080 | 1.00 | 27.25 | L | C |
| ATOM | 3479 | CB | LEU | 53 | 126.355 | 5.366 | 13.631 | 1.00 | 36.82 | L | C |
| ATOM | 3480 | CG | LEU | 53 | 126.949 | 4.324 | 12.682 | 1.00 | 36.82 | L | C |
| ATOM | 3481 | CD1 | LEU | 53 | 127.640 | 3.266 | 13.531 | 1.00 | 36.82 | L | C |
| ATOM | 3482 | CD2 | LEU | 53 | 125.876 | 3.674 | 11.822 | 1.00 | 36.82 | L | C |
| ATOM | 3483 | C | LEU | 53 | 124.938 | 7.312 | 14.219 | 1.00 | 27.25 | L | C |
| ATOM | 3484 | O | LEU | 53 | 125.643 | 8.241 | 14.581 | 1.00 | 27.25 | L | O |
| ATOM | 3485 | N | ALA | 54 | 123.763 | 7.043 | 14.779 | 1.00 | 46.43 | L | N |
| ATOM | 3486 | CA | ALA | 54 | 123.251 | 7.827 | 15.897 | 1.00 | 46.43 | L | C |
| ATOM | 3487 | CB | ALA | 54 | 121.938 | 7.272 | 16.373 | 1.00 | 9.56 | L | C |
| ATOM | 3488 | C | ALA | 54 | 124.267 | 7.728 | 17.008 | 1.00 | 46.43 | L | C |
| ATOM | 3489 | O | ALA | 54 | 125.380 | 7.254 | 16.794 | 1.00 | 46.43 | L | O |
| ATOM | 3490 | N | SER | 55 | 123.891 | 8.140 | 18.208 | 1.00 | 82.41 | L | N |
| ATOM | 3491 | CA | SER | 55 | 124.847 | 8.081 | 19.290 | 1.00 | 82.41 | L | C |
| ATOM | 3492 | CB | SER | 55 | 124.439 | 9.036 | 20.406 | 1.00 | 85.12 | L | C |
| ATOM | 3493 | OG | SER | 55 | 125.561 | 9.342 | 21.215 | 1.00 | 85.12 | L | O |
| ATOM | 3494 | C | SER | 55 | 125.049 | 6.675 | 19.850 | 1.00 | 82.41 | L | C |
| ATOM | 3495 | O | SER | 55 | 126.187 | 6.226 | 20.004 | 1.00 | 82.41 | L | O |
| ATOM | 3496 | N | GLY | 56 | 123.957 | 5.970 | 20.137 | 1.00 | 57.94 | L | N |
| ATOM | 3497 | CA | GLY | 56 | 124.074 | 4.632 | 20.701 | 1.00 | 57.94 | L | C |
| ATOM | 3498 | C | GLY | 56 | 124.408 | 3.486 | 19.758 | 1.00 | 57.94 | L | C |
| ATOM | 3499 | O | GLY | 56 | 125.101 | 2.545 | 20.136 | 1.00 | 57.94 | L | O |
| ATOM | 3500 | N | VAL | 57 | 123.914 | 3.562 | 18.530 | 1.00 | 69.56 | L | N |
| ATOM | 3501 | CA | VAL | 57 | 124.131 | 2.519 | 17.530 | 1.00 | 69.56 | L | C |
| ATOM | 3502 | CB | VAL | 57 | 123.809 | 3.053 | 16.108 | 1.00 | 49.85 | L | C |
| ATOM | 3503 | CG1 | VAL | 57 | 123.682 | 1.898 | 15.128 | 1.00 | 49.85 | L | C |
| ATOM | 3504 | CG2 | VAL | 57 | 122.529 | 3.875 | 16.139 | 1.00 | 49.85 | L | C |

Fig. 19: A-49

| | | | | | | | | | | |
|---|---|---|---|---|---|---|---|---|---|---|
| ATOM | 3505 | C | VAL | 57 | 125.544 | 1.929 | 17.513 | 1.00 | 69.56 | L C |
| ATOM | 3506 | O | VAL | 57 | 126.515 | 2.637 | 17.244 | 1.00 | 69.56 | L O |
| ATOM | 3507 | N | PRO | 58 | 125.674 | 0.618 | 17.799 | 1.00 | 24.22 | L N |
| ATOM | 3508 | CD | PRO | 58 | 124.609 | -0.342 | 18.141 | 1.00 | 44.23 | L C |
| ATOM | 3509 | CA | PRO | 58 | 126.978 | -0.046 | 17.802 | 1.00 | 24.22 | L C |
| ATOM | 3510 | CB | PRO | 58 | 126.638 | -1.472 | 18.237 | 1.00 | 44.23 | L C |
| ATOM | 3511 | CG | PRO | 58 | 125.244 | -1.653 | 17.772 | 1.00 | 44.23 | L C |
| ATOM | 3512 | C | PRO | 58 | 127.609 | 0.017 | 16.415 | 1.00 | 24.22 | L C |
| ATOM | 3513 | O | PRO | 58 | 126.903 | -0.083 | 15.400 | 1.00 | 24.22 | L O |
| ATOM | 3514 | N | SER | 59 | 128.935 | 0.174 | 16.381 | 1.00 | 54.17 | L N |
| ATOM | 3515 | CA | SER | 59 | 129.691 | 0.295 | 15.134 | 1.00 | 54.17 | L C |
| ATOM | 3516 | CB | SER | 59 | 131.184 | 0.489 | 15.438 | 1.00 | 118.98 | L C |
| ATOM | 3517 | OG | SER | 59 | 131.729 | -0.615 | 16.139 | 1.00 | 118.98 | L O |
| ATOM | 3518 | C | SER | 59 | 129.528 | -0.815 | 14.096 | 1.00 | 54.17 | L C |
| ATOM | 3519 | O | SER | 59 | 130.015 | -0.672 | 12.970 | 1.00 | 54.17 | L O |
| ATOM | 3520 | N | ARG | 60 | 128.861 | -1.914 | 14.449 | 1.00 | 62.94 | L N |
| ATOM | 3521 | CA | ARG | 60 | 128.659 | -2.983 | 13.473 | 1.00 | 62.94 | L C |
| ATOM | 3522 | CB | ARG | 60 | 128.247 | -4.291 | 14.159 | 1.00 | 67.90 | L C |
| ATOM | 3523 | CG | ARG | 60 | 127.110 | -4.165 | 15.136 | 1.00 | 67.90 | L C |
| ATOM | 3524 | CD | ARG | 60 | 126.572 | -5.533 | 15.506 | 1.00 | 67.90 | L C |
| ATOM | 3525 | NE | ARG | 60 | 125.638 | -5.453 | 16.621 | 1.00 | 67.90 | L N |
| ATOM | 3526 | CZ | ARG | 60 | 125.978 | -5.050 | 17.840 | 1.00 | 67.90 | L C |
| ATOM | 3527 | NH1 | ARG | 60 | 127.230 | -4.696 | 18.093 | 1.00 | 67.90 | L N |
| ATOM | 3528 | NH2 | ARG | 60 | 125.070 | -5.002 | 18.807 | 1.00 | 67.90 | L N |
| ATOM | 3529 | C | ARG | 60 | 127.596 | -2.555 | 12.459 | 1.00 | 62.94 | L C |
| ATOM | 3530 | O | ARG | 60 | 127.471 | -3.146 | 11.382 | 1.00 | 62.94 | L O |
| ATOM | 3531 | N | PHE | 61 | 126.839 | -1.517 | 12.814 | 1.00 | 65.80 | L N |
| ATOM | 3532 | CA | PHE | 61 | 125.799 | -0.979 | 11.943 | 1.00 | 65.80 | L C |
| ATOM | 3533 | CB | PHE | 61 | 124.718 | -0.270 | 12.752 | 1.00 | 20.54 | L C |
| ATOM | 3534 | CG | PHE | 61 | 123.650 | -1.177 | 13.278 | 1.00 | 20.54 | L C |
| ATOM | 3535 | CD1 | PHE | 61 | 123.613 | -1.519 | 14.628 | 1.00 | 20.54 | L C |
| ATOM | 3536 | CD2 | PHE | 61 | 122.656 | -1.662 | 12.428 | 1.00 | 20.54 | L C |
| ATOM | 3537 | CE1 | PHE | 61 | 122.593 | -2.330 | 15.133 | 1.00 | 20.54 | L C |
| ATOM | 3538 | CE2 | PHE | 61 | 121.627 | -2.476 | 12.914 | 1.00 | 20.54 | L C |
| ATOM | 3539 | CZ | PHE | 61 | 121.594 | -2.809 | 14.270 | 1.00 | 20.54 | L C |
| ATOM | 3540 | C | PHE | 61 | 126.389 | 0.019 | 10.964 | 1.00 | 65.80 | L C |
| ATOM | 3541 | O | PHE | 61 | 127.300 | 0.773 | 11.300 | 1.00 | 65.80 | L O |
| ATOM | 3542 | N | SER | 62 | 125.851 | 0.030 | 9.754 | 1.00 | 31.43 | L N |
| ATOM | 3543 | CA | SER | 62 | 126.317 | 0.941 | 8.722 | 1.00 | 31.43 | L C |
| ATOM | 3544 | CB | SER | 62 | 127.530 | 0.355 | 8.001 | 1.00 | 48.53 | L C |
| ATOM | 3545 | OG | SER | 62 | 127.212 | -0.890 | 7.412 | 1.00 | 48.53 | L O |
| ATOM | 3546 | C | SER | 62 | 125.211 | 1.216 | 7.714 | 1.00 | 31.43 | L C |
| ATOM | 3547 | O | SER | 62 | 124.402 | 0.340 | 7.395 | 1.00 | 31.43 | L O |
| ATOM | 3548 | N | GLY | 63 | 125.177 | 2.443 | 7.216 | 1.00 | 26.27 | L N |
| ATOM | 3549 | CA | GLY | 63 | 124.168 | 2.802 | 6.244 | 1.00 | 26.27 | L C |
| ATOM | 3550 | C | GLY | 63 | 124.870 | 3.245 | 4.988 | 1.00 | 26.27 | L C |
| ATOM | 3551 | O | GLY | 63 | 126.032 | 3.634 | 5.044 | 1.00 | 26.27 | L O |
| ATOM | 3552 | N | SER | 64 | 124.177 | 3.201 | 3.860 | 1.00 | 35.51 | L N |
| ATOM | 3553 | CA | SER | 64 | 124.789 | 3.605 | 2.610 | 1.00 | 35.51 | L C |
| ATOM | 3554 | CB | SER | 64 | 125.824 | 2.565 | 2.193 | 1.00 | 33.46 | L C |
| ATOM | 3555 | OG | SER | 64 | 126.422 | 2.920 | 0.964 | 1.00 | 33.46 | L O |
| ATOM | 3556 | C | SER | 64 | 123.772 | 3.783 | 1.495 | 1.00 | 35.51 | L C |
| ATOM | 3557 | O | SER | 64 | 122.614 | 3.371 | 1.622 | 1.00 | 35.51 | L O |
| ATOM | 3558 | N | GLY | 65 | 124.209 | 4.401 | 0.401 | 1.00 | 29.14 | L N |
| ATOM | 3559 | CA | GLY | 65 | 123.318 | 4.594 | -0.727 | 1.00 | 29.14 | L C |
| ATOM | 3560 | C | GLY | 65 | 123.334 | 5.963 | -1.370 | 1.00 | 29.14 | L C |
| ATOM | 3561 | O | GLY | 65 | 124.127 | 6.837 | -1.024 | 1.00 | 29.14 | L O |
| ATOM | 3562 | N | SER | 66 | 122.439 | 6.137 | -2.329 | 1.00 | 15.93 | L N |
| ATOM | 3563 | CA | SER | 66 | 122.305 | 7.389 | -3.052 | 1.00 | 15.93 | L C |
| ATOM | 3564 | CB | SER | 66 | 123.623 | 7.750 | -3.741 | 1.00 | 32.28 | L C |
| ATOM | 3565 | OG | SER | 66 | 124.127 | 6.657 | -4.482 | 1.00 | 32.28 | L O |
| ATOM | 3566 | C | SER | 66 | 121.171 | 7.264 | -4.076 | 1.00 | 15.93 | L C |
| ATOM | 3567 | O | SER | 66 | 120.609 | 6.184 | -4.284 | 1.00 | 15.93 | L O |
| ATOM | 3568 | N | GLY | 67 | 120.812 | 8.378 | -4.690 | 1.00 | 33.97 | L N |
| ATOM | 3569 | CA | GLY | 67 | 119.751 | 8.349 | -5.673 | 1.00 | 33.97 | L C |
| ATOM | 3570 | C | GLY | 67 | 118.469 | 7.706 | -5.194 | 1.00 | 33.97 | L C |
| ATOM | 3571 | O | GLY | 67 | 117.757 | 8.262 | -4.361 | 1.00 | 33.97 | L O |
| ATOM | 3572 | N | THR | 68 | 118.182 | 6.521 | -5.715 | 1.00 | 25.46 | L N |
| ATOM | 3573 | CA | THR | 68 | 116.954 | 5.828 | -5.366 | 1.00 | 25.46 | L C |
| ATOM | 3574 | CB | THR | 68 | 116.176 | 5.455 | -6.633 | 1.00 | 47.05 | L C |
| ATOM | 3575 | OG1 | THR | 68 | 117.003 | 4.636 | -7.471 | 1.00 | 47.05 | L O |
| ATOM | 3576 | CG2 | THR | 68 | 115.772 | 6.704 | -7.395 | 1.00 | 47.05 | L C |
| ATOM | 3577 | C | THR | 68 | 117.132 | 4.559 | -4.539 | 1.00 | 25.46 | L C |

Fig. 19: A-50

| ATOM | 3578 | O   | THR | 68 | 116.144 |  3.963 | -4.103 | 1.00 | 25.46 | L | O |
|------|------|-----|-----|----|---------|--------|--------|------|-------|---|---|
| ATOM | 3579 | N   | ASP | 69 | 118.374 |  4.134 | -4.327 | 1.00 | 17.04 | L | N |
| ATOM | 3580 | CA  | ASP | 69 | 118.614 |  2.921 | -3.554 | 1.00 | 17.04 | L | C |
| ATOM | 3581 | CB  | ASP | 69 | 119.156 |  1.812 | -4.463 | 1.00 | 63.22 | L | C |
| ATOM | 3582 | CG  | ASP | 69 | 118.129 |  1.354 | -5.490 | 1.00 | 63.22 | L | C |
| ATOM | 3583 | OD1 | ASP | 69 | 117.087 |  0.791 | -5.083 | 1.00 | 63.22 | L | O |
| ATOM | 3584 | OD2 | ASP | 69 | 118.356 |  1.565 | -6.703 | 1.00 | 63.22 | L | O |
| ATOM | 3585 | C   | ASP | 69 | 119.544 |  3.146 | -2.372 | 1.00 | 17.04 | L | C |
| ATOM | 3586 | O   | ASP | 69 | 120.684 |  3.567 | -2.535 | 1.00 | 17.04 | L | O |
| ATOM | 3587 | N   | TYR | 70 | 119.030 |  2.866 | -1.177 | 1.00 | 19.76 | L | N |
| ATOM | 3588 | CA  | TYR | 70 | 119.778 |  3.037 |  0.061 | 1.00 | 19.76 | L | C |
| ATOM | 3589 | CB  | TYR | 70 | 119.130 |  4.151 |  0.895 | 1.00 | 24.73 | L | C |
| ATOM | 3590 | CG  | TYR | 70 | 119.424 |  5.544 |  0.369 | 1.00 | 24.73 | L | C |
| ATOM | 3591 | CD1 | TYR | 70 | 120.547 |  6.255 |  0.809 | 1.00 | 24.73 | L | C |
| ATOM | 3592 | CE1 | TYR | 70 | 120.865 |  7.511 |  0.281 | 1.00 | 24.73 | L | C |
| ATOM | 3593 | CD2 | TYR | 70 | 118.620 |  6.129 | -0.616 | 1.00 | 24.73 | L | C |
| ATOM | 3594 | CE2 | TYR | 70 | 118.931 |  7.384 | -1.153 | 1.00 | 24.73 | L | C |
| ATOM | 3595 | CZ  | TYR | 70 | 120.053 |  8.062 | -0.700 | 1.00 | 24.73 | L | C |
| ATOM | 3596 | OH  | TYR | 70 | 120.371 |  9.275 | -1.247 | 1.00 | 24.73 | L | O |
| ATOM | 3597 | C   | TYR | 70 | 119.812 |  1.727 |  0.840 | 1.00 | 19.76 | L | C |
| ATOM | 3598 | O   | TYR | 70 | 118.997 |  0.828 |  0.599 | 1.00 | 19.76 | L | O |
| ATOM | 3599 | N   | THR | 71 | 120.751 |  1.603 |  1.772 | 1.00 | 26.87 | L | N |
| ATOM | 3600 | CA  | THR | 71 | 120.837 |  0.366 |  2.535 | 1.00 | 26.87 | L | C |
| ATOM | 3601 | CB  | THR | 71 | 121.754 | -0.661 |  1.828 | 1.00 | 34.85 | L | C |
| ATOM | 3602 | OG1 | THR | 71 | 123.107 | -0.192 |  1.860 | 1.00 | 34.85 | L | O |
| ATOM | 3603 | CG2 | THR | 71 | 121.329 | -0.863 |  0.376 | 1.00 | 34.85 | L | C |
| ATOM | 3604 | C   | THR | 71 | 121.333 |  0.483 |  3.977 | 1.00 | 26.87 | L | C |
| ATOM | 3605 | O   | THR | 71 | 122.160 |  1.335 |  4.306 | 1.00 | 26.87 | L | O |
| ATOM | 3606 | N   | LEU | 72 | 120.800 | -0.385 |  4.829 | 1.00 | 24.40 | L | N |
| ATOM | 3607 | CA  | LEU | 72 | 121.204 | -0.467 |  6.222 | 1.00 | 24.40 | L | C |
| ATOM | 3608 | CB  | LEU | 72 | 119.987 | -0.412 |  7.150 | 1.00 | 25.91 | L | C |
| ATOM | 3609 | CG  | LEU | 72 | 120.183 | -0.827 |  8.614 | 1.00 | 25.91 | L | C |
| ATOM | 3610 | CD1 | LEU | 72 | 121.539 | -0.387 |  9.105 | 1.00 | 25.91 | L | C |
| ATOM | 3611 | CD2 | LEU | 72 | 119.097 | -0.207 |  9.470 | 1.00 | 25.91 | L | C |
| ATOM | 3612 | C   | LEU | 72 | 121.875 | -1.837 |  6.296 | 1.00 | 24.40 | L | C |
| ATOM | 3613 | O   | LEU | 72 | 121.386 | -2.803 |  5.707 | 1.00 | 24.40 | L | O |
| ATOM | 3614 | N   | THR | 73 | 123.000 | -1.930 |  6.990 | 1.00 | 38.15 | L | N |
| ATOM | 3615 | CA  | THR | 73 | 123.695 | -3.204 |  7.066 | 1.00 | 38.15 | L | C |
| ATOM | 3616 | CB  | THR | 73 | 124.907 | -3.217 |  6.110 | 1.00 | 35.63 | L | C |
| ATOM | 3617 | OG1 | THR | 73 | 124.556 | -2.566 |  4.885 | 1.00 | 35.63 | L | O |
| ATOM | 3618 | CG2 | THR | 73 | 125.328 | -4.649 |  5.797 | 1.00 | 35.63 | L | C |
| ATOM | 3619 | C   | THR | 73 | 124.189 | -3.542 |  8.467 | 1.00 | 38.15 | L | C |
| ATOM | 3620 | O   | THR | 73 | 124.719 | -2.690 |  9.177 | 1.00 | 38.15 | L | O |
| ATOM | 3621 | N   | ILE | 74 | 123.997 | -4.791 |  8.866 | 1.00 | 31.55 | L | N |
| ATOM | 3622 | CA  | ILE | 74 | 124.467 | -5.246 | 10.158 | 1.00 | 31.55 | L | C |
| ATOM | 3623 | CB  | ILE | 74 | 123.342 | -5.884 | 10.988 | 1.00 | 39.02 | L | C |
| ATOM | 3624 | CG2 | ILE | 74 | 123.734 | -5.878 | 12.461 | 1.00 | 39.02 | L | C |
| ATOM | 3625 | CG1 | ILE | 74 | 122.041 | -5.099 | 10.821 | 1.00 | 39.02 | L | C |
| ATOM | 3626 | CD1 | ILE | 74 | 120.870 | -5.663 | 11.635 | 1.00 | 39.02 | L | C |
| ATOM | 3627 | C   | ILE | 74 | 125.504 | -6.313 |  9.814 | 1.00 | 31.55 | L | C |
| ATOM | 3628 | O   | ILE | 74 | 125.146 | -7.434 |  9.440 | 1.00 | 31.55 | L | O |
| ATOM | 3629 | N   | SER | 75 | 126.782 | -5.951 |  9.921 | 1.00 | 48.74 | L | N |
| ATOM | 3630 | CA  | SER | 75 | 127.888 | -6.857 |  9.605 | 1.00 | 48.74 | L | C |
| ATOM | 3631 | CB  | SER | 75 | 129.209 | -6.106 |  9.727 | 1.00 | 44.70 | L | C |
| ATOM | 3632 | OG  | SER | 75 | 129.306 | -5.485 | 10.994 | 1.00 | 44.70 | L | O |
| ATOM | 3633 | C   | SER | 75 | 127.940 | -8.129 | 10.456 | 1.00 | 48.74 | L | C |
| ATOM | 3634 | O   | SER | 75 | 128.346 | -9.184 |  9.970 | 1.00 | 48.74 | L | O |
| ATOM | 3635 | N   | SER | 76 | 127.544 | -8.021 | 11.722 | 1.00 | 53.77 | L | N |
| ATOM | 3636 | CA  | SER | 76 | 127.530 | -9.165 | 12.635 | 1.00 | 53.77 | L | C |
| ATOM | 3637 | CB  | SER | 76 | 128.773 | -9.166 | 13.521 | 1.00 | 79.21 | L | C |
| ATOM | 3638 | OG  | SER | 76 | 128.707 |-10.224 | 14.463 | 1.00 | 79.21 | L | O |
| ATOM | 3639 | C   | SER | 76 | 126.288 | -9.102 | 13.515 | 1.00 | 53.77 | L | C |
| ATOM | 3640 | O   | SER | 76 | 126.306 | -8.533 | 14.604 | 1.00 | 53.77 | L | O |
| ATOM | 3641 | N   | LEU | 77 | 125.211 | -9.704 | 13.036 | 1.00 | 35.38 | L | N |
| ATOM | 3642 | CA  | LEU | 77 | 123.946 | -9.691 | 13.756 | 1.00 | 35.38 | L | C |
| ATOM | 3643 | CB  | LEU | 77 | 122.955 |-10.639 | 13.085 | 1.00 | 37.68 | L | C |
| ATOM | 3644 | CG  | LEU | 77 | 121.514 |-10.154 | 12.995 | 1.00 | 37.68 | L | C |
| ATOM | 3645 | CD1 | LEU | 77 | 120.623 |-11.329 | 12.638 | 1.00 | 37.68 | L | C |
| ATOM | 3646 | CD2 | LEU | 77 | 121.080 | -9.548 | 14.317 | 1.00 | 37.68 | L | C |
| ATOM | 3647 | C   | LEU | 77 | 124.096 |-10.080 | 15.215 | 1.00 | 35.38 | L | C |
| ATOM | 3648 | O   | LEU | 77 | 124.714 |-11.086 | 15.531 | 1.00 | 35.38 | L | O |
| ATOM | 3649 | N   | GLN | 78 | 123.527 | -9.279 | 16.105 | 1.00 | 50.91 | L | N |
| ATOM | 3650 | CA  | GLN | 78 | 123.589 | -9.577 | 17.527 | 1.00 | 50.91 | L | C |

Fig. 19: A-51

| | | | | | | | | | | |
|---|---|---|---|---|---|---|---|---|---|---|
| ATOM | 3651 | CB | GLN | 78 | 124.201 | -8.408 | 18.290 | 1.00 | 82.93 | L C |
| ATOM | 3652 | CG | GLN | 78 | 125.653 | -8.159 | 17.938 | 1.00 | 82.93 | L C |
| ATOM | 3653 | CD | GLN | 78 | 126.525 | -9.385 | 18.135 | 1.00 | 82.93 | L C |
| ATOM | 3654 | OE1 | GLN | 78 | 126.509 | -10.007 | 19.200 | 1.00 | 82.93 | L O |
| ATOM | 3655 | NE2 | GLN | 78 | 127.299 | -9.736 | 17.109 | 1.00 | 82.93 | L N |
| ATOM | 3656 | C | GLN | 78 | 122.192 | -9.880 | 18.062 | 1.00 | 50.91 | L C |
| ATOM | 3657 | O | GLN | 78 | 121.197 | -9.411 | 17.519 | 1.00 | 50.91 | L O |
| ATOM | 3658 | N | PRO | 79 | 122.104 | -10.680 | 19.135 | 1.00 | 74.65 | L N |
| ATOM | 3659 | CD | PRO | 79 | 123.228 | -11.171 | 19.952 | 1.00 | 43.98 | L C |
| ATOM | 3660 | CA | PRO | 79 | 120.821 | -11.049 | 19.743 | 1.00 | 74.65 | L C |
| ATOM | 3661 | CB | PRO | 79 | 121.243 | -11.963 | 20.887 | 1.00 | 43.98 | L C |
| ATOM | 3662 | CG | PRO | 79 | 122.577 | -11.373 | 21.284 | 1.00 | 43.98 | L C |
| ATOM | 3663 | C | PRO | 79 | 120.033 | -9.830 | 20.224 | 1.00 | 74.65 | L C |
| ATOM | 3664 | O | PRO | 79 | 118.855 | -9.922 | 20.577 | 1.00 | 74.65 | L O |
| ATOM | 3665 | N | GLU | 80 | 120.697 | -8.685 | 20.221 | 1.00 | 42.25 | L N |
| ATOM | 3666 | CA | GLU | 80 | 120.080 | -7.451 | 20.659 | 1.00 | 42.25 | L C |
| ATOM | 3667 | CB | GLU | 80 | 121.085 | -6.697 | 21.527 | 1.00 | 40.93 | L C |
| ATOM | 3668 | CG | GLU | 80 | 122.485 | -6.700 | 20.958 | 1.00 | 40.93 | L C |
| ATOM | 3669 | CD | GLU | 80 | 123.424 | -5.786 | 21.726 | 1.00 | 40.93 | L C |
| ATOM | 3670 | OE1 | GLU | 80 | 123.013 | -4.648 | 22.033 | 1.00 | 40.93 | L O |
| ATOM | 3671 | OE2 | GLU | 80 | 124.572 | -6.197 | 22.009 | 1.00 | 40.93 | L O |
| ATOM | 3672 | C | GLU | 80 | 119.602 | -6.575 | 19.489 | 1.00 | 42.25 | L C |
| ATOM | 3673 | O | GLU | 80 | 118.723 | -5.726 | 19.656 | 1.00 | 42.25 | L O |
| ATOM | 3674 | N | ASP | 81 | 120.189 | -6.787 | 18.312 | 1.00 | 42.48 | L N |
| ATOM | 3675 | CA | ASP | 81 | 119.835 | -6.037 | 17.108 | 1.00 | 42.48 | L C |
| ATOM | 3676 | CB | ASP | 81 | 120.867 | -6.254 | 16.005 | 1.00 | 43.12 | L C |
| ATOM | 3677 | CG | ASP | 81 | 122.262 | -5.914 | 16.441 | 1.00 | 43.12 | L C |
| ATOM | 3678 | OD1 | ASP | 81 | 122.422 | -5.003 | 17.281 | 1.00 | 43.12 | L O |
| ATOM | 3679 | OD2 | ASP | 81 | 123.205 | -6.549 | 15.924 | 1.00 | 43.12 | L O |
| ATOM | 3680 | C | ASP | 81 | 118.495 | -6.488 | 16.564 | 1.00 | 42.48 | L C |
| ATOM | 3681 | O | ASP | 81 | 118.086 | -6.063 | 15.488 | 1.00 | 42.48 | L O |
| ATOM | 3682 | N | PHE | 82 | 117.810 | -7.351 | 17.299 | 1.00 | 48.53 | L N |
| ATOM | 3683 | CA | PHE | 82 | 116.544 | -7.856 | 16.822 | 1.00 | 48.53 | L C |
| ATOM | 3684 | CB | PHE | 82 | 116.337 | -9.265 | 17.368 | 1.00 | 189.91 | L C |
| ATOM | 3685 | CG | PHE | 82 | 117.320 | -10.260 | 16.810 | 1.00 | 189.91 | L C |
| ATOM | 3686 | CD1 | PHE | 82 | 117.227 | -10.676 | 15.485 | 1.00 | 189.91 | L C |
| ATOM | 3687 | CD2 | PHE | 82 | 118.369 | -10.741 | 17.587 | 1.00 | 189.91 | L C |
| ATOM | 3688 | CE1 | PHE | 82 | 118.164 | -11.554 | 14.940 | 1.00 | 189.91 | L C |
| ATOM | 3689 | CE2 | PHE | 82 | 119.311 | -11.622 | 17.048 | 1.00 | 189.91 | L C |
| ATOM | 3690 | CZ | PHE | 82 | 119.207 | -12.027 | 15.725 | 1.00 | 189.91 | L C |
| ATOM | 3691 | C | PHE | 82 | 115.359 | -6.953 | 17.094 | 1.00 | 48.53 | L C |
| ATOM | 3692 | O | PHE | 82 | 114.857 | -6.863 | 18.216 | 1.00 | 48.53 | L O |
| ATOM | 3693 | N | ALA | 83 | 114.939 | -6.271 | 16.032 | 1.00 | 31.52 | L N |
| ATOM | 3694 | CA | ALA | 83 | 113.813 | -5.350 | 16.052 | 1.00 | 31.52 | L C |
| ATOM | 3695 | CB | ALA | 83 | 114.217 | -4.051 | 16.723 | 1.00 | 63.37 | L C |
| ATOM | 3696 | C | ALA | 83 | 113.398 | -5.090 | 14.605 | 1.00 | 31.52 | L C |
| ATOM | 3697 | O | ALA | 83 | 113.816 | -5.808 | 13.693 | 1.00 | 31.52 | L O |
| ATOM | 3698 | N | THR | 84 | 112.565 | -4.075 | 14.395 | 1.00 | 28.09 | L N |
| ATOM | 3699 | CA | THR | 84 | 112.124 | -3.733 | 13.045 | 1.00 | 28.09 | L C |
| ATOM | 3700 | CB | THR | 84 | 110.572 | -3.799 | 12.928 | 1.00 | 15.50 | L C |
| ATOM | 3701 | OG1 | THR | 84 | 110.127 | -3.002 | 11.822 | 1.00 | 15.50 | L O |
| ATOM | 3702 | CG2 | THR | 84 | 109.922 | -3.332 | 14.207 | 1.00 | 15.50 | L C |
| ATOM | 3703 | C | THR | 84 | 112.664 | -2.346 | 12.659 | 1.00 | 28.09 | L C |
| ATOM | 3704 | O | THR | 84 | 112.505 | -1.373 | 13.400 | 1.00 | 28.09 | L O |
| ATOM | 3705 | N | TYR | 85 | 113.316 | -2.282 | 11.496 | 1.00 | 21.31 | L N |
| ATOM | 3706 | CA | TYR | 85 | 113.935 | -1.055 | 11.000 | 1.00 | 21.31 | L C |
| ATOM | 3707 | CB | TYR | 85 | 115.367 | -1.338 | 10.517 | 1.00 | 19.63 | L C |
| ATOM | 3708 | CG | TYR | 85 | 116.240 | -1.976 | 11.566 | 1.00 | 19.63 | L C |
| ATOM | 3709 | CD1 | TYR | 85 | 115.988 | -3.279 | 12.021 | 1.00 | 19.63 | L C |
| ATOM | 3710 | CE1 | TYR | 85 | 116.718 | -3.834 | 13.061 | 1.00 | 19.63 | L C |
| ATOM | 3711 | CD2 | TYR | 85 | 117.255 | -1.259 | 12.174 | 1.00 | 19.63 | L C |
| ATOM | 3712 | CE2 | TYR | 85 | 117.990 | -1.807 | 13.217 | 1.00 | 19.63 | L C |
| ATOM | 3713 | CZ | TYR | 85 | 117.711 | -3.087 | 13.655 | 1.00 | 19.63 | L C |
| ATOM | 3714 | OH | TYR | 85 | 118.405 | -3.592 | 14.722 | 1.00 | 19.63 | L O |
| ATOM | 3715 | C | TYR | 85 | 113.173 | -0.365 | 9.882 | 1.00 | 21.31 | L C |
| ATOM | 3716 | O | TYR | 85 | 112.768 | -0.996 | 8.900 | 1.00 | 21.31 | L O |
| ATOM | 3717 | N | TYR | 86 | 113.015 | 0.948 | 10.046 | 1.00 | 18.01 | L N |
| ATOM | 3718 | CA | TYR | 86 | 112.321 | 1.806 | 9.090 | 1.00 | 18.01 | L C |
| ATOM | 3719 | CB | TYR | 86 | 111.242 | 2.632 | 9.790 | 1.00 | 24.73 | L C |
| ATOM | 3720 | CG | TYR | 86 | 110.130 | 1.846 | 10.421 | 1.00 | 24.73 | L C |
| ATOM | 3721 | CD1 | TYR | 86 | 109.020 | 1.459 | 9.679 | 1.00 | 24.73 | L C |
| ATOM | 3722 | CE1 | TYR | 86 | 107.971 | 0.756 | 10.278 | 1.00 | 24.73 | L C |
| ATOM | 3723 | CD2 | TYR | 86 | 110.177 | 1.508 | 11.773 | 1.00 | 24.73 | L C |

Fig. 19: A-52

| | | | | | | | | | | | |
|---|---|---|---|---|---|---|---|---|---|---|---|
| ATOM | 3724 | CE2 | TYR | 86 | 109.140 | 0.804 | 12.378 | 1.00 | 24.73 | L | C |
| ATOM | 3725 | CZ | TYR | 86 | 108.042 | 0.438 | 11.628 | 1.00 | 24.73 | L | C |
| ATOM | 3726 | OH | TYR | 86 | 107.002 | -0.204 | 12.238 | 1.00 | 24.73 | L | O |
| ATOM | 3727 | C | TYR | 86 | 113.280 | 2.798 | 8.465 | 1.00 | 18.01 | L | C |
| ATOM | 3728 | O | TYR | 86 | 114.110 | 3.378 | 9.158 | 1.00 | 18.01 | L | O |
| ATOM | 3729 | N | CYS | 87 | 113.170 | 2.996 | 7.158 | 1.00 | 20.53 | L | N |
| ATOM | 3730 | CA | CYS | 87 | 113.989 | 3.999 | 6.494 | 1.00 | 20.53 | L | C |
| ATOM | 3731 | C | CYS | 87 | 113.021 | 5.156 | 6.335 | 1.00 | 20.53 | L | C |
| ATOM | 3732 | O | CYS | 87 | 111.806 | 4.954 | 6.351 | 1.00 | 20.53 | L | O |
| ATOM | 3733 | CB | CYS | 87 | 114.509 | 3.527 | 5.133 | 1.00 | 17.33 | L | C |
| ATOM | 3734 | SG | CYS | 87 | 113.306 | 2.900 | 3.921 | 1.00 | 17.33 | L | S |
| ATOM | 3735 | N | GLN | 88 | 113.545 | 6.363 | 6.212 | 1.00 | 10.63 | L | N |
| ATOM | 3736 | CA | GLN | 88 | 112.696 | 7.534 | 6.083 | 1.00 | 10.63 | L | C |
| ATOM | 3737 | CB | GLN | 88 | 112.393 | 8.083 | 7.482 | 1.00 | 18.09 | L | C |
| ATOM | 3738 | CG | GLN | 88 | 111.509 | 9.303 | 7.525 | 1.00 | 18.09 | L | C |
| ATOM | 3739 | CD | GLN | 88 | 112.256 | 10.547 | 7.971 | 1.00 | 18.09 | L | C |
| ATOM | 3740 | OE1 | GLN | 88 | 112.946 | 10.539 | 8.987 | 1.00 | 18.09 | L | O |
| ATOM | 3741 | NE2 | GLN | 88 | 112.106 | 11.627 | 7.219 | 1.00 | 18.09 | L | N |
| ATOM | 3742 | C | GLN | 88 | 113.390 | 8.583 | 5.219 | 1.00 | 10.63 | L | C |
| ATOM | 3743 | O | GLN | 88 | 114.626 | 8.680 | 5.198 | 1.00 | 10.63 | L | O |
| ATOM | 3744 | N | GLN | 89 | 112.600 | 9.357 | 4.483 | 1.00 | 11.94 | L | N |
| ATOM | 3745 | CA | GLN | 89 | 113.171 | 10.386 | 3.625 | 1.00 | 11.94 | L | C |
| ATOM | 3746 | CB | GLN | 89 | 112.877 | 10.073 | 2.152 | 1.00 | 25.01 | L | C |
| ATOM | 3747 | CG | GLN | 89 | 111.407 | 10.008 | 1.776 | 1.00 | 25.01 | L | C |
| ATOM | 3748 | CD | GLN | 89 | 110.786 | 11.377 | 1.579 | 1.00 | 25.01 | L | C |
| ATOM | 3749 | OE1 | GLN | 89 | 111.373 | 12.247 | 0.935 | 1.00 | 25.01 | L | O |
| ATOM | 3750 | NE2 | GLN | 89 | 109.591 | 11.571 | 2.119 | 1.00 | 25.01 | L | N |
| ATOM | 3751 | C | GLN | 89 | 112.606 | 11.732 | 4.023 | 1.00 | 11.94 | L | C |
| ATOM | 3752 | O | GLN | 89 | 111.498 | 11.802 | 4.552 | 1.00 | 11.94 | L | O |
| ATOM | 3753 | N | TRP | 90 | 113.375 | 12.794 | 3.792 | 1.00 | 19.62 | L | N |
| ATOM | 3754 | CA | TRP | 90 | 112.948 | 14.144 | 4.145 | 1.00 | 19.62 | L | C |
| ATOM | 3755 | CB | TRP | 90 | 113.773 | 14.667 | 5.336 | 1.00 | 17.27 | L | C |
| ATOM | 3756 | CG | TRP | 90 | 115.220 | 15.018 | 5.023 | 1.00 | 17.27 | L | C |
| ATOM | 3757 | CD2 | TRP | 90 | 116.174 | 15.611 | 5.918 | 1.00 | 17.27 | L | C |
| ATOM | 3758 | CE2 | TRP | 90 | 117.373 | 15.797 | 5.189 | 1.00 | 17.27 | L | C |
| ATOM | 3759 | CE3 | TRP | 90 | 116.132 | 16.005 | 7.267 | 1.00 | 17.27 | L | C |
| ATOM | 3760 | CD1 | TRP | 90 | 115.869 | 14.867 | 3.823 | 1.00 | 17.27 | L | C |
| ATOM | 3761 | NE1 | TRP | 90 | 117.156 | 15.334 | 3.918 | 1.00 | 17.27 | L | N |
| ATOM | 3762 | CZ2 | TRP | 90 | 118.522 | 16.363 | 5.759 | 1.00 | 17.27 | L | C |
| ATOM | 3763 | CZ3 | TRP | 90 | 117.284 | 16.570 | 7.839 | 1.00 | 17.27 | L | C |
| ATOM | 3764 | CH2 | TRP | 90 | 118.462 | 16.741 | 7.080 | 1.00 | 17.27 | L | C |
| ATOM | 3765 | C | TRP | 90 | 113.074 | 15.093 | 2.947 | 1.00 | 19.62 | L | C |
| ATOM | 3766 | O | TRP | 90 | 112.783 | 16.289 | 3.048 | 1.00 | 19.62 | L | O |
| ATOM | 3767 | N | SER | 91 | 113.494 | 14.552 | 1.807 | 1.00 | 12.71 | L | N |
| ATOM | 3768 | CA | SER | 91 | 113.662 | 15.359 | 0.600 | 1.00 | 12.71 | L | C |
| ATOM | 3769 | CB | SER | 91 | 114.504 | 14.587 | -0.414 | 1.00 | 23.55 | L | C |
| ATOM | 3770 | OG | SER | 91 | 115.762 | 14.248 | 0.137 | 1.00 | 23.55 | L | O |
| ATOM | 3771 | C | SER | 91 | 112.344 | 15.800 | -0.054 | 1.00 | 12.71 | L | C |
| ATOM | 3772 | O | SER | 91 | 112.284 | 16.860 | -0.680 | 1.00 | 12.71 | L | O |
| ATOM | 3773 | N | GLY | 92 | 111.297 | 14.986 | 0.096 | 1.00 | 23.24 | L | N |
| ATOM | 3774 | CA | GLY | 92 | 110.008 | 15.310 | -0.493 | 1.00 | 23.24 | L | C |
| ATOM | 3775 | C | GLY | 92 | 108.867 | 15.347 | 0.509 | 1.00 | 23.24 | L | C |
| ATOM | 3776 | O | GLY | 92 | 108.931 | 14.718 | 1.567 | 1.00 | 23.24 | L | O |
| ATOM | 3777 | N | ASN | 93 | 107.811 | 16.078 | 0.169 | 1.00 | 31.94 | L | N |
| ATOM | 3778 | CA | ASN | 93 | 106.663 | 16.206 | 1.048 | 1.00 | 31.94 | L | C |
| ATOM | 3779 | CB | ASN | 93 | 106.307 | 17.670 | 1.203 | 1.00 | 23.71 | L | C |
| ATOM | 3780 | CG | ASN | 93 | 107.400 | 18.448 | 1.896 | 1.00 | 23.71 | L | C |
| ATOM | 3781 | OD1 | ASN | 93 | 107.790 | 19.525 | 1.445 | 1.00 | 23.71 | L | O |
| ATOM | 3782 | ND2 | ASN | 93 | 107.905 | 17.905 | 3.006 | 1.00 | 23.71 | L | N |
| ATOM | 3783 | C | ASN | 93 | 105.478 | 15.454 | 0.507 | 1.00 | 31.94 | L | C |
| ATOM | 3784 | O | ASN | 93 | 105.227 | 15.478 | -0.692 | 1.00 | 31.94 | L | O |
| ATOM | 3785 | N | PRO | 94 | 104.724 | 14.779 | 1.386 | 1.00 | 29.10 | L | N |
| ATOM | 3786 | CD | PRO | 94 | 103.575 | 13.939 | 1.009 | 1.00 | 1.87 | L | C |
| ATOM | 3787 | CA | PRO | 94 | 104.950 | 14.713 | 2.830 | 1.00 | 29.10 | L | C |
| ATOM | 3788 | CB | PRO | 94 | 103.651 | 14.113 | 3.340 | 1.00 | 1.87 | L | C |
| ATOM | 3789 | CG | PRO | 94 | 103.336 | 13.137 | 2.269 | 1.00 | 1.87 | L | C |
| ATOM | 3790 | C | PRO | 94 | 106.131 | 13.823 | 3.167 | 1.00 | 29.10 | L | C |
| ATOM | 3791 | O | PRO | 94 | 106.516 | 12.987 | 2.361 | 1.00 | 29.10 | L | O |
| ATOM | 3792 | N | TRP | 95 | 106.711 | 14.011 | 4.349 | 1.00 | 16.41 | L | N |
| ATOM | 3793 | CA | TRP | 95 | 107.810 | 13.155 | 4.772 | 1.00 | 16.41 | L | C |
| ATOM | 3794 | CB | TRP | 95 | 108.425 | 13.629 | 6.094 | 1.00 | 13.37 | L | C |
| ATOM | 3795 | CG | TRP | 95 | 109.201 | 14.906 | 5.979 | 1.00 | 13.37 | L | C |
| ATOM | 3796 | CD2 | TRP | 95 | 109.284 | 15.950 | 6.954 | 1.00 | 13.37 | L | C |

Fig. 19: A-53

| | | | | | | | | | | |
|---|---|---|---|---|---|---|---|---|---|---|
| ATOM | 3797 | CE2 | TRP | 95 | 110.104 | 16.960 | 6.412 | 1.00 | 13.37 | L C |
| ATOM | 3798 | CE3 | TRP | 95 | 108.743 | 16.132 | 8.229 | 1.00 | 13.37 | L C |
| ATOM | 3799 | CD1 | TRP | 95 | 109.963 | 15.312 | 4.917 | 1.00 | 13.37 | L C |
| ATOM | 3800 | NE1 | TRP | 95 | 110.504 | 16.543 | 5.168 | 1.00 | 13.37 | L N |
| ATOM | 3801 | CZ2 | TRP | 95 | 110.394 | 18.144 | 7.107 | 1.00 | 13.37 | L C |
| ATOM | 3802 | CZ3 | TRP | 95 | 109.030 | 17.305 | 8.919 | 1.00 | 13.37 | L C |
| ATOM | 3803 | CH2 | TRP | 95 | 109.845 | 18.297 | 8.358 | 1.00 | 13.37 | L C |
| ATOM | 3804 | C | TRP | 95 | 107.226 | 11.751 | 4.942 | 1.00 | 16.41 | L C |
| ATOM | 3805 | O | TRP | 95 | 106.136 | 11.575 | 5.484 | 1.00 | 16.41 | L O |
| ATOM | 3806 | N | THR | 96 | 107.956 | 10.748 | 4.481 | 1.00 | 6.71 | L N |
| ATOM | 3807 | CA | THR | 96 | 107.465 | 9.388 | 4.563 | 1.00 | 6.71 | L C |
| ATOM | 3808 | CB | THR | 96 | 106.963 | 8.932 | 3.172 | 1.00 | 11.59 | L C |
| ATOM | 3809 | OG1 | THR | 96 | 108.045 | 8.991 | 2.235 | 1.00 | 11.59 | L O |
| ATOM | 3810 | CG2 | THR | 96 | 105.859 | 9.852 | 2.674 | 1.00 | 11.59 | L C |
| ATOM | 3811 | C | THR | 96 | 108.489 | 8.369 | 5.087 | 1.00 | 6.71 | L C |
| ATOM | 3812 | O | THR | 96 | 109.703 | 8.621 | 5.121 | 1.00 | 6.71 | L O |
| ATOM | 3813 | N | PHE | 97 | 107.966 | 7.222 | 5.513 | 1.00 | 24.36 | L N |
| ATOM | 3814 | CA | PHE | 97 | 108.777 | 6.119 | 6.013 | 1.00 | 24.36 | L C |
| ATOM | 3815 | CB | PHE | 97 | 108.327 | 5.689 | 7.418 | 1.00 | 11.10 | L C |
| ATOM | 3816 | CG | PHE | 97 | 108.422 | 6.762 | 8.461 | 1.00 | 11.10 | L C |
| ATOM | 3817 | CD1 | PHE | 97 | 107.541 | 7.831 | 8.460 | 1.00 | 11.10 | L C |
| ATOM | 3818 | CD2 | PHE | 97 | 109.391 | 6.685 | 9.470 | 1.00 | 11.10 | L C |
| ATOM | 3819 | CE1 | PHE | 97 | 107.612 | 8.821 | 9.453 | 1.00 | 11.10 | L C |
| ATOM | 3820 | CE2 | PHE | 97 | 109.475 | 7.665 | 10.468 | 1.00 | 11.10 | L C |
| ATOM | 3821 | CZ | PHE | 97 | 108.577 | 8.738 | 10.456 | 1.00 | 11.10 | L C |
| ATOM | 3822 | C | PHE | 97 | 108.532 | 4.950 | 5.062 | 1.00 | 24.36 | L C |
| ATOM | 3823 | O | PHE | 97 | 107.613 | 4.990 | 4.241 | 1.00 | 24.36 | L O |
| ATOM | 3824 | N | GLY | 98 | 109.362 | 3.919 | 5.168 | 1.00 | 21.54 | L N |
| ATOM | 3825 | CA | GLY | 98 | 109.183 | 2.727 | 4.350 | 1.00 | 21.54 | L C |
| ATOM | 3826 | C | GLY | 98 | 108.266 | 1.849 | 5.184 | 1.00 | 21.54 | L C |
| ATOM | 3827 | O | GLY | 98 | 107.977 | 2.196 | 6.339 | 1.00 | 21.54 | L O |
| ATOM | 3828 | N | GLN | 99 | 107.796 | 0.728 | 4.645 | 1.00 | 11.59 | L N |
| ATOM | 3829 | CA | GLN | 99 | 106.894 | -0.114 | 5.442 | 1.00 | 11.59 | L C |
| ATOM | 3830 | CB | GLN | 99 | 106.211 | -1.197 | 4.593 | 1.00 | 37.88 | L C |
| ATOM | 3831 | CG | GLN | 99 | 106.810 | -1.403 | 3.238 | 1.00 | 37.88 | L C |
| ATOM | 3832 | CD | GLN | 99 | 108.266 | -1.748 | 3.319 | 1.00 | 37.88 | L C |
| ATOM | 3833 | OE1 | GLN | 99 | 108.638 | -2.821 | 3.796 | 1.00 | 37.88 | L O |
| ATOM | 3834 | NE2 | GLN | 99 | 109.110 | -0.832 | 2.866 | 1.00 | 37.88 | L N |
| ATOM | 3835 | C | GLN | 99 | 107.586 | -0.758 | 6.634 | 1.00 | 11.59 | L C |
| ATOM | 3836 | O | GLN | 99 | 106.943 | -1.317 | 7.508 | 1.00 | 11.59 | L O |
| ATOM | 3837 | N | GLY | 100 | 108.902 | -0.640 | 6.684 | 1.00 | 24.72 | L N |
| ATOM | 3838 | CA | GLY | 100 | 109.633 | -1.225 | 7.785 | 1.00 | 24.72 | L C |
| ATOM | 3839 | C | GLY | 100 | 110.055 | -2.630 | 7.425 | 1.00 | 24.72 | L C |
| ATOM | 3840 | O | GLY | 100 | 109.402 | -3.279 | 6.606 | 1.00 | 24.72 | L O |
| ATOM | 3841 | N | THR | 101 | 111.157 | -3.084 | 8.017 | 1.00 | 23.77 | L N |
| ATOM | 3842 | CA | THR | 101 | 111.685 | -4.424 | 7.780 | 1.00 | 23.77 | L C |
| ATOM | 3843 | CB | THR | 101 | 113.019 | -4.382 | 7.040 | 1.00 | 10.18 | L C |
| ATOM | 3844 | OG1 | THR | 101 | 112.790 | -4.076 | 5.659 | 1.00 | 10.18 | L O |
| ATOM | 3845 | CG2 | THR | 101 | 113.735 | -5.716 | 7.173 | 1.00 | 10.18 | L C |
| ATOM | 3846 | C | THR | 101 | 111.908 | -5.076 | 9.129 | 1.00 | 23.77 | L C |
| ATOM | 3847 | O | THR | 101 | 112.689 | -4.582 | 9.942 | 1.00 | 23.77 | L O |
| ATOM | 3848 | N | LYS | 102 | 111.223 | -6.188 | 9.365 | 1.00 | 19.34 | L N |
| ATOM | 3849 | CA | LYS | 102 | 111.347 | -6.858 | 10.641 | 1.00 | 19.34 | L C |
| ATOM | 3850 | CB | LYS | 102 | 110.009 | -7.496 | 11.027 | 1.00 | 36.70 | L C |
| ATOM | 3851 | CG | LYS | 102 | 109.872 | -7.774 | 12.521 | 1.00 | 36.70 | L C |
| ATOM | 3852 | CD | LYS | 102 | 108.464 | -8.244 | 12.876 | 1.00 | 36.70 | L C |
| ATOM | 3853 | CE | LYS | 102 | 108.313 | -8.467 | 14.372 | 1.00 | 36.70 | L C |
| ATOM | 3854 | NZ | LYS | 102 | 108.632 | -7.218 | 15.120 | 1.00 | 36.70 | L N |
| ATOM | 3855 | C | LYS | 102 | 112.449 | -7.907 | 10.608 | 1.00 | 19.34 | L C |
| ATOM | 3856 | O | LYS | 102 | 112.530 | -8.703 | 9.661 | 1.00 | 19.34 | L O |
| ATOM | 3857 | N | VAL | 103 | 113.304 | -7.894 | 11.634 | 1.00 | 20.01 | L N |
| ATOM | 3858 | CA | VAL | 103 | 114.378 | -8.868 | 11.714 | 1.00 | 20.01 | L C |
| ATOM | 3859 | CB | VAL | 103 | 115.793 | -8.188 | 11.567 | 1.00 | 24.69 | L C |
| ATOM | 3860 | CG1 | VAL | 103 | 115.696 | -6.991 | 10.636 | 1.00 | 24.69 | L C |
| ATOM | 3861 | CG2 | VAL | 103 | 116.361 | -7.780 | 12.908 | 1.00 | 24.69 | L C |
| ATOM | 3862 | C | VAL | 103 | 114.280 | -9.654 | 13.031 | 1.00 | 20.01 | L C |
| ATOM | 3863 | O | VAL | 103 | 114.380 | -9.075 | 14.117 | 1.00 | 20.01 | L O |
| ATOM | 3864 | N | GLU | 104 | 114.047 | -10.969 | 12.927 | 1.00 | 25.78 | L N |
| ATOM | 3865 | CA | GLU | 104 | 113.948 | -11.831 | 14.106 | 1.00 | 25.78 | L C |
| ATOM | 3866 | CB | GLU | 104 | 112.662 | -12.666 | 14.098 | 1.00 | 117.28 | L C |
| ATOM | 3867 | CG | GLU | 104 | 112.589 | -13.728 | 13.022 | 1.00 | 117.28 | L C |
| ATOM | 3868 | CD | GLU | 104 | 112.095 | -13.176 | 11.705 | 1.00 | 117.28 | L C |
| ATOM | 3869 | OE1 | GLU | 104 | 112.047 | -13.942 | 10.717 | 1.00 | 117.28 | L O |

Fig. 19: A-54

| ATOM | 3870 | OE2 | GLU | 104 | 111.747 | -11.975 | 11.660 | 1.00 | 117.28 | L | O |
|---|---|---|---|---|---|---|---|---|---|---|---|
| ATOM | 3871 | C | GLU | 104 | 115.148 | -12.759 | 14.179 | 1.00 | 25.78 | L | C |
| ATOM | 3872 | O | GLU | 104 | 115.852 | -12.955 | 13.185 | 1.00 | 25.78 | L | O |
| ATOM | 3873 | N | ILE | 105 | 115.368 | -13.324 | 15.365 | 1.00 | 16.82 | L | N |
| ATOM | 3874 | CA | ILE | 105 | 116.489 | -14.228 | 15.621 | 1.00 | 16.82 | L | C |
| ATOM | 3875 | CB | ILE | 105 | 116.771 | -14.386 | 17.124 | 1.00 | 41.57 | L | C |
| ATOM | 3876 | CG2 | ILE | 105 | 118.226 | -14.701 | 17.335 | 1.00 | 41.57 | L | C |
| ATOM | 3877 | CG1 | ILE | 105 | 116.372 | -13.111 | 17.873 | 1.00 | 41.57 | L | C |
| ATOM | 3878 | CD1 | ILE | 105 | 116.594 | -13.151 | 19.385 | 1.00 | 41.57 | L | C |
| ATOM | 3879 | C | ILE | 105 | 116.204 | -15.611 | 15.102 | 1.00 | 16.82 | L | C |
| ATOM | 3880 | O | ILE | 105 | 115.251 | -16.250 | 15.543 | 1.00 | 16.82 | L | O |
| ATOM | 3881 | N | LYS | 106 | 117.008 | -16.076 | 14.153 | 1.00 | 39.65 | L | N |
| ATOM | 3882 | CA | LYS | 106 | 116.807 | -17.422 | 13.653 | 1.00 | 39.65 | L | C |
| ATOM | 3883 | CB | LYS | 106 | 117.310 | -17.587 | 12.217 | 1.00 | 48.57 | L | C |
| ATOM | 3884 | CG | LYS | 106 | 116.947 | -18.952 | 11.631 | 1.00 | 48.57 | L | C |
| ATOM | 3885 | CD | LYS | 106 | 117.401 | -19.148 | 10.179 | 1.00 | 48.57 | L | C |
| ATOM | 3886 | CE | LYS | 106 | 117.087 | -20.579 | 9.702 | 1.00 | 48.57 | L | C |
| ATOM | 3887 | NZ | LYS | 106 | 117.672 | -20.948 | 8.369 | 1.00 | 48.57 | L | N |
| ATOM | 3888 | C | LYS | 106 | 117.598 | -18.310 | 14.600 | 1.00 | 39.65 | L | C |
| ATOM | 3889 | O | LYS | 106 | 118.804 | -18.122 | 14.782 | 1.00 | 38.70 | L | O |
| ATOM | 3890 | N | ARG | 107 | 116.894 | -19.242 | 15.235 | 1.00 | 14.86 | L | N |
| ATOM | 3891 | CA | ARG | 107 | 117.492 | -20.178 | 16.174 | 1.00 | 14.86 | L | C |
| ATOM | 3892 | CB | ARG | 107 | 117.158 | -19.771 | 17.605 | 1.00 | 20.96 | L | C |
| ATOM | 3893 | CG | ARG | 107 | 115.687 | -19.532 | 17.832 | 1.00 | 20.96 | L | C |
| ATOM | 3894 | CD | ARG | 107 | 115.296 | -19.930 | 19.239 | 1.00 | 20.96 | L | C |
| ATOM | 3895 | NE | ARG | 107 | 115.615 | -21.335 | 19.502 | 1.00 | 20.96 | L | N |
| ATOM | 3896 | CZ | ARG | 107 | 115.513 | -21.910 | 20.692 | 1.00 | 20.96 | L | C |
| ATOM | 3897 | NH1 | ARG | 107 | 115.096 | -21.206 | 21.732 | 1.00 | 20.96 | L | N |
| ATOM | 3898 | NH2 | ARG | 107 | 115.843 | -23.182 | 20.840 | 1.00 | 20.96 | L | N |
| ATOM | 3899 | C | ARG | 107 | 116.986 | -21.595 | 15.899 | 1.00 | 14.86 | L | C |
| ATOM | 3900 | O | ARG | 107 | 116.062 | -21.796 | 15.107 | 1.00 | 14.86 | L | O |
| ATOM | 3901 | N | THR | 108 | 117.606 | -22.575 | 16.545 | 1.00 | 15.74 | L | N |
| ATOM | 3902 | CA | THR | 108 | 117.220 | -23.963 | 16.354 | 1.00 | 15.74 | L | C |
| ATOM | 3903 | CB | THR | 108 | 118.025 | -24.921 | 17.260 | 1.00 | 26.88 | L | C |
| ATOM | 3904 | OG1 | THR | 108 | 118.232 | -24.320 | 18.548 | 1.00 | 26.88 | L | O |
| ATOM | 3905 | CG2 | THR | 108 | 119.347 | -25.257 | 16.618 | 1.00 | 26.88 | L | C |
| ATOM | 3906 | C | THR | 108 | 115.756 | -24.161 | 16.653 | 1.00 | 15.74 | L | C |
| ATOM | 3907 | O | THR | 108 | 115.179 | -23.450 | 17.481 | 1.00 | 15.74 | L | O |
| ATOM | 3908 | N | VAL | 109 | 115.170 | -25.134 | 15.963 | 1.00 | 14.98 | L | N |
| ATOM | 3909 | CA | VAL | 109 | 113.775 | -25.469 | 16.136 | 1.00 | 12.60 | L | C |
| ATOM | 3910 | CB | VAL | 109 | 113.368 | -26.593 | 15.189 | 1.00 | 15.46 | L | C |
| ATOM | 3911 | CG1 | VAL | 109 | 111.987 | -27.105 | 15.527 | 1.00 | 14.41 | L | C |
| ATOM | 3912 | CG2 | VAL | 109 | 113.383 | -26.074 | 13.789 | 1.00 | 13.59 | L | C |
| ATOM | 3913 | C | VAL | 109 | 113.517 | -25.909 | 17.565 | 1.00 | 13.54 | L | C |
| ATOM | 3914 | O | VAL | 109 | 114.393 | -26.477 | 18.236 | 1.00 | 21.28 | L | O |
| ATOM | 3915 | N | ALA | 110 | 112.313 | -25.637 | 18.036 | 1.00 | 11.81 | L | N |
| ATOM | 3916 | CA | ALA | 110 | 111.953 | -26.001 | 19.383 | 1.00 | 12.99 | L | C |
| ATOM | 3917 | CB | ALA | 110 | 112.312 | -24.878 | 20.330 | 1.00 | 8.30 | L | C |
| ATOM | 3918 | C | ALA | 110 | 110.463 | -26.281 | 19.426 | 1.00 | 13.63 | L | C |
| ATOM | 3919 | O | ALA | 110 | 109.654 | -25.390 | 19.158 | 1.00 | 15.92 | L | O |
| ATOM | 3920 | N | ALA | 111 | 110.112 | -27.525 | 19.758 | 1.00 | 25.70 | L | N |
| ATOM | 3921 | CA | ALA | 111 | 108.715 | -27.951 | 19.838 | 1.00 | 26.75 | L | C |
| ATOM | 3922 | CB | ALA | 111 | 108.641 | -29.446 | 20.087 | 1.00 | 23.32 | L | C |
| ATOM | 3923 | C | ALA | 111 | 107.981 | -27.198 | 20.936 | 1.00 | 25.59 | L | C |
| ATOM | 3924 | O | ALA | 111 | 108.525 | -26.932 | 22.008 | 1.00 | 29.44 | L | O |
| ATOM | 3925 | N | PRO | 112 | 106.720 | -26.857 | 20.686 | 1.00 | 20.76 | L | N |
| ATOM | 3926 | CD | PRO | 112 | 105.901 | -27.063 | 19.477 | 1.00 | 26.01 | L | C |
| ATOM | 3927 | CA | PRO | 112 | 105.975 | -26.125 | 21.707 | 1.00 | 26.81 | L | C |
| ATOM | 3928 | CB | PRO | 112 | 104.938 | -25.381 | 20.882 | 1.00 | 26.37 | L | C |
| ATOM | 3929 | CG | PRO | 112 | 104.550 | -26.457 | 19.876 | 1.00 | 24.71 | L | C |
| ATOM | 3930 | C | PRO | 112 | 105.322 | -27.058 | 22.703 | 1.00 | 30.67 | L | C |
| ATOM | 3931 | O | PRO | 112 | 104.936 | -28.166 | 22.353 | 1.00 | 31.28 | L | O |
| ATOM | 3932 | N | SER | 113 | 105.220 | -26.618 | 23.947 | 1.00 | 12.97 | L | N |
| ATOM | 3933 | CA | SER | 113 | 104.530 | -27.410 | 24.944 | 1.00 | 16.57 | L | C |
| ATOM | 3934 | CB | SER | 113 | 105.027 | -27.079 | 26.334 | 1.00 | 14.96 | L | C |
| ATOM | 3935 | OG | SER | 113 | 106.427 | -27.165 | 26.370 | 1.00 | 27.37 | L | O |
| ATOM | 3936 | C | SER | 113 | 103.099 | -26.913 | 24.815 | 1.00 | 15.10 | L | C |
| ATOM | 3937 | O | SER | 113 | 102.884 | -25.708 | 24.770 | 1.00 | 12.98 | L | O |
| ATOM | 3938 | N | VAL | 114 | 102.111 | -27.792 | 24.731 | 1.00 | 10.23 | L | N |
| ATOM | 3939 | CA | VAL | 114 | 100.766 | -27.258 | 24.630 | 1.00 | 9.98 | L | C |
| ATOM | 3940 | CB | VAL | 114 | 99.989 | -27.808 | 23.413 | 1.00 | 7.82 | L | C |
| ATOM | 3941 | CG1 | VAL | 114 | 100.921 | -27.972 | 22.212 | 1.00 | 4.17 | L | C |
| ATOM | 3942 | CG2 | VAL | 114 | 99.331 | -29.100 | 23.777 | 1.00 | 9.35 | L | C |

Fig. 19: A-55

| ATOM | 3943 | C | VAL | 114 | 99.992 | -27.558 | 25.899 | 1.00 | 9.84 | L | C |
|---|---|---|---|---|---|---|---|---|---|---|---|
| ATOM | 3944 | O | VAL | 114 | 100.318 | -28.494 | 26.628 | 1.00 | 12.49 | L | O |
| ATOM | 3945 | N | PHE | 115 | 98.981 | -26.728 | 26.153 | 1.00 | 26.11 | L | N |
| ATOM | 3946 | CA | PHE | 115 | 98.109 | -26.840 | 27.318 | 1.00 | 30.12 | L | C |
| ATOM | 3947 | CB | PHE | 115 | 98.581 | -25.896 | 28.416 | 1.00 | 36.06 | L | C |
| ATOM | 3948 | CG | PHE | 115 | 100.030 | -26.015 | 28.706 | 1.00 | 35.84 | L | C |
| ATOM | 3949 | CD1 | PHE | 115 | 100.505 | -27.040 | 29.513 | 1.00 | 38.16 | L | C |
| ATOM | 3950 | CD2 | PHE | 115 | 100.935 | -25.146 | 28.115 | 1.00 | 34.45 | L | C |
| ATOM | 3951 | CE1 | PHE | 115 | 101.854 | -27.203 | 29.723 | 1.00 | 41.30 | L | C |
| ATOM | 3952 | CE2 | PHE | 115 | 102.287 | -25.302 | 28.319 | 1.00 | 38.56 | L | C |
| ATOM | 3953 | CZ | PHE | 115 | 102.749 | -26.335 | 29.126 | 1.00 | 39.82 | L | C |
| ATOM | 3954 | C | PHE | 115 | 96.727 | -26.410 | 26.873 | 1.00 | 32.06 | L | C |
| ATOM | 3955 | O | PHE | 115 | 96.590 | -25.543 | 26.017 | 1.00 | 32.56 | L | O |
| ATOM | 3956 | N | ILE | 116 | 95.694 | -27.018 | 27.432 | 1.00 | 24.34 | L | N |
| ATOM | 3957 | CA | ILE | 116 | 94.354 | -26.608 | 27.069 | 1.00 | 18.54 | L | C |
| ATOM | 3958 | CB | ILE | 116 | 93.606 | -27.735 | 26.309 | 1.00 | 15.62 | L | C |
| ATOM | 3959 | CG2 | ILE | 116 | 93.239 | -28.855 | 27.249 | 1.00 | 4.34 | L | C |
| ATOM | 3960 | CG1 | ILE | 116 | 92.377 | -27.145 | 25.615 | 1.00 | 12.45 | L | C |
| ATOM | 3961 | CD1 | ILE | 116 | 91.695 | -28.089 | 24.646 | 1.00 | 4.28 | L | C |
| ATOM | 3962 | C | ILE | 116 | 93.661 | -26.233 | 28.371 | 1.00 | 19.64 | L | C |
| ATOM | 3963 | O | ILE | 116 | 93.931 | -26.834 | 29.412 | 1.00 | 19.05 | L | O |
| ATOM | 3964 | N | PHE | 117 | 92.802 | -25.217 | 28.308 | 1.00 | 17.52 | L | N |
| ATOM | 3965 | CA | PHE | 117 | 92.066 | -24.715 | 29.475 | 1.00 | 21.17 | L | C |
| ATOM | 3966 | CB | PHE | 117 | 92.501 | -23.295 | 29.828 | 1.00 | 22.98 | L | C |
| ATOM | 3967 | CG | PHE | 117 | 93.922 | -23.177 | 30.280 | 1.00 | 26.62 | L | C |
| ATOM | 3968 | CD1 | PHE | 117 | 94.293 | -23.562 | 31.559 | 1.00 | 29.31 | L | C |
| ATOM | 3969 | CD2 | PHE | 117 | 94.882 | -22.653 | 29.433 | 1.00 | 28.01 | L | C |
| ATOM | 3970 | CE1 | PHE | 117 | 95.599 | -23.421 | 31.988 | 1.00 | 28.27 | L | C |
| ATOM | 3971 | CE2 | PHE | 117 | 96.186 | -22.511 | 29.854 | 1.00 | 26.58 | L | C |
| ATOM | 3972 | CZ | PHE | 117 | 96.550 | -22.895 | 31.134 | 1.00 | 28.58 | L | C |
| ATOM | 3973 | C | PHE | 117 | 90.585 | -24.642 | 29.194 | 1.00 | 24.71 | L | C |
| ATOM | 3974 | O | PHE | 117 | 90.167 | -23.964 | 28.261 | 1.00 | 29.18 | L | O |
| ATOM | 3975 | N | PRO | 118 | 89.768 | -25.323 | 30.007 | 1.00 | 23.78 | L | N |
| ATOM | 3976 | CD | PRO | 118 | 90.235 | -26.376 | 30.926 | 1.00 | 9.40 | L | C |
| ATOM | 3977 | CA | PRO | 118 | 88.300 | -25.354 | 29.883 | 1.00 | 26.26 | L | C |
| ATOM | 3978 | CB | PRO | 118 | 87.907 | -26.568 | 30.718 | 1.00 | 9.92 | L | C |
| ATOM | 3979 | CG | PRO | 118 | 89.159 | -27.404 | 30.763 | 1.00 | 12.26 | L | C |
| ATOM | 3980 | C | PRO | 118 | 87.660 | -24.081 | 30.455 | 1.00 | 29.72 | L | C |
| ATOM | 3981 | O | PRO | 118 | 88.231 | -23.440 | 31.338 | 1.00 | 31.19 | L | O |
| ATOM | 3982 | N | PRO | 119 | 86.464 | -23.699 | 29.966 | 1.00 | 9.50 | L | N |
| ATOM | 3983 | CD | PRO | 119 | 85.678 | -24.330 | 28.892 | 1.00 | 26.21 | L | C |
| ATOM | 3984 | CA | PRO | 119 | 85.787 | -22.493 | 30.479 | 1.00 | 9.82 | L | C |
| ATOM | 3985 | CB | PRO | 119 | 84.413 | -22.555 | 29.826 | 1.00 | 24.20 | L | C |
| ATOM | 3986 | CG | PRO | 119 | 84.703 | -23.219 | 28.519 | 1.00 | 27.52 | L | C |
| ATOM | 3987 | C | PRO | 119 | 85.682 | -22.566 | 32.001 | 1.00 | 15.21 | L | C |
| ATOM | 3988 | O | PRO | 119 | 85.463 | -23.630 | 32.561 | 1.00 | 17.89 | L | O |
| ATOM | 3989 | N | SER | 120 | 85.843 | -21.435 | 32.665 | 1.00 | 31.09 | L | N |
| ATOM | 3990 | CA | SER | 120 | 85.765 | -21.378 | 34.118 | 1.00 | 35.08 | L | C |
| ATOM | 3991 | CB | SER | 120 | 86.299 | -20.027 | 34.586 | 1.00 | 17.54 | L | C |
| ATOM | 3992 | OG | SER | 120 | 85.709 | -18.983 | 33.832 | 1.00 | 27.86 | L | O |
| ATOM | 3993 | C | SER | 120 | 84.334 | -21.550 | 34.623 | 1.00 | 35.73 | L | C |
| ATOM | 3994 | O | SER | 120 | 83.370 | -21.381 | 33.869 | 1.00 | 35.32 | L | O |
| ATOM | 3995 | N | ASP | 121 | 84.185 | -21.896 | 35.897 | 1.00 | 24.20 | L | N |
| ATOM | 3996 | CA | ASP | 121 | 82.842 | -22.015 | 36.465 | 1.00 | 27.07 | L | C |
| ATOM | 3997 | CB | ASP | 121 | 82.897 | -22.458 | 37.937 | 1.00 | 55.35 | L | C |
| ATOM | 3998 | CG | ASP | 121 | 83.160 | -23.950 | 38.101 | 1.00 | 60.98 | L | C |
| ATOM | 3999 | OD1 | ASP | 121 | 82.573 | -24.736 | 37.331 | 1.00 | 62.35 | L | O |
| ATOM | 4000 | OD2 | ASP | 121 | 83.934 | -24.337 | 39.008 | 1.00 | 63.66 | L | O |
| ATOM | 4001 | C | ASP | 121 | 82.194 | -20.627 | 36.384 | 1.00 | 26.11 | L | C |
| ATOM | 4002 | O | ASP | 121 | 81.053 | -20.474 | 35.941 | 1.00 | 23.12 | L | O |
| ATOM | 4003 | N | GLU | 122 | 82.954 | -19.617 | 36.794 | 1.00 | 48.87 | L | N |
| ATOM | 4004 | CA | GLU | 122 | 82.490 | -18.234 | 36.797 | 1.00 | 47.43 | L | C |
| ATOM | 4005 | CB | GLU | 122 | 83.596 | -17.328 | 37.348 | 1.00 | 56.26 | L | C |
| ATOM | 4006 | CG | GLU | 122 | 83.180 | -15.870 | 37.529 | 1.00 | 59.80 | L | C |
| ATOM | 4007 | CD | GLU | 122 | 84.328 | -14.966 | 37.984 | 1.00 | 63.49 | L | C |
| ATOM | 4008 | OE1 | GLU | 122 | 84.099 | -13.741 | 38.109 | 1.00 | 64.12 | L | O |
| ATOM | 4009 | OE2 | GLU | 122 | 85.453 | -15.472 | 38.213 | 1.00 | 63.98 | L | O |
| ATOM | 4010 | C | GLU | 122 | 82.018 | -17.703 | 35.434 | 1.00 | 47.22 | L | C |
| ATOM | 4011 | O | GLU | 122 | 80.884 | -17.232 | 35.303 | 1.00 | 45.96 | L | O |
| ATOM | 4012 | N | GLN | 123 | 82.881 | -17.774 | 34.424 | 1.00 | 34.52 | L | N |
| ATOM | 4013 | CA | GLN | 123 | 82.523 | -17.273 | 33.102 | 1.00 | 32.32 | L | C |
| ATOM | 4014 | CB | GLN | 123 | 83.643 | -17.511 | 32.097 | 1.00 | 23.68 | L | C |
| ATOM | 4015 | CG | GLN | 123 | 83.286 | -17.000 | 30.723 | 1.00 | 24.85 | L | C |

Fig. 19: A-56

| | | | | | | | | | | |
|---|---|---|---|---|---|---|---|---|---|---|
| ATOM | 4016 | CD | GLN | 123 | 84.089 | -17.644 | 29.635 | 1.00 | 26.94 | L | C |
| ATOM | 4017 | OE1 | GLN | 123 | 83.877 | -17.369 | 28.463 | 1.00 | 23.36 | L | O |
| ATOM | 4018 | NE2 | GLN | 123 | 85.017 | -18.511 | 30.010 | 1.00 | 24.66 | L | N |
| ATOM | 4019 | C | GLN | 123 | 81.256 | -17.909 | 32.565 | 1.00 | 32.32 | L | C |
| ATOM | 4020 | O | GLN | 123 | 80.424 | -17.233 | 31.969 | 1.00 | 29.27 | L | O |
| ATOM | 4021 | N | LEU | 124 | 81.128 | -19.218 | 32.745 | 1.00 | 36.22 | L | N |
| ATOM | 4022 | CA | LEU | 124 | 79.938 | -19.926 | 32.288 | 1.00 | 37.57 | L | C |
| ATOM | 4023 | CB | LEU | 124 | 80.075 | -21.425 | 32.570 | 1.00 | 20.16 | L | C |
| ATOM | 4024 | CG | LEU | 124 | 80.878 | -22.173 | 31.498 | 1.00 | 19.96 | L | C |
| ATOM | 4025 | CD1 | LEU | 124 | 81.099 | -23.623 | 31.892 | 1.00 | 15.21 | L | C |
| ATOM | 4026 | CD2 | LEU | 124 | 80.123 | -22.085 | 30.176 | 1.00 | 18.53 | L | C |
| ATOM | 4027 | C | LEU | 124 | 78.722 | -19.355 | 33.003 | 1.00 | 41.33 | L | C |
| ATOM | 4028 | O | LEU | 124 | 77.648 | -19.204 | 32.417 | 1.00 | 43.14 | L | O |
| ATOM | 4029 | N | LYS | 125 | 78.912 | -19.022 | 34.274 | 1.00 | 101.23 | L | N |
| ATOM | 4030 | CA | LYS | 125 | 77.856 | -18.441 | 35.090 | 1.00 | 102.45 | L | C |
| ATOM | 4031 | CB | LYS | 125 | 78.355 | -18.285 | 36.534 | 1.00 | 60.11 | L | C |
| ATOM | 4032 | CG | LYS | 125 | 77.286 | -18.376 | 37.612 | 1.00 | 62.95 | L | C |
| ATOM | 4033 | CD | LYS | 125 | 76.737 | -19.797 | 37.713 | 1.00 | 68.67 | L | C |
| ATOM | 4034 | CE | LYS | 125 | 75.726 | -19.942 | 38.847 | 1.00 | 73.14 | L | C |
| ATOM | 4035 | NZ | LYS | 125 | 75.101 | -21.299 | 38.895 | 1.00 | 74.11 | L | N |
| ATOM | 4036 | C | LYS | 125 | 77.545 | -17.065 | 34.494 | 1.00 | 104.22 | L | C |
| ATOM | 4037 | O | LYS | 125 | 77.004 | -16.195 | 35.168 | 1.00 | 105.97 | L | O |
| ATOM | 4038 | N | SER | 126 | 77.892 | -16.880 | 33.222 | 1.00 | 44.02 | L | N |
| ATOM | 4039 | CA | SER | 126 | 77.693 | -15.614 | 32.522 | 1.00 | 43.14 | L | C |
| ATOM | 4040 | CB | SER | 126 | 79.045 | -14.925 | 32.308 | 1.00 | 48.89 | L | C |
| ATOM | 4041 | OG | SER | 126 | 78.953 | -13.915 | 31.324 | 1.00 | 52.18 | L | O |
| ATOM | 4042 | C | SER | 126 | 76.995 | -15.769 | 31.176 | 1.00 | 41.22 | L | C |
| ATOM | 4043 | O | SER | 126 | 76.469 | -14.802 | 30.631 | 1.00 | 40.32 | L | O |
| ATOM | 4044 | N | GLY | 127 | 77.007 | -16.978 | 30.626 | 1.00 | 29.57 | L | N |
| ATOM | 4045 | CA | GLY | 127 | 76.340 | -17.190 | 29.355 | 1.00 | 30.30 | L | C |
| ATOM | 4046 | C | GLY | 127 | 77.266 | -17.332 | 28.168 | 1.00 | 29.68 | L | C |
| ATOM | 4047 | O | GLY | 127 | 76.818 | -17.391 | 27.022 | 1.00 | 30.41 | L | O |
| ATOM | 4048 | N | THR | 128 | 78.564 | -17.375 | 28.432 | 1.00 | 60.53 | L | N |
| ATOM | 4049 | CA | THR | 128 | 79.530 | -17.531 | 27.360 | 1.00 | 57.77 | L | C |
| ATOM | 4050 | CB | THR | 128 | 80.105 | -16.180 | 26.921 | 1.00 | 55.78 | L | C |
| ATOM | 4051 | OG1 | THR | 128 | 79.080 | -15.424 | 26.264 | 1.00 | 56.94 | L | O |
| ATOM | 4052 | CG2 | THR | 128 | 81.259 | -16.381 | 25.960 | 1.00 | 54.81 | L | C |
| ATOM | 4053 | C | THR | 128 | 80.643 | -18.434 | 27.830 | 1.00 | 56.24 | L | C |
| ATOM | 4054 | O | THR | 128 | 80.979 | -18.446 | 29.015 | 1.00 | 51.99 | L | O |
| ATOM | 4055 | N | ALA | 129 | 81.201 | -19.203 | 26.901 | 1.00 | 18.93 | L | N |
| ATOM | 4056 | CA | ALA | 129 | 82.275 | -20.125 | 27.232 | 1.00 | 17.83 | L | C |
| ATOM | 4057 | CB | ALA | 129 | 81.779 | -21.558 | 27.108 | 1.00 | 65.23 | L | C |
| ATOM | 4058 | C | ALA | 129 | 83.512 | -19.937 | 26.374 | 1.00 | 17.59 | L | C |
| ATOM | 4059 | O | ALA | 129 | 83.443 | -19.993 | 25.148 | 1.00 | 23.96 | L | O |
| ATOM | 4060 | N | SER | 130 | 84.652 | -19.729 | 27.020 | 1.00 | 24.31 | L | N |
| ATOM | 4061 | CA | SER | 130 | 85.905 | -19.560 | 26.298 | 1.00 | 19.76 | L | C |
| ATOM | 4062 | CB | SER | 130 | 86.565 | -18.256 | 26.741 | 1.00 | 18.21 | L | C |
| ATOM | 4063 | OG | SER | 130 | 85.724 | -17.142 | 26.477 | 1.00 | 20.32 | L | O |
| ATOM | 4064 | C | SER | 130 | 86.835 | -20.755 | 26.573 | 1.00 | 16.63 | L | C |
| ATOM | 4065 | O | SER | 130 | 87.037 | -21.141 | 27.732 | 1.00 | 19.43 | L | O |
| ATOM | 4066 | N | VAL | 131 | 87.370 | -21.371 | 25.521 | 1.00 | 11.62 | L | N |
| ATOM | 4067 | CA | VAL | 131 | 88.294 | -22.502 | 25.686 | 1.00 | 9.15 | L | C |
| ATOM | 4068 | CB | VAL | 131 | 87.848 | -23.743 | 24.872 | 1.00 | 17.04 | L | C |
| ATOM | 4069 | CG1 | VAL | 131 | 88.738 | -24.927 | 25.196 | 1.00 | 21.32 | L | C |
| ATOM | 4070 | CG2 | VAL | 131 | 86.413 | -24.081 | 25.180 | 1.00 | 16.62 | L | C |
| ATOM | 4071 | C | VAL | 131 | 89.647 | -22.030 | 25.156 | 1.00 | 9.42 | L | C |
| ATOM | 4072 | O | VAL | 131 | 89.731 | -21.557 | 24.025 | 1.00 | 13.02 | L | O |
| ATOM | 4073 | N | VAL | 132 | 90.704 | -22.146 | 25.956 | 1.00 | 21.24 | L | N |
| ATOM | 4074 | CA | VAL | 132 | 92.011 | -21.677 | 25.501 | 1.00 | 16.30 | L | C |
| ATOM | 4075 | CB | VAL | 132 | 92.573 | -20.538 | 26.414 | 1.00 | 43.77 | L | C |
| ATOM | 4076 | CG1 | VAL | 132 | 93.958 | -20.122 | 25.934 | 1.00 | 47.77 | L | C |
| ATOM | 4077 | CG2 | VAL | 132 | 91.645 | -19.324 | 26.393 | 1.00 | 44.24 | L | C |
| ATOM | 4078 | C | VAL | 132 | 93.081 | -22.743 | 25.374 | 1.00 | 17.14 | L | C |
| ATOM | 4079 | O | VAL | 132 | 93.372 | -23.482 | 26.320 | 1.00 | 14.49 | L | O |
| ATOM | 4080 | N | CYS | 133 | 93.662 | -22.793 | 24.178 | 1.00 | 23.86 | L | N |
| ATOM | 4081 | CA | CYS | 133 | 94.737 | -23.713 | 23.822 | 1.00 | 24.13 | L | C |
| ATOM | 4082 | C | CYS | 133 | 96.034 | -22.880 | 23.891 | 1.00 | 24.10 | L | C |
| ATOM | 4083 | O | CYS | 133 | 96.072 | -21.744 | 23.425 | 1.00 | 27.83 | L | O |
| ATOM | 4084 | CB | CYS | 133 | 94.486 | -24.219 | 22.399 | 1.00 | 19.56 | L | C |
| ATOM | 4085 | SG | CYS | 133 | 95.558 | -25.537 | 21.738 | 1.00 | 32.96 | L | S |
| ATOM | 4086 | N | LEU | 134 | 97.085 | -23.432 | 24.482 | 1.00 | 36.02 | L | N |
| ATOM | 4087 | CA | LEU | 134 | 98.343 | -22.709 | 24.591 | 1.00 | 34.35 | L | C |
| ATOM | 4088 | CB | LEU | 134 | 98.658 | -22.383 | 26.058 | 1.00 | 16.71 | L | C |

Fig. 19: A-57

```
ATOM   4089  CG   LEU   134     100.079  -21.843   26.376  1.00   12.52    L   C
ATOM   4090  CD1  LEU   134     100.297  -20.468   25.729  1.00    9.26    L   C
ATOM   4091  CD2  LEU   134     100.275  -21.746   27.892  1.00    9.75    L   C
ATOM   4092  C    LEU   134      99.532  -23.457   24.001  1.00   33.88    L   C
ATOM   4093  O    LEU   134      99.820  -24.595   24.378  1.00   33.96    L   O
ATOM   4094  N    LEU   135     100.206  -22.802   23.060  1.00   23.69    L   N
ATOM   4095  CA   LEU   135     101.406  -23.336   22.441  1.00   29.22    L   C
ATOM   4096  CB   LEU   135     101.353  -23.150   20.926  1.00    1.87    L   C
ATOM   4097  CG   LEU   135     100.337  -24.016   20.168  1.00    4.32    L   C
ATOM   4098  CD1  LEU   135      98.962  -23.751   20.672  1.00    5.12    L   C
ATOM   4099  CD2  LEU   135     100.392  -23.713   18.681  1.00    3.70    L   C
ATOM   4100  C    LEU   135     102.454  -22.437   23.097  1.00   29.43    L   C
ATOM   4101  O    LEU   135     102.401  -21.216   22.977  1.00   30.81    L   O
ATOM   4102  N    ASN   136     103.394  -23.047   23.810  1.00   17.75    L   N
ATOM   4103  CA   ASN   136     104.393  -22.299   24.550  1.00   20.05    L   C
ATOM   4104  CB   ASN   136     104.179  -22.576   26.016  1.00   15.03    L   C
ATOM   4105  CG   ASN   136     104.905  -21.615   26.885  1.00   19.57    L   C
ATOM   4106  OD1  ASN   136     105.767  -22.017   27.666  1.00   25.01    L   O
ATOM   4107  ND2  ASN   136     104.569  -20.327   26.769  1.00   19.54    L   N
ATOM   4108  C    ASN   136     105.856  -22.526   24.212  1.00   18.78    L   C
ATOM   4109  O    ASN   136     106.283  -23.651   23.963  1.00   17.25    L   O
ATOM   4110  N    ASN   137     106.619  -21.436   24.240  1.00   28.11    L   N
ATOM   4111  CA   ASN   137     108.053  -21.425   23.950  1.00   27.19    L   C
ATOM   4112  CB   ASN   137     108.869  -21.844   25.173  1.00   13.82    L   C
ATOM   4113  CG   ASN   137     108.594  -20.986   26.387  1.00   24.17    L   C
ATOM   4114  OD1  ASN   137     108.027  -19.901   26.281  1.00   19.30    L   O
ATOM   4115  ND2  ASN   137     109.009  -21.468   27.558  1.00   29.25    L   N
ATOM   4116  C    ASN   137     108.486  -22.292   22.783  1.00   25.42    L   C
ATOM   4117  O    ASN   137     109.125  -23.324   22.977  1.00   28.31    L   O
ATOM   4118  N    PHE   138     108.152  -21.880   21.571  1.00   45.01    L   N
ATOM   4119  CA   PHE   138     108.557  -22.652   20.412  1.00   41.21    L   C
ATOM   4120  CB   PHE   138     107.362  -23.361   19.777  1.00   23.11    L   C
ATOM   4121  CG   PHE   138     106.230  -22.452   19.442  1.00   20.89    L   C
ATOM   4122  CD1  PHE   138     105.342  -22.043   20.433  1.00   18.63    L   C
ATOM   4123  CD2  PHE   138     106.055  -21.993   18.137  1.00   19.93    L   C
ATOM   4124  CE1  PHE   138     104.289  -21.189   20.134  1.00   11.59    L   C
ATOM   4125  CE2  PHE   138     105.010  -21.138   17.818  1.00   16.52    L   C
ATOM   4126  CZ   PHE   138     104.118  -20.730   18.818  1.00   14.07    L   C
ATOM   4127  C    PHE   138     109.248  -21.794   19.369  1.00   36.81    L   C
ATOM   4128  O    PHE   138     109.456  -20.594   19.559  1.00   35.37    L   O
ATOM   4129  N    TYR   139     109.606  -22.437   18.267  1.00   17.70    L   N
ATOM   4130  CA   TYR   139     110.283  -21.797   17.159  1.00   20.93    L   C
ATOM   4131  CB   TYR   139     111.660  -21.300   17.579  1.00   31.56    L   C
ATOM   4132  CG   TYR   139     112.317  -20.472   16.502  1.00   31.46    L   C
ATOM   4133  CD1  TYR   139     112.207  -19.083   16.502  1.00   26.49    L   C
ATOM   4134  CE1  TYR   139     112.725  -18.327   15.462  1.00   25.20    L   C
ATOM   4135  CD2  TYR   139     112.974  -21.083   15.428  1.00   25.20    L   C
ATOM   4136  CE2  TYR   139     113.490  -20.336   14.386  1.00   25.20    L   C
ATOM   4137  CZ   TYR   139     113.358  -18.960   14.407  1.00   25.20    L   C
ATOM   4138  OH   TYR   139     113.820  -18.216   13.353  1.00   28.00    L   O
ATOM   4139  C    TYR   139     110.447  -22.917   16.166  1.00   20.32    L   C
ATOM   4140  O    TYR   139     110.798  -24.022   16.550  1.00   25.25    L   O
ATOM   4141  N    PRO   140     110.223  -22.662   14.876  1.00   34.32    L   N
ATOM   4142  CD   PRO   140     110.342  -23.783   13.937  1.00    6.42    L   C
ATOM   4143  CA   PRO   140     109.824  -21.443   14.171  1.00   30.02    L   C
ATOM   4144  CB   PRO   140     109.691  -21.901   12.723  1.00    2.76    L   C
ATOM   4145  CG   PRO   140     110.570  -23.070   12.643  1.00    4.42    L   C
ATOM   4146  C    PRO   140     108.502  -20.939   14.685  1.00   31.53    L   C
ATOM   4147  O    PRO   140     107.830  -21.612   15.466  1.00   29.36    L   O
ATOM   4148  N    ARG   141     108.119  -19.764   14.203  1.00   22.83    L   N
ATOM   4149  CA   ARG   141     106.871  -19.115   14.588  1.00   27.99    L   C
ATOM   4150  CB   ARG   141     106.931  -17.657   14.148  1.00   21.70    L   C
ATOM   4151  CG   ARG   141     105.753  -16.783   14.473  1.00   25.87    L   C
ATOM   4152  CD   ARG   141     106.157  -15.358   14.129  1.00   37.20    L   C
ATOM   4153  NE   ARG   141     105.187  -14.366   14.564  1.00   43.19    L   N
ATOM   4154  CZ   ARG   141     104.001  -14.188   13.995  1.00   43.90    L   C
ATOM   4155  NH1  ARG   141     103.642  -14.941   12.960  1.00   39.57    L   N
ATOM   4156  NH2  ARG   141     103.173  -13.262   14.464  1.00   42.44    L   N
ATOM   4157  C    ARG   141     105.668  -19.798   13.960  1.00   30.81    L   C
ATOM   4158  O    ARG   141     104.585  -19.815   14.537  1.00   34.71    L   O
ATOM   4159  N    GLU   142     105.860  -20.365   12.776  1.00   28.20    L   N
ATOM   4160  CA   GLU   142     104.756  -21.013   12.091  1.00   24.33    L   C
ATOM   4161  CB   GLU   142     105.171  -21.552   10.725  1.00    7.98    L   C
```

Fig. 19: A-58

```
ATOM   4162  CG   GLU  142     105.741 -20.523   9.781  1.00   19.00    L  C
ATOM   4163  CD   GLU  142     107.096 -20.051  10.217  1.00   27.12    L  C
ATOM   4164  OE1  GLU  142     107.152 -18.970  10.837  1.00   31.02    L  O
ATOM   4165  OE2  GLU  142     108.095 -20.772   9.952  1.00   33.88    L  O
ATOM   4166  C    GLU  142     104.154 -22.151  12.878  1.00   22.94    L  C
ATOM   4167  O    GLU  142     104.753 -23.220  13.021  1.00   26.95    L  O
ATOM   4168  N    ALA  143     102.958 -21.909  13.386  1.00   30.55    L  N
ATOM   4169  CA   ALA  143     102.238 -22.914  14.130  1.00   32.81    L  C
ATOM   4170  CB   ALA  143     102.260 -22.593  15.640  1.00   21.32    L  C
ATOM   4171  C    ALA  143     100.819 -22.862  13.579  1.00   34.94    L  C
ATOM   4172  O    ALA  143     100.373 -21.832  13.058  1.00   38.69    L  O
ATOM   4173  N    LYS  144     100.120 -23.981  13.677  1.00   46.96    L  N
ATOM   4174  CA   LYS  144      98.761 -24.047  13.197  1.00   49.64    L  C
ATOM   4175  CB   LYS  144      98.734 -24.807  11.870  1.00   34.36    L  C
ATOM   4176  CG   LYS  144      97.631 -24.370  10.922  1.00   44.31    L  C
ATOM   4177  CD   LYS  144      97.441 -25.358   9.772  1.00   55.06    L  C
ATOM   4178  CE   LYS  144      96.888 -26.699  10.279  1.00   57.35    L  C
ATOM   4179  NZ   LYS  144      96.807 -27.761   9.225  1.00   58.76    L  N
ATOM   4180  C    LYS  144      97.934 -24.771  14.266  1.00   52.97    L  C
ATOM   4181  O    LYS  144      98.340 -25.822  14.775  1.00   51.55    L  O
ATOM   4182  N    VAL  145      96.791 -24.194  14.630  1.00   15.87    L  N
ATOM   4183  CA   VAL  145      95.927 -24.813  15.629  1.00   21.71    L  C
ATOM   4184  CB   VAL  145      95.790 -23.937  16.905  1.00    8.53    L  C
ATOM   4185  CG1  VAL  145      94.817 -24.597  17.889  1.00    7.53    L  C
ATOM   4186  CG2  VAL  145      97.151 -23.769  17.570  1.00    8.28    L  C
ATOM   4187  C    VAL  145      94.536 -25.074  15.073  1.00   25.32    L  C
ATOM   4188  O    VAL  145      93.909 -24.193  14.497  1.00   27.49    L  O
ATOM   4189  N    GLN  146      94.055 -26.296  15.231  1.00   39.17    L  N
ATOM   4190  CA   GLN  146      92.729 -26.611  14.743  1.00   38.70    L  C
ATOM   4191  CB   GLN  146      92.798 -27.679  13.653  1.00   72.09    L  C
ATOM   4192  CG   GLN  146      93.678 -27.281  12.482  1.00   76.00    L  C
ATOM   4193  CD   GLN  146      93.630 -28.276  11.339  1.00   75.94    L  C
ATOM   4194  OE1  GLN  146      92.616 -28.399  10.654  1.00   76.92    L  O
ATOM   4195  NE2  GLN  146      94.730 -28.997  11.130  1.00   77.33    L  N
ATOM   4196  C    GLN  146      91.880 -27.094  15.904  1.00   37.70    L  C
ATOM   4197  O    GLN  146      92.302 -27.965  16.667  1.00   34.46    L  O
ATOM   4198  N    TRP  147      90.699 -26.498  16.048  1.00   30.86    L  N
ATOM   4199  CA   TRP  147      89.777 -26.878  17.102  1.00   30.91    L  C
ATOM   4200  CB   TRP  147      88.947 -25.687  17.556  1.00   36.68    L  C
ATOM   4201  CG   TRP  147      89.689 -24.788  18.432  1.00   34.29    L  C
ATOM   4202  CD2  TRP  147      89.927 -24.969  19.825  1.00   32.37    L  C
ATOM   4203  CE2  TRP  147      90.723 -23.885  20.258  1.00   33.31    L  C
ATOM   4204  CE3  TRP  147      89.552 -25.943  20.752  1.00   31.13    L  C
ATOM   4205  CD1  TRP  147      90.326 -23.641  18.077  1.00   36.68    L  C
ATOM   4206  NE1  TRP  147      90.951 -23.086  19.168  1.00   33.41    L  N
ATOM   4207  CZ2  TRP  147      91.150 -23.747  21.587  1.00   31.66    L  C
ATOM   4208  CZ3  TRP  147      89.977 -25.808  22.073  1.00   33.39    L  C
ATOM   4209  CH2  TRP  147      90.767 -24.716  22.476  1.00   33.58    L  C
ATOM   4210  C    TRP  147      88.844 -27.963  16.611  1.00   33.36    L  C
ATOM   4211  O    TRP  147      88.440 -27.968  15.453  1.00   34.42    L  O
ATOM   4212  N    LYS  148      88.495 -28.877  17.501  1.00   28.86    L  N
ATOM   4213  CA   LYS  148      87.609 -29.958  17.147  1.00   29.96    L  C
ATOM   4214  CB   LYS  148      88.431 -31.196  16.787  1.00   35.94    L  C
ATOM   4215  CG   LYS  148      88.353 -31.585  15.320  1.00   39.31    L  C
ATOM   4216  CD   LYS  148      89.726 -31.865  14.715  1.00   45.24    L  C
ATOM   4217  CE   LYS  148      90.421 -33.078  15.337  1.00   45.54    L  C
ATOM   4218  NZ   LYS  148      91.826 -33.267  14.818  1.00   44.96    L  N
ATOM   4219  C    LYS  148      86.712 -30.227  18.340  1.00   32.40    L  C
ATOM   4220  O    LYS  148      87.197 -30.505  19.438  1.00   31.51    L  O
ATOM   4221  N    VAL  149      85.404 -30.124  18.118  1.00   22.85    L  N
ATOM   4222  CA   VAL  149      84.406 -30.352  19.161  1.00   20.04    L  C
ATOM   4223  CB   VAL  149      83.453 -29.167  19.269  1.00    1.90    L  C
ATOM   4224  CG1  VAL  149      82.408 -29.440  20.364  1.00    1.90    L  C
ATOM   4225  CG2  VAL  149      84.242 -27.899  19.563  1.00    1.90    L  C
ATOM   4226  C    VAL  149      83.580 -31.605  18.862  1.00   23.24    L  C
ATOM   4227  O    VAL  149      82.835 -31.642  17.883  1.00   24.43    L  O
ATOM   4228  N    ASP  150      83.679 -32.611  19.731  1.00   18.00    L  N
ATOM   4229  CA   ASP  150      82.974 -33.863  19.502  1.00   21.30    L  C
ATOM   4230  CB   ASP  150      81.464 -33.661  19.459  1.00   45.33    L  C
ATOM   4231  CG   ASP  150      80.862 -33.543  20.840  1.00   50.39    L  C
ATOM   4232  OD1  ASP  150      81.334 -34.248  21.760  1.00   51.76    L  O
ATOM   4233  OD2  ASP  150      79.910 -32.756  21.007  1.00   53.67    L  O
ATOM   4234  C    ASP  150      83.487 -34.293  18.152  1.00   22.51    L  C
```

Fig. 19: A-59

```
ATOM   4235  O    ASP  150     82.737 -34.683  17.268  1.00  23.76   L  O
ATOM   4236  N    ASN  151     84.800 -34.161  18.007  1.00  36.79   L  N
ATOM   4237  CA   ASN  151     85.493 -34.524  16.789  1.00  39.62   L  C
ATOM   4238  CB   ASN  151     85.425 -36.041  16.614  1.00  29.22   L  C
ATOM   4239  CG   ASN  151     86.220 -36.776  17.683  1.00  38.58   L  C
ATOM   4240  OD1  ASN  151     87.450 -36.736  17.686  1.00  42.16   L  O
ATOM   4241  ND2  ASN  151     85.522 -37.430  18.608  1.00  39.63   L  N
ATOM   4242  C    ASN  151     84.985 -33.778  15.557  1.00  37.90   L  C
ATOM   4243  O    ASN  151     85.224 -34.183  14.425  1.00  41.98   L  O
ATOM   4244  N    ALA  152     84.293 -32.672  15.793  1.00  26.76   L  N
ATOM   4245  CA   ALA  152     83.802 -31.838  14.703  1.00  29.16   L  C
ATOM   4246  CB   ALA  152     82.421 -31.261  15.034  1.00   1.87   L  C
ATOM   4247  C    ALA  152     84.801 -30.698  14.501  1.00  30.47   L  C
ATOM   4248  O    ALA  152     84.940 -29.813  15.355  1.00  32.16   L  O
ATOM   4249  N    LEU  153     85.502 -30.724  13.375  1.00  37.66   L  N
ATOM   4250  CA   LEU  153     86.470 -29.684  13.073  1.00  38.47   L  C
ATOM   4251  CB   LEU  153     87.021 -29.896  11.656  1.00  33.69   L  C
ATOM   4252  CG   LEU  153     87.944 -28.864  11.005  1.00  36.76   L  C
ATOM   4253  CD1  LEU  153     87.112 -27.705  10.466  1.00  35.54   L  C
ATOM   4254  CD2  LEU  153     88.999 -28.394  12.004  1.00  35.80   L  C
ATOM   4255  C    LEU  153     85.796 -28.315  13.206  1.00  37.05   L  C
ATOM   4256  O    LEU  153     84.632 -28.150  12.870  1.00  37.53   L  O
ATOM   4257  N    GLN  154     86.524 -27.342  13.732  1.00  42.87   L  N
ATOM   4258  CA   GLN  154     85.984 -26.006  13.885  1.00  41.76   L  C
ATOM   4259  CB   GLN  154     86.346 -25.438  15.255  1.00  24.84   L  C
ATOM   4260  CG   GLN  154     85.653 -26.133  16.403  1.00  25.94   L  C
ATOM   4261  CD   GLN  154     84.146 -26.162  16.225  1.00  28.42   L  C
ATOM   4262  OE1  GLN  154     83.495 -25.115  16.127  1.00  30.98   L  O
ATOM   4263  NE2  GLN  154     83.584 -27.365  16.176  1.00  27.76   L  N
ATOM   4264  C    GLN  154     86.574 -25.139  12.793  1.00  40.20   L  C
ATOM   4265  O    GLN  154     87.702 -25.363  12.350  1.00  39.24   L  O
ATOM   4266  N    SER  155     85.813 -24.146  12.359  1.00  42.27   L  N
ATOM   4267  CA   SER  155     86.269 -23.257  11.306  1.00  44.34   L  C
ATOM   4268  CB   SER  155     85.770 -23.768   9.952  1.00  47.84   L  C
ATOM   4269  OG   SER  155     86.319 -23.035   8.872  1.00  49.98   L  O
ATOM   4270  C    SER  155     85.693 -21.888  11.600  1.00  40.94   L  C
ATOM   4271  O    SER  155     86.208 -20.864  11.160  1.00  39.18   L  O
ATOM   4272  N    GLY  156     84.621 -21.877  12.374  1.00  21.85   L  N
ATOM   4273  CA   GLY  156     83.986 -20.619  12.702  1.00  22.33   L  C
ATOM   4274  C    GLY  156     84.732 -19.585  13.544  1.00  22.19   L  C
ATOM   4275  O    GLY  156     85.518 -18.793  13.032  1.00  19.16   L  O
ATOM   4276  N    ASN  157     84.484 -19.595  14.850  1.00  39.06   L  N
ATOM   4277  CA   ASN  157     85.088 -18.595  15.697  1.00  40.50   L  C
ATOM   4278  CB   ASN  157     83.992 -17.700  16.281  1.00 106.22   L  C
ATOM   4279  CG   ASN  157     83.201 -16.977  15.200  1.00 109.22   L  C
ATOM   4280  OD1  ASN  157     83.779 -16.402  14.277  1.00 109.54   L  O
ATOM   4281  ND2  ASN  157     81.874 -16.999  15.313  1.00 114.95   L  N
ATOM   4282  C    ASN  157     86.059 -18.997  16.790  1.00  41.01   L  C
ATOM   4283  O    ASN  157     85.713 -19.566  17.827  1.00  40.41   L  O
ATOM   4284  N    SER  158     87.299 -18.635  16.520  1.00  42.44   L  N
ATOM   4285  CA   SER  158     88.409 -18.862  17.405  1.00  35.84   L  C
ATOM   4286  CB   SER  158     89.078 -20.173  17.047  1.00  10.55   L  C
ATOM   4287  OG   SER  158     89.643 -20.069  15.757  1.00  10.12   L  O
ATOM   4288  C    SER  158     89.326 -17.691  17.059  1.00  34.29   L  C
ATOM   4289  O    SER  158     89.197 -17.092  15.992  1.00  32.27   L  O
ATOM   4290  N    GLN  159     90.238 -17.345  17.952  1.00  34.35   L  N
ATOM   4291  CA   GLN  159     91.133 -16.250  17.652  1.00  31.73   L  C
ATOM   4292  CB   GLN  159     90.538 -14.932  18.130  1.00  20.18   L  C
ATOM   4293  CG   GLN  159     89.399 -14.413  17.266  1.00  21.46   L  C
ATOM   4294  CD   GLN  159     89.053 -12.981  17.608  1.00  25.67   L  C
ATOM   4295  OE1  GLN  159     88.796 -12.658  18.762  1.00  28.88   L  O
ATOM   4296  NE2  GLN  159     89.051 -12.114  16.606  1.00  25.13   L  N
ATOM   4297  C    GLN  159     92.502 -16.452  18.255  1.00  29.74   L  C
ATOM   4298  O    GLN  159     92.647 -16.711  19.449  1.00  28.24   L  O
ATOM   4299  N    GLU  160     93.514 -16.327  17.414  1.00  31.36   L  N
ATOM   4300  CA   GLU  160     94.872 -16.510  17.865  1.00  24.49   L  C
ATOM   4301  CB   GLU  160     95.646 -17.316  16.834  1.00  58.94   L  C
ATOM   4302  CG   GLU  160     94.977 -18.617  16.476  1.00  59.06   L  C
ATOM   4303  CD   GLU  160     95.890 -19.506  15.678  1.00  67.10   L  C
ATOM   4304  OE1  GLU  160     95.463 -20.619  15.285  1.00  71.37   L  O
ATOM   4305  OE2  GLU  160     97.043 -19.078  15.452  1.00  65.02   L  O
ATOM   4306  C    GLU  160     95.591 -15.199  18.140  1.00  20.89   L  C
ATOM   4307  O    GLU  160     95.211 -14.141  17.654  1.00  14.39   L  O
```

Fig. 19: A-60

| ATOM | 4308 | N | SER | 161 | 96.639 | -15.293 | 18.941 | 1.00 | 19.35 | L | N |
|---|---|---|---|---|---|---|---|---|---|---|---|
| ATOM | 4309 | CA | SER | 161 | 97.456 | -14.151 | 19.310 | 1.00 | 16.36 | L | C |
| ATOM | 4310 | CB | SER | 161 | 96.953 | -13.486 | 20.597 | 1.00 | 26.12 | L | C |
| ATOM | 4311 | OG | SER | 161 | 97.935 | -12.623 | 21.157 | 1.00 | 26.54 | L | O |
| ATOM | 4312 | C | SER | 161 | 98.811 | -14.751 | 19.556 | 1.00 | 11.36 | L | C |
| ATOM | 4313 | O | SER | 161 | 98.934 | -15.799 | 20.191 | 1.00 | 11.86 | L | O |
| ATOM | 4314 | N | VAL | 162 | 99.833 | -14.086 | 19.053 | 1.00 | 21.19 | L | N |
| ATOM | 4315 | CA | VAL | 162 | 101.170 | -14.592 | 19.215 | 1.00 | 22.81 | L | C |
| ATOM | 4316 | CB | VAL | 162 | 101.764 | -14.965 | 17.832 | 1.00 | 29.37 | L | C |
| ATOM | 4317 | CG1 | VAL | 162 | 101.449 | -13.865 | 16.834 | 1.00 | 33.68 | L | C |
| ATOM | 4318 | CG2 | VAL | 162 | 103.270 | -15.178 | 17.933 | 1.00 | 33.85 | L | C |
| ATOM | 4319 | C | VAL | 162 | 101.997 | -13.524 | 19.877 | 1.00 | 25.31 | L | C |
| ATOM | 4320 | O | VAL | 162 | 101.835 | -12.319 | 19.566 | 1.00 | 32.55 | L | O |
| ATOM | 4321 | N | THR | 163 | 102.861 | -13.928 | 20.805 | 1.00 | 22.97 | L | N |
| ATOM | 4322 | CA | THR | 163 | 103.735 | -12.975 | 21.475 | 1.00 | 21.36 | L | C |
| ATOM | 4323 | CB | THR | 163 | 104.424 | -13.567 | 22.719 | 1.00 | 4.31 | L | C |
| ATOM | 4324 | OG1 | THR | 163 | 105.214 | -14.705 | 22.342 | 1.00 | 10.67 | L | O |
| ATOM | 4325 | CG2 | THR | 163 | 103.411 | -13.966 | 23.748 | 1.00 | 4.70 | L | C |
| ATOM | 4326 | C | THR | 163 | 104.842 | -12.550 | 20.520 | 1.00 | 20.43 | L | C |
| ATOM | 4327 | O | THR | 163 | 104.880 | -12.951 | 19.350 | 1.00 | 20.01 | L | O |
| ATOM | 4328 | N | GLU | 164 | 105.741 | -11.722 | 21.022 | 1.00 | 16.64 | L | N |
| ATOM | 4329 | CA | GLU | 164 | 106.844 | -11.283 | 20.211 | 1.00 | 24.33 | L | C |
| ATOM | 4330 | CB | GLU | 164 | 107.182 | -9.828 | 20.515 | 1.00 | 53.60 | L | C |
| ATOM | 4331 | CG | GLU | 164 | 107.982 | -9.187 | 19.415 | 1.00 | 64.34 | L | C |
| ATOM | 4332 | CD | GLU | 164 | 107.202 | -9.144 | 18.126 | 1.00 | 70.19 | L | C |
| ATOM | 4333 | OE1 | GLU | 164 | 106.337 | -8.252 | 17.994 | 1.00 | 69.97 | L | O |
| ATOM | 4334 | OE2 | GLU | 164 | 107.442 | -10.011 | 17.257 | 1.00 | 73.61 | L | O |
| ATOM | 4335 | C | GLU | 164 | 107.989 | -12.190 | 20.635 | 1.00 | 22.81 | L | C |
| ATOM | 4336 | O | GLU | 164 | 107.990 | -12.697 | 21.765 | 1.00 | 25.48 | L | O |
| ATOM | 4337 | N | GLN | 165 | 108.948 | -12.407 | 19.734 | 1.00 | 26.35 | L | N |
| ATOM | 4338 | CA | GLN | 165 | 110.100 | -13.261 | 20.018 | 1.00 | 31.24 | L | C |
| ATOM | 4339 | CB | GLN | 165 | 111.181 | -13.024 | 18.967 | 1.00 | 24.53 | L | C |
| ATOM | 4340 | CG | GLN | 165 | 111.927 | -14.274 | 18.584 | 1.00 | 20.02 | L | C |
| ATOM | 4341 | CD | GLN | 165 | 112.911 | -14.054 | 17.454 | 1.00 | 22.62 | L | C |
| ATOM | 4342 | OE1 | GLN | 165 | 113.487 | -15.005 | 16.930 | 1.00 | 23.83 | L | O |
| ATOM | 4343 | NE2 | GLN | 165 | 113.118 | -12.794 | 17.080 | 1.00 | 19.11 | L | N |
| ATOM | 4344 | C | GLN | 165 | 110.633 | -12.941 | 21.412 | 1.00 | 35.11 | L | C |
| ATOM | 4345 | O | GLN | 165 | 110.857 | -11.783 | 21.739 | 1.00 | 31.98 | L | O |
| ATOM | 4346 | N | ASP | 166 | 110.826 | -13.963 | 22.236 | 1.00 | 20.85 | L | N |
| ATOM | 4347 | CA | ASP | 166 | 111.311 | -13.741 | 23.592 | 1.00 | 27.22 | L | C |
| ATOM | 4348 | CB | ASP | 166 | 111.206 | -15.030 | 24.402 | 1.00 | 40.40 | L | C |
| ATOM | 4349 | CG | ASP | 166 | 111.513 | -14.813 | 25.872 | 1.00 | 48.39 | L | C |
| ATOM | 4350 | OD1 | ASP | 166 | 112.706 | -14.808 | 26.246 | 1.00 | 51.89 | L | O |
| ATOM | 4351 | OD2 | ASP | 166 | 110.555 | -14.631 | 26.655 | 1.00 | 52.06 | L | O |
| ATOM | 4352 | C | ASP | 166 | 112.741 | -13.205 | 23.656 | 1.00 | 29.80 | L | C |
| ATOM | 4353 | O | ASP | 166 | 113.659 | -13.787 | 23.079 | 1.00 | 33.62 | L | O |
| ATOM | 4354 | N | SER | 167 | 112.923 | -12.098 | 24.371 | 1.00 | 40.62 | L | N |
| ATOM | 4355 | CA | SER | 167 | 114.238 | -11.463 | 24.521 | 1.00 | 38.35 | L | C |
| ATOM | 4356 | CB | SER | 167 | 114.089 | -10.092 | 25.191 | 1.00 | 42.38 | L | C |
| ATOM | 4357 | OG | SER | 167 | 113.564 | -10.221 | 26.499 | 1.00 | 53.10 | L | O |
| ATOM | 4358 | C | SER | 167 | 115.229 | -12.312 | 25.325 | 1.00 | 40.21 | L | C |
| ATOM | 4359 | O | SER | 167 | 116.373 | -11.913 | 25.544 | 1.00 | 45.86 | L | O |
| ATOM | 4360 | N | LYS | 168 | 114.777 | -13.475 | 25.782 | 1.00 | 39.00 | L | N |
| ATOM | 4361 | CA | LYS | 168 | 115.637 | -14.383 | 26.527 | 1.00 | 40.59 | L | C |
| ATOM | 4362 | CB | LYS | 168 | 114.968 | -14.809 | 27.837 | 1.00 | 73.78 | L | C |
| ATOM | 4363 | CG | LYS | 168 | 115.002 | -13.726 | 28.916 | 1.00 | 80.20 | L | C |
| ATOM | 4364 | CD | LYS | 168 | 114.141 | -12.523 | 28.554 | 1.00 | 89.23 | L | C |
| ATOM | 4365 | CE | LYS | 168 | 112.663 | -12.805 | 28.778 | 1.00 | 96.32 | L | C |
| ATOM | 4366 | NZ | LYS | 168 | 112.355 | -13.017 | 30.222 | 1.00 | 95.77 | L | N |
| ATOM | 4367 | C | LYS | 168 | 115.959 | -15.597 | 25.650 | 1.00 | 39.39 | L | C |
| ATOM | 4368 | O | LYS | 168 | 117.046 | -15.671 | 25.077 | 1.00 | 43.53 | L | O |
| ATOM | 4369 | N | ASP | 169 | 115.011 | -16.522 | 25.506 | 1.00 | 18.93 | L | N |
| ATOM | 4370 | CA | ASP | 169 | 115.240 | -17.716 | 24.686 | 1.00 | 15.08 | L | C |
| ATOM | 4371 | CB | ASP | 169 | 114.476 | -18.913 | 25.262 | 1.00 | 29.81 | L | C |
| ATOM | 4372 | CG | ASP | 169 | 112.992 | -18.648 | 25.407 | 1.00 | 32.60 | L | C |
| ATOM | 4373 | OD1 | ASP | 169 | 112.397 | -18.049 | 24.488 | 1.00 | 27.93 | L | O |
| ATOM | 4374 | OD2 | ASP | 169 | 112.415 | -19.054 | 26.441 | 1.00 | 29.85 | L | O |
| ATOM | 4375 | C | ASP | 169 | 114.914 | -17.596 | 23.193 | 1.00 | 15.61 | L | C |
| ATOM | 4376 | O | ASP | 169 | 115.038 | -18.571 | 22.459 | 1.00 | 9.73 | L | O |
| ATOM | 4377 | N | SER | 170 | 114.490 | -16.418 | 22.747 | 1.00 | 28.98 | L | N |
| ATOM | 4378 | CA | SER | 170 | 114.170 | -16.202 | 21.331 | 1.00 | 26.94 | L | C |
| ATOM | 4379 | CB | SER | 170 | 115.401 | -16.487 | 20.433 | 1.00 | 15.64 | L | C |
| ATOM | 4380 | OG | SER | 170 | 116.466 | -15.560 | 20.636 | 1.00 | 17.90 | L | O |

Fig. 19: A-61

| ATOM | 4381 | C | SER | 170 | 112.995 | -17.042 | 20.825 | 1.00 | 25.42 | L | C |
| ATOM | 4382 | O | SER | 170 | 112.916 | -17.345 | 19.636 | 1.00 | 25.18 | L | O |
| ATOM | 4383 | N | THR | 171 | 112.071 | -17.411 | 21.702 | 1.00 | 22.07 | L | N |
| ATOM | 4384 | CA | THR | 171 | 110.946 | -18.222 | 21.247 | 1.00 | 22.16 | L | C |
| ATOM | 4385 | CB | THR | 171 | 110.658 | -19.406 | 22.212 | 1.00 | 16.53 | L | C |
| ATOM | 4386 | OG1 | THR | 171 | 110.127 | -18.911 | 23.452 | 1.00 | 18.93 | L | O |
| ATOM | 4387 | CG2 | THR | 171 | 111.939 | -20.191 | 22.471 | 1.00 | 18.13 | L | C |
| ATOM | 4388 | C | THR | 171 | 109.657 | -17.437 | 21.064 | 1.00 | 26.03 | L | C |
| ATOM | 4389 | O | THR | 171 | 109.601 | -16.235 | 21.327 | 1.00 | 31.48 | L | O |
| ATOM | 4390 | N | TYR | 172 | 108.633 | -18.147 | 20.596 | 1.00 | 7.82 | L | N |
| ATOM | 4391 | CA | TYR | 172 | 107.297 | -17.600 | 20.373 | 1.00 | 6.45 | L | C |
| ATOM | 4392 | CB | TYR | 172 | 106.934 | -17.706 | 18.894 | 1.00 | 43.65 | L | C |
| ATOM | 4393 | CG | TYR | 172 | 107.809 | -16.890 | 17.974 | 1.00 | 37.38 | L | C |
| ATOM | 4394 | CD1 | TYR | 172 | 107.652 | -15.507 | 17.865 | 1.00 | 32.97 | L | C |
| ATOM | 4395 | CE1 | TYR | 172 | 108.438 | -14.759 | 16.977 | 1.00 | 32.97 | L | C |
| ATOM | 4396 | CD2 | TYR | 172 | 108.776 | -17.508 | 17.181 | 1.00 | 37.97 | L | C |
| ATOM | 4397 | CE2 | TYR | 172 | 109.565 | -16.774 | 16.296 | 1.00 | 34.76 | L | C |
| ATOM | 4398 | CZ | TYR | 172 | 109.391 | -15.405 | 16.194 | 1.00 | 32.97 | L | C |
| ATOM | 4399 | OH | TYR | 172 | 110.163 | -14.703 | 15.294 | 1.00 | 32.97 | L | O |
| ATOM | 4400 | C | TYR | 172 | 106.255 | -18.364 | 21.212 | 1.00 | 6.45 | L | C |
| ATOM | 4401 | O | TYR | 172 | 106.431 | -19.539 | 21.528 | 1.00 | 9.78 | L | O |
| ATOM | 4402 | N | SER | 173 | 105.183 | -17.687 | 21.600 | 1.00 | 23.67 | L | N |
| ATOM | 4403 | CA | SER | 173 | 104.123 | -18.323 | 22.370 | 1.00 | 25.48 | L | C |
| ATOM | 4404 | CB | SER | 173 | 104.165 | -17.902 | 23.834 | 1.00 | 31.18 | L | C |
| ATOM | 4405 | OG | SER | 173 | 105.281 | -18.492 | 24.468 | 1.00 | 25.15 | L | O |
| ATOM | 4406 | C | SER | 173 | 102.836 | -17.886 | 21.728 | 1.00 | 26.94 | L | C |
| ATOM | 4407 | O | SER | 173 | 102.611 | -16.699 | 21.473 | 1.00 | 27.36 | L | O |
| ATOM | 4408 | N | LEU | 174 | 101.980 | -18.857 | 21.474 | 1.00 | 22.39 | L | N |
| ATOM | 4409 | CA | LEU | 174 | 100.734 | -18.593 | 20.791 | 1.00 | 25.49 | L | C |
| ATOM | 4410 | CB | LEU | 174 | 100.836 | -19.238 | 19.399 | 1.00 | 22.33 | L | C |
| ATOM | 4411 | CG | LEU | 174 | 99.682 | -19.165 | 18.422 | 1.00 | 13.39 | L | C |
| ATOM | 4412 | CD1 | LEU | 174 | 100.207 | -19.296 | 17.013 | 1.00 | 17.21 | L | C |
| ATOM | 4413 | CD2 | LEU | 174 | 98.663 | -20.257 | 18.769 | 1.00 | 10.23 | L | C |
| ATOM | 4414 | C | LEU | 174 | 99.510 | -19.075 | 21.562 | 1.00 | 27.64 | L | C |
| ATOM | 4415 | O | LEU | 174 | 99.542 | -20.111 | 22.229 | 1.00 | 30.82 | L | O |
| ATOM | 4416 | N | SER | 175 | 98.433 | -18.306 | 21.470 | 1.00 | 22.56 | L | N |
| ATOM | 4417 | CA | SER | 175 | 97.200 | -18.651 | 22.162 | 1.00 | 25.61 | L | C |
| ATOM | 4418 | CB | SER | 175 | 96.913 | -17.644 | 23.292 | 1.00 | 28.99 | L | C |
| ATOM | 4419 | OG | SER | 175 | 96.487 | -16.378 | 22.794 | 1.00 | 32.45 | L | O |
| ATOM | 4420 | C | SER | 175 | 96.009 | -18.693 | 21.214 | 1.00 | 29.48 | L | C |
| ATOM | 4421 | O | SER | 175 | 95.733 | -17.718 | 20.511 | 1.00 | 30.81 | L | O |
| ATOM | 4422 | N | SER | 176 | 95.316 | -19.829 | 21.181 | 1.00 | 31.99 | L | N |
| ATOM | 4423 | CA | SER | 176 | 94.125 | -19.957 | 20.346 | 1.00 | 32.77 | L | C |
| ATOM | 4424 | CB | SER | 176 | 94.154 | -21.247 | 19.514 | 1.00 | 10.71 | L | C |
| ATOM | 4425 | OG | SER | 176 | 93.247 | -21.176 | 18.421 | 1.00 | 10.34 | L | O |
| ATOM | 4426 | C | SER | 176 | 92.985 | -19.991 | 21.352 | 1.00 | 29.41 | L | C |
| ATOM | 4427 | O | SER | 176 | 93.042 | -20.712 | 22.350 | 1.00 | 29.56 | L | O |
| ATOM | 4428 | N | THR | 177 | 91.963 | -19.183 | 21.118 | 1.00 | 38.41 | L | N |
| ATOM | 4429 | CA | THR | 177 | 90.846 | -19.136 | 22.042 | 1.00 | 37.60 | L | C |
| ATOM | 4430 | CB | THR | 177 | 90.742 | -17.741 | 22.706 | 1.00 | 7.23 | L | C |
| ATOM | 4431 | OG1 | THR | 177 | 92.000 | -17.399 | 23.318 | 1.00 | 10.12 | L | O |
| ATOM | 4432 | CG2 | THR | 177 | 89.631 | -17.728 | 23.773 | 1.00 | 2.94 | L | C |
| ATOM | 4433 | C | THR | 177 | 89.551 | -19.455 | 21.311 | 1.00 | 35.94 | L | C |
| ATOM | 4434 | O | THR | 177 | 89.133 | -18.709 | 20.425 | 1.00 | 37.02 | L | O |
| ATOM | 4435 | N | LEU | 178 | 88.941 | -20.584 | 21.669 | 1.00 | 33.89 | L | N |
| ATOM | 4436 | CA | LEU | 178 | 87.682 | -21.015 | 21.072 | 1.00 | 32.44 | L | C |
| ATOM | 4437 | CB | LEU | 178 | 87.587 | -22.542 | 21.069 | 1.00 | 26.21 | L | C |
| ATOM | 4438 | CG | LEU | 178 | 86.291 | -23.170 | 20.539 | 1.00 | 27.24 | L | C |
| ATOM | 4439 | CD1 | LEU | 178 | 86.077 | -22.824 | 19.070 | 1.00 | 27.77 | L | C |
| ATOM | 4440 | CD2 | LEU | 178 | 86.367 | -24.683 | 20.730 | 1.00 | 15.35 | L | C |
| ATOM | 4441 | C | LEU | 178 | 86.552 | -20.412 | 21.901 | 1.00 | 32.70 | L | C |
| ATOM | 4442 | O | LEU | 178 | 86.476 | -20.589 | 23.120 | 1.00 | 29.14 | L | O |
| ATOM | 4443 | N | THR | 179 | 85.669 | -19.683 | 21.244 | 1.00 | 21.74 | L | N |
| ATOM | 4444 | CA | THR | 179 | 84.598 | -19.059 | 21.983 | 1.00 | 27.65 | L | C |
| ATOM | 4445 | CB | THR | 179 | 84.804 | -17.547 | 22.031 | 1.00 | 33.66 | L | C |
| ATOM | 4446 | OG1 | THR | 179 | 83.651 | -16.929 | 22.608 | 1.00 | 34.46 | L | O |
| ATOM | 4447 | CG2 | THR | 179 | 85.056 | -17.005 | 20.633 | 1.00 | 33.07 | L | C |
| ATOM | 4448 | C | THR | 179 | 83.223 | -19.377 | 21.430 | 1.00 | 32.00 | L | C |
| ATOM | 4449 | O | THR | 179 | 82.928 | -19.104 | 20.271 | 1.00 | 32.92 | L | O |
| ATOM | 4450 | N | LEU | 180 | 82.398 | -19.981 | 22.278 | 1.00 | 32.07 | L | N |
| ATOM | 4451 | CA | LEU | 180 | 81.035 | -20.349 | 21.922 | 1.00 | 33.73 | L | C |
| ATOM | 4452 | CB | LEU | 180 | 80.936 | -21.831 | 21.528 | 1.00 | 30.85 | L | C |
| ATOM | 4453 | CG | LEU | 180 | 82.059 | -22.804 | 21.881 | 1.00 | 33.56 | L | C |

Fig. 19: A-62

```
ATOM   4454  CD1 LEU  180      82.518 -22.589  23.309  1.00  36.03      L    C
ATOM   4455  CD2 LEU  180      81.552 -24.220  21.697  1.00  34.15      L    C
ATOM   4456  C   LEU  180      80.093 -20.062  23.084  1.00  37.58      L    C
ATOM   4457  O   LEU  180      80.526 -19.899  24.229  1.00  37.41      L    O
ATOM   4458  N   SER  181      78.801 -20.000  22.772  1.00  28.10      L    N
ATOM   4459  CA  SER  181      77.778 -19.711  23.770  1.00  31.26      L    C
ATOM   4460  CB  SER  181      76.433 -19.537  23.087  1.00  22.13      L    C
ATOM   4461  OG  SER  181      76.019 -20.764  22.513  1.00  25.39      L    O
ATOM   4462  C   SER  181      77.655 -20.802  24.815  1.00  33.74      L    C
ATOM   4463  O   SER  181      77.917 -21.978  24.533  1.00  33.98      L    O
ATOM   4464  N   LYS  182      77.247 -20.402  26.019  1.00  29.35      L    N
ATOM   4465  CA  LYS  182      77.060 -21.339  27.120  1.00  30.58      L    C
ATOM   4466  CB  LYS  182      76.375 -20.647  28.307  1.00  27.86      L    C
ATOM   4467  CG  LYS  182      76.341 -21.446  29.627  1.00  29.57      L    C
ATOM   4468  CD  LYS  182      74.912 -21.752  30.107  1.00  31.50      L    C
ATOM   4469  CE  LYS  182      74.863 -22.027  31.619  1.00  34.15      L    C
ATOM   4470  NZ  LYS  182      73.622 -22.756  32.099  1.00  38.40      L    N
ATOM   4471  C   LYS  182      76.167 -22.438  26.573  1.00  28.49      L    C
ATOM   4472  O   LYS  182      76.358 -23.618  26.878  1.00  20.36      L    O
ATOM   4473  N   ALA  183      75.206 -22.030  25.743  1.00  42.67      L    N
ATOM   4474  CA  ALA  183      74.252 -22.937  25.108  1.00  43.14      L    C
ATOM   4475  CB  ALA  183      73.319 -22.150  24.203  1.00  20.20      L    C
ATOM   4476  C   ALA  183      74.929 -24.053  24.313  1.00  42.26      L    C
ATOM   4477  O   ALA  183      74.645 -25.229  24.531  1.00  43.50      L    O
ATOM   4478  N   ASP  184      75.820 -23.691  23.395  1.00  37.65      L    N
ATOM   4479  CA  ASP  184      76.523 -24.692  22.587  1.00  39.98      L    C
ATOM   4480  CB  ASP  184      77.271 -24.023  21.434  1.00  60.24      L    C
ATOM   4481  CG  ASP  184      76.362 -23.219  20.545  1.00  66.97      L    C
ATOM   4482  OD1 ASP  184      75.360 -23.784  20.055  1.00  70.29      L    O
ATOM   4483  OD2 ASP  184      76.653 -22.023  20.335  1.00  70.50      L    O
ATOM   4484  C   ASP  184      77.519 -25.525  23.395  1.00  38.91      L    C
ATOM   4485  O   ASP  184      77.531 -26.753  23.308  1.00  36.50      L    O
ATOM   4486  N   TYR  185      78.362 -24.849  24.167  1.00  50.74      L    N
ATOM   4487  CA  TYR  185      79.352 -25.544  24.972  1.00  51.74      L    C
ATOM   4488  CB  TYR  185      80.011 -24.589  25.965  1.00  23.76      L    C
ATOM   4489  CG  TYR  185      81.104 -25.256  26.771  1.00  21.08      L    C
ATOM   4490  CD1 TYR  185      82.328 -25.552  26.192  1.00  16.43      L    C
ATOM   4491  CE1 TYR  185      83.332 -26.186  26.915  1.00  15.99      L    C
ATOM   4492  CD2 TYR  185      80.905 -25.613  28.104  1.00  17.64      L    C
ATOM   4493  CE2 TYR  185      81.902 -26.244  28.839  1.00  14.97      L    C
ATOM   4494  CZ  TYR  185      83.118 -26.526  28.235  1.00  14.93      L    C
ATOM   4495  OH  TYR  185      84.141 -27.119  28.944  1.00  16.56      L    O
ATOM   4496  C   TYR  185      78.729 -26.695  25.756  1.00  52.88      L    C
ATOM   4497  O   TYR  185      79.364 -27.728  25.978  1.00  52.42      L    O
ATOM   4498  N   GLU  186      77.484 -26.505  26.177  1.00  52.93      L    N
ATOM   4499  CA  GLU  186      76.787 -27.509  26.965  1.00  54.71      L    C
ATOM   4500  CB  GLU  186      75.643 -26.870  27.748  1.00  28.62      L    C
ATOM   4501  CG  GLU  186      76.067 -26.060  28.955  1.00  35.11      L    C
ATOM   4502  CD  GLU  186      74.876 -25.493  29.702  1.00  38.66      L    C
ATOM   4503  OE1 GLU  186      75.089 -24.850  30.746  1.00  41.21      L    O
ATOM   4504  OE2 GLU  186      73.725 -25.689  29.245  1.00  36.89      L    O
ATOM   4505  C   GLU  186      76.242 -28.694  26.190  1.00  52.40      L    C
ATOM   4506  O   GLU  186      76.029 -29.755  26.769  1.00  48.88      L    O
ATOM   4507  N   LYS  187      76.004 -28.538  24.895  1.00  35.74      L    N
ATOM   4508  CA  LYS  187      75.472 -29.662  24.147  1.00  37.64      L    C
ATOM   4509  CB  LYS  187      74.507 -29.173  23.057  1.00  53.22      L    C
ATOM   4510  CG  LYS  187      75.138 -28.512  21.849  1.00  54.27      L    C
ATOM   4511  CD  LYS  187      74.055 -27.941  20.930  1.00  53.80      L    C
ATOM   4512  CE  LYS  187      74.665 -27.203  19.740  1.00  49.76      L    C
ATOM   4513  NZ  LYS  187      73.707 -26.272  19.069  1.00  48.24      L    N
ATOM   4514  C   LYS  187      76.568 -30.553  23.549  1.00  36.73      L    C
ATOM   4515  O   LYS  187      76.287 -31.436  22.732  1.00  37.96      L    O
ATOM   4516  N   HIS  188      77.813 -30.339  23.972  1.00  23.77      L    N
ATOM   4517  CA  HIS  188      78.934 -31.124  23.468  1.00  21.36      L    C
ATOM   4518  CB  HIS  188      79.811 -30.257  22.562  1.00  41.13      L    C
ATOM   4519  CG  HIS  188      79.099 -29.774  21.338  1.00  42.53      L    C
ATOM   4520  CD2 HIS  188      78.800 -28.524  20.913  1.00  44.25      L    C
ATOM   4521  ND1 HIS  188      78.562 -30.633  20.405  1.00  41.45      L    N
ATOM   4522  CE1 HIS  188      77.961 -29.935  19.458  1.00  45.45      L    C
ATOM   4523  NE2 HIS  188      78.090 -28.652  19.743  1.00  43.75      L    N
ATOM   4524  C   HIS  188      79.743 -31.715  24.610  1.00  19.53      L    C
ATOM   4525  O   HIS  188      79.648 -31.253  25.751  1.00  19.70      L    O
ATOM   4526  N   LYS  189      80.521 -32.747  24.294  1.00  33.83      L    N
```

Fig. 19: A-63

```
ATOM   4527  CA   LYS   189      81.334  -33.445   25.281  1.00   33.86      L    C
ATOM   4528  CB   LYS   189      81.136  -34.957   25.152  1.00   43.10      L    C
ATOM   4529  CG   LYS   189      79.898  -35.516   25.815  1.00   47.03      L    C
ATOM   4530  CD   LYS   189      79.974  -37.041   25.887  1.00   53.76      L    C
ATOM   4531  CE   LYS   189      79.997  -37.680   24.505  1.00   59.30      L    C
ATOM   4532  NZ   LYS   189      78.694  -37.545   23.794  1.00   59.64      L    N
ATOM   4533  C    LYS   189      82.831  -33.155   25.201  1.00   33.18      L    C
ATOM   4534  O    LYS   189      83.435  -32.657   26.155  1.00   36.85      L    O
ATOM   4535  N    VAL   190      83.435  -33.482   24.069  1.00   39.67      L    N
ATOM   4536  CA   VAL   190      84.860  -33.260   23.916  1.00   35.33      L    C
ATOM   4537  CB   VAL   190      85.516  -34.439   23.214  1.00   33.71      L    C
ATOM   4538  CG1  VAL   190      85.356  -35.648   24.059  1.00   26.86      L    C
ATOM   4539  CG2  VAL   190      84.880  -34.657   21.855  1.00   36.79      L    C
ATOM   4540  C    VAL   190      85.249  -31.992   23.170  1.00   35.17      L    C
ATOM   4541  O    VAL   190      84.656  -31.641   22.141  1.00   36.62      L    O
ATOM   4542  N    TYR   191      86.256  -31.319   23.718  1.00   27.65      L    N
ATOM   4543  CA   TYR   191      86.811  -30.105   23.152  1.00   26.85      L    C
ATOM   4544  CB   TYR   191      86.554  -28.934   24.095  1.00   16.61      L    C
ATOM   4545  CG   TYR   191      85.109  -28.475   24.056  1.00   23.44      L    C
ATOM   4546  CD1  TYR   191      84.654  -27.650   23.030  1.00   27.57      L    C
ATOM   4547  CE1  TYR   191      83.322  -27.300   22.929  1.00   29.06      L    C
ATOM   4548  CD2  TYR   191      84.178  -28.937   24.991  1.00   24.37      L    C
ATOM   4549  CE2  TYR   191      82.838  -28.592   24.894  1.00   25.88      L    C
ATOM   4550  CZ   TYR   191      82.419  -27.773   23.859  1.00   28.22      L    C
ATOM   4551  OH   TYR   191      81.097  -27.419   23.745  1.00   30.91      L    O
ATOM   4552  C    TYR   191      88.295  -30.381   23.010  1.00   28.07      L    C
ATOM   4553  O    TYR   191      88.946  -30.821   23.960  1.00   29.13      L    O
ATOM   4554  N    ALA   192      88.837  -30.159   21.822  1.00   17.93      L    N
ATOM   4555  CA   ALA   192      90.246  -30.425   21.621  1.00   13.94      L    C
ATOM   4556  CB   ALA   192      90.424  -31.850   21.160  1.00   12.32      L    C
ATOM   4557  C    ALA   192      90.921  -29.489   20.640  1.00   14.27      L    C
ATOM   4558  O    ALA   192      90.271  -28.885   19.784  1.00   14.89      L    O
ATOM   4559  N    CYS   193      92.234  -29.362   20.787  1.00   20.91      L    N
ATOM   4560  CA   CYS   193      93.015  -28.544   19.883  1.00   19.50      L    C
ATOM   4561  C    CYS   193      94.268  -29.301   19.502  1.00   17.29      L    C
ATOM   4562  O    CYS   193      95.057  -29.729   20.352  1.00   15.43      L    O
ATOM   4563  CB   CYS   193      93.361  -27.183   20.490  1.00   44.80      L    C
ATOM   4564  SG   CYS   193      94.412  -27.194   21.962  1.00   52.58      L    S
ATOM   4565  N    GLU   194      94.411  -29.480   18.195  1.00   24.90      L    N
ATOM   4566  CA   GLU   194      95.522  -30.193   17.600  1.00   25.90      L    C
ATOM   4567  CB   GLU   194      95.004  -30.956   16.384  1.00   66.26      L    C
ATOM   4568  CG   GLU   194      95.979  -31.887   15.718  1.00   77.97      L    C
ATOM   4569  CD   GLU   194      95.392  -32.479   14.461  1.00   83.25      L    C
ATOM   4570  OE1  GLU   194      95.276  -31.738   13.462  1.00   80.00      L    O
ATOM   4571  OE2  GLU   194      95.028  -33.674   14.477  1.00   89.05      L    O
ATOM   4572  C    GLU   194      96.546  -29.158   17.175  1.00   25.27      L    C
ATOM   4573  O    GLU   194      96.204  -28.171   16.538  1.00   23.30      L    O
ATOM   4574  N    VAL   195      97.798  -29.373   17.537  1.00   38.95      L    N
ATOM   4575  CA   VAL   195      98.850  -28.443   17.168  1.00   34.83      L    C
ATOM   4576  CB   VAL   195      99.715  -28.048   18.403  1.00   15.18      L    C
ATOM   4577  CG1  VAL   195     100.911  -27.210   17.971  1.00   11.26      L    C
ATOM   4578  CG2  VAL   195      98.869  -27.268   19.395  1.00   16.15      L    C
ATOM   4579  C    VAL   195      99.730  -29.115   16.126  1.00   34.14      L    C
ATOM   4580  O    VAL   195      99.964  -30.319   16.180  1.00   32.63      L    O
ATOM   4581  N    THR   196     100.190  -28.340   15.157  1.00   43.12      L    N
ATOM   4582  CA   THR   196     101.063  -28.876   14.135  1.00   42.44      L    C
ATOM   4583  CB   THR   196     100.411  -28.867   12.764  1.00   26.65      L    C
ATOM   4584  OG1  THR   196      99.001  -28.673   12.909  1.00   36.35      L    O
ATOM   4585  CG2  THR   196     100.671  -30.180   12.067  1.00   28.65      L    C
ATOM   4586  C    THR   196     102.233  -27.927   14.121  1.00   42.04      L    C
ATOM   4587  O    THR   196     102.049  -26.710   14.053  1.00   37.83      L    O
ATOM   4588  N    HIS   197     103.437  -28.479   14.186  1.00   32.41      L    N
ATOM   4589  CA   HIS   197     104.623  -27.653   14.217  1.00   27.77      L    C
ATOM   4590  CB   HIS   197     104.867  -27.172   15.651  1.00   21.71      L    C
ATOM   4591  CG   HIS   197     105.914  -26.113   15.762  1.00   23.27      L    C
ATOM   4592  CD2  HIS   197     105.817  -24.761   15.753  1.00   17.64      L    C
ATOM   4593  ND1  HIS   197     107.257  -26.402   15.868  1.00   25.39      L    N
ATOM   4594  CE1  HIS   197     107.944  -25.274   15.923  1.00   22.67      L    C
ATOM   4595  NE2  HIS   197     107.093  -24.264   15.854  1.00   24.76      L    N
ATOM   4596  C    HIS   197     105.825  -28.417   13.708  1.00   24.98      L    C
ATOM   4597  O    HIS   197     105.932  -29.629   13.885  1.00   29.24      L    O
ATOM   4598  N    GLN   198     106.728  -27.687   13.070  1.00   28.46      L    N
ATOM   4599  CA   GLN   198     107.944  -28.252   12.515  1.00   26.49      L    C
```

Fig. 19: A-64

```
ATOM   4600  CB   GLN  198    108.840  -27.114  12.048  1.00  34.42  L  C
ATOM   4601  CG   GLN  198    110.091  -27.549  11.333  1.00  36.17  L  C
ATOM   4602  CD   GLN  198    110.868  -26.365  10.821  1.00  48.65  L  C
ATOM   4603  OE1  GLN  198    110.286  -25.414  10.299  1.00  57.22  L  O
ATOM   4604  NE2  GLN  198    112.185  -26.414  10.956  1.00  51.65  L  N
ATOM   4605  C    GLN  198    108.681  -29.107  13.541  1.00  29.43  L  C
ATOM   4606  O    GLN  198    109.331  -30.088  13.182  1.00  31.15  L  O
ATOM   4607  N    GLY  199    108.568  -28.728  14.815  1.00  31.39  L  N
ATOM   4608  CA   GLY  199    109.234  -29.452  15.887  1.00  36.65  L  C
ATOM   4609  C    GLY  199    108.465  -30.636  16.444  1.00  39.08  L  C
ATOM   4610  O    GLY  199    108.880  -31.244  17.425  1.00  43.81  L  O
ATOM   4611  N    LEU  200    107.339  -30.961  15.823  1.00  25.48  L  N
ATOM   4612  CA   LEU  200    106.510  -32.087  16.247  1.00  22.67  L  C
ATOM   4613  CB   LEU  200    105.094  -31.597  16.570  1.00  31.49  L  C
ATOM   4614  CG   LEU  200    104.868  -31.002  17.964  1.00  34.60  L  C
ATOM   4615  CD1  LEU  200    106.036  -30.149  18.361  1.00  37.97  L  C
ATOM   4616  CD2  LEU  200    103.592  -30.188  17.967  1.00  34.28  L  C
ATOM   4617  C    LEU  200    106.463  -33.152  15.144  1.00  23.29  L  C
ATOM   4618  O    LEU  200    106.089  -32.869  14.003  1.00  24.15  L  O
ATOM   4619  N    SER  201    106.860  -34.372  15.499  1.00  21.11  L  N
ATOM   4620  CA   SER  201    106.886  -35.503  14.570  1.00  24.08  L  C
ATOM   4621  CB   SER  201    107.367  -36.747  15.311  1.00  27.13  L  C
ATOM   4622  OG   SER  201    106.702  -36.875  16.561  1.00  28.99  L  O
ATOM   4623  C    SER  201    105.510  -35.761  13.957  1.00  24.14  L  C
ATOM   4624  O    SER  201    105.392  -36.267  12.835  1.00  25.49  L  O
ATOM   4625  N    SER  202    104.476  -35.405  14.717  1.00  17.09  L  N
ATOM   4626  CA   SER  202    103.086  -35.562  14.302  1.00  21.15  L  C
ATOM   4627  CB   SER  202    102.636  -37.010  14.522  1.00  43.22  L  C
ATOM   4628  OG   SER  202    103.011  -37.462  15.810  1.00  46.12  L  O
ATOM   4629  C    SER  202    102.265  -34.603  15.155  1.00  21.60  L  C
ATOM   4630  O    SER  202    102.656  -34.296  16.282  1.00  27.36  L  O
ATOM   4631  N    PRO  203    101.119  -34.121  14.636  1.00  22.94  L  N
ATOM   4632  CD   PRO  203    100.457  -34.478  13.368  1.00  32.35  L  C
ATOM   4633  CA   PRO  203    100.290  -33.187  15.407  1.00  18.89  L  C
ATOM   4634  CB   PRO  203     98.971  -33.177  14.643  1.00  26.47  L  C
ATOM   4635  CG   PRO  203     99.416  -33.370  13.223  1.00  29.48  L  C
ATOM   4636  C    PRO  203    100.128  -33.646  16.836  1.00  18.90  L  C
ATOM   4637  O    PRO  203    100.178  -34.842  17.100  1.00  21.86  L  O
ATOM   4638  N    VAL  204     99.980  -32.693  17.753  1.00  28.11  L  N
ATOM   4639  CA   VAL  204     99.794  -32.996  19.172  1.00  29.99  L  C
ATOM   4640  CB   VAL  204    100.759  -32.201  20.081  1.00  20.42  L  C
ATOM   4641  CG1  VAL  204    100.254  -32.204  21.512  1.00  20.30  L  C
ATOM   4642  CG2  VAL  204    102.141  -32.819  20.036  1.00  15.23  L  C
ATOM   4643  C    VAL  204     98.393  -32.574  19.514  1.00  33.93  L  C
ATOM   4644  O    VAL  204     97.887  -31.601  18.963  1.00  35.36  L  O
ATOM   4645  N    THR  205     97.755  -33.293  20.422  1.00  45.34  L  N
ATOM   4646  CA   THR  205     96.402  -32.933  20.787  1.00  46.97  L  C
ATOM   4647  CB   THR  205     95.386  -33.896  20.137  1.00  14.48  L  C
ATOM   4648  OG1  THR  205     95.275  -33.587  18.747  1.00  10.44  L  O
ATOM   4649  CG2  THR  205     94.013  -33.761  20.769  1.00  11.16  L  C
ATOM   4650  C    THR  205     96.169  -32.886  22.280  1.00  47.18  L  C
ATOM   4651  O    THR  205     96.596  -33.763  23.032  1.00  49.19  L  O
ATOM   4652  N    LYS  206     95.513  -31.822  22.709  1.00  22.09  L  N
ATOM   4653  CA   LYS  206     95.167  -31.681  24.108  1.00  26.52  L  C
ATOM   4654  CB   LYS  206     95.791  -30.422  24.710  1.00  41.08  L  C
ATOM   4655  CG   LYS  206     97.208  -30.641  25.215  1.00  44.88  L  C
ATOM   4656  CD   LYS  206     97.269  -31.688  26.312  1.00  47.36  L  C
ATOM   4657  CE   LYS  206     98.654  -31.760  26.957  1.00  49.27  L  C
ATOM   4658  NZ   LYS  206     99.723  -32.144  25.997  1.00  50.40  L  N
ATOM   4659  C    LYS  206     93.653  -31.602  24.100  1.00  29.29  L  C
ATOM   4660  O    LYS  206     93.063  -30.939  23.246  1.00  34.45  L  O
ATOM   4661  N    SER  207     93.026  -32.304  25.033  1.00  32.39  L  N
ATOM   4662  CA   SER  207     91.578  -32.324  25.083  1.00  29.18  L  C
ATOM   4663  CB   SER  207     91.046  -33.364  24.080  1.00  31.23  L  C
ATOM   4664  OG   SER  207     91.613  -34.655  24.294  1.00  31.62  L  O
ATOM   4665  C    SER  207     91.039  -32.624  26.476  1.00  28.78  L  C
ATOM   4666  O    SER  207     91.798  -32.938  27.397  1.00  29.47  L  O
ATOM   4667  N    PHE  208     89.719  -32.517  26.606  1.00  33.89  L  N
ATOM   4668  CA   PHE  208     89.013  -32.777  27.852  1.00  39.79  L  C
ATOM   4669  CB   PHE  208     89.217  -31.615  28.842  1.00  17.06  L  C
ATOM   4670  CG   PHE  208     88.662  -30.300  28.353  1.00  14.11  L  C
ATOM   4671  CD1  PHE  208     89.409  -29.482  27.499  1.00  18.84  L  C
ATOM   4672  CD2  PHE  208     87.376  -29.906  28.690  1.00  11.57  L  C
```

Fig. 19: A-65

| | | | | | | | | | | |
|---|---|---|---|---|---|---|---|---|---|---|
| ATOM | 4673 | CE1 | PHE | 208 | 88.879 | -28.298 | 26.990 | 1.00 | 19.93 | L C |
| ATOM | 4674 | CE2 | PHE | 208 | 86.846 | -28.729 | 28.182 | 1.00 | 14.34 | L C |
| ATOM | 4675 | CZ | PHE | 208 | 87.602 | -27.925 | 27.330 | 1.00 | 20.99 | L C |
| ATOM | 4676 | C | PHE | 208 | 87.536 | -32.873 | 27.472 | 1.00 | 45.59 | L C |
| ATOM | 4677 | O | PHE | 208 | 87.168 | -32.576 | 26.335 | 1.00 | 47.78 | L O |
| ATOM | 4678 | N | ASN | 209 | 86.703 | -33.293 | 28.420 | 1.00 | 24.67 | L N |
| ATOM | 4679 | CA | ASN | 209 | 85.257 | -33.398 | 28.213 | 1.00 | 28.33 | L C |
| ATOM | 4680 | CB | ASN | 209 | 84.751 | -34.785 | 28.623 | 1.00 | 27.05 | L C |
| ATOM | 4681 | CG | ASN | 209 | 85.664 | -35.913 | 28.172 | 1.00 | 33.97 | L C |
| ATOM | 4682 | OD1 | ASN | 209 | 85.777 | -36.941 | 28.841 | 1.00 | 34.19 | L O |
| ATOM | 4683 | ND2 | ASN | 209 | 86.304 | -35.732 | 27.031 | 1.00 | 37.01 | L N |
| ATOM | 4684 | C | ASN | 209 | 84.630 | -32.370 | 29.160 | 1.00 | 29.95 | L C |
| ATOM | 4685 | O | ASN | 209 | 85.203 | -32.108 | 30.218 | 1.00 | 31.18 | L O |
| ATOM | 4686 | N | ARG | 210 | 83.473 | -31.800 | 28.805 | 1.00 | 15.88 | L N |
| ATOM | 4687 | CA | ARG | 210 | 82.810 | -30.829 | 29.687 | 1.00 | 19.72 | L C |
| ATOM | 4688 | CB | ARG | 210 | 81.337 | -30.721 | 29.371 | 1.00 | 31.19 | L C |
| ATOM | 4689 | CG | ARG | 210 | 81.027 | -29.666 | 28.361 | 1.00 | 32.77 | L C |
| ATOM | 4690 | CD | ARG | 210 | 79.655 | -29.104 | 28.627 | 1.00 | 36.35 | L C |
| ATOM | 4691 | NE | ARG | 210 | 78.656 | -30.166 | 28.633 | 1.00 | 41.72 | L N |
| ATOM | 4692 | CZ | ARG | 210 | 77.502 | -30.095 | 29.282 | 1.00 | 45.49 | L C |
| ATOM | 4693 | NH1 | ARG | 210 | 77.204 | -29.008 | 29.981 | 1.00 | 46.04 | L N |
| ATOM | 4694 | NH2 | ARG | 210 | 76.655 | -31.112 | 29.232 | 1.00 | 47.73 | L N |
| ATOM | 4695 | C | ARG | 210 | 82.964 | -31.252 | 31.137 | 1.00 | 22.05 | L C |
| ATOM | 4696 | O | ARG | 210 | 82.962 | -32.440 | 31.428 | 1.00 | 23.93 | L O |
| ATOM | 4697 | N | GLY | 211 | 83.096 | -30.291 | 32.048 | 1.00 | 53.99 | L N |
| ATOM | 4698 | CA | GLY | 211 | 83.297 | -30.638 | 33.447 | 1.00 | 53.99 | L C |
| ATOM | 4699 | C | GLY | 211 | 84.740 | -31.088 | 33.630 | 1.00 | 53.99 | L C |
| ATOM | 4700 | O | GLY | 211 | 85.665 | -30.312 | 33.387 | 1.00 | 53.99 | L O |
| ATOM | 4701 | N | GLU | 212 | 84.942 | -32.336 | 34.046 | 1.00 | 80.95 | L N |
| ATOM | 4702 | CA | GLU | 212 | 86.287 | -32.890 | 34.236 | 1.00 | 80.95 | L C |
| ATOM | 4703 | CB | GLU | 212 | 86.995 | -33.004 | 32.871 | 1.00 | 34.07 | L C |
| ATOM | 4704 | CG | GLU | 212 | 88.259 | -33.888 | 32.849 | 1.00 | 34.07 | L C |
| ATOM | 4705 | CD | GLU | 212 | 88.691 | -34.311 | 31.435 | 1.00 | 34.07 | L C |
| ATOM | 4706 | OE1 | GLU | 212 | 89.803 | -34.863 | 31.296 | 1.00 | 34.07 | L O |
| ATOM | 4707 | OE2 | GLU | 212 | 87.923 | -34.113 | 30.468 | 1.00 | 34.07 | L O |
| ATOM | 4708 | C | GLU | 212 | 87.134 | -32.080 | 35.227 | 1.00 | 80.95 | L C |
| ATOM | 4709 | O | GLU | 212 | 86.690 | -31.043 | 35.732 | 1.00 | 80.95 | L O |
| ATOM | 4710 | N | CYS | 213 | 88.341 | -32.566 | 35.516 | 1.00 | 81.74 | L N |
| ATOM | 4711 | CA | CYS | 213 | 89.243 | -31.893 | 36.450 | 1.00 | 81.74 | L C |
| ATOM | 4712 | CB | CYS | 213 | 88.990 | -32.374 | 37.883 | 1.00 | 54.42 | L C |
| ATOM | 4713 | SG | CYS | 213 | 87.479 | -31.701 | 38.656 | 1.00 | 54.42 | L S |
| ATOM | 4714 | C | CYS | 213 | 90.715 | -32.123 | 36.095 | 1.00 | 81.74 | L C |
| ATOM | 4715 | O | CYS | 213 | 90.996 | -32.758 | 35.051 | 1.00 | 81.74 | L O |
| ATOM | 4716 | OXT | CYS | 213 | 91.581 | -31.647 | 36.863 | 1.00 | 72.88 | L O |
| ATOM | 4717 | MN | MN | 400 | 117.831 | 24.682 | 6.345 | 1.00 | 34.24 | M |
| ATOM | 4718 | CB | THR | 145 | 114.226 | 73.843 | 15.327 | 1.00 | 72.71 | B C |
| ATOM | 4719 | OG1 | THR | 145 | 113.673 | 74.174 | 16.611 | 1.00 | 72.71 | B O |
| ATOM | 4720 | CG2 | THR | 145 | 114.208 | 75.069 | 14.426 | 1.00 | 72.71 | B C |
| ATOM | 4721 | C | THR | 145 | 113.665 | 71.399 | 15.485 | 1.00 | 109.74 | B C |
| ATOM | 4722 | O | THR | 145 | 113.590 | 70.290 | 14.948 | 1.00 | 110.14 | B O |
| ATOM | 4723 | N | THR | 145 | 111.957 | 72.996 | 14.632 | 1.00 | 108.12 | B N |
| ATOM | 4724 | CA | THR | 145 | 113.414 | 72.677 | 14.686 | 1.00 | 107.72 | B C |
| ATOM | 4725 | N | GLN | 146 | 113.963 | 71.561 | 16.769 | 1.00 | 79.22 | B N |
| ATOM | 4726 | CA | GLN | 146 | 114.224 | 70.425 | 17.633 | 1.00 | 77.37 | B C |
| ATOM | 4727 | CB | GLN | 146 | 115.554 | 70.620 | 18.378 | 1.00 | 80.28 | B C |
| ATOM | 4728 | CG | GLN | 146 | 115.640 | 71.886 | 19.208 | 1.00 | 80.28 | B C |
| ATOM | 4729 | CD | GLN | 146 | 116.952 | 72.001 | 19.955 | 1.00 | 80.28 | B C |
| ATOM | 4730 | OE1 | GLN | 146 | 117.150 | 72.929 | 20.742 | 1.00 | 80.28 | B O |
| ATOM | 4731 | NE2 | GLN | 146 | 117.858 | 71.059 | 19.712 | 1.00 | 80.28 | B N |
| ATOM | 4732 | C | GLN | 146 | 113.077 | 70.200 | 18.620 | 1.00 | 77.79 | B C |
| ATOM | 4733 | O | GLN | 146 | 112.818 | 71.018 | 19.511 | 1.00 | 79.65 | B O |
| ATOM | 4734 | N | LEU | 147 | 112.383 | 69.081 | 18.432 | 1.00 | 43.47 | B N |
| ATOM | 4735 | CA | LEU | 147 | 111.265 | 68.710 | 19.288 | 1.00 | 42.60 | B C |
| ATOM | 4736 | CB | LEU | 147 | 109.936 | 68.755 | 18.525 | 1.00 | 51.95 | B C |
| ATOM | 4737 | CG | LEU | 147 | 109.450 | 69.952 | 17.707 | 1.00 | 52.14 | B C |
| ATOM | 4738 | CD1 | LEU | 147 | 110.464 | 70.296 | 16.632 | 1.00 | 47.35 | B C |
| ATOM | 4739 | CD2 | LEU | 147 | 108.114 | 69.607 | 17.060 | 1.00 | 51.99 | B C |
| ATOM | 4740 | C | LEU | 147 | 111.461 | 67.281 | 19.756 | 1.00 | 41.58 | B C |
| ATOM | 4741 | O | LEU | 147 | 112.077 | 66.470 | 19.058 | 1.00 | 42.88 | B O |
| ATOM | 4742 | N | ASP | 148 | 110.944 | 66.988 | 20.945 | 1.00 | 31.29 | B N |
| ATOM | 4743 | CA | ASP | 148 | 110.974 | 65.640 | 21.493 | 1.00 | 28.75 | B C |
| ATOM | 4744 | CB | ASP | 148 | 111.394 | 65.642 | 22.960 | 1.00 | 32.78 | B C |
| ATOM | 4745 | CG | ASP | 148 | 112.897 | 65.718 | 23.133 | 1.00 | 32.40 | B C |

Fig. 19: A-66

| ATOM | 4746 | OD1 | ASP | 148 | 113.366 | 65.715 | 24.290 | 1.00 | 31.51 | B | O |
| --- | --- | --- | --- | --- | --- | --- | --- | --- | --- | --- | --- |
| ATOM | 4747 | OD2 | ASP | 148 | 113.616 | 65.777 | 22.116 | 1.00 | 30.58 | B | O |
| ATOM | 4748 | C | ASP | 148 | 109.526 | 65.181 | 21.358 | 1.00 | 25.13 | B | C |
| ATOM | 4749 | O | ASP | 148 | 108.664 | 65.583 | 22.128 | 1.00 | 24.43 | B | O |
| ATOM | 4750 | N | ILE | 149 | 109.260 | 64.368 | 20.345 | 1.00 | 21.33 | B | N |
| ATOM | 4751 | CA | ILE | 149 | 107.918 | 63.885 | 20.105 | 1.00 | 20.27 | B | C |
| ATOM | 4752 | CB | ILE | 149 | 107.610 | 63.880 | 18.605 | 1.00 | 13.57 | B | C |
| ATOM | 4753 | CG2 | ILE | 149 | 106.140 | 63.573 | 18.378 | 1.00 | 8.58 | B | C |
| ATOM | 4754 | CG1 | ILE | 149 | 107.932 | 65.234 | 17.998 | 1.00 | 9.29 | B | C |
| ATOM | 4755 | CD1 | ILE | 149 | 107.697 | 65.263 | 16.508 | 1.00 | 12.04 | B | C |
| ATOM | 4756 | C | ILE | 149 | 107.723 | 62.464 | 20.629 | 1.00 | 21.92 | B | C |
| ATOM | 4757 | O | ILE | 149 | 108.507 | 61.563 | 20.315 | 1.00 | 22.32 | B | O |
| ATOM | 4758 | N | VAL | 150 | 106.680 | 62.271 | 21.433 | 1.00 | 32.56 | B | N |
| ATOM | 4759 | CA | VAL | 150 | 106.357 | 60.950 | 21.956 | 1.00 | 34.12 | B | C |
| ATOM | 4760 | CB | VAL | 150 | 106.256 | 60.940 | 23.492 | 1.00 | 12.90 | B | C |
| ATOM | 4761 | CG1 | VAL | 150 | 105.775 | 59.579 | 23.967 | 1.00 | 15.09 | B | C |
| ATOM | 4762 | CG2 | VAL | 150 | 107.620 | 61.256 | 24.110 | 1.00 | 14.71 | B | C |
| ATOM | 4763 | C | VAL | 150 | 105.001 | 60.604 | 21.381 | 1.00 | 31.68 | B | C |
| ATOM | 4764 | O | VAL | 150 | 104.057 | 61.380 | 21.523 | 1.00 | 29.83 | B | O |
| ATOM | 4765 | N | ILE | 151 | 104.904 | 59.459 | 20.714 | 1.00 | 36.82 | B | N |
| ATOM | 4766 | CA | ILE | 151 | 103.640 | 59.037 | 20.115 | 1.00 | 35.62 | B | C |
| ATOM | 4767 | CB | ILE | 151 | 103.862 | 58.436 | 18.709 | 1.00 | 31.63 | B | C |
| ATOM | 4768 | CG2 | ILE | 151 | 102.537 | 58.084 | 18.081 | 1.00 | 27.99 | B | C |
| ATOM | 4769 | CG1 | ILE | 151 | 104.582 | 59.454 | 17.817 | 1.00 | 30.05 | B | C |
| ATOM | 4770 | CD1 | ILE | 151 | 104.981 | 58.916 | 16.457 | 1.00 | 32.03 | B | C |
| ATOM | 4771 | C | ILE | 151 | 102.978 | 58.008 | 21.016 | 1.00 | 33.74 | B | C |
| ATOM | 4772 | O | ILE | 151 | 103.593 | 57.013 | 21.394 | 1.00 | 33.98 | B | O |
| ATOM | 4773 | N | VAL | 152 | 101.725 | 58.254 | 21.368 | 1.00 | 29.85 | B | N |
| ATOM | 4774 | CA | VAL | 152 | 100.996 | 57.347 | 22.243 | 1.00 | 30.70 | B | C |
| ATOM | 4775 | CB | VAL | 152 | 100.279 | 58.127 | 23.344 | 1.00 | 30.57 | B | C |
| ATOM | 4776 | CG1 | VAL | 152 | 99.721 | 57.170 | 24.385 | 1.00 | 29.70 | B | C |
| ATOM | 4777 | CG2 | VAL | 152 | 101.245 | 59.134 | 23.962 | 1.00 | 27.01 | B | C |
| ATOM | 4778 | C | VAL | 152 | 99.966 | 56.560 | 21.451 | 1.00 | 28.60 | B | C |
| ATOM | 4779 | O | VAL | 152 | 98.867 | 57.044 | 21.194 | 1.00 | 22.20 | B | O |
| ATOM | 4780 | N | LEU | 153 | 100.324 | 55.336 | 21.083 | 1.00 | 26.94 | B | N |
| ATOM | 4781 | CA | LEU | 153 | 99.451 | 54.479 | 20.289 | 1.00 | 27.05 | B | C |
| ATOM | 4782 | CB | LEU | 153 | 100.312 | 53.600 | 19.370 | 1.00 | 31.93 | B | C |
| ATOM | 4783 | CG | LEU | 153 | 100.518 | 54.010 | 17.910 | 1.00 | 33.71 | B | C |
| ATOM | 4784 | CD1 | LEU | 153 | 100.287 | 55.490 | 17.732 | 1.00 | 34.22 | B | C |
| ATOM | 4785 | CD2 | LEU | 153 | 101.914 | 53.616 | 17.481 | 1.00 | 36.25 | B | C |
| ATOM | 4786 | C | LEU | 153 | 98.475 | 53.597 | 21.058 | 1.00 | 28.11 | B | C |
| ATOM | 4787 | O | LEU | 153 | 98.837 | 52.930 | 22.035 | 1.00 | 27.11 | B | O |
| ATOM | 4788 | N | ASP | 154 | 97.228 | 53.602 | 20.604 | 1.00 | 33.48 | B | N |
| ATOM | 4789 | CA | ASP | 154 | 96.199 | 52.768 | 21.204 | 1.00 | 32.96 | B | C |
| ATOM | 4790 | CB | ASP | 154 | 94.809 | 53.341 | 20.911 | 1.00 | 34.05 | B | C |
| ATOM | 4791 | CG | ASP | 154 | 93.686 | 52.502 | 21.505 | 1.00 | 33.25 | B | C |
| ATOM | 4792 | OD1 | ASP | 154 | 93.959 | 51.385 | 21.985 | 1.00 | 36.76 | B | O |
| ATOM | 4793 | OD2 | ASP | 154 | 92.523 | 52.960 | 21.489 | 1.00 | 29.57 | B | O |
| ATOM | 4794 | C | ASP | 154 | 96.362 | 51.412 | 20.515 | 1.00 | 36.30 | B | C |
| ATOM | 4795 | O | ASP | 154 | 96.349 | 51.326 | 19.285 | 1.00 | 32.62 | B | O |
| ATOM | 4796 | N | GLY | 155 | 96.539 | 50.361 | 21.303 | 1.00 | 16.68 | B | N |
| ATOM | 4797 | CA | GLY | 155 | 96.700 | 49.039 | 20.732 | 1.00 | 18.75 | B | C |
| ATOM | 4798 | C | GLY | 155 | 95.706 | 48.058 | 21.321 | 1.00 | 20.01 | B | C |
| ATOM | 4799 | O | GLY | 155 | 95.856 | 46.845 | 21.177 | 1.00 | 22.50 | B | O |
| ATOM | 4800 | N | SER | 156 | 94.692 | 48.595 | 21.992 | 1.00 | 30.46 | B | N |
| ATOM | 4801 | CA | SER | 156 | 93.653 | 47.780 | 22.612 | 1.00 | 35.04 | B | C |
| ATOM | 4802 | CB | SER | 156 | 92.616 | 48.670 | 23.302 | 1.00 | 22.70 | B | C |
| ATOM | 4803 | OG | SER | 156 | 91.999 | 49.542 | 22.372 | 1.00 | 25.62 | B | O |
| ATOM | 4804 | C | SER | 156 | 92.962 | 46.891 | 21.584 | 1.00 | 32.03 | B | C |
| ATOM | 4805 | O | SER | 156 | 93.057 | 47.122 | 20.379 | 1.00 | 35.21 | B | O |
| ATOM | 4806 | N | ASN | 157 | 92.257 | 45.879 | 22.074 | 1.00 | 34.08 | B | N |
| ATOM | 4807 | CA | ASN | 157 | 91.565 | 44.927 | 21.216 | 1.00 | 31.16 | B | C |
| ATOM | 4808 | CB | ASN | 157 | 90.632 | 44.046 | 22.047 | 1.00 | 34.61 | B | C |
| ATOM | 4809 | CG | ASN | 157 | 91.378 | 42.971 | 22.811 | 1.00 | 36.10 | B | C |
| ATOM | 4810 | OD1 | ASN | 157 | 90.795 | 42.270 | 23.638 | 1.00 | 33.17 | B | O |
| ATOM | 4811 | ND2 | ASN | 157 | 92.672 | 42.832 | 22.536 | 1.00 | 33.38 | B | N |
| ATOM | 4812 | C | ASN | 157 | 90.783 | 45.529 | 20.069 | 1.00 | 29.13 | B | C |
| ATOM | 4813 | O | ASN | 157 | 90.806 | 45.003 | 18.956 | 1.00 | 27.11 | B | O |
| ATOM | 4814 | N | SER | 158 | 90.094 | 46.631 | 20.339 | 1.00 | 20.01 | B | N |
| ATOM | 4815 | CA | SER | 158 | 89.275 | 47.285 | 19.324 | 1.00 | 18.22 | B | C |
| ATOM | 4816 | CB | SER | 158 | 88.506 | 48.464 | 19.936 | 1.00 | 15.08 | B | C |
| ATOM | 4817 | OG | SER | 158 | 89.356 | 49.363 | 20.616 | 1.00 | 17.79 | B | O |
| ATOM | 4818 | C | SER | 158 | 90.035 | 47.739 | 18.087 | 1.00 | 18.99 | B | C |

Fig. 19: A-67

| ATOM | 4819 | O | SER | 158 | 89.527 | 47.602 | 16.984 | 1.00 | 16.16 | B | O |
|---|---|---|---|---|---|---|---|---|---|---|---|
| ATOM | 4820 | N | ILE | 159 | 91.245 | 48.269 | 18.257 | 1.00 | 19.55 | B | N |
| ATOM | 4821 | CA | ILE | 159 | 92.033 | 48.722 | 17.110 | 1.00 | 24.15 | B | C |
| ATOM | 4822 | CB | ILE | 159 | 93.423 | 49.203 | 17.541 | 1.00 | 21.45 | B | C |
| ATOM | 4823 | CG2 | ILE | 159 | 94.256 | 49.546 | 16.307 | 1.00 | 21.36 | B | C |
| ATOM | 4824 | CG1 | ILE | 159 | 93.293 | 50.411 | 18.471 | 1.00 | 26.23 | B | C |
| ATOM | 4825 | CD1 | ILE | 159 | 92.779 | 51.664 | 17.787 | 1.00 | 31.39 | B | C |
| ATOM | 4826 | C | ILE | 159 | 92.204 | 47.597 | 16.089 | 1.00 | 28.46 | B | C |
| ATOM | 4827 | O | ILE | 159 | 92.638 | 46.502 | 16.434 | 1.00 | 27.87 | B | O |
| ATOM | 4828 | N | TYR | 160 | 91.863 | 47.876 | 14.832 | 1.00 | 56.09 | B | N |
| ATOM | 4829 | CA | TYR | 160 | 91.959 | 46.886 | 13.756 | 1.00 | 58.22 | B | C |
| ATOM | 4830 | CB | TYR | 160 | 90.931 | 45.768 | 13.980 | 1.00 | 40.50 | B | C |
| ATOM | 4831 | CG | TYR | 160 | 90.932 | 44.654 | 12.939 | 1.00 | 37.26 | B | C |
| ATOM | 4832 | CD1 | TYR | 160 | 91.606 | 43.449 | 13.172 | 1.00 | 39.68 | B | C |
| ATOM | 4833 | CE1 | TYR | 160 | 91.602 | 42.423 | 12.225 | 1.00 | 37.28 | B | C |
| ATOM | 4834 | CD2 | TYR | 160 | 90.254 | 44.803 | 11.722 | 1.00 | 34.91 | B | C |
| ATOM | 4835 | CE2 | TYR | 160 | 90.251 | 43.782 | 10.770 | 1.00 | 38.62 | B | C |
| ATOM | 4836 | CZ | TYR | 160 | 90.926 | 42.598 | 11.030 | 1.00 | 37.97 | B | C |
| ATOM | 4837 | OH | TYR | 160 | 90.922 | 41.597 | 10.095 | 1.00 | 42.97 | B | O |
| ATOM | 4838 | C | TYR | 160 | 91.696 | 47.533 | 12.400 | 1.00 | 59.94 | B | C |
| ATOM | 4839 | O | TYR | 160 | 90.730 | 48.276 | 12.232 | 1.00 | 65.86 | B | O |
| ATOM | 4840 | N | PRO | 161 | 92.548 | 47.241 | 11.407 | 1.00 | 26.83 | B | N |
| ATOM | 4841 | CD | PRO | 161 | 92.182 | 47.499 | 10.002 | 1.00 | 24.03 | B | C |
| ATOM | 4842 | CA | PRO | 161 | 93.721 | 46.362 | 11.479 | 1.00 | 25.11 | B | C |
| ATOM | 4843 | CB | PRO | 161 | 93.784 | 45.785 | 10.075 | 1.00 | 28.41 | B | C |
| ATOM | 4844 | CG | PRO | 161 | 93.364 | 46.960 | 9.239 | 1.00 | 31.57 | B | C |
| ATOM | 4845 | C | PRO | 161 | 95.008 | 47.109 | 11.857 | 1.00 | 23.77 | B | C |
| ATOM | 4846 | O | PRO | 161 | 95.234 | 48.238 | 11.413 | 1.00 | 23.09 | B | O |
| ATOM | 4847 | N | TRP | 162 | 95.856 | 46.463 | 12.654 | 1.00 | 23.22 | B | N |
| ATOM | 4848 | CA | TRP | 162 | 97.108 | 47.062 | 13.111 | 1.00 | 24.29 | B | C |
| ATOM | 4849 | CB | TRP | 162 | 97.922 | 46.022 | 13.878 | 1.00 | 29.42 | B | C |
| ATOM | 4850 | CG | TRP | 162 | 99.067 | 46.586 | 14.670 | 1.00 | 29.94 | B | C |
| ATOM | 4851 | CD2 | TRP | 162 | 99.004 | 47.603 | 15.676 | 1.00 | 24.78 | B | C |
| ATOM | 4852 | CE2 | TRP | 162 | 100.308 | 47.769 | 16.185 | 1.00 | 28.33 | B | C |
| ATOM | 4853 | CE3 | TRP | 162 | 97.973 | 48.389 | 16.201 | 1.00 | 24.19 | B | C |
| ATOM | 4854 | CD1 | TRP | 162 | 100.369 | 46.192 | 14.611 | 1.00 | 29.13 | B | C |
| ATOM | 4855 | NE1 | TRP | 162 | 101.123 | 46.898 | 15.516 | 1.00 | 31.00 | B | N |
| ATOM | 4856 | CZ2 | TRP | 162 | 100.607 | 48.687 | 17.195 | 1.00 | 26.87 | B | C |
| ATOM | 4857 | CZ3 | TRP | 162 | 98.274 | 49.303 | 17.208 | 1.00 | 22.52 | B | C |
| ATOM | 4858 | CH2 | TRP | 162 | 99.580 | 49.441 | 17.691 | 1.00 | 27.43 | B | C |
| ATOM | 4859 | C | TRP | 162 | 97.961 | 47.663 | 11.988 | 1.00 | 26.07 | B | C |
| ATOM | 4860 | O | TRP | 162 | 98.554 | 48.734 | 12.161 | 1.00 | 25.22 | B | O |
| ATOM | 4861 | N | GLU | 163 | 98.010 | 46.979 | 10.843 | 1.00 | 39.64 | B | N |
| ATOM | 4862 | CA | GLU | 163 | 98.797 | 47.432 | 9.693 | 1.00 | 41.42 | B | C |
| ATOM | 4863 | CB | GLU | 163 | 98.585 | 46.509 | 8.485 | 1.00 | 121.98 | B | C |
| ATOM | 4864 | CG | GLU | 163 | 97.219 | 46.612 | 7.826 | 1.00 | 128.29 | B | C |
| ATOM | 4865 | CD | GLU | 163 | 97.206 | 46.043 | 6.418 | 1.00 | 130.43 | B | C |
| ATOM | 4866 | OE1 | GLU | 163 | 97.894 | 46.611 | 5.541 | 1.00 | 132.14 | B | O |
| ATOM | 4867 | OE2 | GLU | 163 | 96.512 | 45.029 | 6.187 | 1.00 | 129.39 | B | O |
| ATOM | 4868 | C | GLU | 163 | 98.491 | 48.867 | 9.280 | 1.00 | 41.08 | B | C |
| ATOM | 4869 | O | GLU | 163 | 99.390 | 49.609 | 8.881 | 1.00 | 37.25 | B | O |
| ATOM | 4870 | N | SER | 164 | 97.225 | 49.262 | 9.368 | 1.00 | 24.58 | B | N |
| ATOM | 4871 | CA | SER | 164 | 96.850 | 50.620 | 8.989 | 1.00 | 21.77 | B | C |
| ATOM | 4872 | CB | SER | 164 | 95.320 | 50.772 | 8.984 | 1.00 | 53.34 | B | C |
| ATOM | 4873 | OG | SER | 164 | 94.722 | 49.950 | 7.992 | 1.00 | 59.23 | B | O |
| ATOM | 4874 | C | SER | 164 | 97.484 | 51.619 | 9.956 | 1.00 | 22.53 | B | C |
| ATOM | 4875 | O | SER | 164 | 97.993 | 52.661 | 9.536 | 1.00 | 25.73 | B | O |
| ATOM | 4876 | N | VAL | 165 | 97.451 | 51.286 | 11.247 | 1.00 | 28.47 | B | N |
| ATOM | 4877 | CA | VAL | 165 | 98.027 | 52.137 | 12.280 | 1.00 | 27.86 | B | C |
| ATOM | 4878 | CB | VAL | 165 | 97.841 | 51.525 | 13.680 | 1.00 | 11.01 | B | C |
| ATOM | 4879 | CG1 | VAL | 165 | 98.722 | 52.245 | 14.697 | 1.00 | 12.40 | B | C |
| ATOM | 4880 | CG2 | VAL | 165 | 96.376 | 51.622 | 14.089 | 1.00 | 14.01 | B | C |
| ATOM | 4881 | C | VAL | 165 | 99.509 | 52.334 | 12.028 | 1.00 | 29.02 | B | C |
| ATOM | 4882 | O | VAL | 165 | 100.032 | 53.444 | 12.137 | 1.00 | 30.84 | B | O |
| ATOM | 4883 | N | ILE | 166 | 100.184 | 51.248 | 11.678 | 1.00 | 20.94 | B | N |
| ATOM | 4884 | CA | ILE | 166 | 101.613 | 51.305 | 11.400 | 1.00 | 20.26 | B | C |
| ATOM | 4885 | CB | ILE | 166 | 102.211 | 49.894 | 11.330 | 1.00 | 40.92 | B | C |
| ATOM | 4886 | CG2 | ILE | 166 | 103.697 | 49.962 | 10.986 | 1.00 | 40.13 | B | C |
| ATOM | 4887 | CG1 | ILE | 166 | 102.017 | 49.214 | 12.687 | 1.00 | 40.78 | B | C |
| ATOM | 4888 | CD1 | ILE | 166 | 102.580 | 47.823 | 12.762 | 1.00 | 37.18 | B | C |
| ATOM | 4889 | C | ILE | 166 | 101.920 | 52.073 | 10.121 | 1.00 | 19.71 | B | C |
| ATOM | 4890 | O | ILE | 166 | 102.909 | 52.792 | 10.059 | 1.00 | 21.46 | B | O |
| ATOM | 4891 | N | ALA | 167 | 101.076 | 51.927 | 9.106 | 1.00 | 22.08 | B | N |

Fig. 19: A-68

| | | | | | | | | | | |
|---|---|---|---|---|---|---|---|---|---|---|
| ATOM | 4892 | CA | ALA | 167 | 101.271 | 52.670 | 7.866 | 1.00 | 22.68 | B C |
| ATOM | 4893 | CB | ALA | 167 | 100.207 | 52.309 | 6.859 | 1.00 | 1.87 | B C |
| ATOM | 4894 | C | ALA | 167 | 101.165 | 54.150 | 8.224 | 1.00 | 23.89 | B C |
| ATOM | 4895 | O | ALA | 167 | 101.881 | 54.989 | 7.684 | 1.00 | 20.49 | B O |
| ATOM | 4896 | N | PHE | 168 | 100.261 | 54.458 | 9.147 | 1.00 | 25.99 | B N |
| ATOM | 4897 | CA | PHE | 168 | 100.083 | 55.823 | 9.583 | 1.00 | 24.51 | B C |
| ATOM | 4898 | CB | PHE | 168 | 98.964 | 55.902 | 10.623 | 1.00 | 28.51 | B C |
| ATOM | 4899 | CG | PHE | 168 | 98.962 | 57.185 | 11.406 | 1.00 | 27.01 | B C |
| ATOM | 4900 | CD1 | PHE | 168 | 99.549 | 57.240 | 12.671 | 1.00 | 28.61 | B C |
| ATOM | 4901 | CD2 | PHE | 168 | 98.409 | 58.341 | 10.872 | 1.00 | 25.32 | B C |
| ATOM | 4902 | CE1 | PHE | 168 | 99.587 | 58.424 | 13.392 | 1.00 | 27.09 | B C |
| ATOM | 4903 | CE2 | PHE | 168 | 98.442 | 59.529 | 11.587 | 1.00 | 27.14 | B C |
| ATOM | 4904 | CZ | PHE | 168 | 99.034 | 59.570 | 12.853 | 1.00 | 29.63 | B C |
| ATOM | 4905 | C | PHE | 168 | 101.397 | 56.325 | 10.178 | 1.00 | 25.37 | B C |
| ATOM | 4906 | O | PHE | 168 | 101.832 | 57.446 | 9.908 | 1.00 | 21.81 | B O |
| ATOM | 4907 | N | LEU | 169 | 102.030 | 55.488 | 10.990 | 1.00 | 25.37 | B N |
| ATOM | 4908 | CA | LEU | 169 | 103.286 | 55.867 | 11.611 | 1.00 | 27.96 | B C |
| ATOM | 4909 | CB | LEU | 169 | 103.749 | 54.790 | 12.585 | 1.00 | 24.35 | B C |
| ATOM | 4910 | CG | LEU | 169 | 103.127 | 54.723 | 13.977 | 1.00 | 23.51 | B C |
| ATOM | 4911 | CD1 | LEU | 169 | 103.983 | 53.810 | 14.831 | 1.00 | 19.97 | B C |
| ATOM | 4912 | CD2 | LEU | 169 | 103.079 | 56.105 | 14.609 | 1.00 | 20.37 | B C |
| ATOM | 4913 | C | LEU | 169 | 104.357 | 56.081 | 10.555 | 1.00 | 30.26 | B C |
| ATOM | 4914 | O | LEU | 169 | 105.055 | 57.095 | 10.555 | 1.00 | 31.69 | B O |
| ATOM | 4915 | N | ASN | 170 | 104.488 | 55.115 | 9.655 | 1.00 | 28.40 | B N |
| ATOM | 4916 | CA | ASN | 170 | 105.470 | 55.208 | 8.591 | 1.00 | 25.53 | B C |
| ATOM | 4917 | CB | ASN | 170 | 105.243 | 54.077 | 7.580 | 1.00 | 72.75 | B C |
| ATOM | 4918 | CG | ASN | 170 | 106.484 | 53.768 | 6.747 | 1.00 | 76.17 | B C |
| ATOM | 4919 | OD1 | ASN | 170 | 106.703 | 54.346 | 5.680 | 1.00 | 71.70 | B O |
| ATOM | 4920 | ND2 | ASN | 170 | 107.307 | 52.854 | 7.242 | 1.00 | 74.08 | B N |
| ATOM | 4921 | C | ASN | 170 | 105.335 | 56.578 | 7.913 | 1.00 | 25.54 | B C |
| ATOM | 4922 | O | ASN | 170 | 106.242 | 57.408 | 7.992 | 1.00 | 25.75 | B O |
| ATOM | 4923 | N | ASP | 171 | 104.189 | 56.819 | 7.275 | 1.00 | 35.44 | B N |
| ATOM | 4924 | CA | ASP | 171 | 103.940 | 58.079 | 6.581 | 1.00 | 37.56 | B C |
| ATOM | 4925 | CB | ASP | 171 | 102.467 | 58.179 | 6.168 | 1.00 | 72.00 | B C |
| ATOM | 4926 | CG | ASP | 171 | 102.163 | 57.427 | 4.880 | 1.00 | 79.65 | B C |
| ATOM | 4927 | OD1 | ASP | 171 | 102.448 | 56.213 | 4.805 | 1.00 | 81.87 | B O |
| ATOM | 4928 | OD2 | ASP | 171 | 101.635 | 58.055 | 3.937 | 1.00 | 81.51 | B O |
| ATOM | 4929 | C | ASP | 171 | 104.309 | 59.289 | 7.418 | 1.00 | 39.05 | B C |
| ATOM | 4930 | O | ASP | 171 | 104.975 | 60.202 | 6.937 | 1.00 | 37.77 | B O |
| ATOM | 4931 | N | LEU | 172 | 103.881 | 59.289 | 8.674 | 1.00 | 36.54 | B N |
| ATOM | 4932 | CA | LEU | 172 | 104.152 | 60.403 | 9.570 | 1.00 | 37.22 | B C |
| ATOM | 4933 | CB | LEU | 172 | 103.410 | 60.204 | 10.891 | 1.00 | 36.27 | B C |
| ATOM | 4934 | CG | LEU | 172 | 102.901 | 61.423 | 11.674 | 1.00 | 35.76 | B C |
| ATOM | 4935 | CD1 | LEU | 172 | 103.145 | 61.178 | 13.158 | 1.00 | 33.36 | B C |
| ATOM | 4936 | CD2 | LEU | 172 | 103.593 | 62.706 | 11.237 | 1.00 | 33.93 | B C |
| ATOM | 4937 | C | LEU | 172 | 105.642 | 60.561 | 9.849 | 1.00 | 37.56 | B C |
| ATOM | 4938 | O | LEU | 172 | 106.212 | 61.628 | 9.627 | 1.00 | 37.55 | B O |
| ATOM | 4939 | N | LEU | 173 | 106.269 | 59.493 | 10.337 | 1.00 | 40.49 | B N |
| ATOM | 4940 | CA | LEU | 173 | 107.692 | 59.520 | 10.669 | 1.00 | 43.24 | B C |
| ATOM | 4941 | CB | LEU | 173 | 108.115 | 58.215 | 11.364 | 1.00 | 18.13 | B C |
| ATOM | 4942 | CG | LEU | 173 | 107.801 | 57.866 | 12.826 | 1.00 | 19.48 | B C |
| ATOM | 4943 | CD1 | LEU | 173 | 108.033 | 59.060 | 13.729 | 1.00 | 23.00 | B C |
| ATOM | 4944 | CD2 | LEU | 173 | 106.380 | 57.395 | 12.943 | 1.00 | 20.03 | B C |
| ATOM | 4945 | C | LEU | 173 | 108.650 | 59.772 | 9.503 | 1.00 | 44.67 | B C |
| ATOM | 4946 | O | LEU | 173 | 109.601 | 60.537 | 9.642 | 1.00 | 41.39 | B O |
| ATOM | 4947 | N | LYS | 174 | 108.409 | 59.135 | 8.360 | 1.00 | 37.56 | B N |
| ATOM | 4948 | CA | LYS | 174 | 109.304 | 59.291 | 7.221 | 1.00 | 37.78 | B C |
| ATOM | 4949 | CB | LYS | 174 | 108.836 | 58.421 | 6.047 | 1.00 | 42.14 | B C |
| ATOM | 4950 | CG | LYS | 174 | 107.739 | 58.988 | 5.169 | 1.00 | 42.47 | B C |
| ATOM | 4951 | CD | LYS | 174 | 107.472 | 58.022 | 4.008 | 1.00 | 41.72 | B C |
| ATOM | 4952 | CE | LYS | 174 | 106.689 | 58.660 | 2.852 | 1.00 | 36.97 | B C |
| ATOM | 4953 | NZ | LYS | 174 | 105.297 | 59.097 | 3.187 | 1.00 | 33.44 | B N |
| ATOM | 4954 | C | LYS | 174 | 109.511 | 60.738 | 6.774 | 1.00 | 36.14 | B C |
| ATOM | 4955 | O | LYS | 174 | 110.571 | 61.078 | 6.245 | 1.00 | 37.01 | B O |
| ATOM | 4956 | N | ARG | 175 | 108.514 | 61.589 | 7.004 | 1.00 | 41.42 | B N |
| ATOM | 4957 | CA | ARG | 175 | 108.587 | 63.006 | 6.653 | 1.00 | 43.65 | B C |
| ATOM | 4958 | CB | ARG | 175 | 107.182 | 63.634 | 6.654 | 1.00 | 108.28 | B C |
| ATOM | 4959 | CG | ARG | 175 | 106.189 | 63.149 | 5.589 | 1.00 | 115.21 | B C |
| ATOM | 4960 | CD | ARG | 175 | 104.762 | 63.613 | 5.939 | 1.00 | 119.49 | B C |
| ATOM | 4961 | NE | ARG | 175 | 103.895 | 63.818 | 4.775 | 1.00 | 124.39 | B N |
| ATOM | 4962 | CZ | ARG | 175 | 103.454 | 62.856 | 3.969 | 1.00 | 127.97 | B C |
| ATOM | 4963 | NH1 | ARG | 175 | 103.793 | 61.593 | 4.182 | 1.00 | 128.17 | B N |
| ATOM | 4964 | NH2 | ARG | 175 | 102.666 | 63.162 | 2.945 | 1.00 | 128.87 | B N |

Fig. 19: A-69

| | | | | | | | | | | |
|---|---|---|---|---|---|---|---|---|---|---|
| ATOM | 4965 | C | ARG | 175 | 109.471 | 63.798 | 7.611 | 1.00 | 41.18 | B C |
| ATOM | 4966 | O | ARG | 175 | 109.696 | 64.986 | 7.411 | 1.00 | 41.02 | B O |
| ATOM | 4967 | N | MET | 176 | 109.970 | 63.145 | 8.660 | 1.00 | 47.15 | B N |
| ATOM | 4968 | CA | MET | 176 | 110.777 | 63.821 | 9.678 | 1.00 | 43.63 | B C |
| ATOM | 4969 | CB | MET | 176 | 110.320 | 63.383 | 11.065 | 1.00 | 33.29 | B C |
| ATOM | 4970 | CG | MET | 176 | 108.969 | 63.920 | 11.456 | 1.00 | 30.19 | B C |
| ATOM | 4971 | SD | MET | 176 | 108.444 | 63.366 | 13.073 | 1.00 | 34.33 | B S |
| ATOM | 4972 | CE | MET | 176 | 107.041 | 62.339 | 12.619 | 1.00 | 27.84 | B C |
| ATOM | 4973 | C | MET | 176 | 112.284 | 63.663 | 9.611 | 1.00 | 47.14 | B C |
| ATOM | 4974 | O | MET | 176 | 112.795 | 62.707 | 9.037 | 1.00 | 47.21 | B O |
| ATOM | 4975 | N | ASP | 177 | 112.991 | 64.617 | 10.213 | 1.00 | 51.06 | B N |
| ATOM | 4976 | CA | ASP | 177 | 114.451 | 64.590 | 10.276 | 1.00 | 53.55 | B C |
| ATOM | 4977 | CB | ASP | 177 | 115.047 | 65.944 | 9.881 | 1.00 | 101.95 | B C |
| ATOM | 4978 | CG | ASP | 177 | 115.065 | 66.158 | 8.381 | 1.00 | 104.90 | B C |
| ATOM | 4979 | OD1 | ASP | 177 | 115.635 | 67.174 | 7.934 | 1.00 | 104.57 | B O |
| ATOM | 4980 | OD2 | ASP | 177 | 114.511 | 65.310 | 7.647 | 1.00 | 106.55 | B O |
| ATOM | 4981 | C | ASP | 177 | 114.851 | 64.249 | 11.706 | 1.00 | 53.47 | B C |
| ATOM | 4982 | O | ASP | 177 | 115.107 | 65.133 | 12.519 | 1.00 | 53.19 | B O |
| ATOM | 4983 | N | ILE | 178 | 114.888 | 62.954 | 12.003 | 1.00 | 55.91 | B N |
| ATOM | 4984 | CA | ILE | 178 | 115.236 | 62.465 | 13.331 | 1.00 | 56.05 | B C |
| ATOM | 4985 | CB | ILE | 178 | 114.719 | 61.004 | 13.543 | 1.00 | 33.37 | B C |
| ATOM | 4986 | CG2 | ILE | 178 | 115.323 | 60.410 | 14.790 | 1.00 | 31.65 | B C |
| ATOM | 4987 | CG1 | ILE | 178 | 113.191 | 60.985 | 13.665 | 1.00 | 34.43 | B C |
| ATOM | 4988 | CD1 | ILE | 178 | 112.464 | 60.671 | 12.376 | 1.00 | 36.27 | B C |
| ATOM | 4989 | C | ILE | 178 | 116.743 | 62.502 | 13.583 | 1.00 | 55.19 | B C |
| ATOM | 4990 | O | ILE | 178 | 117.543 | 62.224 | 12.686 | 1.00 | 57.18 | B O |
| ATOM | 4991 | N | GLY | 179 | 117.117 | 62.846 | 14.812 | 1.00 | 23.09 | B N |
| ATOM | 4992 | CA | GLY | 179 | 118.521 | 62.912 | 15.178 | 1.00 | 22.81 | B C |
| ATOM | 4993 | C | GLY | 179 | 118.736 | 63.508 | 16.560 | 1.00 | 23.57 | B C |
| ATOM | 4994 | O | GLY | 179 | 117.931 | 64.325 | 17.012 | 1.00 | 21.72 | B O |
| ATOM | 4995 | N | PRO | 180 | 119.815 | 63.113 | 17.265 | 1.00 | 39.73 | B N |
| ATOM | 4996 | CD | PRO | 180 | 120.782 | 62.068 | 16.873 | 1.00 | 73.51 | B C |
| ATOM | 4997 | CA | PRO | 180 | 120.124 | 63.620 | 18.606 | 1.00 | 40.79 | B C |
| ATOM | 4998 | CB | PRO | 180 | 121.542 | 63.113 | 18.840 | 1.00 | 72.35 | B C |
| ATOM | 4999 | CG | PRO | 180 | 121.502 | 61.776 | 18.184 | 1.00 | 74.74 | B C |
| ATOM | 5000 | C | PRO | 180 | 120.019 | 65.135 | 18.697 | 1.00 | 42.57 | B C |
| ATOM | 5001 | O | PRO | 180 | 119.718 | 65.680 | 19.761 | 1.00 | 43.21 | B O |
| ATOM | 5002 | N | LYS | 181 | 120.268 | 65.810 | 17.578 | 1.00 | 56.97 | B N |
| ATOM | 5003 | CA | LYS | 181 | 120.186 | 67.265 | 17.534 | 1.00 | 57.39 | B C |
| ATOM | 5004 | CB | LYS | 181 | 121.522 | 67.867 | 17.092 | 1.00 | 83.43 | B C |
| ATOM | 5005 | CG | LYS | 181 | 122.677 | 67.613 | 18.052 | 1.00 | 84.03 | B C |
| ATOM | 5006 | CD | LYS | 181 | 122.430 | 68.205 | 19.442 | 1.00 | 82.89 | B C |
| ATOM | 5007 | CE | LYS | 181 | 123.580 | 67.868 | 20.394 | 1.00 | 85.41 | B C |
| ATOM | 5008 | NZ | LYS | 181 | 123.351 | 68.348 | 21.790 | 1.00 | 84.98 | B N |
| ATOM | 5009 | C | LYS | 181 | 119.070 | 67.736 | 16.597 | 1.00 | 56.74 | B C |
| ATOM | 5010 | O | LYS | 181 | 118.973 | 68.917 | 16.274 | 1.00 | 55.06 | B O |
| ATOM | 5011 | N | GLN | 182 | 118.225 | 66.804 | 16.167 | 1.00 | 33.36 | B N |
| ATOM | 5012 | CA | GLN | 182 | 117.112 | 67.117 | 15.279 | 1.00 | 32.02 | B C |
| ATOM | 5013 | CB | GLN | 182 | 117.152 | 66.219 | 14.044 | 1.00 | 74.94 | B C |
| ATOM | 5014 | CG | GLN | 182 | 118.512 | 66.050 | 13.424 | 1.00 | 76.22 | B C |
| ATOM | 5015 | CD | GLN | 182 | 119.037 | 67.334 | 12.850 | 1.00 | 77.84 | B C |
| ATOM | 5016 | OE1 | GLN | 182 | 119.266 | 68.305 | 13.573 | 1.00 | 78.68 | B O |
| ATOM | 5017 | NE2 | GLN | 182 | 119.230 | 67.356 | 11.537 | 1.00 | 79.20 | B N |
| ATOM | 5018 | C | GLN | 182 | 115.831 | 66.826 | 16.046 | 1.00 | 30.93 | B C |
| ATOM | 5019 | O | GLN | 182 | 115.638 | 67.278 | 17.173 | 1.00 | 35.26 | B O |
| ATOM | 5020 | N | THR | 183 | 114.961 | 66.046 | 15.419 | 1.00 | 29.87 | B N |
| ATOM | 5021 | CA | THR | 183 | 113.706 | 65.648 | 16.025 | 1.00 | 26.79 | B C |
| ATOM | 5022 | CB | THR | 183 | 112.612 | 65.493 | 14.962 | 1.00 | 31.40 | B C |
| ATOM | 5023 | OG1 | THR | 183 | 112.484 | 66.721 | 14.231 | 1.00 | 27.85 | B O |
| ATOM | 5024 | CG2 | THR | 183 | 111.285 | 65.127 | 15.610 | 1.00 | 29.08 | B C |
| ATOM | 5025 | C | THR | 183 | 113.957 | 64.288 | 16.666 | 1.00 | 26.45 | B C |
| ATOM | 5026 | O | THR | 183 | 114.624 | 63.428 | 16.077 | 1.00 | 24.98 | B O |
| ATOM | 5027 | N | GLN | 184 | 113.464 | 64.102 | 17.883 | 1.00 | 44.27 | B N |
| ATOM | 5028 | CA | GLN | 184 | 113.619 | 62.822 | 18.546 | 1.00 | 39.92 | B C |
| ATOM | 5029 | CB | GLN | 184 | 114.254 | 62.981 | 19.920 | 1.00 | 33.99 | B C |
| ATOM | 5030 | CG | GLN | 184 | 115.752 | 63.197 | 19.878 | 1.00 | 33.74 | B C |
| ATOM | 5031 | CD | GLN | 184 | 116.427 | 62.766 | 21.163 | 1.00 | 33.21 | B C |
| ATOM | 5032 | OE1 | GLN | 184 | 116.097 | 63.258 | 22.244 | 1.00 | 28.91 | B O |
| ATOM | 5033 | NE2 | GLN | 184 | 117.375 | 61.835 | 21.053 | 1.00 | 31.51 | B N |
| ATOM | 5034 | C | GLN | 184 | 112.227 | 62.240 | 18.670 | 1.00 | 40.30 | B C |
| ATOM | 5035 | O | GLN | 184 | 111.249 | 62.978 | 18.834 | 1.00 | 37.69 | B O |
| ATOM | 5036 | N | VAL | 185 | 112.131 | 60.918 | 18.574 | 1.00 | 24.17 | B N |
| ATOM | 5037 | CA | VAL | 185 | 110.837 | 60.255 | 18.649 | 1.00 | 22.54 | B C |

Fig. 19: A-70

| ATOM | 5038 | CB | VAL | 185 | 110.345 | 59.858 | 17.235 | 1.00 | 12.44 | B | C |
|---|---|---|---|---|---|---|---|---|---|---|---|
| ATOM | 5039 | CG1 | VAL | 185 | 109.105 | 58.990 | 17.335 | 1.00 | 12.43 | B | C |
| ATOM | 5040 | CG2 | VAL | 185 | 110.052 | 61.103 | 16.425 | 1.00 | 1.87 | B | C |
| ATOM | 5041 | C | VAL | 185 | 110.840 | 59.025 | 19.536 | 1.00 | 23.13 | B | C |
| ATOM | 5042 | O | VAL | 185 | 111.756 | 58.206 | 19.510 | 1.00 | 20.28 | B | O |
| ATOM | 5043 | N | GLY | 186 | 109.789 | 58.914 | 20.328 | 1.00 | 27.91 | B | N |
| ATOM | 5044 | CA | GLY | 186 | 109.630 | 57.782 | 21.213 | 1.00 | 29.54 | B | C |
| ATOM | 5045 | C | GLY | 186 | 108.200 | 57.319 | 21.045 | 1.00 | 27.52 | B | C |
| ATOM | 5046 | O | GLY | 186 | 107.308 | 58.138 | 20.839 | 1.00 | 32.88 | B | O |
| ATOM | 5047 | N | ILE | 187 | 107.970 | 56.017 | 21.105 | 1.00 | 20.77 | B | N |
| ATOM | 5048 | CA | ILE | 187 | 106.617 | 55.519 | 20.958 | 1.00 | 19.36 | B | C |
| ATOM | 5049 | CB | ILE | 187 | 106.460 | 54.729 | 19.642 | 1.00 | 17.70 | B | C |
| ATOM | 5050 | CG2 | ILE | 187 | 105.081 | 54.079 | 19.577 | 1.00 | 15.03 | B | C |
| ATOM | 5051 | CG1 | ILE | 187 | 106.639 | 55.676 | 18.454 | 1.00 | 18.22 | B | C |
| ATOM | 5052 | CD1 | ILE | 187 | 106.437 | 55.033 | 17.100 | 1.00 | 19.27 | B | C |
| ATOM | 5053 | C | ILE | 187 | 106.160 | 54.674 | 22.143 | 1.00 | 18.65 | B | C |
| ATOM | 5054 | O | ILE | 187 | 106.852 | 53.763 | 22.590 | 1.00 | 17.55 | B | O |
| ATOM | 5055 | N | VAL | 188 | 104.984 | 55.015 | 22.649 | 1.00 | 23.72 | B | N |
| ATOM | 5056 | CA | VAL | 188 | 104.370 | 54.332 | 23.774 | 1.00 | 23.39 | B | C |
| ATOM | 5057 | CB | VAL | 188 | 104.053 | 55.333 | 24.911 | 1.00 | 24.28 | B | C |
| ATOM | 5058 | CG1 | VAL | 188 | 103.055 | 54.728 | 25.896 | 1.00 | 19.55 | B | C |
| ATOM | 5059 | CG2 | VAL | 188 | 105.320 | 55.715 | 25.625 | 1.00 | 24.70 | B | C |
| ATOM | 5060 | C | VAL | 188 | 103.055 | 53.702 | 23.303 | 1.00 | 21.93 | B | C |
| ATOM | 5061 | O | VAL | 188 | 102.274 | 54.341 | 22.591 | 1.00 | 21.34 | B | O |
| ATOM | 5062 | N | GLN | 189 | 102.815 | 52.453 | 23.686 | 1.00 | 21.90 | B | N |
| ATOM | 5063 | CA | GLN | 189 | 101.580 | 51.785 | 23.312 | 1.00 | 21.58 | B | C |
| ATOM | 5064 | CB | GLN | 189 | 101.857 | 50.545 | 22.463 | 1.00 | 19.75 | B | C |
| ATOM | 5065 | CG | GLN | 189 | 100.577 | 49.784 | 22.128 | 1.00 | 17.26 | B | C |
| ATOM | 5066 | CD | GLN | 189 | 100.819 | 48.495 | 21.377 | 1.00 | 17.97 | B | C |
| ATOM | 5067 | OE1 | GLN | 189 | 99.930 | 47.647 | 21.283 | 1.00 | 19.19 | B | O |
| ATOM | 5068 | NE2 | GLN | 189 | 102.022 | 48.340 | 20.831 | 1.00 | 19.01 | B | N |
| ATOM | 5069 | C | GLN | 189 | 100.820 | 51.386 | 24.572 | 1.00 | 18.57 | B | C |
| ATOM | 5070 | O | GLN | 189 | 101.423 | 50.980 | 25.567 | 1.00 | 16.93 | B | O |
| ATOM | 5071 | N | TYR | 190 | 99.494 | 51.500 | 24.524 | 1.00 | 20.56 | B | N |
| ATOM | 5072 | CA | TYR | 190 | 98.671 | 51.159 | 25.680 | 1.00 | 24.08 | B | C |
| ATOM | 5073 | CB | TYR | 190 | 98.255 | 52.432 | 26.418 | 1.00 | 22.72 | B | C |
| ATOM | 5074 | CG | TYR | 190 | 97.213 | 53.255 | 25.687 | 1.00 | 17.37 | B | C |
| ATOM | 5075 | CD1 | TYR | 190 | 95.849 | 53.072 | 25.929 | 1.00 | 15.48 | B | C |
| ATOM | 5076 | CE1 | TYR | 190 | 94.882 | 53.820 | 25.244 | 1.00 | 17.37 | B | C |
| ATOM | 5077 | CD2 | TYR | 190 | 97.586 | 54.207 | 24.739 | 1.00 | 13.48 | B | C |
| ATOM | 5078 | CE2 | TYR | 190 | 96.624 | 54.957 | 24.051 | 1.00 | 14.90 | B | C |
| ATOM | 5079 | CZ | TYR | 190 | 95.279 | 54.760 | 24.311 | 1.00 | 15.79 | B | C |
| ATOM | 5080 | OH | TYR | 190 | 94.340 | 55.527 | 23.663 | 1.00 | 14.38 | B | O |
| ATOM | 5081 | C | TYR | 190 | 97.428 | 50.342 | 25.344 | 1.00 | 25.93 | B | C |
| ATOM | 5082 | O | TYR | 190 | 97.000 | 50.260 | 24.195 | 1.00 | 26.01 | B | O |
| ATOM | 5083 | N | GLY | 191 | 96.860 | 49.746 | 26.385 | 1.00 | 24.69 | B | N |
| ATOM | 5084 | CA | GLY | 191 | 95.675 | 48.920 | 26.270 | 1.00 | 22.44 | B | C |
| ATOM | 5085 | C | GLY | 191 | 95.277 | 48.649 | 27.701 | 1.00 | 23.88 | B | C |
| ATOM | 5086 | O | GLY | 191 | 94.720 | 49.532 | 28.348 | 1.00 | 27.26 | B | O |
| ATOM | 5087 | N | GLU | 192 | 95.572 | 47.446 | 28.197 | 1.00 | 23.59 | B | N |
| ATOM | 5088 | CA | GLU | 192 | 95.284 | 47.084 | 29.584 | 1.00 | 25.60 | B | C |
| ATOM | 5089 | CB | GLU | 192 | 95.232 | 45.574 | 29.758 | 1.00 | 40.14 | B | C |
| ATOM | 5090 | CG | GLU | 192 | 94.135 | 44.871 | 29.002 | 1.00 | 40.52 | B | C |
| ATOM | 5091 | CD | GLU | 192 | 94.134 | 43.382 | 29.273 | 1.00 | 40.71 | B | C |
| ATOM | 5092 | OE1 | GLU | 192 | 93.230 | 42.690 | 28.759 | 1.00 | 43.60 | B | O |
| ATOM | 5093 | OE2 | GLU | 192 | 95.038 | 42.906 | 29.999 | 1.00 | 38.58 | B | O |
| ATOM | 5094 | C | GLU | 192 | 96.465 | 47.608 | 30.390 | 1.00 | 25.41 | B | C |
| ATOM | 5095 | O | GLU | 192 | 96.325 | 48.027 | 31.536 | 1.00 | 26.78 | B | O |
| ATOM | 5096 | N | ASN | 193 | 97.637 | 47.569 | 29.770 | 1.00 | 17.36 | B | N |
| ATOM | 5097 | CA | ASN | 193 | 98.862 | 48.041 | 30.395 | 1.00 | 18.57 | B | C |
| ATOM | 5098 | CB | ASN | 193 | 99.814 | 46.877 | 30.653 | 1.00 | 57.60 | B | C |
| ATOM | 5099 | CG | ASN | 193 | 99.159 | 45.755 | 31.418 | 1.00 | 60.77 | B | C |
| ATOM | 5100 | OD1 | ASN | 193 | 98.225 | 45.115 | 30.933 | 1.00 | 64.88 | B | O |
| ATOM | 5101 | ND2 | ASN | 193 | 99.644 | 45.509 | 32.626 | 1.00 | 62.88 | B | N |
| ATOM | 5102 | C | ASN | 193 | 99.510 | 49.007 | 29.425 | 1.00 | 16.75 | B | C |
| ATOM | 5103 | O | ASN | 193 | 98.917 | 49.360 | 28.413 | 1.00 | 17.75 | B | O |
| ATOM | 5104 | N | VAL | 194 | 100.735 | 49.418 | 29.728 | 1.00 | 23.63 | B | N |
| ATOM | 5105 | CA | VAL | 194 | 101.454 | 50.346 | 28.866 | 1.00 | 25.97 | B | C |
| ATOM | 5106 | CB | VAL | 194 | 101.516 | 51.750 | 29.490 | 1.00 | 24.85 | B | C |
| ATOM | 5107 | CG1 | VAL | 194 | 102.014 | 52.745 | 28.459 | 1.00 | 25.88 | B | C |
| ATOM | 5108 | CG2 | VAL | 194 | 100.153 | 52.147 | 30.032 | 1.00 | 22.12 | B | C |
| ATOM | 5109 | C | VAL | 194 | 102.887 | 49.864 | 28.661 | 1.00 | 23.74 | B | C |
| ATOM | 5110 | O | VAL | 194 | 103.535 | 49.384 | 29.597 | 1.00 | 21.86 | B | O |

Fig. 19: A-71

| | | | | | | | | | | |
|---|---|---|---|---|---|---|---|---|---|---|
| ATOM | 5111 | N | THR | 195 | 103.397 | 49.986 | 27.444 | 1.00 | 25.03 | B N |
| ATOM | 5112 | CA | THR | 195 | 104.758 | 49.552 | 27.197 | 1.00 | 26.21 | B C |
| ATOM | 5113 | CB | THR | 195 | 104.797 | 48.182 | 26.450 | 1.00 | 38.61 | B C |
| ATOM | 5114 | OG1 | THR | 195 | 104.420 | 48.360 | 25.081 | 1.00 | 42.62 | B O |
| ATOM | 5115 | CG2 | THR | 195 | 103.828 | 47.195 | 27.087 | 1.00 | 40.24 | B C |
| ATOM | 5116 | C | THR | 195 | 105.511 | 50.599 | 26.391 | 1.00 | 27.05 | B C |
| ATOM | 5117 | O | THR | 195 | 104.944 | 51.254 | 25.514 | 1.00 | 29.64 | B O |
| ATOM | 5118 | N | HIS | 196 | 106.791 | 50.765 | 26.716 | 1.00 | 33.64 | B N |
| ATOM | 5119 | CA | HIS | 196 | 107.656 | 51.713 | 26.029 | 1.00 | 33.74 | B C |
| ATOM | 5120 | CB | HIS | 196 | 108.815 | 52.119 | 26.942 | 1.00 | 34.91 | B C |
| ATOM | 5121 | CG | HIS | 196 | 108.417 | 53.011 | 28.079 | 1.00 | 31.41 | B C |
| ATOM | 5122 | CD2 | HIS | 196 | 108.084 | 52.725 | 29.360 | 1.00 | 32.04 | B C |
| ATOM | 5123 | ND1 | HIS | 196 | 108.322 | 54.382 | 27.955 | 1.00 | 30.06 | B N |
| ATOM | 5124 | CE1 | HIS | 196 | 107.949 | 54.901 | 29.111 | 1.00 | 26.78 | B C |
| ATOM | 5125 | NE2 | HIS | 196 | 107.797 | 53.918 | 29.979 | 1.00 | 24.99 | B N |
| ATOM | 5126 | C | HIS | 196 | 108.219 | 51.017 | 24.806 | 1.00 | 33.60 | B C |
| ATOM | 5127 | O | HIS | 196 | 109.201 | 50.289 | 24.932 | 1.00 | 32.26 | B O |
| ATOM | 5128 | N | GLU | 197 | 107.609 | 51.216 | 23.636 | 1.00 | 34.73 | B N |
| ATOM | 5129 | CA | GLU | 197 | 108.123 | 50.583 | 22.417 | 1.00 | 32.06 | B C |
| ATOM | 5130 | CB | GLU | 197 | 107.313 | 50.999 | 21.193 | 1.00 | 45.57 | B C |
| ATOM | 5131 | CG | GLU | 197 | 105.913 | 50.386 | 21.130 | 1.00 | 45.91 | B C |
| ATOM | 5132 | CD | GLU | 197 | 105.911 | 48.876 | 21.303 | 1.00 | 44.98 | B C |
| ATOM | 5133 | OE1 | GLU | 197 | 106.869 | 48.228 | 20.834 | 1.00 | 43.56 | B O |
| ATOM | 5134 | OE2 | GLU | 197 | 104.949 | 48.331 | 21.892 | 1.00 | 46.64 | B O |
| ATOM | 5135 | C | GLU | 197 | 109.595 | 50.958 | 22.245 | 1.00 | 29.53 | B C |
| ATOM | 5136 | O | GLU | 197 | 110.447 | 50.081 | 22.151 | 1.00 | 34.73 | B O |
| ATOM | 5137 | N | PHE | 198 | 109.898 | 52.254 | 22.203 | 1.00 | 32.40 | B N |
| ATOM | 5138 | CA | PHE | 198 | 111.293 | 52.691 | 22.126 | 1.00 | 34.20 | B C |
| ATOM | 5139 | CB | PHE | 198 | 111.881 | 52.501 | 20.714 | 1.00 | 23.77 | B C |
| ATOM | 5140 | CG | PHE | 198 | 111.239 | 53.331 | 19.636 | 1.00 | 22.02 | B C |
| ATOM | 5141 | CD1 | PHE | 198 | 111.379 | 54.711 | 19.614 | 1.00 | 28.16 | B C |
| ATOM | 5142 | CD2 | PHE | 198 | 110.539 | 52.715 | 18.597 | 1.00 | 16.76 | B C |
| ATOM | 5143 | CE1 | PHE | 198 | 110.837 | 55.468 | 18.571 | 1.00 | 24.19 | B C |
| ATOM | 5144 | CE2 | PHE | 198 | 109.990 | 53.460 | 17.548 | 1.00 | 22.67 | B C |
| ATOM | 5145 | CZ | PHE | 198 | 110.140 | 54.838 | 17.536 | 1.00 | 26.47 | B C |
| ATOM | 5146 | C | PHE | 198 | 111.471 | 54.120 | 22.642 | 1.00 | 36.88 | B C |
| ATOM | 5147 | O | PHE | 198 | 110.631 | 54.973 | 22.398 | 1.00 | 38.17 | B O |
| ATOM | 5148 | N | ASN | 199 | 112.552 | 54.366 | 23.386 | 1.00 | 21.75 | B N |
| ATOM | 5149 | CA | ASN | 199 | 112.810 | 55.686 | 23.971 | 1.00 | 22.04 | B C |
| ATOM | 5150 | CB | ASN | 199 | 113.924 | 55.613 | 25.007 | 1.00 | 33.57 | B C |
| ATOM | 5151 | CG | ASN | 199 | 113.636 | 54.633 | 26.105 | 1.00 | 34.83 | B C |
| ATOM | 5152 | OD1 | ASN | 199 | 112.614 | 54.717 | 26.785 | 1.00 | 36.36 | B O |
| ATOM | 5153 | ND2 | ASN | 199 | 114.549 | 53.688 | 26.295 | 1.00 | 33.71 | B N |
| ATOM | 5154 | C | ASN | 199 | 113.159 | 56.792 | 22.996 | 1.00 | 24.50 | B C |
| ATOM | 5155 | O | ASN | 199 | 113.569 | 56.546 | 21.862 | 1.00 | 22.31 | B O |
| ATOM | 5156 | N | LEU | 200 | 113.004 | 58.023 | 23.473 | 1.00 | 27.41 | B N |
| ATOM | 5157 | CA | LEU | 200 | 113.286 | 59.215 | 22.685 | 1.00 | 29.37 | B C |
| ATOM | 5158 | CB | LEU | 200 | 113.094 | 60.467 | 23.542 | 1.00 | 22.93 | B C |
| ATOM | 5159 | CG | LEU | 200 | 111.694 | 61.088 | 23.545 | 1.00 | 20.78 | B C |
| ATOM | 5160 | CD1 | LEU | 200 | 111.613 | 62.208 | 24.578 | 1.00 | 25.90 | B C |
| ATOM | 5161 | CD2 | LEU | 200 | 111.375 | 61.607 | 22.140 | 1.00 | 21.95 | B C |
| ATOM | 5162 | C | LEU | 200 | 114.685 | 59.223 | 22.104 | 1.00 | 29.77 | B C |
| ATOM | 5163 | O | LEU | 200 | 114.899 | 59.698 | 20.992 | 1.00 | 30.79 | B O |
| ATOM | 5164 | N | ASN | 201 | 115.635 | 58.685 | 22.856 | 1.00 | 32.06 | B N |
| ATOM | 5165 | CA | ASN | 201 | 117.027 | 58.660 | 22.426 | 1.00 | 33.91 | B C |
| ATOM | 5166 | CB | ASN | 201 | 117.920 | 59.105 | 23.578 | 1.00 | 34.75 | B C |
| ATOM | 5167 | CG | ASN | 201 | 117.838 | 58.168 | 24.769 | 1.00 | 37.03 | B C |
| ATOM | 5168 | OD1 | ASN | 201 | 118.389 | 58.443 | 25.832 | 1.00 | 37.17 | B O |
| ATOM | 5169 | ND2 | ASN | 201 | 117.147 | 57.052 | 24.592 | 1.00 | 34.87 | B N |
| ATOM | 5170 | C | ASN | 201 | 117.517 | 57.309 | 21.936 | 1.00 | 33.96 | B C |
| ATOM | 5171 | O | ASN | 201 | 118.723 | 57.111 | 21.825 | 1.00 | 29.86 | B O |
| ATOM | 5172 | N | LYS | 202 | 116.603 | 56.382 | 21.653 | 1.00 | 35.80 | B N |
| ATOM | 5173 | CA | LYS | 202 | 116.990 | 55.051 | 21.183 | 1.00 | 35.92 | B C |
| ATOM | 5174 | CB | LYS | 202 | 115.786 | 54.107 | 21.160 | 1.00 | 34.30 | B C |
| ATOM | 5175 | CG | LYS | 202 | 116.107 | 52.652 | 20.788 | 1.00 | 35.84 | B C |
| ATOM | 5176 | CD | LYS | 202 | 116.841 | 51.929 | 21.898 | 1.00 | 37.75 | B C |
| ATOM | 5177 | CE | LYS | 202 | 116.185 | 52.179 | 23.273 | 1.00 | 43.50 | B C |
| ATOM | 5178 | NZ | LYS | 202 | 114.729 | 51.801 | 23.388 | 1.00 | 42.52 | B N |
| ATOM | 5179 | C | LYS | 202 | 117.617 | 55.071 | 19.800 | 1.00 | 34.79 | B C |
| ATOM | 5180 | O | LYS | 202 | 118.667 | 54.472 | 19.589 | 1.00 | 32.07 | B O |
| ATOM | 5181 | N | TYR | 203 | 116.977 | 55.747 | 18.852 | 1.00 | 23.81 | B N |
| ATOM | 5182 | CA | TYR | 203 | 117.509 | 55.815 | 17.491 | 1.00 | 23.49 | B C |
| ATOM | 5183 | CB | TYR | 203 | 116.466 | 55.300 | 16.499 | 1.00 | 32.41 | B C |

Fig. 19: A-72

| | | | | | | | | | | |
|---|---|---|---|---|---|---|---|---|---|---|
| ATOM | 5184 | CG | TYR | 203 | 115.907 | 53.951 | 16.886 | 1.00 | 31.08 | B C |
| ATOM | 5185 | CD1 | TYR | 203 | 114.665 | 53.844 | 17.509 | 1.00 | 31.69 | B C |
| ATOM | 5186 | CE1 | TYR | 203 | 114.179 | 52.613 | 17.930 | 1.00 | 28.16 | B C |
| ATOM | 5187 | CD2 | TYR | 203 | 116.649 | 52.784 | 16.689 | 1.00 | 33.97 | B C |
| ATOM | 5188 | CE2 | TYR | 203 | 116.173 | 51.550 | 17.109 | 1.00 | 36.72 | B C |
| ATOM | 5189 | CZ | TYR | 203 | 114.940 | 51.474 | 17.730 | 1.00 | 36.34 | B C |
| ATOM | 5190 | OH | TYR | 203 | 114.466 | 50.262 | 18.169 | 1.00 | 41.34 | B O |
| ATOM | 5191 | C | TYR | 203 | 117.957 | 57.230 | 17.114 | 1.00 | 24.13 | B C |
| ATOM | 5192 | O | TYR | 203 | 117.268 | 58.211 | 17.387 | 1.00 | 22.30 | B O |
| ATOM | 5193 | N | SER | 204 | 119.122 | 57.323 | 16.484 | 1.00 | 32.64 | B N |
| ATOM | 5194 | CA | SER | 204 | 119.693 | 58.608 | 16.089 | 1.00 | 34.49 | B C |
| ATOM | 5195 | CB | SER | 204 | 121.199 | 58.588 | 16.320 | 1.00 | 50.27 | B C |
| ATOM | 5196 | OG | SER | 204 | 121.780 | 57.499 | 15.621 | 1.00 | 52.10 | B O |
| ATOM | 5197 | C | SER | 204 | 119.432 | 58.924 | 14.632 | 1.00 | 37.07 | B C |
| ATOM | 5198 | O | SER | 204 | 119.922 | 59.919 | 14.118 | 1.00 | 37.58 | B O |
| ATOM | 5199 | N | SER | 205 | 118.657 | 58.082 | 13.966 | 1.00 | 56.25 | B N |
| ATOM | 5200 | CA | SER | 205 | 118.379 | 58.289 | 12.558 | 1.00 | 55.91 | B C |
| ATOM | 5201 | CB | SER | 205 | 119.256 | 57.357 | 11.734 | 1.00 | 30.45 | B C |
| ATOM | 5202 | OG | SER | 205 | 118.818 | 57.302 | 10.393 | 1.00 | 35.94 | B O |
| ATOM | 5203 | C | SER | 205 | 116.918 | 58.067 | 12.195 | 1.00 | 54.04 | B C |
| ATOM | 5204 | O | SER | 205 | 116.208 | 57.320 | 12.866 | 1.00 | 50.30 | B O |
| ATOM | 5205 | N | THR | 206 | 116.477 | 58.718 | 11.122 | 1.00 | 22.26 | B N |
| ATOM | 5206 | CA | THR | 206 | 115.105 | 58.589 | 10.661 | 1.00 | 23.61 | B C |
| ATOM | 5207 | CB | THR | 206 | 114.799 | 59.611 | 9.560 | 1.00 | 36.04 | B C |
| ATOM | 5208 | OG1 | THR | 206 | 114.968 | 60.935 | 10.086 | 1.00 | 34.85 | B O |
| ATOM | 5209 | CG2 | THR | 206 | 113.364 | 59.438 | 9.047 | 1.00 | 34.41 | B C |
| ATOM | 5210 | C | THR | 206 | 114.780 | 57.188 | 10.144 | 1.00 | 24.20 | B C |
| ATOM | 5211 | O | THR | 206 | 113.676 | 56.683 | 10.363 | 1.00 | 26.99 | B O |
| ATOM | 5212 | N | GLU | 207 | 115.719 | 56.554 | 9.447 | 1.00 | 31.43 | B N |
| ATOM | 5213 | CA | GLU | 207 | 115.444 | 55.210 | 8.964 | 1.00 | 30.59 | B C |
| ATOM | 5214 | CB | GLU | 207 | 116.448 | 54.791 | 7.893 | 1.00 | 74.76 | B C |
| ATOM | 5215 | CG | GLU | 207 | 117.897 | 54.985 | 8.248 | 1.00 | 75.48 | B C |
| ATOM | 5216 | CD | GLU | 207 | 118.817 | 54.402 | 7.189 | 1.00 | 76.89 | B C |
| ATOM | 5217 | OE1 | GLU | 207 | 118.595 | 54.668 | 5.982 | 1.00 | 76.12 | B O |
| ATOM | 5218 | OE2 | GLU | 207 | 119.765 | 53.679 | 7.565 | 1.00 | 75.79 | B O |
| ATOM | 5219 | C | GLU | 207 | 115.462 | 54.237 | 10.141 | 1.00 | 31.09 | B C |
| ATOM | 5220 | O | GLU | 207 | 114.647 | 53.315 | 10.194 | 1.00 | 31.04 | B O |
| ATOM | 5221 | N | GLU | 208 | 116.373 | 54.449 | 11.093 | 1.00 | 40.73 | B N |
| ATOM | 5222 | CA | GLU | 208 | 116.441 | 53.584 | 12.267 | 1.00 | 42.46 | B C |
| ATOM | 5223 | CB | GLU | 208 | 117.542 | 54.038 | 13.230 | 1.00 | 57.02 | B C |
| ATOM | 5224 | CG | GLU | 208 | 118.951 | 53.899 | 12.682 | 1.00 | 54.49 | B C |
| ATOM | 5225 | CD | GLU | 208 | 120.022 | 54.254 | 13.703 | 1.00 | 54.01 | B C |
| ATOM | 5226 | OE1 | GLU | 208 | 121.217 | 54.253 | 13.333 | 1.00 | 59.78 | B O |
| ATOM | 5227 | OE2 | GLU | 208 | 119.669 | 54.533 | 14.873 | 1.00 | 52.73 | B O |
| ATOM | 5228 | C | GLU | 208 | 115.100 | 53.611 | 12.991 | 1.00 | 43.16 | B C |
| ATOM | 5229 | O | GLU | 208 | 114.637 | 52.584 | 13.489 | 1.00 | 44.16 | B O |
| ATOM | 5230 | N | VAL | 209 | 114.478 | 54.787 | 13.046 | 1.00 | 30.06 | B N |
| ATOM | 5231 | CA | VAL | 209 | 113.190 | 54.922 | 13.709 | 1.00 | 28.98 | B C |
| ATOM | 5232 | CB | VAL | 209 | 112.879 | 56.399 | 14.058 | 1.00 | 17.77 | B C |
| ATOM | 5233 | CG1 | VAL | 209 | 111.379 | 56.612 | 14.232 | 1.00 | 18.10 | B C |
| ATOM | 5234 | CG2 | VAL | 209 | 113.575 | 56.762 | 15.349 | 1.00 | 18.79 | B C |
| ATOM | 5235 | C | VAL | 209 | 112.098 | 54.359 | 12.820 | 1.00 | 27.00 | B C |
| ATOM | 5236 | O | VAL | 209 | 111.198 | 53.660 | 13.296 | 1.00 | 25.96 | B O |
| ATOM | 5237 | N | LEU | 210 | 112.187 | 54.655 | 11.529 | 1.00 | 33.19 | B N |
| ATOM | 5238 | CA | LEU | 210 | 111.207 | 54.164 | 10.570 | 1.00 | 33.52 | B C |
| ATOM | 5239 | CB | LEU | 210 | 111.557 | 54.643 | 9.168 | 1.00 | 15.67 | B C |
| ATOM | 5240 | CG | LEU | 210 | 110.629 | 55.672 | 8.535 | 1.00 | 15.91 | B C |
| ATOM | 5241 | CD1 | LEU | 210 | 111.182 | 55.981 | 7.171 | 1.00 | 12.46 | B C |
| ATOM | 5242 | CD2 | LEU | 210 | 109.191 | 55.157 | 8.437 | 1.00 | 9.36 | B C |
| ATOM | 5243 | C | LEU | 210 | 111.152 | 52.639 | 10.571 | 1.00 | 31.78 | B C |
| ATOM | 5244 | O | LEU | 210 | 110.090 | 52.042 | 10.382 | 1.00 | 32.55 | B O |
| ATOM | 5245 | N | VAL | 211 | 112.307 | 52.017 | 10.779 | 1.00 | 24.37 | B N |
| ATOM | 5246 | CA | VAL | 211 | 112.404 | 50.569 | 10.809 | 1.00 | 24.13 | B C |
| ATOM | 5247 | CB | VAL | 211 | 113.852 | 50.123 | 10.575 | 1.00 | 20.01 | B C |
| ATOM | 5248 | CG1 | VAL | 211 | 114.002 | 48.647 | 10.897 | 1.00 | 22.19 | B C |
| ATOM | 5249 | CG2 | VAL | 211 | 114.239 | 50.405 | 9.118 | 1.00 | 20.62 | B C |
| ATOM | 5250 | C | VAL | 211 | 111.913 | 49.997 | 12.129 | 1.00 | 23.38 | B C |
| ATOM | 5251 | O | VAL | 211 | 111.260 | 48.958 | 12.164 | 1.00 | 24.06 | B O |
| ATOM | 5252 | N | ALA | 212 | 112.230 | 50.674 | 13.221 | 1.00 | 40.83 | B N |
| ATOM | 5253 | CA | ALA | 212 | 111.803 | 50.203 | 14.526 | 1.00 | 39.81 | B C |
| ATOM | 5254 | CB | ALA | 212 | 112.489 | 51.000 | 15.612 | 1.00 | 28.52 | B C |
| ATOM | 5255 | C | ALA | 212 | 110.295 | 50.339 | 14.650 | 1.00 | 37.62 | B C |
| ATOM | 5256 | O | ALA | 212 | 109.626 | 49.493 | 15.256 | 1.00 | 37.56 | B O |

Fig. 19: A-73

| ATOM | 5257 | N | ALA | 213 | 109.759 | 51.408 | 14.069 | 1.00 | 31.97 | B | N |
|---|---|---|---|---|---|---|---|---|---|---|---|
| ATOM | 5258 | CA | ALA | 213 | 108.324 | 51.658 | 14.122 | 1.00 | 33.14 | B | C |
| ATOM | 5259 | CB | ALA | 213 | 107.999 | 52.998 | 13.459 | 1.00 | 19.99 | B | C |
| ATOM | 5260 | C | ALA | 213 | 107.530 | 50.535 | 13.458 | 1.00 | 31.94 | B | C |
| ATOM | 5261 | O | ALA | 213 | 106.556 | 50.029 | 14.025 | 1.00 | 29.57 | B | O |
| ATOM | 5262 | N | ASN | 214 | 107.954 | 50.142 | 12.258 | 1.00 | 35.89 | B | N |
| ATOM | 5263 | CA | ASN | 214 | 107.264 | 49.091 | 11.524 | 1.00 | 39.76 | B | C |
| ATOM | 5264 | CB | ASN | 214 | 107.804 | 48.970 | 10.100 | 1.00 | 79.46 | B | C |
| ATOM | 5265 | CG | ASN | 214 | 107.278 | 50.049 | 9.190 | 1.00 | 81.19 | B | C |
| ATOM | 5266 | OD1 | ASN | 214 | 107.668 | 51.210 | 9.296 | 1.00 | 83.12 | B | O |
| ATOM | 5267 | ND2 | ASN | 214 | 106.379 | 49.676 | 8.289 | 1.00 | 81.61 | B | N |
| ATOM | 5268 | C | ASN | 214 | 107.348 | 47.738 | 12.207 | 1.00 | 42.15 | B | C |
| ATOM | 5269 | O | ASN | 214 | 106.583 | 46.829 | 11.891 | 1.00 | 42.87 | B | O |
| ATOM | 5270 | N | LYS | 215 | 108.271 | 47.596 | 13.148 | 1.00 | 30.37 | B | N |
| ATOM | 5271 | CA | LYS | 215 | 108.418 | 46.326 | 13.856 | 1.00 | 30.81 | B | C |
| ATOM | 5272 | CB | LYS | 215 | 109.892 | 46.059 | 14.209 | 1.00 | 46.54 | B | C |
| ATOM | 5273 | CG | LYS | 215 | 110.791 | 45.922 | 12.978 | 1.00 | 54.12 | B | C |
| ATOM | 5274 | CD | LYS | 215 | 112.062 | 45.124 | 13.256 | 1.00 | 57.66 | B | C |
| ATOM | 5275 | CE | LYS | 215 | 112.950 | 45.778 | 14.311 | 1.00 | 61.12 | B | C |
| ATOM | 5276 | NZ | LYS | 215 | 114.249 | 45.057 | 14.483 | 1.00 | 62.11 | B | N |
| ATOM | 5277 | C | LYS | 215 | 107.560 | 46.274 | 15.113 | 1.00 | 28.94 | B | C |
| ATOM | 5278 | O | LYS | 215 | 107.568 | 45.277 | 15.832 | 1.00 | 30.16 | B | O |
| ATOM | 5279 | N | ILE | 216 | 106.809 | 47.341 | 15.377 | 1.00 | 44.32 | B | N |
| ATOM | 5280 | CA | ILE | 216 | 105.945 | 47.362 | 16.553 | 1.00 | 41.14 | B | C |
| ATOM | 5281 | CB | ILE | 216 | 105.443 | 48.776 | 16.874 | 1.00 | 15.33 | B | C |
| ATOM | 5282 | CG2 | ILE | 216 | 104.492 | 48.730 | 18.038 | 1.00 | 12.11 | B | C |
| ATOM | 5283 | CG1 | ILE | 216 | 106.616 | 49.674 | 17.243 | 1.00 | 12.01 | B | C |
| ATOM | 5284 | CD1 | ILE | 216 | 106.191 | 51.073 | 17.602 | 1.00 | 10.70 | B | C |
| ATOM | 5285 | C | ILE | 216 | 104.740 | 46.447 | 16.369 | 1.00 | 39.58 | B | C |
| ATOM | 5286 | O | ILE | 216 | 104.035 | 46.498 | 15.361 | 1.00 | 40.28 | B | O |
| ATOM | 5287 | N | VAL | 217 | 104.524 | 45.611 | 17.372 | 1.00 | 36.13 | B | N |
| ATOM | 5288 | CA | VAL | 217 | 103.436 | 44.647 | 17.392 | 1.00 | 37.90 | B | C |
| ATOM | 5289 | CB | VAL | 217 | 103.949 | 43.284 | 17.887 | 1.00 | 59.95 | B | C |
| ATOM | 5290 | CG1 | VAL | 217 | 102.793 | 42.367 | 18.217 | 1.00 | 59.95 | B | C |
| ATOM | 5291 | CG2 | VAL | 217 | 104.837 | 42.666 | 16.829 | 1.00 | 59.95 | B | C |
| ATOM | 5292 | C | VAL | 217 | 102.316 | 45.111 | 18.311 | 1.00 | 39.06 | B | C |
| ATOM | 5293 | O | VAL | 217 | 102.565 | 45.725 | 19.352 | 1.00 | 38.52 | B | O |
| ATOM | 5294 | N | GLN | 218 | 101.084 | 44.809 | 17.914 | 1.00 | 32.14 | B | N |
| ATOM | 5295 | CA | GLN | 218 | 99.907 | 45.181 | 18.687 | 1.00 | 32.80 | B | C |
| ATOM | 5296 | CB | GLN | 218 | 98.646 | 44.976 | 17.850 | 1.00 | 28.44 | B | C |
| ATOM | 5297 | CG | GLN | 218 | 97.378 | 45.433 | 18.528 | 1.00 | 28.44 | B | C |
| ATOM | 5298 | CD | GLN | 218 | 96.153 | 45.273 | 17.644 | 1.00 | 28.44 | B | C |
| ATOM | 5299 | OE1 | GLN | 218 | 95.096 | 45.843 | 17.928 | 1.00 | 28.44 | B | O |
| ATOM | 5300 | NE2 | GLN | 218 | 96.283 | 44.490 | 16.571 | 1.00 | 28.44 | B | N |
| ATOM | 5301 | C | GLN | 218 | 99.856 | 44.288 | 19.913 | 1.00 | 32.25 | B | C |
| ATOM | 5302 | O | GLN | 218 | 99.948 | 43.079 | 19.792 | 1.00 | 36.00 | B | O |
| ATOM | 5303 | N | ARG | 219 | 99.709 | 44.883 | 21.091 | 1.00 | 14.17 | B | N |
| ATOM | 5304 | CA | ARG | 219 | 99.664 | 44.114 | 22.330 | 1.00 | 13.82 | B | C |
| ATOM | 5305 | CB | ARG | 219 | 100.490 | 44.828 | 23.394 | 1.00 | 43.11 | B | C |
| ATOM | 5306 | CG | ARG | 219 | 101.627 | 45.640 | 22.823 | 1.00 | 43.11 | B | C |
| ATOM | 5307 | CD | ARG | 219 | 102.594 | 46.039 | 23.901 | 1.00 | 43.11 | B | C |
| ATOM | 5308 | NE | ARG | 219 | 103.597 | 45.007 | 24.124 | 1.00 | 43.11 | B | N |
| ATOM | 5309 | CZ | ARG | 219 | 104.694 | 44.867 | 23.384 | 1.00 | 43.11 | B | C |
| ATOM | 5310 | NH1 | ARG | 219 | 104.921 | 45.705 | 22.369 | 1.00 | 43.11 | B | N |
| ATOM | 5311 | NH2 | ARG | 219 | 105.566 | 43.900 | 23.661 | 1.00 | 43.11 | B | N |
| ATOM | 5312 | C | ARG | 219 | 98.221 | 43.910 | 22.821 | 1.00 | 15.03 | B | C |
| ATOM | 5313 | O | ARG | 219 | 97.976 | 43.309 | 23.871 | 1.00 | 15.04 | B | O |
| ATOM | 5314 | N | GLY | 220 | 97.269 | 44.423 | 22.048 | 1.00 | 30.91 | B | N |
| ATOM | 5315 | CA | GLY | 220 | 95.868 | 44.283 | 22.402 | 1.00 | 30.52 | B | C |
| ATOM | 5316 | C | GLY | 220 | 95.495 | 44.884 | 23.742 | 1.00 | 30.19 | B | C |
| ATOM | 5317 | O | GLY | 220 | 96.246 | 45.674 | 24.327 | 1.00 | 28.53 | B | O |
| ATOM | 5318 | N | GLY | 221 | 94.316 | 44.511 | 24.222 | 1.00 | 22.15 | B | N |
| ATOM | 5319 | CA | GLY | 221 | 93.852 | 45.009 | 25.500 | 1.00 | 20.72 | B | C |
| ATOM | 5320 | C | GLY | 221 | 92.348 | 44.902 | 25.652 | 1.00 | 21.14 | B | C |
| ATOM | 5321 | O | GLY | 221 | 91.598 | 45.328 | 24.776 | 1.00 | 17.94 | B | O |
| ATOM | 5322 | N | ARG | 222 | 91.897 | 44.327 | 26.760 | 1.00 | 28.36 | B | N |
| ATOM | 5323 | CA | ARG | 222 | 90.467 | 44.199 | 27.011 | 1.00 | 29.07 | B | C |
| ATOM | 5324 | CB | ARG | 222 | 90.204 | 43.114 | 28.053 | 1.00 | 26.86 | B | C |
| ATOM | 5325 | CG | ARG | 222 | 90.365 | 41.713 | 27.491 | 1.00 | 26.86 | B | C |
| ATOM | 5326 | CD | ARG | 222 | 90.427 | 40.663 | 28.578 | 1.00 | 26.86 | B | C |
| ATOM | 5327 | NE | ARG | 222 | 91.679 | 40.734 | 29.316 | 1.00 | 26.86 | B | N |
| ATOM | 5328 | CZ | ARG | 222 | 92.021 | 39.885 | 30.274 | 1.00 | 26.86 | B | C |
| ATOM | 5329 | NH1 | ARG | 222 | 91.201 | 38.895 | 30.612 | 1.00 | 26.86 | B | N |

Fig. 19: A-74

```
ATOM   5330  NH2 ARG  222      93.184  40.027  30.893  1.00  26.86     B  N
ATOM   5331  C   ARG  222      89.899  45.529  27.482  1.00  29.12     B  C
ATOM   5332  O   ARG  222      88.686  45.686  27.599  1.00  29.89     B  O
ATOM   5333  N   GLN  223      90.792  46.477  27.756  1.00  34.74     B  N
ATOM   5334  CA  GLN  223      90.423  47.826  28.182  1.00  33.03     B  C
ATOM   5335  CB  GLN  223      90.700  48.050  29.677  1.00  36.16     B  C
ATOM   5336  CG  GLN  223      89.723  47.394  30.641  1.00  37.60     B  C
ATOM   5337  CD  GLN  223      90.065  45.957  30.915  1.00  38.01     B  C
ATOM   5338  OE1 GLN  223      91.209  45.635  31.230  1.00  38.41     B  O
ATOM   5339  NE2 GLN  223      89.075  45.080  30.811  1.00  38.45     B  N
ATOM   5340  C   GLN  223      91.221  48.849  27.372  1.00  33.77     B  C
ATOM   5341  O   GLN  223      92.122  48.487  26.619  1.00  33.25     B  O
ATOM   5342  N   THR  224      90.893  50.126  27.535  1.00  56.95     B  N
ATOM   5343  CA  THR  224      91.572  51.197  26.820  1.00  54.83     B  C
ATOM   5344  CB  THR  224      90.628  51.834  25.793  1.00   7.14     B  C
ATOM   5345  OG1 THR  224      90.118  50.811  24.930  1.00   7.13     B  O
ATOM   5346  CG2 THR  224      91.357  52.895  24.965  1.00   4.73     B  C
ATOM   5347  C   THR  224      92.002  52.252  27.829  1.00  51.84     B  C
ATOM   5348  O   THR  224      91.290  53.221  28.067  1.00  48.33     B  O
ATOM   5349  N   MET  225      93.175  52.061  28.419  1.00  27.08     B  N
ATOM   5350  CA  MET  225      93.679  52.980  29.426  1.00  27.97     B  C
ATOM   5351  CB  MET  225      94.712  52.269  30.301  1.00  32.79     B  C
ATOM   5352  CG  MET  225      94.280  50.804  30.301  1.00  30.22     B  C
ATOM   5353  SD  MET  225      92.971  50.963  31.995  1.00  37.96     B  S
ATOM   5354  CE  MET  225      93.153  49.343  32.760  1.00  34.54     B  C
ATOM   5355  C   MET  225      94.304  54.237  28.846  1.00  29.00     B  C
ATOM   5356  O   MET  225      95.442  54.561  29.180  1.00  30.46     B  O
ATOM   5357  N   THR  226      93.571  54.953  27.997  1.00  32.08     B  N
ATOM   5358  CA  THR  226      94.102  56.178  27.393  1.00  31.55     B  C
ATOM   5359  CB  THR  226      93.013  56.963  26.655  1.00  28.80     B  C
ATOM   5360  OG1 THR  226      92.395  56.132  25.665  1.00  30.82     B  O
ATOM   5361  CG2 THR  226      93.620  58.170  25.976  1.00  26.52     B  C
ATOM   5362  C   THR  226      94.735  57.104  28.438  1.00  30.15     B  C
ATOM   5363  O   THR  226      95.804  57.672  28.216  1.00  24.84     B  O
ATOM   5364  N   ALA  227      94.075  57.249  29.581  1.00  17.95     B  N
ATOM   5365  CA  ALA  227      94.594  58.094  30.645  1.00  16.89     B  C
ATOM   5366  CB  ALA  227      93.655  58.069  31.829  1.00  18.36     B  C
ATOM   5367  C   ALA  227      95.975  57.633  31.076  1.00  17.55     B  C
ATOM   5368  O   ALA  227      96.898  58.439  31.199  1.00  18.35     B  O
ATOM   5369  N   LEU  228      96.111  56.331  31.307  1.00  19.16     B  N
ATOM   5370  CA  LEU  228      97.384  55.752  31.728  1.00  17.60     B  C
ATOM   5371  CB  LEU  228      97.206  54.252  32.017  1.00   6.84     B  C
ATOM   5372  CG  LEU  228      98.453  53.498  32.483  1.00  14.73     B  C
ATOM   5373  CD1 LEU  228      99.020  54.157  33.734  1.00  12.32     B  C
ATOM   5374  CD2 LEU  228      98.097  52.064  32.732  1.00  11.78     B  C
ATOM   5375  C   LEU  228      98.463  55.955  30.662  1.00  16.78     B  C
ATOM   5376  O   LEU  228      99.605  56.321  30.971  1.00  19.76     B  O
ATOM   5377  N   GLY  229      98.094  55.713  29.408  1.00  21.79     B  N
ATOM   5378  CA  GLY  229      99.033  55.877  28.318  1.00  24.15     B  C
ATOM   5379  C   GLY  229      99.620  57.267  28.293  1.00  26.71     B  C
ATOM   5380  O   GLY  229     100.843  57.422  28.296  1.00  27.30     B  O
ATOM   5381  N   ILE  230      98.756  58.281  28.280  1.00  20.54     B  N
ATOM   5382  CA  ILE  230      99.216  59.666  28.259  1.00  21.87     B  C
ATOM   5383  CB  ILE  230      98.039  60.677  28.160  1.00  18.79     B  C
ATOM   5384  CG2 ILE  230      98.595  62.090  28.034  1.00  18.79     B  C
ATOM   5385  CG1 ILE  230      97.174  60.370  26.933  1.00  18.79     B  C
ATOM   5386  CD1 ILE  230      95.945  61.225  26.807  1.00  18.79     B  C
ATOM   5387  C   ILE  230     100.042  60.007  29.505  1.00  22.13     B  C
ATOM   5388  O   ILE  230     101.101  60.634  29.402  1.00  20.06     B  O
ATOM   5389  N   ASP  231      99.566  59.595  30.677  1.00  30.92     B  N
ATOM   5390  CA  ASP  231     100.286  59.876  31.916  1.00  29.32     B  C
ATOM   5391  CB  ASP  231      99.494  59.354  33.116  1.00  27.91     B  C
ATOM   5392  CG  ASP  231      99.993  59.917  34.442  1.00  34.91     B  C
ATOM   5393  OD1 ASP  231      99.939  61.155  34.644  1.00  33.67     B  O
ATOM   5394  OD2 ASP  231     100.432  59.112  35.288  1.00  38.45     B  O
ATOM   5395  C   ASP  231     101.676  59.231  31.884  1.00  30.30     B  C
ATOM   5396  O   ASP  231     102.669  59.838  32.318  1.00  27.52     B  O
ATOM   5397  N   THR  232     101.741  58.007  31.361  1.00  43.37     B  N
ATOM   5398  CA  THR  232     102.998  57.276  31.260  1.00  42.16     B  C
ATOM   5399  CB  THR  232     102.768  55.830  30.801  1.00  59.43     B  C
ATOM   5400  OG1 THR  232     101.963  55.148  31.771  1.00  57.94     B  O
ATOM   5401  CG2 THR  232     104.097  55.098  30.645  1.00  52.97     B  C
ATOM   5402  C   THR  232     103.939  57.959  30.274  1.00  42.79     B  C
```

Fig. 19: A-75

| ATOM | 5403 | O | THR | 232 | 105.153 | 58.050 | 30.509 | 1.00 | 42.96 | B | O |
|---|---|---|---|---|---|---|---|---|---|---|---|
| ATOM | 5404 | N | ALA | 233 | 103.383 | 58.427 | 29.161 | 1.00 | 22.02 | B | N |
| ATOM | 5405 | CA | ALA | 233 | 104.202 | 59.116 | 28.179 | 1.00 | 24.67 | B | C |
| ATOM | 5406 | CB | ALA | 233 | 103.373 | 59.472 | 26.961 | 1.00 | 49.88 | B | C |
| ATOM | 5407 | C | ALA | 233 | 104.752 | 60.385 | 28.836 | 1.00 | 26.98 | B | C |
| ATOM | 5408 | O | ALA | 233 | 105.862 | 60.834 | 28.532 | 1.00 | 28.89 | B | O |
| ATOM | 5409 | N | ARG | 234 | 103.967 | 60.947 | 29.751 | 1.00 | 50.27 | B | N |
| ATOM | 5410 | CA | ARG | 234 | 104.361 | 62.165 | 30.431 | 1.00 | 53.37 | B | C |
| ATOM | 5411 | CB | ARG | 234 | 103.146 | 62.842 | 31.077 | 1.00 | 50.29 | B | C |
| ATOM | 5412 | CG | ARG | 234 | 103.377 | 64.312 | 31.390 | 1.00 | 50.29 | B | C |
| ATOM | 5413 | CD | ARG | 234 | 102.536 | 64.816 | 32.561 | 1.00 | 50.29 | B | C |
| ATOM | 5414 | NE | ARG | 234 | 103.103 | 64.432 | 33.852 | 1.00 | 50.29 | B | N |
| ATOM | 5415 | CZ | ARG | 234 | 102.668 | 63.418 | 34.592 | 1.00 | 50.29 | B | C |
| ATOM | 5416 | NH1 | ARG | 234 | 101.650 | 62.682 | 34.172 | 1.00 | 50.29 | B | N |
| ATOM | 5417 | NH2 | ARG | 234 | 103.258 | 63.135 | 35.744 | 1.00 | 50.29 | B | N |
| ATOM | 5418 | C | ARG | 234 | 105.406 | 61.904 | 31.498 | 1.00 | 55.50 | B | C |
| ATOM | 5419 | O | ARG | 234 | 106.556 | 62.316 | 31.368 | 1.00 | 55.55 | B | O |
| ATOM | 5420 | N | LYS | 235 | 105.009 | 61.196 | 32.547 | 1.00 | 27.28 | B | N |
| ATOM | 5421 | CA | LYS | 235 | 105.914 | 60.939 | 33.660 | 1.00 | 27.23 | B | C |
| ATOM | 5422 | CB | LYS | 235 | 105.129 | 60.356 | 34.848 | 1.00 | 39.45 | B | C |
| ATOM | 5423 | CG | LYS | 235 | 104.888 | 58.857 | 34.831 | 1.00 | 40.60 | B | C |
| ATOM | 5424 | CD | LYS | 235 | 104.027 | 58.450 | 36.030 | 1.00 | 40.42 | B | C |
| ATOM | 5425 | CE | LYS | 235 | 104.119 | 56.955 | 36.346 | 1.00 | 41.22 | B | C |
| ATOM | 5426 | NZ | LYS | 235 | 103.715 | 56.073 | 35.205 | 1.00 | 41.98 | B | N |
| ATOM | 5427 | C | LYS | 235 | 107.149 | 60.078 | 33.375 | 1.00 | 27.37 | B | C |
| ATOM | 5428 | O | LYS | 235 | 108.112 | 60.118 | 34.130 | 1.00 | 27.71 | B | O |
| ATOM | 5429 | N | GLU | 236 | 107.133 | 59.313 | 32.290 | 1.00 | 28.33 | B | N |
| ATOM | 5430 | CA | GLU | 236 | 108.264 | 58.454 | 31.964 | 1.00 | 29.95 | B | C |
| ATOM | 5431 | CB | GLU | 236 | 107.803 | 56.992 | 31.884 | 1.00 | 47.54 | B | C |
| ATOM | 5432 | CG | GLU | 236 | 107.861 | 56.249 | 33.216 | 1.00 | 50.31 | B | C |
| ATOM | 5433 | CD | GLU | 236 | 107.031 | 54.965 | 33.245 | 1.00 | 52.79 | B | C |
| ATOM | 5434 | OE1 | GLU | 236 | 107.194 | 54.118 | 32.342 | 1.00 | 52.88 | B | O |
| ATOM | 5435 | OE2 | GLU | 236 | 106.219 | 54.797 | 34.184 | 1.00 | 52.63 | B | O |
| ATOM | 5436 | C | GLU | 236 | 108.966 | 58.840 | 30.670 | 1.00 | 28.50 | B | C |
| ATOM | 5437 | O | GLU | 236 | 110.092 | 59.336 | 30.684 | 1.00 | 29.93 | B | O |
| ATOM | 5438 | N | ALA | 237 | 108.287 | 58.617 | 29.552 | 1.00 | 22.73 | B | N |
| ATOM | 5439 | CA | ALA | 237 | 108.860 | 58.901 | 28.248 | 1.00 | 20.20 | B | C |
| ATOM | 5440 | CB | ALA | 237 | 107.783 | 58.831 | 27.180 | 1.00 | 41.37 | B | C |
| ATOM | 5441 | C | ALA | 237 | 109.562 | 60.233 | 28.187 | 1.00 | 19.04 | B | C |
| ATOM | 5442 | O | ALA | 237 | 110.636 | 60.344 | 27.589 | 1.00 | 17.46 | B | O |
| ATOM | 5443 | N | PHE | 238 | 108.962 | 61.242 | 28.810 | 1.00 | 29.57 | B | N |
| ATOM | 5444 | CA | PHE | 238 | 109.530 | 62.580 | 28.795 | 1.00 | 29.00 | B | C |
| ATOM | 5445 | CB | PHE | 238 | 108.419 | 63.620 | 28.752 | 1.00 | 35.30 | B | C |
| ATOM | 5446 | CG | PHE | 238 | 107.856 | 63.854 | 27.381 | 1.00 | 34.33 | B | C |
| ATOM | 5447 | CD1 | PHE | 238 | 106.531 | 63.532 | 27.101 | 1.00 | 35.56 | B | C |
| ATOM | 5448 | CD2 | PHE | 238 | 108.635 | 64.429 | 26.380 | 1.00 | 31.93 | B | C |
| ATOM | 5449 | CE1 | PHE | 238 | 105.985 | 63.780 | 25.841 | 1.00 | 33.36 | B | C |
| ATOM | 5450 | CE2 | PHE | 238 | 108.106 | 64.682 | 25.124 | 1.00 | 38.24 | B | C |
| ATOM | 5451 | CZ | PHE | 238 | 106.778 | 64.359 | 24.850 | 1.00 | 39.66 | B | C |
| ATOM | 5452 | C | PHE | 238 | 110.468 | 62.908 | 29.943 | 1.00 | 30.85 | B | C |
| ATOM | 5453 | O | PHE | 238 | 110.433 | 64.012 | 30.479 | 1.00 | 30.95 | B | O |
| ATOM | 5454 | N | THR | 239 | 111.303 | 61.951 | 30.325 | 1.00 | 29.27 | B | N |
| ATOM | 5455 | CA | THR | 239 | 112.266 | 62.182 | 31.391 | 1.00 | 33.21 | B | C |
| ATOM | 5456 | CB | THR | 239 | 112.113 | 61.150 | 32.520 | 1.00 | 23.55 | B | C |
| ATOM | 5457 | OG1 | THR | 239 | 112.276 | 59.840 | 31.989 | 1.00 | 21.51 | B | O |
| ATOM | 5458 | CG2 | THR | 239 | 110.745 | 61.242 | 33.153 | 1.00 | 26.46 | B | C |
| ATOM | 5459 | C | THR | 239 | 113.660 | 62.084 | 30.770 | 1.00 | 33.47 | B | C |
| ATOM | 5460 | O | THR | 239 | 113.930 | 61.177 | 29.980 | 1.00 | 33.97 | B | O |
| ATOM | 5461 | N | GLU | 240 | 114.531 | 63.030 | 31.117 | 1.00 | 17.24 | B | N |
| ATOM | 5462 | CA | GLU | 240 | 115.890 | 63.085 | 30.580 | 1.00 | 17.49 | B | C |
| ATOM | 5463 | CB | GLU | 240 | 116.748 | 64.003 | 31.444 | 1.00 | 74.12 | B | C |
| ATOM | 5464 | CG | GLU | 240 | 118.007 | 64.483 | 30.758 | 1.00 | 78.76 | B | C |
| ATOM | 5465 | CD | GLU | 240 | 118.634 | 65.654 | 31.479 | 1.00 | 81.67 | B | C |
| ATOM | 5466 | OE1 | GLU | 240 | 117.904 | 66.627 | 31.774 | 1.00 | 81.77 | B | O |
| ATOM | 5467 | OE2 | GLU | 240 | 119.853 | 65.605 | 31.746 | 1.00 | 81.74 | B | O |
| ATOM | 5468 | C | GLU | 240 | 116.555 | 61.712 | 30.465 | 1.00 | 18.84 | B | C |
| ATOM | 5469 | O | GLU | 240 | 117.323 | 61.444 | 29.530 | 1.00 | 20.05 | B | O |
| ATOM | 5470 | N | ALA | 241 | 116.234 | 60.839 | 31.415 | 1.00 | 54.75 | B | N |
| ATOM | 5471 | CA | ALA | 241 | 116.784 | 59.491 | 31.446 | 1.00 | 55.60 | B | C |
| ATOM | 5472 | CB | ALA | 241 | 116.331 | 58.783 | 32.723 | 1.00 | 26.00 | B | C |
| ATOM | 5473 | C | ALA | 241 | 116.387 | 58.678 | 30.212 | 1.00 | 55.07 | B | C |
| ATOM | 5474 | O | ALA | 241 | 117.093 | 57.751 | 29.823 | 1.00 | 56.53 | B | O |
| ATOM | 5475 | N | ARG | 242 | 115.259 | 59.024 | 29.598 | 1.00 | 25.17 | B | N |

Fig. 19: A-76

| ATOM | 5476 | CA | ARG | 242 | 114.805 | 58.305 | 28.417 | 1.00 | 24.91 | B | C |
|------|------|----|-----|-----|---------|--------|--------|------|-------|---|---|
| ATOM | 5477 | CB | ARG | 242 | 113.337 | 57.917 | 28.570 | 1.00 | 45.62 | B | C |
| ATOM | 5478 | CG | ARG | 242 | 113.136 | 56.644 | 29.392 | 1.00 | 45.82 | B | C |
| ATOM | 5479 | CD | ARG | 242 | 111.684 | 56.188 | 29.334 | 1.00 | 46.68 | B | C |
| ATOM | 5480 | NE | ARG | 242 | 111.525 | 54.733 | 29.424 | 1.00 | 47.88 | B | N |
| ATOM | 5481 | CZ | ARG | 242 | 111.348 | 54.055 | 30.557 | 1.00 | 47.08 | B | C |
| ATOM | 5482 | NH1 | ARG | 242 | 111.307 | 54.695 | 31.721 | 1.00 | 46.13 | B | N |
| ATOM | 5483 | NH2 | ARG | 242 | 111.187 | 52.738 | 30.526 | 1.00 | 49.10 | B | N |
| ATOM | 5484 | C | ARG | 242 | 115.039 | 59.088 | 27.120 | 1.00 | 26.11 | B | C |
| ATOM | 5485 | O | ARG | 242 | 114.450 | 58.796 | 26.076 | 1.00 | 29.12 | B | O |
| ATOM | 5486 | N | GLY | 243 | 115.919 | 60.079 | 27.194 | 1.00 | 41.48 | B | N |
| ATOM | 5487 | CA | GLY | 243 | 116.226 | 60.863 | 26.014 | 1.00 | 39.63 | B | C |
| ATOM | 5488 | C | GLY | 243 | 115.497 | 62.187 | 25.893 | 1.00 | 37.91 | B | C |
| ATOM | 5489 | O | GLY | 243 | 115.454 | 62.774 | 24.810 | 1.00 | 37.53 | B | O |
| ATOM | 5490 | N | ALA | 244 | 114.913 | 62.665 | 26.986 | 1.00 | 32.61 | B | N |
| ATOM | 5491 | CA | ALA | 244 | 114.209 | 63.941 | 26.939 | 1.00 | 30.61 | B | C |
| ATOM | 5492 | CB | ALA | 244 | 113.253 | 64.074 | 28.124 | 1.00 | 2.29 | B | C |
| ATOM | 5493 | C | ALA | 244 | 115.262 | 65.033 | 26.984 | 1.00 | 32.49 | B | C |
| ATOM | 5494 | O | ALA | 244 | 115.867 | 65.266 | 28.021 | 1.00 | 31.95 | B | O |
| ATOM | 5495 | N | ARG | 245 | 115.491 | 65.690 | 25.854 | 1.00 | 46.10 | B | N |
| ATOM | 5496 | CA | ARG | 245 | 116.482 | 66.760 | 25.768 | 1.00 | 46.93 | B | C |
| ATOM | 5497 | CB | ARG | 245 | 116.690 | 67.163 | 24.309 | 1.00 | 24.44 | B | C |
| ATOM | 5498 | CG | ARG | 245 | 117.460 | 66.126 | 23.503 | 1.00 | 26.91 | B | C |
| ATOM | 5499 | CD | ARG | 245 | 117.553 | 66.517 | 22.054 | 1.00 | 27.12 | B | C |
| ATOM | 5500 | NE | ARG | 245 | 116.229 | 66.560 | 21.457 | 1.00 | 21.54 | B | N |
| ATOM | 5501 | CZ | ARG | 245 | 115.999 | 66.826 | 20.179 | 1.00 | 21.36 | B | C |
| ATOM | 5502 | NH1 | ARG | 245 | 117.016 | 67.074 | 19.370 | 1.00 | 20.56 | B | N |
| ATOM | 5503 | NH2 | ARG | 245 | 114.756 | 66.834 | 19.708 | 1.00 | 18.65 | B | N |
| ATOM | 5504 | C | ARG | 245 | 116.101 | 67.986 | 26.585 | 1.00 | 45.30 | B | C |
| ATOM | 5505 | O | ARG | 245 | 114.975 | 68.480 | 26.496 | 1.00 | 41.41 | B | O |
| ATOM | 5506 | N | ARG | 246 | 117.051 | 68.476 | 27.376 | 1.00 | 48.54 | B | N |
| ATOM | 5507 | CA | ARG | 246 | 116.830 | 69.640 | 28.229 | 1.00 | 51.33 | B | C |
| ATOM | 5508 | CB | ARG | 246 | 118.096 | 69.982 | 29.012 | 1.00 | 83.48 | B | C |
| ATOM | 5509 | CG | ARG | 246 | 117.975 | 71.269 | 29.811 | 1.00 | 88.84 | B | C |
| ATOM | 5510 | CD | ARG | 246 | 119.295 | 71.647 | 30.449 | 1.00 | 94.76 | B | C |
| ATOM | 5511 | NE | ARG | 246 | 119.896 | 70.525 | 31.165 | 1.00 | 97.67 | B | N |
| ATOM | 5512 | CZ | ARG | 246 | 119.288 | 69.828 | 32.123 | 1.00 | 100.78 | B | C |
| ATOM | 5513 | NH1 | ARG | 246 | 118.047 | 70.132 | 32.491 | 1.00 | 100.47 | B | N |
| ATOM | 5514 | NH2 | ARG | 246 | 119.923 | 68.825 | 32.717 | 1.00 | 101.56 | B | N |
| ATOM | 5515 | C | ARG | 246 | 116.415 | 70.871 | 27.448 | 1.00 | 49.15 | B | C |
| ATOM | 5516 | O | ARG | 246 | 117.082 | 71.246 | 26.489 | 1.00 | 51.78 | B | O |
| ATOM | 5517 | N | GLY | 247 | 115.311 | 71.489 | 27.868 | 1.00 | 46.59 | B | N |
| ATOM | 5518 | CA | GLY | 247 | 114.825 | 72.705 | 27.233 | 1.00 | 49.17 | B | C |
| ATOM | 5519 | C | GLY | 247 | 114.381 | 72.609 | 25.787 | 1.00 | 49.24 | B | C |
| ATOM | 5520 | O | GLY | 247 | 114.531 | 73.560 | 25.019 | 1.00 | 52.20 | B | O |
| ATOM | 5521 | N | VAL | 248 | 113.836 | 71.462 | 25.407 | 1.00 | 57.57 | B | N |
| ATOM | 5522 | CA | VAL | 248 | 113.357 | 71.266 | 24.049 | 1.00 | 55.58 | B | C |
| ATOM | 5523 | CB | VAL | 248 | 114.012 | 70.043 | 23.407 | 1.00 | 22.85 | B | C |
| ATOM | 5524 | CG1 | VAL | 248 | 113.384 | 69.765 | 22.056 | 1.00 | 20.50 | B | C |
| ATOM | 5525 | CG2 | VAL | 248 | 115.499 | 70.287 | 23.266 | 1.00 | 14.62 | B | C |
| ATOM | 5526 | C | VAL | 248 | 111.855 | 71.056 | 24.094 | 1.00 | 58.60 | B | C |
| ATOM | 5527 | O | VAL | 248 | 111.343 | 70.403 | 25.005 | 1.00 | 62.65 | B | O |
| ATOM | 5528 | N | LYS | 249 | 111.147 | 71.607 | 23.115 | 1.00 | 37.34 | B | N |
| ATOM | 5529 | CA | LYS | 249 | 109.698 | 71.464 | 23.086 | 1.00 | 38.25 | B | C |
| ATOM | 5530 | CB | LYS | 249 | 109.115 | 72.122 | 21.832 | 1.00 | 57.29 | B | C |
| ATOM | 5531 | CG | LYS | 249 | 107.594 | 72.204 | 21.869 | 1.00 | 62.81 | B | C |
| ATOM | 5532 | CD | LYS | 249 | 107.103 | 72.892 | 23.155 | 1.00 | 63.88 | B | C |
| ATOM | 5533 | CE | LYS | 249 | 105.634 | 72.579 | 23.450 | 1.00 | 66.24 | B | C |
| ATOM | 5534 | NZ | LYS | 249 | 105.067 | 73.292 | 24.636 | 1.00 | 69.06 | B | N |
| ATOM | 5535 | C | LYS | 249 | 109.244 | 69.998 | 23.173 | 1.00 | 36.91 | B | C |
| ATOM | 5536 | O | LYS | 249 | 109.790 | 69.112 | 22.505 | 1.00 | 36.73 | B | O |
| ATOM | 5537 | N | LYS | 250 | 108.238 | 69.755 | 24.009 | 1.00 | 33.42 | B | N |
| ATOM | 5538 | CA | LYS | 250 | 107.706 | 68.419 | 24.208 | 1.00 | 33.07 | B | C |
| ATOM | 5539 | CB | LYS | 250 | 107.603 | 68.147 | 25.710 | 1.00 | 46.37 | B | C |
| ATOM | 5540 | CG | LYS | 250 | 108.970 | 68.151 | 26.374 | 1.00 | 44.97 | B | C |
| ATOM | 5541 | CD | LYS | 250 | 108.918 | 68.429 | 27.872 | 1.00 | 46.52 | B | C |
| ATOM | 5542 | CE | LYS | 250 | 108.389 | 67.256 | 28.686 | 1.00 | 45.68 | B | C |
| ATOM | 5543 | NZ | LYS | 250 | 108.578 | 67.474 | 30.157 | 1.00 | 47.50 | B | N |
| ATOM | 5544 | C | LYS | 250 | 106.355 | 68.263 | 23.506 | 1.00 | 32.42 | B | C |
| ATOM | 5545 | O | LYS | 250 | 105.380 | 68.931 | 23.842 | 1.00 | 32.10 | B | O |
| ATOM | 5546 | N | VAL | 251 | 106.320 | 67.372 | 22.519 | 1.00 | 37.83 | B | N |
| ATOM | 5547 | CA | VAL | 251 | 105.121 | 67.115 | 21.730 | 1.00 | 37.74 | B | C |
| ATOM | 5548 | CB | VAL | 251 | 105.403 | 67.373 | 20.248 | 1.00 | 28.71 | B | C |

Fig. 19: A-77

| ATOM | 5549 | CG1 | VAL | 251 | 104.180 | 67.017 | 19.410 | 1.00 | 26.86 | B | C |
|------|------|-----|-----|-----|---------|--------|--------|------|-------|---|---|
| ATOM | 5550 | CG2 | VAL | 251 | 105.819 | 68.822 | 20.057 | 1.00 | 29.92 | B | C |
| ATOM | 5551 | C   | VAL | 251 | 104.591 | 65.689 | 21.866 | 1.00 | 36.22 | B | C |
| ATOM | 5552 | O   | VAL | 251 | 105.339 | 64.715 | 21.714 | 1.00 | 32.22 | B | O |
| ATOM | 5553 | N   | MET | 252 | 103.289 | 65.572 | 22.122 | 1.00 | 42.57 | B | N |
| ATOM | 5554 | CA  | MET | 252 | 102.651 | 64.269 | 22.275 | 1.00 | 43.55 | B | C |
| ATOM | 5555 | CB  | MET | 252 | 102.013 | 64.160 | 23.660 | 1.00 | 27.32 | B | C |
| ATOM | 5556 | CG  | MET | 252 | 101.440 | 62.787 | 23.998 | 1.00 | 26.01 | B | C |
| ATOM | 5557 | SD  | MET | 252 | 100.740 | 62.725 | 25.675 | 1.00 | 30.06 | B | S |
| ATOM | 5558 | CE  | MET | 252 | 102.222 | 63.011 | 26.691 | 1.00 | 21.37 | B | C |
| ATOM | 5559 | C   | MET | 252 | 101.583 | 64.060 | 21.217 | 1.00 | 42.57 | B | C |
| ATOM | 5560 | O   | MET | 252 | 100.761 | 64.937 | 20.982 | 1.00 | 44.94 | B | O |
| ATOM | 5561 | N   | VAL | 253 | 101.604 | 62.900 | 20.573 | 1.00 | 21.89 | B | N |
| ATOM | 5562 | CA  | VAL | 253 | 100.607 | 62.580 | 19.558 | 1.00 | 23.04 | B | C |
| ATOM | 5563 | CB  | VAL | 253 | 101.267 | 62.281 | 18.187 | 1.00 | 9.79  | B | C |
| ATOM | 5564 | CG1 | VAL | 253 | 100.191 | 61.900 | 17.168 | 1.00 | 11.21 | B | C |
| ATOM | 5565 | CG2 | VAL | 253 | 102.044 | 63.490 | 17.701 | 1.00 | 9.43  | B | C |
| ATOM | 5566 | C   | VAL | 253 | 99.819  | 61.353 | 20.015 | 1.00 | 22.61 | B | C |
| ATOM | 5567 | O   | VAL | 253 | 100.383 | 60.276 | 20.161 | 1.00 | 21.05 | B | O |
| ATOM | 5568 | N   | ILE | 254 | 98.522  | 61.516 | 20.252 | 1.00 | 29.50 | B | N |
| ATOM | 5569 | CA  | ILE | 254 | 97.692  | 60.403 | 20.701 | 1.00 | 26.40 | B | C |
| ATOM | 5570 | CB  | ILE | 254 | 96.820  | 60.777 | 21.925 | 1.00 | 25.01 | B | C |
| ATOM | 5571 | CG2 | ILE | 254 | 96.017  | 59.564 | 22.369 | 1.00 | 21.48 | B | C |
| ATOM | 5572 | CG1 | ILE | 254 | 97.697  | 61.256 | 23.089 | 1.00 | 23.59 | B | C |
| ATOM | 5573 | CD1 | ILE | 254 | 98.231  | 62.661 | 22.921 | 1.00 | 23.22 | B | C |
| ATOM | 5574 | C   | ILE | 254 | 96.757  | 59.905 | 19.611 | 1.00 | 24.49 | B | C |
| ATOM | 5575 | O   | ILE | 254 | 96.163  | 60.692 | 18.876 | 1.00 | 26.36 | B | O |
| ATOM | 5576 | N   | VAL | 255 | 96.628  | 58.587 | 19.516 | 1.00 | 26.63 | B | N |
| ATOM | 5577 | CA  | VAL | 255 | 95.758  | 57.981 | 18.521 | 1.00 | 25.37 | B | C |
| ATOM | 5578 | CB  | VAL | 255 | 96.553  | 57.259 | 17.428 | 1.00 | 15.78 | B | C |
| ATOM | 5579 | CG1 | VAL | 255 | 95.672  | 57.064 | 16.198 | 1.00 | 14.23 | B | C |
| ATOM | 5580 | CG2 | VAL | 255 | 97.805  | 58.036 | 17.089 | 1.00 | 16.42 | B | C |
| ATOM | 5581 | C   | VAL | 255 | 94.907  | 56.947 | 19.221 | 1.00 | 23.12 | B | C |
| ATOM | 5582 | O   | VAL | 255 | 95.444  | 56.089 | 19.916 | 1.00 | 25.12 | B | O |
| ATOM | 5583 | N   | THR | 256 | 93.591  | 57.012 | 19.036 | 1.00 | 8.41  | B | N |
| ATOM | 5584 | CA  | THR | 256 | 92.709  | 56.052 | 19.689 | 1.00 | 8.83  | B | C |
| ATOM | 5585 | CB  | THR | 256 | 92.529  | 56.416 | 21.189 | 1.00 | 19.33 | B | C |
| ATOM | 5586 | OG1 | THR | 256 | 91.459  | 55.645 | 21.755 | 1.00 | 15.37 | B | O |
| ATOM | 5587 | CG2 | THR | 256 | 92.255  | 57.908 | 21.344 | 1.00 | 18.18 | B | C |
| ATOM | 5588 | C   | THR | 256 | 91.353  | 55.955 | 18.992 | 1.00 | 12.31 | B | C |
| ATOM | 5589 | O   | THR | 256 | 90.941  | 56.881 | 18.308 | 1.00 | 8.47  | B | O |
| ATOM | 5590 | N   | ASP | 257 | 90.673  | 54.824 | 19.162 | 1.00 | 17.26 | B | N |
| ATOM | 5591 | CA  | ASP | 257 | 89.375  | 54.601 | 18.530 | 1.00 | 17.64 | B | C |
| ATOM | 5592 | CB  | ASP | 257 | 89.491  | 53.474 | 17.491 | 1.00 | 29.20 | B | C |
| ATOM | 5593 | CG  | ASP | 257 | 89.534  | 52.074 | 18.122 | 1.00 | 34.56 | B | C |
| ATOM | 5594 | OD1 | ASP | 257 | 89.894  | 51.957 | 19.313 | 1.00 | 35.03 | B | O |
| ATOM | 5595 | OD2 | ASP | 257 | 89.220  | 51.084 | 17.421 | 1.00 | 39.83 | B | O |
| ATOM | 5596 | C   | ASP | 257 | 88.267  | 54.259 | 19.535 | 1.00 | 14.23 | B | C |
| ATOM | 5597 | O   | ASP | 257 | 87.243  | 53.660 | 19.169 | 1.00 | 13.47 | B | O |
| ATOM | 5598 | N   | GLY | 258 | 88.462  | 54.634 | 20.798 | 1.00 | 26.33 | B | N |
| ATOM | 5599 | CA  | GLY | 258 | 87.450  | 54.331 | 21.793 | 1.00 | 28.75 | B | C |
| ATOM | 5600 | C   | GLY | 258 | 87.546  | 55.109 | 23.088 | 1.00 | 32.57 | B | C |
| ATOM | 5601 | O   | GLY | 258 | 88.615  | 55.601 | 23.476 | 1.00 | 28.29 | B | O |
| ATOM | 5602 | N   | GLU | 259 | 86.404  | 55.231 | 23.755 | 1.00 | 39.52 | B | N |
| ATOM | 5603 | CA  | GLU | 259 | 86.335  | 55.931 | 25.025 | 1.00 | 41.40 | B | C |
| ATOM | 5604 | CB  | GLU | 259 | 84.905  | 55.925 | 25.555 | 1.00 | 36.52 | B | C |
| ATOM | 5605 | CG  | GLU | 259 | 83.950  | 56.783 | 24.749 | 1.00 | 44.30 | B | C |
| ATOM | 5606 | CD  | GLU | 259 | 82.509  | 56.415 | 24.994 | 1.00 | 48.11 | B | C |
| ATOM | 5607 | OE1 | GLU | 259 | 81.625  | 57.175 | 24.546 | 1.00 | 54.86 | B | O |
| ATOM | 5608 | OE2 | GLU | 259 | 82.262  | 55.360 | 25.626 | 1.00 | 48.13 | B | O |
| ATOM | 5609 | C   | GLU | 259 | 87.240  | 55.210 | 26.003 | 1.00 | 40.26 | B | C |
| ATOM | 5610 | O   | GLU | 259 | 87.125  | 53.999 | 26.194 | 1.00 | 37.43 | B | O |
| ATOM | 5611 | N   | SER | 260 | 88.155  | 55.953 | 26.610 | 1.00 | 34.06 | B | N |
| ATOM | 5612 | CA  | SER | 260 | 89.067  | 55.369 | 27.576 | 1.00 | 37.22 | B | C |
| ATOM | 5613 | CB  | SER | 260 | 90.041  | 56.432 | 28.083 | 1.00 | 50.00 | B | C |
| ATOM | 5614 | OG  | SER | 260 | 89.341  | 57.516 | 28.666 | 1.00 | 50.51 | B | O |
| ATOM | 5615 | C   | SER | 260 | 88.261  | 54.814 | 28.740 | 1.00 | 37.12 | B | C |
| ATOM | 5616 | O   | SER | 260 | 87.177  | 55.300 | 29.043 | 1.00 | 33.15 | B | O |
| ATOM | 5617 | N   | HIS | 261 | 88.781  | 53.787 | 29.392 | 1.00 | 36.47 | B | N |
| ATOM | 5618 | CA  | HIS | 261 | 88.084  | 53.212 | 30.527 | 1.00 | 40.82 | B | C |
| ATOM | 5619 | CB  | HIS | 261 | 88.509  | 51.755 | 30.728 | 1.00 | 21.13 | B | C |
| ATOM | 5620 | CG  | HIS | 261 | 87.908  | 50.809 | 29.732 | 1.00 | 24.33 | B | C |
| ATOM | 5621 | CD2 | HIS | 261 | 88.345  | 50.398 | 28.519 | 1.00 | 23.44 | B | C |

Fig. 19: A-78

| ATOM | 5622 | ND1 | HIS | 261 | 86.688 | 50.197 | 29.925 | 1.00 | 25.81 | B | N |
|---|---|---|---|---|---|---|---|---|---|---|---|
| ATOM | 5623 | CE1 | HIS | 261 | 86.400 | 49.448 | 28.876 | 1.00 | 25.88 | B | C |
| ATOM | 5624 | NE2 | HIS | 261 | 87.390 | 49.554 | 28.009 | 1.00 | 23.15 | B | N |
| ATOM | 5625 | C | HIS | 261 | 88.394 | 54.045 | 31.761 | 1.00 | 41.88 | B | C |
| ATOM | 5626 | O | HIS | 261 | 87.711 | 53.940 | 32.779 | 1.00 | 39.10 | B | O |
| ATOM | 5627 | N | ASP | 262 | 89.425 | 54.880 | 31.657 | 1.00 | 49.36 | B | N |
| ATOM | 5628 | CA | ASP | 262 | 89.825 | 55.758 | 32.753 | 1.00 | 54.33 | B | C |
| ATOM | 5629 | CB | ASP | 262 | 91.343 | 55.676 | 32.985 | 1.00 | 33.92 | B | C |
| ATOM | 5630 | CG | ASP | 262 | 92.124 | 55.281 | 31.733 | 1.00 | 33.92 | B | C |
| ATOM | 5631 | OD1 | ASP | 262 | 91.724 | 55.659 | 30.611 | 1.00 | 33.92 | B | O |
| ATOM | 5632 | OD2 | ASP | 262 | 93.162 | 54.600 | 31.875 | 1.00 | 33.92 | B | O |
| ATOM | 5633 | C | ASP | 262 | 89.418 | 57.218 | 32.507 | 1.00 | 54.38 | B | C |
| ATOM | 5634 | O | ASP | 262 | 90.221 | 58.134 | 32.700 | 1.00 | 54.24 | B | O |
| ATOM | 5635 | N | ASN | 263 | 88.171 | 57.424 | 32.085 | 1.00 | 68.10 | B | N |
| ATOM | 5636 | CA | ASN | 263 | 87.646 | 58.765 | 31.813 | 1.00 | 69.27 | B | C |
| ATOM | 5637 | CB | ASN | 263 | 86.123 | 58.734 | 31.630 | 1.00 | 82.52 | B | C |
| ATOM | 5638 | CG | ASN | 263 | 85.660 | 57.631 | 30.707 | 1.00 | 86.89 | B | C |
| ATOM | 5639 | OD1 | ASN | 263 | 85.981 | 57.626 | 29.519 | 1.00 | 88.39 | B | O |
| ATOM | 5640 | ND2 | ASN | 263 | 84.893 | 56.686 | 31.249 | 1.00 | 81.39 | B | N |
| ATOM | 5641 | C | ASN | 263 | 87.948 | 59.670 | 32.998 | 1.00 | 69.91 | B | C |
| ATOM | 5642 | O | ASN | 263 | 88.360 | 60.822 | 32.841 | 1.00 | 68.81 | B | O |
| ATOM | 5643 | N | TYR | 264 | 87.732 | 59.122 | 34.187 | 1.00 | 59.82 | B | N |
| ATOM | 5644 | CA | TYR | 264 | 87.925 | 59.837 | 35.432 | 1.00 | 57.67 | B | C |
| ATOM | 5645 | CB | TYR | 264 | 87.914 | 58.853 | 36.590 | 1.00 | 108.49 | B | C |
| ATOM | 5646 | CG | TYR | 264 | 86.626 | 58.083 | 36.660 | 1.00 | 108.49 | B | C |
| ATOM | 5647 | CD1 | TYR | 264 | 86.284 | 57.171 | 35.663 | 1.00 | 108.49 | B | C |
| ATOM | 5648 | CE1 | TYR | 264 | 85.074 | 56.490 | 35.698 | 1.00 | 108.49 | B | C |
| ATOM | 5649 | CD2 | TYR | 264 | 85.723 | 58.292 | 37.699 | 1.00 | 108.49 | B | C |
| ATOM | 5650 | CE2 | TYR | 264 | 84.509 | 57.615 | 37.744 | 1.00 | 108.49 | B | C |
| ATOM | 5651 | CZ | TYR | 264 | 84.190 | 56.717 | 36.741 | 1.00 | 108.49 | B | C |
| ATOM | 5652 | OH | TYR | 264 | 82.987 | 56.052 | 36.783 | 1.00 | 108.49 | B | O |
| ATOM | 5653 | C | TYR | 264 | 89.156 | 60.710 | 35.512 | 1.00 | 56.32 | B | C |
| ATOM | 5654 | O | TYR | 264 | 89.047 | 61.935 | 35.549 | 1.00 | 53.45 | B | O |
| ATOM | 5655 | N | ARG | 265 | 90.331 | 60.098 | 35.527 | 1.00 | 41.74 | B | N |
| ATOM | 5656 | CA | ARG | 265 | 91.544 | 60.892 | 35.641 | 1.00 | 40.64 | B | C |
| ATOM | 5657 | CB | ARG | 265 | 92.610 | 60.127 | 36.427 | 1.00 | 58.89 | B | C |
| ATOM | 5658 | CG | ARG | 265 | 93.152 | 58.875 | 35.779 | 1.00 | 59.34 | B | C |
| ATOM | 5659 | CD | ARG | 265 | 94.501 | 58.614 | 36.400 | 1.00 | 61.17 | B | C |
| ATOM | 5660 | NE | ARG | 265 | 95.183 | 57.456 | 35.851 | 1.00 | 66.56 | B | N |
| ATOM | 5661 | CZ | ARG | 265 | 96.506 | 57.349 | 35.784 | 1.00 | 66.73 | B | C |
| ATOM | 5662 | NH1 | ARG | 265 | 97.281 | 58.334 | 36.227 | 1.00 | 71.36 | B | N |
| ATOM | 5663 | NH2 | ARG | 265 | 97.059 | 56.256 | 35.280 | 1.00 | 70.70 | B | N |
| ATOM | 5664 | C | ARG | 265 | 92.147 | 61.423 | 34.347 | 1.00 | 39.89 | B | C |
| ATOM | 5665 | O | ARG | 265 | 93.311 | 61.833 | 34.319 | 1.00 | 41.20 | B | O |
| ATOM | 5666 | N | LEU | 266 | 91.360 | 61.433 | 33.278 | 1.00 | 45.12 | B | N |
| ATOM | 5667 | CA | LEU | 266 | 91.855 | 61.947 | 32.007 | 1.00 | 46.69 | B | C |
| ATOM | 5668 | CB | LEU | 266 | 90.885 | 61.580 | 30.886 | 1.00 | 30.69 | B | C |
| ATOM | 5669 | CG | LEU | 266 | 91.357 | 61.919 | 29.480 | 1.00 | 29.90 | B | C |
| ATOM | 5670 | CD1 | LEU | 266 | 92.760 | 61.369 | 29.232 | 1.00 | 32.24 | B | C |
| ATOM | 5671 | CD2 | LEU | 266 | 90.347 | 61.344 | 28.500 | 1.00 | 26.36 | B | C |
| ATOM | 5672 | C | LEU | 266 | 91.989 | 63.466 | 32.139 | 1.00 | 49.51 | B | C |
| ATOM | 5673 | O | LEU | 266 | 92.861 | 64.093 | 31.541 | 1.00 | 49.39 | B | O |
| ATOM | 5674 | N | LYS | 267 | 91.107 | 64.041 | 32.945 | 1.00 | 50.12 | B | N |
| ATOM | 5675 | CA | LYS | 267 | 91.097 | 65.473 | 33.206 | 1.00 | 52.43 | B | C |
| ATOM | 5676 | CB | LYS | 267 | 89.927 | 65.807 | 34.136 | 1.00 | 99.33 | B | C |
| ATOM | 5677 | CG | LYS | 267 | 89.719 | 67.279 | 34.431 | 1.00 | 99.33 | B | C |
| ATOM | 5678 | CD | LYS | 267 | 88.623 | 67.863 | 33.558 | 1.00 | 99.33 | B | C |
| ATOM | 5679 | CE | LYS | 267 | 88.211 | 69.242 | 34.049 | 1.00 | 99.33 | B | C |
| ATOM | 5680 | NZ | LYS | 267 | 87.044 | 69.788 | 33.293 | 1.00 | 99.33 | B | N |
| ATOM | 5681 | C | LYS | 267 | 92.417 | 65.835 | 33.882 | 1.00 | 51.92 | B | C |
| ATOM | 5682 | O | LYS | 267 | 93.126 | 66.738 | 33.440 | 1.00 | 51.44 | B | O |
| ATOM | 5683 | N | GLN | 268 | 92.736 | 65.115 | 34.956 | 1.00 | 36.69 | B | N |
| ATOM | 5684 | CA | GLN | 268 | 93.968 | 65.338 | 35.709 | 1.00 | 35.66 | B | C |
| ATOM | 5685 | CB | GLN | 268 | 94.098 | 64.324 | 36.841 | 1.00 | 127.61 | B | C |
| ATOM | 5686 | CG | GLN | 268 | 93.032 | 64.387 | 37.906 | 1.00 | 127.61 | B | C |
| ATOM | 5687 | CD | GLN | 268 | 93.203 | 63.286 | 38.941 | 1.00 | 127.61 | B | C |
| ATOM | 5688 | OE1 | GLN | 268 | 92.487 | 63.236 | 39.939 | 1.00 | 127.61 | B | O |
| ATOM | 5689 | NE2 | GLN | 268 | 94.158 | 62.392 | 38.702 | 1.00 | 127.61 | B | N |
| ATOM | 5690 | C | GLN | 268 | 95.203 | 65.210 | 34.824 | 1.00 | 31.41 | B | C |
| ATOM | 5691 | O | GLN | 268 | 96.044 | 66.108 | 34.788 | 1.00 | 32.59 | B | O |
| ATOM | 5692 | N | VAL | 269 | 95.308 | 64.085 | 34.114 | 1.00 | 29.89 | B | N |
| ATOM | 5693 | CA | VAL | 269 | 96.457 | 63.831 | 33.256 | 1.00 | 27.64 | B | C |
| ATOM | 5694 | CB | VAL | 269 | 96.321 | 62.467 | 32.516 | 1.00 | 26.10 | B | C |

Fig. 19: A-79

| ATOM | 5695 | CG1 | VAL | 269 | 97.551 | 62.215 | 31.663 | 1.00 | 21.75 | B | C |
| --- | --- | --- | --- | --- | --- | --- | --- | --- | --- | --- | --- |
| ATOM | 5696 | CG2 | VAL | 269 | 96.161 | 61.338 | 33.520 | 1.00 | 23.96 | B | C |
| ATOM | 5697 | C | VAL | 269 | 96.683 | 64.956 | 32.246 | 1.00 | 27.23 | B | C |
| ATOM | 5698 | O | VAL | 269 | 97.784 | 65.502 | 32.174 | 1.00 | 30.07 | B | O |
| ATOM | 5699 | N | ILE | 270 | 95.658 | 65.306 | 31.471 | 1.00 | 16.50 | B | N |
| ATOM | 5700 | CA | ILE | 270 | 95.797 | 66.379 | 30.487 | 1.00 | 17.12 | B | C |
| ATOM | 5701 | CB | ILE | 270 | 94.459 | 66.696 | 29.777 | 1.00 | 35.19 | B | C |
| ATOM | 5702 | CG2 | ILE | 270 | 94.594 | 67.973 | 28.937 | 1.00 | 29.81 | B | C |
| ATOM | 5703 | CG1 | ILE | 270 | 94.060 | 65.520 | 28.885 | 1.00 | 32.75 | B | C |
| ATOM | 5704 | CD1 | ILE | 270 | 95.062 | 65.231 | 27.778 | 1.00 | 33.87 | B | C |
| ATOM | 5705 | C | ILE | 270 | 96.275 | 67.631 | 31.210 | 1.00 | 20.99 | B | C |
| ATOM | 5706 | O | ILE | 270 | 97.060 | 68.413 | 30.670 | 1.00 | 19.77 | B | O |
| ATOM | 5707 | N | GLN | 271 | 95.802 | 67.796 | 32.444 | 1.00 | 57.05 | B | N |
| ATOM | 5708 | CA | GLN | 271 | 96.169 | 68.935 | 33.269 | 1.00 | 59.11 | B | C |
| ATOM | 5709 | CB | GLN | 271 | 95.440 | 68.865 | 34.610 | 1.00 | 85.78 | B | C |
| ATOM | 5710 | CG | GLN | 271 | 95.525 | 70.134 | 35.439 | 1.00 | 87.68 | B | C |
| ATOM | 5711 | CD | GLN | 271 | 94.967 | 71.338 | 34.708 | 1.00 | 90.18 | B | C |
| ATOM | 5712 | OE1 | GLN | 271 | 95.614 | 71.898 | 33.822 | 1.00 | 90.51 | B | O |
| ATOM | 5713 | NE2 | GLN | 271 | 93.752 | 71.735 | 35.065 | 1.00 | 91.75 | B | N |
| ATOM | 5714 | C | GLN | 271 | 97.673 | 68.932 | 33.495 | 1.00 | 61.57 | B | C |
| ATOM | 5715 | O | GLN | 271 | 98.359 | 69.896 | 33.172 | 1.00 | 64.26 | B | O |
| ATOM | 5716 | N | ASP | 272 | 98.184 | 67.837 | 34.042 | 1.00 | 39.03 | B | N |
| ATOM | 5717 | CA | ASP | 272 | 99.612 | 67.716 | 34.304 | 1.00 | 40.31 | B | C |
| ATOM | 5718 | CB | ASP | 272 | 99.922 | 66.338 | 34.890 | 1.00 | 54.12 | B | C |
| ATOM | 5719 | CG | ASP | 272 | 99.275 | 66.122 | 36.255 | 1.00 | 55.74 | B | C |
| ATOM | 5720 | OD1 | ASP | 272 | 99.087 | 64.949 | 36.647 | 1.00 | 57.81 | B | O |
| ATOM | 5721 | OD2 | ASP | 272 | 98.961 | 67.123 | 36.939 | 1.00 | 62.00 | B | O |
| ATOM | 5722 | C | ASP | 272 | 100.420 | 67.937 | 33.033 | 1.00 | 41.11 | B | C |
| ATOM | 5723 | O | ASP | 272 | 101.550 | 68.418 | 33.083 | 1.00 | 38.56 | B | O |
| ATOM | 5724 | N | CYS | 273 | 99.843 | 67.587 | 31.891 | 1.00 | 49.56 | B | N |
| ATOM | 5725 | CA | CYS | 273 | 100.538 | 67.776 | 30.629 | 1.00 | 47.99 | B | C |
| ATOM | 5726 | CB | CYS | 273 | 99.824 | 67.028 | 29.503 | 1.00 | 39.07 | B | C |
| ATOM | 5727 | SG | CYS | 273 | 100.050 | 65.235 | 29.538 | 1.00 | 37.17 | B | S |
| ATOM | 5728 | C | CYS | 273 | 100.628 | 69.257 | 30.291 | 1.00 | 48.36 | B | C |
| ATOM | 5729 | O | CYS | 273 | 101.602 | 69.695 | 29.686 | 1.00 | 42.67 | B | O |
| ATOM | 5730 | N | GLU | 274 | 99.609 | 70.022 | 30.682 | 1.00 | 40.12 | B | N |
| ATOM | 5731 | CA | GLU | 274 | 99.584 | 71.467 | 30.425 | 1.00 | 42.92 | B | C |
| ATOM | 5732 | CB | GLU | 274 | 98.187 | 72.055 | 30.703 | 1.00 | 40.77 | B | C |
| ATOM | 5733 | CG | GLU | 274 | 97.285 | 72.151 | 29.470 | 1.00 | 45.89 | B | C |
| ATOM | 5734 | CD | GLU | 274 | 97.830 | 73.108 | 28.405 | 1.00 | 51.00 | B | C |
| ATOM | 5735 | OE1 | GLU | 274 | 97.269 | 73.155 | 27.284 | 1.00 | 52.87 | B | O |
| ATOM | 5736 | OE2 | GLU | 274 | 98.816 | 73.818 | 28.691 | 1.00 | 55.56 | B | O |
| ATOM | 5737 | C | GLU | 274 | 100.615 | 72.172 | 31.293 | 1.00 | 45.34 | B | C |
| ATOM | 5738 | O | GLU | 274 | 101.309 | 73.081 | 30.842 | 1.00 | 47.54 | B | O |
| ATOM | 5739 | N | ASP | 275 | 100.711 | 71.735 | 32.542 | 1.00 | 77.40 | B | N |
| ATOM | 5740 | CA | ASP | 275 | 101.656 | 72.302 | 33.495 | 1.00 | 76.14 | B | C |
| ATOM | 5741 | CB | ASP | 275 | 101.456 | 71.665 | 34.871 | 1.00 | 72.98 | B | C |
| ATOM | 5742 | CG | ASP | 275 | 100.070 | 71.900 | 35.432 | 1.00 | 74.25 | B | C |
| ATOM | 5743 | OD1 | ASP | 275 | 99.160 | 72.258 | 34.656 | 1.00 | 77.95 | B | O |
| ATOM | 5744 | OD2 | ASP | 275 | 99.887 | 71.712 | 36.652 | 1.00 | 75.91 | B | O |
| ATOM | 5745 | C | ASP | 275 | 103.093 | 72.050 | 33.046 | 1.00 | 75.13 | B | C |
| ATOM | 5746 | O | ASP | 275 | 104.021 | 72.707 | 33.512 | 1.00 | 70.68 | B | O |
| ATOM | 5747 | N | GLU | 276 | 103.275 | 71.091 | 32.146 | 1.00 | 44.46 | B | N |
| ATOM | 5748 | CA | GLU | 276 | 104.606 | 70.757 | 31.668 | 1.00 | 44.11 | B | C |
| ATOM | 5749 | CB | GLU | 276 | 104.846 | 69.258 | 31.847 | 1.00 | 54.99 | B | C |
| ATOM | 5750 | CG | GLU | 276 | 104.556 | 68.799 | 33.266 | 1.00 | 54.86 | B | C |
| ATOM | 5751 | CD | GLU | 276 | 105.018 | 67.383 | 33.547 | 1.00 | 55.96 | B | C |
| ATOM | 5752 | OE1 | GLU | 276 | 104.861 | 66.934 | 34.705 | 1.00 | 56.67 | B | O |
| ATOM | 5753 | OE2 | GLU | 276 | 105.538 | 66.724 | 32.616 | 1.00 | 52.90 | B | O |
| ATOM | 5754 | C | GLU | 276 | 104.843 | 71.175 | 30.222 | 1.00 | 42.94 | B | C |
| ATOM | 5755 | O | GLU | 276 | 105.823 | 70.759 | 29.597 | 1.00 | 44.05 | B | O |
| ATOM | 5756 | N | ASN | 277 | 103.938 | 71.997 | 29.700 | 1.00 | 43.81 | B | N |
| ATOM | 5757 | CA | ASN | 277 | 104.043 | 72.505 | 28.338 | 1.00 | 43.78 | B | C |
| ATOM | 5758 | CB | ASN | 277 | 105.229 | 73.464 | 28.233 | 1.00 | 55.27 | B | C |
| ATOM | 5759 | CG | ASN | 277 | 105.219 | 74.514 | 29.311 | 1.00 | 60.19 | B | C |
| ATOM | 5760 | OD1 | ASN | 277 | 104.288 | 75.315 | 29.403 | 1.00 | 60.01 | B | O |
| ATOM | 5761 | ND2 | ASN | 277 | 106.256 | 74.518 | 30.145 | 1.00 | 59.15 | B | N |
| ATOM | 5762 | C | ASN | 277 | 104.188 | 71.428 | 27.261 | 1.00 | 40.13 | B | C |
| ATOM | 5763 | O | ASN | 277 | 105.083 | 71.515 | 26.416 | 1.00 | 41.11 | B | O |
| ATOM | 5764 | N | ILE | 278 | 103.309 | 70.427 | 27.278 | 1.00 | 17.87 | B | N |
| ATOM | 5765 | CA | ILE | 278 | 103.366 | 69.361 | 26.289 | 1.00 | 18.32 | B | C |
| ATOM | 5766 | CB | ILE | 278 | 103.110 | 67.975 | 26.928 | 1.00 | 22.06 | B | C |
| ATOM | 5767 | CG2 | ILE | 278 | 103.120 | 66.897 | 25.854 | 1.00 | 23.45 | B | C |

Fig. 19: A-80

```
ATOM   5768  CG1 ILE   278     104.172  67.675  27.987  1.00  19.51  B  C
ATOM   5769  CD1 ILE   278     103.941  66.373  28.707  1.00  21.79  B  C
ATOM   5770  C   ILE   278     102.316  69.579  25.213  1.00  18.92  B  C
ATOM   5771  O   ILE   278     101.132  69.378  25.463  1.00  19.26  B  O
ATOM   5772  N   GLN   279     102.749  69.994  24.024  1.00  49.21  B  N
ATOM   5773  CA  GLN   279     101.831  70.198  22.908  1.00  48.81  B  C
ATOM   5774  CB  GLN   279     102.579  70.633  21.652  1.00  63.04  B  C
ATOM   5775  CG  GLN   279     103.187  71.998  21.752  1.00  68.82  B  C
ATOM   5776  CD  GLN   279     102.173  73.043  22.155  1.00  72.74  B  C
ATOM   5777  OE1 GLN   279     101.233  73.328  21.410  1.00  66.98  B  O
ATOM   5778  NE2 GLN   279     102.352  73.618  23.345  1.00  72.33  B  N
ATOM   5779  C   GLN   279     101.175  68.864  22.640  1.00  46.68  B  C
ATOM   5780  O   GLN   279     101.861  67.859  22.467  1.00  43.60  B  O
ATOM   5781  N   ARG   280      99.851  68.848  22.595  1.00  28.30  B  N
ATOM   5782  CA  ARG   280      99.138  67.605  22.363  1.00  29.82  B  C
ATOM   5783  CB  ARG   280      98.276  67.277  23.575  1.00  38.67  B  C
ATOM   5784  CG  ARG   280      99.036  67.225  24.874  1.00  37.30  B  C
ATOM   5785  CD  ARG   280      98.068  67.012  26.018  1.00  36.97  B  C
ATOM   5786  NE  ARG   280      97.070  68.075  26.073  1.00  34.02  B  N
ATOM   5787  CZ  ARG   280      97.288  69.298  26.557  1.00  37.93  B  C
ATOM   5788  NH1 ARG   280      98.483  69.627  27.041  1.00  40.85  B  N
ATOM   5789  NH2 ARG   280      96.307  70.192  26.554  1.00  42.87  B  N
ATOM   5790  C   ARG   280      98.264  67.579  21.111  1.00  29.48  B  C
ATOM   5791  O   ARG   280      97.406  68.437  20.912  1.00  29.21  B  O
ATOM   5792  N   PHE   281      98.501  66.582  20.266  1.00  31.71  B  N
ATOM   5793  CA  PHE   281      97.713  66.392  19.066  1.00  33.70  B  C
ATOM   5794  CB  PHE   281      98.594  66.335  17.826  1.00  18.70  B  C
ATOM   5795  CG  PHE   281      99.324  67.604  17.555  1.00  21.73  B  C
ATOM   5796  CD1 PHE   281     100.438  67.950  18.308  1.00  25.58  B  C
ATOM   5797  CD2 PHE   281      98.887  68.469  16.551  1.00  23.46  B  C
ATOM   5798  CE1 PHE   281     101.111  69.136  18.070  1.00  25.64  B  C
ATOM   5799  CE2 PHE   281      99.554  69.665  16.301  1.00  21.19  B  C
ATOM   5800  CZ  PHE   281     100.669  69.999  17.064  1.00  22.62  B  C
ATOM   5801  C   PHE   281      97.025  65.060  19.266  1.00  34.41  B  C
ATOM   5802  O   PHE   281      97.677  64.053  19.509  1.00  36.78  B  O
ATOM   5803  N   SER   282      95.704  65.061  19.202  1.00  16.00  B  N
ATOM   5804  CA  SER   282      94.962  63.835  19.374  1.00  17.85  B  C
ATOM   5805  CB  SER   282      93.973  63.973  20.528  1.00  14.79  B  C
ATOM   5806  OG  SER   282      93.036  64.997  20.286  1.00  11.34  B  O
ATOM   5807  C   SER   282      94.231  63.507  18.093  1.00  19.73  B  C
ATOM   5808  O   SER   282      93.909  64.389  17.306  1.00  23.59  B  O
ATOM   5809  N   ILE   283      93.986  62.224  17.881  1.00  19.27  B  N
ATOM   5810  CA  ILE   283      93.288  61.779  16.693  1.00  17.19  B  C
ATOM   5811  CB  ILE   283      94.245  61.146  15.697  1.00   9.92  B  C
ATOM   5812  CG2 ILE   283      93.501  60.806  14.425  1.00  10.73  B  C
ATOM   5813  CG1 ILE   283      95.377  62.118  15.383  1.00   6.39  B  C
ATOM   5814  CD1 ILE   283      96.630  61.446  14.894  1.00   9.95  B  C
ATOM   5815  C   ILE   283      92.278  60.748  17.127  1.00  16.26  B  C
ATOM   5816  O   ILE   283      92.574  59.886  17.947  1.00  16.12  B  O
ATOM   5817  N   ALA   284      91.078  60.836  16.584  1.00  18.66  B  N
ATOM   5818  CA  ALA   284      90.050  59.896  16.955  1.00  18.68  B  C
ATOM   5819  CB  ALA   284      88.903  60.627  17.622  1.00  45.12  B  C
ATOM   5820  C   ALA   284      89.542  59.107  15.759  1.00  16.81  B  C
ATOM   5821  O   ALA   284      89.045  59.681  14.792  1.00  15.47  B  O
ATOM   5822  N   ILE   285      89.691  57.788  15.826  1.00  23.61  B  N
ATOM   5823  CA  ILE   285      89.205  56.922  14.772  1.00  17.81  B  C
ATOM   5824  CB  ILE   285      89.960  55.564  14.741  1.00  12.20  B  C
ATOM   5825  CG2 ILE   285      89.210  54.576  13.862  1.00   7.02  B  C
ATOM   5826  CG1 ILE   285      91.380  55.738  14.204  1.00   7.53  B  C
ATOM   5827  CD1 ILE   285      92.342  56.334  15.179  1.00   8.67  B  C
ATOM   5828  C   ILE   285      87.745  56.678  15.148  1.00  21.13  B  C
ATOM   5829  O   ILE   285      87.466  56.108  16.201  1.00  22.87  B  O
ATOM   5830  N   LEU   286      86.820  57.112  14.297  1.00  18.22  B  N
ATOM   5831  CA  LEU   286      85.399  56.937  14.581  1.00  18.70  B  C
ATOM   5832  CB  LEU   286      84.615  58.129  14.039  1.00  27.86  B  C
ATOM   5833  CG  LEU   286      85.105  59.512  14.456  1.00  30.68  B  C
ATOM   5834  CD1 LEU   286      84.112  60.536  13.961  1.00  33.24  B  C
ATOM   5835  CD2 LEU   286      85.249  59.599  15.963  1.00  32.35  B  C
ATOM   5836  C   LEU   286      84.774  55.645  14.044  1.00  19.15  B  C
ATOM   5837  O   LEU   286      83.552  55.458  14.122  1.00  19.99  B  O
ATOM   5838  N   GLY   287      85.609  54.752  13.520  1.00  37.37  B  N
ATOM   5839  CA  GLY   287      85.115  53.501  12.967  1.00  36.15  B  C
ATOM   5840  C   GLY   287      84.059  52.745  13.760  1.00  33.73  B  C
```

Fig. 19: A-81

```
ATOM   5841  O    GLY  287      82.899  52.681  13.367  1.00  37.83      B    O
ATOM   5842  N    HIS  288      84.464  52.162  14.878  1.00  34.79      B    N
ATOM   5843  CA   HIS  288      83.563  51.376  15.700  1.00  32.75      B    C
ATOM   5844  CB   HIS  288      84.272  51.016  16.996  1.00  68.63      B    C
ATOM   5845  CG   HIS  288      85.486  50.181  16.763  1.00  70.54      B    C
ATOM   5846  CD2  HIS  288      85.781  48.912  17.123  1.00  66.91      B    C
ATOM   5847  ND1  HIS  288      86.520  50.600  15.955  1.00  65.20      B    N
ATOM   5848  CE1  HIS  288      87.397  49.623  15.821  1.00  65.56      B    C
ATOM   5849  NE2  HIS  288      86.972  48.586  16.519  1.00  64.05      B    N
ATOM   5850  C    HIS  288      82.214  52.006  15.968  1.00  30.23      B    C
ATOM   5851  O    HIS  288      81.180  51.398  15.711  1.00  29.80      B    O
ATOM   5852  N    TYR  289      82.219  53.233  16.461  1.00  26.68      B    N
ATOM   5853  CA   TYR  289      80.982  53.912  16.754  1.00  27.59      B    C
ATOM   5854  CB   TYR  289      81.287  55.288  17.309  1.00  20.91      B    C
ATOM   5855  CG   TYR  289      81.803  55.203  18.717  1.00  23.71      B    C
ATOM   5856  CD1  TYR  289      83.163  55.293  18.997  1.00  24.30      B    C
ATOM   5857  CE1  TYR  289      83.633  55.127  20.281  1.00  27.49      B    C
ATOM   5858  CD2  TYR  289      80.928  54.947  19.764  1.00  26.60      B    C
ATOM   5859  CE2  TYR  289      81.381  54.776  21.047  1.00  21.41      B    C
ATOM   5860  CZ   TYR  289      82.733  54.866  21.303  1.00  23.14      B    C
ATOM   5861  OH   TYR  289      83.166  54.686  22.597  1.00  27.79      B    O
ATOM   5862  C    TYR  289      80.039  54.015  15.572  1.00  29.36      B    C
ATOM   5863  O    TYR  289      78.849  53.720  15.692  1.00  28.55      B    O
ATOM   5864  N    ASN  290      80.551  54.414  14.419  1.00  30.33      B    N
ATOM   5865  CA   ASN  290      79.681  54.538  13.264  1.00  29.82      B    C
ATOM   5866  CB   ASN  290      80.390  55.290  12.141  1.00  19.88      B    C
ATOM   5867  CG   ASN  290      80.582  56.750  12.466  1.00  23.09      B    C
ATOM   5868  OD1  ASN  290      79.681  57.395  13.005  1.00  24.51      B    O
ATOM   5869  ND2  ASN  290      81.748  57.286  12.133  1.00  26.61      B    N
ATOM   5870  C    ASN  290      79.142  53.214  12.746  1.00  28.65      B    C
ATOM   5871  O    ASN  290      78.008  53.153  12.264  1.00  35.25      B    O
ATOM   5872  N    ARG  291      79.944  52.155  12.842  1.00  46.80      B    N
ATOM   5873  CA   ARG  291      79.513  50.850  12.362  1.00  46.11      B    C
ATOM   5874  CB   ARG  291      80.694  49.867  12.337  1.00  45.84      B    C
ATOM   5875  CG   ARG  291      81.661  50.063  11.152  1.00  50.80      B    C
ATOM   5876  CD   ARG  291      82.722  48.943  11.054  1.00  54.88      B    C
ATOM   5877  NE   ARG  291      83.916  49.157  11.883  1.00  47.06      B    N
ATOM   5878  CZ   ARG  291      84.884  50.030  11.603  1.00  56.55      B    C
ATOM   5879  NH1  ARG  291      84.813  50.787  10.515  1.00  55.39      B    N
ATOM   5880  NH2  ARG  291      85.936  50.131  12.401  1.00  53.31      B    N
ATOM   5881  C    ARG  291      78.367  50.296  13.207  1.00  43.91      B    C
ATOM   5882  O    ARG  291      77.338  49.876  12.676  1.00  47.17      B    O
ATOM   5883  N    GLY  292      78.531  50.306  14.523  1.00  18.83      B    N
ATOM   5884  CA   GLY  292      77.476  49.795  15.374  1.00  19.08      B    C
ATOM   5885  C    GLY  292      76.427  50.857  15.628  1.00  26.45      B    C
ATOM   5886  O    GLY  292      75.874  50.947  16.722  1.00  32.58      B    O
ATOM   5887  N    ASN  293      76.151  51.664  14.610  1.00  32.56      B    N
ATOM   5888  CA   ASN  293      75.177  52.740  14.724  1.00  34.89      B    C
ATOM   5889  CB   ASN  293      73.785  52.239  14.339  1.00  18.98      B    C
ATOM   5890  CG   ASN  293      73.623  52.066  12.846  1.00  25.56      B    C
ATOM   5891  OD1  ASN  293      74.249  52.776  12.063  1.00  27.19      B    O
ATOM   5892  ND2  ASN  293      72.767  51.132  12.440  1.00  26.33      B    N
ATOM   5893  C    ASN  293      75.116  53.389  16.111  1.00  36.22      B    C
ATOM   5894  O    ASN  293      74.054  53.448  16.722  1.00  31.70      B    O
ATOM   5895  N    LEU  294      76.247  53.875  16.614  1.00  40.17      B    N
ATOM   5896  CA   LEU  294      76.260  54.525  17.921  1.00  39.32      B    C
ATOM   5897  CB   LEU  294      77.141  53.737  18.901  1.00  27.66      B    C
ATOM   5898  CG   LEU  294      76.633  52.343  19.291  1.00  26.48      B    C
ATOM   5899  CD1  LEU  294      77.463  51.781  20.440  1.00  27.02      B    C
ATOM   5900  CD2  LEU  294      75.175  52.437  19.714  1.00  27.39      B    C
ATOM   5901  C    LEU  294      76.730  55.985  17.823  1.00  41.69      B    C
ATOM   5902  O    LEU  294      77.579  56.314  16.984  1.00  40.35      B    O
ATOM   5903  N    SER  295      76.158  56.860  18.656  1.00  29.47      B    N
ATOM   5904  CA   SER  295      76.534  58.272  18.644  1.00  29.33      B    C
ATOM   5905  CB   SER  295      75.802  59.063  19.740  1.00  35.11      B    C
ATOM   5906  OG   SER  295      76.336  60.371  19.894  1.00  41.79      B    O
ATOM   5907  C    SER  295      78.022  58.329  18.890  1.00  25.45      B    C
ATOM   5908  O    SER  295      78.583  57.444  19.533  1.00  22.32      B    O
ATOM   5909  N    THR  296      78.661  59.379  18.401  1.00  28.05      B    N
ATOM   5910  CA   THR  296      80.096  59.500  18.559  1.00  28.09      B    C
ATOM   5911  CB   THR  296      80.786  59.452  17.191  1.00  44.94      B    C
ATOM   5912  OG1  THR  296      80.305  60.534  16.383  1.00  50.00      B    O
ATOM   5913  CG2  THR  296      80.485  58.150  16.487  1.00  44.81      B    C
```

Fig. 19: A-82

| ATOM | 5914 | C | THR | 296 | 80.519 | 60.792 | 19.227 | 1.00 | 29.07 | B | C |
|---|---|---|---|---|---|---|---|---|---|---|---|
| ATOM | 5915 | O | THR | 296 | 81.695 | 60.971 | 19.535 | 1.00 | 27.88 | B | O |
| ATOM | 5916 | N | GLU | 297 | 79.581 | 61.705 | 19.451 | 1.00 | 50.64 | B | N |
| ATOM | 5917 | CA | GLU | 297 | 79.970 | 62.978 | 20.038 | 1.00 | 54.10 | B | C |
| ATOM | 5918 | CB | GLU | 297 | 78.781 | 63.943 | 20.111 | 1.00 | 93.12 | B | C |
| ATOM | 5919 | CG | GLU | 297 | 77.787 | 63.695 | 21.213 | 1.00 | 100.15 | B | C |
| ATOM | 5920 | CD | GLU | 297 | 77.036 | 64.960 | 21.569 | 1.00 | 101.40 | B | C |
| ATOM | 5921 | OE1 | GLU | 297 | 76.160 | 64.911 | 22.455 | 1.00 | 104.84 | B | O |
| ATOM | 5922 | OE2 | GLU | 297 | 77.333 | 66.010 | 20.964 | 1.00 | 102.89 | B | O |
| ATOM | 5923 | C | GLU | 297 | 80.639 | 62.849 | 21.399 | 1.00 | 52.14 | B | C |
| ATOM | 5924 | O | GLU | 297 | 81.715 | 63.406 | 21.612 | 1.00 | 51.64 | B | O |
| ATOM | 5925 | N | LYS | 298 | 80.029 | 62.104 | 22.315 | 1.00 | 35.40 | B | N |
| ATOM | 5926 | CA | LYS | 298 | 80.622 | 61.942 | 23.636 | 1.00 | 35.40 | B | C |
| ATOM | 5927 | CB | LYS | 298 | 79.837 | 60.916 | 24.443 | 1.00 | 37.32 | B | C |
| ATOM | 5928 | CG | LYS | 298 | 80.199 | 60.902 | 25.910 | 1.00 | 46.03 | B | C |
| ATOM | 5929 | CD | LYS | 298 | 79.201 | 60.085 | 26.727 | 1.00 | 47.75 | B | C |
| ATOM | 5930 | CE | LYS | 298 | 77.777 | 60.625 | 26.578 | 1.00 | 51.57 | B | C |
| ATOM | 5931 | NZ | LYS | 298 | 77.676 | 62.075 | 26.908 | 1.00 | 55.89 | B | N |
| ATOM | 5932 | C | LYS | 298 | 82.087 | 61.518 | 23.514 | 1.00 | 33.00 | B | C |
| ATOM | 5933 | O | LYS | 298 | 82.939 | 61.933 | 24.310 | 1.00 | 33.88 | B | O |
| ATOM | 5934 | N | PHE | 299 | 82.371 | 60.699 | 22.505 | 1.00 | 29.00 | B | N |
| ATOM | 5935 | CA | PHE | 299 | 83.729 | 60.226 | 22.244 | 1.00 | 27.24 | B | C |
| ATOM | 5936 | CB | PHE | 299 | 83.701 | 59.054 | 21.263 | 1.00 | 39.15 | B | C |
| ATOM | 5937 | CG | PHE | 299 | 85.065 | 58.571 | 20.851 | 1.00 | 31.59 | B | C |
| ATOM | 5938 | CD1 | PHE | 299 | 86.020 | 58.237 | 21.806 | 1.00 | 28.04 | B | C |
| ATOM | 5939 | CD2 | PHE | 299 | 85.396 | 58.435 | 19.505 | 1.00 | 29.32 | B | C |
| ATOM | 5940 | CE1 | PHE | 299 | 87.284 | 57.776 | 21.422 | 1.00 | 27.45 | B | C |
| ATOM | 5941 | CE2 | PHE | 299 | 86.667 | 57.970 | 19.119 | 1.00 | 23.73 | B | C |
| ATOM | 5942 | CZ | PHE | 299 | 87.603 | 57.643 | 20.078 | 1.00 | 22.24 | B | C |
| ATOM | 5943 | C | PHE | 299 | 84.562 | 61.361 | 21.662 | 1.00 | 27.59 | B | C |
| ATOM | 5944 | O | PHE | 299 | 85.625 | 61.702 | 22.183 | 1.00 | 23.40 | B | O |
| ATOM | 5945 | N | VAL | 300 | 84.077 | 61.946 | 20.576 | 1.00 | 13.78 | B | N |
| ATOM | 5946 | CA | VAL | 300 | 84.791 | 63.050 | 19.944 | 1.00 | 18.73 | B | C |
| ATOM | 5947 | CB | VAL | 300 | 83.954 | 63.701 | 18.822 | 1.00 | 24.12 | B | C |
| ATOM | 5948 | CG1 | VAL | 300 | 84.616 | 64.979 | 18.363 | 1.00 | 27.69 | B | C |
| ATOM | 5949 | CG2 | VAL | 300 | 83.814 | 62.731 | 17.646 | 1.00 | 28.13 | B | C |
| ATOM | 5950 | C | VAL | 300 | 85.142 | 64.119 | 20.966 | 1.00 | 17.37 | B | C |
| ATOM | 5951 | O | VAL | 300 | 86.209 | 64.715 | 20.906 | 1.00 | 17.87 | B | O |
| ATOM | 5952 | N | GLU | 301 | 84.248 | 64.359 | 21.914 | 1.00 | 33.19 | B | N |
| ATOM | 5953 | CA | GLU | 301 | 84.520 | 65.377 | 22.915 | 1.00 | 33.85 | B | C |
| ATOM | 5954 | CB | GLU | 301 | 83.255 | 65.707 | 23.706 | 1.00 | 133.49 | B | C |
| ATOM | 5955 | CG | GLU | 301 | 83.426 | 66.851 | 24.703 | 1.00 | 135.76 | B | C |
| ATOM | 5956 | CD | GLU | 301 | 84.115 | 68.077 | 24.108 | 1.00 | 141.57 | B | C |
| ATOM | 5957 | OE1 | GLU | 301 | 83.669 | 68.566 | 23.046 | 1.00 | 141.12 | B | O |
| ATOM | 5958 | OE2 | GLU | 301 | 85.102 | 68.555 | 24.713 | 1.00 | 143.84 | B | O |
| ATOM | 5959 | C | GLU | 301 | 85.634 | 64.925 | 23.847 | 1.00 | 32.42 | B | C |
| ATOM | 5960 | O | GLU | 301 | 86.495 | 65.723 | 24.239 | 1.00 | 30.50 | B | O |
| ATOM | 5961 | N | GLU | 302 | 85.628 | 63.642 | 24.190 | 1.00 | 18.71 | B | N |
| ATOM | 5962 | CA | GLU | 302 | 86.663 | 63.091 | 25.060 | 1.00 | 18.52 | B | C |
| ATOM | 5963 | CB | GLU | 302 | 86.420 | 61.596 | 25.293 | 1.00 | 49.27 | B | C |
| ATOM | 5964 | CG | GLU | 302 | 87.438 | 60.934 | 26.207 | 1.00 | 49.02 | B | C |
| ATOM | 5965 | CD | GLU | 302 | 87.100 | 59.486 | 26.491 | 1.00 | 45.95 | B | C |
| ATOM | 5966 | OE1 | GLU | 302 | 86.051 | 59.237 | 27.118 | 1.00 | 45.93 | B | O |
| ATOM | 5967 | OE2 | GLU | 302 | 87.875 | 58.594 | 26.084 | 1.00 | 50.37 | B | O |
| ATOM | 5968 | C | GLU | 302 | 88.046 | 63.301 | 24.456 | 1.00 | 21.59 | B | C |
| ATOM | 5969 | O | GLU | 302 | 88.964 | 63.720 | 25.150 | 1.00 | 20.85 | B | O |
| ATOM | 5970 | N | ILE | 303 | 88.188 | 63.031 | 23.159 | 1.00 | 30.73 | B | N |
| ATOM | 5971 | CA | ILE | 303 | 89.479 | 63.175 | 22.472 | 1.00 | 30.78 | B | C |
| ATOM | 5972 | CB | ILE | 303 | 89.470 | 62.431 | 21.112 | 1.00 | 21.11 | B | C |
| ATOM | 5973 | CG2 | ILE | 303 | 90.865 | 62.406 | 20.518 | 1.00 | 16.29 | B | C |
| ATOM | 5974 | CG1 | ILE | 303 | 88.932 | 61.003 | 21.306 | 1.00 | 18.71 | B | C |
| ATOM | 5975 | CD1 | ILE | 303 | 89.501 | 60.262 | 22.515 | 1.00 | 15.17 | B | C |
| ATOM | 5976 | C | ILE | 303 | 89.922 | 64.625 | 22.242 | 1.00 | 32.81 | B | C |
| ATOM | 5977 | O | ILE | 303 | 91.097 | 64.955 | 22.415 | 1.00 | 35.30 | B | O |
| ATOM | 5978 | N | LYS | 304 | 88.989 | 65.485 | 21.847 | 1.00 | 41.13 | B | N |
| ATOM | 5979 | CA | LYS | 304 | 89.321 | 66.881 | 21.624 | 1.00 | 41.93 | B | C |
| ATOM | 5980 | CB | LYS | 304 | 88.087 | 67.695 | 21.239 | 1.00 | 34.23 | B | C |
| ATOM | 5981 | CG | LYS | 304 | 87.578 | 67.484 | 19.837 | 1.00 | 40.90 | B | C |
| ATOM | 5982 | CD | LYS | 304 | 86.491 | 68.498 | 19.526 | 1.00 | 42.43 | B | C |
| ATOM | 5983 | CE | LYS | 304 | 85.937 | 68.312 | 18.122 | 1.00 | 45.16 | B | C |
| ATOM | 5984 | NZ | LYS | 304 | 84.893 | 69.323 | 17.799 | 1.00 | 47.34 | B | N |
| ATOM | 5985 | C | LYS | 304 | 89.892 | 67.455 | 22.906 | 1.00 | 38.02 | B | C |
| ATOM | 5986 | O | LYS | 304 | 90.833 | 68.240 | 22.871 | 1.00 | 42.10 | B | O |

Fig. 19: A-83

| ATOM | 5987 | N | SER | 305 | 89.322 | 67.066 | 24.043 | 1.00 | 21.53 | B | N |
|---|---|---|---|---|---|---|---|---|---|---|---|
| ATOM | 5988 | CA | SER | 305 | 89.788 | 67.571 | 25.335 | 1.00 | 18.69 | B | C |
| ATOM | 5989 | CB | SER | 305 | 88.872 | 67.096 | 26.460 | 1.00 | 39.18 | B | C |
| ATOM | 5990 | OG | SER | 305 | 89.039 | 65.715 | 26.696 | 1.00 | 35.86 | B | O |
| ATOM | 5991 | C | SER | 305 | 91.223 | 67.134 | 25.622 | 1.00 | 19.21 | B | C |
| ATOM | 5992 | O | SER | 305 | 91.935 | 67.754 | 26.418 | 1.00 | 21.78 | B | O |
| ATOM | 5993 | N | ILE | 306 | 91.652 | 66.063 | 24.969 | 1.00 | 47.39 | B | N |
| ATOM | 5994 | CA | ILE | 306 | 93.005 | 65.582 | 25.158 | 1.00 | 44.14 | B | C |
| ATOM | 5995 | CB | ILE | 306 | 93.129 | 64.131 | 24.682 | 1.00 | 20.56 | B | C |
| ATOM | 5996 | CG2 | ILE | 306 | 94.584 | 63.769 | 24.454 | 1.00 | 21.29 | B | C |
| ATOM | 5997 | CG1 | ILE | 306 | 92.479 | 63.210 | 25.713 | 1.00 | 23.19 | B | C |
| ATOM | 5998 | CD1 | ILE | 306 | 92.459 | 61.762 | 25.302 | 1.00 | 20.90 | B | C |
| ATOM | 5999 | C | ILE | 306 | 93.966 | 66.469 | 24.378 | 1.00 | 41.90 | B | C |
| ATOM | 6000 | O | ILE | 306 | 95.146 | 66.583 | 24.717 | 1.00 | 42.43 | B | O |
| ATOM | 6001 | N | ALA | 307 | 93.445 | 67.103 | 23.334 | 1.00 | 47.34 | B | N |
| ATOM | 6002 | CA | ALA | 307 | 94.247 | 67.979 | 22.497 | 1.00 | 49.53 | B | C |
| ATOM | 6003 | CB | ALA | 307 | 93.538 | 68.236 | 21.181 | 1.00 | 34.34 | B | C |
| ATOM | 6004 | C | ALA | 307 | 94.526 | 69.296 | 23.200 | 1.00 | 49.19 | B | C |
| ATOM | 6005 | O | ALA | 307 | 93.952 | 69.595 | 24.253 | 1.00 | 48.18 | B | O |
| ATOM | 6006 | N | SER | 308 | 95.415 | 70.078 | 22.604 | 1.00 | 31.36 | B | N |
| ATOM | 6007 | CA | SER | 308 | 95.801 | 71.367 | 23.141 | 1.00 | 34.29 | B | C |
| ATOM | 6008 | CB | SER | 308 | 97.299 | 71.580 | 22.943 | 1.00 | 9.08 | B | C |
| ATOM | 6009 | OG | SER | 308 | 98.040 | 70.819 | 23.867 | 1.00 | 12.47 | B | O |
| ATOM | 6010 | C | SER | 308 | 95.054 | 72.489 | 22.446 | 1.00 | 37.94 | B | C |
| ATOM | 6011 | O | SER | 308 | 94.703 | 72.373 | 21.272 | 1.00 | 35.28 | B | O |
| ATOM | 6012 | N | GLU | 309 | 94.813 | 73.575 | 23.178 | 1.00 | 31.30 | B | N |
| ATOM | 6013 | CA | GLU | 309 | 94.137 | 74.735 | 22.614 | 1.00 | 34.79 | B | C |
| ATOM | 6014 | CB | GLU | 309 | 93.786 | 75.736 | 23.721 | 1.00 | 74.37 | B | C |
| ATOM | 6015 | CG | GLU | 309 | 92.834 | 75.203 | 24.787 | 1.00 | 79.74 | B | C |
| ATOM | 6016 | CD | GLU | 309 | 91.461 | 74.845 | 24.234 | 1.00 | 82.50 | B | C |
| ATOM | 6017 | OE1 | GLU | 309 | 90.533 | 74.618 | 25.043 | 1.00 | 84.83 | B | O |
| ATOM | 6018 | OE2 | GLU | 309 | 91.307 | 74.784 | 22.995 | 1.00 | 86.65 | B | O |
| ATOM | 6019 | C | GLU | 309 | 95.138 | 75.359 | 21.642 | 1.00 | 35.54 | B | C |
| ATOM | 6020 | O | GLU | 309 | 96.321 | 75.480 | 21.971 | 1.00 | 37.19 | B | O |
| ATOM | 6021 | N | PRO | 310 | 94.685 | 75.762 | 20.435 | 1.00 | 19.46 | B | N |
| ATOM | 6022 | CD | PRO | 310 | 95.588 | 76.399 | 19.457 | 1.00 | 19.32 | B | C |
| ATOM | 6023 | CA | PRO | 310 | 93.324 | 75.694 | 19.890 | 1.00 | 19.65 | B | C |
| ATOM | 6024 | CB | PRO | 310 | 93.362 | 76.729 | 18.770 | 1.00 | 21.15 | B | C |
| ATOM | 6025 | CG | PRO | 310 | 94.715 | 76.515 | 18.203 | 1.00 | 20.71 | B | C |
| ATOM | 6026 | C | PRO | 310 | 92.884 | 74.312 | 19.384 | 1.00 | 20.14 | B | C |
| ATOM | 6027 | O | PRO | 310 | 93.368 | 73.816 | 18.374 | 1.00 | 16.93 | B | O |
| ATOM | 6028 | N | THR | 311 | 91.945 | 73.714 | 20.101 | 1.00 | 34.98 | B | N |
| ATOM | 6029 | CA | THR | 311 | 91.410 | 72.410 | 19.764 | 1.00 | 35.85 | B | C |
| ATOM | 6030 | CB | THR | 311 | 89.985 | 72.276 | 20.321 | 1.00 | 54.06 | B | C |
| ATOM | 6031 | OG1 | THR | 311 | 89.327 | 71.159 | 19.711 | 1.00 | 58.22 | B | O |
| ATOM | 6032 | CG2 | THR | 311 | 89.195 | 73.556 | 20.052 | 1.00 | 57.14 | B | C |
| ATOM | 6033 | C | THR | 311 | 91.390 | 72.103 | 18.265 | 1.00 | 37.72 | B | C |
| ATOM | 6034 | O | THR | 311 | 91.801 | 71.022 | 17.847 | 1.00 | 38.89 | B | O |
| ATOM | 6035 | N | GLU | 312 | 90.929 | 73.049 | 17.451 | 1.00 | 45.13 | B | N |
| ATOM | 6036 | CA | GLU | 312 | 90.842 | 72.825 | 16.004 | 1.00 | 43.75 | B | C |
| ATOM | 6037 | CB | GLU | 312 | 90.160 | 74.008 | 15.309 | 1.00 | 94.13 | B | C |
| ATOM | 6038 | CG | GLU | 312 | 90.848 | 75.342 | 15.528 | 1.00 | 95.89 | B | C |
| ATOM | 6039 | CD | GLU | 312 | 90.633 | 76.309 | 14.376 | 1.00 | 95.00 | B | C |
| ATOM | 6040 | OE1 | GLU | 312 | 90.998 | 77.496 | 14.516 | 1.00 | 98.35 | B | O |
| ATOM | 6041 | OE2 | GLU | 312 | 90.109 | 75.880 | 13.327 | 1.00 | 95.87 | B | O |
| ATOM | 6042 | C | GLU | 312 | 92.168 | 72.547 | 15.310 | 1.00 | 42.37 | B | C |
| ATOM | 6043 | O | GLU | 312 | 92.219 | 71.771 | 14.367 | 1.00 | 42.33 | B | O |
| ATOM | 6044 | N | LYS | 313 | 93.240 | 73.180 | 15.763 | 1.00 | 62.67 | B | N |
| ATOM | 6045 | CA | LYS | 313 | 94.537 | 72.966 | 15.141 | 1.00 | 61.87 | B | C |
| ATOM | 6046 | CB | LYS | 313 | 95.368 | 74.255 | 15.192 | 1.00 | 80.35 | B | C |
| ATOM | 6047 | CG | LYS | 313 | 94.954 | 75.308 | 14.167 | 1.00 | 80.23 | B | C |
| ATOM | 6048 | CD | LYS | 313 | 95.351 | 74.917 | 12.745 | 1.00 | 76.53 | B | C |
| ATOM | 6049 | CE | LYS | 313 | 96.790 | 75.307 | 12.430 | 1.00 | 78.57 | B | C |
| ATOM | 6050 | NZ | LYS | 313 | 97.781 | 74.730 | 13.383 | 1.00 | 83.05 | B | N |
| ATOM | 6051 | C | LYS | 313 | 95.308 | 71.832 | 15.800 | 1.00 | 63.02 | B | C |
| ATOM | 6052 | O | LYS | 313 | 96.473 | 71.610 | 15.491 | 1.00 | 65.34 | B | O |
| ATOM | 6053 | N | HIS | 314 | 94.656 | 71.103 | 16.697 | 1.00 | 42.28 | B | N |
| ATOM | 6054 | CA | HIS | 314 | 95.326 | 70.011 | 17.391 | 1.00 | 43.13 | B | C |
| ATOM | 6055 | CB | HIS | 314 | 95.631 | 70.426 | 18.828 | 1.00 | 51.27 | B | C |
| ATOM | 6056 | CG | HIS | 314 | 96.611 | 71.551 | 18.938 | 1.00 | 48.13 | B | C |
| ATOM | 6057 | CD2 | HIS | 314 | 96.423 | 72.880 | 19.111 | 1.00 | 47.60 | B | C |
| ATOM | 6058 | ND1 | HIS | 314 | 97.973 | 71.364 | 18.847 | 1.00 | 47.71 | B | N |
| ATOM | 6059 | CE1 | HIS | 314 | 98.582 | 72.530 | 18.960 | 1.00 | 47.00 | B | C |

Fig. 19: A-84

| ATOM | 6060 | NE2 | HIS | 314 | 97.664 | 73.466 | 19.121 | 1.00 | 47.39 | B | N |
|------|------|-----|-----|-----|--------|--------|--------|------|-------|---|---|
| ATOM | 6061 | C | HIS | 314 | 94.540 | 68.706 | 17.405 | 1.00 | 43.26 | B | C |
| ATOM | 6062 | O | HIS | 314 | 95.034 | 67.690 | 17.896 | 1.00 | 46.66 | B | O |
| ATOM | 6063 | N | PHE | 315 | 93.324 | 68.732 | 16.868 | 1.00 | 55.79 | B | N |
| ATOM | 6064 | CA | PHE | 315 | 92.475 | 67.546 | 16.835 | 1.00 | 55.59 | B | C |
| ATOM | 6065 | CB | PHE | 315 | 91.175 | 67.834 | 17.578 | 1.00 | 29.85 | B | C |
| ATOM | 6066 | CG | PHE | 315 | 90.175 | 66.731 | 17.499 | 1.00 | 24.83 | B | C |
| ATOM | 6067 | CD1 | PHE | 315 | 90.445 | 65.490 | 18.057 | 1.00 | 26.67 | B | C |
| ATOM | 6068 | CD2 | PHE | 315 | 88.944 | 66.942 | 16.890 | 1.00 | 22.91 | B | C |
| ATOM | 6069 | CE1 | PHE | 315 | 89.503 | 64.473 | 18.016 | 1.00 | 21.62 | B | C |
| ATOM | 6070 | CE2 | PHE | 315 | 87.989 | 65.939 | 16.838 | 1.00 | 23.61 | B | C |
| ATOM | 6071 | CZ | PHE | 315 | 88.268 | 64.700 | 17.404 | 1.00 | 25.28 | B | C |
| ATOM | 6072 | C | PHE | 315 | 92.172 | 67.086 | 15.412 | 1.00 | 56.31 | B | C |
| ATOM | 6073 | O | PHE | 315 | 91.948 | 67.903 | 14.516 | 1.00 | 57.71 | B | O |
| ATOM | 6074 | N | PHE | 316 | 92.170 | 65.772 | 15.212 | 1.00 | 44.89 | B | N |
| ATOM | 6075 | CA | PHE | 316 | 91.898 | 65.200 | 13.899 | 1.00 | 41.94 | B | C |
| ATOM | 6076 | CB | PHE | 316 | 93.175 | 64.621 | 13.282 | 1.00 | 20.23 | B | C |
| ATOM | 6077 | CG | PHE | 316 | 94.195 | 65.652 | 12.900 | 1.00 | 23.85 | B | C |
| ATOM | 6078 | CD1 | PHE | 316 | 95.118 | 66.114 | 13.828 | 1.00 | 19.44 | B | C |
| ATOM | 6079 | CD2 | PHE | 316 | 94.229 | 66.165 | 11.605 | 1.00 | 20.70 | B | C |
| ATOM | 6080 | CE1 | PHE | 316 | 96.066 | 67.074 | 13.475 | 1.00 | 22.01 | B | C |
| ATOM | 6081 | CE2 | PHE | 316 | 95.171 | 67.125 | 11.242 | 1.00 | 23.81 | B | C |
| ATOM | 6082 | CZ | PHE | 316 | 96.092 | 67.580 | 12.180 | 1.00 | 24.04 | B | C |
| ATOM | 6083 | C | PHE | 316 | 90.841 | 64.107 | 13.990 | 1.00 | 39.87 | B | C |
| ATOM | 6084 | O | PHE | 316 | 90.845 | 63.302 | 14.910 | 1.00 | 39.11 | B | O |
| ATOM | 6085 | N | ASN | 317 | 89.938 | 64.088 | 13.020 | 1.00 | 36.72 | B | N |
| ATOM | 6086 | CA | ASN | 317 | 88.863 | 63.110 | 12.978 | 1.00 | 37.94 | B | C |
| ATOM | 6087 | CB | ASN | 317 | 87.538 | 63.826 | 12.746 | 1.00 | 58.19 | B | C |
| ATOM | 6088 | CG | ASN | 317 | 86.496 | 63.443 | 13.752 | 1.00 | 61.18 | B | C |
| ATOM | 6089 | OD1 | ASN | 317 | 86.408 | 62.284 | 14.144 | 1.00 | 63.11 | B | O |
| ATOM | 6090 | ND2 | ASN | 317 | 85.688 | 64.411 | 14.176 | 1.00 | 59.44 | B | N |
| ATOM | 6091 | C | ASN | 317 | 89.102 | 62.140 | 11.831 | 1.00 | 38.90 | B | C |
| ATOM | 6092 | O | ASN | 317 | 89.519 | 62.549 | 10.757 | 1.00 | 39.76 | B | O |
| ATOM | 6093 | N | VAL | 318 | 88.840 | 60.858 | 12.045 | 1.00 | 40.86 | B | N |
| ATOM | 6094 | CA | VAL | 318 | 89.027 | 59.872 | 10.981 | 1.00 | 39.49 | B | C |
| ATOM | 6095 | CB | VAL | 318 | 90.348 | 59.096 | 11.156 | 1.00 | 59.32 | B | C |
| ATOM | 6096 | CG1 | VAL | 318 | 90.497 | 58.075 | 10.065 | 1.00 | 59.45 | B | C |
| ATOM | 6097 | CG2 | VAL | 318 | 91.519 | 60.052 | 11.111 | 1.00 | 59.30 | B | C |
| ATOM | 6098 | C | VAL | 318 | 87.861 | 58.894 | 10.987 | 1.00 | 34.64 | B | C |
| ATOM | 6099 | O | VAL | 318 | 87.363 | 58.523 | 12.050 | 1.00 | 35.31 | B | O |
| ATOM | 6100 | N | SER | 319 | 87.417 | 58.482 | 9.803 | 1.00 | 25.74 | B | N |
| ATOM | 6101 | CA | SER | 319 | 86.300 | 57.557 | 9.711 | 1.00 | 25.00 | B | C |
| ATOM | 6102 | CB | SER | 319 | 85.769 | 57.502 | 8.275 | 1.00 | 46.83 | B | C |
| ATOM | 6103 | OG | SER | 319 | 86.801 | 57.222 | 7.348 | 1.00 | 58.78 | B | O |
| ATOM | 6104 | C | SER | 319 | 86.672 | 56.161 | 10.195 | 1.00 | 23.60 | B | C |
| ATOM | 6105 | O | SER | 319 | 85.877 | 55.513 | 10.876 | 1.00 | 21.67 | B | O |
| ATOM | 6106 | N | ASP | 320 | 87.875 | 55.702 | 9.855 | 1.00 | 29.04 | B | N |
| ATOM | 6107 | CA | ASP | 320 | 88.342 | 54.377 | 10.272 | 1.00 | 29.02 | B | C |
| ATOM | 6108 | CB | ASP | 320 | 87.700 | 53.292 | 9.391 | 1.00 | 54.50 | B | C |
| ATOM | 6109 | CG | ASP | 320 | 88.036 | 53.455 | 7.907 | 1.00 | 52.95 | B | C |
| ATOM | 6110 | OD1 | ASP | 320 | 87.708 | 54.505 | 7.318 | 1.00 | 51.63 | B | O |
| ATOM | 6111 | OD2 | ASP | 320 | 88.628 | 52.525 | 7.324 | 1.00 | 53.50 | B | O |
| ATOM | 6112 | C | ASP | 320 | 89.878 | 54.249 | 10.227 | 1.00 | 27.39 | B | C |
| ATOM | 6113 | O | ASP | 320 | 90.574 | 55.142 | 9.734 | 1.00 | 27.17 | B | O |
| ATOM | 6114 | N | GLU | 321 | 90.403 | 53.140 | 10.745 | 1.00 | 32.71 | B | N |
| ATOM | 6115 | CA | GLU | 321 | 91.845 | 52.909 | 10.748 | 1.00 | 33.69 | B | C |
| ATOM | 6116 | CB | GLU | 321 | 92.152 | 51.430 | 11.018 | 1.00 | 76.40 | B | C |
| ATOM | 6117 | CG | GLU | 321 | 92.439 | 51.066 | 12.469 | 1.00 | 70.24 | B | C |
| ATOM | 6118 | CD | GLU | 321 | 91.229 | 51.194 | 13.373 | 1.00 | 69.99 | B | C |
| ATOM | 6119 | OE1 | GLU | 321 | 90.159 | 50.621 | 13.053 | 1.00 | 71.42 | B | O |
| ATOM | 6120 | OE2 | GLU | 321 | 91.357 | 51.862 | 14.418 | 1.00 | 74.03 | B | O |
| ATOM | 6121 | C | GLU | 321 | 92.476 | 53.300 | 9.412 | 1.00 | 37.68 | B | C |
| ATOM | 6122 | O | GLU | 321 | 93.529 | 53.943 | 9.369 | 1.00 | 34.44 | B | O |
| ATOM | 6123 | N | LEU | 322 | 91.820 | 52.905 | 8.323 | 1.00 | 34.24 | B | N |
| ATOM | 6124 | CA | LEU | 322 | 92.310 | 53.175 | 6.971 | 1.00 | 36.93 | B | C |
| ATOM | 6125 | CB | LEU | 322 | 91.345 | 52.598 | 5.937 | 1.00 | 67.00 | B | C |
| ATOM | 6126 | CG | LEU | 322 | 91.361 | 51.081 | 5.743 | 1.00 | 65.63 | B | C |
| ATOM | 6127 | CD1 | LEU | 322 | 92.716 | 50.681 | 5.198 | 1.00 | 67.37 | B | C |
| ATOM | 6128 | CD2 | LEU | 322 | 91.058 | 50.353 | 7.063 | 1.00 | 70.68 | B | C |
| ATOM | 6129 | C | LEU | 322 | 92.566 | 54.632 | 6.643 | 1.00 | 38.52 | B | C |
| ATOM | 6130 | O | LEU | 322 | 93.607 | 54.971 | 6.097 | 1.00 | 41.87 | B | O |
| ATOM | 6131 | N | ALA | 323 | 91.617 | 55.492 | 6.974 | 1.00 | 34.22 | B | N |
| ATOM | 6132 | CA | ALA | 323 | 91.759 | 56.908 | 6.687 | 1.00 | 34.65 | B | C |

Fig. 19: A-85

| | | | | | | | | | | | |
|---|---|---|---|---|---|---|---|---|---|---|---|
| ATOM | 6133 | CB | ALA | 323 | 90.420 | 57.600 | 6.897 | 1.00 | 1.87 | B | C |
| ATOM | 6134 | C | ALA | 323 | 92.859 | 57.644 | 7.476 | 1.00 | 35.06 | B | C |
| ATOM | 6135 | O | ALA | 323 | 93.171 | 58.804 | 7.181 | 1.00 | 35.08 | B | O |
| ATOM | 6136 | N | LEU | 324 | 93.447 | 56.995 | 8.476 | 1.00 | 26.80 | B | N |
| ATOM | 6137 | CA | LEU | 324 | 94.492 | 57.652 | 9.256 | 1.00 | 25.28 | B | C |
| ATOM | 6138 | CB | LEU | 324 | 95.221 | 56.640 | 10.146 | 1.00 | 29.36 | B | C |
| ATOM | 6139 | CG | LEU | 324 | 94.590 | 56.344 | 11.516 | 1.00 | 28.09 | B | C |
| ATOM | 6140 | CD1 | LEU | 324 | 95.288 | 55.158 | 12.170 | 1.00 | 27.23 | B | C |
| ATOM | 6141 | CD2 | LEU | 324 | 94.676 | 57.580 | 12.406 | 1.00 | 26.02 | B | C |
| ATOM | 6142 | C | LEU | 324 | 95.495 | 58.366 | 8.354 | 1.00 | 28.81 | B | C |
| ATOM | 6143 | O | LEU | 324 | 95.822 | 59.521 | 8.588 | 1.00 | 25.35 | B | O |
| ATOM | 6144 | N | VAL | 325 | 95.966 | 57.679 | 7.317 | 1.00 | 52.77 | B | N |
| ATOM | 6145 | CA | VAL | 325 | 96.934 | 58.246 | 6.378 | 1.00 | 56.30 | B | C |
| ATOM | 6146 | CB | VAL | 325 | 97.153 | 57.321 | 5.185 | 1.00 | 36.74 | B | C |
| ATOM | 6147 | CG1 | VAL | 325 | 97.936 | 56.099 | 5.614 | 1.00 | 36.85 | B | C |
| ATOM | 6148 | CG2 | VAL | 325 | 95.810 | 56.923 | 4.599 | 1.00 | 40.13 | B | C |
| ATOM | 6149 | C | VAL | 325 | 96.524 | 59.598 | 5.818 | 1.00 | 59.12 | B | C |
| ATOM | 6150 | O | VAL | 325 | 97.324 | 60.529 | 5.761 | 1.00 | 61.18 | B | O |
| ATOM | 6151 | N | THR | 326 | 95.277 | 59.694 | 5.384 | 1.00 | 40.34 | B | N |
| ATOM | 6152 | CA | THR | 326 | 94.743 | 60.925 | 4.818 | 1.00 | 41.75 | B | C |
| ATOM | 6153 | CB | THR | 326 | 93.298 | 60.706 | 4.344 | 1.00 | 81.94 | B | C |
| ATOM | 6154 | OG1 | THR | 326 | 92.430 | 60.600 | 5.481 | 1.00 | 83.85 | B | O |
| ATOM | 6155 | CG2 | THR | 326 | 93.206 | 59.417 | 3.534 | 1.00 | 84.31 | B | C |
| ATOM | 6156 | C | THR | 326 | 94.744 | 62.070 | 5.836 | 1.00 | 41.76 | B | C |
| ATOM | 6157 | O | THR | 326 | 93.885 | 62.952 | 5.785 | 1.00 | 40.58 | B | O |
| ATOM | 6158 | N | ILE | 327 | 95.705 | 62.052 | 6.755 | 1.00 | 36.65 | B | N |
| ATOM | 6159 | CA | ILE | 327 | 95.812 | 63.075 | 7.792 | 1.00 | 36.84 | B | C |
| ATOM | 6160 | CB | ILE | 327 | 95.078 | 62.604 | 9.085 | 1.00 | 16.25 | B | C |
| ATOM | 6161 | CG2 | ILE | 327 | 95.934 | 62.757 | 10.328 | 1.00 | 17.02 | B | C |
| ATOM | 6162 | CG1 | ILE | 327 | 93.807 | 63.408 | 9.260 | 1.00 | 16.61 | B | C |
| ATOM | 6163 | CD1 | ILE | 327 | 92.943 | 62.878 | 10.372 | 1.00 | 16.28 | B | C |
| ATOM | 6164 | C | ILE | 327 | 97.272 | 63.402 | 8.093 | 1.00 | 37.35 | B | C |
| ATOM | 6165 | O | ILE | 327 | 97.590 | 64.494 | 8.559 | 1.00 | 37.60 | B | O |
| ATOM | 6166 | N | VAL | 328 | 98.158 | 62.455 | 7.804 | 1.00 | 43.89 | B | N |
| ATOM | 6167 | CA | VAL | 328 | 99.575 | 62.643 | 8.060 | 1.00 | 46.03 | B | C |
| ATOM | 6168 | CB | VAL | 328 | 100.407 | 61.469 | 7.510 | 1.00 | 54.81 | B | C |
| ATOM | 6169 | CG1 | VAL | 328 | 99.871 | 60.157 | 8.061 | 1.00 | 56.76 | B | C |
| ATOM | 6170 | CG2 | VAL | 328 | 100.381 | 61.480 | 5.997 | 1.00 | 56.08 | B | C |
| ATOM | 6171 | C | VAL | 328 | 100.121 | 63.943 | 7.481 | 1.00 | 45.95 | B | C |
| ATOM | 6172 | O | VAL | 328 | 100.998 | 64.563 | 8.075 | 1.00 | 45.23 | B | O |
| ATOM | 6173 | N | LYS | 329 | 99.611 | 64.366 | 6.331 | 1.00 | 44.51 | B | N |
| ATOM | 6174 | CA | LYS | 329 | 100.097 | 65.609 | 5.732 | 1.00 | 43.72 | B | C |
| ATOM | 6175 | CB | LYS | 329 | 99.471 | 65.824 | 4.356 | 1.00 | 45.34 | B | C |
| ATOM | 6176 | CG | LYS | 329 | 100.174 | 66.880 | 3.520 | 1.00 | 46.89 | B | C |
| ATOM | 6177 | CD | LYS | 329 | 99.423 | 67.129 | 2.220 | 1.00 | 49.21 | B | C |
| ATOM | 6178 | CE | LYS | 329 | 100.179 | 68.074 | 1.298 | 1.00 | 52.25 | B | C |
| ATOM | 6179 | NZ | LYS | 329 | 101.450 | 67.466 | 0.831 | 1.00 | 55.93 | B | N |
| ATOM | 6180 | C | LYS | 329 | 99.762 | 66.797 | 6.640 | 1.00 | 41.89 | B | C |
| ATOM | 6181 | O | LYS | 329 | 100.640 | 67.552 | 7.056 | 1.00 | 43.10 | B | O |
| ATOM | 6182 | N | ALA | 330 | 98.483 | 66.957 | 6.952 | 1.00 | 14.46 | B | N |
| ATOM | 6183 | CA | ALA | 330 | 98.053 | 68.043 | 7.814 | 1.00 | 14.49 | B | C |
| ATOM | 6184 | CB | ALA | 330 | 96.538 | 68.052 | 7.906 | 1.00 | 26.19 | B | C |
| ATOM | 6185 | C | ALA | 330 | 98.657 | 67.910 | 9.210 | 1.00 | 15.64 | B | C |
| ATOM | 6186 | O | ALA | 330 | 99.090 | 68.896 | 9.796 | 1.00 | 15.54 | B | O |
| ATOM | 6187 | N | LEU | 331 | 98.666 | 66.688 | 9.745 | 1.00 | 29.61 | B | N |
| ATOM | 6188 | CA | LEU | 331 | 99.200 | 66.447 | 11.078 | 1.00 | 27.25 | B | C |
| ATOM | 6189 | CB | LEU | 331 | 99.108 | 64.969 | 11.454 | 1.00 | 20.84 | B | C |
| ATOM | 6190 | CG | LEU | 331 | 99.086 | 64.642 | 12.958 | 1.00 | 17.26 | B | C |
| ATOM | 6191 | CD1 | LEU | 331 | 99.332 | 63.152 | 13.131 | 1.00 | 18.89 | B | C |
| ATOM | 6192 | CD2 | LEU | 331 | 100.130 | 65.436 | 13.722 | 1.00 | 12.95 | B | C |
| ATOM | 6193 | C | LEU | 331 | 100.647 | 66.860 | 11.070 | 1.00 | 27.28 | B | C |
| ATOM | 6194 | O | LEU | 331 | 101.090 | 67.613 | 11.931 | 1.00 | 26.63 | B | O |
| ATOM | 6195 | N | GLY | 332 | 101.374 | 66.358 | 10.079 | 1.00 | 36.12 | B | N |
| ATOM | 6196 | CA | GLY | 332 | 102.784 | 66.666 | 9.949 | 1.00 | 37.22 | B | C |
| ATOM | 6197 | C | GLY | 332 | 103.089 | 68.150 | 9.917 | 1.00 | 37.48 | B | C |
| ATOM | 6198 | O | GLY | 332 | 103.940 | 68.628 | 10.670 | 1.00 | 41.35 | B | O |
| ATOM | 6199 | N | GLU | 333 | 102.398 | 68.892 | 9.058 | 1.00 | 41.72 | B | N |
| ATOM | 6200 | CA | GLU | 333 | 102.653 | 70.317 | 8.967 | 1.00 | 39.78 | B | C |
| ATOM | 6201 | CB | GLU | 333 | 102.052 | 70.889 | 7.683 | 1.00 | 98.89 | B | C |
| ATOM | 6202 | CG | GLU | 333 | 100.546 | 70.988 | 7.678 | 1.00 | 97.26 | B | C |
| ATOM | 6203 | CD | GLU | 333 | 100.018 | 71.598 | 6.400 | 1.00 | 97.28 | B | C |
| ATOM | 6204 | OE1 | GLU | 333 | 98.795 | 71.849 | 6.322 | 1.00 | 99.33 | B | O |
| ATOM | 6205 | OE2 | GLU | 333 | 100.824 | 71.823 | 5.472 | 1.00 | 91.40 | B | O |

Fig. 19: A-86

```
ATOM   6206  C    GLU  333   102.120  71.069  10.179  1.00   38.76  B  C
ATOM   6207  O    GLU  333   102.747  72.010  10.650  1.00   38.38  B  O
ATOM   6208  N    ARG  334   100.969  70.659  10.695  1.00   43.09  B  N
ATOM   6209  CA   ARG  334   100.398  71.340  11.847  1.00   46.47  B  C
ATOM   6210  CB   ARG  334    99.089  70.667  12.265  1.00   41.05  B  C
ATOM   6211  CG   ARG  334    98.167  71.568  13.056  1.00   40.34  B  C
ATOM   6212  CD   ARG  334    96.722  71.432  12.592  1.00   39.10  B  C
ATOM   6213  NE   ARG  334    96.544  71.911  11.222  1.00   34.65  B  N
ATOM   6214  CZ   ARG  334    95.446  71.721  10.488  1.00   38.74  B  C
ATOM   6215  NH1  ARG  334    94.407  71.052  10.987  1.00   35.48  B  N
ATOM   6216  NH2  ARG  334    95.388  72.197   9.246  1.00   44.88  B  N
ATOM   6217  C    ARG  334   101.419  71.321  12.980  1.00   47.77  B  C
ATOM   6218  O    ARG  334   101.633  72.329  13.643  1.00   44.69  B  O
ATOM   6219  N    ILE  335   102.060  70.177  13.192  1.00   95.68  B  N
ATOM   6220  CA   ILE  335   103.084  70.066  14.227  1.00   95.61  B  C
ATOM   6221  CB   ILE  335   103.349  68.565  14.599  1.00   69.44  B  C
ATOM   6222  CG2  ILE  335   103.371  67.701  13.359  1.00   72.22  B  C
ATOM   6223  CG1  ILE  335   104.671  68.420  15.350  1.00   70.66  B  C
ATOM   6224  CD1  ILE  335   105.043  66.983  15.628  1.00   73.45  B  C
ATOM   6225  C    ILE  335   104.346  70.716  13.653  1.00   93.90  B  C
ATOM   6226  O    ILE  335   105.317  70.979  14.364  1.00   96.50  B  O
ATOM   6227  N    PHE  336   104.273  71.011  12.356  1.00  144.26  B  N
ATOM   6228  CA   PHE  336   105.347  71.604  11.560  1.00  143.89  B  C
ATOM   6229  CB   PHE  336   105.336  73.156  11.625  1.00   83.50  B  C
ATOM   6230  CG   PHE  336   105.600  73.748  12.992  1.00   79.82  B  C
ATOM   6231  CD1  PHE  336   106.696  73.355  13.760  1.00   79.24  B  C
ATOM   6232  CD2  PHE  336   104.783  74.762  13.479  1.00   77.77  B  C
ATOM   6233  CE1  PHE  336   106.973  73.966  14.988  1.00   69.57  B  C
ATOM   6234  CE2  PHE  336   105.053  75.377  14.702  1.00   72.13  B  C
ATOM   6235  CZ   PHE  336   106.152  74.977  15.457  1.00   72.59  B  C
ATOM   6236  C    PHE  336   106.737  71.068  11.853  1.00  143.92  B  C
ATOM   6237  O    PHE  336   106.889  70.255  12.788  1.00  123.54  B  O
ATOM   6238  OXT  PHE  336   107.658  71.461  11.111  1.00   66.99  B  O
ATOM   6239  CB   GLU    1    68.990  38.972  10.337  1.00  143.47  X  C
ATOM   6240  CG   GLU    1    68.785  37.653  11.053  1.00  143.47  X  C
ATOM   6241  CD   GLU    1    68.300  36.572  10.118  1.00  143.47  X  C
ATOM   6242  OE1  GLU    1    69.012  36.278   9.134  1.00  143.47  X  O
ATOM   6243  OE2  GLU    1    67.209  36.019  10.363  1.00  143.47  X  O
ATOM   6244  C    GLU    1    71.024  39.462  11.710  1.00   74.19  X  C
ATOM   6245  O    GLU    1    71.492  38.415  11.265  1.00   74.19  X  O
ATOM   6246  N    GLU    1    69.921  41.257  10.328  1.00   74.19  X  N
ATOM   6247  CA   GLU    1    69.711  40.037  11.162  1.00   74.19  X  C
ATOM   6248  N    VAL    2    71.613  40.151  12.681  1.00   55.61  X  N
ATOM   6249  CA   VAL    2    72.858  39.694  13.284  1.00   55.61  X  C
ATOM   6250  CB   VAL    2    73.533  40.812  14.089  1.00   66.95  X  C
ATOM   6251  CG1  VAL    2    74.850  40.323  14.647  1.00   66.95  X  C
ATOM   6252  CG2  VAL    2    73.752  42.021  13.210  1.00   66.95  X  C
ATOM   6253  C    VAL    2    72.566  38.543  14.232  1.00   55.61  X  C
ATOM   6254  O    VAL    2    71.728  38.673  15.127  1.00   55.61  X  O
ATOM   6255  N    GLN    3    73.258  37.421  14.045  1.00   39.72  X  N
ATOM   6256  CA   GLN    3    73.044  36.261  14.908  1.00   39.72  X  C
ATOM   6257  CB   GLN    3    71.807  35.502  14.455  1.00  102.66  X  C
ATOM   6258  CG   GLN    3    71.852  35.144  13.002  1.00  102.66  X  C
ATOM   6259  CD   GLN    3    70.688  34.291  12.604  1.00  102.66  X  C
ATOM   6260  OE1  GLN    3    69.537  34.635  12.873  1.00  102.66  X  O
ATOM   6261  NE2  GLN    3    70.972  33.168  11.955  1.00  102.66  X  N
ATOM   6262  C    GLN    3    74.213  35.288  15.002  1.00   39.72  X  C
ATOM   6263  O    GLN    3    75.064  35.207  14.108  1.00   39.72  X  O
ATOM   6264  N    LEU    4    74.231  34.553  16.109  1.00   34.59  X  N
ATOM   6265  CA   LEU    4    75.260  33.555  16.389  1.00   34.59  X  C
ATOM   6266  CB   LEU    4    76.043  33.931  17.653  1.00   34.08  X  C
ATOM   6267  CG   LEU    4    77.107  35.040  17.665  1.00   34.08  X  C
ATOM   6268  CD1  LEU    4    77.119  35.820  16.353  1.00   34.08  X  C
ATOM   6269  CD2  LEU    4    76.844  35.950  18.863  1.00   34.08  X  C
ATOM   6270  C    LEU    4    74.581  32.212  16.615  1.00   34.59  X  C
ATOM   6271  O    LEU    4    73.737  32.080  17.503  1.00   34.59  X  O
ATOM   6272  N    VAL    5    74.933  31.218  15.806  1.00   36.99  X  N
ATOM   6273  CA   VAL    5    74.350  29.889  15.961  1.00   36.99  X  C
ATOM   6274  CB   VAL    5    73.536  29.456  14.698  1.00   37.13  X  C
ATOM   6275  CG1  VAL    5    74.285  29.815  13.430  1.00   37.13  X  C
ATOM   6276  CG2  VAL    5    73.264  27.963  14.744  1.00   37.13  X  C
ATOM   6277  C    VAL    5    75.429  28.861  16.277  1.00   36.99  X  C
ATOM   6278  O    VAL    5    76.163  28.404  15.398  1.00   36.99  X  O
```

Fig. 19: A-87

```
ATOM   6279  N    GLU   6      75.519   28.517   17.555  1.00   44.32      X   N
ATOM   6280  CA   GLU   6      76.499   27.550   18.020  1.00   44.32      X   C
ATOM   6281  CB   GLU   6      76.924   27.884   19.457  1.00   53.96      X   C
ATOM   6282  CG   GLU   6      75.844   28.531   20.292  1.00   53.96      X   C
ATOM   6283  CD   GLU   6      76.340   28.943   21.659  1.00   53.96      X   C
ATOM   6284  OE1  GLU   6      75.590   29.646   22.368  1.00   53.96      X   O
ATOM   6285  OE2  GLU   6      77.472   28.561   22.028  1.00   53.96      X   O
ATOM   6286  C    GLU   6      76.029   26.095   17.930  1.00   44.32      X   C
ATOM   6287  O    GLU   6      74.856   25.813   17.668  1.00   44.32      X   O
ATOM   6288  N    SER   7      76.980   25.185   18.135  1.00   42.31      X   N
ATOM   6289  CA   SER   7      76.758   23.745   18.091  1.00   42.31      X   C
ATOM   6290  CB   SER   7      76.762   23.261   16.642  1.00   44.31      X   C
ATOM   6291  OG   SER   7      77.832   23.845   15.922  1.00   44.31      X   O
ATOM   6292  C    SER   7      77.919   23.123   18.848  1.00   42.31      X   C
ATOM   6293  O    SER   7      78.889   23.813   19.138  1.00   42.31      X   O
ATOM   6294  N    GLY   8      77.822   21.838   19.178  1.00   39.85      X   N
ATOM   6295  CA   GLY   8      78.908   21.177   19.893  1.00   39.85      X   C
ATOM   6296  C    GLY   8      78.569   20.747   21.313  1.00   39.85      X   C
ATOM   6297  O    GLY   8      79.330   20.016   21.962  1.00   39.85      X   O
ATOM   6298  N    GLY   9      77.417   21.199   21.795  1.00   54.13      X   N
ATOM   6299  CA   GLY   9      76.998   20.852   23.138  1.00   54.13      X   C
ATOM   6300  C    GLY   9      76.467   19.439   23.283  1.00   54.13      X   C
ATOM   6301  O    GLY   9      75.390   19.102   22.783  1.00   54.13      X   O
ATOM   6302  N    GLY  10      77.235   18.606   23.972  1.00   51.55      X   N
ATOM   6303  CA   GLY  10      76.825   17.236   24.195  1.00   51.55      X   C
ATOM   6304  C    GLY  10      77.359   16.807   25.544  1.00   51.55      X   C
ATOM   6305  O    GLY  10      77.723   17.651   26.370  1.00   51.55      X   O
ATOM   6306  N    LEU  11      77.409   15.500   25.776  1.00   54.73      X   N
ATOM   6307  CA   LEU  11      77.930   14.981   27.032  1.00   54.73      X   C
ATOM   6308  CB   LEU  11      76.994   13.903   27.583  1.00   40.69      X   C
ATOM   6309  CG   LEU  11      77.583   13.086   28.735  1.00   40.69      X   C
ATOM   6310  CD1  LEU  11      78.170   14.011   29.795  1.00   40.69      X   C
ATOM   6311  CD2  LEU  11      76.508   12.198   29.317  1.00   40.69      X   C
ATOM   6312  C    LEU  11      79.341   14.412   26.852  1.00   54.73      X   C
ATOM   6313  O    LEU  11      79.664   13.853   25.806  1.00   54.73      X   O
ATOM   6314  N    VAL  12      80.177   14.576   27.872  1.00   43.40      X   N
ATOM   6315  CA   VAL  12      81.552   14.079   27.848  1.00   43.40      X   C
ATOM   6316  CB   VAL  12      82.538   15.118   27.273  1.00   57.73      X   C
ATOM   6317  CG1  VAL  12      82.222   15.388   25.812  1.00   57.73      X   C
ATOM   6318  CG2  VAL  12      82.473   16.404   28.086  1.00   57.73      X   C
ATOM   6319  C    VAL  12      81.991   13.753   29.269  1.00   43.40      X   C
ATOM   6320  O    VAL  12      81.490   14.344   30.230  1.00   43.40      X   O
ATOM   6321  N    GLN  13      82.931   12.821   29.403  1.00   46.11      X   N
ATOM   6322  CA   GLN  13      83.404   12.420   30.720  1.00   46.11      X   C
ATOM   6323  CB   GLN  13      83.873   10.965   30.676  1.00  148.60      X   C
ATOM   6324  CG   GLN  13      82.843   10.015   30.094  1.00  148.60      X   C
ATOM   6325  CD   GLN  13      83.232    8.560   30.263  1.00  148.60      X   C
ATOM   6326  OE1  GLN  13      84.322    8.145   29.868  1.00  148.60      X   O
ATOM   6327  NE2  GLN  13      82.337    7.774   30.852  1.00  148.60      X   N
ATOM   6328  C    GLN  13      84.532   13.311   31.234  1.00   46.11      X   C
ATOM   6329  O    GLN  13      85.186   14.002   30.454  1.00   46.11      X   O
ATOM   6330  N    PRO  14      84.763   13.319   32.563  1.00   39.23      X   N
ATOM   6331  CD   PRO  14      83.989   12.657   33.630  1.00   55.62      X   C
ATOM   6332  CA   PRO  14      85.831   14.141   33.141  1.00   39.23      X   C
ATOM   6333  CB   PRO  14      85.902   13.648   34.581  1.00   55.62      X   C
ATOM   6334  CG   PRO  14      84.474   13.374   34.887  1.00   55.62      X   C
ATOM   6335  C    PRO  14      87.122   13.905   32.392  1.00   39.23      X   C
ATOM   6336  O    PRO  14      87.357   12.810   31.885  1.00   39.23      X   O
ATOM   6337  N    GLY  15      87.954   14.935   32.320  1.00   28.04      X   N
ATOM   6338  CA   GLY  15      89.220   14.816   31.616  1.00   28.04      X   C
ATOM   6339  C    GLY  15      89.037   14.807   30.109  1.00   28.04      X   C
ATOM   6340  O    GLY  15      89.990   14.979   29.352  1.00   28.04      X   O
ATOM   6341  N    GLY  16      87.801   14.613   29.672  1.00   22.75      X   N
ATOM   6342  CA   GLY  16      87.529   14.583   28.250  1.00   22.75      X   C
ATOM   6343  C    GLY  16      87.705   15.912   27.539  1.00   22.75      X   C
ATOM   6344  O    GLY  16      87.887   16.969   28.155  1.00   22.75      X   O
ATOM   6345  N    SER  17      87.633   15.845   26.217  1.00   36.95      X   N
ATOM   6346  CA   SER  17      87.789   17.014   25.371  1.00   36.95      X   C
ATOM   6347  CB   SER  17      88.962   16.795   24.417  1.00   47.78      X   C
ATOM   6348  OG   SER  17      89.203   17.952   23.645  1.00   47.78      X   O
ATOM   6349  C    SER  17      86.509   17.311   24.581  1.00   36.95      X   C
ATOM   6350  O    SER  17      85.817   16.402   24.106  1.00   36.95      X   O
ATOM   6351  N    LEU  18      86.199   18.593   24.429  1.00   50.75      X   N
```

Fig. 19: A-88

```
ATOM   6352  CA   LEU   18      84.995  18.978  23.719  1.00  50.75      X   C
ATOM   6353  CB   LEU   18      83.833  18.944  24.701  1.00  37.38      X   C
ATOM   6354  CG   LEU   18      82.463  19.285  24.146  1.00  37.38      X   C
ATOM   6355  CD1  LEU   18      82.177  18.476  22.874  1.00  37.38      X   C
ATOM   6356  CD2  LEU   18      81.442  19.012  25.239  1.00  37.38      X   C
ATOM   6357  C    LEU   18      85.107  20.355  23.069  1.00  50.75      X   C
ATOM   6358  O    LEU   18      85.530  21.313  23.714  1.00  50.75      X   O
ATOM   6359  N    ARG   19      84.737  20.454  21.792  1.00  27.07      X   N
ATOM   6360  CA   ARG   19      84.805  21.739  21.097  1.00  27.07      X   C
ATOM   6361  CB   ARG   19      85.774  21.708  19.924  1.00  43.18      X   C
ATOM   6362  CG   ARG   19      85.825  23.068  19.238  1.00  43.18      X   C
ATOM   6363  CD   ARG   19      86.689  23.075  18.015  1.00  43.18      X   C
ATOM   6364  NE   ARG   19      86.060  22.389  16.896  1.00  43.18      X   N
ATOM   6365  CZ   ARG   19      86.564  22.371  15.666  1.00  43.18      X   C
ATOM   6366  NH1  ARG   19      87.708  23.006  15.407  1.00  43.18      X   N
ATOM   6367  NH2  ARG   19      85.924  21.725  14.696  1.00  43.18      X   N
ATOM   6368  C    ARG   19      83.501  22.302  20.558  1.00  27.07      X   C
ATOM   6369  O    ARG   19      82.895  21.745  19.625  1.00  27.07      X   O
ATOM   6370  N    LEU   20      83.109  23.438  21.135  1.00  30.57      X   N
ATOM   6371  CA   LEU   20      81.908  24.150  20.731  1.00  30.57      X   C
ATOM   6372  CB   LEU   20      81.354  24.965  21.896  1.00  36.53      X   C
ATOM   6373  CG   LEU   20      80.981  24.196  23.159  1.00  36.53      X   C
ATOM   6374  CD1  LEU   20      80.415  25.142  24.218  1.00  36.53      X   C
ATOM   6375  CD2  LEU   20      79.964  23.135  22.802  1.00  36.53      X   C
ATOM   6376  C    LEU   20      82.304  25.098  19.618  1.00  30.57      X   C
ATOM   6377  O    LEU   20      83.313  25.784  19.723  1.00  30.57      X   O
ATOM   6378  N    SER   21      81.527  25.122  18.544  1.00  31.77      X   N
ATOM   6379  CA   SER   21      81.789  26.024  17.426  1.00  31.77      X   C
ATOM   6380  CB   SER   21      81.876  25.252  16.117  1.00  32.65      X   C
ATOM   6381  OG   SER   21      80.580  24.896  15.682  1.00  32.65      X   O
ATOM   6382  C    SER   21      80.593  26.971  17.383  1.00  31.77      X   C
ATOM   6383  O    SER   21      79.591  26.738  18.057  1.00  31.77      X   O
ATOM   6384  N    CYS   22      80.673  28.024  16.585  1.00  49.03      X   N
ATOM   6385  CA   CYS   22      79.580  28.981  16.526  1.00  49.03      X   C
ATOM   6386  C    CYS   22      79.725  29.812  15.272  1.00  49.03      X   C
ATOM   6387  O    CYS   22      80.743  30.484  15.096  1.00  49.03      X   O
ATOM   6388  CB   CYS   22      79.643  29.849  17.788  1.00  49.62      X   C
ATOM   6389  SG   CYS   22      78.993  31.555  17.774  1.00  49.62      X   S
ATOM   6390  N    ALA   23      78.724  29.744  14.389  1.00  43.82      X   N
ATOM   6391  CA   ALA   23      78.742  30.509  13.136  1.00  43.82      X   C
ATOM   6392  CB   ALA   23      78.022  29.768  12.021  1.00   1.87      X   C
ATOM   6393  C    ALA   23      78.093  31.854  13.329  1.00  43.82      X   C
ATOM   6394  O    ALA   23      77.118  31.999  14.070  1.00  43.82      X   O
ATOM   6395  N    ALA   24      78.644  32.843  12.645  1.00  28.70      X   N
ATOM   6396  CA   ALA   24      78.129  34.190  12.735  1.00  28.70      X   C
ATOM   6397  CB   ALA   24      79.199  35.129  13.323  1.00  18.49      X   C
ATOM   6398  C    ALA   24      77.725  34.659  11.356  1.00  28.70      X   C
ATOM   6399  O    ALA   24      78.213  34.160  10.345  1.00  28.70      X   O
ATOM   6400  N    SER   25      76.816  35.620  11.338  1.00  39.45      X   N
ATOM   6401  CA   SER   25      76.338  36.218  10.108  1.00  39.45      X   C
ATOM   6402  CB   SER   25      75.279  35.322   9.443  1.00  48.28      X   C
ATOM   6403  OG   SER   25      74.163  35.090  10.287  1.00  48.28      X   O
ATOM   6404  C    SER   25      75.751  37.575  10.486  1.00  39.45      X   C
ATOM   6405  O    SER   25      75.425  37.819  11.656  1.00  39.45      X   O
ATOM   6406  N    GLY   26      75.651  38.464   9.506  1.00  15.13      X   N
ATOM   6407  CA   GLY   26      75.093  39.773   9.767  1.00  15.13      X   C
ATOM   6408  C    GLY   26      76.061  40.808  10.313  1.00  15.13      X   C
ATOM   6409  O    GLY   26      75.650  41.692  11.070  1.00  15.13      X   O
ATOM   6410  N    PHE   27      77.336  40.697   9.941  1.00  51.25      X   N
ATOM   6411  CA   PHE   27      78.375  41.638  10.358  1.00  51.25      X   C
ATOM   6412  CB   PHE   27      78.322  41.921  11.860  1.00  33.43      X   C
ATOM   6413  CG   PHE   27      78.647  40.736  12.720  1.00  33.43      X   C
ATOM   6414  CD1  PHE   27      77.696  39.749  12.958  1.00  33.43      X   C
ATOM   6415  CD2  PHE   27      79.891  40.629  13.337  1.00  33.43      X   C
ATOM   6416  CE1  PHE   27      77.978  38.673  13.810  1.00  33.43      X   C
ATOM   6417  CE2  PHE   27      80.186  39.558  14.190  1.00  33.43      X   C
ATOM   6418  CZ   PHE   27      79.227  38.581  14.428  1.00  33.43      X   C
ATOM   6419  C    PHE   27      79.748  41.100  10.012  1.00  51.25      X   C
ATOM   6420  O    PHE   27      79.966  39.894  10.027  1.00  51.25      X   O
ATOM   6421  N    THR   28      80.671  42.006   9.707  1.00  31.93      X   N
ATOM   6422  CA   THR   28      82.031  41.637   9.348  1.00  31.93      X   C
ATOM   6423  CB   THR   28      82.821  42.872   8.910  1.00  48.89      X   C
ATOM   6424  OG1  THR   28      82.126  43.520   7.836  1.00  48.89      X   O
```

Fig. 19: A-89

| | | | | | | | | | | |
|---|---|---|---|---|---|---|---|---|---|---|
| ATOM | 6425 | CG2 | THR | 28 | 84.212 | 42.474 | 8.454 | 1.00 | 48.89 | X C |
| ATOM | 6426 | C | THR | 28 | 82.744 | 40.981 | 10.519 | 1.00 | 31.93 | X C |
| ATOM | 6427 | O | THR | 28 | 83.431 | 41.640 | 11.286 | 1.00 | 31.93 | X O |
| ATOM | 6428 | N | PHE | 29 | 82.576 | 39.671 | 10.636 | 1.00 | 37.68 | X N |
| ATOM | 6429 | CA | PHE | 29 | 83.166 | 38.876 | 11.712 | 1.00 | 37.68 | X C |
| ATOM | 6430 | CB | PHE | 29 | 83.068 | 37.386 | 11.352 | 1.00 | 38.41 | X C |
| ATOM | 6431 | CG | PHE | 29 | 83.484 | 36.454 | 12.462 | 1.00 | 38.41 | X C |
| ATOM | 6432 | CD1 | PHE | 29 | 82.795 | 36.440 | 13.676 | 1.00 | 38.41 | X C |
| ATOM | 6433 | CD2 | PHE | 29 | 84.570 | 35.587 | 12.296 | 1.00 | 38.41 | X C |
| ATOM | 6434 | CE1 | PHE | 29 | 83.183 | 35.577 | 14.709 | 1.00 | 38.41 | X C |
| ATOM | 6435 | CE2 | PHE | 29 | 84.967 | 34.718 | 13.324 | 1.00 | 38.41 | X C |
| ATOM | 6436 | CZ | PHE | 29 | 84.272 | 34.715 | 14.530 | 1.00 | 38.41 | X C |
| ATOM | 6437 | C | PHE | 29 | 84.616 | 39.225 | 12.021 | 1.00 | 37.68 | X C |
| ATOM | 6438 | O | PHE | 29 | 84.958 | 39.552 | 13.160 | 1.00 | 37.68 | X O |
| ATOM | 6439 | N | SER | 30 | 85.462 | 39.160 | 10.998 | 1.00 | 22.05 | X N |
| ATOM | 6440 | CA | SER | 30 | 86.890 | 39.421 | 11.157 | 1.00 | 22.05 | X C |
| ATOM | 6441 | CB | SER | 30 | 87.553 | 39.545 | 9.783 | 1.00 | 37.79 | X C |
| ATOM | 6442 | OG | SER | 30 | 86.886 | 40.481 | 8.959 | 1.00 | 37.79 | X O |
| ATOM | 6443 | C | SER | 30 | 87.270 | 40.622 | 12.014 | 1.00 | 22.05 | X C |
| ATOM | 6444 | O | SER | 30 | 88.326 | 40.634 | 12.639 | 1.00 | 22.05 | X O |
| ATOM | 6445 | N | ARG | 31 | 86.395 | 41.615 | 12.063 | 1.00 | 29.69 | X N |
| ATOM | 6446 | CA | ARG | 31 | 86.651 | 42.846 | 12.801 | 1.00 | 29.69 | X C |
| ATOM | 6447 | CB | ARG | 31 | 85.819 | 43.956 | 12.162 | 1.00 | 51.15 | X C |
| ATOM | 6448 | CG | ARG | 31 | 86.068 | 45.323 | 12.719 | 1.00 | 51.15 | X C |
| ATOM | 6449 | CD | ARG | 31 | 84.999 | 46.281 | 12.231 | 1.00 | 51.15 | X C |
| ATOM | 6450 | NE | ARG | 31 | 84.964 | 46.383 | 10.772 | 1.00 | 51.15 | X N |
| ATOM | 6451 | CZ | ARG | 31 | 85.899 | 46.974 | 10.038 | 1.00 | 51.15 | X C |
| ATOM | 6452 | NH1 | ARG | 31 | 86.959 | 47.523 | 10.621 | 1.00 | 51.15 | X N |
| ATOM | 6453 | NH2 | ARG | 31 | 85.764 | 47.027 | 8.722 | 1.00 | 51.15 | X N |
| ATOM | 6454 | C | ARG | 31 | 86.425 | 42.833 | 14.329 | 1.00 | 29.69 | X C |
| ATOM | 6455 | O | ARG | 31 | 87.226 | 43.399 | 15.080 | 1.00 | 29.69 | X O |
| ATOM | 6456 | N | TYR | 32 | 85.352 | 42.185 | 14.785 | 1.00 | 39.46 | X N |
| ATOM | 6457 | CA | TYR | 32 | 85.009 | 42.144 | 16.217 | 1.00 | 39.46 | X C |
| ATOM | 6458 | CB | TYR | 32 | 83.506 | 41.880 | 16.409 | 1.00 | 51.56 | X C |
| ATOM | 6459 | CG | TYR | 32 | 82.601 | 42.689 | 15.516 | 1.00 | 51.56 | X C |
| ATOM | 6460 | CD1 | TYR | 32 | 82.540 | 42.437 | 14.148 | 1.00 | 51.56 | X C |
| ATOM | 6461 | CE1 | TYR | 32 | 81.721 | 43.181 | 13.316 | 1.00 | 51.56 | X C |
| ATOM | 6462 | CD2 | TYR | 32 | 81.811 | 43.714 | 16.034 | 1.00 | 51.56 | X C |
| ATOM | 6463 | CE2 | TYR | 32 | 80.985 | 44.467 | 15.209 | 1.00 | 51.56 | X C |
| ATOM | 6464 | CZ | TYR | 32 | 80.946 | 44.193 | 13.851 | 1.00 | 51.56 | X C |
| ATOM | 6465 | OH | TYR | 32 | 80.135 | 44.929 | 13.015 | 1.00 | 51.56 | X O |
| ATOM | 6466 | C | TYR | 32 | 85.761 | 41.108 | 17.037 | 1.00 | 39.46 | X C |
| ATOM | 6467 | O | TYR | 32 | 86.159 | 40.072 | 16.515 | 1.00 | 39.46 | X O |
| ATOM | 6468 | N | THR | 33 | 85.943 | 41.386 | 18.328 | 1.00 | 29.44 | X N |
| ATOM | 6469 | CA | THR | 33 | 86.611 | 40.421 | 19.191 | 1.00 | 29.44 | X C |
| ATOM | 6470 | CB | THR | 33 | 87.510 | 41.080 | 20.315 | 1.00 | 20.65 | X C |
| ATOM | 6471 | OG1 | THR | 33 | 86.749 | 41.242 | 21.514 | 1.00 | 20.65 | X O |
| ATOM | 6472 | CG2 | THR | 33 | 88.072 | 42.437 | 19.866 | 1.00 | 20.65 | X C |
| ATOM | 6473 | C | THR | 33 | 85.483 | 39.614 | 19.835 | 1.00 | 29.44 | X C |
| ATOM | 6474 | O | THR | 33 | 84.632 | 40.167 | 20.536 | 1.00 | 29.44 | X O |
| ATOM | 6475 | N | MET | 34 | 85.484 | 38.307 | 19.568 | 1.00 | 30.35 | X N |
| ATOM | 6476 | CA | MET | 34 | 84.474 | 37.391 | 20.084 | 1.00 | 30.35 | X C |
| ATOM | 6477 | CB | MET | 34 | 84.235 | 36.284 | 19.067 | 1.00 | 43.39 | X C |
| ATOM | 6478 | CG | MET | 34 | 84.070 | 36.798 | 17.652 | 1.00 | 43.39 | X C |
| ATOM | 6479 | SD | MET | 34 | 82.775 | 38.029 | 17.525 | 1.00 | 43.39 | X S |
| ATOM | 6480 | CE | MET | 34 | 81.376 | 37.024 | 17.198 | 1.00 | 43.39 | X C |
| ATOM | 6481 | C | MET | 34 | 84.867 | 36.785 | 21.430 | 1.00 | 30.35 | X C |
| ATOM | 6482 | O | MET | 34 | 86.049 | 36.761 | 21.790 | 1.00 | 30.35 | X O |
| ATOM | 6483 | N | SER | 35 | 83.866 | 36.293 | 22.164 | 1.00 | 35.95 | X N |
| ATOM | 6484 | CA | SER | 35 | 84.073 | 35.701 | 23.487 | 1.00 | 35.95 | X C |
| ATOM | 6485 | CB | SER | 35 | 83.875 | 36.765 | 24.580 | 1.00 | 34.42 | X C |
| ATOM | 6486 | OG | SER | 35 | 84.740 | 37.878 | 24.420 | 1.00 | 34.42 | X O |
| ATOM | 6487 | C | SER | 35 | 83.105 | 34.548 | 23.761 | 1.00 | 35.95 | X C |
| ATOM | 6488 | O | SER | 35 | 82.191 | 34.290 | 22.978 | 1.00 | 35.95 | X O |
| ATOM | 6489 | N | TRP | 36 | 83.323 | 33.856 | 24.879 | 1.00 | 43.17 | X N |
| ATOM | 6490 | CA | TRP | 36 | 82.457 | 32.758 | 25.309 | 1.00 | 43.17 | X C |
| ATOM | 6491 | CB | TRP | 36 | 83.159 | 31.383 | 25.200 | 1.00 | 32.84 | X C |
| ATOM | 6492 | CG | TRP | 36 | 83.355 | 30.875 | 23.782 | 1.00 | 32.84 | X C |
| ATOM | 6493 | CD2 | TRP | 36 | 82.419 | 30.118 | 22.998 | 1.00 | 32.84 | X C |
| ATOM | 6494 | CE2 | TRP | 36 | 82.982 | 29.957 | 21.711 | 1.00 | 32.84 | X C |
| ATOM | 6495 | CE3 | TRP | 36 | 81.153 | 29.564 | 23.257 | 1.00 | 32.84 | X C |
| ATOM | 6496 | CD1 | TRP | 36 | 84.419 | 31.124 | 22.962 | 1.00 | 32.84 | X C |
| ATOM | 6497 | NE1 | TRP | 36 | 84.201 | 30.579 | 21.716 | 1.00 | 32.84 | X N |

Fig. 19: A-90

```
ATOM   6498  CZ2 TRP   36      82.324  29.267  20.681  1.00   32.84    X   C
ATOM   6499  CZ3 TRP   36      80.495  28.877  22.228  1.00   32.84    X   C
ATOM   6500  CH2 TRP   36      81.086  28.738  20.957  1.00   32.84    X   C
ATOM   6501  C   TRP   36      82.056  33.022  26.764  1.00   43.17    X   C
ATOM   6502  O   TRP   36      82.908  33.298  27.615  1.00   43.17    X   O
ATOM   6503  N   VAL   37      80.751  32.958  27.026  1.00   29.19    X   N
ATOM   6504  CA  VAL   37      80.177  33.175  28.360  1.00   29.19    X   C
ATOM   6505  CB  VAL   37      79.213  34.419  28.353  1.00    8.00    X   C
ATOM   6506  CG1 VAL   37      78.350  34.467  29.621  1.00    8.00    X   C
ATOM   6507  CG2 VAL   37      80.026  35.689  28.240  1.00    8.00    X   C
ATOM   6508  C   VAL   37      79.412  31.907  28.760  1.00   29.19    X   C
ATOM   6509  O   VAL   37      78.629  31.381  27.971  1.00   29.19    X   O
ATOM   6510  N   ARG   38      79.651  31.415  29.974  1.00   61.80    X   N
ATOM   6511  CA  ARG   38      78.992  30.198  30.454  1.00   61.80    X   C
ATOM   6512  CB  ARG   38      80.036  29.167  30.899  1.00   27.50    X   C
ATOM   6513  CG  ARG   38      80.926  29.688  32.011  1.00   27.50    X   C
ATOM   6514  CD  ARG   38      81.370  28.603  32.965  1.00   27.50    X   C
ATOM   6515  NE  ARG   38      82.222  27.579  32.364  1.00   27.50    X   N
ATOM   6516  CZ  ARG   38      83.391  27.181  32.874  1.00   27.50    X   C
ATOM   6517  NH1 ARG   38      83.862  27.725  33.992  1.00   27.50    X   N
ATOM   6518  NH2 ARG   38      84.087  26.217  32.281  1.00   27.50    X   N
ATOM   6519  C   ARG   38      78.053  30.468  31.628  1.00   61.80    X   C
ATOM   6520  O   ARG   38      78.104  31.528  32.245  1.00   61.80    X   O
ATOM   6521  N   GLN   39      77.204  29.491  31.934  1.00   39.46    X   N
ATOM   6522  CA  GLN   39      76.269  29.597  33.049  1.00   39.46    X   C
ATOM   6523  CB  GLN   39      74.982  30.269  32.588  1.00   44.48    X   C
ATOM   6524  CG  GLN   39      73.997  30.530  33.708  1.00   44.48    X   C
ATOM   6525  CD  GLN   39      72.916  31.497  33.294  1.00   44.48    X   C
ATOM   6526  OE1 GLN   39      72.269  31.320  32.252  1.00   44.48    X   O
ATOM   6527  NE2 GLN   39      72.709  32.532  34.106  1.00   44.48    X   N
ATOM   6528  C   GLN   39      75.955  28.224  33.663  1.00   39.46    X   C
ATOM   6529  O   GLN   39      75.233  27.404  33.076  1.00   39.46    X   O
ATOM   6530  N   ALA   40      76.514  27.984  34.846  1.00   47.11    X   N
ATOM   6531  CA  ALA   40      76.324  26.727  35.558  1.00   47.11    X   C
ATOM   6532  CB  ALA   40      77.241  26.678  36.773  1.00   19.87    X   C
ATOM   6533  C   ALA   40      74.875  26.592  35.995  1.00   47.11    X   C
ATOM   6534  O   ALA   40      74.296  27.542  36.512  1.00   47.11    X   O
ATOM   6535  N   PRO   41      74.271  25.403  35.802  1.00   63.91    X   N
ATOM   6536  CD  PRO   41      74.879  24.157  35.299  1.00   66.56    X   C
ATOM   6537  CA  PRO   41      72.875  25.168  36.187  1.00   63.91    X   C
ATOM   6538  CB  PRO   41      72.793  23.649  36.244  1.00   66.56    X   C
ATOM   6539  CG  PRO   41      73.667  23.254  35.115  1.00   66.56    X   C
ATOM   6540  C   PRO   41      72.507  25.826  37.508  1.00   63.91    X   C
ATOM   6541  O   PRO   41      73.186  25.637  38.522  1.00   63.91    X   O
ATOM   6542  N   GLY   42      71.432  26.608  37.478  1.00   63.56    X   N
ATOM   6543  CA  GLY   42      70.979  27.297  38.671  1.00   63.56    X   C
ATOM   6544  C   GLY   42      71.963  28.342  39.165  1.00   63.56    X   C
ATOM   6545  O   GLY   42      71.920  28.732  40.334  1.00   63.56    X   O
ATOM   6546  N   LYS   43      72.846  28.793  38.276  1.00  103.79    X   N
ATOM   6547  CA  LYS   43      73.852  29.802  38.607  1.00  103.79    X   C
ATOM   6548  CB  LYS   43      75.248  29.168  38.641  1.00   95.84    X   C
ATOM   6549  CG  LYS   43      75.752  28.830  40.037  1.00   95.84    X   C
ATOM   6550  CD  LYS   43      74.840  27.853  40.755  1.00   95.84    X   C
ATOM   6551  CE  LYS   43      75.225  27.734  42.222  1.00   95.84    X   C
ATOM   6552  NZ  LYS   43      75.138  29.048  42.920  1.00   95.84    X   N
ATOM   6553  C   LYS   43      73.848  30.984  37.634  1.00  103.79    X   C
ATOM   6554  O   LYS   43      73.085  31.013  36.668  1.00  103.79    X   O
ATOM   6555  N   GLY   44      74.714  31.956  37.899  1.00   36.05    X   N
ATOM   6556  CA  GLY   44      74.796  33.131  37.055  1.00   36.05    X   C
ATOM   6557  C   GLY   44      75.710  33.025  35.845  1.00   36.05    X   C
ATOM   6558  O   GLY   44      76.150  31.931  35.477  1.00   36.05    X   O
ATOM   6559  N   LEU   45      76.003  34.186  35.249  1.00   24.14    X   N
ATOM   6560  CA  LEU   45      76.832  34.316  34.046  1.00   24.14    X   C
ATOM   6561  CB  LEU   45      76.343  35.504  33.214  1.00   15.59    X   C
ATOM   6562  CG  LEU   45      74.932  35.346  32.638  1.00   15.59    X   C
ATOM   6563  CD1 LEU   45      74.470  36.606  31.917  1.00   15.59    X   C
ATOM   6564  CD2 LEU   45      74.942  34.179  31.677  1.00   15.59    X   C
ATOM   6565  C   LEU   45      78.316  34.474  34.311  1.00   24.14    X   C
ATOM   6566  O   LEU   45      78.732  35.324  35.095  1.00   24.14    X   O
ATOM   6567  N   GLU   46      79.110  33.661  33.624  1.00   56.59    X   N
ATOM   6568  CA  GLU   46      80.557  33.686  33.774  1.00   56.59    X   C
ATOM   6569  CB  GLU   46      81.034  32.373  34.412  1.00   46.99    X   C
ATOM   6570  CG  GLU   46      82.536  32.308  34.666  1.00   46.99    X   C
```

Fig. 19: A-91

| ATOM | 6571 | CD | GLU | 46 | 82.953 | 31.066 | 35.438 | 1.00 | 46.99 | X | C |
|------|------|-----|-----|----|--------|--------|--------|------|-------|---|---|
| ATOM | 6572 | OE1 | GLU | 46 | 82.642 | 29.952 | 34.970 | 1.00 | 46.99 | X | O |
| ATOM | 6573 | OE2 | GLU | 46 | 83.594 | 31.201 | 36.508 | 1.00 | 46.99 | X | O |
| ATOM | 6574 | C | GLU | 46 | 81.272 | 33.904 | 32.439 | 1.00 | 56.59 | X | C |
| ATOM | 6575 | O | GLU | 46 | 80.821 | 33.433 | 31.393 | 1.00 | 56.59 | X | O |
| ATOM | 6576 | N | TRP | 47 | 82.385 | 34.632 | 32.489 | 1.00 | 30.60 | X | N |
| ATOM | 6577 | CA | TRP | 47 | 83.188 | 34.910 | 31.300 | 1.00 | 30.60 | X | C |
| ATOM | 6578 | CB | TRP | 47 | 83.889 | 36.273 | 31.426 | 1.00 | 23.41 | X | C |
| ATOM | 6579 | CG | TRP | 47 | 84.944 | 36.481 | 30.385 | 1.00 | 23.41 | X | C |
| ATOM | 6580 | CD2 | TRP | 47 | 86.358 | 36.500 | 30.601 | 1.00 | 23.41 | X | C |
| ATOM | 6581 | CE2 | TRP | 47 | 86.971 | 36.591 | 29.328 | 1.00 | 23.41 | X | C |
| ATOM | 6582 | CE3 | TRP | 47 | 87.170 | 36.441 | 31.746 | 1.00 | 23.41 | X | C |
| ATOM | 6583 | CD1 | TRP | 47 | 84.759 | 36.570 | 29.031 | 1.00 | 23.41 | X | C |
| ATOM | 6584 | NE1 | TRP | 47 | 85.969 | 36.633 | 28.392 | 1.00 | 23.41 | X | N |
| ATOM | 6585 | CZ2 | TRP | 47 | 88.365 | 36.622 | 29.165 | 1.00 | 23.41 | X | C |
| ATOM | 6586 | CZ3 | TRP | 47 | 88.553 | 36.470 | 31.587 | 1.00 | 23.41 | X | C |
| ATOM | 6587 | CH2 | TRP | 47 | 89.137 | 36.560 | 30.304 | 1.00 | 23.41 | X | C |
| ATOM | 6588 | C | TRP | 47 | 84.231 | 33.810 | 31.153 | 1.00 | 30.60 | X | C |
| ATOM | 6589 | O | TRP | 47 | 84.965 | 33.516 | 32.097 | 1.00 | 30.60 | X | O |
| ATOM | 6590 | N | VAL | 48 | 84.317 | 33.219 | 29.967 | 1.00 | 24.17 | X | N |
| ATOM | 6591 | CA | VAL | 48 | 85.270 | 32.128 | 29.755 | 1.00 | 24.17 | X | C |
| ATOM | 6592 | CB | VAL | 48 | 84.589 | 30.924 | 29.011 | 1.00 | 22.03 | X | C |
| ATOM | 6593 | CG1 | VAL | 48 | 85.589 | 29.786 | 28.790 | 1.00 | 22.03 | X | C |
| ATOM | 6594 | CG2 | VAL | 48 | 83.408 | 30.436 | 29.805 | 1.00 | 22.03 | X | C |
| ATOM | 6595 | C | VAL | 48 | 86.550 | 32.490 | 29.006 | 1.00 | 24.17 | X | C |
| ATOM | 6596 | O | VAL | 48 | 87.640 | 32.477 | 29.579 | 1.00 | 24.17 | X | O |
| ATOM | 6597 | N | ALA | 49 | 86.407 | 32.800 | 27.724 | 1.00 | 21.43 | X | N |
| ATOM | 6598 | CA | ALA | 49 | 87.550 | 33.118 | 26.885 | 1.00 | 21.43 | X | C |
| ATOM | 6599 | CB | ALA | 49 | 87.953 | 31.884 | 26.094 | 1.00 | 38.48 | X | C |
| ATOM | 6600 | C | ALA | 49 | 87.228 | 34.257 | 25.934 | 1.00 | 21.43 | X | C |
| ATOM | 6601 | O | ALA | 49 | 86.066 | 34.661 | 25.825 | 1.00 | 21.43 | X | O |
| ATOM | 6602 | N | THR | 50 | 88.257 | 34.745 | 25.235 | 1.00 | 24.70 | X | N |
| ATOM | 6603 | CA | THR | 50 | 88.115 | 35.856 | 24.286 | 1.00 | 24.70 | X | C |
| ATOM | 6604 | CB | THR | 50 | 87.952 | 37.202 | 25.048 | 1.00 | 38.80 | X | C |
| ATOM | 6605 | OG1 | THR | 50 | 86.711 | 37.215 | 25.763 | 1.00 | 38.80 | X | O |
| ATOM | 6606 | CG2 | THR | 50 | 87.981 | 38.369 | 24.087 | 1.00 | 38.80 | X | C |
| ATOM | 6607 | C | THR | 50 | 89.298 | 36.039 | 23.324 | 1.00 | 24.70 | X | C |
| ATOM | 6608 | O | THR | 50 | 90.456 | 35.935 | 23.738 | 1.00 | 24.70 | X | O |
| ATOM | 6609 | N | ILE | 51 | 89.010 | 36.300 | 22.047 | 1.00 | 32.54 | X | N |
| ATOM | 6610 | CA | ILE | 51 | 90.075 | 36.599 | 21.074 | 1.00 | 32.54 | X | C |
| ATOM | 6611 | CB | ILE | 51 | 90.333 | 35.495 | 19.998 | 1.00 | 54.98 | X | C |
| ATOM | 6612 | CG2 | ILE | 51 | 90.567 | 34.178 | 20.661 | 1.00 | 54.98 | X | C |
| ATOM | 6613 | CG1 | ILE | 51 | 89.180 | 35.415 | 18.997 | 1.00 | 54.98 | X | C |
| ATOM | 6614 | CD1 | ILE | 51 | 87.893 | 34.921 | 19.582 | 1.00 | 54.98 | X | C |
| ATOM | 6615 | C | ILE | 51 | 89.674 | 37.865 | 20.335 | 1.00 | 32.54 | X | C |
| ATOM | 6616 | O | ILE | 51 | 88.516 | 38.024 | 19.937 | 1.00 | 32.54 | X | O |
| ATOM | 6617 | N | SER | 52 | 90.628 | 38.774 | 20.167 | 1.00 | 43.61 | X | N |
| ATOM | 6618 | CA | SER | 52 | 90.361 | 40.024 | 19.477 | 1.00 | 43.61 | X | C |
| ATOM | 6619 | CB | SER | 52 | 91.374 | 41.081 | 19.910 | 1.00 | 24.33 | X | C |
| ATOM | 6620 | OG | SER | 52 | 92.684 | 40.702 | 19.528 | 1.00 | 24.33 | X | O |
| ATOM | 6621 | C | SER | 52 | 90.450 | 39.789 | 17.973 | 1.00 | 43.61 | X | C |
| ATOM | 6622 | O | SER | 52 | 90.677 | 38.663 | 17.533 | 1.00 | 43.61 | X | O |
| ATOM | 6623 | N | GLY | 53 | 90.243 | 40.843 | 17.187 | 1.00 | 34.59 | X | N |
| ATOM | 6624 | CA | GLY | 53 | 90.336 | 40.707 | 15.747 | 1.00 | 34.59 | X | C |
| ATOM | 6625 | C | GLY | 53 | 91.800 | 40.559 | 15.381 | 1.00 | 34.59 | X | C |
| ATOM | 6626 | O | GLY | 53 | 92.152 | 40.020 | 14.332 | 1.00 | 34.59 | X | O |
| ATOM | 6627 | N | GLY | 54 | 92.658 | 41.047 | 16.266 | 1.00 | 29.30 | X | N |
| ATOM | 6628 | CA | GLY | 54 | 94.079 | 40.949 | 16.033 | 1.00 | 29.30 | X | C |
| ATOM | 6629 | C | GLY | 54 | 94.555 | 39.550 | 16.359 | 1.00 | 29.30 | X | C |
| ATOM | 6630 | O | GLY | 54 | 95.642 | 39.135 | 15.954 | 1.00 | 29.30 | X | O |
| ATOM | 6631 | N | GLY | 55 | 93.747 | 38.811 | 17.103 | 1.00 | 15.27 | X | N |
| ATOM | 6632 | CA | GLY | 55 | 94.139 | 37.465 | 17.437 | 1.00 | 15.27 | X | C |
| ATOM | 6633 | C | GLY | 55 | 94.596 | 37.254 | 18.867 | 1.00 | 15.27 | X | C |
| ATOM | 6634 | O | GLY | 55 | 94.878 | 36.105 | 19.231 | 1.00 | 15.27 | X | O |
| ATOM | 6635 | N | HIS | 56 | 94.676 | 38.319 | 19.675 | 1.00 | 13.76 | X | N |
| ATOM | 6636 | CA | HIS | 56 | 95.101 | 38.181 | 21.076 | 1.00 | 13.76 | X | C |
| ATOM | 6637 | CB | HIS | 56 | 95.268 | 39.543 | 21.741 | 1.00 | 60.58 | X | C |
| ATOM | 6638 | CG | HIS | 56 | 96.115 | 40.490 | 20.957 | 1.00 | 60.58 | X | C |
| ATOM | 6639 | CD2 | HIS | 56 | 97.417 | 40.838 | 21.087 | 1.00 | 60.58 | X | C |
| ATOM | 6640 | ND1 | HIS | 56 | 95.638 | 41.180 | 19.862 | 1.00 | 60.58 | X | N |
| ATOM | 6641 | CE1 | HIS | 56 | 96.611 | 41.913 | 19.351 | 1.00 | 60.58 | X | C |
| ATOM | 6642 | NE2 | HIS | 56 | 97.701 | 41.724 | 20.075 | 1.00 | 60.58 | X | N |
| ATOM | 6643 | C | HIS | 56 | 94.071 | 37.383 | 21.857 | 1.00 | 13.76 | X | C |

Fig. 19: A-92

```
ATOM   6644  O    HIS  56      92.864  37.621  21.736  1.00  13.76      X    O
ATOM   6645  N    THR  57      94.529  36.438  22.671  1.00  20.05      X    N
ATOM   6646  CA   THR  57      93.583  35.632  23.436  1.00  20.05      X    C
ATOM   6647  CB   THR  57      93.759  34.123  23.096  1.00  15.53      X    C
ATOM   6648  OG1  THR  57      95.015  33.651  23.587  1.00  15.53      X    O
ATOM   6649  CG2  THR  57      93.734  33.929  21.593  1.00  15.53      X    C
ATOM   6650  C    THR  57      93.655  35.876  24.952  1.00  20.05      X    C
ATOM   6651  O    THR  57      94.716  36.142  25.512  1.00  20.05      X    O
ATOM   6652  N    TYR  58      92.500  35.808  25.603  1.00  19.06      X    N
ATOM   6653  CA   TYR  58      92.410  36.037  27.040  1.00  19.06      X    C
ATOM   6654  CB   TYR  58      91.829  37.428  27.304  1.00  22.48      X    C
ATOM   6655  CG   TYR  58      92.614  38.542  26.661  1.00  22.48      X    C
ATOM   6656  CD1  TYR  58      93.565  39.252  27.384  1.00  22.48      X    C
ATOM   6657  CE1  TYR  58      94.308  40.265  26.788  1.00  22.48      X    C
ATOM   6658  CD2  TYR  58      92.423  38.871  25.316  1.00  22.48      X    C
ATOM   6659  CE2  TYR  58      93.167  39.886  24.703  1.00  22.48      X    C
ATOM   6660  CZ   TYR  58      94.105  40.580  25.447  1.00  22.48      X    C
ATOM   6661  OH   TYR  58      94.828  41.611  24.876  1.00  22.48      X    O
ATOM   6662  C    TYR  58      91.513  34.973  27.656  1.00  19.06      X    C
ATOM   6663  O    TYR  58      90.442  34.660  27.123  1.00  19.06      X    O
ATOM   6664  N    TYR  59      91.945  34.437  28.792  1.00  29.06      X    N
ATOM   6665  CA   TYR  59      91.199  33.378  29.456  1.00  29.06      X    C
ATOM   6666  CB   TYR  59      91.988  32.080  29.371  1.00  21.37      X    C
ATOM   6667  CG   TYR  59      92.252  31.641  27.969  1.00  21.37      X    C
ATOM   6668  CD1  TYR  59      91.352  30.813  27.303  1.00  21.37      X    C
ATOM   6669  CE1  TYR  59      91.573  30.428  25.988  1.00  21.37      X    C
ATOM   6670  CD2  TYR  59      93.382  32.076  27.286  1.00  21.37      X    C
ATOM   6671  CE2  TYR  59      93.608  31.698  25.968  1.00  21.37      X    C
ATOM   6672  CZ   TYR  59      92.697  30.874  25.330  1.00  21.37      X    C
ATOM   6673  OH   TYR  59      92.897  30.495  24.027  1.00  21.37      X    O
ATOM   6674  C    TYR  59      90.857  33.605  30.910  1.00  29.06      X    C
ATOM   6675  O    TYR  59      91.575  34.287  31.648  1.00  29.06      X    O
ATOM   6676  N    LEU  60      89.745  33.002  31.308  1.00  26.45      X    N
ATOM   6677  CA   LEU  60      89.309  33.048  32.689  1.00  26.45      X    C
ATOM   6678  CB   LEU  60      87.927  32.397  32.826  1.00  24.21      X    C
ATOM   6679  CG   LEU  60      87.411  32.193  34.252  1.00  24.21      X    C
ATOM   6680  CD1  LEU  60      87.173  33.538  34.911  1.00  24.21      X    C
ATOM   6681  CD2  LEU  60      86.135  31.380  34.223  1.00  24.21      X    C
ATOM   6682  C    LEU  60      90.382  32.189  33.360  1.00  26.45      X    C
ATOM   6683  O    LEU  60      90.822  31.191  32.781  1.00  26.45      X    O
ATOM   6684  N    ASP  61      90.822  32.570  34.553  1.00  64.06      X    N
ATOM   6685  CA   ASP  61      91.865  31.810  35.240  1.00  64.06      X    C
ATOM   6686  CB   ASP  61      92.297  32.556  36.502  1.00  60.41      X    C
ATOM   6687  CG   ASP  61      92.984  33.865  36.183  1.00  60.41      X    C
ATOM   6688  OD1  ASP  61      93.262  34.650  37.114  1.00  60.41      X    O
ATOM   6689  OD2  ASP  61      93.250  34.106  34.986  1.00  60.41      X    O
ATOM   6690  C    ASP  61      91.477  30.371  35.576  1.00  64.06      X    C
ATOM   6691  O    ASP  61      92.337  29.503  35.701  1.00  64.06      X    O
ATOM   6692  N    SER  62      90.181  30.122  35.707  1.00  57.78      X    N
ATOM   6693  CA   SER  62      89.681  28.791  36.028  1.00  57.78      X    C
ATOM   6694  CB   SER  62      88.196  28.868  36.386  1.00  42.55      X    C
ATOM   6695  OG   SER  62      87.643  27.575  36.556  1.00  42.55      X    O
ATOM   6696  C    SER  62      89.872  27.787  34.894  1.00  57.78      X    C
ATOM   6697  O    SER  62      90.000  26.590  35.142  1.00  57.78      X    O
ATOM   6698  N    VAL  63      89.890  28.269  33.655  1.00  47.11      X    N
ATOM   6699  CA   VAL  63      90.047  27.383  32.504  1.00  47.11      X    C
ATOM   6700  CB   VAL  63      88.796  27.464  31.555  1.00  39.29      X    C
ATOM   6701  CG1  VAL  63      87.513  27.472  32.375  1.00  39.29      X    C
ATOM   6702  CG2  VAL  63      88.863  28.700  30.679  1.00  39.29      X    C
ATOM   6703  C    VAL  63      91.318  27.660  31.686  1.00  47.11      X    C
ATOM   6704  O    VAL  63      91.504  27.093  30.603  1.00  47.11      X    O
ATOM   6705  N    LYS  64      92.200  28.511  32.208  1.00  47.01      X    N
ATOM   6706  CA   LYS  64      93.424  28.843  31.483  1.00  47.01      X    C
ATOM   6707  CB   LYS  64      94.116  30.063  32.107  1.00  84.46      X    C
ATOM   6708  CG   LYS  64      95.038  30.797  31.135  1.00  84.46      X    C
ATOM   6709  CD   LYS  64      95.670  32.025  31.766  1.00  84.46      X    C
ATOM   6710  CE   LYS  64      96.370  32.907  30.725  1.00  84.46      X    C
ATOM   6711  NZ   LYS  64      95.419  33.654  29.833  1.00  84.46      X    N
ATOM   6712  C    LYS  64      94.388  27.666  31.441  1.00  47.01      X    C
ATOM   6713  O    LYS  64      94.757  27.113  32.479  1.00  47.01      X    O
ATOM   6714  N    GLY  65      94.795  27.289  30.231  1.00  35.35      X    N
ATOM   6715  CA   GLY  65      95.704  26.167  30.073  1.00  35.35      X    C
ATOM   6716  C    GLY  65      94.953  24.919  29.652  1.00  35.35      X    C
```

Fig. 19: A-93

```
ATOM   6717  O    GLY  65   95.547  23.945  29.195  1.00  35.35  X  O
ATOM   6718  N    ARG  66   93.634  24.956  29.809  1.00  33.32  X  N
ATOM   6719  CA   ARG  66   92.791  23.833  29.450  1.00  33.32  X  C
ATOM   6720  CB   ARG  66   91.881  23.470  30.616  1.00  43.17  X  C
ATOM   6721  CG   ARG  66   92.594  23.386  31.958  1.00  43.17  X  C
ATOM   6722  CD   ARG  66   91.684  22.813  33.050  1.00  43.17  X  C
ATOM   6723  NE   ARG  66   90.548  23.679  33.367  1.00  43.17  X  N
ATOM   6724  CZ   ARG  66   89.277  23.296  33.305  1.00  43.17  X  C
ATOM   6725  NH1  ARG  66   88.973  22.061  32.932  1.00  43.17  X  N
ATOM   6726  NH2  ARG  66   88.309  24.144  33.630  1.00  43.17  X  N
ATOM   6727  C    ARG  66   91.945  24.169  28.232  1.00  33.32  X  C
ATOM   6728  O    ARG  66   91.775  23.336  27.346  1.00  33.32  X  O
ATOM   6729  N    PHE  67   91.411  25.389  28.191  1.00  33.69  X  N
ATOM   6730  CA   PHE  67   90.567  25.834  27.074  1.00  33.69  X  C
ATOM   6731  CB   PHE  67   89.444  26.750  27.587  1.00  42.44  X  C
ATOM   6732  CG   PHE  67   88.346  26.030  28.330  1.00  42.44  X  C
ATOM   6733  CD1  PHE  67   88.573  24.802  28.943  1.00  42.44  X  C
ATOM   6734  CD2  PHE  67   87.074  26.594  28.426  1.00  42.44  X  C
ATOM   6735  CE1  PHE  67   87.547  24.145  29.637  1.00  42.44  X  C
ATOM   6736  CE2  PHE  67   86.038  25.940  29.122  1.00  42.44  X  C
ATOM   6737  CZ   PHE  67   86.278  24.717  29.724  1.00  42.44  X  C
ATOM   6738  C    PHE  67   91.393  26.578  26.027  1.00  33.69  X  C
ATOM   6739  O    PHE  67   92.405  27.194  26.344  1.00  33.69  X  O
ATOM   6740  N    THR  68   90.949  26.526  24.779  1.00  56.59  X  N
ATOM   6741  CA   THR  68   91.646  27.201  23.689  1.00  56.59  X  C
ATOM   6742  CB   THR  68   92.454  26.193  22.846  1.00  46.98  X  C
ATOM   6743  OG1  THR  68   93.611  25.781  23.578  1.00  46.98  X  O
ATOM   6744  CG2  THR  68   92.870  26.808  21.512  1.00  46.98  X  C
ATOM   6745  C    THR  68   90.661  27.913  22.768  1.00  56.59  X  C
ATOM   6746  O    THR  68   89.899  27.270  22.047  1.00  56.59  X  O
ATOM   6747  N    ILE  69   90.672  29.239  22.781  1.00  20.15  X  N
ATOM   6748  CA   ILE  69   89.760  29.975  21.918  1.00  20.15  X  C
ATOM   6749  CB   ILE  69   89.287  31.289  22.607  1.00  31.46  X  C
ATOM   6750  CG2  ILE  69   90.480  32.153  22.953  1.00  31.46  X  C
ATOM   6751  CG1  ILE  69   88.283  32.028  21.722  1.00  31.46  X  C
ATOM   6752  CD1  ILE  69   87.574  33.159  22.446  1.00  31.46  X  C
ATOM   6753  C    ILE  69   90.464  30.262  20.591  1.00  20.15  X  C
ATOM   6754  O    ILE  69   91.672  30.481  20.559  1.00  20.15  X  O
ATOM   6755  N    SER  70   89.724  30.223  19.489  1.00  21.14  X  N
ATOM   6756  CA   SER  70   90.319  30.482  18.182  1.00  21.14  X  C
ATOM   6757  CB   SER  70   91.105  29.263  17.693  1.00  37.41  X  C
ATOM   6758  OG   SER  70   90.228  28.236  17.253  1.00  37.41  X  O
ATOM   6759  C    SER  70   89.242  30.824  17.163  1.00  21.14  X  C
ATOM   6760  O    SER  70   88.045  30.637  17.413  1.00  21.14  X  O
ATOM   6761  N    ARG  71   89.673  31.322  16.009  1.00  30.73  X  N
ATOM   6762  CA   ARG  71   88.734  31.687  14.966  1.00  30.73  X  C
ATOM   6763  CB   ARG  71   88.369  33.178  15.073  1.00  24.51  X  C
ATOM   6764  CG   ARG  71   89.546  34.139  14.901  1.00  24.51  X  C
ATOM   6765  CD   ARG  71   89.071  35.503  14.453  1.00  24.51  X  C
ATOM   6766  NE   ARG  71   88.464  36.278  15.534  1.00  24.51  X  N
ATOM   6767  CZ   ARG  71   87.604  37.283  15.351  1.00  24.51  X  C
ATOM   6768  NH1  ARG  71   87.229  37.643  14.131  1.00  24.51  X  N
ATOM   6769  NH2  ARG  71   87.132  37.948  16.391  1.00  24.51  X  N
ATOM   6770  C    ARG  71   89.259  31.393  13.560  1.00  30.73  X  C
ATOM   6771  O    ARG  71   90.464  31.415  13.301  1.00  30.73  X  O
ATOM   6772  N    ASP  72   88.326  31.106  12.663  1.00  55.72  X  N
ATOM   6773  CA   ASP  72   88.619  30.836  11.268  1.00  55.72  X  C
ATOM   6774  CB   ASP  72   88.219  29.405  10.902  1.00  83.09  X  C
ATOM   6775  CG   ASP  72   88.255  29.153   9.409  1.00  83.09  X  C
ATOM   6776  OD1  ASP  72   89.282  29.466   8.773  1.00  83.09  X  O
ATOM   6777  OD2  ASP  72   87.256  28.637   8.870  1.00  83.09  X  O
ATOM   6778  C    ASP  72   87.749  31.837  10.528  1.00  55.72  X  C
ATOM   6779  O    ASP  72   86.613  31.539  10.162  1.00  55.72  X  O
ATOM   6780  N    ASN  73   88.284  33.036  10.340  1.00  57.89  X  N
ATOM   6781  CA   ASN  73   87.552  34.098   9.673  1.00  57.89  X  C
ATOM   6782  CB   ASN  73   88.426  35.345   9.558  1.00  43.96  X  C
ATOM   6783  CG   ASN  73   88.777  35.928  10.912  1.00  43.96  X  C
ATOM   6784  OD1  ASN  73   88.021  35.794  11.879  1.00  43.96  X  O
ATOM   6785  ND2  ASN  73   89.919  36.593  10.986  1.00  43.96  X  N
ATOM   6786  C    ASN  73   87.020  33.715   8.306  1.00  57.89  X  C
ATOM   6787  O    ASN  73   85.949  34.173   7.903  1.00  57.89  X  O
ATOM   6788  N    SER  74   87.756  32.870   7.594  1.00  50.09  X  N
ATOM   6789  CA   SER  74   87.324  32.451   6.268  1.00  50.09  X  C
```

Fig. 19: A-94

```
ATOM   6790  CB   SER   74      88.277  31.398   5.705  1.00  34.87      X    C
ATOM   6791  OG   SER   74      88.179  30.197   6.441  1.00  34.87      X    O
ATOM   6792  C    SER   74      85.910  31.880   6.303  1.00  50.09      X    C
ATOM   6793  O    SER   74      85.141  32.050   5.356  1.00  50.09      X    O
ATOM   6794  N    LYS   75      85.572  31.209   7.400  1.00  50.16      X    N
ATOM   6795  CA   LYS   75      84.257  30.597   7.551  1.00  50.16      X    C
ATOM   6796  CB   LYS   75      84.418  29.097   7.814  1.00  60.89      X    C
ATOM   6797  CG   LYS   75      85.206  28.372   6.729  1.00  60.89      X    C
ATOM   6798  CD   LYS   75      85.356  26.884   7.009  1.00  60.89      X    C
ATOM   6799  CE   LYS   75      86.046  26.195   5.840  1.00  60.89      X    C
ATOM   6800  NZ   LYS   75      85.341  26.459   4.551  1.00  60.89      X    N
ATOM   6801  C    LYS   75      83.423  31.226   8.663  1.00  50.16      X    C
ATOM   6802  O    LYS   75      82.470  30.618   9.142  1.00  50.16      X    O
ATOM   6803  N    ASN   76      83.786  32.441   9.066  1.00  54.49      X    N
ATOM   6804  CA   ASN   76      83.075  33.165  10.117  1.00  54.49      X    C
ATOM   6805  CB   ASN   76      81.812  33.818   9.559  1.00  41.29      X    C
ATOM   6806  CG   ASN   76      82.116  34.956   8.620  1.00  41.29      X    C
ATOM   6807  OD1  ASN   76      81.399  35.956   8.592  1.00  41.29      X    O
ATOM   6808  ND2  ASN   76      83.181  34.812   7.839  1.00  41.29      X    N
ATOM   6809  C    ASN   76      82.684  32.285  11.286  1.00  54.49      X    C
ATOM   6810  O    ASN   76      81.523  32.278  11.706  1.00  54.49      X    O
ATOM   6811  N    THR   77      83.645  31.550  11.827  1.00  48.88      X    N
ATOM   6812  CA   THR   77      83.325  30.675  12.938  1.00  48.88      X    C
ATOM   6813  CB   THR   77      83.321  29.215  12.481  1.00  67.62      X    C
ATOM   6814  OG1  THR   77      82.318  29.048  11.469  1.00  67.62      X    O
ATOM   6815  CG2  THR   77      83.028  28.284  13.653  1.00  67.62      X    C
ATOM   6816  C    THR   77      84.245  30.817  14.132  1.00  48.88      X    C
ATOM   6817  O    THR   77      85.463  30.858  13.990  1.00  48.88      X    O
ATOM   6818  N    LEU   78      83.641  30.900  15.313  1.00  25.08      X    N
ATOM   6819  CA   LEU   78      84.387  31.014  16.562  1.00  25.08      X    C
ATOM   6820  CB   LEU   78      83.739  32.047  17.488  1.00  24.57      X    C
ATOM   6821  CG   LEU   78      84.362  32.022  18.881  1.00  24.57      X    C
ATOM   6822  CD1  LEU   78      85.757  32.625  18.789  1.00  24.57      X    C
ATOM   6823  CD2  LEU   78      83.507  32.770  19.868  1.00  24.57      X    C
ATOM   6824  C    LEU   78      84.370  29.653  17.250  1.00  25.08      X    C
ATOM   6825  O    LEU   78      83.312  29.041  17.389  1.00  25.08      X    O
ATOM   6826  N    TYR   79      85.530  29.179  17.687  1.00  41.94      X    N
ATOM   6827  CA   TYR   79      85.595  27.880  18.344  1.00  41.94      X    C
ATOM   6828  CB   TYR   79      86.608  26.963  17.657  1.00  47.62      X    C
ATOM   6829  CG   TYR   79      86.328  26.619  16.226  1.00  47.62      X    C
ATOM   6830  CD1  TYR   79      85.264  25.794  15.887  1.00  47.62      X    C
ATOM   6831  CE1  TYR   79      85.008  25.460  14.559  1.00  47.62      X    C
ATOM   6832  CD2  TYR   79      87.139  27.108  15.207  1.00  47.62      X    C
ATOM   6833  CE2  TYR   79      86.896  26.784  13.878  1.00  47.62      X    C
ATOM   6834  CZ   TYR   79      85.826  25.959  13.559  1.00  47.62      X    C
ATOM   6835  OH   TYR   79      85.564  25.640  12.245  1.00  47.62      X    O
ATOM   6836  C    TYR   79      86.043  27.991  19.779  1.00  41.94      X    C
ATOM   6837  O    TYR   79      86.890  28.824  20.100  1.00  41.94      X    O
ATOM   6838  N    LEU   80      85.470  27.160  20.642  1.00  19.15      X    N
ATOM   6839  CA   LEU   80      85.917  27.110  22.022  1.00  19.15      X    C
ATOM   6840  CB   LEU   80      84.809  27.382  23.047  1.00  21.08      X    C
ATOM   6841  CG   LEU   80      85.271  27.127  24.510  1.00  21.08      X    C
ATOM   6842  CD1  LEU   80      86.500  27.981  24.840  1.00  21.08      X    C
ATOM   6843  CD2  LEU   80      84.142  27.412  25.503  1.00  21.08      X    C
ATOM   6844  C    LEU   80      86.342  25.671  22.129  1.00  19.15      X    C
ATOM   6845  O    LEU   80      85.517  24.769  21.941  1.00  19.15      X    O
ATOM   6846  N    GLN   81      87.631  25.455  22.395  1.00  31.28      X    N
ATOM   6847  CA   GLN   81      88.193  24.111  22.530  1.00  31.28      X    C
ATOM   6848  CB   GLN   81      89.497  24.015  21.738  1.00  68.87      X    C
ATOM   6849  CG   GLN   81      90.141  22.647  21.783  1.00  68.87      X    C
ATOM   6850  CD   GLN   81      89.318  21.580  21.075  1.00  68.87      X    C
ATOM   6851  OE1  GLN   81      89.101  21.648  19.864  1.00  68.87      X    O
ATOM   6852  NE2  GLN   81      88.857  20.588  21.831  1.00  68.87      X    N
ATOM   6853  C    GLN   81      88.448  23.775  24.001  1.00  31.28      X    C
ATOM   6854  O    GLN   81      89.402  24.260  24.604  1.00  31.28      X    O
ATOM   6855  N    MET   82      87.589  22.935  24.569  1.00  32.50      X    N
ATOM   6856  CA   MET   82      87.701  22.541  25.975  1.00  32.50      X    C
ATOM   6857  CB   MET   82      86.297  22.429  26.589  1.00  41.50      X    C
ATOM   6858  CG   MET   82      85.537  23.752  26.653  1.00  41.50      X    C
ATOM   6859  SD   MET   82      83.790  23.594  27.062  1.00  41.50      X    S
ATOM   6860  CE   MET   82      83.088  23.391  25.452  1.00  41.50      X    C
ATOM   6861  C    MET   82      88.463  21.230  26.188  1.00  32.50      X    C
ATOM   6862  O    MET   82      88.239  20.250  25.487  1.00  32.50      X    O
```

Fig. 19: A-95

| | | | | | | | | | | |
|---|---|---|---|---|---|---|---|---|---|---|
| ATOM | 6863 | N | ASN | 83 | 89.369 | 21.224 | 27.160 | 1.00 | 43.69 | X N |
| ATOM | 6864 | CA | ASN | 83 | 90.155 | 20.032 | 27.459 | 1.00 | 43.69 | X C |
| ATOM | 6865 | CB | ASN | 83 | 91.574 | 20.157 | 26.883 | 1.00 | 34.50 | X C |
| ATOM | 6866 | CG | ASN | 83 | 91.574 | 20.391 | 25.383 | 1.00 | 34.50 | X C |
| ATOM | 6867 | OD1 | ASN | 83 | 90.920 | 19.670 | 24.636 | 1.00 | 34.50 | X O |
| ATOM | 6868 | ND2 | ASN | 83 | 92.313 | 21.401 | 24.937 | 1.00 | 34.50 | X N |
| ATOM | 6869 | C | ASN | 83 | 90.225 | 19.855 | 28.967 | 1.00 | 43.69 | X C |
| ATOM | 6870 | O | ASN | 83 | 90.054 | 20.822 | 29.705 | 1.00 | 43.69 | X O |
| ATOM | 6871 | N | SER | 84 | 90.480 | 18.625 | 29.416 | 1.00 | 47.01 | X N |
| ATOM | 6872 | CA | SER | 84 | 90.560 | 18.322 | 30.843 | 1.00 | 47.01 | X C |
| ATOM | 6873 | CB | SER | 84 | 91.748 | 19.045 | 31.482 | 1.00 | 36.84 | X C |
| ATOM | 6874 | OG | SER | 84 | 92.963 | 18.623 | 30.892 | 1.00 | 36.84 | X O |
| ATOM | 6875 | C | SER | 84 | 89.270 | 18.757 | 31.516 | 1.00 | 47.01 | X C |
| ATOM | 6876 | O | SER | 84 | 89.272 | 19.261 | 32.644 | 1.00 | 47.01 | X O |
| ATOM | 6877 | N | LEU | 85 | 88.170 | 18.548 | 30.804 | 1.00 | 35.88 | X N |
| ATOM | 6878 | CA | LEU | 85 | 86.842 | 18.920 | 31.273 | 1.00 | 35.88 | X C |
| ATOM | 6879 | CB | LEU | 85 | 85.800 | 18.466 | 30.250 | 1.00 | 45.16 | X C |
| ATOM | 6880 | CG | LEU | 85 | 85.854 | 19.211 | 28.921 | 1.00 | 45.16 | X C |
| ATOM | 6881 | CD1 | LEU | 85 | 84.875 | 18.608 | 27.936 | 1.00 | 45.16 | X C |
| ATOM | 6882 | CD2 | LEU | 85 | 85.536 | 20.672 | 29.178 | 1.00 | 45.16 | X C |
| ATOM | 6883 | C | LEU | 85 | 86.450 | 18.396 | 32.652 | 1.00 | 35.88 | X C |
| ATOM | 6884 | O | LEU | 85 | 86.175 | 17.208 | 32.818 | 1.00 | 35.88 | X O |
| ATOM | 6885 | N | ARG | 86 | 86.415 | 19.290 | 33.636 | 1.00 | 55.90 | X N |
| ATOM | 6886 | CA | ARG | 86 | 86.022 | 18.907 | 34.985 | 1.00 | 55.90 | X C |
| ATOM | 6887 | CB | ARG | 86 | 86.606 | 19.864 | 36.023 | 1.00 | 50.18 | X C |
| ATOM | 6888 | CG | ARG | 86 | 88.108 | 20.015 | 35.994 | 1.00 | 50.18 | X C |
| ATOM | 6889 | CD | ARG | 86 | 88.620 | 20.357 | 37.385 | 1.00 | 50.18 | X C |
| ATOM | 6890 | NE | ARG | 86 | 89.970 | 20.904 | 37.355 | 1.00 | 50.18 | X N |
| ATOM | 6891 | CZ | ARG | 86 | 90.256 | 22.185 | 37.133 | 1.00 | 50.18 | X C |
| ATOM | 6892 | NH1 | ARG | 86 | 89.280 | 23.066 | 36.926 | 1.00 | 50.18 | X N |
| ATOM | 6893 | NH2 | ARG | 86 | 91.524 | 22.587 | 37.109 | 1.00 | 50.18 | X N |
| ATOM | 6894 | C | ARG | 86 | 84.501 | 18.954 | 35.069 | 1.00 | 55.90 | X C |
| ATOM | 6895 | O | ARG | 86 | 83.818 | 19.086 | 34.055 | 1.00 | 55.90 | X O |
| ATOM | 6896 | N | ALA | 87 | 83.974 | 18.856 | 36.282 | 1.00 | 39.09 | X N |
| ATOM | 6897 | CA | ALA | 87 | 82.533 | 18.893 | 36.485 | 1.00 | 39.09 | X C |
| ATOM | 6898 | CB | ALA | 87 | 82.164 | 18.133 | 37.750 | 1.00 | 69.79 | X C |
| ATOM | 6899 | C | ALA | 87 | 82.028 | 20.325 | 36.578 | 1.00 | 39.09 | X C |
| ATOM | 6900 | O | ALA | 87 | 80.885 | 20.607 | 36.219 | 1.00 | 39.09 | X O |
| ATOM | 6901 | N | GLU | 88 | 82.876 | 21.228 | 37.066 | 1.00 | 49.44 | X N |
| ATOM | 6902 | CA | GLU | 88 | 82.492 | 22.628 | 37.197 | 1.00 | 49.44 | X C |
| ATOM | 6903 | CB | GLU | 88 | 83.586 | 23.435 | 37.899 | 1.00 | 57.40 | X C |
| ATOM | 6904 | CG | GLU | 88 | 84.189 | 22.765 | 39.107 | 1.00 | 57.40 | X C |
| ATOM | 6905 | CD | GLU | 88 | 85.178 | 21.691 | 38.724 | 1.00 | 57.40 | X C |
| ATOM | 6906 | OE1 | GLU | 88 | 86.227 | 22.035 | 38.146 | 1.00 | 57.40 | X O |
| ATOM | 6907 | OE2 | GLU | 88 | 84.906 | 20.504 | 38.993 | 1.00 | 57.40 | X O |
| ATOM | 6908 | C | GLU | 88 | 82.242 | 23.242 | 35.824 | 1.00 | 49.44 | X C |
| ATOM | 6909 | O | GLU | 88 | 81.474 | 24.195 | 35.687 | 1.00 | 49.44 | X O |
| ATOM | 6910 | N | ASP | 89 | 82.892 | 22.698 | 34.803 | 1.00 | 49.12 | X N |
| ATOM | 6911 | CA | ASP | 89 | 82.720 | 23.229 | 33.464 | 1.00 | 49.12 | X C |
| ATOM | 6912 | CB | ASP | 89 | 83.818 | 22.698 | 32.549 | 1.00 | 52.75 | X C |
| ATOM | 6913 | CG | ASP | 89 | 85.194 | 22.903 | 33.124 | 1.00 | 52.75 | X C |
| ATOM | 6914 | OD1 | ASP | 89 | 85.430 | 23.960 | 33.752 | 1.00 | 52.75 | X O |
| ATOM | 6915 | OD2 | ASP | 89 | 86.043 | 22.011 | 32.936 | 1.00 | 52.75 | X O |
| ATOM | 6916 | C | ASP | 89 | 81.348 | 22.914 | 32.871 | 1.00 | 49.12 | X C |
| ATOM | 6917 | O | ASP | 89 | 80.981 | 23.459 | 31.834 | 1.00 | 49.12 | X O |
| ATOM | 6918 | N | THR | 90 | 80.590 | 22.034 | 33.517 | 1.00 | 33.14 | X N |
| ATOM | 6919 | CA | THR | 90 | 79.265 | 21.686 | 33.012 | 1.00 | 33.14 | X C |
| ATOM | 6920 | CB | THR | 90 | 78.652 | 20.480 | 33.766 | 1.00 | 40.77 | X C |
| ATOM | 6921 | CG1 | THR | 90 | 78.585 | 20.770 | 35.162 | 1.00 | 40.77 | X O |
| ATOM | 6922 | CG2 | THR | 90 | 79.498 | 19.257 | 33.590 | 1.00 | 40.77 | X C |
| ATOM | 6923 | C | THR | 90 | 78.361 | 22.899 | 33.174 | 1.00 | 33.14 | X C |
| ATOM | 6924 | O | THR | 90 | 78.260 | 23.486 | 34.263 | 1.00 | 33.14 | X O |
| ATOM | 6925 | N | ALA | 91 | 77.718 | 23.276 | 32.076 | 1.00 | 55.37 | X N |
| ATOM | 6926 | CA | ALA | 91 | 76.832 | 24.428 | 32.058 | 1.00 | 55.37 | X C |
| ATOM | 6927 | CB | ALA | 91 | 77.527 | 25.625 | 32.692 | 1.00 | 7.95 | X C |
| ATOM | 6928 | C | ALA | 91 | 76.504 | 24.732 | 30.609 | 1.00 | 55.37 | X C |
| ATOM | 6929 | O | ALA | 91 | 77.073 | 24.128 | 29.698 | 1.00 | 55.37 | X O |
| ATOM | 6930 | N | VAL | 92 | 75.579 | 25.656 | 30.387 | 1.00 | 44.83 | X N |
| ATOM | 6931 | CA | VAL | 92 | 75.243 | 26.017 | 29.021 | 1.00 | 44.83 | X C |
| ATOM | 6932 | CB | VAL | 92 | 73.747 | 26.429 | 28.878 | 1.00 | 41.51 | X C |
| ATOM | 6933 | CG1 | VAL | 92 | 73.210 | 26.967 | 30.198 | 1.00 | 41.51 | X C |
| ATOM | 6934 | CG2 | VAL | 92 | 73.596 | 27.460 | 27.769 | 1.00 | 41.51 | X C |
| ATOM | 6935 | C | VAL | 92 | 76.182 | 27.145 | 28.591 | 1.00 | 44.83 | X C |

Fig. 19: A-96

```
ATOM   6936  O    VAL   92      76.446  28.085  29.354  1.00  44.83      X   O
ATOM   6937  N    TYR   93      76.701  27.019  27.371  1.00  51.76      X   N
ATOM   6938  CA   TYR   93      77.642  27.978  26.811  1.00  51.76      X   C
ATOM   6939  CB   TYR   93      78.838  27.241  26.227  1.00  15.58      X   C
ATOM   6940  CG   TYR   93      79.743  26.693  27.287  1.00  15.58      X   C
ATOM   6941  CD1  TYR   93      79.520  25.443  27.841  1.00  15.58      X   C
ATOM   6942  CE1  TYR   93      80.339  24.959  28.860  1.00  15.58      X   C
ATOM   6943  CD2  TYR   93      80.802  27.454  27.777  1.00  15.58      X   C
ATOM   6944  CE2  TYR   93      81.618  26.983  28.797  1.00  15.58      X   C
ATOM   6945  CZ   TYR   93      81.384  25.735  29.328  1.00  15.58      X   C
ATOM   6946  OH   TYR   93      82.223  25.253  30.297  1.00  15.58      X   O
ATOM   6947  C    TYR   93      77.091  28.908  25.757  1.00  51.76      X   C
ATOM   6948  O    TYR   93      76.223  28.534  24.972  1.00  51.76      X   O
ATOM   6949  N    TYR   94      77.633  30.121  25.729  1.00  29.82      X   N
ATOM   6950  CA   TYR   94      77.210  31.143  24.774  1.00  29.82      X   C
ATOM   6951  CB   TYR   94      76.448  32.267  25.489  1.00  45.66      X   C
ATOM   6952  CG   TYR   94      75.282  31.829  26.343  1.00  45.66      X   C
ATOM   6953  CD1  TYR   94      74.053  31.494  25.771  1.00  45.66      X   C
ATOM   6954  CE1  TYR   94      72.979  31.108  26.564  1.00  45.66      X   C
ATOM   6955  CD2  TYR   94      75.405  31.763  27.733  1.00  45.66      X   C
ATOM   6956  CE2  TYR   94      74.342  31.376  28.532  1.00  45.66      X   C
ATOM   6957  CZ   TYR   94      73.132  31.051  27.943  1.00  45.66      X   C
ATOM   6958  OH   TYR   94      72.082  30.665  28.743  1.00  45.66      X   O
ATOM   6959  C    TYR   94      78.389  31.799  24.074  1.00  29.82      X   C
ATOM   6960  O    TYR   94      79.360  32.174  24.727  1.00  29.82      X   O
ATOM   6961  N    CYS   95      78.332  31.923  22.752  1.00  22.64      X   N
ATOM   6962  CA   CYS   95      79.394  32.659  22.091  1.00  22.64      X   C
ATOM   6963  C    CYS   95      78.871  34.094  22.103  1.00  22.64      X   C
ATOM   6964  O    CYS   95      77.656  34.337  22.170  1.00  22.64      X   O
ATOM   6965  CB   CYS   95      79.660  32.185  20.660  1.00  55.79      X   C
ATOM   6966  SG   CYS   95      78.222  31.748  19.650  1.00  55.79      X   S
ATOM   6967  N    THR   96      79.778  35.057  22.067  1.00  43.77      X   N
ATOM   6968  CA   THR   96      79.337  36.435  22.107  1.00  43.77      X   C
ATOM   6969  CB   THR   96      79.387  36.985  23.556  1.00  38.47      X   C
ATOM   6970  OG1  THR   96      80.723  36.865  24.069  1.00  38.47      X   O
ATOM   6971  CG2  THR   96      78.421  36.220  24.453  1.00  38.47      X   C
ATOM   6972  C    THR   96      80.130  37.370  21.220  1.00  43.77      X   C
ATOM   6973  O    THR   96      81.328  37.174  20.987  1.00  43.77      X   O
ATOM   6974  N    ARG   97      79.432  38.379  20.709  1.00  52.60      X   N
ATOM   6975  CA   ARG   97      80.068  39.400  19.899  1.00  52.60      X   C
ATOM   6976  CB   ARG   97      79.237  39.799  18.689  1.00  26.06      X   C
ATOM   6977  CG   ARG   97      80.052  40.645  17.733  1.00  26.06      X   C
ATOM   6978  CD   ARG   97      79.235  41.249  16.624  1.00  26.06      X   C
ATOM   6979  NE   ARG   97      78.494  42.412  17.074  1.00  26.06      X   N
ATOM   6980  CZ   ARG   97      77.853  43.231  16.255  1.00  26.06      X   C
ATOM   6981  NH1  ARG   97      77.873  43.004  14.948  1.00  26.06      X   N
ATOM   6982  NH2  ARG   97      77.187  44.271  16.742  1.00  26.06      X   N
ATOM   6983  C    ARG   97      80.142  40.590  20.820  1.00  52.60      X   C
ATOM   6984  O    ARG   97      79.116  41.100  21.260  1.00  52.60      X   O
ATOM   6985  N    GLY   98      81.353  41.020  21.129  1.00  31.82      X   N
ATOM   6986  CA   GLY   98      81.505  42.162  22.004  1.00  31.82      X   C
ATOM   6987  C    GLY   98      81.635  43.450  21.225  1.00  31.82      X   C
ATOM   6988  O    GLY   98      81.903  43.452  20.020  1.00  31.82      X   O
ATOM   6989  N    PHE   99      81.416  44.558  21.913  1.00  20.36      X   N
ATOM   6990  CA   PHE   99      81.554  45.859  21.289  1.00  20.36      X   C
ATOM   6991  CB   PHE   99      80.358  46.753  21.621  1.00  37.93      X   C
ATOM   6992  CG   PHE   99      80.633  48.214  21.431  1.00  37.93      X   C
ATOM   6993  CD1  PHE   99      80.968  49.015  22.517  1.00  37.93      X   C
ATOM   6994  CD2  PHE   99      80.606  48.783  20.158  1.00  37.93      X   C
ATOM   6995  CE1  PHE   99      81.276  50.355  22.339  1.00  37.93      X   C
ATOM   6996  CE2  PHE   99      80.913  50.127  19.967  1.00  37.93      X   C
ATOM   6997  CZ   PHE   99      81.250  50.914  21.058  1.00  37.93      X   C
ATOM   6998  C    PHE   99      82.836  46.468  21.835  1.00  20.36      X   C
ATOM   6999  O    PHE   99      83.239  46.164  22.969  1.00  20.36      X   O
ATOM   7000  N    GLY  100      83.480  47.309  21.030  1.00  25.28      X   N
ATOM   7001  CA   GLY  100      84.704  47.954  21.469  1.00  25.28      X   C
ATOM   7002  C    GLY  100      85.850  46.983  21.672  1.00  25.28      X   C
ATOM   7003  O    GLY  100      86.390  46.466  20.700  1.00  25.28      X   O
ATOM   7004  N    ASP  101      86.231  46.744  22.926  1.00  27.39      X   N
ATOM   7005  CA   ASP  101      87.315  45.814  23.233  1.00  27.39      X   C
ATOM   7006  CB   ASP  101      88.175  46.338  24.396  1.00  32.17      X   C
ATOM   7007  CG   ASP  101      89.037  47.540  24.013  1.00  32.17      X   C
ATOM   7008  OD1  ASP  101      89.287  47.744  22.812  1.00  32.17      X   O
```

Fig. 19: A-97

```
ATOM   7009  OD2 ASP   101      89.483  48.274  24.920  1.00  32.17      X    O
ATOM   7010  C   ASP   101      86.773  44.418  23.596  1.00  27.39      X    C
ATOM   7011  O   ASP   101      87.549  43.518  23.929  1.00  27.39      X    O
ATOM   7012  N   GLY   102      85.449  44.250  23.538  1.00  18.22      X    N
ATOM   7013  CA  GLY   102      84.822  42.973  23.861  1.00  18.22      X    C
ATOM   7014  C   GLY   102      83.925  42.948  25.100  1.00  18.22      X    C
ATOM   7015  O   GLY   102      83.031  42.113  25.198  1.00  18.22      X    O
ATOM   7016  N   GLY   103      84.147  43.870  26.034  1.00  34.16      X    N
ATOM   7017  CA  GLY   103      83.370  43.915  27.268  1.00  34.16      X    C
ATOM   7018  C   GLY   103      81.850  43.964  27.216  1.00  34.16      X    C
ATOM   7019  O   GLY   103      81.182  43.416  28.087  1.00  34.16      X    O
ATOM   7020  N   TYR   104      81.290  44.649  26.230  1.00  25.31      X    N
ATOM   7021  CA  TYR   104      79.839  44.732  26.096  1.00  25.31      X    C
ATOM   7022  CB  TYR   104      79.433  46.131  25.639  1.00  26.21      X    C
ATOM   7023  CG  TYR   104      77.989  46.260  25.234  1.00  26.21      X    C
ATOM   7024  CD1 TYR   104      77.635  46.980  24.087  1.00  26.21      X    C
ATOM   7025  CE1 TYR   104      76.309  47.079  23.677  1.00  26.21      X    C
ATOM   7026  CD2 TYR   104      76.972  45.646  25.972  1.00  26.21      X    C
ATOM   7027  CE2 TYR   104      75.639  45.742  25.573  1.00  26.21      X    C
ATOM   7028  CZ  TYR   104      75.323  46.456  24.422  1.00  26.21      X    C
ATOM   7029  OH  TYR   104      74.025  46.523  23.995  1.00  26.21      X    O
ATOM   7030  C   TYR   104      79.484  43.700  25.037  1.00  25.31      X    C
ATOM   7031  O   TYR   104      79.905  43.810  23.886  1.00  25.31      X    O
ATOM   7032  N   PHE   105      78.728  42.686  25.432  1.00  17.54      X    N
ATOM   7033  CA  PHE   105      78.354  41.616  24.518  1.00  17.54      X    C
ATOM   7034  CB  PHE   105      78.088  40.337  25.309  1.00  20.12      X    C
ATOM   7035  CG  PHE   105      79.154  40.010  26.312  1.00  20.12      X    C
ATOM   7036  CD1 PHE   105      80.478  39.817  25.908  1.00  20.12      X    C
ATOM   7037  CD2 PHE   105      78.832  39.891  27.661  1.00  20.12      X    C
ATOM   7038  CE1 PHE   105      81.472  39.511  26.836  1.00  20.12      X    C
ATOM   7039  CE2 PHE   105      79.808  39.586  28.594  1.00  20.12      X    C
ATOM   7040  CZ  PHE   105      81.136  39.395  28.183  1.00  20.12      X    C
ATOM   7041  C   PHE   105      77.127  41.938  23.669  1.00  17.54      X    C
ATOM   7042  O   PHE   105      75.989  41.689  24.080  1.00  17.54      X    O
ATOM   7043  N   ASP   106      77.376  42.488  22.482  1.00  46.21      X    N
ATOM   7044  CA  ASP   106      76.327  42.840  21.532  1.00  46.21      X    C
ATOM   7045  CB  ASP   106      76.908  43.074  20.143  1.00  54.80      X    C
ATOM   7046  CG  ASP   106      77.456  44.442  19.976  1.00  54.80      X    C
ATOM   7047  OD1 ASP   106      76.774  45.384  20.429  1.00  54.80      X    O
ATOM   7048  OD2 ASP   106      78.552  44.576  19.387  1.00  54.80      X    O
ATOM   7049  C   ASP   106      75.355  41.705  21.399  1.00  46.21      X    C
ATOM   7050  O   ASP   106      74.281  41.707  21.974  1.00  46.21      X    O
ATOM   7051  N   VAL   107      75.769  40.732  20.603  1.00  33.04      X    N
ATOM   7052  CA  VAL   107      74.979  39.559  20.312  1.00  33.04      X    C
ATOM   7053  CB  VAL   107      75.180  39.152  18.858  1.00  31.62      X    C
ATOM   7054  CG1 VAL   107      74.156  38.100  18.457  1.00  31.62      X    C
ATOM   7055  CG2 VAL   107      75.092  40.388  17.980  1.00  31.62      X    C
ATOM   7056  C   VAL   107      75.322  38.379  21.197  1.00  33.04      X    C
ATOM   7057  O   VAL   107      76.413  38.296  21.763  1.00  33.04      X    O
ATOM   7058  N   TRP   108      74.359  37.474  21.306  1.00  37.95      X    N
ATOM   7059  CA  TRP   108      74.501  36.266  22.092  1.00  37.95      X    C
ATOM   7060  CB  TRP   108      73.674  36.351  23.372  1.00  32.89      X    C
ATOM   7061  CG  TRP   108      74.212  37.315  24.368  1.00  32.89      X    C
ATOM   7062  CD2 TRP   108      74.712  37.004  25.668  1.00  32.89      X    C
ATOM   7063  CE2 TRP   108      75.114  38.216  26.261  1.00  32.89      X    C
ATOM   7064  CE3 TRP   108      74.861  35.816  26.390  1.00  32.89      X    C
ATOM   7065  CD1 TRP   108      74.327  38.664  24.225  1.00  32.89      X    C
ATOM   7066  NE1 TRP   108      74.867  39.216  25.358  1.00  32.89      X    N
ATOM   7067  CZ2 TRP   108      75.655  38.278  27.543  1.00  32.89      X    C
ATOM   7068  CZ3 TRP   108      75.402  35.878  27.670  1.00  32.89      X    C
ATOM   7069  CH2 TRP   108      75.792  37.103  28.231  1.00  32.89      X    C
ATOM   7070  C   TRP   108      73.984  35.119  21.260  1.00  37.95      X    C
ATOM   7071  O   TRP   108      73.067  35.296  20.451  1.00  37.95      X    O
ATOM   7072  N   GLY   109      74.568  33.942  21.460  1.00  75.91      X    N
ATOM   7073  CA  GLY   109      74.124  32.770  20.732  1.00  75.91      X    C
ATOM   7074  C   GLY   109      72.791  32.307  21.288  1.00  75.91      X    C
ATOM   7075  O   GLY   109      71.997  33.114  21.780  1.00  75.91      X    O
ATOM   7076  N   GLN   110      72.537  31.007  21.207  1.00  35.37      X    N
ATOM   7077  CA  GLN   110      71.291  30.457  21.724  1.00  35.37      X    C
ATOM   7078  CB  GLN   110      70.652  29.498  20.714  1.00  98.79      X    C
ATOM   7079  CG  GLN   110      71.443  28.228  20.442  1.00  98.79      X    C
ATOM   7080  CD  GLN   110      72.597  28.441  19.485  1.00  98.79      X    C
ATOM   7081  OE1 GLN   110      73.318  27.502  19.152  1.00  98.79      X    O
```

Fig. 19: A-98

```
ATOM   7082  NE2 GLN   110      72.775  29.675  19.031  1.00  98.79      X    N
ATOM   7083  C   GLN   110      71.610  29.708  23.004  1.00  35.37      X    C
ATOM   7084  O   GLN   110      70.793  29.626  23.918  1.00  35.37      X    O
ATOM   7085  N   GLY   111      72.831  29.194  23.067  1.00  45.85      X    N
ATOM   7086  CA  GLY   111      73.257  28.430  24.219  1.00  45.85      X    C
ATOM   7087  C   GLY   111      73.349  26.981  23.781  1.00  45.85      X    C
ATOM   7088  O   GLY   111      72.596  26.540  22.913  1.00  45.85      X    O
ATOM   7089  N   THR   112      74.281  26.243  24.369  1.00  30.06      X    N
ATOM   7090  CA  THR   112      74.480  24.840  24.040  1.00  30.06      X    C
ATOM   7091  CB  THR   112      75.550  24.696  22.962  1.00  24.67      X    C
ATOM   7092  OG1 THR   112      75.636  23.327  22.562  1.00  24.67      X    O
ATOM   7093  CG2 THR   112      76.903  25.177  23.487  1.00  24.67      X    C
ATOM   7094  C   THR   112      74.944  24.184  25.328  1.00  30.06      X    C
ATOM   7095  O   THR   112      75.883  24.658  25.960  1.00  30.06      X    O
ATOM   7096  N   LEU   113      74.292  23.102  25.725  1.00  42.99      X    N
ATOM   7097  CA  LEU   113      74.646  22.449  26.981  1.00  42.99      X    C
ATOM   7098  CB  LEU   113      73.434  21.652  27.499  1.00  32.90      X    C
ATOM   7099  CG  LEU   113      73.366  21.006  28.896  1.00  32.90      X    C
ATOM   7100  CD1 LEU   113      73.914  19.580  28.860  1.00  32.90      X    C
ATOM   7101  CD2 LEU   113      74.109  21.884  29.889  1.00  32.90      X    C
ATOM   7102  C   LEU   113      75.890  21.560  26.932  1.00  42.99      X    C
ATOM   7103  O   LEU   113      76.190  20.899  25.929  1.00  42.99      X    O
ATOM   7104  N   VAL   114      76.621  21.561  28.037  1.00  35.21      X    N
ATOM   7105  CA  VAL   114      77.815  20.754  28.141  1.00  35.21      X    C
ATOM   7106  CB  VAL   114      79.070  21.592  27.837  1.00  43.74      X    C
ATOM   7107  CG1 VAL   114      80.324  20.909  28.384  1.00  43.74      X    C
ATOM   7108  CG2 VAL   114      79.189  21.774  26.331  1.00  43.74      X    C
ATOM   7109  C   VAL   114      77.906  20.141  29.529  1.00  35.21      X    C
ATOM   7110  O   VAL   114      78.064  20.845  30.529  1.00  35.21      X    O
ATOM   7111  N   THR   115      77.788  18.819  29.575  1.00  58.81      X    N
ATOM   7112  CA  THR   115      77.855  18.099  30.829  1.00  58.81      X    C
ATOM   7113  CB  THR   115      76.717  17.098  30.956  1.00  63.66      X    C
ATOM   7114  OG1 THR   115      75.549  17.620  30.311  1.00  63.66      X    O
ATOM   7115  CG2 THR   115      76.412  16.849  32.422  1.00  63.66      X    C
ATOM   7116  C   THR   115      79.161  17.337  30.903  1.00  58.81      X    C
ATOM   7117  O   THR   115      79.831  17.121  29.893  1.00  58.81      X    O
ATOM   7118  N   VAL   116      79.516  16.933  32.114  1.00  73.79      X    N
ATOM   7119  CA  VAL   116      80.741  16.191  32.352  1.00  73.79      X    C
ATOM   7120  CB  VAL   116      81.899  17.135  32.747  1.00  46.90      X    C
ATOM   7121  CG1 VAL   116      83.172  16.339  32.941  1.00  46.90      X    C
ATOM   7122  CG2 VAL   116      82.101  18.194  31.667  1.00  46.90      X    C
ATOM   7123  C   VAL   116      80.478  15.202  33.482  1.00  73.79      X    C
ATOM   7124  O   VAL   116      80.382  15.584  34.649  1.00  73.79      X    O
ATOM   7125  N   SER   117      80.349  13.931  33.114  1.00  65.98      X    N
ATOM   7126  CA  SER   117      80.088  12.858  34.066  1.00  65.98      X    C
ATOM   7127  CB  SER   117      78.608  12.861  34.458  1.00  62.16      X    C
ATOM   7128  OG  SER   117      77.776  12.825  33.308  1.00  62.16      X    O
ATOM   7129  C   SER   117      80.454  11.521  33.427  1.00  65.98      X    C
ATOM   7130  O   SER   117      81.498  11.396  32.789  1.00  65.98      X    O
ATOM   7131  N   SER   118      79.587  10.524  33.594  1.00  80.64      X    N
ATOM   7132  CA  SER   118      79.828   9.208  33.014  1.00  80.64      X    C
ATOM   7133  CB  SER   118      80.556   8.329  34.031  1.00  66.12      X    C
ATOM   7134  OG  SER   118      81.771   8.944  34.438  1.00  66.12      X    O
ATOM   7135  C   SER   118      78.524   8.543  32.563  1.00  80.64      X    C
ATOM   7136  O   SER   118      77.445   9.021  32.973  1.00  79.69      X    O
ATOM   7137  OXT SER   118      78.594   7.553  31.804  1.00  65.17      X    O
ATOM   7138  CB  ILE     2      85.629  44.767  39.417  1.00  24.34      Y    C
ATOM   7139  CG2 ILE     2      84.329  45.456  39.830  1.00  24.34      Y    C
ATOM   7140  CG1 ILE     2      86.754  45.793  39.275  1.00  24.34      Y    C
ATOM   7141  CD1 ILE     2      86.473  46.861  38.237  1.00  24.34      Y    C
ATOM   7142  C   ILE     2      84.812  42.776  40.634  1.00  29.24      Y    C
ATOM   7143  O   ILE     2      84.508  41.962  39.756  1.00  29.24      Y    O
ATOM   7144  N   ILE     2      87.254  42.972  40.068  1.00  29.24      Y    N
ATOM   7145  CA  ILE     2      86.011  43.705  40.462  1.00  29.24      Y    C
ATOM   7146  N   GLN     3      84.122  42.926  41.761  1.00  42.94      Y    N
ATOM   7147  CA  GLN     3      82.960  42.107  42.070  1.00  42.94      Y    C
ATOM   7148  CB  GLN     3      83.156  41.435  43.434  1.00  85.86      Y    C
ATOM   7149  CG  GLN     3      82.045  40.492  43.850  1.00  85.86      Y    C
ATOM   7150  CD  GLN     3      82.371  39.747  45.131  1.00  85.86      Y    C
ATOM   7151  OE1 GLN     3      81.534  39.028  45.670  1.00  85.86      Y    O
ATOM   7152  NE2 GLN     3      83.597  39.911  45.621  1.00  85.86      Y    N
ATOM   7153  C   GLN     3      81.684  42.943  42.059  1.00  42.94      Y    C
ATOM   7154  O   GLN     3      81.626  44.026  42.645  1.00  42.94      Y    O
```

Fig. 19: A-99

| ATOM | 7155 | N | LEU | 4 | 80.666 | 42.426 | 41.380 | 1.00 | 33.35 | Y | N |
|---|---|---|---|---|---|---|---|---|---|---|---|
| ATOM | 7156 | CA | LEU | 4 | 79.378 | 43.098 | 41.269 | 1.00 | 33.35 | Y | C |
| ATOM | 7157 | CB | LEU | 4 | 78.954 | 43.160 | 39.800 | 1.00 | 47.12 | Y | C |
| ATOM | 7158 | CG | LEU | 4 | 79.344 | 44.389 | 38.979 | 1.00 | 47.12 | Y | C |
| ATOM | 7159 | CD1 | LEU | 4 | 80.683 | 44.945 | 39.443 | 1.00 | 47.12 | Y | C |
| ATOM | 7160 | CD2 | LEU | 4 | 79.370 | 44.008 | 37.512 | 1.00 | 47.12 | Y | C |
| ATOM | 7161 | C | LEU | 4 | 78.296 | 42.395 | 42.073 | 1.00 | 33.35 | Y | C |
| ATOM | 7162 | O | LEU | 4 | 78.012 | 41.215 | 41.852 | 1.00 | 33.35 | Y | O |
| ATOM | 7163 | N | THR | 5 | 77.691 | 43.129 | 43.001 | 1.00 | 42.53 | Y | N |
| ATOM | 7164 | CA | THR | 5 | 76.628 | 42.586 | 43.833 | 1.00 | 42.53 | Y | C |
| ATOM | 7165 | CB | THR | 5 | 77.100 | 42.482 | 45.315 | 1.00 | 37.95 | Y | C |
| ATOM | 7166 | OG1 | THR | 5 | 75.992 | 42.697 | 46.196 | 1.00 | 37.95 | Y | O |
| ATOM | 7167 | CG2 | THR | 5 | 78.209 | 43.479 | 45.604 | 1.00 | 37.95 | Y | C |
| ATOM | 7168 | C | THR | 5 | 75.348 | 43.426 | 43.699 | 1.00 | 42.53 | Y | C |
| ATOM | 7169 | O | THR | 5 | 75.306 | 44.593 | 44.089 | 1.00 | 42.53 | Y | O |
| ATOM | 7170 | N | GLN | 6 | 74.318 | 42.806 | 43.119 | 1.00 | 44.79 | Y | N |
| ATOM | 7171 | CA | GLN | 6 | 73.009 | 43.423 | 42.877 | 1.00 | 44.79 | Y | C |
| ATOM | 7172 | CB | GLN | 6 | 72.340 | 42.791 | 41.641 | 1.00 | 23.30 | Y | C |
| ATOM | 7173 | CG | GLN | 6 | 73.239 | 42.643 | 40.421 | 1.00 | 23.30 | Y | C |
| ATOM | 7174 | CD | GLN | 6 | 72.520 | 42.055 | 39.195 | 1.00 | 23.30 | Y | C |
| ATOM | 7175 | OE1 | GLN | 6 | 73.163 | 41.628 | 38.231 | 1.00 | 23.30 | Y | O |
| ATOM | 7176 | NE2 | GLN | 6 | 71.193 | 42.046 | 39.226 | 1.00 | 23.30 | Y | N |
| ATOM | 7177 | C | GLN | 6 | 72.050 | 43.274 | 44.061 | 1.00 | 44.79 | Y | C |
| ATOM | 7178 | O | GLN | 6 | 72.195 | 42.370 | 44.883 | 1.00 | 44.79 | Y | O |
| ATOM | 7179 | N | SER | 7 | 71.057 | 44.156 | 44.128 | 1.00 | 78.31 | Y | N |
| ATOM | 7180 | CA | SER | 7 | 70.069 | 44.113 | 45.201 | 1.00 | 78.31 | Y | C |
| ATOM | 7181 | CB | SER | 7 | 70.640 | 44.715 | 46.480 | 1.00 | 85.46 | Y | C |
| ATOM | 7182 | OG | SER | 7 | 71.028 | 46.058 | 46.262 | 1.00 | 85.46 | Y | O |
| ATOM | 7183 | C | SER | 7 | 68.797 | 44.855 | 44.824 | 1.00 | 78.31 | Y | C |
| ATOM | 7184 | O | SER | 7 | 68.847 | 45.923 | 44.220 | 1.00 | 78.31 | Y | O |
| ATOM | 7185 | N | PRO | 8 | 67.633 | 44.283 | 45.165 | 1.00 | 83.70 | Y | N |
| ATOM | 7186 | CD | PRO | 8 | 66.277 | 44.777 | 44.863 | 1.00 | 54.81 | Y | C |
| ATOM | 7187 | CA | PRO | 8 | 67.571 | 43.000 | 45.865 | 1.00 | 83.70 | Y | C |
| ATOM | 7188 | CB | PRO | 8 | 66.097 | 42.880 | 46.226 | 1.00 | 54.81 | Y | C |
| ATOM | 7189 | CG | PRO | 8 | 65.427 | 43.534 | 45.054 | 1.00 | 54.81 | Y | C |
| ATOM | 7190 | C | PRO | 8 | 68.015 | 41.895 | 44.925 | 1.00 | 83.70 | Y | C |
| ATOM | 7191 | O | PRO | 8 | 68.274 | 42.136 | 43.745 | 1.00 | 83.70 | Y | O |
| ATOM | 7192 | N | SER | 9 | 68.111 | 40.685 | 45.455 | 1.00 | 47.38 | Y | N |
| ATOM | 7193 | CA | SER | 9 | 68.504 | 39.541 | 44.651 | 1.00 | 47.38 | Y | C |
| ATOM | 7194 | CB | SER | 9 | 69.145 | 38.481 | 45.543 | 1.00 | 74.91 | Y | C |
| ATOM | 7195 | OG | SER | 9 | 70.214 | 39.045 | 46.283 | 1.00 | 74.91 | Y | O |
| ATOM | 7196 | C | SER | 9 | 67.232 | 39.002 | 44.025 | 1.00 | 47.38 | Y | C |
| ATOM | 7197 | O | SER | 9 | 67.237 | 38.434 | 42.936 | 1.00 | 47.38 | Y | O |
| ATOM | 7198 | N | SER | 10 | 66.134 | 39.214 | 44.736 | 1.00 | 60.45 | Y | N |
| ATOM | 7199 | CA | SER | 10 | 64.819 | 38.770 | 44.305 | 1.00 | 60.45 | Y | C |
| ATOM | 7200 | CB | SER | 10 | 64.476 | 37.449 | 44.991 | 1.00 | 51.82 | Y | C |
| ATOM | 7201 | OG | SER | 10 | 63.252 | 36.935 | 44.504 | 1.00 | 51.82 | Y | O |
| ATOM | 7202 | C | SER | 10 | 63.797 | 39.840 | 44.691 | 1.00 | 60.45 | Y | C |
| ATOM | 7203 | O | SER | 10 | 63.976 | 40.552 | 45.683 | 1.00 | 60.45 | Y | O |
| ATOM | 7204 | N | LEU | 11 | 62.730 | 39.964 | 43.910 | 1.00 | 65.48 | Y | N |
| ATOM | 7205 | CA | LEU | 11 | 61.710 | 40.964 | 44.206 | 1.00 | 65.48 | Y | C |
| ATOM | 7206 | CB | LEU | 11 | 62.206 | 42.366 | 43.830 | 1.00 | 51.28 | Y | C |
| ATOM | 7207 | CG | LEU | 11 | 62.310 | 42.727 | 42.342 | 1.00 | 51.28 | Y | C |
| ATOM | 7208 | CD1 | LEU | 11 | 60.949 | 43.139 | 41.803 | 1.00 | 51.28 | Y | C |
| ATOM | 7209 | CD2 | LEU | 11 | 63.294 | 43.877 | 42.168 | 1.00 | 51.28 | Y | C |
| ATOM | 7210 | C | LEU | 11 | 60.413 | 40.680 | 43.473 | 1.00 | 65.48 | Y | C |
| ATOM | 7211 | O | LEU | 11 | 60.412 | 40.363 | 42.282 | 1.00 | 65.48 | Y | O |
| ATOM | 7212 | N | SER | 12 | 59.305 | 40.803 | 44.189 | 1.00 | 84.56 | Y | N |
| ATOM | 7213 | CA | SER | 12 | 58.004 | 40.567 | 43.595 | 1.00 | 84.56 | Y | C |
| ATOM | 7214 | CB | SER | 12 | 57.209 | 39.578 | 44.445 | 1.00 | 71.89 | Y | C |
| ATOM | 7215 | OG | SER | 12 | 56.137 | 39.026 | 43.705 | 1.00 | 71.89 | Y | O |
| ATOM | 7216 | C | SER | 12 | 57.273 | 41.902 | 43.507 | 1.00 | 84.56 | Y | C |
| ATOM | 7217 | O | SER | 12 | 57.232 | 42.666 | 44.471 | 1.00 | 84.56 | Y | O |
| ATOM | 7218 | N | ALA | 13 | 56.713 | 42.192 | 42.341 | 1.00 | 109.71 | Y | N |
| ATOM | 7219 | CA | ALA | 13 | 55.997 | 43.442 | 42.152 | 1.00 | 109.71 | Y | C |
| ATOM | 7220 | CB | ALA | 13 | 56.947 | 44.509 | 41.632 | 1.00 | 88.46 | Y | C |
| ATOM | 7221 | C | ALA | 13 | 54.838 | 43.244 | 41.186 | 1.00 | 109.71 | Y | C |
| ATOM | 7222 | O | ALA | 13 | 54.869 | 42.347 | 40.341 | 1.00 | 109.71 | Y | O |
| ATOM | 7223 | N | SER | 14 | 53.816 | 44.084 | 41.315 | 1.00 | 66.55 | Y | N |
| ATOM | 7224 | CA | SER | 14 | 52.632 | 44.000 | 40.461 | 1.00 | 66.55 | Y | C |
| ATOM | 7225 | CB | SER | 14 | 51.370 | 44.265 | 41.290 | 1.00 | 62.23 | Y | C |
| ATOM | 7226 | OG | SER | 14 | 51.506 | 45.449 | 42.059 | 1.00 | 62.23 | Y | O |
| ATOM | 7227 | C | SER | 14 | 52.699 | 44.984 | 39.299 | 1.00 | 66.55 | Y | C |

Fig. 19: A-100

```
ATOM   7228  O    SER  14   53.362  46.015  39.394  1.00   66.55  Y  O
ATOM   7229  N    VAL  15   52.018  44.660  38.202  1.00   56.27  Y  N
ATOM   7230  CA   VAL  15   52.017  45.540  37.037  1.00   56.27  Y  C
ATOM   7231  CB   VAL  15   50.922  45.156  36.016  1.00   42.35  Y  C
ATOM   7232  CG1  VAL  15   51.449  44.089  35.066  1.00   42.35  Y  C
ATOM   7233  CG2  VAL  15   49.679  44.644  36.750  1.00   42.35  Y  C
ATOM   7234  C    VAL  15   51.773  46.964  37.492  1.00   56.27  Y  C
ATOM   7235  O    VAL  15   50.948  47.208  38.369  1.00   56.27  Y  O
ATOM   7236  N    GLY  16   52.509  47.903  36.911  1.00   54.44  Y  N
ATOM   7237  CA   GLY  16   52.343  49.296  37.280  1.00   54.44  Y  C
ATOM   7238  C    GLY  16   53.284  49.795  38.359  1.00   54.44  Y  C
ATOM   7239  O    GLY  16   53.419  51.000  38.542  1.00   54.44  Y  O
ATOM   7240  N    ASP  17   53.931  48.885  39.082  1.00   75.77  Y  N
ATOM   7241  CA   ASP  17   54.863  49.283  40.134  1.00   75.77  Y  C
ATOM   7242  CB   ASP  17   55.212  48.091  41.034  1.00  114.73  Y  C
ATOM   7243  CG   ASP  17   54.035  47.608  41.849  1.00  114.73  Y  C
ATOM   7244  OD1  ASP  17   54.208  46.639  42.623  1.00  114.73  Y  O
ATOM   7245  OD2  ASP  17   52.942  48.198  41.716  1.00  114.73  Y  O
ATOM   7246  C    ASP  17   56.149  49.824  39.525  1.00   75.77  Y  C
ATOM   7247  O    ASP  17   56.476  49.533  38.373  1.00   75.77  Y  O
ATOM   7248  N    ARG  18   56.873  50.616  40.304  1.00   69.15  Y  N
ATOM   7249  CA   ARG  18   58.139  51.161  39.844  1.00   69.15  Y  C
ATOM   7250  CB   ARG  18   58.263  52.634  40.225  1.00   52.23  Y  C
ATOM   7251  CG   ARG  18   59.557  53.291  39.779  1.00   52.23  Y  C
ATOM   7252  CD   ARG  18   59.365  54.788  39.625  1.00   52.23  Y  C
ATOM   7253  NE   ARG  18   60.622  55.478  39.370  1.00   52.23  Y  N
ATOM   7254  CZ   ARG  18   61.621  55.550  40.246  1.00   52.23  Y  C
ATOM   7255  NH1  ARG  18   61.506  54.968  41.436  1.00   52.23  Y  N
ATOM   7256  NH2  ARG  18   62.733  56.209  39.933  1.00   52.23  Y  N
ATOM   7257  C    ARG  18   59.232  50.346  40.514  1.00   69.15  Y  C
ATOM   7258  O    ARG  18   59.318  50.293  41.744  1.00   69.15  Y  O
ATOM   7259  N    VAL  19   60.064  49.706  39.701  1.00   58.62  Y  N
ATOM   7260  CA   VAL  19   61.132  48.871  40.221  1.00   58.62  Y  C
ATOM   7261  CB   VAL  19   61.068  47.477  39.567  1.00   74.00  Y  C
ATOM   7262  CG1  VAL  19   62.050  46.531  40.235  1.00   74.00  Y  C
ATOM   7263  CG2  VAL  19   59.651  46.938  39.664  1.00   74.00  Y  C
ATOM   7264  C    VAL  19   62.518  49.477  40.003  1.00   58.62  Y  C
ATOM   7265  O    VAL  19   62.782  50.096  38.975  1.00   58.62  Y  O
ATOM   7266  N    THR  20   63.399  49.297  40.978  1.00   54.75  Y  N
ATOM   7267  CA   THR  20   64.753  49.815  40.878  1.00   54.75  Y  C
ATOM   7268  CB   THR  20   64.883  51.148  41.639  1.00   56.43  Y  C
ATOM   7269  OG1  THR  20   64.132  52.154  40.955  1.00   56.43  Y  O
ATOM   7270  CG2  THR  20   66.337  51.586  41.726  1.00   56.43  Y  C
ATOM   7271  C    THR  20   65.806  48.834  41.401  1.00   54.75  Y  C
ATOM   7272  O    THR  20   65.963  48.663  42.611  1.00   54.75  Y  O
ATOM   7273  N    ILE  21   66.526  48.194  40.484  1.00   38.23  Y  N
ATOM   7274  CA   ILE  21   67.572  47.250  40.855  1.00   38.23  Y  C
ATOM   7275  CB   ILE  21   67.775  46.182  39.765  1.00   34.57  Y  C
ATOM   7276  CG2  ILE  21   68.753  45.112  40.252  1.00   34.57  Y  C
ATOM   7277  CG1  ILE  21   66.427  45.547  39.426  1.00   34.57  Y  C
ATOM   7278  CD1  ILE  21   66.496  44.426  38.415  1.00   34.57  Y  C
ATOM   7279  C    ILE  21   68.877  48.006  41.047  1.00   38.23  Y  C
ATOM   7280  O    ILE  21   69.215  48.885  40.256  1.00   38.23  Y  O
ATOM   7281  N    THR  22   69.610  47.660  42.100  1.00   41.70  Y  N
ATOM   7282  CA   THR  22   70.880  48.312  42.396  1.00   41.70  Y  C
ATOM   7283  CB   THR  22   70.919  48.826  43.856  1.00   62.77  Y  C
ATOM   7284  OG1  THR  22   69.986  49.903  44.017  1.00   62.77  Y  O
ATOM   7285  CG2  THR  22   72.322  49.303  44.222  1.00   62.77  Y  C
ATOM   7286  C    THR  22   72.052  47.370  42.199  1.00   41.70  Y  C
ATOM   7287  O    THR  22   72.028  46.237  42.674  1.00   41.70  Y  O
ATOM   7288  N    CYS  23   73.077  47.852  41.500  1.00   52.46  Y  N
ATOM   7289  CA   CYS  23   74.289  47.076  41.247  1.00   52.46  Y  C
ATOM   7290  C    CYS  23   75.446  47.833  41.875  1.00   52.46  Y  C
ATOM   7291  O    CYS  23   75.749  48.957  41.476  1.00   52.46  Y  O
ATOM   7292  CB   CYS  23   74.522  46.938  39.744  1.00   61.15  Y  C
ATOM   7293  SG   CYS  23   75.983  45.982  39.184  1.00   61.15  Y  S
ATOM   7294  N    SER  24   76.079  47.219  42.866  1.00   43.95  Y  N
ATOM   7295  CA   SER  24   77.200  47.837  43.556  1.00   43.95  Y  C
ATOM   7296  CB   SER  24   76.992  47.751  45.072  1.00   58.07  Y  C
ATOM   7297  OG   SER  24   75.782  48.379  45.462  1.00   58.07  Y  O
ATOM   7298  C    SER  24   78.495  47.138  43.177  1.00   43.95  Y  C
ATOM   7299  O    SER  24   78.582  45.912  43.222  1.00   43.95  Y  O
ATOM   7300  N    ALA  25   79.503  47.924  42.814  1.00   35.63  Y  N
```

Fig. 19: A-101

| ATOM | 7301 | CA | ALA | 25 | 80.796 | 47.373 | 42.427 | 1.00 | 35.63 | Y | C |
|---|---|---|---|---|---|---|---|---|---|---|---|
| ATOM | 7302 | CB | ALA | 25 | 81.214 | 47.920 | 41.068 | 1.00 | 50.18 | Y | C |
| ATOM | 7303 | C | ALA | 25 | 81.894 | 47.635 | 43.454 | 1.00 | 35.63 | Y | C |
| ATOM | 7304 | O | ALA | 25 | 82.050 | 48.754 | 43.959 | 1.00 | 35.63 | Y | O |
| ATOM | 7305 | N | SER | 26 | 82.650 | 46.579 | 43.742 | 1.00 | 37.44 | Y | N |
| ATOM | 7306 | CA | SER | 26 | 83.746 | 46.616 | 44.697 | 1.00 | 37.44 | Y | C |
| ATOM | 7307 | CB | SER | 26 | 84.492 | 45.280 | 44.672 | 1.00 | 31.41 | Y | C |
| ATOM | 7308 | OG | SER | 26 | 85.018 | 45.005 | 43.381 | 1.00 | 31.41 | Y | O |
| ATOM | 7309 | C | SER | 26 | 84.718 | 47.745 | 44.393 | 1.00 | 37.44 | Y | C |
| ATOM | 7310 | O | SER | 26 | 85.358 | 48.286 | 45.297 | 1.00 | 37.44 | Y | O |
| ATOM | 7311 | N | SER | 27 | 84.835 | 48.088 | 43.116 | 1.00 | 70.39 | Y | N |
| ATOM | 7312 | CA | SER | 27 | 85.726 | 49.157 | 42.687 | 1.00 | 70.39 | Y | C |
| ATOM | 7313 | CB | SER | 27 | 86.941 | 48.581 | 41.954 | 1.00 | 53.81 | Y | C |
| ATOM | 7314 | OG | SER | 27 | 87.574 | 47.567 | 42.716 | 1.00 | 53.81 | Y | O |
| ATOM | 7315 | C | SER | 27 | 84.922 | 50.023 | 41.736 | 1.00 | 70.39 | Y | C |
| ATOM | 7316 | O | SER | 27 | 83.960 | 49.545 | 41.139 | 1.00 | 70.39 | Y | O |
| ATOM | 7317 | N | SER | 28 | 85.306 | 51.290 | 41.595 | 1.00 | 30.73 | Y | N |
| ATOM | 7318 | CA | SER | 28 | 84.598 | 52.194 | 40.695 | 1.00 | 30.73 | Y | C |
| ATOM | 7319 | CB | SER | 28 | 85.060 | 53.628 | 40.920 | 1.00 | 55.81 | Y | C |
| ATOM | 7320 | OG | SER | 28 | 86.448 | 53.723 | 40.688 | 1.00 | 55.81 | Y | O |
| ATOM | 7321 | C | SER | 28 | 84.824 | 51.813 | 39.230 | 1.00 | 30.73 | Y | C |
| ATOM | 7322 | O | SER | 28 | 85.873 | 51.287 | 38.863 | 1.00 | 30.73 | Y | O |
| ATOM | 7323 | N | VAL | 29 | 83.832 | 52.092 | 38.398 | 1.00 | 34.83 | Y | N |
| ATOM | 7324 | CA | VAL | 29 | 83.909 | 51.780 | 36.983 | 1.00 | 34.83 | Y | C |
| ATOM | 7325 | CB | VAL | 29 | 83.173 | 50.443 | 36.682 | 1.00 | 24.96 | Y | C |
| ATOM | 7326 | CG1 | VAL | 29 | 83.891 | 49.286 | 37.382 | 1.00 | 24.96 | Y | C |
| ATOM | 7327 | CG2 | VAL | 29 | 81.717 | 50.518 | 37.153 | 1.00 | 24.96 | Y | C |
| ATOM | 7328 | C | VAL | 29 | 83.267 | 52.929 | 36.208 | 1.00 | 34.83 | Y | C |
| ATOM | 7329 | O | VAL | 29 | 82.397 | 53.621 | 36.738 | 1.00 | 34.83 | Y | O |
| ATOM | 7330 | N | ASN | 30 | 83.689 | 53.134 | 34.963 | 1.00 | 19.83 | Y | N |
| ATOM | 7331 | CA | ASN | 30 | 83.152 | 54.225 | 34.145 | 1.00 | 19.83 | Y | C |
| ATOM | 7332 | CB | ASN | 30 | 84.086 | 54.517 | 32.963 | 1.00 | 44.92 | Y | C |
| ATOM | 7333 | CG | ASN | 30 | 84.524 | 53.261 | 32.254 | 1.00 | 44.92 | Y | C |
| ATOM | 7334 | OD1 | ASN | 30 | 85.235 | 52.431 | 32.832 | 1.00 | 44.92 | Y | O |
| ATOM | 7335 | ND2 | ASN | 30 | 84.097 | 53.099 | 31.001 | 1.00 | 44.92 | Y | N |
| ATOM | 7336 | C | ASN | 30 | 81.740 | 53.976 | 33.634 | 1.00 | 19.83 | Y | C |
| ATOM | 7337 | O | ASN | 30 | 80.998 | 54.926 | 33.381 | 1.00 | 19.83 | Y | O |
| ATOM | 7338 | N | HIS | 31 | 81.367 | 52.708 | 33.475 | 1.00 | 24.55 | Y | N |
| ATOM | 7339 | CA | HIS | 31 | 80.031 | 52.373 | 32.991 | 1.00 | 24.55 | Y | C |
| ATOM | 7340 | CB | HIS | 31 | 80.003 | 52.259 | 31.459 | 1.00 | 41.70 | Y | C |
| ATOM | 7341 | CG | HIS | 31 | 80.061 | 53.572 | 30.737 | 1.00 | 41.70 | Y | C |
| ATOM | 7342 | CD2 | HIS | 31 | 79.124 | 54.233 | 30.016 | 1.00 | 41.70 | Y | C |
| ATOM | 7343 | ND1 | HIS | 31 | 81.196 | 54.351 | 30.692 | 1.00 | 41.70 | Y | N |
| ATOM | 7344 | CE1 | HIS | 31 | 80.958 | 55.435 | 29.973 | 1.00 | 41.70 | Y | C |
| ATOM | 7345 | NE2 | HIS | 31 | 79.708 | 55.387 | 29.551 | 1.00 | 41.70 | Y | N |
| ATOM | 7346 | C | HIS | 31 | 79.548 | 51.058 | 33.567 | 1.00 | 24.55 | Y | C |
| ATOM | 7347 | O | HIS | 31 | 80.274 | 50.392 | 34.305 | 1.00 | 24.55 | Y | O |
| ATOM | 7348 | N | MET | 32 | 78.312 | 50.698 | 33.227 | 1.00 | 16.59 | Y | N |
| ATOM | 7349 | CA | MET | 32 | 77.719 | 49.440 | 33.664 | 1.00 | 16.59 | Y | C |
| ATOM | 7350 | CB | MET | 32 | 76.944 | 49.624 | 34.971 | 1.00 | 29.77 | Y | C |
| ATOM | 7351 | CG | MET | 32 | 76.606 | 48.310 | 35.684 | 1.00 | 29.77 | Y | C |
| ATOM | 7352 | SD | MET | 32 | 78.097 | 47.369 | 36.143 | 1.00 | 29.77 | Y | S |
| ATOM | 7353 | CE | MET | 32 | 78.855 | 48.463 | 37.337 | 1.00 | 29.77 | Y | C |
| ATOM | 7354 | C | MET | 32 | 76.779 | 48.941 | 32.563 | 1.00 | 16.59 | Y | C |
| ATOM | 7355 | O | MET | 32 | 76.138 | 49.734 | 31.871 | 1.00 | 16.59 | Y | O |
| ATOM | 7356 | N | PHE | 33 | 76.706 | 47.629 | 32.383 | 1.00 | 41.04 | Y | N |
| ATOM | 7357 | CA | PHE | 33 | 75.830 | 47.089 | 31.358 | 1.00 | 41.04 | Y | C |
| ATOM | 7358 | CB | PHE | 33 | 76.639 | 46.329 | 30.315 | 1.00 | 16.08 | Y | C |
| ATOM | 7359 | CG | PHE | 33 | 77.695 | 47.161 | 29.657 | 1.00 | 16.08 | Y | C |
| ATOM | 7360 | CD1 | PHE | 33 | 78.846 | 47.528 | 30.354 | 1.00 | 16.08 | Y | C |
| ATOM | 7361 | CD2 | PHE | 33 | 77.524 | 47.609 | 28.350 | 1.00 | 16.08 | Y | C |
| ATOM | 7362 | CE1 | PHE | 33 | 79.810 | 48.328 | 29.763 | 1.00 | 16.08 | Y | C |
| ATOM | 7363 | CE2 | PHE | 33 | 78.484 | 48.414 | 27.745 | 1.00 | 16.08 | Y | C |
| ATOM | 7364 | CZ | PHE | 33 | 79.634 | 48.776 | 28.456 | 1.00 | 16.08 | Y | C |
| ATOM | 7365 | C | PHE | 33 | 74.803 | 46.175 | 31.985 | 1.00 | 41.04 | Y | C |
| ATOM | 7366 | O | PHE | 33 | 75.036 | 45.622 | 33.057 | 1.00 | 41.04 | Y | O |
| ATOM | 7367 | N | TRP | 34 | 73.664 | 46.020 | 31.322 | 1.00 | 26.10 | Y | N |
| ATOM | 7368 | CA | TRP | 34 | 72.604 | 45.168 | 31.843 | 1.00 | 26.10 | Y | C |
| ATOM | 7369 | CB | TRP | 34 | 71.438 | 46.009 | 32.364 | 1.00 | 47.27 | Y | C |
| ATOM | 7370 | CG | TRP | 34 | 71.807 | 46.935 | 33.466 | 1.00 | 47.27 | Y | C |
| ATOM | 7371 | CD2 | TRP | 34 | 71.660 | 46.692 | 34.868 | 1.00 | 47.27 | Y | C |
| ATOM | 7372 | CE2 | TRP | 34 | 72.145 | 47.836 | 35.542 | 1.00 | 47.27 | Y | C |
| ATOM | 7373 | CE3 | TRP | 34 | 71.167 | 45.621 | 35.622 | 1.00 | 47.27 | Y | C |

Fig. 19: A-102

| ATOM | 7374 | CD1 | TRP | 34 | 72.360 | 48.175 | 33.346 | 1.00 | 47.27 | Y | C |
|---|---|---|---|---|---|---|---|---|---|---|---|
| ATOM | 7375 | NE1 | TRP | 34 | 72.567 | 48.725 | 34.589 | 1.00 | 47.27 | Y | N |
| ATOM | 7376 | CZ2 | TRP | 34 | 72.150 | 47.939 | 36.940 | 1.00 | 47.27 | Y | C |
| ATOM | 7377 | CZ3 | TRP | 34 | 71.172 | 45.725 | 37.013 | 1.00 | 47.27 | Y | C |
| ATOM | 7378 | CH2 | TRP | 34 | 71.661 | 46.879 | 37.655 | 1.00 | 47.27 | Y | C |
| ATOM | 7379 | C | TRP | 34 | 72.067 | 44.187 | 30.812 | 1.00 | 26.10 | Y | C |
| ATOM | 7380 | O | TRP | 34 | 71.904 | 44.513 | 29.630 | 1.00 | 26.10 | Y | O |
| ATOM | 7381 | N | TYR | 35 | 71.793 | 42.972 | 31.267 | 1.00 | 43.42 | Y | N |
| ATOM | 7382 | CA | TYR | 35 | 71.248 | 41.964 | 30.381 | 1.00 | 43.42 | Y | C |
| ATOM | 7383 | CB | TYR | 35 | 72.230 | 40.808 | 30.189 | 1.00 | 22.29 | Y | C |
| ATOM | 7384 | CG | TYR | 35 | 73.549 | 41.240 | 29.596 | 1.00 | 22.29 | Y | C |
| ATOM | 7385 | CD1 | TYR | 35 | 74.645 | 41.535 | 30.417 | 1.00 | 22.29 | Y | C |
| ATOM | 7386 | CE1 | TYR | 35 | 75.841 | 41.962 | 29.881 | 1.00 | 22.29 | Y | C |
| ATOM | 7387 | CD2 | TYR | 35 | 73.697 | 41.385 | 28.216 | 1.00 | 22.29 | Y | C |
| ATOM | 7388 | CE2 | TYR | 35 | 74.898 | 41.808 | 27.670 | 1.00 | 22.29 | Y | C |
| ATOM | 7389 | CZ | TYR | 35 | 75.960 | 42.094 | 28.510 | 1.00 | 22.29 | Y | C |
| ATOM | 7390 | OH | TYR | 35 | 77.148 | 42.516 | 27.972 | 1.00 | 22.29 | Y | O |
| ATOM | 7391 | C | TYR | 35 | 69.966 | 41.449 | 30.991 | 1.00 | 43.42 | Y | C |
| ATOM | 7392 | O | TYR | 35 | 69.826 | 41.393 | 32.214 | 1.00 | 43.42 | Y | O |
| ATOM | 7393 | N | GLN | 36 | 69.015 | 41.107 | 30.136 | 1.00 | 45.64 | Y | N |
| ATOM | 7394 | CA | GLN | 36 | 67.760 | 40.567 | 30.607 | 1.00 | 45.64 | Y | C |
| ATOM | 7395 | CB | GLN | 36 | 66.574 | 41.346 | 30.054 | 1.00 | 37.71 | Y | C |
| ATOM | 7396 | CG | GLN | 36 | 65.259 | 40.610 | 30.277 | 1.00 | 37.71 | Y | C |
| ATOM | 7397 | CD | GLN | 36 | 64.189 | 41.002 | 29.287 | 1.00 | 37.71 | Y | C |
| ATOM | 7398 | OE1 | GLN | 36 | 63.601 | 42.072 | 29.391 | 1.00 | 37.71 | Y | O |
| ATOM | 7399 | NE2 | GLN | 36 | 63.936 | 40.137 | 28.314 | 1.00 | 37.71 | Y | N |
| ATOM | 7400 | C | GLN | 36 | 67.664 | 39.138 | 30.118 | 1.00 | 45.64 | Y | C |
| ATOM | 7401 | O | GLN | 36 | 67.725 | 38.881 | 28.910 | 1.00 | 45.64 | Y | O |
| ATOM | 7402 | N | GLN | 37 | 67.522 | 38.205 | 31.050 | 1.00 | 50.28 | Y | N |
| ATOM | 7403 | CA | GLN | 37 | 67.390 | 36.809 | 30.670 | 1.00 | 50.28 | Y | C |
| ATOM | 7404 | CB | GLN | 37 | 68.522 | 35.961 | 31.265 | 1.00 | 34.85 | Y | C |
| ATOM | 7405 | CG | GLN | 37 | 68.392 | 34.487 | 30.904 | 1.00 | 34.85 | Y | C |
| ATOM | 7406 | CD | GLN | 37 | 69.543 | 33.645 | 31.388 | 1.00 | 34.85 | Y | C |
| ATOM | 7407 | OE1 | GLN | 37 | 69.925 | 33.699 | 32.565 | 1.00 | 34.85 | Y | O |
| ATOM | 7408 | NE2 | GLN | 37 | 70.098 | 32.842 | 30.484 | 1.00 | 34.85 | Y | N |
| ATOM | 7409 | C | GLN | 37 | 66.042 | 36.248 | 31.108 | 1.00 | 50.28 | Y | C |
| ATOM | 7410 | O | GLN | 37 | 65.690 | 36.272 | 32.293 | 1.00 | 50.28 | Y | O |
| ATOM | 7411 | N | LYS | 38 | 65.284 | 35.763 | 30.133 | 1.00 | 68.24 | Y | N |
| ATOM | 7412 | CA | LYS | 38 | 63.983 | 35.175 | 30.403 | 1.00 | 68.24 | Y | C |
| ATOM | 7413 | CB | LYS | 38 | 62.991 | 35.530 | 29.291 | 1.00 | 55.54 | Y | C |
| ATOM | 7414 | CG | LYS | 38 | 62.893 | 37.031 | 29.023 | 1.00 | 55.54 | Y | C |
| ATOM | 7415 | CD | LYS | 38 | 61.764 | 37.382 | 28.056 | 1.00 | 55.54 | Y | C |
| ATOM | 7416 | CE | LYS | 38 | 60.394 | 37.298 | 28.726 | 1.00 | 55.54 | Y | C |
| ATOM | 7417 | NZ | LYS | 38 | 60.290 | 38.166 | 29.943 | 1.00 | 55.54 | Y | N |
| ATOM | 7418 | C | LYS | 38 | 64.198 | 33.667 | 30.473 | 1.00 | 68.24 | Y | C |
| ATOM | 7419 | O | LYS | 38 | 64.971 | 33.104 | 29.696 | 1.00 | 68.24 | Y | O |
| ATOM | 7420 | N | PRO | 39 | 63.520 | 32.994 | 31.412 | 1.00 | 67.87 | Y | N |
| ATOM | 7421 | CD | PRO | 39 | 62.478 | 33.563 | 32.282 | 1.00 | 58.47 | Y | C |
| ATOM | 7422 | CA | PRO | 39 | 63.621 | 31.546 | 31.614 | 1.00 | 67.87 | Y | C |
| ATOM | 7423 | CB | PRO | 39 | 62.368 | 31.234 | 32.417 | 1.00 | 58.47 | Y | C |
| ATOM | 7424 | CG | PRO | 39 | 62.247 | 32.446 | 33.271 | 1.00 | 58.47 | Y | C |
| ATOM | 7425 | C | PRO | 39 | 63.717 | 30.714 | 30.338 | 1.00 | 67.87 | Y | C |
| ATOM | 7426 | O | PRO | 39 | 62.898 | 30.859 | 29.425 | 1.00 | 67.87 | Y | O |
| ATOM | 7427 | N | GLY | 40 | 64.730 | 29.847 | 30.288 | 1.00 | 54.98 | Y | N |
| ATOM | 7428 | CA | GLY | 40 | 64.925 | 28.977 | 29.137 | 1.00 | 54.98 | Y | C |
| ATOM | 7429 | C | GLY | 40 | 65.488 | 29.625 | 27.882 | 1.00 | 54.98 | Y | C |
| ATOM | 7430 | O | GLY | 40 | 65.625 | 28.957 | 26.855 | 1.00 | 54.98 | Y | O |
| ATOM | 7431 | N | LYS | 41 | 65.801 | 30.918 | 27.955 | 1.00 | 83.28 | Y | N |
| ATOM | 7432 | CA | LYS | 41 | 66.364 | 31.641 | 26.816 | 1.00 | 83.28 | Y | C |
| ATOM | 7433 | CB | LYS | 41 | 65.414 | 32.754 | 26.354 | 1.00 | 72.06 | Y | C |
| ATOM | 7434 | CG | LYS | 41 | 64.045 | 32.271 | 25.882 | 1.00 | 72.06 | Y | C |
| ATOM | 7435 | CD | LYS | 41 | 63.316 | 33.311 | 25.008 | 1.00 | 72.06 | Y | C |
| ATOM | 7436 | CE | LYS | 41 | 63.035 | 34.642 | 25.726 | 1.00 | 72.06 | Y | C |
| ATOM | 7437 | NZ | LYS | 41 | 64.229 | 35.536 | 25.855 | 1.00 | 72.06 | Y | N |
| ATOM | 7438 | C | LYS | 41 | 67.727 | 32.245 | 27.160 | 1.00 | 83.28 | Y | C |
| ATOM | 7439 | O | LYS | 41 | 68.110 | 32.327 | 28.331 | 1.00 | 83.28 | Y | O |
| ATOM | 7440 | N | ALA | 42 | 68.458 | 32.666 | 26.133 | 1.00 | 55.60 | Y | N |
| ATOM | 7441 | CA | ALA | 42 | 69.776 | 33.261 | 26.326 | 1.00 | 55.60 | Y | C |
| ATOM | 7442 | CB | ALA | 42 | 70.561 | 33.194 | 25.041 | 1.00 | 1.87 | Y | C |
| ATOM | 7443 | C | ALA | 42 | 69.623 | 34.707 | 26.754 | 1.00 | 55.60 | Y | C |
| ATOM | 7444 | O | ALA | 42 | 68.607 | 35.337 | 26.462 | 1.00 | 55.60 | Y | O |
| ATOM | 7445 | N | PRO | 43 | 70.628 | 35.259 | 27.455 | 1.00 | 54.21 | Y | N |
| ATOM | 7446 | CD | PRO | 43 | 71.849 | 34.627 | 27.983 | 1.00 | 18.24 | Y | C |

Fig. 19: A-103

```
ATOM   7447  CA   PRO  43      70.537  36.656  27.889  1.00  54.21      Y   C
ATOM   7448  CB   PRO  43      71.875  36.890  28.594  1.00  18.24      Y   C
ATOM   7449  CG   PRO  43      72.202  35.544  29.149  1.00  18.24      Y   C
ATOM   7450  C    PRO  43      70.349  37.584  26.689  1.00  54.21      Y   C
ATOM   7451  O    PRO  43      70.660  37.219  25.555  1.00  54.21      Y   O
ATOM   7452  N    LYS  44      69.837  38.782  26.946  1.00  55.44      Y   N
ATOM   7453  CA   LYS  44      69.618  39.764  25.892  1.00  55.44      Y   C
ATOM   7454  CB   LYS  44      68.120  39.894  25.601  1.00  46.11      Y   C
ATOM   7455  CG   LYS  44      67.705  39.473  24.199  1.00  46.11      Y   C
ATOM   7456  CD   LYS  44      66.189  39.520  24.018  1.00  46.11      Y   C
ATOM   7457  CE   LYS  44      65.457  38.464  24.865  1.00  46.11      Y   C
ATOM   7458  NZ   LYS  44      65.564  38.665  26.354  1.00  46.11      Y   N
ATOM   7459  C    LYS  44      70.172  41.117  26.328  1.00  55.44      Y   C
ATOM   7460  O    LYS  44      69.930  41.554  27.454  1.00  55.44      Y   O
ATOM   7461  N    PRO  45      70.946  41.785  25.451  1.00  21.39      Y   N
ATOM   7462  CD   PRO  45      71.303  41.365  24.085  1.00  11.37      Y   C
ATOM   7463  CA   PRO  45      71.523  43.103  25.772  1.00  21.39      Y   C
ATOM   7464  CB   PRO  45      72.159  43.539  24.457  1.00  11.37      Y   C
ATOM   7465  CG   PRO  45      72.485  42.234  23.795  1.00  11.37      Y   C
ATOM   7466  C    PRO  45      70.361  44.010  26.138  1.00  21.39      Y   C
ATOM   7467  O    PRO  45      69.407  44.103  25.383  1.00  21.39      Y   O
ATOM   7468  N    TRP  46      70.434  44.676  27.281  1.00  48.64      Y   N
ATOM   7469  CA   TRP  46      69.333  45.532  27.704  1.00  48.64      Y   C
ATOM   7470  CB   TRP  46      68.783  45.038  29.043  1.00  23.18      Y   C
ATOM   7471  CG   TRP  46      67.316  45.220  29.143  1.00  23.18      Y   C
ATOM   7472  CD2  TRP  46      66.330  44.620  28.299  1.00  23.18      Y   C
ATOM   7473  CE2  TRP  46      65.070  45.075  28.739  1.00  23.18      Y   C
ATOM   7474  CE3  TRP  46      66.391  43.736  27.206  1.00  23.18      Y   C
ATOM   7475  CD1  TRP  46      66.637  45.997  30.038  1.00  23.18      Y   C
ATOM   7476  NE1  TRP  46      65.282  45.914  29.803  1.00  23.18      Y   N
ATOM   7477  CZ2  TRP  46      63.881  44.679  28.126  1.00  23.18      Y   C
ATOM   7478  CZ3  TRP  46      65.212  43.342  26.599  1.00  23.18      Y   C
ATOM   7479  CH2  TRP  46      63.973  43.814  27.059  1.00  23.18      Y   C
ATOM   7480  C    TRP  46      69.694  47.007  27.826  1.00  48.64      Y   C
ATOM   7481  O    TRP  46      68.986  47.877  27.324  1.00  48.64      Y   O
ATOM   7482  N    ILE  47      70.785  47.283  28.523  1.00  42.06      Y   N
ATOM   7483  CA   ILE  47      71.238  48.644  28.717  1.00  42.06      Y   C
ATOM   7484  CB   ILE  47      70.801  49.172  30.099  1.00  37.03      Y   C
ATOM   7485  CG2  ILE  47      71.345  50.580  30.325  1.00  37.03      Y   C
ATOM   7486  CG1  ILE  47      69.275  49.168  30.198  1.00  37.03      Y   C
ATOM   7487  CD1  ILE  47      68.749  49.670  31.538  1.00  37.03      Y   C
ATOM   7488  C    ILE  47      72.758  48.641  28.638  1.00  42.06      Y   C
ATOM   7489  O    ILE  47      73.417  47.951  29.414  1.00  42.06      Y   O
ATOM   7490  N    TYR  48      73.310  49.387  27.684  1.00  17.47      Y   N
ATOM   7491  CA   TYR  48      74.753  49.467  27.532  1.00  17.47      Y   C
ATOM   7492  CB   TYR  48      75.189  49.145  26.106  1.00  20.64      Y   C
ATOM   7493  CG   TYR  48      74.613  50.048  25.046  1.00  20.64      Y   C
ATOM   7494  CD1  TYR  48      73.267  49.988  24.710  1.00  20.64      Y   C
ATOM   7495  CE1  TYR  48      72.743  50.792  23.704  1.00  20.64      Y   C
ATOM   7496  CD2  TYR  48      75.425  50.940  24.353  1.00  20.64      Y   C
ATOM   7497  CE2  TYR  48      74.916  51.750  23.347  1.00  20.64      Y   C
ATOM   7498  CZ   TYR  48      73.573  51.671  23.028  1.00  20.64      Y   C
ATOM   7499  OH   TYR  48      73.051  52.476  22.045  1.00  20.64      Y   O
ATOM   7500  C    TYR  48      75.193  50.861  27.892  1.00  17.47      Y   C
ATOM   7501  O    TYR  48      74.365  51.754  28.021  1.00  17.47      Y   O
ATOM   7502  N    LEU  49      76.497  51.044  28.054  1.00  31.07      Y   N
ATOM   7503  CA   LEU  49      77.042  52.337  28.429  1.00  31.07      Y   C
ATOM   7504  CB   LEU  49      77.200  53.247  27.205  1.00  20.44      Y   C
ATOM   7505  CG   LEU  49      78.368  53.044  26.236  1.00  20.44      Y   C
ATOM   7506  CD1  LEU  49      79.662  52.870  27.019  1.00  20.44      Y   C
ATOM   7507  CD2  LEU  49      78.121  51.836  25.385  1.00  20.44      Y   C
ATOM   7508  C    LEU  49      76.173  53.037  29.475  1.00  31.07      Y   C
ATOM   7509  O    LEU  49      75.769  54.178  29.293  1.00  31.07      Y   O
ATOM   7510  N    THR  50      75.861  52.329  30.555  1.00  28.24      Y   N
ATOM   7511  CA   THR  50      75.083  52.870  31.670  1.00  28.24      Y   C
ATOM   7512  CB   THR  50      75.754  54.128  32.230  1.00  41.62      Y   C
ATOM   7513  OG1  THR  50      77.134  53.847  32.495  1.00  41.62      Y   O
ATOM   7514  CG2  THR  50      75.066  54.568  33.522  1.00  41.62      Y   C
ATOM   7515  C    THR  50      73.605  53.187  31.485  1.00  28.24      Y   C
ATOM   7516  O    THR  50      72.761  52.603  32.158  1.00  28.24      Y   O
ATOM   7517  N    SER  51      73.283  54.114  30.595  1.00  28.33      Y   N
ATOM   7518  CA   SER  51      71.889  54.496  30.402  1.00  28.33      Y   C
ATOM   7519  CB   SER  51      71.729  55.981  30.714  1.00  81.44      Y   C
```

Fig. 19: A-104

```
ATOM   7520  OG   SER  51      72.714  56.738  30.034  1.00  81.44      Y  O
ATOM   7521  C    SER  51      71.312  54.190  29.019  1.00  28.33      Y  C
ATOM   7522  O    SER  51      70.092  54.174  28.831  1.00  28.33      Y  O
ATOM   7523  N    ASN  52      72.184  53.941  28.053  1.00  27.44      Y  N
ATOM   7524  CA   ASN  52      71.736  53.648  26.704  1.00  27.44      Y  C
ATOM   7525  CB   ASN  52      72.942  53.523  25.779  1.00  42.81      Y  C
ATOM   7526  CG   ASN  52      73.623  54.849  25.546  1.00  42.81      Y  C
ATOM   7527  OD1  ASN  52      73.059  55.733  24.907  1.00  42.81      Y  O
ATOM   7528  ND2  ASN  52      74.829  55.006  26.076  1.00  42.81      Y  N
ATOM   7529  C    ASN  52      70.896  52.390  26.623  1.00  27.44      Y  C
ATOM   7530  O    ASN  52      71.336  51.320  27.027  1.00  27.44      Y  O
ATOM   7531  N    LEU  53      69.682  52.519  26.100  1.00  46.42      Y  N
ATOM   7532  CA   LEU  53      68.805  51.367  25.954  1.00  46.42      Y  C
ATOM   7533  CB   LEU  53      67.349  51.803  25.887  1.00  19.90      Y  C
ATOM   7534  CG   LEU  53      66.763  52.595  27.051  1.00  19.90      Y  C
ATOM   7535  CD1  LEU  53      65.255  52.685  26.846  1.00  19.90      Y  C
ATOM   7536  CD2  LEU  53      67.071  51.918  28.382  1.00  19.90      Y  C
ATOM   7537  C    LEU  53      69.136  50.610  24.676  1.00  46.42      Y  C
ATOM   7538  O    LEU  53      69.414  51.220  23.644  1.00  46.42      Y  O
ATOM   7539  N    ALA  54      69.101  49.281  24.744  1.00  35.05      Y  N
ATOM   7540  CA   ALA  54      69.378  48.447  23.583  1.00  35.05      Y  C
ATOM   7541  CB   ALA  54      69.220  46.994  23.930  1.00  27.54      Y  C
ATOM   7542  C    ALA  54      68.373  48.829  22.530  1.00  35.05      Y  C
ATOM   7543  O    ALA  54      67.680  49.834  22.666  1.00  35.05      Y  O
ATOM   7544  N    SER  55      68.259  48.026  21.486  1.00  47.40      Y  N
ATOM   7545  CA   SER  55      67.319  48.376  20.443  1.00  47.40      Y  C
ATOM   7546  CB   SER  55      67.689  47.681  19.140  1.00  36.06      Y  C
ATOM   7547  OG   SER  55      67.083  48.359  18.051  1.00  36.06      Y  O
ATOM   7548  C    SER  55      65.866  48.073  20.801  1.00  47.40      Y  C
ATOM   7549  O    SER  55      64.993  48.921  20.631  1.00  47.40      Y  O
ATOM   7550  N    GLY  56      65.599  46.878  21.312  1.00  54.09      Y  N
ATOM   7551  CA   GLY  56      64.225  46.531  21.647  1.00  54.09      Y  C
ATOM   7552  C    GLY  56      63.650  47.071  22.948  1.00  54.09      Y  C
ATOM   7553  O    GLY  56      62.457  47.370  23.025  1.00  54.09      Y  O
ATOM   7554  N    VAL  57      64.497  47.197  23.965  1.00  63.10      Y  N
ATOM   7555  CA   VAL  57      64.082  47.667  25.282  1.00  63.10      Y  C
ATOM   7556  CB   VAL  57      65.311  48.113  26.120  1.00  46.15      Y  C
ATOM   7557  CG1  VAL  57      64.923  48.248  27.588  1.00  46.15      Y  C
ATOM   7558  CG2  VAL  57      66.446  47.118  25.961  1.00  46.15      Y  C
ATOM   7559  C    VAL  57      63.071  48.817  25.251  1.00  63.10      Y  C
ATOM   7560  O    VAL  57      63.363  49.898  24.747  1.00  63.10      Y  O
ATOM   7561  N    PRO  58      61.862  48.594  25.791  1.00  51.01      Y  N
ATOM   7562  CD   PRO  58      61.362  47.365  26.426  1.00  31.12      Y  C
ATOM   7563  CA   PRO  58      60.834  49.639  25.815  1.00  51.01      Y  C
ATOM   7564  CB   PRO  58      59.634  48.929  26.433  1.00  31.12      Y  C
ATOM   7565  CG   PRO  58      60.258  47.899  27.300  1.00  31.12      Y  C
ATOM   7566  C    PRO  58      61.305  50.829  26.643  1.00  51.01      Y  C
ATOM   7567  O    PRO  58      61.992  50.660  27.653  1.00  51.01      Y  O
ATOM   7568  N    SER  59      60.918  52.027  26.216  1.00  33.61      Y  N
ATOM   7569  CA   SER  59      61.330  53.267  26.874  1.00  33.61      Y  C
ATOM   7570  CB   SER  59      60.780  54.482  26.113  1.00  61.12      Y  C
ATOM   7571  OG   SER  59      59.368  54.481  26.096  1.00  61.12      Y  O
ATOM   7572  C    SER  59      61.023  53.411  28.359  1.00  33.61      Y  C
ATOM   7573  O    SER  59      61.495  54.353  28.990  1.00  33.61      Y  O
ATOM   7574  N    ARG  60      60.244  52.500  28.928  1.00  39.70      Y  N
ATOM   7575  CA   ARG  60      59.963  52.599  30.359  1.00  39.70      Y  C
ATOM   7576  CB   ARG  60      58.764  51.731  30.751  1.00  42.51      Y  C
ATOM   7577  CG   ARG  60      58.846  50.293  30.287  1.00  42.51      Y  C
ATOM   7578  CD   ARG  60      57.798  49.425  30.971  1.00  42.51      Y  C
ATOM   7579  NE   ARG  60      57.683  48.120  30.333  1.00  42.51      Y  N
ATOM   7580  CZ   ARG  60      57.277  47.939  29.079  1.00  42.51      Y  C
ATOM   7581  NH1  ARG  60      56.943  48.979  28.324  1.00  42.51      Y  N
ATOM   7582  NH2  ARG  60      57.210  46.718  28.569  1.00  42.51      Y  N
ATOM   7583  C    ARG  60      61.202  52.180  31.158  1.00  39.70      Y  C
ATOM   7584  O    ARG  60      61.311  52.451  32.357  1.00  39.70      Y  O
ATOM   7585  N    PHE  61      62.136  51.522  30.480  1.00  40.60      Y  N
ATOM   7586  CA   PHE  61      63.372  51.086  31.109  1.00  40.60      Y  C
ATOM   7587  CB   PHE  61      63.965  49.886  30.370  1.00  38.42      Y  C
ATOM   7588  CG   PHE  61      63.416  48.563  30.811  1.00  38.42      Y  C
ATOM   7589  CD1  PHE  61      62.493  47.881  30.028  1.00  38.42      Y  C
ATOM   7590  CD2  PHE  61      63.830  47.997  32.010  1.00  38.42      Y  C
ATOM   7591  CE1  PHE  61      61.990  46.652  30.434  1.00  38.42      Y  C
ATOM   7592  CE2  PHE  61      63.332  46.770  32.423  1.00  38.42      Y  C
```

Fig. 19: A-105

```
ATOM   7593  CZ   PHE  61      62.410  46.096  31.634  1.00  38.42   Y  C
ATOM   7594  C    PHE  61      64.399  52.209  31.097  1.00  40.60   Y  C
ATOM   7595  O    PHE  61      64.470  52.989  30.144  1.00  40.60   Y  O
ATOM   7596  N    SER  62      65.202  52.284  32.152  1.00  26.58   Y  N
ATOM   7597  CA   SER  62      66.238  53.306  32.247  1.00  26.58   Y  C
ATOM   7598  CB   SER  62      65.658  54.604  32.802  1.00  47.08   Y  C
ATOM   7599  OG   SER  62      65.071  54.395  34.076  1.00  47.08   Y  O
ATOM   7600  C    SER  62      67.376  52.828  33.145  1.00  26.58   Y  C
ATOM   7601  O    SER  62      67.160  52.123  34.125  1.00  26.58   Y  O
ATOM   7602  N    GLY  63      68.595  53.208  32.797  1.00  30.78   Y  N
ATOM   7603  CA   GLY  63      69.738  52.810  33.591  1.00  30.78   Y  C
ATOM   7604  C    GLY  63      70.426  54.067  34.056  1.00  30.78   Y  C
ATOM   7605  O    GLY  63      70.266  55.122  33.442  1.00  30.78   Y  O
ATOM   7606  N    SER  64      71.195  53.964  35.130  1.00  54.48   Y  N
ATOM   7607  CA   SER  64      71.884  55.130  35.652  1.00  54.48   Y  C
ATOM   7608  CB   SER  64      70.869  56.075  36.290  1.00  25.06   Y  C
ATOM   7609  OG   SER  64      71.519  57.204  36.839  1.00  25.06   Y  O
ATOM   7610  C    SER  64      72.947  54.763  36.675  1.00  54.48   Y  C
ATOM   7611  O    SER  64      73.000  53.632  37.154  1.00  54.48   Y  O
ATOM   7612  N    GLY  65      73.793  55.732  37.007  1.00  43.76   Y  N
ATOM   7613  CA   GLY  65      74.836  55.494  37.984  1.00  43.76   Y  C
ATOM   7614  C    GLY  65      76.218  56.023  37.637  1.00  43.76   Y  C
ATOM   7615  O    GLY  65      76.431  56.698  36.622  1.00  43.76   Y  O
ATOM   7616  N    SER  66      77.167  55.703  38.508  1.00  27.01   Y  N
ATOM   7617  CA   SER  66      78.546  56.110  38.339  1.00  27.01   Y  C
ATOM   7618  CB   SER  66      78.641  57.635  38.286  1.00  58.01   Y  C
ATOM   7619  OG   SER  66      77.927  58.229  39.355  1.00  58.01   Y  O
ATOM   7620  C    SER  66      79.367  55.563  39.498  1.00  27.01   Y  C
ATOM   7621  O    SER  66      78.817  55.039  40.464  1.00  27.01   Y  O
ATOM   7622  N    GLY  67      80.685  55.668  39.385  1.00  73.15   Y  N
ATOM   7623  CA   GLY  67      81.555  55.179  40.436  1.00  73.15   Y  C
ATOM   7624  C    GLY  67      81.312  53.733  40.822  1.00  73.15   Y  C
ATOM   7625  O    GLY  67      81.609  52.814  40.056  1.00  73.15   Y  O
ATOM   7626  N    THR  68      80.758  53.530  42.011  1.00  44.05   Y  N
ATOM   7627  CA   THR  68      80.506  52.186  42.506  1.00  44.05   Y  C
ATOM   7628  CB   THR  68      81.118  52.003  43.894  1.00  42.61   Y  C
ATOM   7629  OG1  THR  68      80.524  52.945  44.793  1.00  42.61   Y  O
ATOM   7630  CG2  THR  68      82.627  52.225  43.845  1.00  42.61   Y  C
ATOM   7631  C    THR  68      79.042  51.786  42.592  1.00  44.05   Y  C
ATOM   7632  O    THR  68      78.743  50.632  42.879  1.00  44.05   Y  O
ATOM   7633  N    ASP  69      78.128  52.720  42.352  1.00  35.15   Y  N
ATOM   7634  CA   ASP  69      76.708  52.392  42.424  1.00  35.15   Y  C
ATOM   7635  CB   ASP  69      76.066  53.103  43.617  1.00  108.02  Y  C
ATOM   7636  CG   ASP  69      76.592  52.591  44.946  1.00  108.02  Y  C
ATOM   7637  OD1  ASP  69      76.357  51.406  45.268  1.00  108.02  Y  O
ATOM   7638  OD2  ASP  69      77.249  53.370  45.667  1.00  108.02  Y  O
ATOM   7639  C    ASP  69      75.942  52.705  41.139  1.00  35.15   Y  C
ATOM   7640  O    ASP  69      75.884  53.850  40.693  1.00  35.15   Y  O
ATOM   7641  N    TYR  70      75.359  51.664  40.551  1.00  27.55   Y  N
ATOM   7642  CA   TYR  70      74.599  51.787  39.317  1.00  27.55   Y  C
ATOM   7643  CB   TYR  70      75.315  51.016  38.191  1.00  25.09   Y  C
ATOM   7644  CG   TYR  70      76.543  51.737  37.662  1.00  25.09   Y  C
ATOM   7645  CD1  TYR  70      76.447  52.637  36.596  1.00  25.09   Y  C
ATOM   7646  CE1  TYR  70      77.562  53.365  36.158  1.00  25.09   Y  C
ATOM   7647  CD2  TYR  70      77.787  51.577  38.275  1.00  25.09   Y  C
ATOM   7648  CE2  TYR  70      78.906  52.299  37.848  1.00  25.09   Y  C
ATOM   7649  CZ   TYR  70      78.785  53.194  36.790  1.00  25.09   Y  C
ATOM   7650  OH   TYR  70      79.873  53.933  36.382  1.00  25.09   Y  O
ATOM   7651  C    TYR  70      73.184  51.267  39.523  1.00  27.55   Y  C
ATOM   7652  O    TYR  70      72.920  50.545  40.488  1.00  27.55   Y  O
ATOM   7653  N    THR  71      72.270  51.635  38.627  1.00  38.36   Y  N
ATOM   7654  CA   THR  71      70.893  51.184  38.767  1.00  38.36   Y  C
ATOM   7655  CB   THR  71      70.074  52.152  39.657  1.00  44.65   Y  C
ATOM   7656  OG1  THR  71      69.921  53.403  38.978  1.00  44.65   Y  O
ATOM   7657  CG2  THR  71      70.770  52.394  40.989  1.00  44.65   Y  C
ATOM   7658  C    THR  71      70.099  50.991  37.473  1.00  38.36   Y  C
ATOM   7659  O    THR  71      70.281  51.707  36.485  1.00  38.36   Y  O
ATOM   7660  N    LEU  72      69.216  50.001  37.499  1.00  32.67   Y  N
ATOM   7661  CA   LEU  72      68.324  49.718  36.385  1.00  32.67   Y  C
ATOM   7662  CB   LEU  72      68.392  48.238  35.985  1.00  53.11   Y  C
ATOM   7663  CG   LEU  72      67.283  47.694  35.073  1.00  53.11   Y  C
ATOM   7664  CD1  LEU  72      66.871  48.731  34.059  1.00  53.11   Y  C
ATOM   7665  CD2  LEU  72      67.769  46.444  34.372  1.00  53.11   Y  C
```

Fig. 19: A-106

| | | | | | | | | | | |
|---|---|---|---|---|---|---|---|---|---|---|
| ATOM | 7666 | C | LEU | 72 | 66.958 | 50.056 | 36.972 | 1.00 | 32.67 | Y C |
| ATOM | 7667 | O | LEU | 72 | 66.688 | 49.738 | 38.129 | 1.00 | 32.67 | Y O |
| ATOM | 7668 | N | THR | 73 | 66.106 | 50.715 | 36.195 | 1.00 | 42.60 | Y N |
| ATOM | 7669 | CA | THR | 73 | 64.795 | 51.100 | 36.700 | 1.00 | 42.60 | Y C |
| ATOM | 7670 | CB | THR | 73 | 64.780 | 52.597 | 37.094 | 1.00 | 57.15 | Y C |
| ATOM | 7671 | OG1 | THR | 73 | 66.018 | 52.943 | 37.730 | 1.00 | 57.15 | Y O |
| ATOM | 7672 | CG2 | THR | 73 | 63.639 | 52.879 | 38.058 | 1.00 | 57.15 | Y C |
| ATOM | 7673 | C | THR | 73 | 63.665 | 50.854 | 35.708 | 1.00 | 42.60 | Y C |
| ATOM | 7674 | O | THR | 73 | 63.791 | 51.132 | 34.516 | 1.00 | 42.60 | Y O |
| ATOM | 7675 | N | ILE | 74 | 62.564 | 50.316 | 36.212 | 1.00 | 51.99 | Y N |
| ATOM | 7676 | CA | ILE | 74 | 61.396 | 50.068 | 35.386 | 1.00 | 51.99 | Y C |
| ATOM | 7677 | CB | ILE | 74 | 60.934 | 48.597 | 35.455 | 1.00 | 52.44 | Y C |
| ATOM | 7678 | CG2 | ILE | 74 | 60.081 | 48.271 | 34.231 | 1.00 | 52.44 | Y C |
| ATOM | 7679 | CG1 | ILE | 74 | 62.138 | 47.656 | 35.471 | 1.00 | 52.44 | Y C |
| ATOM | 7680 | CD1 | ILE | 74 | 61.757 | 46.182 | 35.513 | 1.00 | 52.44 | Y C |
| ATOM | 7681 | C | ILE | 74 | 60.314 | 50.963 | 35.988 | 1.00 | 51.99 | Y C |
| ATOM | 7682 | O | ILE | 74 | 59.739 | 50.639 | 37.030 | 1.00 | 51.99 | Y O |
| ATOM | 7683 | N | SER | 75 | 60.058 | 52.094 | 35.335 | 1.00 | 41.67 | Y N |
| ATOM | 7684 | CA | SER | 75 | 59.069 | 53.066 | 35.801 | 1.00 | 41.67 | Y C |
| ATOM | 7685 | CB | SER | 75 | 59.090 | 54.291 | 34.889 | 1.00 | 51.63 | Y C |
| ATOM | 7686 | OG | SER | 75 | 58.934 | 53.909 | 33.535 | 1.00 | 51.63 | Y O |
| ATOM | 7687 | C | SER | 75 | 57.644 | 52.524 | 35.901 | 1.00 | 41.67 | Y C |
| ATOM | 7688 | O | SER | 75 | 56.885 | 52.924 | 36.777 | 1.00 | 41.67 | Y O |
| ATOM | 7689 | N | SER | 76 | 57.280 | 51.627 | 34.993 | 1.00 | 62.86 | Y N |
| ATOM | 7690 | CA | SER | 76 | 55.950 | 51.032 | 34.996 | 1.00 | 62.86 | Y C |
| ATOM | 7691 | CB | SER | 76 | 55.045 | 51.724 | 33.980 | 1.00 | 71.45 | Y C |
| ATOM | 7692 | OG | SER | 76 | 53.779 | 51.086 | 33.932 | 1.00 | 71.45 | Y O |
| ATOM | 7693 | C | SER | 76 | 56.056 | 49.558 | 34.649 | 1.00 | 62.86 | Y C |
| ATOM | 7694 | O | SER | 76 | 55.970 | 49.176 | 33.480 | 1.00 | 62.86 | Y O |
| ATOM | 7695 | N | LEU | 77 | 56.237 | 48.734 | 35.675 | 1.00 | 53.25 | Y N |
| ATOM | 7696 | CA | LEU | 77 | 56.380 | 47.298 | 35.490 | 1.00 | 53.25 | Y C |
| ATOM | 7697 | CB | LEU | 77 | 56.342 | 46.596 | 36.841 | 1.00 | 41.03 | Y C |
| ATOM | 7698 | CG | LEU | 77 | 57.317 | 45.433 | 37.008 | 1.00 | 41.03 | Y C |
| ATOM | 7699 | CD1 | LEU | 77 | 56.911 | 44.632 | 38.239 | 1.00 | 41.03 | Y C |
| ATOM | 7700 | CD2 | LEU | 77 | 57.310 | 44.548 | 35.766 | 1.00 | 41.03 | Y C |
| ATOM | 7701 | C | LEU | 77 | 55.303 | 46.703 | 34.590 | 1.00 | 53.25 | Y C |
| ATOM | 7702 | O | LEU | 77 | 54.114 | 46.944 | 34.787 | 1.00 | 53.25 | Y O |
| ATOM | 7703 | N | GLN | 78 | 55.723 | 45.921 | 33.602 | 1.00 | 82.27 | Y N |
| ATOM | 7704 | CA | GLN | 78 | 54.781 | 45.285 | 32.691 | 1.00 | 82.27 | Y C |
| ATOM | 7705 | CB | GLN | 78 | 55.094 | 45.667 | 31.243 | 1.00 | 41.92 | Y C |
| ATOM | 7706 | CG | GLN | 78 | 54.907 | 47.148 | 30.956 | 1.00 | 41.92 | Y C |
| ATOM | 7707 | CD | GLN | 78 | 53.508 | 47.627 | 31.288 | 1.00 | 41.92 | Y C |
| ATOM | 7708 | OE1 | GLN | 78 | 52.520 | 47.033 | 30.852 | 1.00 | 41.92 | Y O |
| ATOM | 7709 | NE2 | GLN | 78 | 53.416 | 48.711 | 32.056 | 1.00 | 41.92 | Y N |
| ATOM | 7710 | C | GLN | 78 | 54.830 | 43.774 | 32.852 | 1.00 | 82.27 | Y C |
| ATOM | 7711 | O | GLN | 78 | 55.851 | 43.213 | 33.244 | 1.00 | 82.27 | Y O |
| ATOM | 7712 | N | PRO | 79 | 53.718 | 43.093 | 32.549 | 1.00 | 81.12 | Y N |
| ATOM | 7713 | CD | PRO | 79 | 52.505 | 43.636 | 31.915 | 1.00 | 80.96 | Y C |
| ATOM | 7714 | CA | PRO | 79 | 53.632 | 41.636 | 32.660 | 1.00 | 81.12 | Y C |
| ATOM | 7715 | CB | PRO | 79 | 52.198 | 41.351 | 32.225 | 1.00 | 80.96 | Y C |
| ATOM | 7716 | CG | PRO | 79 | 51.949 | 42.426 | 31.213 | 1.00 | 80.96 | Y C |
| ATOM | 7717 | C | PRO | 79 | 54.663 | 40.914 | 31.792 | 1.00 | 81.12 | Y C |
| ATOM | 7718 | O | PRO | 79 | 54.865 | 39.708 | 31.914 | 1.00 | 81.12 | Y O |
| ATOM | 7719 | N | GLU | 80 | 55.316 | 41.670 | 30.921 | 1.00 | 44.20 | Y N |
| ATOM | 7720 | CA | GLU | 80 | 56.316 | 41.120 | 30.021 | 1.00 | 44.20 | Y C |
| ATOM | 7721 | CB | GLU | 80 | 56.117 | 41.729 | 28.636 | 1.00 | 102.65 | Y C |
| ATOM | 7722 | CG | GLU | 80 | 55.853 | 43.217 | 28.678 | 1.00 | 102.65 | Y C |
| ATOM | 7723 | CD | GLU | 80 | 55.814 | 43.833 | 27.301 | 1.00 | 102.65 | Y C |
| ATOM | 7724 | OE1 | GLU | 80 | 56.717 | 43.528 | 26.494 | 1.00 | 102.65 | Y O |
| ATOM | 7725 | OE2 | GLU | 80 | 54.891 | 44.629 | 27.026 | 1.00 | 102.65 | Y O |
| ATOM | 7726 | C | GLU | 80 | 57.742 | 41.368 | 30.520 | 1.00 | 44.20 | Y C |
| ATOM | 7727 | O | GLU | 80 | 58.672 | 40.652 | 30.145 | 1.00 | 44.20 | Y O |
| ATOM | 7728 | N | ASP | 81 | 57.902 | 42.380 | 31.371 | 1.00 | 52.34 | Y N |
| ATOM | 7729 | CA | ASP | 81 | 59.206 | 42.733 | 31.931 | 1.00 | 52.34 | Y C |
| ATOM | 7730 | CB | ASP | 81 | 59.167 | 44.111 | 32.593 | 1.00 | 55.47 | Y C |
| ATOM | 7731 | CG | ASP | 81 | 58.700 | 45.195 | 31.663 | 1.00 | 55.47 | Y C |
| ATOM | 7732 | OD1 | ASP | 81 | 58.950 | 45.085 | 30.446 | 1.00 | 55.47 | Y O |
| ATOM | 7733 | OD2 | ASP | 81 | 58.099 | 46.171 | 32.156 | 1.00 | 55.47 | Y O |
| ATOM | 7734 | C | ASP | 81 | 59.641 | 41.740 | 32.991 | 1.00 | 52.34 | Y C |
| ATOM | 7735 | O | ASP | 81 | 60.649 | 41.946 | 33.673 | 1.00 | 52.34 | Y O |
| ATOM | 7736 | N | PHE | 82 | 58.884 | 40.664 | 33.138 | 1.00 | 63.15 | Y N |
| ATOM | 7737 | CA | PHE | 82 | 59.207 | 39.685 | 34.158 | 1.00 | 63.15 | Y C |
| ATOM | 7738 | CB | PHE | 82 | 57.917 | 39.041 | 34.647 | 1.00 | 168.46 | Y C |

Fig. 19: A-107

| | | | | | | | | | | |
|---|---|---|---|---|---|---|---|---|---|---|
| ATOM | 7739 | CG | PHE | 82 | 57.024 | 40.004 | 35.381 | 1.00 | 168.46 | Y C |
| ATOM | 7740 | CD1 | PHE | 82 | 57.371 | 40.454 | 36.650 | 1.00 | 168.46 | Y C |
| ATOM | 7741 | CD2 | PHE | 82 | 55.866 | 40.498 | 34.791 | 1.00 | 168.46 | Y C |
| ATOM | 7742 | CE1 | PHE | 82 | 56.579 | 41.384 | 37.321 | 1.00 | 168.46 | Y C |
| ATOM | 7743 | CE2 | PHE | 82 | 55.067 | 41.430 | 35.458 | 1.00 | 168.46 | Y C |
| ATOM | 7744 | CZ | PHE | 82 | 55.425 | 41.872 | 36.724 | 1.00 | 168.46 | Y C |
| ATOM | 7745 | C | PHE | 82 | 60.238 | 38.657 | 33.742 | 1.00 | 63.15 | Y C |
| ATOM | 7746 | O | PHE | 82 | 59.960 | 37.733 | 32.979 | 1.00 | 63.15 | Y O |
| ATOM | 7747 | N | ALA | 83 | 61.447 | 38.867 | 34.256 | 1.00 | 34.42 | Y N |
| ATOM | 7748 | CA | ALA | 83 | 62.601 | 38.015 | 34.000 | 1.00 | 34.42 | Y C |
| ATOM | 7749 | CB | ALA | 83 | 63.138 | 38.260 | 32.595 | 1.00 | 53.93 | Y C |
| ATOM | 7750 | C | ALA | 83 | 63.669 | 38.353 | 35.036 | 1.00 | 34.42 | Y C |
| ATOM | 7751 | O | ALA | 83 | 63.389 | 39.033 | 36.025 | 1.00 | 34.42 | Y O |
| ATOM | 7752 | N | THR | 84 | 64.890 | 37.877 | 34.821 | 1.00 | 50.51 | Y N |
| ATOM | 7753 | CA | THR | 84 | 65.968 | 38.161 | 35.758 | 1.00 | 50.51 | Y C |
| ATOM | 7754 | CB | THR | 84 | 66.566 | 36.849 | 36.323 | 1.00 | 63.35 | Y C |
| ATOM | 7755 | OG1 | THR | 84 | 67.888 | 37.096 | 36.819 | 1.00 | 63.35 | Y O |
| ATOM | 7756 | CG2 | THR | 84 | 66.584 | 35.766 | 35.260 | 1.00 | 63.35 | Y C |
| ATOM | 7757 | C | THR | 84 | 67.028 | 39.021 | 35.065 | 1.00 | 50.51 | Y C |
| ATOM | 7758 | O | THR | 84 | 67.474 | 38.708 | 33.959 | 1.00 | 50.51 | Y O |
| ATOM | 7759 | N | TYR | 85 | 67.401 | 40.119 | 35.723 | 1.00 | 40.66 | Y N |
| ATOM | 7760 | CA | TYR | 85 | 68.364 | 41.076 | 35.187 | 1.00 | 40.66 | Y C |
| ATOM | 7761 | CB | TYR | 85 | 67.819 | 42.503 | 35.330 | 1.00 | 42.00 | Y C |
| ATOM | 7762 | CG | TYR | 85 | 66.476 | 42.693 | 34.668 | 1.00 | 42.00 | Y C |
| ATOM | 7763 | CD1 | TYR | 85 | 65.330 | 42.084 | 35.185 | 1.00 | 42.00 | Y C |
| ATOM | 7764 | CE1 | TYR | 85 | 64.110 | 42.163 | 34.521 | 1.00 | 42.00 | Y C |
| ATOM | 7765 | CD2 | TYR | 85 | 66.363 | 43.401 | 33.472 | 1.00 | 42.00 | Y C |
| ATOM | 7766 | CE2 | TYR | 85 | 65.148 | 43.486 | 32.800 | 1.00 | 42.00 | Y C |
| ATOM | 7767 | CZ | TYR | 85 | 64.028 | 42.860 | 33.327 | 1.00 | 42.00 | Y C |
| ATOM | 7768 | OH | TYR | 85 | 62.841 | 42.889 | 32.633 | 1.00 | 42.00 | Y O |
| ATOM | 7769 | C | TYR | 85 | 69.746 | 41.012 | 35.816 | 1.00 | 40.66 | Y C |
| ATOM | 7770 | O | TYR | 85 | 69.891 | 40.982 | 37.042 | 1.00 | 40.66 | Y O |
| ATOM | 7771 | N | TYR | 86 | 70.756 | 41.016 | 34.949 | 1.00 | 43.34 | Y N |
| ATOM | 7772 | CA | TYR | 86 | 72.159 | 40.970 | 35.349 | 1.00 | 43.34 | Y C |
| ATOM | 7773 | CB | TYR | 86 | 72.890 | 39.833 | 34.633 | 1.00 | 34.52 | Y C |
| ATOM | 7774 | CG | TYR | 86 | 72.406 | 38.441 | 34.941 | 1.00 | 34.52 | Y C |
| ATOM | 7775 | CD1 | TYR | 86 | 72.902 | 37.731 | 36.040 | 1.00 | 34.52 | Y C |
| ATOM | 7776 | CE1 | TYR | 86 | 72.472 | 36.433 | 36.303 | 1.00 | 34.52 | Y C |
| ATOM | 7777 | CD2 | TYR | 86 | 71.466 | 37.820 | 34.118 | 1.00 | 34.52 | Y C |
| ATOM | 7778 | CE2 | TYR | 86 | 71.031 | 36.530 | 34.375 | 1.00 | 34.52 | Y C |
| ATOM | 7779 | CZ | TYR | 86 | 71.538 | 35.841 | 35.462 | 1.00 | 34.52 | Y C |
| ATOM | 7780 | OH | TYR | 86 | 71.124 | 34.549 | 35.683 | 1.00 | 34.52 | Y O |
| ATOM | 7781 | C | TYR | 86 | 72.873 | 42.259 | 34.957 | 1.00 | 43.34 | Y C |
| ATOM | 7782 | O | TYR | 86 | 72.662 | 42.780 | 33.851 | 1.00 | 43.34 | Y O |
| ATOM | 7783 | N | CYS | 87 | 73.706 | 42.773 | 35.862 | 1.00 | 31.05 | Y N |
| ATOM | 7784 | CA | CYS | 87 | 74.499 | 43.945 | 35.548 | 1.00 | 31.05 | Y C |
| ATOM | 7785 | C | CYS | 87 | 75.857 | 43.346 | 35.237 | 1.00 | 31.05 | Y C |
| ATOM | 7786 | O | CYS | 87 | 76.171 | 42.248 | 35.707 | 1.00 | 31.05 | Y O |
| ATOM | 7787 | CB | CYS | 87 | 74.587 | 44.922 | 36.721 | 1.00 | 63.19 | Y C |
| ATOM | 7788 | SG | CYS | 87 | 75.151 | 44.318 | 38.354 | 1.00 | 63.19 | Y S |
| ATOM | 7789 | N | GLN | 88 | 76.653 | 44.040 | 34.431 | 1.00 | 35.54 | Y N |
| ATOM | 7790 | CA | GLN | 88 | 77.964 | 43.536 | 34.058 | 1.00 | 35.54 | Y C |
| ATOM | 7791 | CB | GLN | 88 | 77.834 | 42.732 | 32.769 | 1.00 | 42.46 | Y C |
| ATOM | 7792 | CG | GLN | 88 | 79.114 | 42.125 | 32.259 | 1.00 | 42.46 | Y C |
| ATOM | 7793 | CD | GLN | 88 | 79.594 | 42.783 | 30.983 | 1.00 | 42.46 | Y C |
| ATOM | 7794 | OE1 | GLN | 88 | 78.834 | 42.928 | 30.019 | 1.00 | 42.46 | Y O |
| ATOM | 7795 | NE2 | GLN | 88 | 80.863 | 43.183 | 30.965 | 1.00 | 42.46 | Y N |
| ATOM | 7796 | C | GLN | 88 | 78.930 | 44.691 | 33.873 | 1.00 | 35.54 | Y C |
| ATOM | 7797 | O | GLN | 88 | 78.530 | 45.774 | 33.436 | 1.00 | 35.54 | Y O |
| ATOM | 7798 | N | GLN | 89 | 80.195 | 44.465 | 34.216 | 1.00 | 24.85 | Y N |
| ATOM | 7799 | CA | GLN | 89 | 81.208 | 45.502 | 34.082 | 1.00 | 24.85 | Y C |
| ATOM | 7800 | CB | GLN | 89 | 81.794 | 45.851 | 35.458 | 1.00 | 29.69 | Y C |
| ATOM | 7801 | CG | GLN | 89 | 82.481 | 44.722 | 36.182 | 1.00 | 29.69 | Y C |
| ATOM | 7802 | CD | GLN | 89 | 83.903 | 44.496 | 35.696 | 1.00 | 29.69 | Y C |
| ATOM | 7803 | OE1 | GLN | 89 | 84.676 | 45.442 | 35.535 | 1.00 | 29.69 | Y O |
| ATOM | 7804 | NE2 | GLN | 89 | 84.261 | 43.238 | 35.476 | 1.00 | 29.69 | Y N |
| ATOM | 7805 | C | GLN | 89 | 82.294 | 45.043 | 33.128 | 1.00 | 24.85 | Y C |
| ATOM | 7806 | O | GLN | 89 | 82.527 | 43.853 | 32.990 | 1.00 | 24.85 | Y O |
| ATOM | 7807 | N | TRP | 90 | 82.943 | 45.993 | 32.460 | 1.00 | 39.13 | Y N |
| ATOM | 7808 | CA | TRP | 90 | 84.008 | 45.672 | 31.510 | 1.00 | 39.13 | Y C |
| ATOM | 7809 | CB | TRP | 90 | 83.529 | 45.955 | 30.069 | 1.00 | 30.35 | Y C |
| ATOM | 7810 | CG | TRP | 90 | 83.422 | 47.437 | 29.678 | 1.00 | 30.35 | Y C |
| ATOM | 7811 | CD2 | TRP | 90 | 83.088 | 47.967 | 28.385 | 1.00 | 30.35 | Y C |

Fig. 19: A-108

```
ATOM   7812  CE2 TRP    90      83.122  49.375  28.486  1.00  30.35      Y  C
ATOM   7813  CE3 TRP    90      82.762  47.389  27.152  1.00  30.35      Y  C
ATOM   7814  CD1 TRP    90      83.635  48.523  30.484  1.00  30.35      Y  C
ATOM   7815  NE1 TRP    90      83.460  49.686  29.776  1.00  30.35      Y  N
ATOM   7816  CZ2 TRP    90      82.840  50.217  27.398  1.00  30.35      Y  C
ATOM   7817  CZ3 TRP    90      82.480  48.232  26.063  1.00  30.35      Y  C
ATOM   7818  CH2 TRP    90      82.522  49.627  26.199  1.00  30.35      Y  C
ATOM   7819  C   TRP    90      85.290  46.457  31.816  1.00  39.13      Y  C
ATOM   7820  O   TRP    90      86.293  46.339  31.115  1.00  39.13      Y  O
ATOM   7821  N   SER    91      85.251  47.254  32.876  1.00  18.51      Y  N
ATOM   7822  CA  SER    91      86.395  48.067  33.257  1.00  18.51      Y  C
ATOM   7823  CB  SER    91      85.948  49.152  34.237  1.00  45.24      Y  C
ATOM   7824  OG  SER    91      84.909  49.937  33.686  1.00  45.24      Y  O
ATOM   7825  C   SER    91      87.555  47.267  33.866  1.00  18.51      Y  C
ATOM   7826  O   SER    91      88.717  47.649  33.739  1.00  18.51      Y  O
ATOM   7827  N   GLY    92      87.241  46.166  34.534  1.00  40.34      Y  N
ATOM   7828  CA  GLY    92      88.282  45.360  35.146  1.00  40.34      Y  C
ATOM   7829  C   GLY    92      88.273  43.910  34.687  1.00  40.34      Y  C
ATOM   7830  O   GLY    92      87.248  43.386  34.244  1.00  40.34      Y  O
ATOM   7831  N   ASN    93      89.420  43.249  34.801  1.00  37.36      Y  N
ATOM   7832  CA  ASN    93      89.544  41.863  34.380  1.00  37.36      Y  C
ATOM   7833  CB  ASN    93      90.765  41.702  33.492  1.00  14.59      Y  C
ATOM   7834  CG  ASN    93      90.634  42.451  32.208  1.00  14.59      Y  C
ATOM   7835  OD1 ASN    93      91.556  43.159  31.796  1.00  14.59      Y  O
ATOM   7836  ND2 ASN    93      89.482  42.305  31.552  1.00  14.59      Y  N
ATOM   7837  C   ASN    93      89.668  40.944  35.574  1.00  37.36      Y  C
ATOM   7838  O   ASN    93      90.346  41.265  36.539  1.00  37.36      Y  O
ATOM   7839  N   PRO    94      89.005  39.783  35.525  1.00  28.71      Y  N
ATOM   7840  CD  PRO    94      88.990  38.808  36.629  1.00   9.29      Y  C
ATOM   7841  CA  PRO    94      88.167  39.322  34.412  1.00  28.71      Y  C
ATOM   7842  CB  PRO    94      87.940  37.858  34.745  1.00   9.29      Y  C
ATOM   7843  CG  PRO    94      87.823  37.904  36.251  1.00   9.29      Y  C
ATOM   7844  C   PRO    94      86.845  40.076  34.372  1.00  28.71      Y  C
ATOM   7845  O   PRO    94      86.418  40.640  35.384  1.00  28.71      Y  O
ATOM   7846  N   TRP    95      86.200  40.084  33.206  1.00  37.86      Y  N
ATOM   7847  CA  TRP    95      84.910  40.743  33.082  1.00  37.86      Y  C
ATOM   7848  CB  TRP    95      84.428  40.762  31.629  1.00  24.14      Y  C
ATOM   7849  CG  TRP    95      85.220  41.665  30.744  1.00  24.14      Y  C
ATOM   7850  CD2 TRP    95      85.537  41.458  29.359  1.00  24.14      Y  C
ATOM   7851  CE2 TRP    95      86.285  42.575  28.929  1.00  24.14      Y  C
ATOM   7852  CE3 TRP    95      85.264  40.437  28.440  1.00  24.14      Y  C
ATOM   7853  CD1 TRP    95      85.770  42.867  31.085  1.00  24.14      Y  C
ATOM   7854  NE1 TRP    95      86.411  43.419  30.000  1.00  24.14      Y  N
ATOM   7855  CZ2 TRP    95      86.765  42.697  27.624  1.00  24.14      Y  C
ATOM   7856  CZ3 TRP    95      85.748  40.566  27.133  1.00  24.14      Y  C
ATOM   7857  CH2 TRP    95      86.487  41.685  26.744  1.00  24.14      Y  C
ATOM   7858  C   TRP    95      83.959  39.922  33.941  1.00  37.86      Y  C
ATOM   7859  O   TRP    95      83.997  38.688  33.920  1.00  37.86      Y  O
ATOM   7860  N   THR    96      83.105  40.605  34.695  1.00  19.88      Y  N
ATOM   7861  CA  THR    96      82.192  39.913  35.582  1.00  19.88      Y  C
ATOM   7862  CB  THR    96      82.692  40.028  37.038  1.00  22.31      Y  C
ATOM   7863  OG1 THR    96      82.747  41.408  37.404  1.00  22.31      Y  O
ATOM   7864  CG2 THR    96      84.091  39.443  37.186  1.00  22.31      Y  C
ATOM   7865  C   THR    96      80.759  40.413  35.508  1.00  19.88      Y  C
ATOM   7866  O   THR    96      80.500  41.491  34.998  1.00  19.88      Y  O
ATOM   7867  N   PHE    97      79.839  39.596  36.015  1.00  20.15      Y  N
ATOM   7868  CA  PHE    97      78.420  39.912  36.073  1.00  20.15      Y  C
ATOM   7869  CB  PHE    97      77.580  38.827  35.397  1.00  25.28      Y  C
ATOM   7870  CG  PHE    97      77.890  38.613  33.946  1.00  25.28      Y  C
ATOM   7871  CD1 PHE    97      79.062  37.994  33.554  1.00  25.28      Y  C
ATOM   7872  CD2 PHE    97      76.979  38.990  32.969  1.00  25.28      Y  C
ATOM   7873  CE1 PHE    97      79.322  37.750  32.204  1.00  25.28      Y  C
ATOM   7874  CE2 PHE    97      77.234  38.748  31.611  1.00  25.28      Y  C
ATOM   7875  CZ  PHE    97      78.404  38.128  31.233  1.00  25.28      Y  C
ATOM   7876  C   PHE    97      78.054  39.931  37.557  1.00  20.15      Y  C
ATOM   7877  O   PHE    97      78.841  39.487  38.394  1.00  20.15      Y  O
ATOM   7878  N   GLY    98      76.875  40.460  37.879  1.00  30.22      Y  N
ATOM   7879  CA  GLY    98      76.412  40.488  39.256  1.00  30.22      Y  C
ATOM   7880  C   GLY    98      75.676  39.178  39.406  1.00  30.22      Y  C
ATOM   7881  O   GLY    98      75.506  38.478  38.405  1.00  30.22      Y  O
ATOM   7882  N   GLN    99      75.235  38.819  40.608  1.00  24.51      Y  N
ATOM   7883  CA  GLN    99      74.537  37.541  40.755  1.00  24.51      Y  C
ATOM   7884  CB  GLN    99      74.350  37.163  42.231  1.00  60.71      Y  C
```

Fig. 19: A-109

| | | | | | | | | | | |
|---|---|---|---|---|---|---|---|---|---|---|
| ATOM | 7885 | CG | GLN | 99 | 74.599 | 38.274 | 43.209 | 1.00 | 60.71 | Y | C |
| ATOM | 7886 | CD | GLN | 99 | 73.728 | 39.464 | 42.945 | 1.00 | 60.71 | Y | C |
| ATOM | 7887 | OE1 | GLN | 99 | 72.510 | 39.411 | 43.113 | 1.00 | 60.71 | Y | O |
| ATOM | 7888 | NE2 | GLN | 99 | 74.346 | 40.551 | 42.515 | 1.00 | 60.71 | Y | N |
| ATOM | 7889 | C | GLN | 99 | 73.189 | 37.507 | 40.043 | 1.00 | 24.51 | Y | C |
| ATOM | 7890 | O | GLN | 99 | 72.587 | 36.443 | 39.894 | 1.00 | 24.51 | Y | O |
| ATOM | 7891 | N | GLY | 100 | 72.730 | 38.666 | 39.586 | 1.00 | 42.40 | Y | N |
| ATOM | 7892 | CA | GLY | 100 | 71.455 | 38.725 | 38.900 | 1.00 | 42.40 | Y | C |
| ATOM | 7893 | C | GLY | 100 | 70.355 | 39.043 | 39.886 | 1.00 | 42.40 | Y | C |
| ATOM | 7894 | O | GLY | 100 | 70.483 | 38.749 | 41.074 | 1.00 | 42.40 | Y | O |
| ATOM | 7895 | N | THR | 101 | 69.283 | 39.662 | 39.399 | 1.00 | 27.30 | Y | N |
| ATOM | 7896 | CA | THR | 101 | 68.144 | 40.021 | 40.236 | 1.00 | 27.30 | Y | C |
| ATOM | 7897 | CB | THR | 101 | 68.024 | 41.538 | 40.401 | 1.00 | 28.79 | Y | C |
| ATOM | 7898 | OG1 | THR | 101 | 69.008 | 41.995 | 41.336 | 1.00 | 28.79 | Y | O |
| ATOM | 7899 | CG2 | THR | 101 | 66.646 | 41.907 | 40.892 | 1.00 | 28.79 | Y | C |
| ATOM | 7900 | C | THR | 101 | 66.903 | 39.492 | 39.551 | 1.00 | 27.30 | Y | C |
| ATOM | 7901 | O | THR | 101 | 66.619 | 39.845 | 38.408 | 1.00 | 27.30 | Y | O |
| ATOM | 7902 | N | LYS | 102 | 66.166 | 38.635 | 40.240 | 1.00 | 67.88 | Y | N |
| ATOM | 7903 | CA | LYS | 102 | 64.978 | 38.064 | 39.642 | 1.00 | 67.88 | Y | C |
| ATOM | 7904 | CB | LYS | 102 | 64.806 | 36.618 | 40.106 | 1.00 | 117.75 | Y | C |
| ATOM | 7905 | CG | LYS | 102 | 63.920 | 35.785 | 39.198 | 1.00 | 117.75 | Y | C |
| ATOM | 7906 | CD | LYS | 102 | 63.925 | 34.321 | 39.608 | 1.00 | 117.75 | Y | C |
| ATOM | 7907 | CE | LYS | 102 | 63.094 | 33.485 | 38.651 | 1.00 | 117.75 | Y | C |
| ATOM | 7908 | NZ | LYS | 102 | 63.586 | 33.621 | 37.250 | 1.00 | 117.75 | Y | N |
| ATOM | 7909 | C | LYS | 102 | 63.749 | 38.885 | 39.996 | 1.00 | 67.88 | Y | C |
| ATOM | 7910 | O | LYS | 102 | 63.560 | 39.262 | 41.155 | 1.00 | 67.88 | Y | O |
| ATOM | 7911 | N | VAL | 103 | 62.926 | 39.176 | 38.989 | 1.00 | 55.50 | Y | N |
| ATOM | 7912 | CA | VAL | 103 | 61.706 | 39.941 | 39.208 | 1.00 | 55.50 | Y | C |
| ATOM | 7913 | CB | VAL | 103 | 61.779 | 41.349 | 38.510 | 1.00 | 68.46 | Y | C |
| ATOM | 7914 | CG1 | VAL | 103 | 63.207 | 41.865 | 38.530 | 1.00 | 68.46 | Y | C |
| ATOM | 7915 | CG2 | VAL | 103 | 61.258 | 41.290 | 37.084 | 1.00 | 68.46 | Y | C |
| ATOM | 7916 | C | VAL | 103 | 60.489 | 39.141 | 38.709 | 1.00 | 55.50 | Y | C |
| ATOM | 7917 | O | VAL | 103 | 60.378 | 38.828 | 37.517 | 1.00 | 55.50 | Y | O |
| ATOM | 7918 | N | GLU | 104 | 59.597 | 38.779 | 39.633 | 1.00 | 70.95 | Y | N |
| ATOM | 7919 | CA | GLU | 104 | 58.395 | 38.025 | 39.281 | 1.00 | 70.95 | Y | C |
| ATOM | 7920 | CB | GLU | 104 | 58.243 | 36.764 | 40.145 | 1.00 | 145.77 | Y | C |
| ATOM | 7921 | CG | GLU | 104 | 57.957 | 37.019 | 41.616 | 1.00 | 145.77 | Y | C |
| ATOM | 7922 | CD | GLU | 104 | 59.215 | 37.263 | 42.418 | 1.00 | 145.77 | Y | C |
| ATOM | 7923 | OE1 | GLU | 104 | 59.106 | 37.542 | 43.631 | 1.00 | 145.77 | Y | O |
| ATOM | 7924 | OE2 | GLU | 104 | 60.315 | 37.167 | 41.839 | 1.00 | 145.77 | Y | O |
| ATOM | 7925 | C | GLU | 104 | 57.157 | 38.897 | 39.443 | 1.00 | 70.95 | Y | C |
| ATOM | 7926 | O | GLU | 104 | 57.197 | 39.939 | 40.108 | 1.00 | 70.95 | Y | O |
| ATOM | 7927 | N | ILE | 105 | 56.058 | 38.459 | 38.834 | 1.00 | 139.77 | Y | N |
| ATOM | 7928 | CA | ILE | 105 | 54.791 | 39.184 | 38.876 | 1.00 | 139.77 | Y | C |
| ATOM | 7929 | CB | ILE | 105 | 53.838 | 38.730 | 37.757 | 1.00 | 105.35 | Y | C |
| ATOM | 7930 | CG2 | ILE | 105 | 52.923 | 39.875 | 37.373 | 1.00 | 105.35 | Y | C |
| ATOM | 7931 | CG1 | ILE | 105 | 54.633 | 38.232 | 36.553 | 1.00 | 105.35 | Y | C |
| ATOM | 7932 | CD1 | ILE | 105 | 53.775 | 37.746 | 35.397 | 1.00 | 105.35 | Y | C |
| ATOM | 7933 | C | ILE | 105 | 54.047 | 38.952 | 40.180 | 1.00 | 139.77 | Y | C |
| ATOM | 7934 | O | ILE | 105 | 53.763 | 37.810 | 40.533 | 1.00 | 139.77 | Y | O |
| ATOM | 7935 | N | LYS | 106 | 53.706 | 40.031 | 40.880 | 1.00 | 101.75 | Y | N |
| ATOM | 7936 | CA | LYS | 106 | 52.969 | 39.916 | 42.135 | 1.00 | 101.75 | Y | C |
| ATOM | 7937 | CB | LYS | 106 | 53.545 | 40.870 | 43.189 | 1.00 | 95.13 | Y | C |
| ATOM | 7938 | CG | LYS | 106 | 52.954 | 40.690 | 44.584 | 1.00 | 95.13 | Y | C |
| ATOM | 7939 | CD | LYS | 106 | 53.556 | 41.665 | 45.586 | 1.00 | 95.13 | Y | C |
| ATOM | 7940 | CE | LYS | 106 | 52.939 | 41.482 | 46.965 | 1.00 | 95.13 | Y | C |
| ATOM | 7941 | NZ | LYS | 106 | 53.446 | 42.478 | 47.948 | 1.00 | 95.13 | Y | N |
| ATOM | 7942 | C | LYS | 106 | 51.492 | 40.235 | 41.897 | 1.00 | 101.75 | Y | C |
| ATOM | 7943 | O | LYS | 106 | 51.148 | 40.637 | 40.765 | 1.00 | 100.80 | Y | O |
| ATOM | 7944 | OXT | LYS | 106 | 50.694 | 40.080 | 42.844 | 1.00 | 94.18 | Y | O |
| ATOM | 7945 | MN | MN | 400 | 89.864 | 50.249 | 22.621 | 1.00 | 34.24 | N | |

END

US 7,910,099 B2

ANTIBODIES TO VLA-1

CROSS-REFERENCE TO RELATED APPLICATIONS

This application is a divisional application of U.S. application Ser. No. 12/015,213, filed Jan. 16, 2008 (which issued as U.S. Pat. No. 7,723,073 on May 25, 2010), which is a divisional application of U.S. application Ser. No. 10/474,832, filed Oct. 14, 2003 (which issued as U.S. Pat. No. 7,358,054 on Apr. 15, 2008), which is the National Stage filing under 35 U.S.C. §371 of International Application No. PCT/US02/11521, filed Apr. 12, 2002, which claims benefit under 35 U.S.C. §119(e) of United States provisional application Nos. 60/283,794, filed Apr. 13, 2001, and 60/303,689, filed Jul. 6, 2001.

FIELD OF THE INVENTION

This invention relates to antibodies to VLA-1 integrin and the use of these antibodies in treating inflammatory diseases and other immunological disorders.

This invention also relates to the crystal structure of the complex between one such antibody and the α1-I domain of VLA-1, and to the use of this structural information for computational drug design.

BACKGROUND OF THE INVENTION

Integrins are a superfamily of cell surface receptors that mediate cell-cell and cell-matrix adhesion. These proteins are known to provide anchorage as well as signals for cellular growth, migration and differentiation during development and tissue repair. They have been implicated in immune and inflammatory processes.

Integrins are heterodimeric proteins composed of two non-covalently linked polypeptide chains, α and β. The amino terminus of each chain forms a globular head that contributes to interchain linking and to ligand binding. The globular heads are connected to the transmembrane segments by stalks. The cytoplasmic tails are usually less than 50 amino acid residues long. Integrin subfamilies were originally defined on the basis of which β subunit was used to form the heterodimers. The β1-containing integrins are also called VLA molecules, referring to "very late activation" antigens. VLA-1 to VLA-6 refer to β1 subfamily members containing α1 to α6 (i.e., CD49a to CD49f), respectively. For general review, see Cellular and Molecular Immunology, eds. Abul K. Abbas et al., W. B. Saunders Company, Philadelphia, Pa., 2000.

Collagen (both types I and IV) and laminin are known ligands of α1β1 integrin (i.e., VLA-1). VLA-1 has been implicated in cell adhesion and migration on collagen (Keely et al., 1995, J. Cell Sci. 108:595-607; and Gotwals et al., 1996, J. Clin. Invest. 97:2469-2477); in promoting contraction and reorganization of collagen matrices, a critical component of wound healing (Gotwals et al., supra; and Chiro, 1991, Cell 67:403-410); and in regulating the expression of genes involved in extracellular matrix remodeling (Riikonen et al., 1995, J. Biol. Chem. 270:1-5; and Langholz et al., 1995, J. Cell Biol. 131:1903-1915). Thus, improper regulation of VLA-1 may result in certain pathological conditions such as fibrosis.

Moreover, it has been suggested that VLA-1 may play a role in T cell/monocyte-driven diseases. Anti-VLA-1 antibodies block T-cell dependent cytokine expression (Miyake et al., 1993, J. Exp. Med. 177:863-868). Expression of VLA-1 is increased in persistently activated, 2 to 4 week old cultured T cells (Hemler et al., 1985, Eur. J. Immunol. 15:502-508). VLA-1 is also expressed on a high percentage of T cells isolated from the synovium of patients with rheumatoid arthritis (Hemler et al., 1986, J. Clin. Invest. 78:692-702).

Several crystal structures of integrin α subunits have been determined, including the structures of the α2-I domain of α2β1 (PDB accession code 1aox; Emsley et al., 1997, J. Biol. Chem. 272:28512-28517); the α1-I domain of rat α1β1 (PDB accession number 1ck4; Nolte et al., 1999, FEBS Lett. 452:379-85; WO 00/20459); the a1 subunit of human α1β1 (PDB accession code 1qc5; Rich et al., 1999, J. Biol. Chem. 274:24906-24913); the αL-I and αM-I domains; and vWF-A3 (Lee et al., 1995, Cell 80:631-635; Lee et al., 1995, Structure 3:1333-1340; Qu et al., 1995, Proc. Natl. Acad. Sci. USA 92:10277-10281; Qu et al., 1996, Structure 4:931-942). The α2β1 structure revealed a helix (i.e., the C-helix) that created a trench or groove on one face of the protein at the metal-ion binding site (Emsley et al., supra). The crystal structure of the α2-I domain complexed to a short collagen-based triple helical peptide revealed that the collagen-based peptide was bound to that trench, where the α2-I amino acids that made intermolecular or metal contacts included Asp151, Asn154, Tyr157, Gln215, Asp219, Leu220, Thr221, Asp254, Glu256, His258, Tyr285, Leu286, Asn289, Leu291, Asn295, and Lys298 (PDB accession code 1dzi; Emsley et al., 2000, Cell 101:47-56; WO 01/73444). The amino acid numbering immediately above is based on PDB accession code 1dzi and herein referred to as "crystal numbering." The crystal structures of the rat and human α1-I domains revealed a similar trench.

SUMMARY OF THE INVENTION

The present invention provides anti-VLA-1 antibodies and methods of using these antibodies to treat a variety of inflammatory and immunological disorders.

Specifically, the invention embraces an antibody that specifically binds to VLA-1 (e.g., human VLA-1). This antibody contains light chain complementarity determining regions ("CDR"s) defined by amino acid residues 24 to 33, 49 to 55, and 88 to 96 of SEQ ID NO:1, and/or heavy chain complementarity determining regions defined by amino acid residues 31 to 35, 50 to 65, and 98 to 107 of SEQ ID NO:2. These CDRs may contain mutations (e.g., deletions, insertions and/or substitutions) in the non-antigen-contacting portions, as determined from the crystal structure disclosed herein, without affecting the VLA-1-binding activity of the antibody. Exemplary mutations are S24N, G92S and D101A in the light chain CDRs, and G55S in the heavy chain CDR2. In one embodiment, the antibody of this invention contains a light chain variable domain sequence of SEQ ID NO:1 and/or a heavy chain variable domain sequence of SEQ ID NO:2.

In a related embodiment, the antibody of this invention contains the same heavy and light chain polypeptide sequences as an antibody produced by hybridoma mAQC2, deposited on Apr. 18, 2001 at the American Type Culture Collection ("ATCC"), 10801 University Boulevard, Manassas, Va. 20110-2209 and having ATCC accession number PTA3273. (All ATCC deposits recited herein were made under the Budapest Treaty). This antibody can be produced by, for example, hybridoma mAQC2, or cells containing nucleic acid sequences isolated from that hybridoma that encode the heavy and light chains of the mAQC2 monoclonal antibody.

In another embodiment, the antibody is a humanized antibody comprising at least one (e.g., 2, 3, 4, or 5) of the following residues in its light chain: Q1, L4, P46, W47 and Y71; or at least one (e.g., 2, 3, 4, 5, 6 or 7) of the following residues in its heavy chain: D1, V12, S28, F29, A49, T93, R94 (Kabat numbering convention). For instance, the antibody comprises Q1, L4 and Y71 in the light chain; and/or (i) F29, A49, T93 and R94, or (ii) A49 and T93, in the heavy chain.

The humanized antibody of this invention may contain a light chain variable domain sequence defined by amino acid residues 1 to 106 of SEQ ID NO:3, and/or a heavy chain variable domain sequence defined by amino acid residues 1 to 118 of SEQ ID NO:4. The humanized antibody may comprise the same heavy and/or light chain polypeptide sequences as an antibody produced by cell line hAQC2 (ATCC accession number PTA3275; deposited on Apr. 18, 2001).

In another embodiment, the humanized antibody of this invention may contain a mutation (e.g., deletion, substitution or addition) at one or more (e.g., 2, 3, 4, 5, 6, 7 or 8) of certain positions in the heavy chain such that an effector function of the antibody (e.g., the ability of the antibody to bind to a Fc receptor or a complement factor) is altered without affecting the antibody's ability to bind to VLA-1 (U.S. Pat. No. 5,648, 260). These heavy chain positions include, without limitation, residues 234, 235, 236, 237, 297, 318, 320 and 322 (EU numbering system). The humanized antibody can, for instance, contain the mutations L234A (i.e., replacing leucine at position 234 of an unmodified antibody with alanine) and L235A (EU numbering system) in its heavy chain. In one related embodiment, the antibody comprises the same heavy chain polypeptide sequence as an antibody produced by cell line hsAQC2 (ATCC accession number PTA3356; deposited on May 4, 2001).

In yet another embodiment, the humanized antibody of this invention may contain a mutation (e.g., deletion or substitution) at an amino acid residue that is a site for glycosylation, such that the glycosylation site is eliminated. Such an antibody may be clinically beneficial for having reduced effector functions or other undesired functions while retaining its VLA-1 binding affinity. Mutations of glycosylation sites can also be beneficial for process development (e.g., protein expression and purification). For instance, the heavy chain of the antibody may contain the mutation N297Q (EU numbering system) such that the heavy chain can no longer be glycosylated at this site. In one related embodiment, the humanized antibody may comprise the same heavy chain polypeptide sequence as an antibody produced by cell line haAQC2 (ATCC accession number PTA3274; deposited on Apr. 18, 2001).

In still other embodiments, the heavy and/or light chains of the antibody of this invention contain mutations that increase affinity for binding to VLA-1 and thereby increase potency for treating VLA-1-mediated disorders.

Embraced in this invention are also a composition containing an antibody of the invention and a pharmaceutically acceptable carrier; an isolated nucleic acid containing a coding sequence for SEQ ID NO:1; an isolated nucleic acid containing a coding sequence for SEQ ID NO:2; an isolated nucleic acid containing a coding sequence for the light chain of an antibody produced by hybridoma mAQC2; an isolated nucleic acid containing a coding sequence for the heavy chain of an antibody produced by hybridoma mAQC2; an isolated nucleic acid containing a coding sequence for the light chain of an antibody produced by cell line hAQC2; an isolated nucleic acid containing a coding sequence for the heavy chain of an antibody produced by cell line hAQC2; an isolated nucleic acid containing a coding sequence for the heavy chain of an antibody produced by cell line haAQC2; an isolated nucleic acid containing a coding sequence for the heavy chain of an antibody produced by cell line hsAQC2; an isolated nucleic acid containing a coding sequence for residues 1 to 106 of SEQ ID NO:3; an isolated nucleic acid containing a coding sequence for residues 1 to 118 of SEQ ID NO:4; cells of hybridoma mAQC2; cells from cell line hAQC2; cells from cell line haAQC2; and cells from cell line hsAQC2.

The present invention also provides a method of treating a subject with an immunological disorder mediated by VLA-1, including administering to the subject an effective amount of an antibody of this invention. For instance, this method is used to treat a human subject to palliate, ameliorate, stabilize, reverse, prevent, slow or delay progression of the disorder. Alternatively, this method is used prophylactically to treat a human subject at risk for developing this immunological disorder so as to prevent or delay the onset of the disorder. An "effective amount" of the composition can be administered in one or more dosages.

VLA-1 mediated immunological disorders include, but are not limited to, disorders in which the VLA-1 activity level is elevated in one or more tissues as compared to a normal subject. Examples of such disorders are skin related conditions (e.g., psoriasis, eczema, burns, dermatitis, and abnormal proliferation of hair follicle cells), fibrosis (e.g., kidney or lung fibrosis), allergic rhinitis, respiratory distress syndrome, asthma, bronchitis, tendinitis, bursitis, fever, migraine headaches, gastrointestinal conditions (e.g., inflammatory bowel disease, Crohn's disease, gastritis, irritable bowel syndrome, colitis and colorectal cancer), vascular diseases (e.g., atherosclerosis), periarteritis nodosa, thyroiditis, aplastic anemia, Hodgkin's Disease, rheumatic fever, osteoarthritis, autoimmune diseases (e.g., type I diabetes, myasthenia gravis, rheumatoid arthritis, systemic lupus erythematosus, and multiple sclerosis), sarcoidosis, nephrotic syndrome, renal failure, Bechet's Syndrome, polymyositis, gingivitis, hypersensitivity (e.g., delayed type hypersensitivity or immediate hypersensitivity), graft and transplant rejections, graft versus host disease (GVHD), conjunctivitis, swelling occurring after injury, myocardial ischemia, and endotoxin shock syndrome.

The present invention also provides a method of determining the level of VLA-1 in a tissue (e.g., tissue specimen and body fluid) comprising contacting the tissue (e.g., in vivo or in vitro) with the antibody of the invention, and then detecting the binding of the antibody to the tissue, thereby determining the level of VLA-1 in the tissue.

As used herein, the antibody of this invention can be, for instance, a murine antibody, a humanized antibody, or a chimeric antibody. It can be a whole antibody (i.e., with two full length light chains and two full length heavy chains) of any isotype and subtypes (e.g., IgM, IgD, $IgG_1$, $IgG_2$, $IgG_3$, $IgG_4$, IgE, $IgA_1$, and $IgA_2$; with either kappa or lambda light chain). Alternatively, the antibody of this invention refers to an antigen-binding fragment (e.g., Fab, $F(ab')_2$, and single chain Fv) of a whole antibody.

The present invention further provides crystallizable compositions and crystals of complexes formed by a rat-human chimeric α1-I domain (mutant RΔH) and a hAQC2 Fab fragment, and methods for using such compositions and crystals. This invention also provides the structure coordinates and binding sites of the chimeric domain and the hAQC2 Fab fragment. The atomic coordinates derived from the crystal structure described herein provide a structural basis for the biological activities of hAQC2 as well as a basis for rational design of VLA-1 agonists or antagonists with predicted biological activities (e.g., small molecule compounds or antibodies such as hAQC2 variants).

The crystal structure disclosed herein is the first crystal structure of an α1-I domain of an α1β1 integrin/Fab complex.

This structure shows the residues critical for Fab binding by α1-I domain. In addition, the Fab binds in the putative collagen-binding site and inhibits collagen binding. Amino acid residues found in the binding site on the α1-I domain include Asp154, Ser156, Asn157, Ser158, Tyr160, Glu192, Glu218, Arg219, Gly220, Gly221, Arg222, Gln223, Thr224, Asp257, His261, Asn263, and Leu294 (crystal numbering). Residues on the Fab fragment found to bind to the α1-I domain include light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering).

This invention also provides a computer for producing a three-dimensional representation of a molecular complex, where the molecular complex is defined by the set of structure coordinates of a complex of a chimeric I domain of an α1β1 integrin RΔH and humanized antibody hAQC2, according to FIG. 19; or a homologue of the molecular complex, the homologue having a root mean square deviation from the backbone atoms of the amino acids of not more than 0.65 Å. The computer includes a machine-readable data storage medium including a data storage material encoded with machine-readable data, where the data contains at least a portion of the structure coordinates of the complex according to FIG. 19; a working memory for storing instructions for processing the machine-readable data; a central processing unit coupled to the working memory and to the machine-readable data storage medium for processing the machine readable data into the three-dimensional representations; and a display coupled to the central-processing unit for displaying the three-dimensional representation.

This invention further provides a computer for producing a three-dimensional representation of a molecule or molecular complex including a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19; or a homologue of the molecule or molecular complex, where the homologue includes a binding site that has a root mean square deviation from the backbone atoms of the hAQC2 amino acids of not more than 1.10 Å. This invention also provides a computer for producing a three-dimensional representation of: a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19; a binding site of a homologue that has a root mean square deviation from the backbone atoms of the hAQC2 amino acids of not more than 1.10 Å.

This invention also provides a method for identifying an inhibitor of an I domain of an integrin including the steps of using structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg39, Trp47, Ser52, Gly53, His56, Tyr58, Phe99, Gly100 and Asp101 (crystal numbering), according to FIG. 19 or ±a root mean square deviation from the backbone atoms of the hAQC2 amino acids not more than 1.10 Å, to generate a three-dimensional structure of a binding site; employing the three-dimensional structure to design or select a potential antagonist; synthesizing the potential antagonist; and contacting the potential antagonist with hAQC2 to determine the ability of the potential antagonist to interact with hAQC2, where the ability of the potential antagonist to interact with hAQC2 indicates that the potential antagonist is an inhibitor of the I domain. This invention further provides an inhibitor of I domain of integrin identified by this method.

This invention also provides a computer for producing a three-dimensional representation of a molecule or molecular complex including: a binding site defined by structure coordinates of I domain amino acid residues Asp 154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a homologue of the molecule or molecular complex, where the homologue includes a second binding site that has a root mean square deviation from the backbone atoms of the I domain amino acids not more than 0.65 Å. This invention also provides a computer for producing a three-dimensional representation of: a first binding site defined by structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a binding site of a homologue that has a root mean square deviation from the backbone atoms of the I domain amino acids not more than 0.65 Å.

This invention also provides a computer for producing a three-dimensional representation of a molecule or molecular complex including: a binding site defined by structure coordinates of I domain amino acids including at least three of residues Glu192, Gln218, Arg219, Gly220, and Gly221 (crystal numbering), according to FIG. 19; or a homologue of the molecule or molecular complex, where the homologue includes a second binding site that has a root mean square deviation from the backbone atoms of the I domain amino acids not more than 1.0 Å. The invention further provides a computer for producing a three-dimensional representation of a binding site defined by structure coordinates of I domain amino acids including at least three of residues Glu192, Gln218, Arg219, Gly220, and Gly221 (crystal numbering), according to FIG. 19; or a binding site of a homologue that has a root mean square deviation from the backbone atoms of the I domain amino acids not more than 1.0 Å.

This invention further provides methods for using these three-dimensional representations to design chemical entities that associate with the chimeric domain or the hAQC2 Fab fragment, or portions thereof; and act as potential inhibitors of the chimeric domain or the hAQC2 Fab fragment, or portions thereof. This invention also relates to compositions including chemical entities, such as inhibitors and variants of the chimeric domain or variants of the hAQC2 Fab fragment, where such chemical entities and variants are rationally designed by means of the structure coordinates of the chimeric domain or the hAQC2 Fab fragment, or binding sites. The invention further relates to use of the above-identified chemical entities to treat or prevent conditions associated with inappropriate or abnormal α1β1 activity in a subject.

This invention further provides a method for identifying an inhibitor of an I domain of an integrin including the steps of using the structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain, where the ability of the potential antagonist to interact with the I domain indicates that the potential antagonist is an inhibitor of the I domain.

This invention also provides a method for identifying an inhibitor of an I domain of an integrin including the steps of using the structure coordinates of at least three of I domain amino acids including residues Glu192, Gln218, Arg219, Gly220, and Gly221 (crystal numbering), according to FIG. 19, or ±a root mean square deviation from the backbone atoms of the I domain amino acids not more than 0.65 Å, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain of integrin, where the ability of the potential antagonist to interact with the I domain indicates that the potential antagonist is an inhibitor of the I domain. This invention also provides an inhibitor of I domain of integrin identified by this method.

Other features and advantages of the invention will be apparent from the following detailed description, and from the claims.

Arthritis was apparent by day 6 and continued for several weeks. Mice were treated i.p. with mAbs (250 μg) or Ig fusion protein (200 μg) every 3rd day starting on day 4. Mice received either mAb (Ha4/8 isotype control or Ha31/8 anti-α1), Ig fusion protein (Isotype control Ig or TNF-R55-Ig) or a combination of both (250 ug Ha31/8 and 200 ug TNF-R55-Ig). Each limb was evaluated and scored on a 0 to 4 scale every 3rd day. Results are expressed as the mean arthritic score per limb (maximum score of 4). Groups of 4 mice per condition were used.

FIG. 11. Location of the Epitope for the anti-α1 I domain Blocking mAbs. A. Amino acid sequence of the rat (top; SEQ ID NO:63) and human (below; residues of SEQ ID NO:64, which are different from rat are shown) α1-I domain. The residues that comprise the MIDAS (metal ion dependent adhesion site) motif are shown in bold. The human amino acids that replaced the corresponding rat residues (RΔH) are shown below the rat sequence in the boxed region. For clarity, residue numbering in the text refers to this figure, unless otherwise designated, e.g., as crystal numbering. B. Increasing concentrations of mAb AJH10 (ATCC No. PTA-3580; deposited under the Budapest Treaty with the American Type Culture Collection, Manassas, Va., USA on Aug. 2, 2001) were bound to plates coated with 30 μg/ml human (circles), rat (triangles) or RΔH (squares) α1-I domain. Data shown is representative of three experiments.

Figure 12:
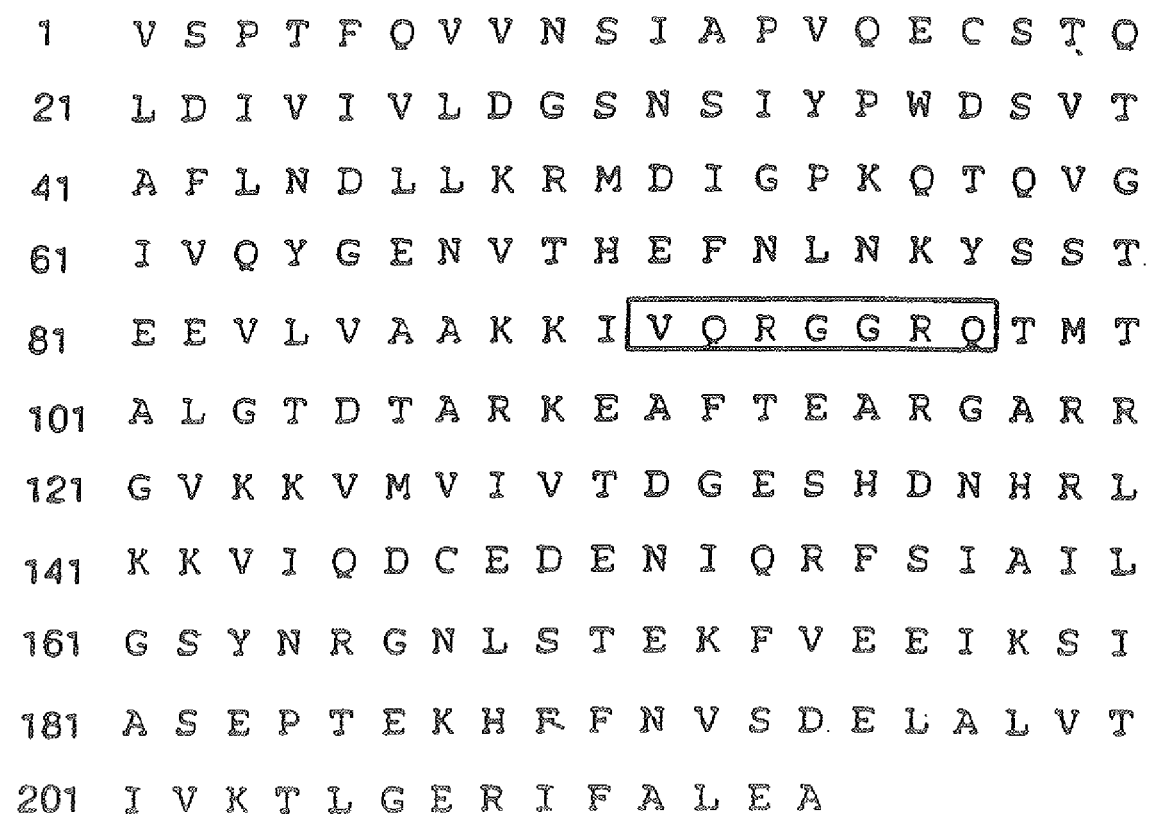

FIG. 12. Amino acid sequence of the human α1-I domain (SEQ ID NO:64).

Figure 13A:
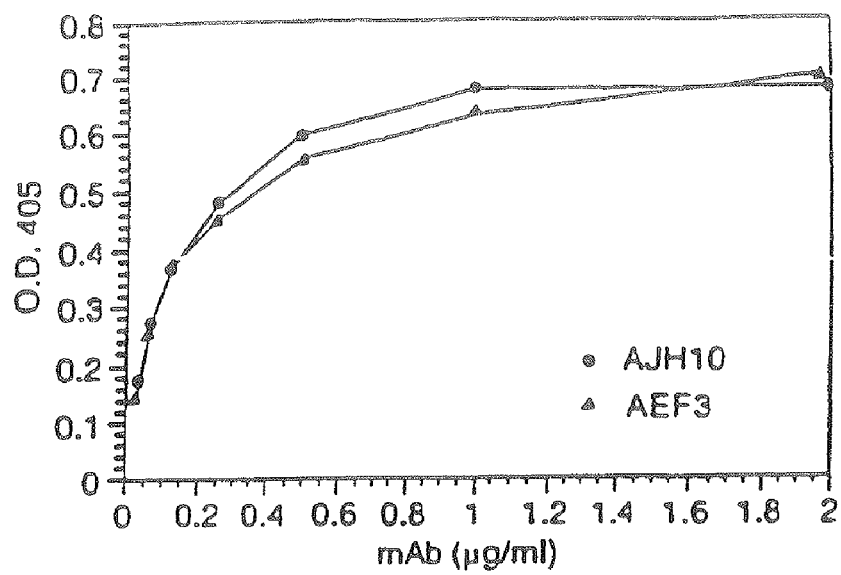
Figure 13B:
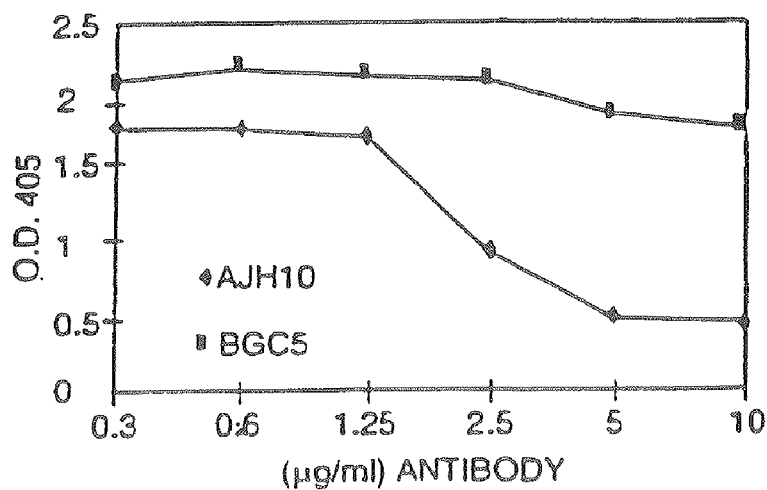
Figure 13C:
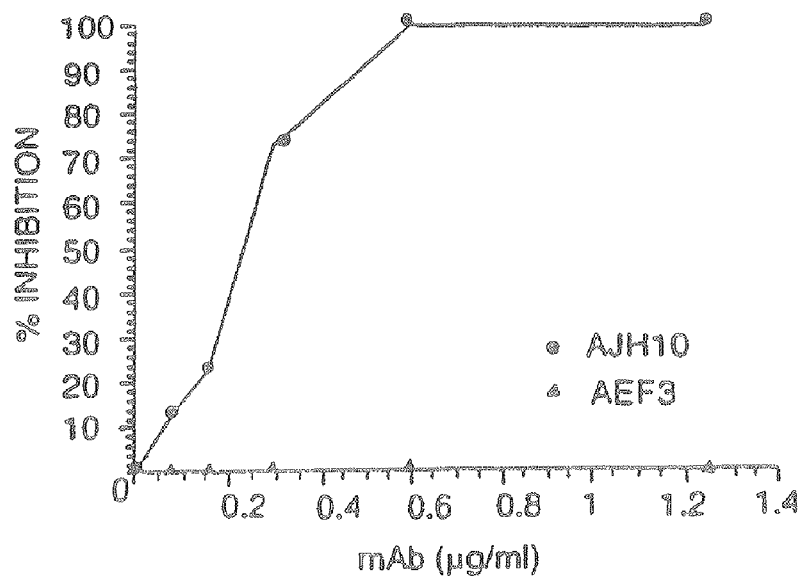

FIG. 13. Identification of a blocking mAb to the α1-I domain. A. Increasing concentration of mAbs AEF3 (triangles) or AJH10 (circles) were bound to plates coated with 30 μg/ml α1-I domain. B. The α1-I domain was treated with increasing concentrations of mAb AJH10 (diamonds) or mAb BGC5 (squares) and bound collagen IV (2 μg/ml) coated plates. C. K562-α1 cell were treated with increasing concentration of mAbs AEF3 (triangles) or AJH10 (circles) and bound to collagen IV (5 μg/ml) coated plates. 45-50% of cells added to each well adhered to collagen IV. Data shown is representative of three independent experiments.

FIG. 14. Species Cross-reactivity of the blocking mAbs analyzed by fluorescence activated cell sorter (FACS). Rabbit vascular smooth muscle cells were incubated with either mAb AJH10 (bottom) or murine IgG control (top) and analyzed by fluorescence activated cell sorter (FACS).

FIG. 15. The α1-I domain binds collagen. A. Increasing concentrations of the human α1-I domain were bound to plates previously coated with 1 μg/ml collagen I (squares) or collagen IV (circles). Values shown have been corrected for background binding to BSA. B. 2 μg/ml human α1-I domain was mixed with increasing concentration of an anti-human α1-I integrin antibody 5E8D9 (squares) or an anti-human α2-integrin antibody A2IIE10 (circles), and then bound to plates previously coated with 1 μg/ml collagen IV. C. Plates were coated with 1 μg/ml collagen TV or 3% BSA. α1-I domain (2 μg/ml) was subsequently bound to coated plates in the presence of 1 mM $Mn^{2+}$, 1 mM $Mg^{2+}$, or 5 mM EDTA. Data shown is representative of three independent experiments.

FIG. 16. Characterization of Humanized AQC2 Forms. mAQC2 (triangles), chAQC2 (circles), hAQC2 (inverted triangles) and hAQC2' (squares) were evaluated.
  A. Inhibition of VLA-1 binding to type IV collagen.
  B. Inhibition of α1-I domain binding to type IV collagen.
  C. Binding to immobilized α1-I domain.
  D. Competition with biotinylated mAQC2 for binding to immobilized α1-I domain.

Figure 17:
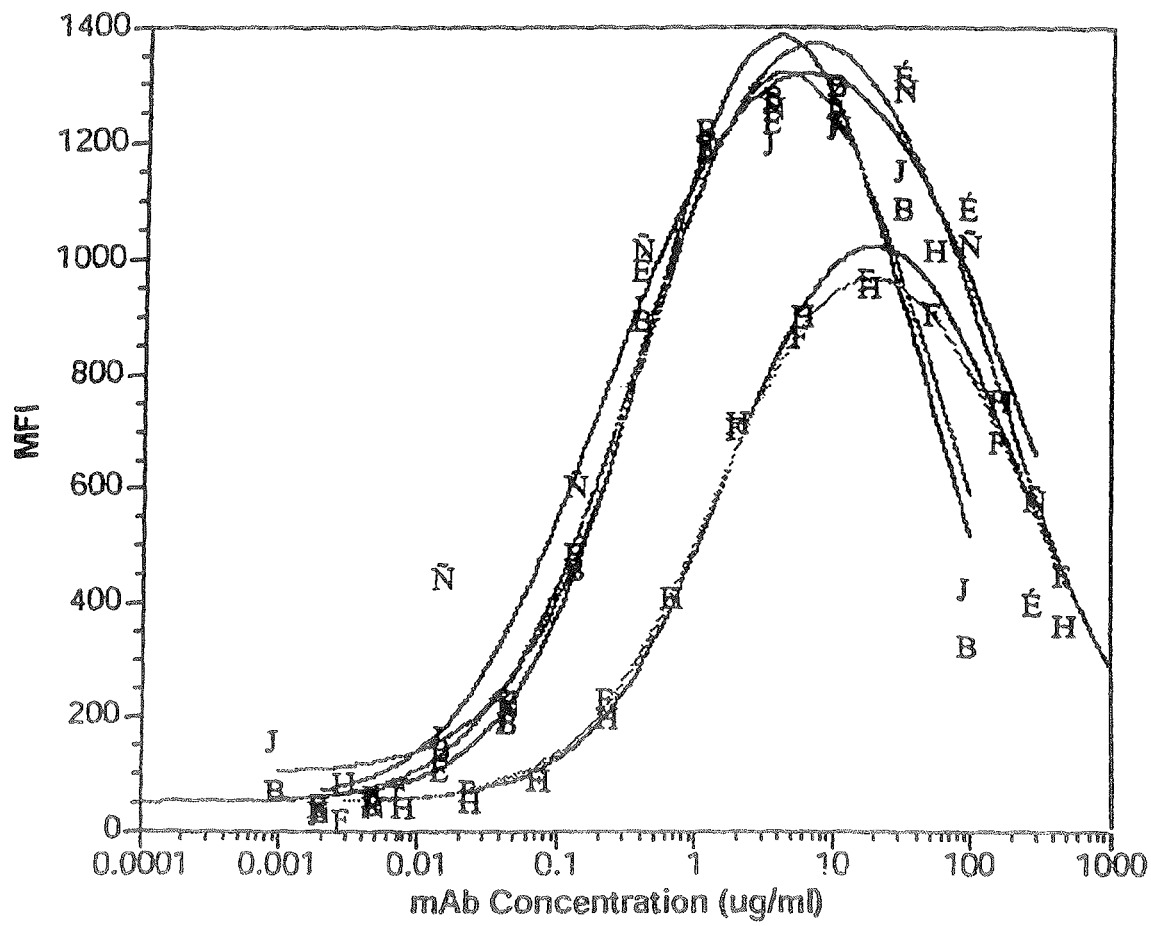

FIG. 17. Characterization of Humanized AQC2 Forms by FACS.

Figure 18:
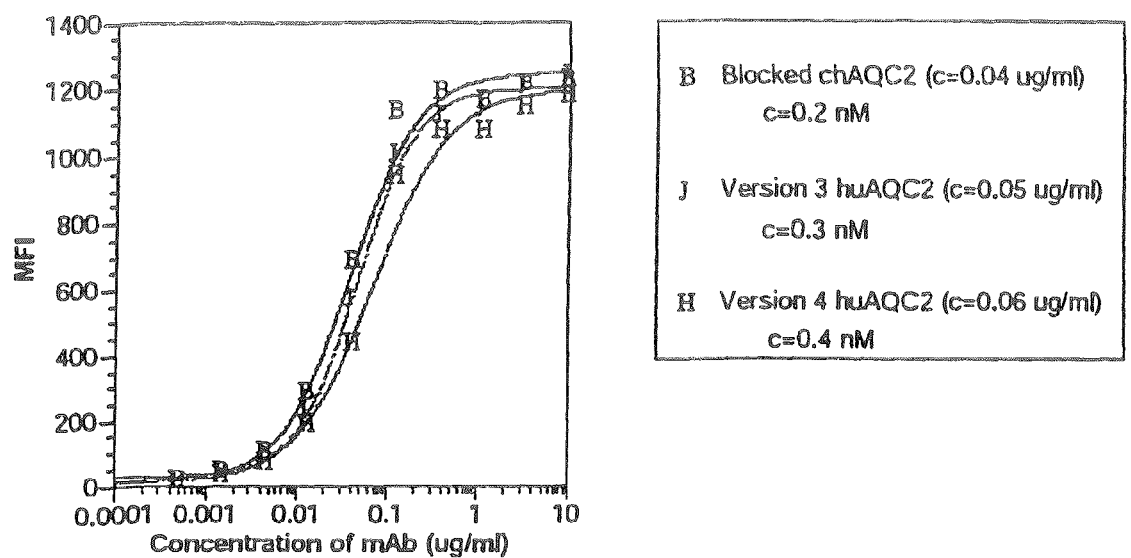

FIG. 18. Characterization of Humanized AQC2 Forms by FACS.

Figure 20:
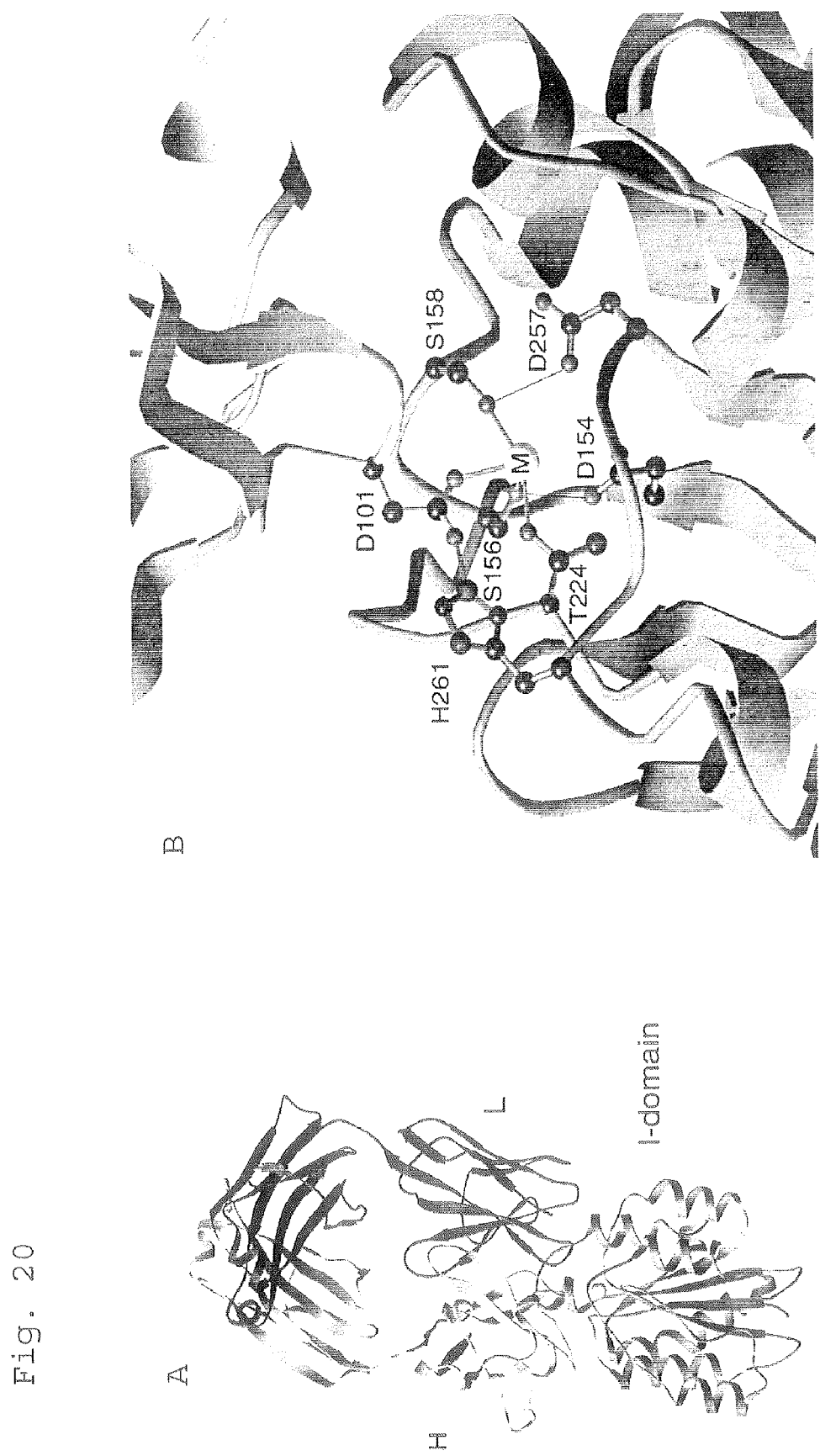

FIG. 19. Atomic structure coordinates for the α1-I domain/Fab complex, as derived by X-ray crystallography from crystals of that complex in Protein Data Bank (PDB) format. The coordinates of the two complexes in the asymmetric unit are listed as follows.
  Complex 1: molecule A=I domain of integrin
  molecule H=heavy chain of hAQC2 Fab
  molecule L=light chain of hAQC2 Fab
  molecule M=$Mn^{+2}$
  Complex 2: molecule B=I domain of integrin
  molecule X=heavy chain of hAQC2 Fab
  molecule Y=light chain of hAQC2 Fab
  molecule M=$Mn^{+2}$ FIG. 20. I domain-Fab complex. A. Ribbon diagram of the I domain-Fab complex. The I domain and the antibody heavy and light chain are labeled. The $Mn^{+2}$ ion is shown as a sphere. B. Close-up of the MIDAS (Metal-Ion-Dependent-Adhesion-Site) site showing the coordination of the metal ion (sphere) by Asp101 (crystal numbering). The protein backbones are shown as ribbons and the side chains in the ball-and-stick representation. The cylinders represent interactions between the metal ion and protein atoms. The thin lines represent H-bonds. FIG. 20 was made with the software program RIBBONS (Carson, 1991, J. Appl. Cryst, 24:958-961).

Figure 21:
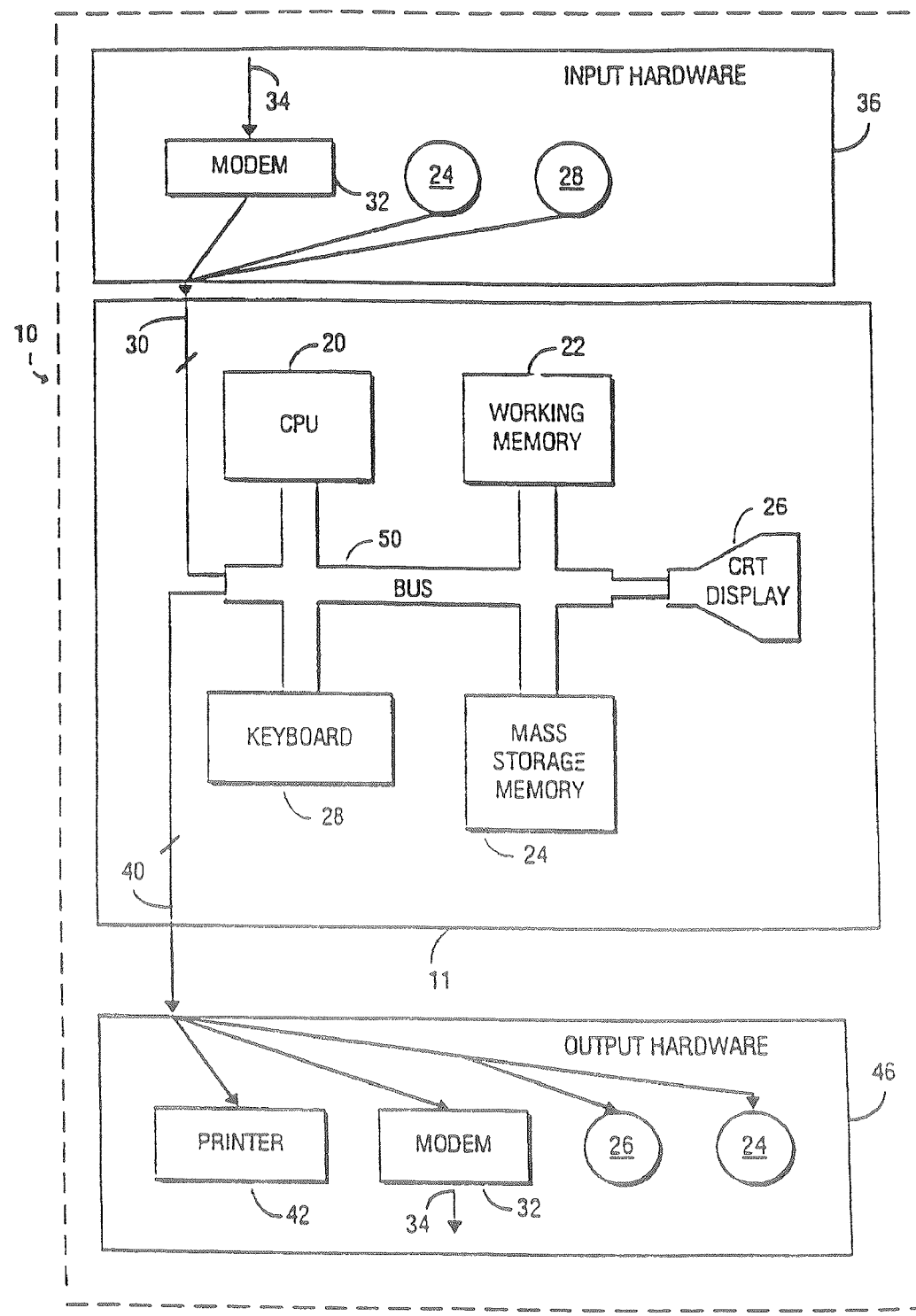

FIG. 21. A diagram of a system used to carry out the instructions encoded by the storage medium of FIGS. 22 and 23.

Figure 22:
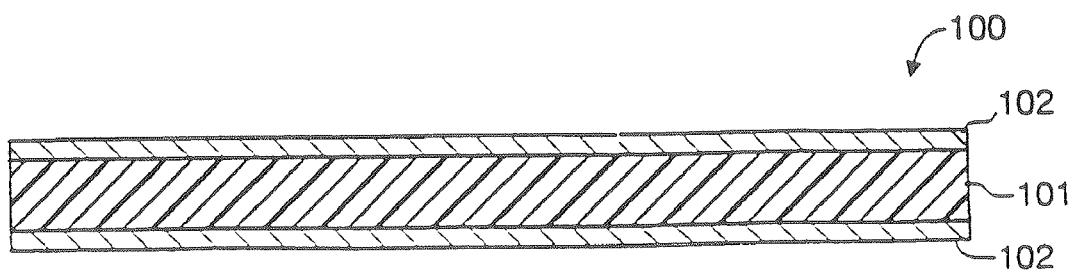

FIG. 22. A cross section of a magnetic storage medium.

Figure 23:
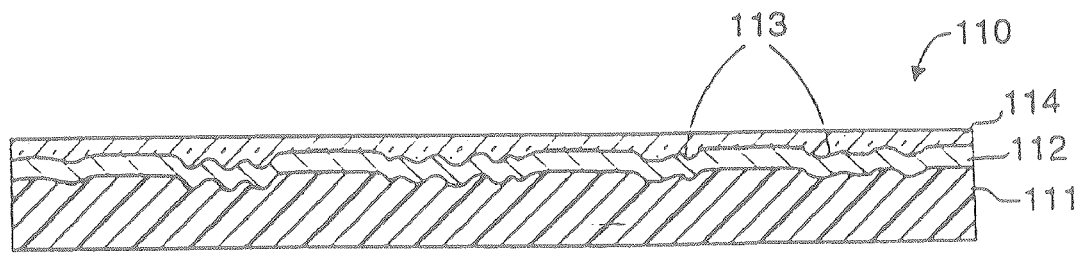

FIG. 23. A cross section of an optically-readable data storage medium.

DETAILED DESCRIPTION OF THE INVENTION

It is a discovery of the present invention that an antibody to an integrin (e.g., VLA-1) and fragment thereof, particularly, an α1-integrin subunit, can block the interaction of pro-inflammatory leukocytes with components of the extracellular matrix including, but not limited to collagens, laminin and fibronectin. This discovery illustrates the importance of adhesion molecules of the integrin family, particularly α1β1, in the peripheral tissue environment during conditions related to inflammation. It also extends the role of integrins family and fragments thereof in inflammation beyond leukocyte attachment and extravasation at the endothelial interface by highlighting the importance of the matrix-rich peripheral tissue environment to immune responses and it reveals peripheral tissues as a new point of intervention for adhesion based therapies.

I. Anti-Integrin Antibodies

The methods of the present invention contemplate the use of antibodies to integrins where the integrins contemplated include molecules which comprise a β chain, including but not limited to β1, β2, β3, β4, β5, β6, β7, β8, non-covalently bound to an α chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:
  α1β1, α2β1, α3β1, α4β1, α5β1, α6β1, α7β1, α8β1, α9β1, α10β1, αVβ1, αLβ1, αMβ1, αXβ1, αDβ1, αEβ1;
  α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β8, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an α chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1β1 (Briesewitz et al., 1993, J. Biol. Chem. 268:2989); α2β1 (Takada and Hemler, 1989, J Cell Biol 109:397), αLβ2 (Larson et al., 1989, J Cell Biol 108:703), αMβ2 (Corbi et al., 1988, J Biol Chem 263:12403), αXβ2 (Corbi et al., 1987, EMBO J 6:4023), αDβ2 (Grayson et al., 1988, J Exp Med 188:2187), αEβ7 (Shaw et al., 1994, J Biol Chem 269:6016). In one embodiment, the α1-I domain antigenic determinant includes an amino acid sequence of at least 6 contiguous amino acids, wherein the contiguous sequence is found within the sequence of FIG. 12. In a related embodiment, the contiguous sequence is Val-Gln-Arg-Gly-Gly-Arg (residues 91-96 of SEQ ID NO:64).

Methods for producing integrins for use in the present invention are known to those of skill in the art (see, e.g., Springer et al., 1990, Nature 346:425-434).

Embodiments of the present invention further include anti-integrin polyclonal and monoclonal antibodies. Embodiments of the present invention include a monoclonal antibody such an anti-α1 monoclonal antibody. Antibodies for treatment, in particular for human treatment, include human antibodies, humanized antibodies, chimeric antibodies, and antigen-binding fragments of whole antibodies such as Fab, Fab', F(ab')2 and F(v) antibody fragments. Some antibodies of this invention may also include proteins containing one or more immunoglobulin light chains and/or heavy chains, such as monomers and homo- or hetero-multimers (e.g., dimers or trimers) of these chains, where these chains are optionally disulfide-bonded or otherwise cross-linked. These antibodies may be capable of binding to one or more antigens (e.g., α1, α2, α6 or alpha-I domain containing integrin subunits).

An α1β1 function blocking antibody as used herein refers to an antibody that binds to the α1-I domain, for example, residues 91-97 of FIG. 12, and blocks α1β1 function as tested, for example, by their ability to inhibit K562-α1 dependent adhesion to Collagen IV (see Example 15).

The following describes the various methods of making the antibodies of this invention. Methods that are known in the art but not specifically described herein are also within the scope of this invention. For instance, antibodies of this invention can also be identified using phage-displayed antibody libraries, such as those described in Smith, 1985, Science 228:1315-7; U.S. Pat. Nos. 5,565,332, 5,733,743, 6,291,650, and 6,303,313. Additional antibodies of this invention can be made by coupling the heavy chains identified herein with a noncognate light chain, e.g., a light chain identified by phage display technology.

II. Non-Human Hybridoma Antibodies

The monoclonal antibodies of this invention can be generated by well known hybridoma technology. For instance, $\beta_1$-/- animals (e.g., mice, rats or rabbits) can be immunized with purified or crude $\alpha_1\beta_1$ preparations, cells transfected with cDNA constructs encoding $\alpha_1$, $\beta_1$ or both antigens, cells that constitutively express $\alpha_1\beta_1$, and the like. The antigen can be delivered as purified protein, protein expressed on cells, protein fragment or peptide thereof, or as naked DNA or viral vectors encoding the protein, protein fragment, or peptide. Sera of the immunized animals are then tested for the presence of anti-$\alpha_1\beta_1$ antibodies. B cells are isolated from animals that test positive, and hybridomas are made with these B cells.

Antibodies secreted by the hybridomas are screened for their ability to bind specifically to VLA-1 (e.g., binding to $\alpha_1$-transfected cells and not to untransfected parent cells) and for any other desired features, e.g., having the desired CDR consensus sequences, inhibiting (or not inhibiting in the case of nonblockers) the binding between collagen and VLA-1.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

III. Chimeric Antibodies

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art. Human constant regions include those derived from IgG1 and IgG4.

IV. Fully Human Antibodies

The monoclonal antibodies of this invention also include fully human antibodies. They may be prepared using in vitro-primed human splenocytes, as described by Boerner et al., 1991, J. Immunol. 147:8695, or using phage-displayed antibody libraries, as described in, e.g., U.S. Pat. No. 6,300,064.

Alternatively, fully human antibodies may be prepared by repertoire cloning as described by Persson et al., 1991, Proc. Nat. Acad. Sci. USA 88: 2432-2436; and Huang and Stollar, 1991, J. Immunol, Methods 141: 227-236. In addition, U.S. Pat. No. 5,798,230 (Aug. 25, 1998) describes preparation of human monoclonal antibodies from human B cells, wherein human antibody-producing B cells are immortalized by infection with an Epstein-Ban virus, or a derivative thereof, that expresses Epstein Barr virus nuclear antigen 2 (EBNA2), a protein required for immortalization. The EBNA2 function is subsequently shut off, resulting in an increase in antibody production.

Some other methods for producing fully human antibodies involve the use of nonhuman animals that have inactivated endogenous Ig loci and are transgenic for un-rearranged human antibody heavy chain and light chain genes. Such transgenic animals can be immunized with $\alpha_1\beta_1$ and hybridomas are then made from B cells derived therefrom. These methods are described in, e.g., the various GenPharm/Medarex (Palo Alto, Calif.) publications/patents concerning transgenic mice containing human Ig miniloci (e.g., Lonberg U.S. Pat. No. 5,789,650); the various Abgenix (Fremont, Calif.) publications/patents with respect to XENOMICE (e.g., Kucherlapati U.S. Pat. Nos. 6,075,181, 6,150,584 and 6,162,963; Green et al., 1994, Nature Genetics 7:13-21; and Mendez et al., 1997, Nature Genetics 15(2):146-56); and the various Kirin (Japan) publications/patents concerning "transomic" mice (e.g., EP 843 961, and Tomizuka et al., 1997, Nature Genetics 16:133-1443).

V. Humanized Antibodies

The monoclonal antibodies of this invention also include humanized versions of cognate anti-$\alpha_1\beta_1$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer nonhuman components.

The methods for making humanized antibodies are described in, e.g., Winter E P 239 400; Jones et al., 1986, Nature 321:522-525; Riechmann et al., 1988, Nature 332: 323-327 (1988); Verhoeyen et al., 1988, Science 239:1534-1536; Queen et al., 1989, Proc. Nat. Acad. Sci. USA 86:10029; U.S. Pat. No. 6,180,370; and Orlandi et al., 1989, Proc. Natl. Acad. Sci. USA 86:3833. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g, $\gamma 1$ for CH and k for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., 1991, Proc. Nat. Acad. Sci. USA 88:2869-2873, and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the nonhuman donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, 1991, Biotechnology 9: 266-271. Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

VI. Other Moieties

The monoclonal antibodies of this invention may further include other moieties to effect the desired functions. For instance, the antibodies may include a toxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026). The antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 regions).

VII. Crystallizable Compositions and Crystals

This invention also provides a crystallizable composition containing a complex of: (1) a rat-human chimeric α1-I domain (e.g., mutant RΔH), or a portion thereof (e.g., a polypeptide including 135 to 336 amino acids of the rat-human chimeric α1-I domain); and (2) a Fab fragment of hAQC2, or a portion thereof (e.g., a polypeptide including 3 to 213 amino acids of the light chain and/or a polypeptide including 3 to 219 amino acids of the heavy chain). An exemplary complex is shown in FIG. 20. The RΔH α1-I domain can include, e.g., amino acid residues 145 to 336 (crystal numbering) (SEQ ID NO:59, infra) of the rat α1 subunit. The hAQC2 Fab fragments may include light chain amino acid residues 1 to 106 (e.g., 1-213) of SEQ ID NO:3 and heavy chain amino acid residues 1 to 118 (e.g., 1-219) of SEQ ID NO:4. The hAQC2 Fab fragments may be obtained by papain digestion of the whole antibody or made by recombinant methods. The Fab fragments include at least an antigen-binding portion of the variable domains of the light chain and/or the heavy chains of hAQC2.

```
                                                   (SEQ ID NO: 59)
145 TQLDIV

151 IVLDGSNSIY PWESVIAFLN DLLKRMDIGP KQTQVGIVQY

191 GENVTHEFNL NKYSSTEEVL VAANKIVQRG GRQTMTALGI

231 DTARKEAFTE ARGARRGVKK VMVIVTDGES HDNYRLKQVI

271 QDCEDENIQR FSIAILGHYN RGNLSTEKFV EEIKSIASEP

311 TEKHPENVSD ELALVTIVKA LGERIF
```

Some crystallizable compositions and crystals of this invention may contain a molecule or molecular complex that is homologous to the α1-I domain and/or the hAQC2 Fab fragment by amino acid sequence or by three-dimensional structure. Examples of homologues include, but are not limited to: the α1-I domain and/or the hAQC2 Fab fragment with mutations, such as conservative substitutions, additions, deletions or a combination thereof. "Conservative substitutions" refer to replacement residues that are physically similar in size, shape, hydrophobicity, charge, and/or chemical properties to the corresponding reference residues. Methods for identifying a "corresponding" amino acid are known in the art and are based upon sequence, structural alignment, its functional position or a combination thereof as compared to the crystal structure solved in the present invention. For example, corresponding amino acids may be identified by superimposing the backbone atoms of the amino acids in the α1-I domain/hAQC2 complex and a α1-I domain and/or hAQC2 homologue using well known software applications, such as QUANTA (Molecular Simulations, Inc., San Diego, Calif. ©1998, 2000). The corresponding amino acids may also be identified using sequence alignment programs such as the "bestfit" program available from the Genetics Computer Group, which uses the local homology algorithm described by Smith and Waterman in Adv. Appl. Math. 2:482 (1981).

Crystallizable compositions of this invention may further include one or more components that promote crystallization and/or is compatible with crystallization conditions. Such components may include, but are not limited to, buffer, salts, precipitating agents and other reagents. One component can be 30% weight/volume Polyethylene Glycol 1500 (PEG1500).

The instant invention also provides methods of making crystals from crystallizable compositions including a complex of α1-I domain and an antigen-binding portion of hAQC2 (e.g., Fab, Fab' or other fragments, supra). Various techniques of crystallization can be used in the claimed invention, including, but not limited to, vapor-diffusion, dialysis, microbatch, batch, and liquid-liquid diffusion. Vapor diffusion methods include, but are not limited too, sitting-drop, hanging-drop and sandwich-drop techniques. Vapor-diffusion methods can use techniques to control the rate of crystallization, such as the addition of oils on the drops or reservoir solution. Crystallization methods can include mixing a reservoir solution containing precipitating agent with an aqueous solution of a complex of α1-I domain and an antigen-binding portion of hAQC2 to produce a crystallizable composition. The mixture or crystallizable composition may then be crystallized using the various above-listed techniques. The crystallizable composition of this invention may be an aqueous solution of a complex of α1-I domain and an antigen-binding portion of hAQC2 containing the complex at a concentration of about 1 to 50 mg per mL, such as a concentration of about 5 to 115 mg per mL (e.g., 11 mg per mL).

VIII. Crystal Structures and Structure Coordinates

This invention further provides the three-dimensional structure of a crystal including a complex of mutant RΔH, and a hAQC2 Fab fragment at 2.8 Å resolution (Example 24, infra). The three-dimensional structures of other related crystals may also be determined using techniques described herein and those known in the art. The three-dimensional structure of this complex is defined by a set of structure coordinates set forth in FIG. 19. These structure coordinates are Cartesian atomic coordinates derived from mathematical equations related to the patterns obtained from diffraction of a monochromatic beam of X-rays by the atoms or scattering centers of the crystalline complex of the α1-I domain and the hAQC2 Fab fragment. Diffraction data are first used to calculate an electron density map of the repeating unit of the crystal. The electron density map is then used to establish the positions of individual atoms of the complex.

This invention provides a molecule or a molecular complex defined by all or part of the structure coordinates of all amino acids set forth in FIG. 19, as well as a homologue of the molecule or molecular complex, where the homologue has a root mean square deviation from the backbone atoms of these amino acids between 0.00 Å and 0.65 Å, such as between 0.00 Å and 0.60 Å (e.g., between 0.00 Å and 0.50 Å). The term "root mean square deviation" or "r.m.s. deviation" means the square root of the arithmetic mean of the squares of the deviations from the mean. It is a way to express the deviation or variation from a trend or object. For purposes of this invention, the "root mean square deviation" or "r.m.s. positional deviation" defines the variation in the backbone of a protein from the relevant portion of the backbone of the polypeptide as defined by the structure coordinates described herein.

A molecule or a molecular complex of this invention may also include a binding site defined by structure coordinates of at least seven amino acids of the hAQC2 Fab fragment selected from the group including of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19; or a homologue of the molecule or molecular complex, where the homologue includes a binding site that has a root mean square deviation from the backbone atoms of one or more of these amino acids between 0.00 Å and 1.10 Å, such as between 0.00 Å and 1.00 Å (e.g., between 0.00 Å and 0.50 Å.). The term "binding site" as used herein, refers to a region of a molecule or molecular complex that, as a result of its shape and charge, favorably associates with another chemical entity. The term "site" includes, but is not limited to, trench, cleft, channel or pocket. For instance, binding sites on the α1-I domain may include a collagen-binding site (Emsley et al., 1997, supra), an antibody-binding site, and an allosteric (or IDAS) binding site (Huth et al., 2000, Proc. Natl. Acad. Sci. U.S.A. 97:5231-5236). The term "chemical entity" includes, but is not limited to, any molecule, molecular complex, compound or fragment thereof. The term "associate with" refers to an association or binding in a condition of proximity between a chemical entity, or portions thereof, and a binding pocket or binding site on a protein. The association may be non-covalent—where the juxtaposition is energetically favored by hydrogen bonding or van der Waals or electrostatic interactions or it may be covalent.

A molecule or molecular complex of this invention can include a binding site defined by structure coordinates of α1-I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19, or a homologue of the molecule or molecular complex, where the homologue includes a binding site that has a root mean square deviation from the backbone atoms of the α1-I domain amino acids between 0.00 Å and 0.92 Å.

A molecule or molecular complex of this invention also may include a binding site defined by structure coordinates of α1-I domain amino acids selected from the group consisting of residues Glu192, Gln218, Arg219, Gly220, and Gly221 (crystal numbering), according to FIG. 19; or a homologue of the molecule or molecular complex, where the homologue includes a binding site that has a root mean square deviation from the backbone atoms of the α1-I domain amino acids between 0.00 Å and 0.30 Å.

Those of skill in the art will understand that a set of structure coordinates for a polypeptide is a relative set of points that define a shape in three dimensions. Thus, it is possible that an entirely different set of coordinates that define a similar or identical shape could be generated using mathematical manipulations of the structure coordinates in FIG. 19. For example, the structure coordinates could be manipulated by crystallographic permutations of the structure coordinates, fractionalization of the structure coordinates, integer additions or subtractions to sets of the structure coordinates, inversion of the structure coordinates, or any combination thereof. Moreover, slight variations in the individual coordinates will have little effect on overall shape.

Alternatively, modification in the crystal structure due to mutations, such as additions, substitutions, and/or deletions of amino acids, or other changes in any of the polypeptide components (e.g., a hAQC2 Fab fragment or a α1-I domain) that make up the crystal can also account for variations in structure coordinates. If such variations are within an acceptable standard error as compared to the original coordinates, the resulting three-dimensional shape is considered to be the same as that of the unmodified crystal.

It is therefore necessary to determine whether an entity is sufficiently similar to all or parts of the structure described herein as to be considered the same. Such analyses may be carried out using current software applications, such as QUANTA (Accelrys, Inc. and Molecular Simulations, Inc., San Diego, Calif. ©1998,2000) and O (Jones et al., 1991, Acta Cryst. A47:110-119), and accompanying User Guides. The Molecular Similarity application of QUANTA and the LSQ application of O permit comparisons between different structures, different conformations of the same structure, and different parts of the same structure. The general procedure used in both applications is to input the structures to be compared, define the equivalent atomic positions in these structures, perform a fitting operation, and analyze the results.

When each structure is input into the application, it is given a name, and identified as the fixed structure or a moving structures. Atom equivalency is usually defined by equivalent atoms such as protein backbone atoms (N, Cα, C and O) for all conserved residues between the two structures being compared. The moving structure is translated and rotated to obtain an optimum or least-squares fit with the fixed structure. The root mean square difference of the fit over the specified pairs of equivalent atom is reported by both programs in angstroms.

For the purpose of this invention, any molecular complex that has a root mean square deviation of conserved residue backbone atoms (N, Cα, C, O) between 0.00 Å and 1.50 Å, such as between 0.00 Å and 1.00 Å (e.g., between 0.00 Å and 0.50 Å), when superimposed on the relevant backbone atoms described by structure coordinates listed in FIG. 19 are considered identical.

IX. Determining Other Crystal Structures

The structure coordinates set forth in FIG. 19 can also be used to aid in obtaining structural information about another crystallized molecular entity, such as another hAQC2 containing amino acid substitutions in one of its CDRs. This may be achieved by any well-known techniques, including molecular replacement, an especially useful method for determining the structures of mutants and homologues of α1-I domain/Fab.

The structure coordinates set forth in FIG. 19 can also be used for determining at least a portion of the three-dimensional structure of molecular entities that contain at least some structural features similar to at least a portion of the α1-I domain or the hAQC2 Fab. Therefore, another embodiment of this invention provides a method of utilizing molecular replacement to obtain structural information about a crystallized molecule or molecular complex with unknown structure including the steps of: (a) generating an X-ray diffraction pattern from the crystallized molecule or molecular complex; and (b) applying at least a portion of the structure coordinates set forth in FIG. 19 to the X-ray diffraction pattern to generate a three-dimensional electron density map of the molecule or molecular complex with unknown structure.

By using molecular replacement, all or part of the structure coordinates set forth in FIG. 19 can be used to determine the unknown structure of a crystallized molecular entity more rapidly and efficiently than attempting to determine such information ab initio. Molecular replacement provides an accurate estimation of the phases for an unknown structure. Phases are a factor in equations used to solve crystal structures that cannot be determined directly. Obtaining accurate values for the phases, by methods other than molecular replacement, can often be a time-consuming process that involves iterative cycles of approximations and refinements and greatly hinders the solution of crystal structures. However, when the crystal structure of a protein containing at least a homologous portion has been solved, the phases from the known structure can often provide a satisfactory estimate of the phases for the unknown structure.

Thus, molecular replacement involves generating a preliminary model of a molecule or molecular complex whose structure coordinates are unknown, by orienting and positioning the relevant portion of the complex according to FIG. 19 within the unit cell of the crystal of the unknown molecule or molecular complex, so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, 1985, Meth. Enzymol. 115:55-77; Rossmann, ed., "The Molecular Replacement Method", Int. Sci. Rev. Ser., No. 13, Gordon & Breach, New York, 1972). The structure of any portion of any crystallized molecule or molecular complex that is sufficiently homologous to any portion of the α1-I domain and/or the hAQC2 Fab fragment (according to FIG. 19) can be solved by this method.

X. Computer and Storage Medium

To use the structure coordinates of this invention, e.g., those set forth in FIG. 19, it is usually necessary to convert the coordinates into a three-dimensional representation or shape. Commercially available graphical software programs including, but not limited to, O (Jones et al., 1991, Acta Cryst. A47:110-119) and ISIGHTII (©Accelrys, Inc. and Molecular Simulations, Inc., San Diego, Calif.) are capable of generating three-dimensional representations of molecules or molecular complexes, or portions thereof, from a set of structure coordinates.

In accordance with the present invention, the structure coordinates of the molecular entities of this invention are stored in a storage medium readable by machine (e.g., a computer). Using a computer and appropriate software, such data may be used for a variety of purposes, such as drug discovery and X-ray crystallographic analysis of other protein crystals.

Accordingly, a machine-readable data storage medium may include a data storage material encoded with machine-readable data including at least a portion of the structure coordinates set forth in FIG. 19. The computer may further include instructions to produce three-dimensional representations of the molecular complexes of α1-I domain and the hAQC2 Fab fragment by processing the machine-readable data of this invention. The computer of this invention may also include a display, a graphical interface for displaying, or an input device for moving and manipulating the three-dimensional graphical representation of the structure coordinates.

This invention also provides a computer for determining at least a portion of the structure coordinates corresponding to X-ray diffraction data obtained from a molecular complex of α1β1 integrin and the Fab fragment of hAQC2 antibody, where the computer includes a machine-readable data storage medium including a data storage material encoded with machine-readable data, where the data includes at least a portion of the structure coordinates of the molecular complex of α1-I domain and the hAQC2 Fab fragment according to FIG. 19, or X-ray diffraction data obtained from the crystalline molecular complex. The computer further includes instructions for performing a Fourier transform of the machine readable coordinate data, and instructions for processing this machine readable diffraction data into structure coordinates. This computer may further include: a working memory for storing instructions for processing the machine-readable data; a central-processing unit coupled to the working memory and to the machine-readable data; and optionally a graphical interface or display coupled to the central-processing unit for displaying the three-dimensional graphical representation of the structure coordinates of the molecule or molecular complex.

This invention further provides a computer for producing a three-dimensional representation of: a molecule or a molecular complex defined by at least a portion or all of the structure coordinates of all the α1-I domain and the AQC2 Fab fragment amino acids set forth in FIG. 19, or a homologue of the molecule or molecular complex, where the homologue has a root mean square deviation from the backbone atoms of the amino acids of between 0.00 Å than 1.50 Å, such as between 0.00 Å and 1.00 Å, (e.g., between 0.00 Å and 0.50 Å). Further in this invention the computer includes: a machine-readable data storage medium including a data storage material encoded with machine-readable data, where the data includes at least a portion or all of the structure coordinates of all of the α1-I domain and the Fab hAQC2 fragment amino acids set forth in FIG. 19.

A computer of this invention may also produce a three-dimensional representation of a molecule or molecular complex including a binding site. The binding site may be defined by structure coordinates of at least seven amino acids of: the hAQC2 Fab fragment selected from the group including light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19; or a homologue of the molecule or molecular complex, where the homologue includes a binding site that has a root mean square deviation from the backbone atoms of the at least one amino acid of the hAQC2 Fab fragment of between 0.00 Å and 1.10 Å, such as between 0.00 Å and 1.00 Å, (e.g., between 0.00 Å and 0.50 Å). Further, the computer of this invention includes: a machine-readable data storage medium including a data storage material encoded with machine-readable data, where the data includes the structure coordinates of at least seven amino acids of the hAQC2 Fab fragment selected from the group consisting of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19.

This invention also provides a computer for producing a three-dimensional representation of: a molecule or molecular complex including a binding site defined by structure coordinates I domain amino acids selected from the group consisting of residues Asp154, Ser156, Asn157, Ser158, Tyr160, Glu192, Gln218, Arg219, Gly220, Arg222, Gln223, Thr224, Asp257, His261, Asn263, Arg291, and Leu294 (crystal numbering), according to FIG. 19; or a homologue of the molecule or molecular complex, where the homologue includes a binding site that has a root mean square deviation from the backbone atoms of the I domain amino acids between 0.00 Å and 0.92 Å. Further in this invention, the computer includes: a machine-readable data storage medium including a data storage material encoded with machine-readable data, where the data includes the structure coordinates of I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19.

This invention also provides a computer for producing a three-dimensional representation of a molecule or molecular complex including a binding site defined by structure coordinates of I domain amino acids selected from the group consisting of residues Glu192, Gln218, Arg219, Gly220, and Gly221 (crystal numbering), according to FIG. 19; or a homologue of the molecule or molecular complex, where the homologue includes a binding site that has a root mean square deviation from the backbone atoms of I domain amino acids between 0.00 Å and 0.30 Å. Further in this invention the computer includes: a machine-readable data storage medium including a data storage material encoded with machine-readable data, where the data includes the structure coordinates I domain amino acids selected from the group consisting of residues Glu192, Gln218, Arg219, Gly220, and Gly221 (crystal numbering), according to FIG. 19.

FIG. 21 demonstrates one such embodiment. System 10 includes a computer 11 including a central-processing unit ("CPU") 20, a working memory 22 which may be, e.g., Ram (random-access memory) or "core" memory, mass storage memory 24 (such as one or more disk or tape drives or CD-ROM or DVD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may include CD-ROM or DVD-ROM drives or tape or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding site of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 22 shows a cross-section of a magnetic data storage medium 100 which can be encoded with machine-readable data that can be carried out by a system such as system 10 of FIG. 21. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 11 of FIG. 21.

FIG. 23 shows a cross-section of an optically-readable data storage medium 110 which also can be encoded with such machine-readable data, or a set of instructions, which can be carried out by a system such as system 10 of FIG. 21. Medium 110 can be a conventional compact disk or DVD disk read only memory (CD-ROM or DVD-ROM) or a rewritable medium, such as a magneto-optical disk which is optically readable and magneto-optically writable. Medium 100 has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

XI. Rational Drug Design

The present invention permits the use of structure-based and rational drug design techniques to design, select, and synthesize or isolate chemical entities, such as inhibitors of the α1-I domain and to improve known inhibitors of this domain. These inhibitors may be capable of blocking the collagen-binding site of VLA-1. This invention also permits the use of structure-based and rational drug design techniques to design variants that may act as inhibitors of collagen binding.

The three-dimensional representation of this invention can be used experimentally or computationally to design potential inhibitors, other chemical entities, variants of the Fab fragment or combinations of chemical entities that may bind to and effect the biological functions of the hAQC2 Fab fragment or the chimeric α1-I domain of the current invention.

One skilled in the art can use one of several methods to screen chemical entities for their ability to associate with the complex of the hAQC2 Fab fragment or the chimeric α1-I domain of the current invention and more particularly with a binding site of either the I domain or the Fab fragment. This process may begin by visual inspection of, for example, the binding site for either the I domain or the Fab fragment on the computer screen, based on the coordinates of the complex in FIG. 19. Selected chemical entities may then be positioned in a variety of orientations, or docked, within an individual binding site of either the I domain or the Fab fragment. Docking may be accomplished using software such as QUANTA, followed by energy minimization and molecular dynamics with standard molecular mechanics forcefields, such as CHARMM (Molecular Simulations, Inc., Burlington, Mass. ©1994) and AMBER (P. A. Kollman, University of California at San Francisco, ©1994).

Specialized computer programs may also assist in the process of selecting chemical entities. These include, inter alia:
1. GRID (Goodford, P. J., 1985, J. Med. Chem. 28:849-857).
   GRID is available from Oxford University, Oxford, UK.
2. MCSS (Miranker, A. and M. Karplus, 1991, Proteins: Structure, Function and Genetics 11:29-34). MCSS is available from Molecular Simulations, Burlington, Mass.
3. AUTODOCK (Goodsell, D. S, and A. J. Olsen, 1990, Proteins: Structure, Function, and Genetics 8:195-202). AUTODOCK is available from Scripps Research Institute, La Jolla, Calif.

4. DOCK (Kuntz, I. D. et al., 1982, J. Mol. Biol. 161:269-288). DOCK is available from University of California, San Francisco, Calif.

Once suitable chemical entities have been selected, they can be assembled into a single compound. Assembly may proceed by visual inspection of the relationship of the entities to each other on the three-dimensional image displayed on a computer screen in relation to the structure coordinates of the complex of hAQC2 Fab fragment and the chimeric α1-I domain. This is followed by manual model building using software such as Quanta or Sybyl.

The above-described evaluation process for chemical entities may be performed in a similar fashion for compounds or for variants that may bind the α1-I domain.

Useful programs to aid one of skill in the art in connecting the individual chemical entities include:
1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., 1989, Royal Chem. Soc., 78:182-196). CAVEAT is available from the University of California, Berkeley, Calif.
2. 3D Database systems such as MACCS-3D (MDL Information Systems, San Leandro, Calif.). This area is reviewed in Martin, Y. C., 1992, J. Med. Chem. 35:2145-2154.
3. HOOK (available from Molecular Simulations, Burlington, Mass.).

Instead of proceeding to build an inhibitor or binding compound in a step-wise fashion one chemical entity at a time, as described above, binding compounds may be designed as a whole or "de novo" using either an empty binding site (such as a binding site of the α1-I domain or the hAQC2 Fab fragment) or optionally including some portion(s) of a known α1-I domain or the hAQC2 Fab fragment binding compound. These methods include:
1. LUDI (Bohm, H.-J., 1992, J. Comp. Aid. Molec. Design 6:61-78). LUDI is available from Biosym Technologies, San Diego, Calif.
2. LEGEND (Nishibata, Y. and A. Itai, 1991, Tetrahedron 47:8985). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., 1990, J. Med. Chem. 33:883-894. See also Navia, M. A. and M. A. Murcko, 1992, Curr. Opin. Struct. Biol. 2:202-210.

Once an entity has been designed or selected by the above methods, the efficiency with which that entity may bind to the α1-I domain or the hAQC2 Fab fragment can be tested and optimized by computational evaluation. For example, a compound that has been designed or selected to function as α1-I domain binding compound can traverse a volume not overlapping that occupied by the binding site when it is bound to the chimeric α1-I domain. An effective α1-I domain binding compound can demonstrate a relatively small difference in energy between its bound and free states (i.e., a small deformation energy of binding). Thus, the most efficient α1-I domain binding compound should be designed with a deformation energy of binding of not greater than about 10 kcal/mole, e.g., not greater than 7 kcal/mole. α1-I domain binding compounds may interact with the α1-I domain in more than one conformation that is similar in overall binding energy. In those cases, the deformation energy of binding is taken to be the difference between the energy of the free compound and the average energy of the conformations observed when the compound binds to the protein.

A compound designed or selected as binding to α1-I domain may be further computationally optimized so that in its bound state it would lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the protein when the compound is bound to α1-I domain, should make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa. ©1992); AMBER, version 4.0 (P. A. Kollman, University of California at San Francisco, ©1994); QUANTA/CHARMM (Molecular Simulations, Inc., Burlington, Mass. 1994); and Insight II/Discover (Biosysm Technologies Inc., San Diego, Calif. ©1994). These programs may be implemented, for instance, using a Silicon Graphics workstation. Other hardware systems and software packages will be known to those skilled in the alt.

One other useful drug design technique enabled by this invention is iterative drug design. Iterative drug design is a method for optimizing associations between a protein and a compound (that compound includes an antibody) by determining and evaluating the three-dimensional structures of successive sets of protein/compound complexes. In iterative drug design, a series of crystals of a protein complexed with entities that bind the protein are obtained and then the three-dimensional structure of each molecular complex is solved. Such an approach provides insight into the associations between the proteins and other entities of each complex. This is accomplished by selecting chemical entities with inhibitory activity, obtaining crystals of these new complexes, solving the three-dimensional structure of the complexes, and comparing the associations between the new complexes and the previously solved complex. Associations within a complex can be optimized by observing how changes in the components of the complex affect associations.

In some cases, iterative drug design is carried out by forming successive complexes and then crystallizing each new complex. Alternatively, a pre-formed protein crystal is soaked in the presence of another chemical entity, thereby forming a complex and obviating the need to crystallize each individual complex.

XII. Pharmaceutical Compositions

The pharmaceutical compositions of this invention contains one or more VLA-1 antagonists of the present invention (e.g., anti-VLA-1 antibodies and the small molecular VLA-1 antagonists identified by the above-described rational drug design methods), or pharmaceutically acceptable derivatives thereof. The compositions may further contain a pharmaceutically acceptable carrier, such as an adjuvant, a vehicle, a buffer, and a stabilizer.

The pharmaceutical compositions of this invention may be given orally, topically, intravenously, subcutaneously, intraperitoneally, intramuscularly, intramedullarily, intraarterially, intra-articularly, intra-synovially, intrasternally, intrathecally, intrahepatically, intraspinally, intracranially as desired, or just locally at sites of inflammation or tumor growth. The pharmaceutical compositions of this invention may also be administered by inhalation through the use of, e.g., a nebulizer, a dry powder inhaler or a metered dose inhaler, or by implantation of an infusion pump or a biocompatible sustained release implant into the subject.

The pharmaceutical compositions may be in the form of a sterile injectable preparation, for example a sterile injectable aqueous or oleaginous suspension. This suspension may be formulated according to techniques known in the art using suitable dispersing, wetting, and suspending agents. If given orally, the pharmaceutical compositions can be administered in form of capsules, tablets, aqueous suspensions or solutions. For topical applications, the pharmaceutical compositions may be formulated in a suitable ointment.

The dosage and dose rate of the VLA-1 antagonists of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

XIII. Diseased Conditions and Animal Models

The VLA-1 antagonists of the invention are useful in the treatment, including prevention, of $\alpha_1\beta_1$-mediated diseases such as those enumerated above. The treatments of this invention are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

The efficacy of the VLA-1 antagonists of the invention can be tested in various animal models. For instance, useful psoriasis and arthritis models include those described in WO 00/72881. Kidney fibrosis models include those described in WO 99/61040, the Alport's syndrome kidney model described in Cosgove et al., 2000, Am. J. Path. 157:1649-1659, and the SNF1 mouse model of lupus nephritis described in Kalled et al., 2001, Lupus 10:9-22. Vascular fibrosis models for restenosis include a rat carotid balloon injury model described in Smith et al., 1999, Circ. Res. 84:1212-1222. Lung fibrosis models for idiopathic pulmonary fibrosis and scleroderma-associated pulmonary fibrosis include a bleomycin-induced pulmonary fibrosis model described in Wang et al., 1999, Thorax 54:805-812. Liver cirrhosis models for hepatitis C- or alcohol-induced cirrhosis include the bile duct ligation model described in George et al., 1999, Proc. Natl. Acad. Sci. USA 96:12719-12724 and the CCL4-induced liver fibrosis model described in Shi et al., 1997, Proc. Natl. Acad. Sci. USA 94:10663-10668.

The efficacy of the treatments of this invention may be measured by a number of available diagnostic tools, including physical examination, blood tests, proteinuria measurements, creatinine levels and creatinine clearance, pulmonary function tests, chest X-rays, bronchoscopy, bronchioalveolar lavage, lung biopsy, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

XIV. Diagnostic Methods

The antibodies of this invention can be used to diagnose diseased conditions associated with altered a1 expression levels. A tissue sample from a subject, such as a tissue biopsy, body fluid sample or lavage (e.g., alveolar lavage), can be tested in an antigen capture assay, ELISA, immunohistochemistry assay, and the like using the antibodies. A tissue sample from a normal individual is used as control.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition (Sambrook et al., Eds.), 1989; Oligonucleotide Synthesis, (M. J. Gait, Ed.), 1984; U.S. Pat. No. 4,683,195 to Mullis et al.; Nucleic Acid Hybridization, (B. D. Hames and S. J. Higgins), 1984; Transcription and Translation, (B. D. Hames and S. J. Higgins), 1984; Culture of Animal Cells (R. I. Freshney, Ed.), 1987; Immobilized Cells and Enzymes, IRL Press, 1986; A Practical Guide to Molecular Cloning (B. Perbal), 1984; Methods in Enzymology, Volumes 154 and 155 (Wu et al., Eds.), Academic Press, New York; Gene Transfer Vectors for Mammalian Cells (J. H. Miller and M. P. Calos, Eds.), 1987; Immunochemical Methods in Cell and Molecular Biology (Mayer and Walker, Eds.), 1987; Handbook of Experiment Immunology, Volumes I-IV (D. M. Weir and C. C. Blackwell, Eds.), 1986; Manipulating the Mouse Embryo, 1986.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

The following Examples are provided to illustrate the present invention, and should not be construed as limiting thereof.

EXAMPLES

Chemical Reagents

Fluorescein isothiocyanate (FITC) was purchased from Sigma Chemical Co. (St. Louis, Mo.). Croton oil was purchased from ICN Biochemicals (Aurora, Ohio). Whole sheep blood in Alsevers solution was obtained from East Acres Biologicals (Southbridge, Mass.). Type I rat tail collagen and type IV mouse collagen were purchased from Collaborative Research Inc. (Bedford, Mass.) and Gibco (Gaithersburg, Md.), respectively.

Balb/c female mice of 6-8 weeks of age were purchased from Taconic (Germantown, N.Y.) and the α1β1 integrin-deficient mice on a Balb/c background were as previously described (3).

Example 1

Monoclonal Antibodies. Function-blocking mAbs to murine antigens were prepared in an azide-free and low endotoxin format: Ha31/8 (hamster anti-CD49a; integrin α1) (Mendrick et al. 1995. Lab. Invest. 72:367-375), Ha1/29 (hamster anti-CD49b; integrin α2)(β1) (Mendrick et al. 1995. Lab. Invest. 72:367-375; Mendrick, D. L. and D. M. Kelly 1993 Lab. Invest. 69:690-702), hamster group II control mAb Ha4/8 (hamster anti-KLH) (Mendrick, D. L. and D. M. Kelly 1993 Lab. Invest. 69:690-702), and PS/2 (rat anti-CD49d; integrin α4β1 chain) (Miyake et al. 1991 J. Exp. Med. 173: 599-607). In addition, the following function-blocking mAbs to murine antigens were purchased as no-azide/low endotoxin preparations from Pharmingen (San Diego, Calif.): HMβ1-1 (hamster anti-CD29; integrin β1 chain) (Noto et al. 1995 Int. Immunol. 7:835-842), Ha2/5 (hamster anti-CD29; integrin β1 chain) (Mendrick, D. L. and D. M. Kelly 1993 Lab. Invest. 69:690-702), 3E2 (hamster anti-CD54, ICAM-1) (Scheynius et al. 1993 J. Immunol. 150:655-663), 5H10-27 (rat anti-CD49e; integrin α5) (Kinashi, T., and T. A. Springer. 1994. Blood Cells. 20:25-44), GoH3 (rat anti-CD49f; integrin α6) (Sonnenberg et al. 1987 J. Biol. Chem. 262:10376-10383), and the rat isotype control mAbs R35-95 (rat IgG2a) and R35-38 (rat IgG2b).

Adhesion Assay. Splenocytes from Balb/c mice were cultured with 20 ng/ml IL-2 for 7-12 d. Adhesion of cells to type I and type TV collagen was as previously described (Gotwals et al. 1996 J. Clin. Invest. 97:2469-2477). Briefly, 96-well Maxisorp plates (Nunc, Napierville, Ill.) were coated with either 10 μg/ml type IV or 5 μg/ml type I collagen and non-specific sites blocked with 1% BSA. IL-2 activated splenocytes were labeled with 2 μM BCECF [2',7'-bis(carboxyethyl)-5(6) carboxyl fluorescein penta acetoxymethylester] (Molecular Probes, Eugene, Oreg.) and incubated with 10 μg/ml of indicated mAbs for 15 min. $10^5$ cells in 0.25% BSA in RPMI were then added to coated wells and incubated for 60 min at 37° C. Unbound cells were removed by washing three times with 0.25% BSA in RPMI. Adhesion was quantified using a CytoFluor 2350 fluorescent plate reader (Millipore, Bedford, Mass.). The ratio of bound cells to input cells was measured and percent adhesion relative to control mAb-treated cells (normalized to 100%) calculated. Background values due to cell adhesion on wells coated with BSA alone were subtracted.

Figure 1A:
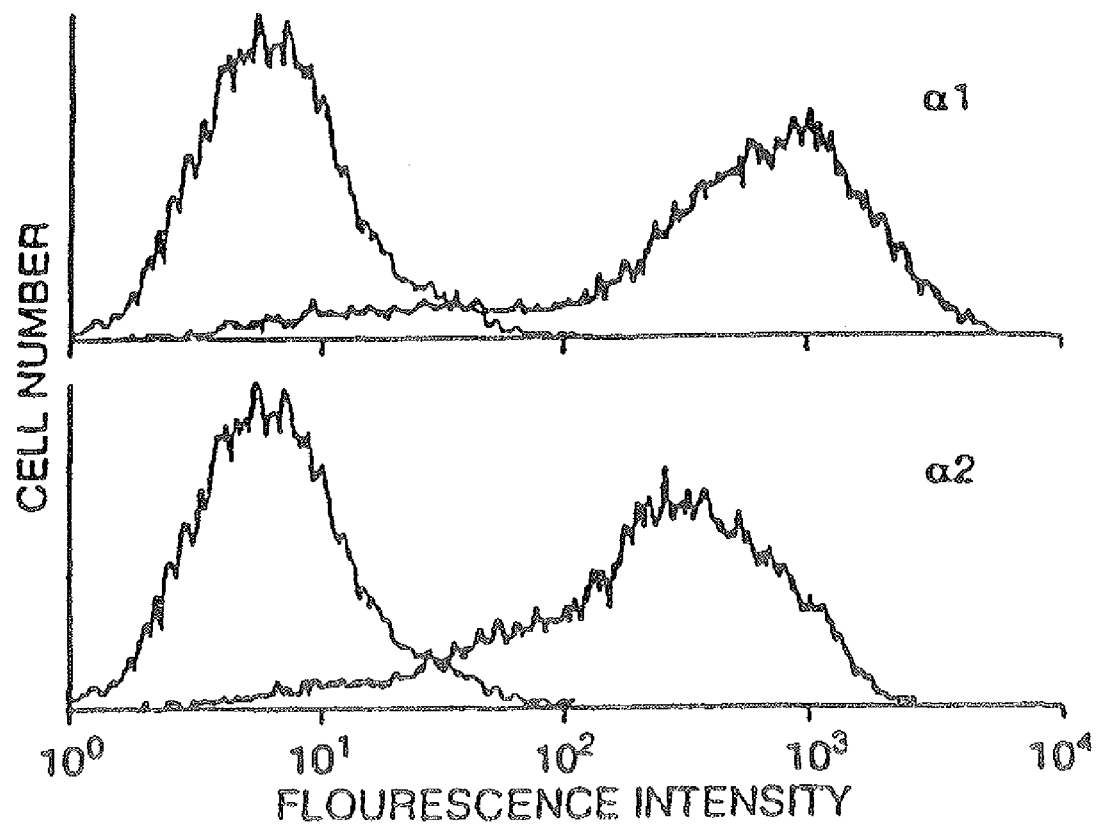
FIG. 1. Collagen-binding integrins α1β1 and α2β1 on activated leukocytes. (A). Flow cytometric analysis of α1 and α2β1 integrin expression on IL-2-activated splenocytes (d 11). Cells were labeled with either anti-α1 mAb, anti-α2 mAb, or non-binding control mAb (grey lines), and followed by FITC-anti-hamster immunoglobulin. (B) Effect of anti-α1 and anti-α2 mAbs on leukocyte adhesion to collagen. $10^5$ IL-2 activated splenocytes were treated with indicated mAbs for 15 min before plating onto either type IV or type I collagen-coated wells for 1 h at 37° C. Adhesion was calculated as illustrated in Example 1, and expressed as % adhesion relative to control mAb-treated cells. Adhesion assays were done in triplicate, and at least three independent experiments were performed. One representative experiment is shown.
Figure 1B:
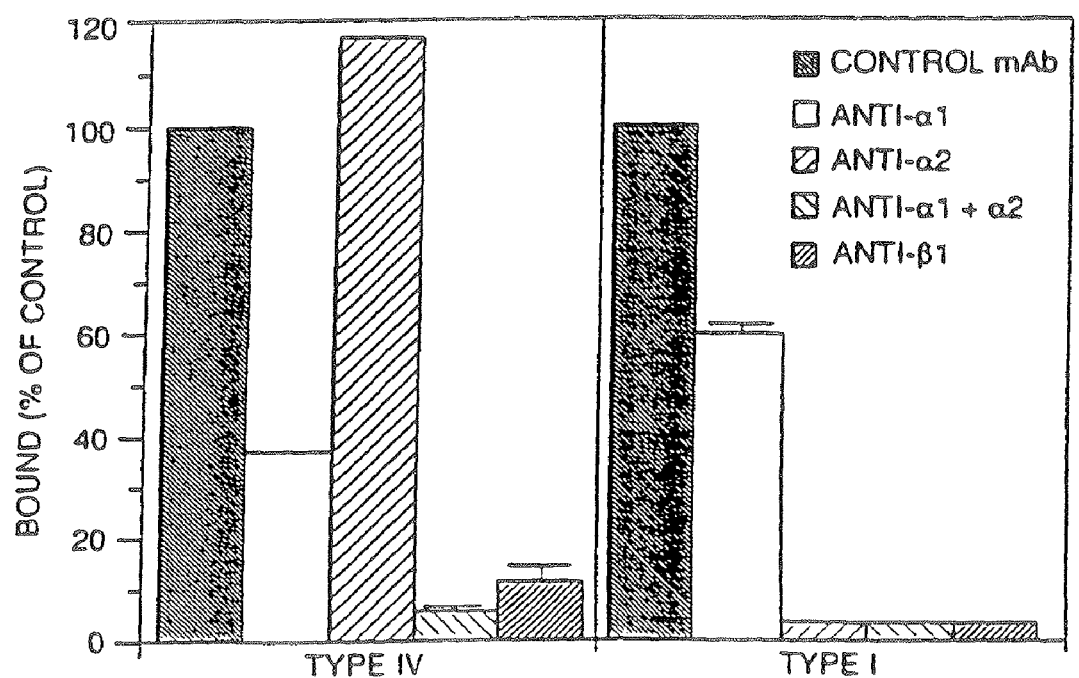

Expression and functional blockade of α1β1 and α2β1 on activated leukocytes. Given the key role leukocytes play in inflammation, we decided to test whether anti-α1 and anti-α2 mAbs were capable of blocking leukocyte adhesion to collagens. In order to obtain leukocytes expressing high levels of both α1 and α2, murine T cells were stimulated in vitro with IL-2 for 7-12 d. These cells expressed high levels of both α1 and α2 (FIG. 1A), and bound well to both collagen type IV and type I-coated surfaces (FIG. 1B). Adhesion to type IV collagen was partially inhibited by anti-α1 mAb alone and was not inhibited by anti-α2 mAb alone. In contrast, adhesion to type I collagen was completely inhibited by anti-α2 mAb and anti-α1 mAb alone showed only partial inhibition. Both anti-β1 mAb and the combination of anti-α1 and anti-α2 mAbs completely inhibited adhesion to types I and IV collagen. Having demonstrated that the α1β1 and α2β1 integrins are expressed on activated T cells and that anti-α1 and α2 mAbs are able to functionally block leukocyte adhesion to collagens, we used these mAbs to investigate the in vivo role of these integrins in animal models of inflammatory disorders.

Example 2

Inhibition of DTH responses by anti-integrin mAbs. SRBC-induced delayed type hypersensitivity (DTH) responses were adapted from a previously published protocol (Hurtrel et al., 1992, Cell. Immunol. 142:252-263). Briefly, mice were immunized s.c. in the back with $2 \times 10^7$ SRBC in 100 ul PBS on d 0. The mice were challenged on d 5 by injecting $1 \times 10^8$ SRBC in 25 ul PBS s.c into the right hind footpad. Footpad thickness was measured with an engineer's caliper (Mitutoyo/MTI, Paramus, N.J.) 20 h after antigen challenge, and the degree of footpad swelling calculated. Results are reported as the mean percent increase footpad thickness±SEM and calculated as % increase=[1=(Right footpad thickness 20 h after antigen challenge/Uninjected left footpad thickness 20 h after antigen challenge)]×100. To block the effector phase of the SRBC-induced DTH response, therapeutic or control mAb (100 ug), which were prepared according to the methods described in Example 1, was given i.p. 1 h prior to antigen challenge on d 5.

Figure 2:
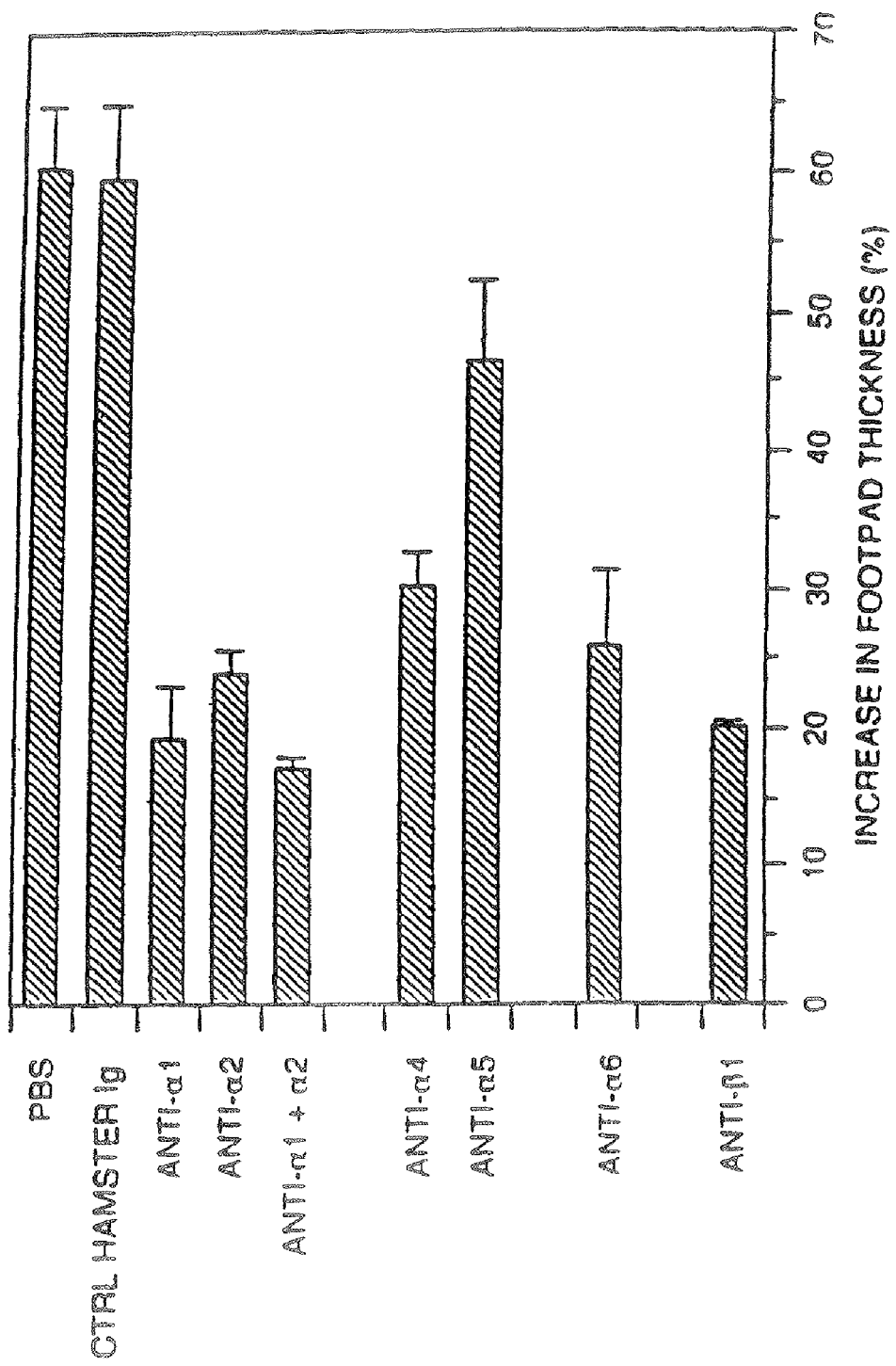
FIG. 2. Effect of anti-integrin mAbs on the effector phase of delayed-type hypersensitivity. SRBC-sensitized mice were injected i.p. with the indicated mAbs 1 h prior to SRBC challenge. Footpad thickness was measured 20 h after antigen challenge, and results shown as % increase in footpad thickness±SEM as illustrated in Example 2. These data represent a summary of eight experiments with n=79 (PBS), 68 (control hamster Ig), 68 (anti-α1), 29 (anti-α2), 18 (anti-α1+ anti-α2), 45 (anti-α4), 18 (anti-α5), 20 (anti-α6), and 10 (anti-β1). The mAbs used were: Ha4/8 (control hamster Ig group 2), Ha31/8 (anti-α1), Ha1/29 (anti-α2), PS/2 (anti-α4), 5H10-27 (anti-α5), GoH3 (anti-α6), and HM β1-1 (anti-β1).

SRBC-induced DTH is a well characterized in vivo model of inflammation, and in particular psoriasis, that has been used to demonstrate the importance of a variety of cytokines and adhesion molecules in inflammation (Tedder et al., 1995, J. Exp. Med. 181:2259-2264, Terashita et al., 1996, J Immunol 156:4638-4643). SRBC-sensitized mice received anti-integrin mAbs 1 h prior to footpad antigen challenge and inflammation was assessed 20 h later as measured by increased footpad thickness. PBS and control hamster Ig-treated mice showed a 60-70% increase in footpad thickness 20 h after antigen challenge (FIG. 2). Compared to control hamster Ig treatment, anti-α1 or anti-α2 mAbs resulted in a 68% and 60% inhibition in footpad thickness, respectively. The combination of anti-α1 and α2 mAbs resulted in 71% inhibition, demonstrating little additive effect over anti-α1 or anti-α2 mAbs alone. Treatment with other anti-integrin mAbs was also effective at inhibiting DTH effector response. The degree of inhibition seen with the various mAb treatments was 49% (anti-α4), 23% (anti-α5), and 57% (anti-α6). Lastly, mAb blockade of the common β1 integrin subunit (mAb HMBI-1) inhibited the effector DTH response by 67%.

Example 3

Inhibition of CHS effector responses by anti-integrin mAbs. Contact hypersensitivity (CHS) to FITC was assayed as previously described (Gaspari et al., 1991, In Current Protocols in Immunology. J. E. Coligan, A. M. Kruisbeek, D. H. Margulies, E. M. Shevach, and W. Strober, editors. John Wiley & Sons, New York. Section 4.2:1). Briefly, mice were sensitized by painting 100 ul 0.5% FITC in 1:1 acetone/dibutylphthalate onto the shaved back on d 0.10 d later, animals were challenged by applying 5 ul 0.5% FITC onto both sides of each ear. Ear swelling response was determined by ear thickness measured with an engineer's caliper (Mitutoyo/MTI, Paramus, N.J.) at the time of antigen challenge (d 10) and 24 h later, and the results reported as mean percent increase in baseline ear thickness±SEM. Increase in ear thickness was calculated as % increase=[1=(Ear thickness 24 h after antigen challenge/Ear thickness at the time of antigen challenge)]×100. To block the effector phase of the CHS response, therapeutic or control in mAb (250 ug) was given i.p. 4 h prior to antigen challenge on d 10. Mice that were antigen-sensitized and ear challenged with vehicle only (vehicle control) or mice that were ear challenged without prior sensitization (irritant control) served as negative controls (never exceeded 2% increase in ear thickness).

Figure 3:
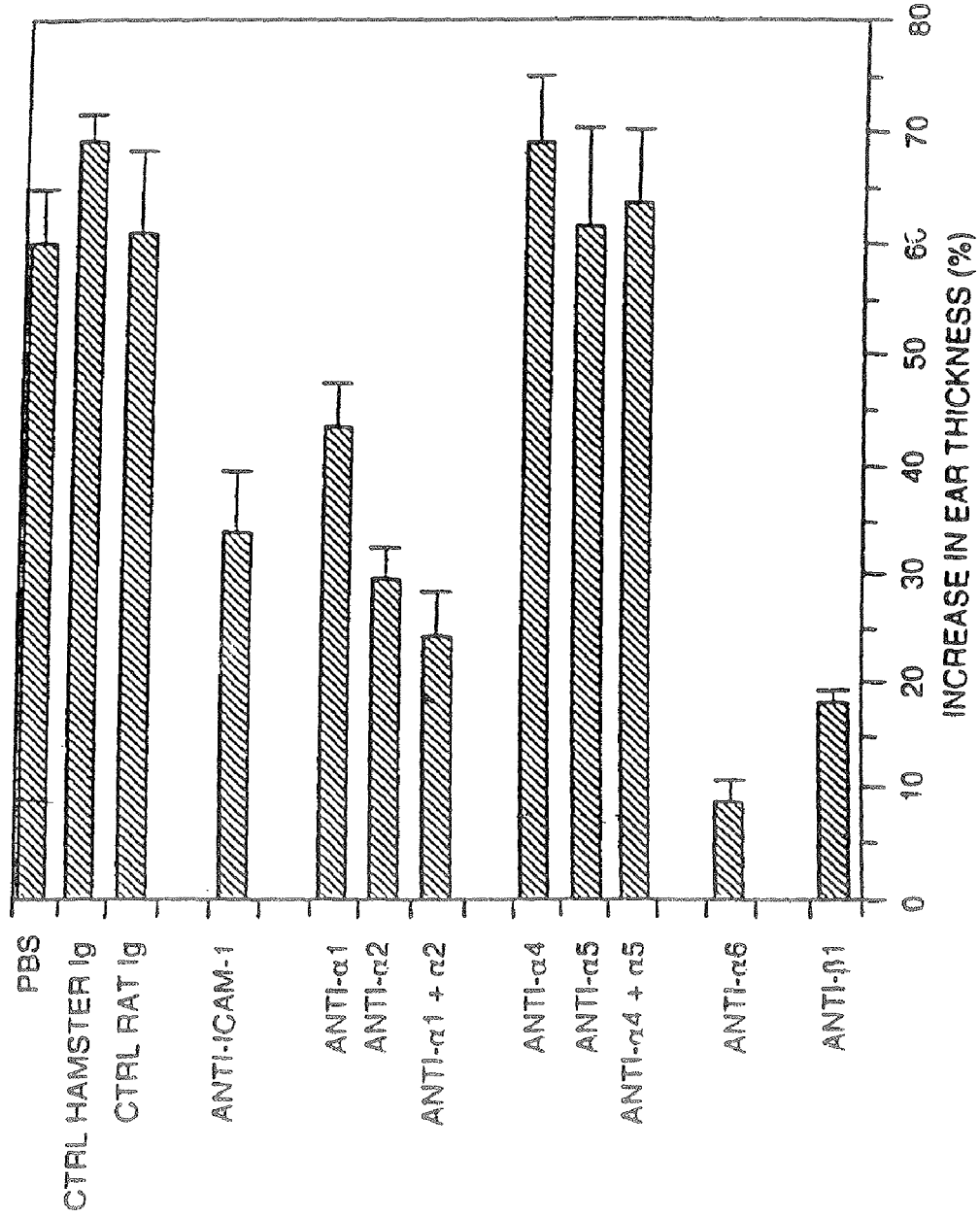
FIG. 3. Effect of anti-integrin mAbs on the effector phase of contact hypersensitivity. FITC-sensitized mice were injected i.p. with the indicated mAbs 4 h prior to FITC challenge. Ear thickness was measured at baseline and 24 h later, and results shown as % increase in ear thickness±SEM as illustrated in Example 3. These data represent a summary of nine experiments with n=74 (PBS), 60 (control hamster Ig), 26 (anti-ICAM-1), 44 (anti-α1), 44 (anti-α2), 38 (anti-α1+ anti-α2), 36 (anti-α4), 16 (anti-α5), 26 (anti-α4+anti-α5), 24 (anti-α6), and 22 (anti-β1). The hamster mAbs used were: Ha4/8 (control hamster Ig group 2), Ha31/8 (anti-α1), Ha1/29 (anti-α2), HMβ1-1 (anti-β1), 3E2 (anti-ICAM-1); the rat mAbs used were: R35-95 and R35-38 (control rat IgG2a and rat IgG2b, respectively), PS/2 (anti-α4), 5H10-27 (anti-α5), GoH3 (anti-α6).

Given that CHS is mechanistically distinct from DTH and involves different effector cells, we investigated what effect anti-integrin mAbs had on the effector phase of abacks, followed 10 d later with FITC challenge to the ear resulting in an inflammatory response the next day. FITC-sensitized mice demonstrated a 60-70% increase in thickness 24 h after antigen challenge (FIG. 3). Consistent with published results (Scheynius et al., J. Immunol. 150:655-663), anti-ICAM-1 mAb treatment resulted in 51% inhibition of ear swelling. Compared to control hamster mAb, treatment of mice with anti-α1 or anti-α2 mAb 4 h prior to antigen challenge resulted in 37% and 57% inhibition in ear swelling, respectively (FIG. 3). The combination of anti-α1 and anti-α2 mAbs resulted in slightly greater inhibition of ear swelling (65%). Treatment with other mAbs to β1 integrins revealed that while anti-α4 and anti-α5 mAbs resulted in no inhibition of FITC-induced CHS effector response when compared to control rat mAb, treatment with anti-α6 mAb resulted in an 86% inhibition of effector responses. Lastly, mAb blockade of the common β1 integrin subunit inhibited CHS effector responses by 74%. Similar CHS results were obtained using different strains of mice (C57/BL6, 129/Sv) and a different sensitizing agent (oxazolone) (data not shown). Similar to the results seen in the SRBC-induced DTH model, histologic analysis of inflamed ears revealed that both edema formation and leukocytic infiltration were inhibited by anti-α1 and anti-α2 mAb treatment.

Consistent with the finding that α1β1 and α2β1 can be expressed on IL-2-activated splenocytes, analysis of lymph nodes from antigen-sensitized mice (FITC or oxazolone) revealed of α1β1 and α2β1 to be expressed exclusively on $CD44^{hi}$ $LFA-1^{hi}$ activated CD4+ and CD8+ T cells (data not shown). Treatment of mice with anti-α1 and anti-α2 mAbs did not result in deletion of these cells, as the numbers of activated T cells in both spleen and lymph nodes seen in response to antigen sensitization in the CHS model was unaffected. In addition, effector cells were not functionally deleted as prolonged treatment of antigen-sensitized mice with anti-α1 and anti-α2 mAbs (d 10-16) did not affect the inflammatory response of mice challenged with antigen at d 20 (data not shown).

Example 4

Figure 4:
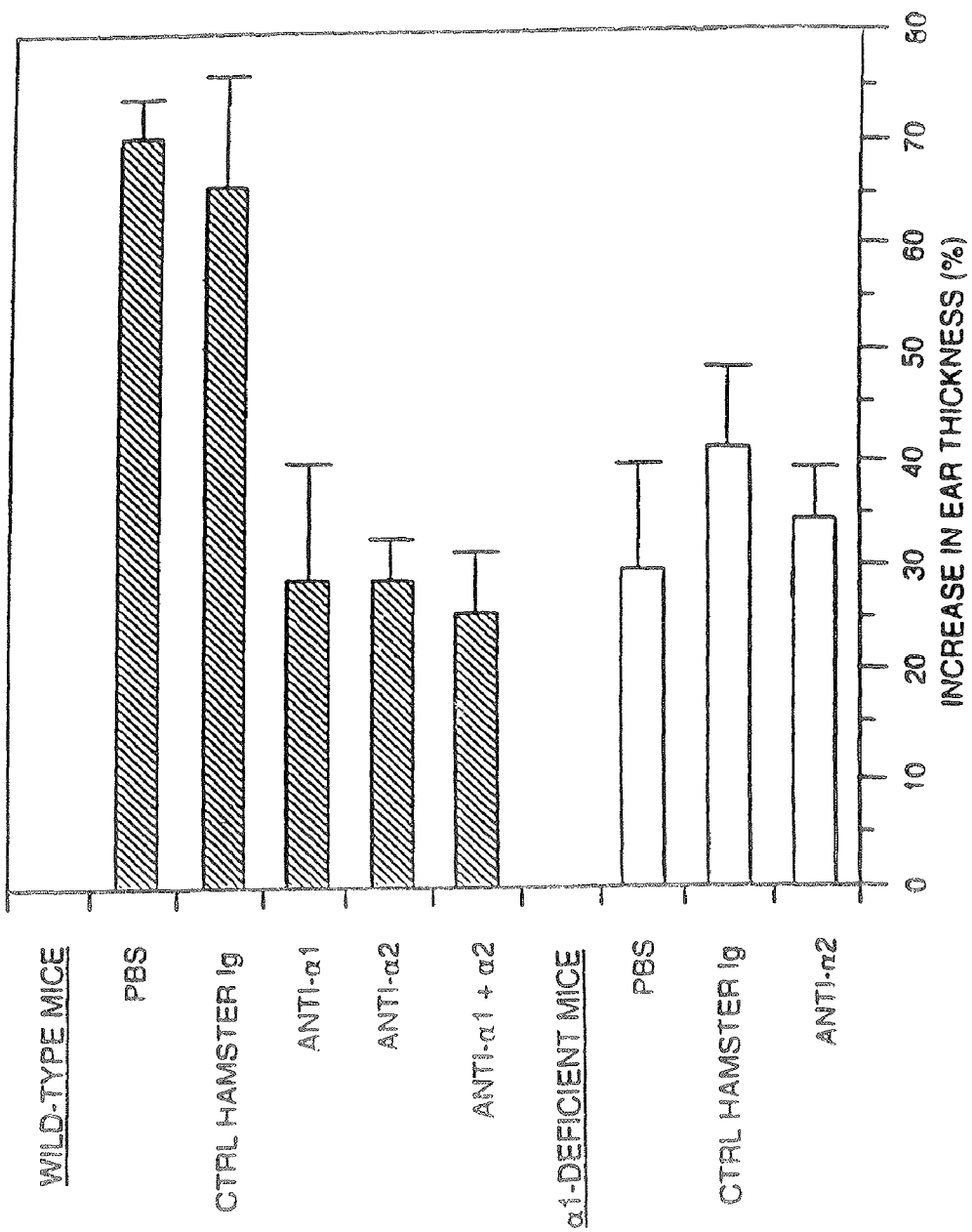
FIG. 4. Contact hypersensitivity responses in α1-deficient mice compared to wild-type mice. FITC-sensitized mice were injected i.p. with indicated mAbs 4 h prior to FITC challenge. Ear thickness was measured at baseline and 24 h later, and results shown as % increase in ear thickness±SEM as illustrated in Example 4. Groups of four to five mice per condition were used, and all experiments were performed a minimum of three times. One representative experiment is shown.

CHS effector responses are decreased in α1β3-deficient mice. To exclude the possibility that the inhibitory role of α1β1 in the effector response of FITC-mediated CHS was mAb-mediated, experiments were carried out in wild-type and α1β1 integrin deficient mice (FIG. 4). MAb inhibition of the effector phase in wild-type mice was consistent with previous results with 56% inhibition in ear thickness seen with anti-α1, 56% with anti-α2 and 62% with a combination of anti-α1 and anti-α2. The effector phase of CHS was significantly reduced in untreated α1β1-deficient mice as compared to untreated wild-type mice (30% vs 71% increase in ear thickness, respectively). As expected, the level of ear swelling in untreated α1β1-deficient mice was equivalent to the level of ear swelling seen in anti-α1 mAb-treated wild-type mice. Lastly, mAb blockade of α2β1 in the α1β1-deficient mice resulted in only slightly increased inhibition of ear swelling, consistent with the results seen in wild-type mice treated with a combination of anti-α1 and anti-α2 mAbs.

Example 5

To further exclude the possibility that the inhibitory effect of the anti-integrin mAbs seen in both the DTH and CHS models of inflammation is caused by a general anti-inflammatory effect mediated by the anti-α1 and anti-α2 mAbs, the effect of these mAbs on irritant dermatitis was studied.

To assess irritant dermatitis, mice were painted with 5 ul of 0.8% croton oil in acetone on both sides of each ear. Therapeutic or control antibodies were given 4 h prior to the application of the irritant. Ear swelling was measured 24 h later as described above and compared to ear thickness prior to croton oil application. Results are reported as mean percent increase in baseline ear thickness±SEM as described above. Mice painted with acetone only (vehicle control) served as a negative control.

Figure 5:
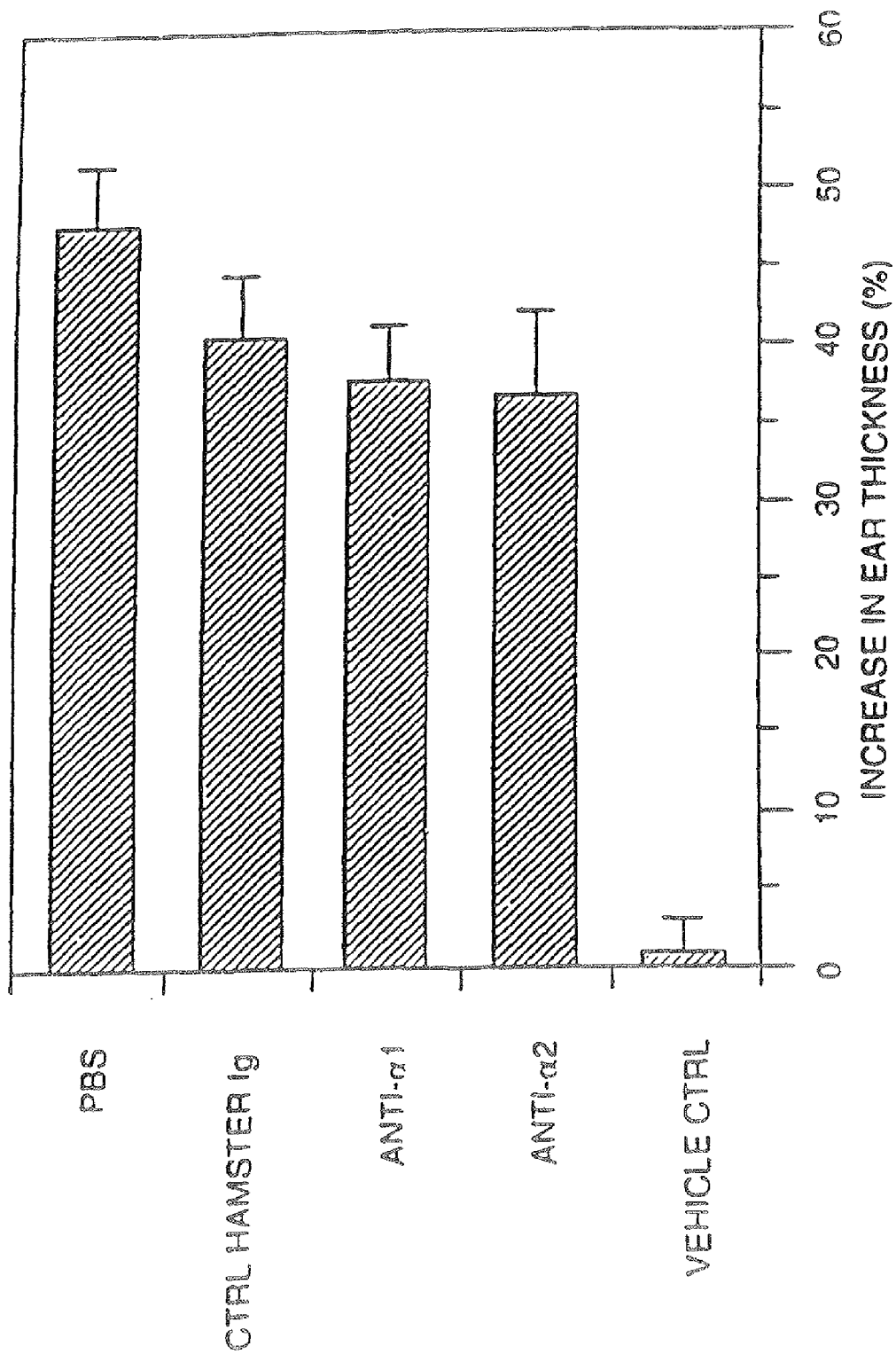
FIG. 5. Effect of anti-α1and anti-α2 mAbs on croton oil-induced non-specific inflammation. Mice were injected i.p. with indicated mAbs 4 h prior to ear painting with croton oil. Ear thickness was measured at baseline and 24 h later, and results shown as % increase in ear thickness±SEM as illustrated in Example 5. Groups of four to five mice per condition were used, and all experiments were performed a minimum of three times. One representative experiment is shown.

24 h later, ears of mice treated with croton oil showed a significant increase in ear thickness (48%), when compared to mice receiving vehicle only (acetone). Toxic ear swelling caused by croton oil was not significantly affected in mice pretreated with anti-α1 or anti-α2 mAbs when compared to either PBS or control mAb-treated animals (FIG. 5). Histologic examination of the croton oil-treated ears revealed no differences in numbers or types of infiltrating cells or edema formation in mice treated with anti-α1 or anti-α2 mAbs, as compared to control mAb-treated mice or PBS-treated mice (data not shown).

Example 6

Inhibition of arthritis bar α1β1 and α2β1. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, J. Immunol. 148:2103-2108; Terato et al., 1995, Autoimmunity 22:137-147).

Arthrogen-CIA Antibody kits were purchased from Stratagene (La Jolla, Calif.) and arthritis induced using a well established protocol (Terato et al., 1992, J. Immunol. 148:2103-2108; Terato et al., 1995, Autoimmunity 22:137-147). Briefly, arthritis was induced through i.p. injection of a cocktail of 4 anti-collagen type II mAbs (1 mg each) on d 0, followed by i.p. injection of 50 ug LPS on d 3. Over the course of the next 3-4 d, the mice developed swollen wrists, ankles and digits. Therapeutic or control mAb (250 ug) was administered i.p. 4 h prior to injection of the anti-collagen mAbs on d 0, and again 4 h prior to LPS administration on d 3, and then continuing every $3^{rd}$ day for the length of the experiment. Beginning on d 3, mice were evaluated for the development of arthritis. Severity of arthritis in each limb was scored using a four point system. 0=normal; 1=mild redness, slight swelling of ankle or wrist; 2=moderate swelling of ankle or wrist; 3=severe swelling including some digits, ankle, and foot; 4=maximally inflamed.

Figure 6:
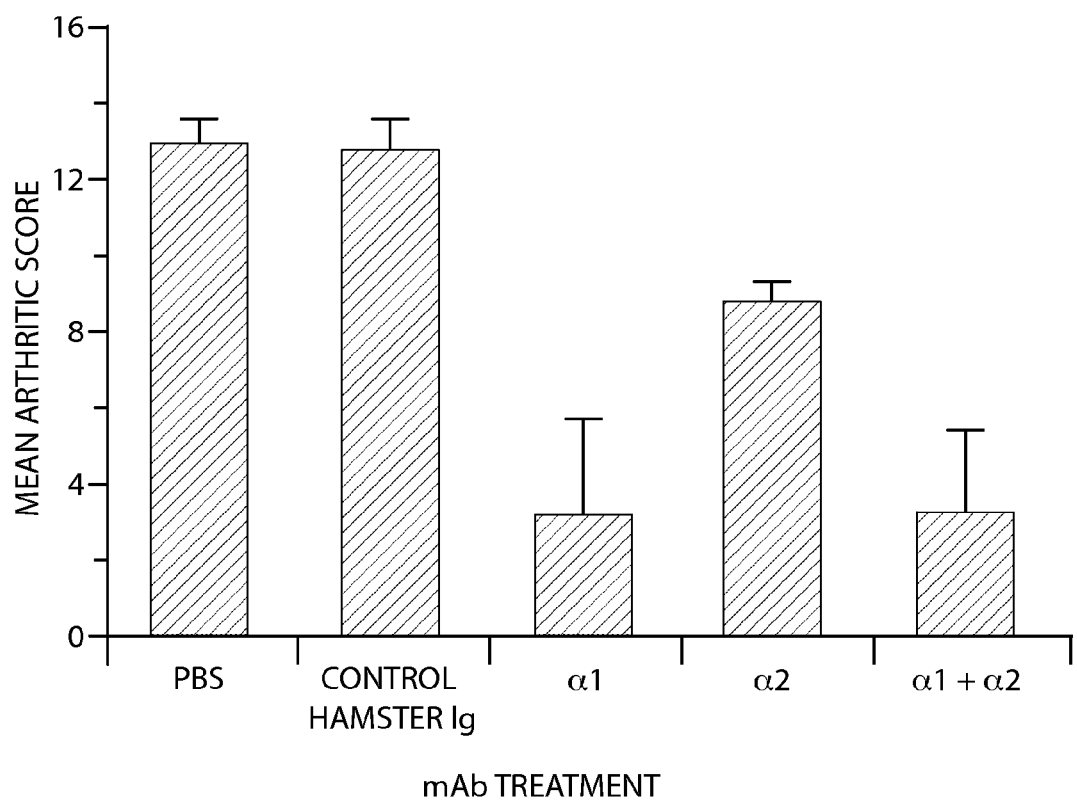
FIG. 6. Effect of anti-α1 and α2mAbs in collagen mAb-induced arthritis. Mice were injected i.p. with anti-collagen mAbs at d 0, followed by LPS on day 3. Mice were injected i.p. with indicated mAbs every $3^{rd}$ day starting on d 0. Clinical arthritis was apparent 2-3 d following LPS injection and continued for several weeks. Each limb was evaluated on a 0 to 4 scale every $3^{rd}$ day as illustrated in Example 6 and results are expressed as the mean arthritic score between d 9 and d 15 (±SEM) of all four limbs. These data represent a summary of four experiments with each experiment consisting of groups of three to four mice per condition.

Severe arthritis in Balb/c mice developed within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 6). In contrast, treatment with anti-α1 mAb alone resulted in a marked reduction (78%) in arthritis, lasting the duration of the experiment. Treatment with anti-α2 mAb alone also had a beneficial effect, resulting in a 32% decrease in the arthritic score as compared to control b-treated mice. The combination of anti-α1 and anti-α2 mAbs resulted in a similar degree of inhibition as seen with anti-α1 mAb alone.

Example 7

Histological analysis of effect of anti-α1 and anti-α2 mAb treatment on the inflammatory cellular infiltrate. Further histological analysis of the SRBC-induced DTH response confirmed the ability of anti-α1 and anti-α2 mAb treatment to modulate the elicited inflammatory response. An unchallenged footpad from an SRBC-sensitized mouse showed virtually no inflammatory cellular infiltrate when compared to an SRBC-challenged footpad from the same mouse. Treatment of SRBC-sensitized mice with anti-α1 and anti-α2 mAbs either alone or combined greatly reduced the number of these infiltrating cells found in SRBC-challenged footpads when compared to control mAb-treated mice. Closer examination of the infiltrating cells revealed most cells to be composed of neutrophils, with some monocytes and lymphocytes present, and confirmed that anti-α1 and anti-α2 mAb treatment greatly decreased the numbers of these cells.

Example 8

Immunohistochemical demonstration of α1-expressing cells in the inflammatory cellular infiltrate. Immunohistochemistry was performed to more precisely determine the nature of the infiltrating cells and whether they express collagen-binding integrins. Infiltrating cells from an inflamed footpad of an untreated mouse were examined for expression of α1β1 integrin and cell lineage markers. α1β1 integrin was found to be expressed on many infiltrating leukocytes. Dual immunohistochemistry was utilized to identify the nature of the infiltrating cells and the distribution of α1β1 expression. Using cell lineage markers, the infiltrate was found to be composed largely of granulocyte/monocytes (Mac-1+), with many of these cells being neutrophils (Gr1+), along with a smaller number of T lymphocytes (CD3+). Expression of α1β1 integrin was found among all three subsets of cells, with α1 expressed on a subset of Mac-1+ granulocyte/monocytes, a subset of Gr1+ neutrophils, and on the majority of infiltrating CD3+ T lymphocytes. Detailed immunohistochemical analysis revealed that although anti-α1 and anti-α2 mAb treatment reduced the numbers of infiltrating cells, no change in the cellular composition of the infiltrate was seen (data not shown). Immunohistochemistry staining with a FITC anti-hamster mAb confirmed the ability of the anti-α1 and antis α2 mAb to localize to the inflamed footpad (data not shown).

Example 9

Figure 7:
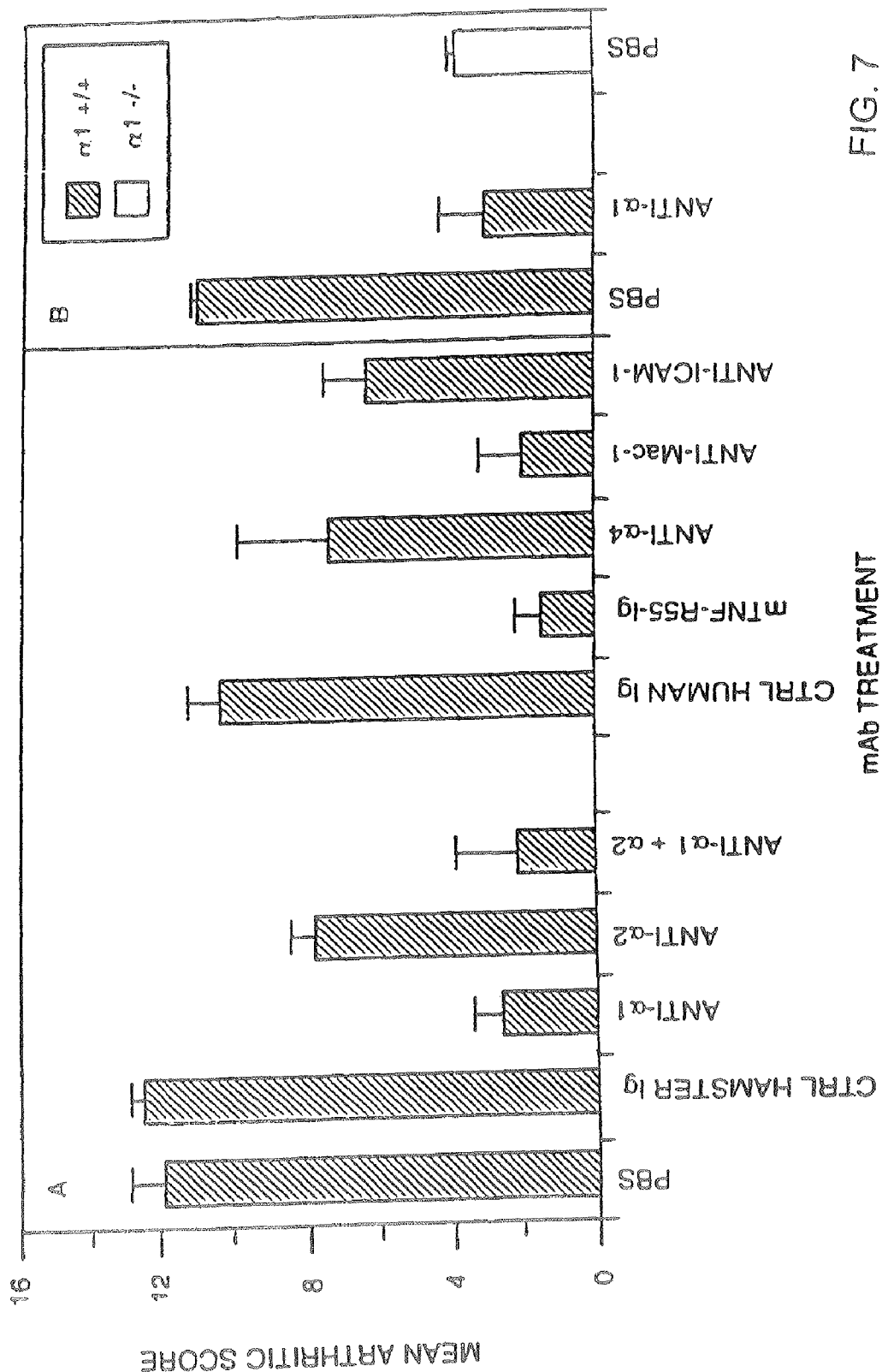
FIG. 7. Effect of anti-α1 and α2 mAbs in collagen mAb-induced arthritis. A. Preventative treatment of mice with either anti-α1 or anti-α2 mAb decreases arthritic score. Mice were treated with anti-collagen mAbs at d 0, followed by LPS on d 3. Arthritis was apparent by d 6 and continued for several weeks. Mice were treated with the indicated mAbs every $3^{rd}$ day starting on d 0. Each limb was evaluated and scored on a 0 to 4 scale every $3^{rd}$ day. Results are expressed as the mean arthritic score between d 9 and d 15 (±SEM) of all four limbs (maximum score of 16). Groups of 4 mice per condition were used; the average of 12 experiments is shown. B. α1-deficient mice have a reduced arthritic score comparable to anti-α1 mAb-treated wild-type mice. Experimental details and scoring are as outlined above. Groups of 4 mice per condition were used; the average of 2 experiments is shown.

Inhibition of arthritis by mAbs to α1β1 and α2β1 and in α1-deficient mice. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, J. Immunol 148:2103-2108; Terato et al., 1995, Autoimmunity 22:137-147). This model involves injection of a cocktail of anti-collagen type II mAbs into mice, followed later by LPS administration, resulting in the development of arthritis over the next 3-7 d. Mice were given mAb every $3^{rd}$ day starting at d 0, and scored for the development of arthritis every $3^{rd}$ day. Severe arthritis developed in all mice within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 7). In contrast, treatment with anti-α1 mAb alone resulted in a marked reduction (79% and higher) in arthritis, lasting the duration of the experiment. Treatment with anti-α2 mAb alone also had a beneficial effect, resulting in a 37% decrease in the arthritic score as compared to control mAb-treated mice. The combination of anti-α1 and anti-α2 mAbs resulted in a similar degree of inhibition as seen with anti-α1 mAb alone. Reduction of arthritic score with anti-α1 mAb treatment was seen in all mice and compares favorably with several other mAb-based treatments for arthritis such as soluble TNF receptor Ig fusion protein (Mori et al., 1996, J. Immunol. 157:3178-3182), anti-Mac-1 (Taylor et al., 1996, Immunology. 88:315-321), anti-α4 (Seiffge, 1996, J. Rheumatol. 23:2086-2091), and anti-ICAM-1 (Kakimoto et al., 1992, Cell Immunol. 142:326-337). In agreement with mAb-based data showing an important role for α1β1 in arthritis, untreated i-deficient mice showed significant reduction in arthritic score when compared to wild-type mice.

Example 10

Effect of anti-α1 mAb treatment on the immunopathology of arthritic joints. Joints from wild-type arthritic mice (day 8) receiving either control mAb or anti-α1 mAb treatment were compared visually and histologically to joints from a normal untreated mouse. Visually, joints from control mAb-treated mice demonstrated redness and swelling of the entire foot including digits, while anti-α1 mAb-treated mice showed little if any signs of inflammation in either joints or digits. Histologic examination showed severe changes in control mAb-treated arthritic joints, with extensive infiltration of the subsynovial tissue with inflammatory cells, adherence of cells to the joint surface, and marked cartilage destruction as evidenced by proteoglycan loss. Consistent with previous reports (Terato et al., 1992, J. Immunol 148:2103-2108; Terato et al., 1995, Autoimmunity 22:137-147), the majority of the infiltrating cells in this model are neutrophils. Anti-α1 mAb treatment of mice dramatically reduced the amount of inflammatory infiltrate and the degree of cartilage destruction.

Example 11

Figure 8:
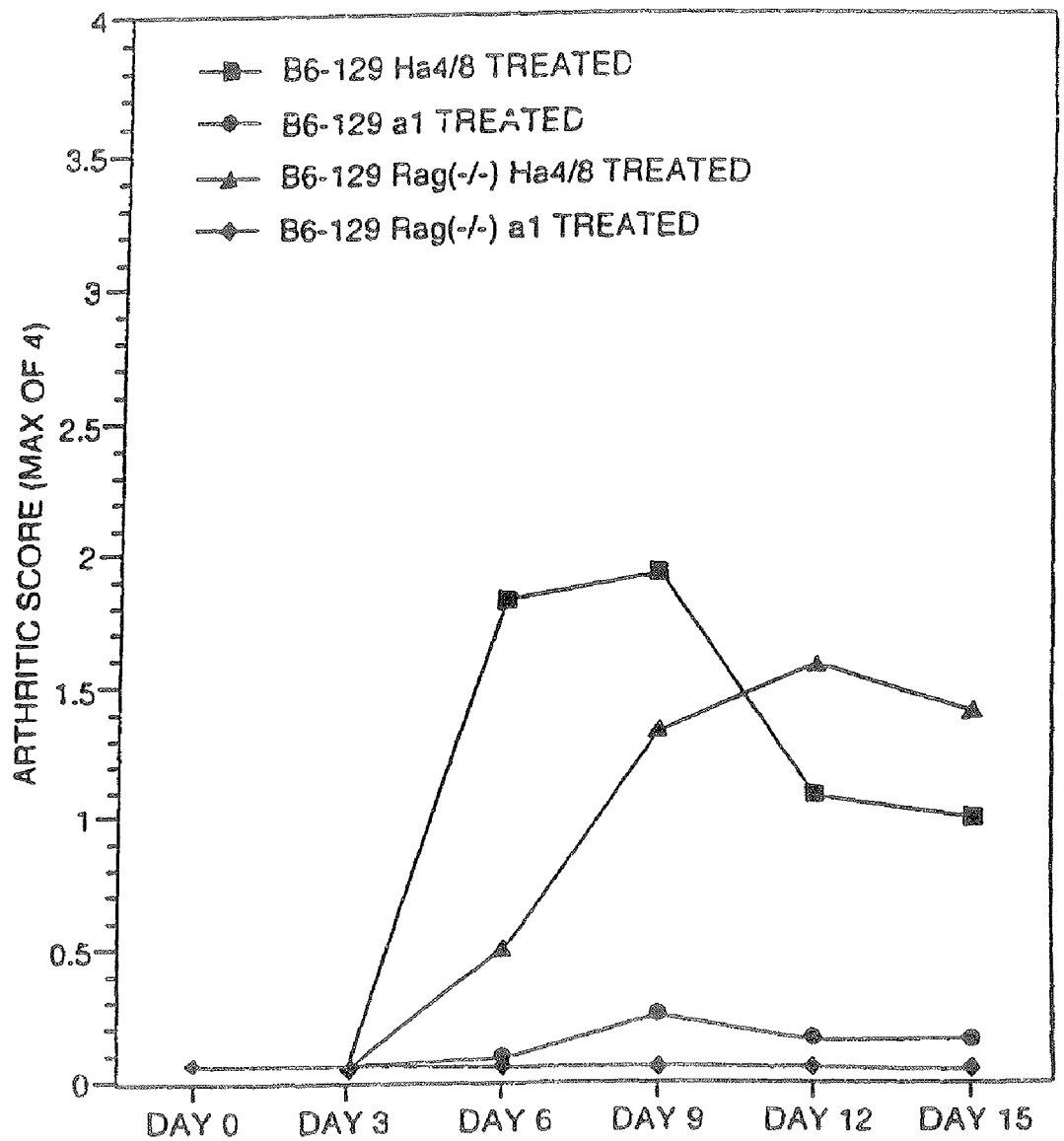
FIG. 8. Development of arthritis is delayed in the absence of lymphocytes and inhibition of arthritis by anti-al mAb occurs in the absence of lymphocytes. Wild-type B6,129 or RAG-1-deficient B6,129 mice were treated with anti-collagen mAbs at day 0, followed by LPS on day 3. Arthritis was apparent by day 6 and continued for several weeks. Mice were treated with the indicated mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Development of arthritis is delayed in the absence of lymphocytes and inhibition of arthritis by anti-α1 mAb occurs in the absence of lymphocytes. To determine what cell types might be important in the collagen mAb-induced arthritis model we compared the ability of wild-type B6-129 mice and RAG-1-deficient B6-129 mice to develop arthritis (FIG. 8). Genetic deletion of the RAG-1 (recombination activating gene-1) gene results in a complete loss of mature T and B lymphocytes (Mombaerts et al., 1992, Cell 68:869-877). Both the wild-type and RAG-1-deficient mice developed arthritis, though the kinetics of induction in the RAG-1-deficient mice is significantly slower (FIG. 8). These results suggest that while lymphocytes are involved in this model of arthritis, they are not required for the development and progression of the disease. Published reports examining the effect of the RAG-1-deficient mice in other models of arthritis also found that loss of T and B lymphocytes delayed the onset of arthritis (Plows et al., 1999, J. Immunol. 162:1018-1023). Treatment of either wild-type or RAG-1-deficient mice with anti-α1 mAb completely inhibited arthritis (FIG. 8). These results demonstrate that the effectiveness of anti-α1 mAb in this model is not dependent on the presence of lymphocytes, and that as suggested by previous experiments (FIG. 7), the efficacy of anti-α1 mAb in preventing disease may be through its action on other α1-expressing cells, such as macrophages and neutrophils.

Example 12

Figure 9:
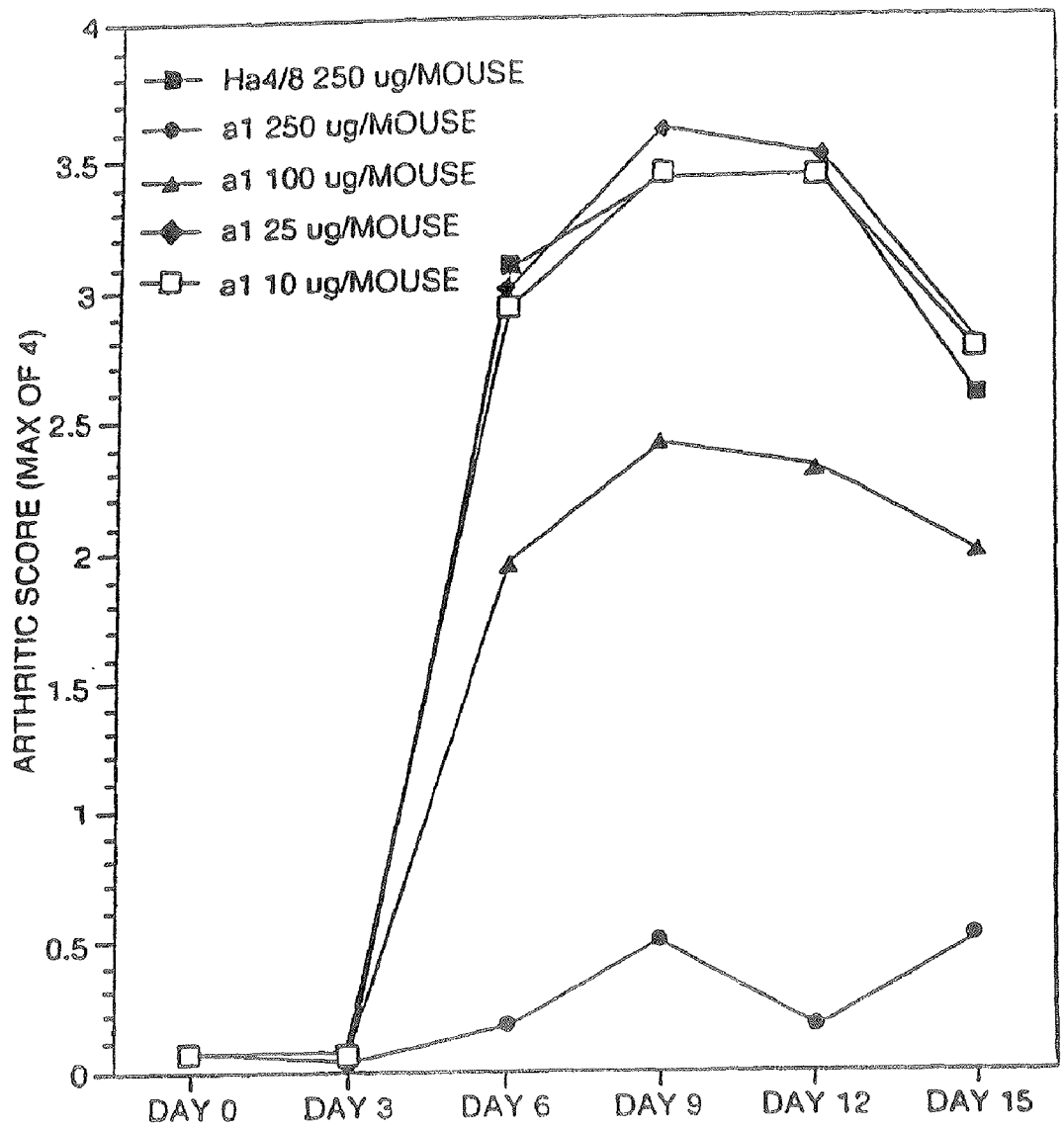
FIG. 9. Dose response of anti-α1 mAb inhibition of arthritis. Wild-type Balb/c mice were treated with anti-collagen mAbs at day 0, followed by LPS on day 3. Arthritis was apparent by day 6 and continued for several weeks. Mice were treated i.p. with the indicated dose of either Ha4/8 (isotype control) or Ha31/8 (anti-al) mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Dose response of anti-α1 mAb inhibition of arthritis. Given the striking effects of anti-α1 mAb treatment on preventing arthritis, we extended these studies to include a dose response analysis (FIG. 9). Different doses of mAb were administered i.p. every $3^{rd}$ day starting at day 0. In agreement with earlier data, a 250 ug dose of anti-α1 mAb resulted in near complete prevention of arthritis. A lower dose of 100 ug of anti-α1 mAb was partially effective at preventing arthritis in this model, while lower doses did not have any discernable effect on arthritic score (FIG. 9).

Example 13

Figure 10:
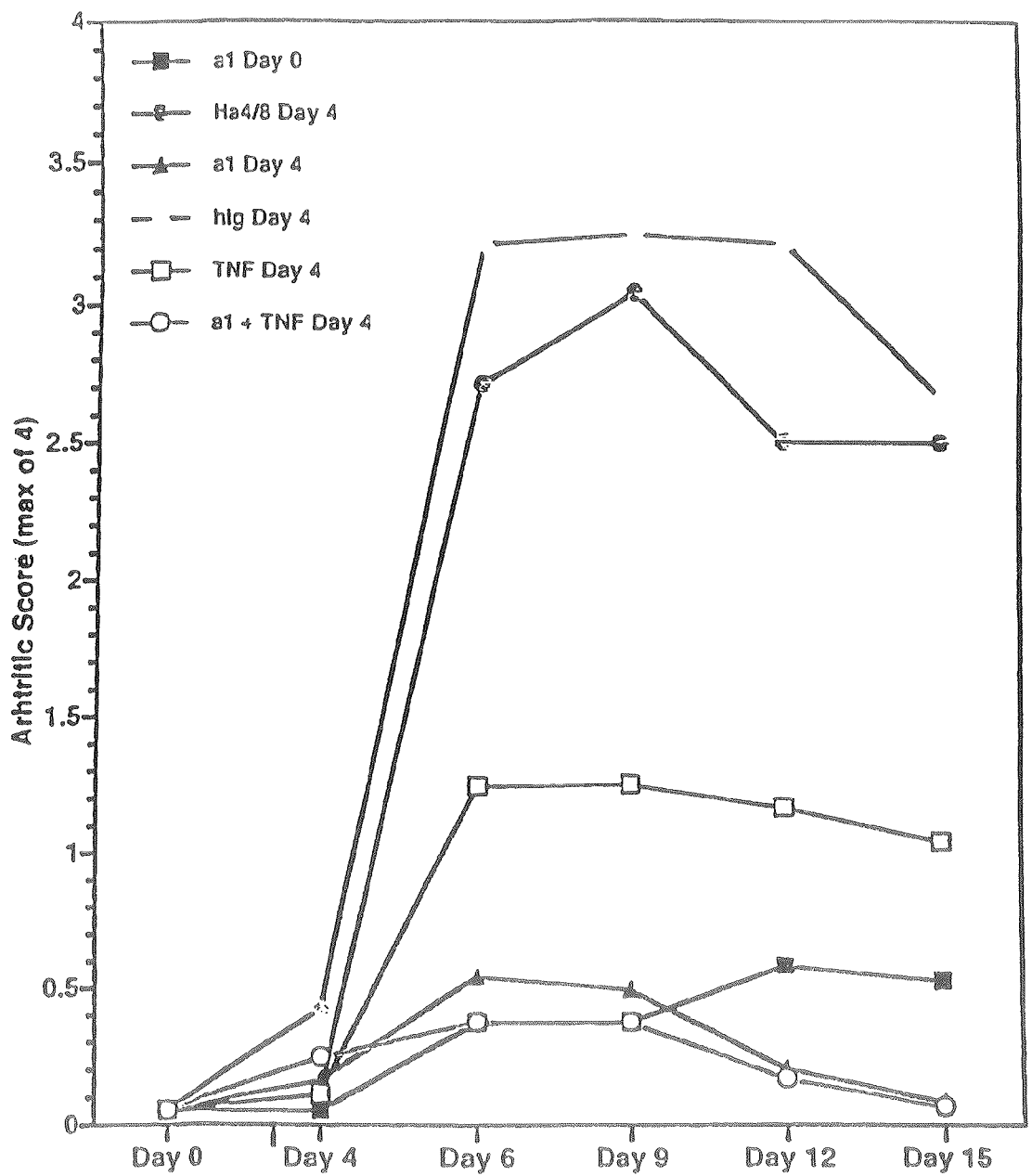
FIG. 10. Therapeutic treatment with anti-α1 mAb can decrease arthritic score. Wild-type Balb/c mice were treated with anti-collagen mAbs at day 0, followed by LPS on day 3.

Therapeutic treatment with anti-α1 mAb can decrease arthritic score. Given the effectiveness of anti-α1 mAb in preventing arthritis, we attempted to treat mice that are on their way to develop disease. Arthritis was induced in mice by injection of a cocktail of anti-collagen type II mAbs on day 0, followed by LPS administration on day 3. Mice were then treated with either anti-α1 mAb or a soluble TNF receptor Ig fusion protein starting on day 4. Progression of arthritis was completely blocked in mice receiving anti-α1 mAb starting at day 4, when compared to mice receiving control hamster mAb starting at day 4 (FIG. 10). The degree of inhibition seen with therapeutic administration of anti-α1 mAb was complete and was equal to that seen with preventative treatment of anti-α1 mAb (started at day 0) (FIG. 10). In comparison, treatment with TN receptor Ig fusion protein from day 4 onwards resulted in only a 60-70% inhibition in arthritic score when compared to control Ig fusion protein (FIG. 10). Combined treatment of anti-α1 mAb and TNF receptor Ig fusion together was effective at completely inhibiting arthritic score, which is not surprising given the complete effectiveness of anti-α1 mAb treatment alone in suppressing arthritis. In summary, these results indicate that therapeutic treatment with anti-α1 mAb is effective at inhibiting arthritic score, and compares favorably to therapeutic treatment with a TNF antagonist.

Example 14

Cloning and mutagenesis of the α1-I domain. Human and rat α1β1 integrin I domain sequences were amplified from full length cDNAs (Kem, et al., 1994, J. Biol. Chem. 269, 22811-22816; Ignatius et al., 1990, J. Cell Biol. 111, 709-720) by the polymerase chain reaction (PCR) (PCR CORE Kit; Boehringer Mannheim, GmbH Germany), using either human specific primers, 5'-CAGGATCCGTCAGCCCCA-CATTTCAA-3' [forward] (SEQ ED NO:7), and 5'-TCCTC-GAGGGCTTGCAGGGCAAATAT-3' [reverse] (SEQ ID NO:8), or rat specific primers, 5'-CAGGATCCGTCAGTC-CTACATTTCAA-3' [forward] (SEQ ID NO:9), and 5'-TC-CTCGAGCGCTTCCAAAGCGAATAT-3' [reverse] (SEQ ID NO:10).

The resulting PCR amplified products were purified, ligated into pGEX4t-i (Pharmacia), and transformed into competent DH5α cells (Life Technologies). Ampicillin resistant colonies were screened for the expression of the .about.45 kDa glutathione S-transferase-I domain fusion protein. The sequences from inserts of plasmid DNA of clones that were selected for further characterization were confirmed by DNA sequencing.

A rat/human chimeric α1-I domain (RΔH) was generated (MORPH Mutagenesis kit; 5 prime-3 prime), exchanging the rat residues G91, R92, Q93, and L96 (FIG. 11) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 12.

Example 15

Generation of mAbs specific to the α1-I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996) Structure 4, 931-942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 .μg of purified human α1β1 (Edwards et al., 1995, J. Biol. Chem. 270, 12635-12640; Gotwals et al., 1999, Biochemistry 38:8280-8) emulsified with complete Freund's adjuvant (LifeTechnologies). They were boosted three times i.p. with 25 .μg of α1β1 emulsified with incomplete Freund's adjuvant (LifeTechnologies). The mouse with the highest anti-α1-I domain titer was boosted i.p. with 100 μg of α1β1 three days prior to fusion, and intravenously with 50 μg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the D subunit. Subsequently, $3-5\times10^4$ K562 cells transfected with the α1 integrin subunit (K562-α1) suspended in FACS buffer (1% fetal calf serum (FCS) in PBS containing 0.5% $NaN_3$) were incubated with supernatant for 45 minutes at 4° C., washed and incubated with antis mouse IgG conjugated to phycoerythrin. After washing twice with FACS buffer, cells were analyzed in a Becton Dickinson Flow Cytometer.

Supernatants from the resulting hybridomas were screened for binding to the α1-I domain. Briefly, 50 μl of 30 μg/ml human α1-I-domain-(GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (pNPP) in 0.1 M glycine, 1 mM $ZnCl_2$, and 1 mM $MgCl_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7'(bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 mM $MgCl_2$ at a final concentration of $1 \times 10^6$ cells/mL. 50 µl of supernatant was incubated with an equal volume of $2 \times 10^5$ K562-α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

Figure 16A:
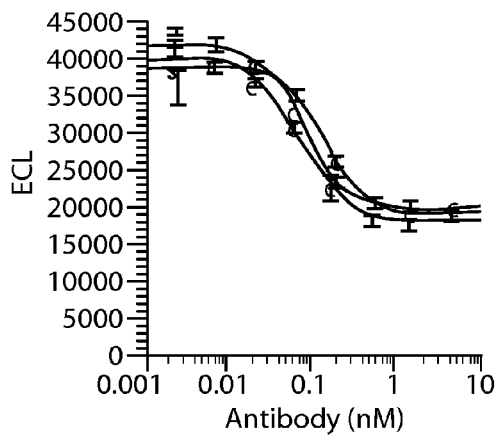
Figure 16B:
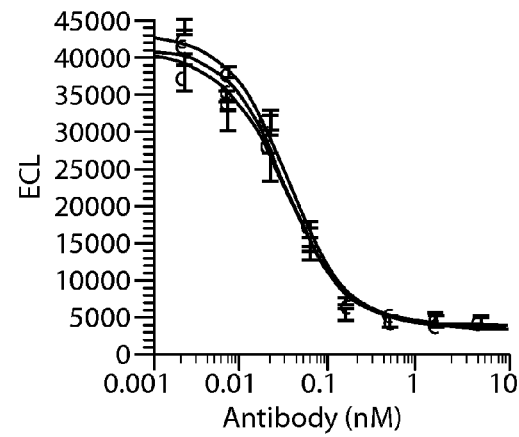
Figure 16C:
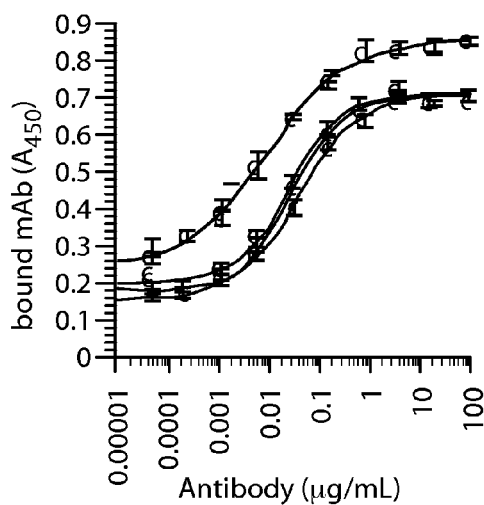
Figure 16D:
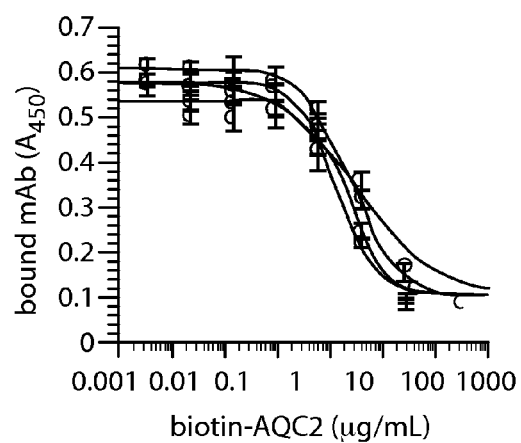

We initially identified 19 hybridomas, the supernatants of which bound to human leukemia K562 cells expressing the α1β1 integrin (K562-α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGC5, AQC2 and AJH10 bind the α1-I domain (FIG. 13A, data not shown for BGC5), only mAbs AJH10 and AQC2 inhibit α1-I domain-dependent (FIG. 13B; FIG. 16B) or K562-α1 (FIG. 13C; FIG. 16C) adhesion to collagen IV.

Sequencing of the Complementarity Determining Regions. To establish the clonal origin of this panel of mAbs, we amplified by PCR and sequenced the CDRs from 12 of the 19 antibodies (data not shown).

2 µg of mRNA, isolated from $10^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al., 1993, Cell 72:857-867); light chain, VK4FOR, which defines four separate oligos (Kern et al., 1994, J. Biol. Chem. 269:22811-22816). For each hybridoma, heavy and light chains were amplified in four separate PCR reactions using various combination of the following oligos: 1) Heavy chain: VH1FR1K (Kamata et al., 1995, J. of Biol. Chem. 270:12531-12535), VH1BACK, VH1BACK (Baldwin et al. (1998) Structure 6, 923-935), $V_H$fr1a, $V_H$fr1b, $V_H$fr1e, $V_H$fr1f, $V_H$fr1g (Ignatius et al. (1990) J. Cell Biol. 111, 709-720), or VH1FOR-2 (Michishita, M., Videm, V., and Arnaout, M. A. (1993) Cell 72, 857-867); 2) Light chain: VK1BACK (Baldwin et al. (1998) Structure 6, 923-935), VK4FOR, VK2BACK oligos (Kern et al. (1994) J. Biol. Chem. 269, 22811-22816), or $V_K$fr1a, $V_H$fr1c, $V_H$fr1e, $V_H$fr1f (Ignatius et al. (1990) J. Cell Biol. 111, 709-720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 16

Immunoblotting and FACS Analysis. Sequences of the variable regions of the non-blocking antibodies were markedly different from the clonally related family of sequences found for the blocking antibodies. As the blocking antibodies appear to originate from a single clone, we chose two (AJH10 and AQC2) to characterize further.

Immunoblotting. The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl fluoride (PMSF), 20 µg/ml aprotinin, 10 µg/ml leupeptin, 10 mM ethylenediaminetetraacetic acid (EDTA). Samples were subjected to 4-20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% $NaN_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Immunoblotting and FACS analysis (FIG. 14) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 17

Binding of the α1-I Domain to Collagen is Divalent Cation-Dependent

A. Purification of the α1-I Domains.

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) Structure 3, 1333-1340, 871 Da) by electrospray ionization-mass spectrometry (ESI-MS), migrated as a single band by SDS-PAGE, and the protein eluted as a single peak of appropriate size by size exclusion chromatography on a Superose 6 FPLC column (Pharmacia).

B. Functional Analysis 96 well plates were coated overnight at 4° C. with 1 µg/ml collagen IV (Sigma) or collagen Type I (Collaborative Biomedical), washed with Triton buffer (0.1% Triton X-100; 1 mM $MnCl_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM MnCl.sub.2 and 3% BSA were incubated on the coated plates at room temperature for 1 hour, and washed in Triton buffer. Bound α1-I domain was detected with serial additions of 10 µg/ml biotinylated anti-GST polyclonal antibody (Pharmacia); ExtrAvidin-horseradish peroxidase (Sigma) diluted 1:3000 in TBS containing 1 mM $MnCl_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results.

Figure 15A:
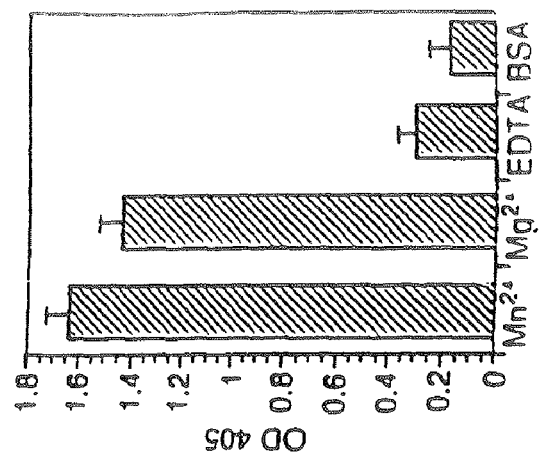
Figure 15B:
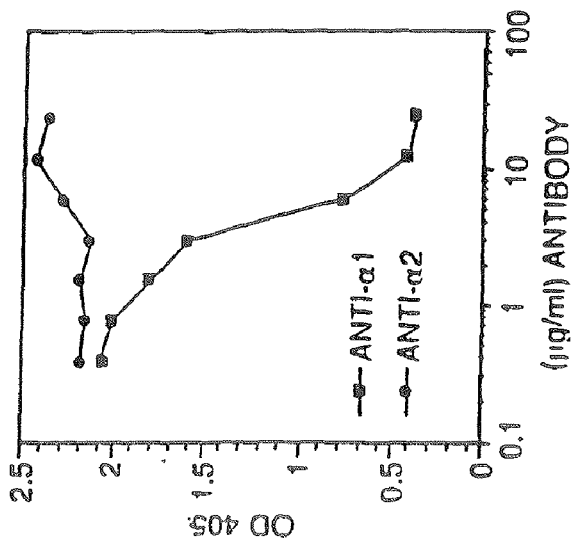
Figure 15C:
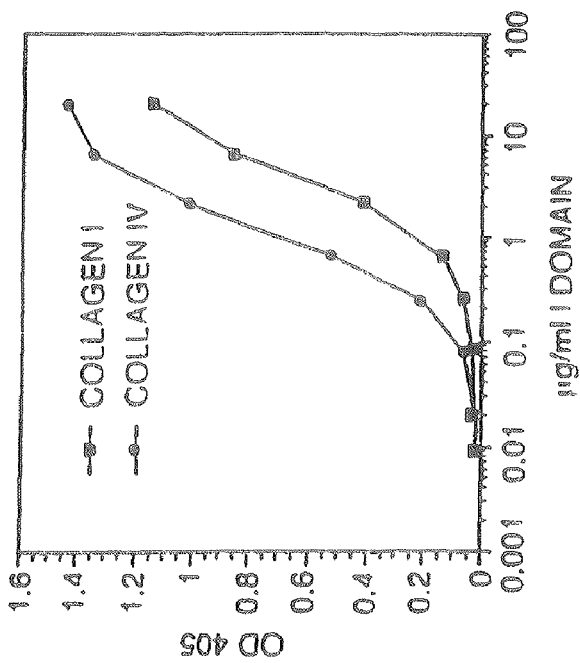

The human and rat (95% identity to human) α1-I domains were expressed in *E. coli* as GST-fusion proteins and purified over glutathione sepharose. Both proteins were examined for binding to collagen I and IV using a variation of an ELISA-based assay previously described (Qu, A., and Leahy, D. J. (1995) Proc. Natl. Acad. Sci. USA 92, 10277-10281). The human α1-I domain binds collagen IV with better efficiency than collagen I (FIG. 15A). An antibody specific to the α1-I domain, but not an antibody specific to the α2-I domain (FIG. 15B) abrogated binding to both ligands (data for collagen I is not shown). Both $Mn^{2+}$ and $Mg^{2+}$ stimulated binding, and EDTA reduced binding to background levels (FIG. 15C). No measurable differences in ligand binding were detected between the human and rat α1-I domains suggesting that the sequence differences between species are not functionally relevant (data not shown). Thus, the α1-I domain, specifically, require cation for efficient ligand binding.

Example 18

Figures 11A, 11B:
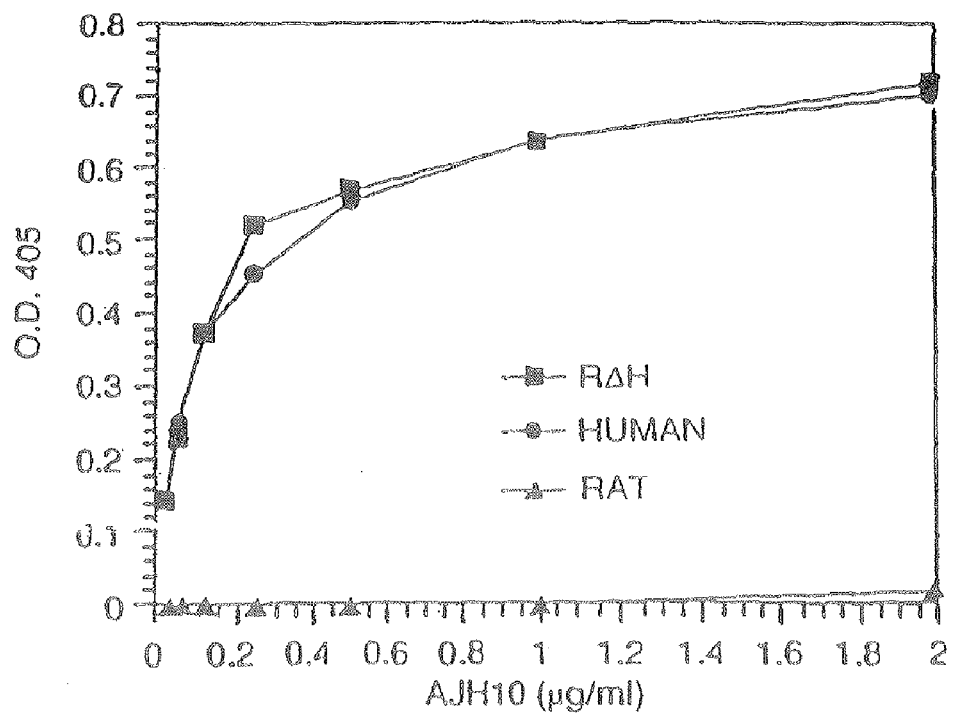

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 92-97, FIG. 11A) adjacent to the critical threonine (FIG. 11A, aa 98) within the MIDAS motif. To test the hypothesis that the 6 amino acid residues, Val-Gln-Arg-Gly-Gly-Arg (residues 91-96 of SEQ ID NO:64), comprise the epitope for the blocking mAbs, we constructed a chimeric I domain (RΔH), exchanging the rat residues G91, R92, Q93, and L96, for the corresponding human residues, V, Q, R, and R, respectively. AJH10, along with all the function-blocking mAbs, recognizes the chimeric I domain (RΔH; FIG. 11B).

To orient these residues with respect to the MIDAS domain in the tertiary structure of the α1-I domain, we modeled the α1-I domain using the coordinates of the crystal structure of the α2 I domain.

A homology model of the human α2 I-domain was built using the X ray crystal structure of the human α2 I-domain (Ward et al. (1989) Nature 341, 544-546). The model was built using the homology modeling module of Insight II (version 2.3.5; Biosym Technologies). The program CHARMM (Clackson et al. (1991) Nature 352, 624-628) was used with the all-hydrogen parameter set 22 with a distant dependent dielectric constant of two times the atom separation distance. We first did 1000 steps of steepest descent minimization with mass-weighted harmonic positional constraints of 1 kcal/(mol $Å^2$) on all atoms of the α1-I domain. This minimization was followed by another 1000 steps of steepest descent and 5000 steps of Adopted-Basis Newton Raphson with constraints of 0.1 kcal/(mol $Å^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 11A) hydrogen bonds with the carbonyl group of I33, the residue adjacent to S32. Thus, the loop that contains the epitope may play a functional role in stabilizing the MIDAS region.

Example 19

Monoclonal antibody AQC2 (i.e., mAQC2; "m" for murine) (Example 15, supra) is an $IgG_1$, kappa antibody. To identify the nucleotide sequences encoding the heavy and light chains of this antibody, total cellular RNA from AQC2 murine hybridoma cells was obtained by using a QIAGEN RNEASY midi kit in accordance with the manufacturer's instructions. Then cDNAs encoding the variable regions of the heavy and light chains were cloned by RT-PCR from total cellular RNA using a GIBCO BRL SUPERSCRIPT Preamplification System for First Strand cDNA Synthesis following the manufacturer's recommended protocol. Random hexamers were used for priming.

The heavy chain variable domain of mAQC2 was amplified by PCR from the first strand cDNA with the primers: 5' TGA GGA GAC GGT GAC CGT GGC CCT TGG CCC C 3' (SEQ ID NO:11) and 5' AGG TSM ARC TGC AGS AGT CWG G 3' (S=C/G, M=A/C, R=A/G, and W=A/T) (SEQ ID NO:12). The PCR was subjected to 30 cycles using Clontech's Advantage Taq polymerase: denature 30 sec at 94° C., anneal 1 min at 50° C., and elongate 1.5 min at 68° C. The mAQC2 light chain with its signal sequence was amplified by PCR using the primers: 5' ACT AGT CGA CAT GGA TTT WCA GGT GCA GAT TWT CAG CTT C 3' (W=A/T) (SEQ ID NO:13) and 5' ACT GGA TGG TGG GAA GAT GGA 3' (SEQ ID NO:14). The PCR was subjected to 30 cycles using Stratagene's cloned Pfu polymerase: denature 1 min at 94° C., anneal 1 min at 50° C., and elongate 2 min at 72° C. The PCR products for the heavy and light chains were gel-purified using a QIAGEN QIAQUICK gel extraction kit following the manufacturer's recommended protocol.

Purified heavy chain product was subcloned into Invitrogen's pCR2.1-TOPO TA vector using its TOPO TA cloning kit. Purified light chain was subcloned into Invitrogen's pCR-bluntIITOPO vector using its Zero blunt TOPO cloning kit following the manufacturer's recommended protocol. Inserts from multiple independent subclones were sequenced. With the exception of degenerate positions within the PCR primers, the insert sequences of the independent subclones were identical.

The polypeptide sequences of mAQC2 were deduced from their coding sequences. The N-terminal amino acid sequence for the mature light chain predicted by the cDNA sequence from the PCR product amplified with a signal sequence exactly matched the N-terminal sequence of purified mAQC2 light chain derived from Edman degradation (DVKVVESGG; SEQ ID NO:15). BLAST analyses of the variable domain sequences confirmed their immunoglobulin identity.

The polypeptide sequence of the light chain variable domain of mAQC2 is shown below:

```
                                                    (SEQ ID NO: 1)
  1 QIVLTQFPAL MSASPGEKVT MTCSASSSVN HMFWYQQKPK

41 SSPKPWIYLT SNLASGVPAR FSGSGSGTSY SLTISSMEAE

81 DAATYYCQQW SGNPWTFGGG TKLEIK 106
```

The CDRs are shown in boldface. The CDRs are defined according to Kabat et al., Sequences of Proteins of Immunological Interest, 5th Edition, The United States Department of Health and Human Services, The United States Government Printing Office, 1991. Using the Kabat numbering system, SEQ ID NO:1 is represented as follows, where a dash denotes the absence of an amino acid:

```
  1  QIVLTQFPAL MSASPGEKVT MTCSASS-SV NHMFWYQQKP
 41  KSSPKPWIYL TSNLASGVPA RFSGSGSGTS YSLTISSMEA
 81  EDAATYYCQQ WSGNPWTFGG GTKLEIK 107
```

The polypeptide sequence of the heavy chain variable domain of mAQC2 is:

```
                                                 (SEQ ID NO: 2)
  1  DVKVVESGGG LVKPGGSLKL ACAASGFSFS RYTMSWVRQI
 41  PEKRLEWVAT ISGGGHTYYL DSVKGRFTIS RDNAKNTLYL
 81  QMSSLRSEDT AMYYCTRGFG DGGYFDVWGQ GTTVTVSS
```

The CDRs are shown in boldface. Using the Kabat numbering system, SEQ ID NO:2 is represented as follows, where positions numbers are consecutive numerals unless otherwise indicated:

```
  1      DVKVVESGGG LVKPGGSLKL ACAASGFSFS RYTMSWVRQI
 41      PEKRLEWVAT ISGGGHTYYL DSVKGRFTIS RDNAKNTLYL
 81      QM
 82a-c   SSL
 83      RSEDTAMY YCTRGFGDGG
100a-b   YF
101      DVWGQGTTVT VSS 113
```

As used herein, residue position numbers of variable domains are designated in accordance with the Kabat numbering system unless otherwise indicated.

Example 20

This example describes the generation of a murine-human chimeric antibody, chAQC2.

The cDNAs encoding the variable regions of the mAQC2 heavy and light chains were used to construct chAQC2 expression vectors, in which the mAQC2 variable regions were linked to human IgG$_1$ and kappa constant regions.

The heavy chain chimera was constructed as follows. A 0.33 kb PstI-BstEII fragment from the mAQC2 heavy chain plasmid pAND083 was subcloned into the phosphatased 2.82 kb PstI-BstEII vector fragment from the 5a8 heavy chain plasmid pLCB7, so as to add a murine heavy chain signal-encoding sequence and a murine splice donor site to the cDNA of the mAQC2 heavy chain variable region. 5a8 is a molecularly cloned CD4-specific mAb (see, e.g., Boon et al., 2002, Toxicology 172:191-203). In the mature heavy chain encoded by the resultant plasmid (pAND092), the N-terminus differed by five residues from the N-terminus (DVKVVE; SEQ ID NO:16) of the cognate mAQC2 heavy chain.

To correct the heavy chain N-terminus, pAND092 was subjected to unique site elimination (USE) mutagenesis using an USE mutagenesis kit (Amersham Pharmacia Biotech) following the manufacturer's recommended protocol. The Q1D, Q3K, L4V, Q5V, Q6E substitutions were encoded by the mutagenic primer 5' GCA CCA GGT GCC CAC TCC GAC GTC AAG GTG GTG GAG TCA GGG GGA GGC TTA GTG 3' (SEQ ID NO:17). Mutated plasmid clones were identified by their new AatII and HinfI sites and eliminated PstI site. The heavy chain coding sequence was then confirmed by DNA sequencing. The correctly mutated plasmid was called pAND094. The 0.43 kb NotI-HindIII fragment from pAND094 and the 1.21 kb HindIII-NotI fragment from the plasmid pEAG964 (containing a coding sequence for a human IgG$_1$ constant region) were subcloned into the NotI site of pCH269, a plasmid derived from the pCEP4 EBV expression vector (Invitrogen). The resultant plasmid was named pAND099.

The light chain chimera was generated as follows. A 0.46 kb EcoRI fragment from the mAQC2 light chain variable domain plasmid pAND081 was subcloned into the phosphatased 2.7 kb vector fragment of the pUC-derived pNN09 cloning vector, to add a 5' NotI site. The resulting plasmid, pAND091, was subjected to mutagenesis using the Amersham USE kit (supra) to introduce a BglII site at the 3' end of the coding sequence. The mutagenic primer had the sequence 5' GGA GGC ACC AAG CTG GAG ATC TAA CGG GCT GAT GCT GC 3' (SEQ TD NO: 18). The correctly mutated plasmid was identified by its BglII and BstYI site changes. The light chain coding sequence in the resultant plasmid pAND093 was confirmed by DNA sequencing. Then the 0.44 kb NotI-BglII light chain variable domain fragment from pAND093 and the 0.68 kb BclI-NotI fragment from the plasmid pEAG963 (containing a coding sequence for a human kappa light chain constant domain) were subcloned into the NotI site of pCH269 (supra), producing plasmid pAND102. To create an unblocked kappa light chain (Q1E), pAND093 was subjected to USE mutagenesis with the mutagenic primer 5' CAT MT GTC CAG GGG AGA AAT TGT TCT CAC CCA G 3' (SEQ ID NO:19), to introduce an XmnI site. The mutated plasmid was identified by screening for an XmnI site change. The light chain sequence in the resultant plasmid pAND097 was confirmed by DNA sequencing. The 0.44 kb NotI-BglII light chain variable domain fragment from pAND097 and the 0.68 kb BclI-NotI fragment from the plasmid pEAG963 (containing a human kappa light chain constant domain) were subcloned into the NotI site of pCH269, producing plasmid pAND098.

To generate chAQC2 antibodies, expression vectors (chAQC2 heavy chain vector pAND099-I chAQC2 light chain vector pAND102, and chAQC2 heavy chain vector pAND099+chAQC2 unblocked light chain vector pAND098) were co-transfected into 293-EBNA cells. The transfectants were tested for antibody secretion and specificity. The controls were cells transfected with the corresponding vectors without an insert or with DNA constructs encoding ch5c8 (a molecularly cloned CD154-specific mAb described in, e.g., Elster et al., 2001, Transplantation 72:1473-1478) or chCBE11 (a molecularly cloned LTβR-specific mAb described in, e.g., Browning et al., 1996, J. Biol. Chem. 271:24934-24938).

Then transfectants with the desired antibody secretion were lysed, and protein A immunoprecipitation was performed on the lysates and conditioned medium. Western blot analysis of the precipitates performed with anti-human heavy and light chain antibodies indicated that chAQC2-transfected cells synthesized and efficiently secreted heavy and light chains at levels similar to ch5c8-transfected and chCBE11-transfected cells. Further, huVLA-1-expressing K562α1 cells were stained with the conditioned medium from the transfected cells, and FACS analysis was performed on the stained cells. The results indicated that the chAQC2 antibody produced staining patterns similar to those of mAQC2, while conditioned media from mock-transfected and ch5c8-transfected cells failed to stain K562α1 cells. Chimeric AQC2 produced from scaled-up transient transfection was purified and shown to bind to VLA-1 by FACS titration. Chimeric AQC2 with either a wildtype or a genetically unblocked light chain bound to VLA-1. See also FIGS. 16A-D (discussed below).

Example 21

This example describes a method of humanizing the mAQC2 monoclonal antibody.

Analysis of the mAQC2 variable domains. The variable domains in the light and heavy chains of mAQC2 were compared with the consensus sequences for mouse and human subgroups (Kabat et al, supra) using the software program FASTA. The light chain variable domain was found to be a member of mouse subgroup VI with 89% identity in a 109 amino acid overlap. This domain also corresponded to human subgroup I with 72% identity in a 113 amino acid overlap. The heavy chain variable domain was found to be a member of mouse subgroup IIId with 86% identity in a 129 amino acid overlap. This heavy chain variable domain also corresponded to human subgroup III with 79% identity in a 130 amino acid overlap.

The CDRs were categorized into canonical classes according to Chothia et al., Nature 342, pp. 877-883 (1989). The key residues defining each canonical class determine to a large extent the structural conformation of the CDR loop, and thus should be retained in the reshaped antibody. The L1 loop of mAQC2 fell into canonical class 1 (10 residue loop), L2 into class 1 (7 residue loop) and L3 into class 1 (9 residue loop). The H1 loop fell into class 1 (5 residue loop) and the H2 loop into class 1 (16 residue loop) residues. The H3 loop did not seem to belong to any canonical class. The canonical residues important for these classes were all included in the humanized antibodies.

Unusual framework residues in mAQC2 were determined by analyzing all mouse and human variable chain sequences in the September 1999 version of the Kabat database. It was believed that mAQC2-specific differences might indicate somatic mutations that enhance binding affinity if these differences were close to the binding site. Unusual mAQC2 residues further away from the binding site and unusual human framework residues were removed in case they would create immunogenic epitopes in the humanized antibody. Unusual framework residues found in mAQC2 were 7(F), 10(L), and 41(K) in the light chain; and 4(V), 21(A), and 40(I) in the heavy chain. None of these unusual mouse framework residues were retained the humanized antibodies.

Modeling the structure of the variable regions. The light and heavy chains of mAQC2 were aligned against a nonredundant database to determine which structural frames to use to construct three-dimensional models of the mAQC2 light and heavy chains. Using FASTA, the light chain was found to have 82% sequence identity to monoclonal murine antibody ab57 (1CLOL), whereas the heavy chain was found to have 76% sequence identity to murine 6d9 Fab fragment (1HYY). Using the molecular modeling software package SYBYL (Tripos Inc.), the approximate three dimensional structures of the mAQC2 light and heavy chains were built using the light chain of ab57 and the heavy chain of 6d9, respectively. The structural integrity of the models was assessed at the console and was found to be reasonable.

Design of the reshaped variable regions. Two approaches were used to choose human acceptor frameworks to "accept" mAQC2's CDRs. The first approach was by homology matching and the other by using consensus human Ig sequences. Under the homology approach, the Kabat database, the nonredundant database from NCBI, ENTREZ (The National Institutes of Health), and the Incyte database were searched using the software programs FASTA and BLAST. The choice of human acceptor frameworks was made based on sequence identity between mAQC2 frameworks and human frameworks (excluding frameworks from previously humanized antibodies) and the source of the antibody.

The frameworks from an immunoglobulin variable region gene having a GENBANK accession number of gi:587330 (human kappa subgroup I Vκ-1c147) were eventually chosen for the light chain of the humanized antibody (Welschof et al., J. Immunol. Meth. 179:203-14 (1995)). The frameworks from Amulc11 (Kabat E D 044469; human subgroup III) were chosen for the heavy chain of the humanized antibody (Huang et al., J. Immunol. 151:5290-300 (1993)).

Back mutations of the human frameworks. Strategies for determining which back mutations to make are available on the Humanization by Design web sites under mirrored urls on the worldwide web at mathbio.nimr.mrc.ac.uk/jsaldan and cryst.bbk.ac.uk/~ubcg07s. Previous experiments have shown that it is important to retain canonical residues, interface packing residues and unusual murine residues that are close to the binding site. In addition, residues in the "Vernier Zone," which forms a platform on which the CDRs rest (Foote et al., J. Mol. Biol. 224, p. 487 (1992)) and those close to CDR H3 should be considered.

Four reshaped versions were designed for each of the variable light and heavy chains, as shown in Table 1. Two of the four versions for each chain were designed by homology matching (designated huAQC2-h1 and -h2) and the other two versions by consensus matching (huAQC2-c1 and c2). It should be noted that the sequences for huAQC-h1 heavy chain and huAQC-c1 heavy chain are identical.

TABLE 1

Sequences of mAQC2, huAQC2, and human frameworks

LIGHT CHAIN

|  | FR1 |
|---|---|
| Vk-1c147 | D--M--S-SSL---V-DR--I--* |
| huAQC2-h2 | ------S-SSL---V-DR--I-- |
| huAQC2-h1 | ------S-SSL---V-DR--I-- |
| mAQC2 | QIVLTQFPALMSASPGEKVTMTC |
| huAQC2-c1 | --Q---S-SSL---V-DR--I-- |
| huAQC2-c2 | --Q---S-SSL---V-DR--I-- |

TABLE 1-continued

Sequences of mAQC2, huAQC2, and human frameworks

```
              CDR1              FR2
Vk-1c147      R---Q-ISYLN       ------GKA--LL-- huAQC2-h2     ----------------  ------GKA--LL-- huAQC2-h1     ----------------  ------GKA-------- mAQC2         SASSSVNHMF        WYQQKPKSSPKPWIY huAQC2-c1     ----------------  ------GKA-------- huAQC2-c2     ----------------  ------GKA--LL--

CDR2      FR3
Vk-1c147      AA-S-Q-   ---S---------DFT-----LQP--F----- huAQC2-h2     -------   ---S---------D-T-----LQP--F----- huAQC2-h1     -------   ---S---------D-T-----LQP--F----- mAQC2         LTSNLAS   GVPARFSGSGSGTSYSLTISSMEAEDAATYYC huAQC2-c1     -------   ---S---------D-T-----LQP--F----- huAQC2-c2     -------   ---S---------D-T-----LQP--F-----

CDR3       FR4           Framework Changes
Vk-1c147      --SYST-L-  ------V---    25 huAQC2-h2     -------    ------V---    21 huAQC2-h1     -------    ------V---    19 mAQC2         QQWSGNPWT  FGGGTKLEIK**  0 huAQC2-c1     -------    --Q---V---    21 huAQC2-c2     -------    --Q---V---    23
```

SEQ ID NOs: 65, 51, 49, 1, 66, and 54, respectively,
in order of appearance.

HEAVY CHAIN:

```
              FR1                               CDR1
AMU1C11       E-QL--------IQ-----R-S------TV-   SNY-- huAQC2-h2     E-QL--------IQ-----R-S------T--   ----- huAQC2-h1     ---QL--------Q-----R-S----------  ----- mAQC2         DVKVVESGGGLVKPGGSLKLACAASGFSFS    RYTMS huAQC2-c1     ---QL--------Q-----R-S----------  ----- huAQC2-c2     E-QL--------Q-----R-S--------T--  -----

FR2              CDR2
AMU1C11       ----A-G-G----S   V-YS-S---A--------------- huAQC2-h2     ----A-G-G------  ------------------------ huAQC2-h1     ----A-G-G------  ------------------------ mAQC2         WVRQIPEKRLEWVA   TISGGGHTYYLDSVKG huAQC2-c1     ----A-G-G------  ------------------------ huAQC2-c2     ----A-G-G------  ------------------------

FR3                                   CDR3
AMU1C11       --------S---------N---A----V---AS     IRFLEWS--Y huAQC2-h2     --------S---------N---A----V---       ---------- huAQC2-h1     --------S---------N---A----V-------   ---------- mAQC2         RFTISRDNAKNTLYLQMSSLRSEDTAMYYCTR       GFGDGGYFDV
```

TABLE 1-continued

Sequences of mAQC2, huAQC2, and human frameworks

```
huAQC2-c1    --------S---------N---A----V-------  ----------------- huAQC2-c2    --------S---------N---A----V-------  -----------------

FR4                  Framework changes
  AMU1C11    -----L-----          20 huAQC2-h2  -----L-----          16 huAQC2-h1  -----L-----          13 mAQC2      WGQGTTVTVSS***        0 huAQC2-c1  -----L-----          13 huAQC2-c2  -----L-----          15
```

*Dashes indicate identity with the mAQC2 amino acid sequence.
*Part of SEQ ID NO: 1.
***Part of SEQ ID NO: 2.
SEQ ID NOs: 67, 44, 42, 2, 42 and 68, respectively, in order of appearance.

Some of the back mutations are discussed below.
(1) Light Chain:

| | |
|---|---|
| 1 D->Q | This mutation was made in all versions since previous reshaping experiments (e.g. Kolbinger et al, Protein Eng. 6, p. 971 (1993)) suggested its importance for antigen binding. |
| 4 M->L | This is a vernier residue and was retained in all versions. |
| 46 L->P | This residue is both an interfacial and vernier residue and was retained only in h1 and c1. |
| 47 L->W | This is a vernier residue and was retained only in h1 and c1. |
| 71 F>Y | This residue is in an important canonical position and was retained in all versions. |

(2) Heavy Chain:

| | |
|---|---|
| 1 E->D | This back mutation was made in h1 (i.e., c1) only. |
| 12 I->V | The residue I is unusual in human and was retained in the h2 only. |
| 28 T->S | This is a vernier residue and was retained in h1 only. |
| 29 V->F | This is a canonical residue and was retained in all versions. |
| 49 S->A | This is a vernier residue and was retained in all versions. |
| 93 A->T | This is a vernier residue and interfacial and was retained in all versions. |
| 94 S->R | This is a canonical residue and was retained in both versions. |

The huAQC2 variable regions were made by USE mutagenesis as described above, using the chAQC2 variable domain plasmids as starting templates. The human acceptor framework ("FR") cDNA sequences were Kabat #Z37334 for the light chain and Kabat #U00490 for the heavy chain. To facilitate identification of mutated plasmids, silent mutations were introduced to change restriction sites. Mutated plasmids were identified by the restriction site changes. The variable region cDNA sequences in the resultant plasmids were confirmed by DNA sequencing.

The h1 and c1 versions of heavy chain (which were identical) were made by using plasmid pAND094 as template. The mutagenic primers were: FR1 primer 5'GGT GCC CAC TCC GAC GTC CAG CTG GTC GAG TCA GGG GGA GGC TTA GTC CAC CCT GGA GGG TCC CTG AGA CTC TCC TGT GCA GCC TCT GGA TTC 3' (SEQ ID NO:20), which introduced TaqI and PvuII sites, and eliminated a DdeI site; FR2 primer 5' ATG TCT TGG GTT CGC CAG GCT CCG GGG AAG GGG CTG GAG TGG GTC GCA ACC 3' (SEQ ID NO:21), which introduced a NciI site, and eliminated BspEI and EarI sites; FR3 primer 5' TTC ACC ATC TCC AGA GAC AAT TCC AAG AAC ACC CTG TAC CTG CAG ATG AAC AGT CTG AGG GCC GAG GAC ACA GCC GTG TAT TAC TGT ACA AGA 3' (SEQ ID NO:22), which introduced PstI and DdeI sites; and FR4 primer 5' TGG GGC CAA GGT ACC CTG GTC ACC GTC TCC TCA GGT GAG 3' (SEQ ID NO:23), which introduced KpnI and Eco0109I sites. The resultant h1 (i.e., c1) heavy chain plasmid was designated pAND104.

The c2 version of heavy chain were made by using pAND104 as template with the following mutagenic primers: FR1 primer 5' TCC TGT GCA GCC TCT GGA TTC ACC TTC AGT AGG TAT ACT ATG TCT TGG GTT 3' (SEQ ID NO:24), which introduced an AccI site; and FR1 primer 5' GCA CCA GGT GCG CAC TCC GAG GTC CAG CTG GTC GAG TCA 3' (SEQ ID NO:25), which introduced an FspI site and eliminated an AatII site. The resultant c2 heavy chain plasmid was designated pAND115.

The h2 version of heavy chain were made by using pAND115 as template with the following primer: FR1 primer 5' GAG TCA GGG GGA GGC TTA ATC CAG CCT GGA GGG TCC CTG 3' (SEQ ID NO:26), which eliminated a DdeI site. The resultant h2 heavy chain plasmid was designated pAND113.

To generate expression vectors for the huAQC2 heavy chains, the 0.43 kb NotI-HindIII heavy chain variable domain fragment from pAND104, pAND115, or pAND113, and the 1.21 kb HindIII-NotI fragment from pEAG964 (supra) were subcloned into the NotI site of pCH269 (supra). The resultant heavy chain expression plasmids were designated pAND114 (h1), pAND121 (c2), and pAND124 (h2), respectively.

The h1 version of light chain were made by using plasmid pAND093 as template. The mutagenic primers were: FR1 primer 5' CAA ATT GTT CTC ACC CAG TCT CCA TCC TCC CTG TCT GCG TCT GTA GGG GAC AGA GTC ACC ATC ACA TGC AGT GCC AGC TCA 3' (SEQ ID NO:27), which removed BstEII and PstI sites; FW primer 5' TTC TGG TAT CAG CAG AAG CCC GGG AAA GCC CCC AAA CCC TGG ATT 3' (SEQ ID NO:28), which introduced an NciI site; FR3 primer 5 GCT TCT GGA GTC CCT TCA CGC TTC AGT GGC AGT GGG TCT GGG ACA GAT TAC ACT CTC ACA ATC AGC AGC CTG CAA CCT GAA GAT TTT GCC ACT TAT TAC TGC CAG 3' (SEQ ID NO:29), which introduced a DdeI site and eliminated Eco0109I and AvaII sites; and FR4 primer 5S GGT GGA GGC ACT AAG GTG GAG ATC TAA CGG GCT 3' (SEQ ID NO:30), which introduced DdeI and StyI sites. The resultant h1 light chain plasmid was designated pAND103.

The h2 version of light chain were made by using pAND103 as template with the following primer: FR2 primer 5' CCC GGG AAA GCG CCC AAA CTC CTG ATT TAT CTC ACA TCC 3' (SEQ ID NO:31), which introduced HhaI and HaeII sites. The resultant h2 light chain plasmid was designated pAND116.

The c1 version of light chain used plasmid pAND103 template with the following primers: FR1 primer 5' GCC TCA GTC ATA ATG TCC CGG GGA CAA ATT CAG CTC ACC CAG TCT CCA TCC 3' (SEQ ID NO:32), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:33), which introduced a Bsp1286I site. The resultant c1 light chain plasmid was designated pAND118.

The c2 version of light chain were made by using plasmid pAND116 template with the following primers: FR1 primer 5' GCC TCA GTC ATA ATG TCC CGG GGA CAA ATT CAG CTC ACC CAG TCT CCA TCC 3' (SEQ ID NO:34), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:35), which introduced a Bsp1286I site. The resultant c2 light chain plasmid was designated pAND119.

To generate expression vectors for the huAQC2 light chains, the 0.44 kb NotI-BglII light chain variable domain fragment from pAND103, pAND116, pAND118, or pAND119, and the 0.68 kb BclI-NotI fragment from pEAG963 (supra) were subcloned into the NotI site of pCH269 (supra). The resultant light chain expression vectors were designated pAND117 (h1), pAND120 (h2), pAND122 (c1), and pAND123 (c2), respectively.

The expression vectors were co-transfected into 293-EBNA cells, and transfected cells were tested for antibody secretion and specificity. Cells transfected with an empty vector served as negative control. The whole cell lysates and the conditioned medium were immuno-precipitated with protein A. Western blot analysis of the precipitates (developed with anti-human heavy and light chain antibodies) indicated that huAQC2-transfected cells synthesized and efficiently secreted heavy and light chains at levels similar to chAQC2-transfected cells.

FACS analysis of VLA-1 expressing K 562α1 cells stained with conditioned medium from the transfected cells was then performed. To do so, the K562α1 cells were incubated with the conditioned medium on ice for 120 min. The cells were then washed three times with a FACS buffer (PBS with 5% FBS and 0.05% sodium azide). The washed cells were resuspended in the buffer and incubated with PE-conjugated anti-human IgG (H+L) (Jackson ImmunoResearch Laboratories, Inc.) on ice for 30 min on ice. After the incubation, the cells were washed three times with the FACS buffer, and resuspended in the FACS buffer for analysis. The data are shown in Table 2, in which HuAQC2-h1 refers to an mAb consisting of the h1 version of the huAQC2 heavy chain (HC) and the h1 version of the huAQC2 light chain (LC) (see Table 1). Likewise, huAQC2-h2 is an mAb consisting of the h2 versions of the heavy and light chains, huAQC2-c1 the c1 versions, and huAQC2-c2 the c2 versions. In the table, relative MFI refers to mean MFI normalized to that observed for chAQC2 blocked. Data shown represents the average from two independent transfections. These data indicated that the huAQC2-h2 and -c2 mAbs bound less well than huAQC2-h1 and -c1 relative to chAQC2.

TABLE 2

FACS staining of K562α1 cells by chAQC2 and huAQC2

| | Light chain | Heavy chain | Relative MFI |
|---|---|---|---|
| chAQC2 | pAND102 | pAND099 | 1.00 |
| huAQC2-h1 | pAND117 | pAND114 | 1.50 |
| huAQC2-h2 | pAND120 | pAND124 | 0.64 |
| huAQC2-c1 | pAND122 | pAND114 | 1.50 |
| huAQC2-c2 | pAND123 | pAND121 | 0.68 |
| huAQC2 LC c1/HC c2 | pAND122 | pAND121 | 2.21 |
| huAQC2 LC c2/HC c1 | pAND123 | pAND114 | 0.76 |
| huAQC2 LC unblocked c1/HC c2 | pAND150* | pAND121 | 0.75 |
| huAQC2 LC L46P c2/HC c2 | pAND133** | pAND121 | 1.50 |
| huAQC2 LC L47W c2/HC c2 | pAND132*** | pAND121 | 1.00 |

*It encodes huAQC2 LC c1 with an unblocked N-terminus Q1D.
**It encodes huAQC2 LC c2 with L46P.
***It encodes huAQC2 LC c2 with L47W.

Co-transfections of 293-EBNA cells with chAQC2 and huAQC2h1, -h2, -c1 and -c2 were scaled up. Antibodies in the conditioned media were purified with Protein A-Sepharose. Purified mAbs were assayed by FACS for activity. The protocol as follows.

1. Count cells from flask that was split 1:4 on the day prior to the assay.
2. Pellet cells and resuspend at 2.5e5 cells/ml in FACS buffer (5% FBS in PBS with 0.02% NaAzide).
3. Pipette 100 μl of cells into the wells of a 96 well V bottom plate.
4. Prepare 1:3 serial dilutions of AQC2 starting at 3 μg/ml in FACS buffer.
5. Pellet the cells for 5 minutes at 800×g and flick plate to remove buffer.
6. Resuspend the cells in 100 μl of the diluted antibody series.
7. Incubate for 2 hours on ice.
8. Wash plate. Pellet the cells for 3 minutes at 800×g and flick plate to remove buffer.
9. Resuspend the cells in 100 μl of secondary antibody (diluted 1:100 in FACS buffer).
10. Incubate for 30 minutes on ice.
11. Wash plate (see above).
12. Resuspend cells in 25 μl of FACS buffer.
13. Centrifuge the FACS tubes briefly to ensure that the 50 μl is in the bottom of the tubes.
14. Vortex each tube vigorously and collect 5000 events.

The data are shown in FIG. 17. These data confirmed that huAQC2-h2 and -c2 bound less well than huAQC2-h1 and c1 relative to chAQC2.

The consensus versions of huAQC2 were studied further because they would be less immunogenic when used to treat patients with chronic indications. Mix-and-match cotransfections were performed to identify whether a single chain was responsible for the apparent decrease in binding seen with huAQC2-c2. The co-transfections suggested that the reduction could be attributed to the c2 light chain (encoded by pAND123), which differed from the c1 light chain (encoded by pAND122) at only two residues in the FR region: P46L and W47L.

To examine the individual contributions of each of these two changes, new c2 light chain expression vectors were constructed. Plasmid pAND125, the LA7W variant of the c2 light chain was made using pAND119 as a template with the following mutagenic primer: FR2 primer 5' GGG AAA GCA CCC AAA CTC TGG ATC TAT CTC ACA TCC AAC 3' (SEQ ID NO:36), which introduced HhaI and HaeII sites. Plasmid pAND126, the L46P variant of the c2 light chain, was made by using pAND119 as a template with the following mutagenic primer: FR2 primer 5' AAG CCC GGG AAG GCG CCC AAA CCC CTG ATT TAT CTC ACA TCC AAC 3' (SEQ ID NO:37), which introduced BsaHI, BanI, and NarI sites. Expression vectors for these new huAQC2 light chains were made by subcloning the 0.44 kb NotI-BglII light chain variable domain fragment from pAND125 or pAND126, and the 0.68 kb BclI-NotI fragment from pEAG963 (supra) into the NotI site of pCH269 (supra). The resultant plasmids were designated pAND132 (c2 with L47W) (SEQ ID NO:47), and pAND133 (c2 with L46P) (SEQ ID NO:70), respectively.

Co-transfections of the new light chain plasmids with each of the huAQC2 heavy chain plasmids were performed. VLA-1 binding was examined by FACS. The data demonstrate that the L47W back mutation failed to improve binding. The LA6P mutation improved the peak of the binding curve, but the EC50 was still right-shifted relative to the behavior of huAQC2 version 1 (Table 2, supra). These results suggested that both back mutations were needed for full binding activity.

A genetically unblocked c1 light chain was also made, since the Q1D variant would be one residue more "humanized." The Q1D mutant, designated pAND148, was made with the template pAND118 with the following mutagenic primer: FR1 primer 5' GTC ATA ATG TCC CGG GGA GAT ATC CAG CTC ACC CAG TCT 3' (SEQ ID NO:38), which introduced a new EcoRI site and removed an ApoI site. An expression vector for this last variant of the huAQC2 light chain was made by subcloning the 0.44 kb NotI-BglII light chain variable domain fragment from pAND148 and the 0.68 kb BclI-NotI fragment from pEAG963 into the NotI site of pCH269, producing the light chain expression vector pAND150 (c1 with unblocked N-terminus Q1D). Co-expression of the genetically unblocked light chain with the c2 heavy chain (i.e., "huAQC2 LC c1 unblocked/HC c2"; designated huAQC2c4) was equivalent to that of "huAQC2 LC c1/HC c2" (designated as huAQC2-c3). VLA-1 binding was confirmed by FACS on VLA1-expressing K562α1 cells (Table 2).

Co-transfections of 293EBNA cells with chAQC2 and huAQC2h1, -h2, -c1, -c2, -c3, and -c4 Antibodies in the conditioned media were purified on Protein A-Sepharose. The purified mAbs were assayed for activity (FIGS. 17 and 18). HuAQC2-c3 was chosen as the drug candidate, since its properties were more similar to chAQC2. Vectors were then designed for stable expression of huAQC2-c3 in CHO cells. The vectors contained a cDNA for the huAQC2 c1 LC or c2 HC, with the 5' and 3' UTRs eliminated and the heavy chain C-terminal lysine genetically deleted to ensure product homogeneity. The final vectors were pAND162 (light chain), pAND160 (heavy chain). As used herein, huAQC2-c3 is also called hAQC2.

The full polypeptide sequences of hAQC2 are as follows.

Light Chain (Plasmid: pAND162)

(SEQ ID NO: 3)

```
  1 QIQLTQSPSS LSASVGDRVT ITCSASSSVN HMFWYQQKPG
    KAPKPWIYLT

51 SNLASGVPSR FSGSGSGTDY TLTISSLQPE DFATYYCQQW
    SGNPWTFGQG

101 TKVEIKRTVA APSVFIFPPS DEQLKSGTAS VVCLLNNFYP
    REAKVQWKVD

151 NALQSGNSQE SVTEQDSKDS TYSLSSTLTL SKADYEKHKV
    YACEVTHQGL

201 SSPVTKSNR GEC
```

Heavy Chain (Plasmid: pAND160) (SEQ ID NO:4)

(SEQ ID NO: 4)

```
  1 EVQLVFSGGG LVQPGGSLRL SCAASGFTFS RYTMSWVRQA
    PGKGLEWVAT

51 ISGGGHTYYL DSVKGRFTIS RDNSKNTLYL QMNSLRAEDT
    AVYYCTRGFG

101 DGGYFDVNGQ GTLVTVSSAS TKGPSVFPLA PSSKSTSGGT
    AALGCLVKDY

151 FPEPVTVSWN SGALTSGVHT PPAVLQSSGL YSLSSVVTVP
    SSSLGTQTYI

201 CNVNHKPSNT KVDKKVEPKS CDKTHTCPPC PAPELLGGPS
    VFLFPPKPKD

251 TLMISRTPEV TCVVVDVSHE DPEVKFNWYV DGVEVHNAKT
    KPREEQYNST

301 YRVVSVLTVL HQDWLNGKEY KCKVSNKALP APIEKTISKA
    KGQPREPQVY

351 TLPPSRDELT KHQVSLTCLV KGFYPSDTAV EWESNGQPEN
    NYKTTPPVLD

401 SDGSFFLYSK LTVDKSRWQQ GNVFSCSVMH EALHNHYTQK
    SLSLSPG
```

Other heavy and light chain polypeptide and nucleotide sequences are shown below.

A. chAQC2 heavy chain (Pand099) (SEQ ID NOs:39 and 40. The former No refers to the nucleotide sequence and the latter to the polypeptide sequence. The same order is used in the following numbering.)

```
  1 GACGTCAAGGTGGTGGAGTCAGGGGGAGGCTTAGTGAAGCCTGGAGGGTCC
    CTGAAACTC D V K V V E S G G G L V K P G G S L K L

61 GCCTGTGCAGCCTCTGGATTCAGTTTCAGTAGATATACTATGTCTTGGGTTCG
    CCAGATT A C A A S G F S F S R Y T M S W V R Q I

121 CCGGAGAAGAGGCTGGAGTGGGTCGCAACCATTAGTGGTGGTGGTCACACCT
    ACTATCTA P E K R L E W V A T I S G G G H T Y Y L

181 GACAGTGTGAAGGGCCGATTCACCATCTCCAGAGACAATGCCAAGAACACCC
    TGTACCTG D S V K G R F T I S R D N A K N T L Y L
```

```
241  CAAATGAGCAGTCTGAGGTCTGAGGACACAGCCATGTATTACTGTACAAGAG
     GTTTTGGA  Q M S S L R S E D T A M Y Y C T R G F G

301  GACGGGGGTACTTCGATGTCTGGGCCAAGGGACCACGGTCACCGTCTCCT
     CA  D G G Y F D V W G Q G T T V T V S S
```

B. hAQC2 HC h1 and c1 (pAND114) (SEQ ID NOs:41 and 42)

```
  1  GACGTCCAGCTGGTCGACTCAGGGGAGGCTTAGTCCAGCCTGGAGGGTCCC
     TGAGACTC  D V Q L V E S G G G L V Q P G G S L R L

61  TCCTGTGCACCCTCTGGATTCAGTTTCAGTAGATATACTATGTCTTGGGTTCG
     CCAGGCT  S C A A S G F S F S R Y T M S W V R Q A

121  CCGGGGAAGGGGCTGGAGTGGGTCGCAACCATTAGTGGTGGTGGTCACACCT
     ACTATCTA  P G K G L E W V A T I S G G G H T Y Y L

181  GACAGTGTGAAGGGCCGATTCACCATCTCCAGAGACAATTCCAAGAACACCC
     TGTACCTG  D S V K G R F T I S R D N S K N T L Y L

241  CAGATGAACAGTCTGAGGGCCGAGGACACAGCCGTGTATTACTGTACAAGAG
     GTTTTGGA  Q M N S L R A E D T A V Y Y C T R G F G

301  GACGGGGGTACTTCGATGTCTGGGCCAAGGTACCCTGGTCACCGTCTCCT
     CA  D G G Y F D V W G Q G T L V T V S S
```

C. hAQC2 h2 Heavy Chain (pAND124) (SEQ ID NOs:43 and 44)

```
  1  GAGGTCCAGCTGGTCGAGTCAGGGGAGGCTTAATCCAGCCTGGAGGGTCCC
     TGAGACTC  E V Q L V E S G G G L I Q P G G S L R L

61  TCCTGTGCAGCCTCTGGATTCACCTTCAGTAGGTATACTATGTCTTGGGTTCG
     CCAGGCT  S C A A S G F T F S R Y T M S W V R Q A

121  CCGGGGAAGGGGCTGGAGTGGGTCGCAACCATTAGTGGTGGTGGTCACACCT
     ACTATCTA  P G K G L E W V A T I S G G G H T Y Y L

181  GACAGTGTGAAGGGCCGATTCACCATCTCCAGAGACAATTCCAAGAACACCC
     TGTACCTG  D S V K G R F T I S R D N S K N T L Y L

241  CAGATGAACAGTCTGAGGGCCGAGGACACAGCCGTGTATTACTGTACAAGAG
     GTTTTGGA  Q M N S L R A E D T A V Y Y C T R G F G

301  GACGGGGGTACTTCGATGTCTGGGCCAAGGTACCCTGGTCACCGTCTCCT
     CAGG  D G G Y F D V W G Q G T L V T V S S
```

D. hAQC2 c2 Heavy Chain (pAND121) (SEQ ID NOs:45 and 68)

```
  1  GAGGTCCAGCTGGTCGAGTCAGGGGAGGCTTAGTCCAGCCTGGAGGGTCCC
     TGAGACTC  E V Q L V E S G G G L V Q P G G S L R L

61  TCCTGTGCAGCCTCTGGATTCACCTTCAGTAGGTATACTATGTCTTGGGTTCG
     CCAGGCT  S C A A S G F T F S R Y T M S W V R Q A

121  CCGGGGAAGGGGCTGGAGTGGGTCGCAACCATTAGTGGTGGTGGTCACACCT
     ACTATCTA  P G K G L E W V A T I S G G G H T Y Y L

181  GACAGTGTGAAGGGCCGATTCACCATCTCCAGAGACAATTCCAAGAACACCC
     TGTACCTG  D S V K G R F T I S R D N S K N T L Y L

241  CAGATGAACAGTCTGAGGGCCGAGGACACAGCCGTGTATTACTGTACAAGAG
     GTTTTGGA  Q M N S L R A E D T A V Y Y C T R G F G

301  GACGGGGGTACTTCGATGTCTGGGCCAAGGTACCCTGGTCACCGTCTCCT
     CAGG  D G G Y F D V W G Q G T L V T V S S
```

E. chAQC2 Blocked Light Chain (Pand102) (SEQ ID NOs: 46 and 1)

```
  1   CAAATTGTTCTCACCCAGTTTCCAGCACTCATGTCTGCGTCTCCAGGGGAGAA
      GCTCACC  Q I V L T Q F P A L M S A S P G E K V T

61   ATGACCTGCAGTGCCAGCTCAAGTGTAAATCACATGTTCTGGTATCAGCAGA
      AGCCAAAA  M T C S A S S S V N H M F W Y Q Q K P K

121   TCCTCCCCCAAACCCTGGATTTATCTCACATCCAACCTGGCTTCTGGAGTCCC
      TGCTCGC   S S P K P W I Y L T S N L A S G V P A R

181   TTCAGTGGCAGTGGGTCTGGGACCTCTTACTCTCTCACAATCAGCAGCATGGA
      GGCTGAA   F S G S G S G T S Y S L T I S S M E A E

241   GATGCTGCCACTTATTACTGCCAGCAGTGGAGTGGTAACCCGTGGACGTTCG
      GTGGAGGC  D A A T Y Y C Q Q W S G N P W T F G G G

301   ACCAAGCTGGAGATCAAA  T K L E I K
```

F. hAQC2 h1 Light Chain (pAND117) (SEQ ID NOs: 48 and 49)

```
  1   CAAATTGTTCTCACCCAGTCTCCATCCTCCCTGTCTGCGTCTGTAGGgGACAG
      AGTCACC   Q I V L T Q S P S S L S A S V G D R V T

61   ATCACATGCAGTGCCAGCTCAAGTGTAAATCACATGTTCTGGTATCAGCAGA
      AGCCCGGGIT C S A S S S V N H M F W Y Q Q K P G

121   AAAGCCCCCAAACCCTGGATTTATCTCACATCCAACCTGGCTTCTGGAGTCCC
      TTCACGC   K A P K P W I Y L T S N L A S G V P S R

181   TTCAGTGGCAGTGGGTCTGGGACAGATTACACTCTCACAATCAGCAGCCTGC
      AACCTGAA  F S G S G S G T D Y T L T I S S L Q P E

241   GATTTTGCCACTTATTACTGCCAGCAGTGGAGTGGTAACCCGTGGACGTTCGG
      TGGAGGC   D F A T Y Y C Q Q W S G N P W T F G G G

301   ACTAAGGTGGAGATCAAA  T K V E I K
```

G. hAQC2 h2 Light Chain (pAND120) (SEQ ID NOs: 50 and 51)

```
  1   CAAATTGTTCTCACCCAGTCTCCATCCTCCCTGTCTGCGTCTGTAGGGGACAG
      AGTCACC   Q I V L T Q S P S S L S A S V G D R V T

61   ATCACATGCAGTGCCAGCTCAAGTGTAAATCACATGTTCTGGTATCAGCAGA
      AGCCCGGG  I T C S A S S S V N H M F W Y Q Q K P G

121   AAAGCGCCCAAACTCCTGATTTATCTCACATCCAACCTGGCTTCTGGAGTCCC
      TTCACGC   K A P K L L I Y L T S N L A S G V P S R

181   TTCAGTGGCAGTGGGTCTGGGACAGATTACACTCTCACAATCAGCAGCCTGC
      AACCTGAA  F S G S G S G T D Y T L T I S S L Q P E

241   GATTTTGCCACTTATTACTGCCAGCAGTGGAGTGGTAACCCGTGGACGTTCGG
      TGGAGGC   D F A T Y Y C Q Q W S G N P W T F G G G

301   ACTAAGGTGGAGATCAAA  T K V E I K
```

H. hAQC2 c1 Light Chain (pAND122) (SEQ ID NOs: 52 and 66)

```
  1   CAAATTCAGCTCACCCAGTCTCCATCCTCCCTGTCTGCGTCTGTAGGGGACAG
      AGTCACC   Q I Q L T Q S P S S L S A S V G D R V T

61   ATCACATGCAGTGCCAGCTCAAGTGTAAATCACATGTTCTGGTATCAGCAGA
      AGCCCGGG  I T C S A S S S V N H M F W Y Q Q K P G

121   AAAGCCCCCAAACCCTGGATTTATCTCACATCCAACCTGGCTTCTGGAGTCCC
      TTCACGC   K A P K P W I Y L T S N L A S G V P S R

181   TTCACTGGCAGTGGGTCTGGGACAGATTACACTCTCACAATCAGCAGCCTGC
      AACCTGAA  F S G S G S G T D Y T L T I S S L Q P E
```

-continued

```
241  GATTTTGCCACTTATTACTGCCAGCAGTGGAGTGGTAACCCGTGGACGTTCGG
     TCAGGGC  D  F  A  T  Y  Y  C  Q  Q  W  S  G  N  P  W  T  F  G  Q  G

301  ACTAAGGTGGAGATCAAA  T  K  V  E  I  K
```

I. hAQC2 c2 Light Chain (pAND123) (SEQ ID NOs:53 and 54)

```
  1  CAAATTCAGCTCACCCAGTCTCCATCCTCCCTGTCTGCGTCTGTAGGGGACAG
     AGTCACC  Q  I  Q  L  T  Q  S  P  S  S  L  S  A  S  V  G  D  R  V  T

61  ATCACATGCAGTGCCAGCTCAAGTGTAAATCACATGTTCTGGTATCAGCAGA
     AGCCCGGG  I  T  C  S  A  S  S  S  V  N  H  M  F  W  Y  Q  Q  K  P  G

121  AAAGCGCCCAAACTCCTGATTTATCTCACATCCAACCTGGCTTCTGGAGTCCC
     TTCACGC  K  A  P  K  L  L  I  Y  L  T  S  N  L  A  S  G  V  P  S  R

181  TTCAGTGGCAGTGGGTCTGGGACAGATTACACTCTCACAATCAGCAGCCTGC
     AACCTGAA  F  S  G  S  G  S  G  T  D  Y  T  L  T  I  S  S  L  Q  P  E

241  GATTTTGCCACTTATTACTGCCAGCAGTGGAGTGGTAACCCGTGGACGTTCGG
     TCAGGGC  D  F  A  T  Y  Y  C  Q  Q  W  S  G  N  P  W  T  F  G  Q  G

301  ACTAAGGTGGAGATCAAA  T  K  V  E  I  K
```

J. chAQC2 Unblocked Light Chain (pAND098) (SEQ ID NOs:55 and 56)

```
  1  GAAATTGTTCTCACCCAGTTTCCAGCACTCATGTCTGCGTCTCCAGGGGAGAA
     GGTCACC  E  I  V  L  T  Q  F  P  A  L  M  S  A  S  P  G  E  K  V  T

61  ATGACCTGCAGTGCCAGCTCAAGTGTAAATCACATGTTCTGGTATCAGCAGA
     AGCCAAAA  M  T  C  S  A  S  S  S  V  N  H  M  F  W  Y  Q  Q  K  P  K

121  TCCTCCCCCAAACCCTGGATTTATCTCACATCCAACCTGGCTTCTGGAGTCCC
     TGCTCGC  S  S  P  K  P  W  I  Y  L  T  S  N  L  A  S  G  V  P  A  R

181  TTCAGTGGCAGTGGGTCTGGGACCTCTTACTCTCTCACAATCAGCAGCATGGA
     GGCTGAA  F  S  G  S  G  S  G  T  S  Y  S  L  T  I  S  S  M  E  A  E

241  GATGCTGCCACTTATTACTGCCAGCAGTGGAGTGGTAACCCGTGGACGTTCG
     GTGGAGGC  D  A  A  T  Y  Y  C  Q  Q  W  S  G  N  P  W  T  F  G  G  G

301  ACCAAGCTGGAGATCAAA  T  K  L  E  I  K
```

K. huAQC2 Unblocked c1 Light Chain (pAND150) (SEQ ID NOs:57 and 58)

```
  1  GATATCCAGCTCACCCAGTCTCCATCCTCCCTGTCTGCGTCTGTAGGGGACAG
     AGTCACC  D  I  Q  L  T  Q  S  P  S  S  L  S  A  S  V  G  D  R  V  T

61  ATCACATGCAGTGCCAGCTCAAGTGTAAATCACATGTTCTGGTATCAGCAGA
     AGCCCGGG  I  T  C  S  A  S  S  S  V  N  H  M  F  W  Y  Q  Q  K  P  G

121  AAAGCCCCCAAACCCTGGATTTATCTCACATCCAACCTGGCTTCTGGAGTCCC
     TTCACGC  K  A  P  K  P  W  I  Y  L  T  S  N  L  A  S  G  V  P  S  R

181  TTCAGTGGCAGTGGGTCTGGGACAGATTACACTCTCACAATCAGCAGCCTGC
     AACCTGAA  F  S  G  S  G  S  G  T  D  Y  T  L  T  I  S  S  L  Q  P  E

241  GATTTTGCCACTTATTACTGCCAGCAGTGGAGTGGTAACCCGTGGACGTTCGG
     TCAGGGC  D  F  A  T  Y  Y  C  Q  Q  W  S  G  N  P  W  T  F  G  Q  G

301  ACTAAGGTGGAGATCAAA  T  K  V  E  I  K
```

Example 22

This example describes the characterization of various AQC2 antibodies of the invention.

Solid-phase assay for α1 I domain binding. Fifty μl of 10 mg/ml α1 I domain-GST fusion protein was added to a CORNING COSTAR EASY WASH polystyrene 96-well plate (Gotwals et al., Biochemistry, 38, 8280-8 (1999)). Following incubation at 4° C. for 16 hrs, the plate was washed four times with 350 μl of 0.1% Tween-20 in PBS in a plate washer. The plate was blocked by addition of 180 μl of 3% BSA in TBS at 25° C. for 60 min, and then washed as above. Dilutions of antibodies (50 μl/well) in TBS containing 1 mg/ml BSA (assay buffer) were prepared in a 96-well round-bottom plate, transferred to the α1 I domain-coated plate, and incubated for 60 min at 25° C. Following a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Electrochemiluminescence assays for binding of α1β1 integrin or α1 I domain to collagen. Tosyl-activated DYNABEADS M-280 (Dynal, Inc.) were coated with 100 µg/ml type IV collagen (Sigma) according to the manufacturer's instructions. Cell lysates from α1-transfected K562 cells were prepared as follows. Cells were collected by centrifugation, resuspended at $10^8$ cells/ml in a lysis buffer containing 25 mM Tris, pH 7.4, 1% NP-40, 1 mM CaCl.sub.2, 1 mM MnCl.sub.2, 1 mM MgCl.sub.2, 2% BSA, and 1 mM PMSF, and incubated at 4° C. for 60 min. Cell debris was removed by centrifugation at 12,000 rpm for 30 min and the resulting supernatant was used in subsequent experiments. Anti-β1 activating antibody TS2/16 and polyclonal anti-GST antibody (Pharmacia) were labeled with TAG-NHS ester (IGEN International, Inc., Gaithersburg, Md.) according to the manufacturer's instructions. Labeled antibodies were purified by gel filtration chromatography on SEPHADEX G25M (Pharmacia).

To carry out the binding assay, collagen-coated beads (1 mg/ml) were blocked for 5 min with 8% Lewis rat plasma in an assay buffer containing 50 mM HEPES, pH 7.5, 150 mM NaCl, and 0.1% Triton X-100. For the α1β1 binding assay, serial dilutions of antibodies were incubated with 10 µg of beads, cell lysate prepared from $10^5$ α1-transfected K562 cells (supra), and 0.1 µg/ml of TAG-TS2/16 in an assay buffer containing 1 mM MnCl$_2$. For the α1 I domain binding assay, the antibodies were incubated with 10 µg of beads, 0.1 µg/ml α1 I domain GST fusion protein, and 1 µg/ml of TAG-anti-GST in an assay buffer containing 1 mM MnCl$_2$. After one to two hours of agitation at room temperature, 200 µl of the assay buffer was added and the samples were read on an ORIGEN 1.5 electrochemiluminescence detector (IGEN). Plots are presented with arbitrary electrochemiluminescence units (ECL) on the ordinate axis.

Biotinylated mAQC2 competition assay. A 96-well plate was coated with 50 µl of 5 µg/ml α1 I domain GST fusion protein and blocked with 3% BSA in TBS as described above. Dilutions of antibodies (60 µl/well) in the assay buffer were prepared in a 96-well roundbottom plate, and 60 µl of 0.1 µg/ml biotinylated murine AQC2 in the assay buffer was added. Fifty microliters from each well was transferred to the coated plate and incubated for 3 hrs at 25° C. The plate was then washed as above, 50 µl of 1 µg/ml peroxidase-conjugated EXTRAVIDIN (Sigma) was added, and the plate was incubated another 2 hrs at 25° C. After a final wash, 100 µl/well of TMB reagent (Pierce) was added. After 10 min, 100 µl of 1 M sulfuric acid was added, and the absorbance at 450 nm was read on a UV-Vis 96-well spectrophotometer.

Experimental results. The experimental results are shown in FIGS. 16A-D and Table 3. The ability of mAQC2, chAQC2, hAQC2, and hAQC2' (i.e., huAQC2-c4; differing from hAQC2 only in that residue 1 of the hAQC2' light chain was D instead of Q) to (1) bind to human α1-transfected K562 cells (by FACS); (2) bind to immobilized α1-I domain (by ELISA); (3) compete with mAQC2 for binding to α1-I domain (ELISA); (4) block α1β1 domain binding to collagen (Electrochemiluminescence assay); or (5) block a α1β1 integrin binding to collagen (Electrochemiluminescence assay) was determined. The results are shown in FIGS. 16A-D, and calculated IC50 (for inhibition) or EC50 (for binding) values are given in Table 3. In each assay, each of the humanized AQC2 forms showed a similar ability to either bind VLA1 (or the α1 domain) or block binding to collagen (Note that in panel C, the observed difference in intensity between mAQC2 and the humanized forms derives from the use of an anti-murine-IgG secondary antibody, instead of an anti-human-IgG).

TABLE 3

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| mAQC2 | n.d. | 0.0726 (±0.014) | 0.029 (±0.011) | 0.061 (±0.015) | 38 (±8.7) |
| Chimera | 0.25 | 0.071 (±0.002) | 0.027 (±0.007) | 0.176 (±0.058) | 30 (±6.9) |
| hAQC2 | 0.29 | 0.129 (±0.005) | 0.035 (±0.005) | 0.190 (±0.010) | 65 (±2.2) |
| hAQC2' | 0.43 | 0.125 (±0.018) | 0.037 (±0.001) | 0.313 (±0.072) | 69 (±25.7) |

We next tested whether changes at certain conservative residues in the CDRs could preserve the VLA-1 binding activity of hAQC2, DNA constructs encoding variants of hAQC2 with the following mutations were made by site-directed mutagenesis: (1) G55S in the heavy chain CDR2; (2) S24N in the light chain CDR1 (introducing an occupied N-linked glycosylation site); (3) G92S in the light chain CDR3; (4) a combination of (1) and (2); and (5) a combination of (1) and (3). The DNA constructs encoding both the heavy and light chains were then co-transfected into 293-EBNA cells, and the conditioned medium of the transfectants was assayed for antibody expression by Western blot and ELISA. The results indicated that the hAQC2 variants were expressed as efficiently as cognate h-AQC2. FACS analysis using VLA-1-expressing K562 cells further showed that the VLA-1 binding activities of these variants were similar to hAQC2 itself. In sum, the amino acid substitutions did not alter the VLA-1 binding activity of hAQC2. Indeed, X-ray crystal structure of the RΔH/hAQC2 Fab complex (infra) shows that S24 and G92 of the light chain and G55 of the heavy chain are not in the binding pocket that is in contact with the α1-I domain.

Example 23

The effector functions of an immunoglobulin couple the immunoglobulin's antigen-binding activity to the inflammatory, cytotoxic and stimulatory arms of the immune system. Effector functions may impair the safety and efficacy of an immunoglobulin therapeutic product. To reduce the potential effector functions of h-AQC2, mutations of L234A and L235A were made to its heavy chain to generate hsAQC2. For the same reason, a single mutation of N298Q (numbering according to SEQ ID NO:5) was made in the heavy chain of hAQC2 to generate an aglycosylated form of hAQC2, named haAQC2. Studies can be done to compare their efficacy, residual effector function, stability and immunogenicity to cognate hAQC2. Unless otherwise indicated, residue position numbers in constant regions as used herein are designated in accordance with the EU numbering convention.

The heavy chain polypeptide sequence of haAQC2 is as follows (Plasmid: pAND161):

(SEQ ID NO: 5)

```
  1 EVQLVESGGG LVQPGGSLRL SCAASGFTFS RYTMSWVRQA
    PGKGLEWVAT

51 ISGGGHTYYL DSVKGRFTIS RDNSKNTLYL QMNSLRAEDT
    AVYYCTRGFG

101 DGGYFDVWGQ GTLVTVSSAS TKGPSVFPLA PSSKSTSGGT
    AALGCLVKDY

151 FPEPVTVSWN SGALTSGVHT FPAVLQSSGL YSLSSVVTVP SSSLGTQTYI

201 CNVNHKPSNT KVDKKVEPKS CDKTHTCPPC PAPELLGGPS
    VFLFPPKPKD

251 TLMISRTPEV TCVVVDVSHE DPEVKFNWYV DGVEVHNAKT
    KPREEQYQST

301 YRVVSVLTVL HQDWLNGKEY KCKVSNKALP APIEKTISKA
    KGQPREPQVY

351 TLPPSRDELT KNQVSLTCLV KGFYPSDIAV EWESNGQPEN
    NYKTTPPVLD

401 SDGSFFLYSK LTVDKSRWQQ GNVFSCSVMH EALHNHYTQK SLSLSPG
```

The heavy chain polypeptide sequence of hsAQC2 is as follows (Plasmid: pAND171):

(SEQ ID NO: 6)

```
  1 EVQLVESGGG LVQPGGSLRL SCAASGFTFS RYTMSWVRQA
    PGKGLEWVAT

51 ISGGGHTYYL DSVKGRFTIS RDNSKNTLYL QMNSLRAEDT
    AVYYCTRGFG

101 DGGYPDVWCQ GTLVTVSSAS TKGPSVFPLA PSSKSTSGGT
    AALGCLVKDY

151 FPEPVTVSWN SGALTSGVHT FPAVLQSSGL YSLSSVVTVP SSSLGTQTYI

201 CNVNHKPSNT KVDKKVEPKS CDKTHTCPPC PAPEAAGGPS
    VFLFPPKPKD

251 TLMISRTPEV TCVVVDVSHE DPEVKFNWYV DGVEVHNAKT
    KPREEQYNST

301 YRVVSVLTVL HQDWLNGKEY KCKVSNKALP APIEKTISKA
    KGQPREPQVY

351 TLPPSRDELT KNQVSLTCLV KGFYPLDIAV EWESNGQPEN
    NYKTTPPVLD

401 SDGSFFLYSK LTVDKSRWQQ GNVFSCSVMH EALHNHYTQK SLSLSPG
```

Example 24

This example describes a method for determining the crystal structure of the complex of a rat/human chimeric α1-I domain of the α1β1 integrin and the hAQC2 Fab fragment.

Preparation of the Protein Complex

The hAQC2 Fab fragment was prepared from hAQC2 antibody using a variation of the procedure of the IMMUNOPURE® Fab preparation kit (Cat #44885, Pierce, Rockford, Ill.). The intact hAQC2 antibody was concentrated to 12 mg/ml in a buffer containing 20 mM phosphate, 10 mM EDTA and 25 mM cysteine (pH 7.0). Immobilized papain was added at an enzyme to substrate ratio of 1:50, and digestion was allowed to occur overnight at 37° C. The immobilized papain was removed and the crude digest was dialyzed against 20 mM sodium acetate buffer (pH 4.5). The Fab fragment was separated from residual intact antibody, dimeric Fab fragment, and Fc fragment by cation exchange chromatography using a S-column (Poros HS/M, PERSEPTIVE Biosystems #PO42M26) with a shallow salt gradient. The Fab fragment was then exchanged into 0.1 M Hepes buffer (pH 8.0).

The chimeric α1-I domain used in the present invention is a rat/human chimeric I domain construct (mutant RΔH) containing residues Thr145-Phe336 of the rat α1 integrin chain, where residues Gly217, Arg218, Gln219 and Leu222 (crystal numbering) have been substituted with equivalent human residues Val, Gln, Arg and Arg, respectively, in order to restore antibody binding. The amino acid sequences of chimeric RΔH, rat, and human α1-I domains are given below in SEQ ID NOs:59, 60 and 61, respectively. Recombinant α1-I domain was expressed in E. coli as a GST-fusion protein. The RΔH α1-I domain was cleaved with thrombin and purified from a Pichia pastoris clone as described previously (Gotwals et al., 1999, Biochemistry 38:8280-8288).

```
                                          (SEQ ID NO: 59)
145 TQLDIV

151 IVLDGSNSIY PWESVIAFLN DLLKRMDIGP KQTQVGIVQY

191 GENVTHEFNL NKYSSTEEVL VAANKIVQRG GRQTMTALGI

231 DTARKEAFTE ARGARRGVKK VMVIVTDGES HDNYRLKQVI

271 QDCEDENIQR FSIAILGHYN RGNLSTEKFV EEIKSIASEP

311 TEKHFFNVSD ELALVTIVKA LGERIF (SEQ ID NO: 60)
145 TQLDIV

151 IVLDGSNSIY PWESVIAFLN DLLKRMDIGP KQTQVGIVQY

191 GENVTHEFNL NKYSSTEEVL VAANKIGRQG GLQTMTALGI

231 DTARKEAFTE ARGARRGVKK VMVIVTDGES HDNYRLKQVI

271 QDCEDENIQR FSIAILGHYN RGNLSTEKFV EEIKSIASEP

311 TEKHFFNVSD ELALVTIVKA LGERIF (SEQ ID NO: 61)
145 TQLDIV

151 IVLDGSNSIY PWDSVTAFLN DLLKRMDIGP KQTQVGIVQY

191 GENVTHEFNL NKYSSTEEVL VAAKKIVQRG GRQTMTALGI

231 DTARKEAFTE ARGARRGVKK VMVIVTDGES HDNHRLKKVI

271 QDCEDENIQR FSIAILGSYN RGNLSTEKFV EEIKSIASEP

311 TEKHFFNVSD EIALVTIVKT LGERIF
```

The hAQC2 Fab fragment was mixed with excess chimeric α1-I domain and incubated at 37° C. for 15 minutes. The saturated α1/Fab complexes were separated from uncomplexed α1-I domain by size exclusion chromatography using a S200 Sephacryl column (Pharmacia, Gibco). The complex was further concentrated to 11 mg/ml in a 20 mM Tris (pH 7.4) 150 mM NaCl 1 mM MnCl$_2$, 5 mM β-mercaptoethanol.

Preparation of Crystals

Crystallization conditions were found using the CRYSTAL SCREEN™ KITs from Hampton Research (Laguna Niguel, Calif.). Crystals of the complex described above were grown at 20° C. by vapor diffusion using an equal amount of protein complex solution and a 20-30% PEG 1500 reservoir solution. Typically, 2 μL of protein complex was added to 2 μL of well solution to yield drops of 4 μL. Crystals grew in two to seven days as hexagonal rods with dimensions 0.8× 0.05×0.05 mm$^3$. The presence of the α1-I domain and hAQC2 Fab fragment was confirmed by SDS-PAGE analysis of dissolved crystals. In order to reduce the inherent radiation damage during data collection, X-ray diffraction data was collected at approximately 100 K. To prepare the crystals for data collection at this low temperature, crystals were gradually equilibrated into a cryoprotectant solution containing 25% PEG 400 and 30% PEG 1500, and flash cooled in liquid nitrogen.

Structure Determination

Native X-ray diffraction data to 2.8 Å resolution were collected from a single crystal at about 100 K using an ADSC Quantum 4 charged-coupled device detector at beamline X4A of the Brookhaven National Laboratory (BNL) National Synchrotron Light Source (NSLS). Data was processed using the software programs DENZO and SCALEPACK (Otwinowski & Minor, 1997, Methods in Enzymol. 276:307-326). Crystals belonged to the space group P6.sub.1 or its enantiomorph P6.sub.5, with unit cell dimensions a=b=255.09 Å, c=38.64 Å. The data set was 96.6% complete and had an R-merge of 8.3%. The Matthews coefficient (Matthews, 1968, J. Mol. Biol. 33:491-497) was 2.59 Å$^3$ Da$^{-1}$ with a solvent content of 52.1%, which indicated that there were two complexes in the asymmetric unit. The two complexes in the asymmetric unit were related by non-crystallographic 2-fold symmetry. Data statistics are shown in Table 4.

Molecular replacement searches were done with the program AMoRe (Navaza, 1994, Acta Cryst. A50:157-163) from the CCP4 program package (Collaborative Computational Project No. 4. The CCP4 Suite: programs for protein crystallography. 1994, Acta Cryst. D50:760-763), and molecular graphics manipulations were done with the program QUANTA. A single α1-I domain from the structure of the rat α1-I domain of α1β1 integrin (Protein Data Bank (PDB) accession number 1ck4; Nolte et al., 1999, FEBS Lett. 452: 379-385) was used as a model or probe for rotation and translation searches. The translation function search indicated that the 1$^{st}$ and 9$^{th}$ highest peaks of the rotation function corresponded to the correct solutions for the two α1-I domains in the asymmetric unit (correlation coefficient (cc) =21.1%, R=53.1%) and that the space group was P6$_5$. Subsequently, searches for the hAQC2 Fab fragments were done, keeping the I domain solutions fixed and using a model of the Fv domain of the hAQC2 Fab as a search probe. A clear solution was found for one of the two Fv domains (cc=22.1%, R=52.6%), but the second Fv could not be located. The position of the second Fv was derived using the non-crystallographic 2-fold symmetry. Rigid body refinement of the two I domains and two Fv domains reduced the R-factor to 43.6% (R-free=42.7%). An 2Fo-Fc electron density map showed clear electron density for the constant domain (Fconst) of the first Fab fragment, but no density for the Fconst domain of the second Fab fragment. A model of the Fconst domain of the first Fab was manually fit in the observed electron density. Subsequent rigid body refinement with the software program CNX (Accelrys Inc., San Diego, Calif. ©2000; Brunger, 1998, Acta Cryst. D54:905-921), using data in the 500-2.8 Å resolution range, optimized the position of all domains, reducing the R-factor to 39.7% (R-free=38.9%).

All subsequent refinement steps were carried out with the CNX program. To reduce model bias, partial models were used for 2Fo-Fc map calculation and model refinement. The initial partial model, was subjected to simulated annealing and grouped B-factor refinement with non-crystallographic symmetry restraints. The R-working and R-free factors dropped to 28.3% and 32.9%, respectively. Several cycles consisting of iterative model building, maximum likelihood positional refinement and B-factor refinement followed. Only model adjustments that resulted in a drop in the R-free factor were accepted. A bulk-solvent correction was employed after the complete model was built. The R-working and R-free factors of the final model are 21.3% and 27.2%, respectively for the data (F>2σ) in the 500-2.8 Å resolution range.

The final 2Fo-Fc electron density map is of good quality for most of the complex with the exception of amino acid residues 288-295 of one I domain fragment (molecule A in FIG. 19) that are associated with weak electron density and have not been included in the model. In addition, the entire constant domain of one Fab fragment has no visible electron density, which indicates that it is disordered. This appears to be consequence of the absence of crystal contacts for the constant domain of the Fab fragment due to its position within a large solvent channel. This domain was also not included in the final model that consists of 1030 amino acid residues, constituting 6 polypeptide chains, and 2 manganese ions. The r.m.s. positional deviation between equivalent residues from the two complexes in the asymmetric unit is small (0.37 Å for 1660 equivalent main chain atoms). Stereochemistry statistics were calculated with the software programs PROCHECK (Laskowski et al., 1993, J. Appl. Cryst. 26:283-291; Morris et al., 1992, Proteins 12:345-364) and CNX. Hydrogen bonds (<3.6 Å) were found with the program CONTACT (Tadeusz Skarzvnski, Imperial College, London, Jan. 12, 1988; Collaborative Computational Project No. 4. The CCP4 Suite: programs for protein crystallography. 1994, Acta Cryst. D50, 760-763). All non-glycine residues (except residue Thr50 of the L chain that will be discussed below) are in the allowed regions of the Ramachandran diagram and 86% of the residues are in the most favored regions. The average B-factor of the main chain atoms is 38.5 $Å^2$. Crystallographic analysis data are in Table 4.

TABLE 4

Summary of Data Statistics and Crystallographic Analysis

| Data collection | |
|---|---|
| Cell dimensions a, b, c (Å) | 255.09, 255.09, 38.64 |
| Space group | $P6_5$ |
| Resolution (Å) | 500-2.8 (2.9-2.8)† |
| Unique reflections | 35275 |
| Completeness (%) | 96.6 (87.7)† |
| Average I/s | 11.92 (2.29)† |
| Rmerge* (%) | 8.3 (30.9)† |
| Model | |
| Number of non-H atoms | 7950 |
| Number of protein residues | 1030 |
| Contents of asymmetric unit | 2 I domains, 1 Fab fragment, 1 Fv domain |
| Average B-factor ($Å^2$) | 38.5 |
| Refinement | |
| Resolution range used (F > 2δ) | 500-2.8 |
| R-factor (R-working) (%) | 21.3 |
| R-free†† (%) | 27.2 |
| Stereochemistry | |
| RMS deviations | |
| Bond lengths (Å) | 0.007 |
| Angles (°) | 1.43 |

*Rmerge = $\Sigma_h\Sigma_i|I_{hi} - I_h|/\Sigma_{hi}I_{hi}$
†Values for the highest resolution shell given in parenthesis.
††8% of the data were allocated for the calculation of R-free factor.

Example 25

This example describes the crystal structure of the complex of a rat/human chimeric α1-I domain of the α1β1 integrin and the hAQC2 Fab fragment.

Architecture of Crystal Structure

The crystal structure of the complex of the rat/human chimeric α1-I domain of the α1β1 integrin and the hAQC2 Fab fragment has an elongated shape (FIG. 20). The dimensions of the complex are 100 Å×50 Å×35 Å.

The Fab fragment exhibits the typical immunoglobulin fold. The light chain and heavy chains of the Fab fragment each form two broad sheets of anti-parallel β-strands which pack tightly together to form a scaffold for the complementarity determining region (CDR) loops which extend from the packed sheets. Both the light chain and the heavy chain contain three CDR loops. The light chain loops are called L1, L2 and L3, while the heavy chain loops are referred to as H1, H2 and H3. The complementarity determining region (CDR) loops correspond to canonical structure 1 for light chain L1, L2 and L3 loops and for heavy chain H1 and H2 loops (Chothia et al., 1989, Nature 342:877-883). The heavy chain H3 loop has a tight β-hairpin-like conformation that is stabilized by internal hydrogen bonds as well as two aromatic residues (Tyr104 and Phe105) that are packed against the light chain. Residue Thr50 of L2 adopts mainchain dihedral angles that fall in the disallowed regions of the Ramachandran diagram. The same observation for the corresponding residue has been made for other antibodies (Muller et al., 1998, Structure 6, pp. 1153-11567) which indicates that this is a natural characteristic of L2 loops.

The α1-I domain in the present invention has a structure very similar to the uncomplexed α1-I domain (PDB accession number 1ck4; Nolte et al., 1999, FEBS Lett. 452:379-385; PDB accession code 1qc5; Rich et al., 1999, J. Biol. Chem. 274:24906-24913). The I domain structure exhibits a "dinucleotide-binding" or "Rossman" fold (Rao & Rossman, 1973, J. Mol. Biol. 76:241-256) in which a central sheet of five parallel β-strands and one small antiparallel-strand is surrounded on both sides by a total of seven α-helices. The six β-strands of the structure in this invention will be referred to as βA, βB, βC, βD, βE, and βF and the seven α-helices are called α1, α2, α3, α4, α5, α6 and α7.

Three characteristic structural features exist for 1 domains. The first characteristic feature is the presence of an inserted small helix in the βE-α6 loop, termed as the C helix. Most of the C helix loop of molecule A (FIG. 19) in the present invention is associated with weak electron density, which suggests disorder. This appears to be a consequence of absence of crystal contacts or contacts with the Fab that would have stabilized the loop. However, the same loop in molecule B (FIG. 19) in the present invention has well-defined electron density and has been included in the model. The second characteristic feature of α1-I domains is the MIDAS or Metal-Ion-Dependent-Adhesion-Site where metal ions and ligands are implicated to bind to the I domain. Five key residues which form part of the MIDAS are referred to as the "DxSxS-T-D" motif. These residues, which are completely conserved among I domains, coordinate the metal ion (Gotwals et al., 1999, Biochemistry 38:8280-8288). The crystals in the present invention were grown in the presence of manganese and the MIDAS site of the I domain in this structure is observed to contain a $Mn^{+2}$ metal ion. The ion is directly coordinated by the side chains of residues Ser156, Ser158 and Thr224. The 2Fo-Fc electron density map shows no evidence that MIDAS residues Asp 154 and Asp257 make water-mediated indirect coordination of the metal ion (FIG. 20). However, the apparent absence of water molecules could be a consequence of the limited resolution (2.8 Å) of the electron density map. The third feature of X domains is that all determined structures of I domains belong to one of two conformations called "open" and "closed". The differences between the open and closed conformation include a different mode of metal ion coordination and a significant (about 10 Å) positional shift of the C-terminal helix of the I domain. The I domain in the complex in the present invention is in the closed conformation.

In the structure of the complex in the present invention, the Fab fragment binds to its epitope on the front upper surface of the I domain with a footprint 35 Å by 30 Å. The total buried surface area in the antibody-antigen interface is 1534 $Å^2$ which is typical of other antibody-antigen complexes (Davies et al., 1996, Proc. Natl. Acad. Sci. USA 93:7-12; Jones & Thornton, 1996, Proc. Natl. Acad. Sci. USA 93:13-20). The surface is 25% hydrophobic and 75% hydrophilic in character. The heavy chain contributes 65% of the buried surface area for the complex, while the remaining 35% is contributed by the light chain. The antibody epitope consists of residues located in four loops of the I domain (Emsley et al., 2000, Cell 101:47-56). Three of the loops form the MIDAS site: loop 1 (βA-α1) which contains the conserved DXSXS sequence, loop 2 (α3-α4) which contains the MIDAS Thr224 and loop 3 (βD-α5) that contains MIDAS residue Asp257. The fourth loop is the C-helix loop and is involved in only in minor contacts.

The central feature of the antigen-antibody interaction is the coordination of the MIDAS site metal ion by Asp101 from the CDR H3 of the antibody (FIG. 20). The distance between the ion and Oδ1 of Asp101 is 2.4 Å. In addition, the Oδ2 atom of Asp101 is interacting with His261 of the I domain. Interestingly, the CDR H3 contains several glycine residues adjacent to Asp101 (sequence GFGDGGY) (SEQ ID NO:62), presumably to allow enough flexibility to the CDR loop to permit proper coordination of the metal ion. The CDR H3 sequence is essentially invariant in monoclonal antibodies that were raised against the same antigen and found to belong in the same class. Most of the antibody residues that are involved in antibody-antigen contacts are located in L3, H1, H2 and H3 CDR loops. A few residues from the L1 (Asn30) and L2 (Tyr48) loops appear to form minor Van Der Waals contacts. L3 primarily contributes to contacts through two large hydrophobic residues, Trp90 and Trp95. In addition, Asn93 from L3 forms hydrogen bonds with Gln223 of the I domain. The side chains of His56 and Tyr58 from the H2 loop form hydrogen bonds with main chain atoms of loop 2 of the I domain. Arg31 of H1 is in contact with Arg291 of loop 4 of the I domain. Arg222 from loop 2 of the I domain is sandwiched between several antibody residues including Tyr58, Trp95 and Asn93. This is the only residue out of the four mutated in the RΔH I domain, that is involved in contacts with the Fab. It is therefore likely to be the only residue responsible for restoring the binding of the antibody after the mutagenesis.

Comparison of the Crystal Structure of the Complex of a Rat/Human Chimeric α1-I Domain and the hAQC2 Fab Fragment with Other I Domain Structures The chimeric RΔH α1-I domain has four sequence differences with the rat α1-I domain (rat residues: 217G, 218R, 219Q and 222L), eight sequence differences with the human α1-I domain (human residues: 163D, 166T, 214K, 264H, 268K, 288S, 322I and 380T), and ten sequence differences with the clone used in the crystal structure studies of human α1-I domain (clone residues: 163D, 166T, 174E, 214K, 230I, 264H, 268K, 288S, 322I and 380T). In the unliganded rat α1β1 α1-I domain crystal structure (PDB accession code 1ck4; Nolte et al., 1999, FEBS Lett. 452:379-385), the α1-I domain contains no bound metal ions and adopts the "closed" conformation. In the unliganded human α1-I domain crystal structure (accession code 1qc5; Rich et al., 1999, J. Biol. Chem. 274:24906-24913), the α1-I domain contains bound $Mg^{+2}$ and similarly adopts the closed conformation. Superimposition of these two structures with the complexed chimeric α1-I domain indicates that there are only minor conformational changes upon hAQC2 antibody binding. The r.m.s. positional deviation between the rat and chimeric α1-I domain is 1.04 Å for all 768 main chain atoms. The r.m.s. positional deviation between the human and chimeric α1-I domain is 0.69 Å for all 764 main chain atoms. The biggest differences (human and chimeric α1-I domain pair) are observed in loop 1 (r.m.s. deviations 1.24 Å for main chain atoms of residues 154-161) and the loop 4 (C helix loop) of the α1-I domain (r.m.s. deviations 1.55 Å for main chain atoms of residues 288-296). However, these differences can be more accurately described as shifts of the whole secondary structure elements rather than complex conformational changes. These are likely to be within the normal range of conformational flexibility of proteins. The r.m.s. positional deviation between the human and chimeric α1-I domain for backbone atoms of amino acid residues Glu192, Gln218, Arg219, Gly220, and Gly221 (crystal numbering) is 0.33 Å. The r.m.s. positional deviation between the rat and chimeric α1-I domain for backbone atoms of amino acid residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering) is 0.97 Å.

The I domain maintains the "closed" I domain conformation that has been observed only for unliganded I domains crystallized in the absence of ligands or pseudo-ligands bound to the MIDAS site. The r.m.s. positional deviation of the C-terminal helices of the human and chimeric I domains (calculated for the main chain atoms of residues 321-335) is 0.64 Å. A simulated annealing omit map calculated for the final refined model unambiguously confirms that the position of the C-terminal helix and adjacent structural elements are consistent with the closed conformation.

In order to investigate the effects of ligand binding to the modes of metal ion coordination, the structure of the present invention was superimposed with the structures of the unliganded α2-I domain (PDB accession code 1aox; Emsley et al., 1997, J. Biol. Chem. 272:28512-28517) and the α2-I domain complexed with a collagen peptide (PDB accession code 1dzi; Emsley et al., 2000, Cell 101:47-56). The coordination of the metal ion by Asp101 from the antibody is remarkably similar to the coordination of the metal ion of the α2-I domain by a glutamic acid from the collagen peptide. Another feature that is conserved is the simultaneous interaction of the acidic group with His261 (His258 in the α2-I domain). All MIDAS residues of the I domain-Fab complex except Ser156 and Ser158 adopt conformations very similar to those observed in the unliganded I domain. In contrast, the side chains of Ser156 and Ser158, as well as the metal, adopt conformations similar with those of the liganded I domain. It is clear that the coordination of the metal ion by Asp101 does not allow the ion to maintain the position and coordination distances that are observed in the unliganded state. Thus, the metal ion is not directly coordinated by Asp257, a fact that permits the ion to maintain high electrophilicity.

Biological Implications

In the present invention, there is no direct coordination of the metal by Asp257, which may permit high affinity binding by lowering the energy barrier between a closed (no ligand bound) and open (ligand bound) conformation. However, the coordination of the metal by an aspartic acid from the antibody is not sufficient to induce the open conformation to the I domain in the present invention. The I domain-Fab complex structure indicates that it is possible to have strong binding to the I domain that adopts the closed conformation and that coordination of the metal ion by an acidic residue from the ligand may be necessary but not sufficient to induce a conformational change to the open state. Binding of the antibody is expected to stabilize the low affinity state of the integrin and prevent the outside-in signaling that would have accompanied integrin binding to collagen.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention.

What is claimed is:

1. A method of treating a subject with rheumatoid arthritis comprising administering to the subject a composition comprising an anti-VLA-1 antibody or antigen binding fragment thereof, and a pharmaceutically acceptable carrier, wherein the antibody or antigen binding fragment comprises light chain complementarity determining regions defined by amino acid residues 24 to 33, 49 to 55 and 88 to 96 of SEQ ID NO:1, and heavy chain complementarity determining regions defined by amino acid residues 31 to 35, 50 to 65 and 98 to 107 of SEQ ID NO:2.

2. The method of claim 1, wherein the anti-VLA-1 antibody or antigen binding fragment thereof comprises a light chain variable domain sequence of SEQ ID NO:1 and a heavy chain variable domain sequence of SEQ ID NO:2.

3. The method of claim 1, wherein the anti-VLA-1 antibody or antigen binding fragment thereof comprises the same heavy and light chain polypeptide sequences as an antibody produced by hybridoma mAQC2 which is deposited under ATCC accession number PTA3273.

4. The method of claim 1, wherein the anti-VLA-1 antibody or antigen binding fragment thereof is a humanized or chimeric antibody or antigen-binding fragment thereof.

5. The method of claim 4, wherein the anti-VLA-1 antibody or antigen binding fragment thereof comprises at least one of the following residues in its light chain: Q1, L4, P45, W46 and Y70 of SEQ ID NO:1; or at least one of the following residues in its heavy chain: D1, V12, S28, F29, A49, T96, and R97 of SEQ ID NO:2.

6. The method of claim 4, wherein the anti-VLA-1 antibody or antigen binding fragment thereof comprises a light chain variable domain sequence defined by amino acid residues 1 to 106 of SEQ ID NO:3, and a heavy chain variable domain sequence defined by amino acid residues 1 to 118 of SEQ ID NO:4.

7. The method of claim 4, wherein the anti-VLA-1 antibody or antigen binding fragment thereof comprises the same heavy and light chain polypeptide sequences as an antibody produced by cell line hAQC2 which is deposited under ATCC accession number PTA3275.

8. The method of claim 4, wherein the anti-VLA-1 antibody or antigen binding fragment thereof comprises the same heavy and light polypeptide sequences as an antibody produced by cell line hsAQC2 which is deposited under ATCC accession number PTA3356.

9. The method of claim 4, wherein the anti-VLA-1 antibody or antigen binding fragment thereof comprises the same heavy and light chain polypeptide sequences as an antibody produced by cell line haAQC2 which is deposited under ATCC accession number PTA3274.

10. The method of claim 1, wherein the anti-VLA-1 antibody or antigen binding fragment thereof comprises an antibody or antigen-binding fragment thereof produced by cell line mAQC2 which is deposited under ATCC accession number PTA3273.

11. The method of claim 4, wherein the anti-VLA-1 antibody or antigen binding fragment thereof comprises an antibody or antigen-binding fragment thereof produced by cell line hAQC2 which is deposited under ATCC accession number PTA3275.

12. The method of claim 4, wherein the anti-VLA-1 antibody or antigen binding fragment thereof comprises an antibody or antigen-binding fragment thereof produced by cell line hsAQC2 which is deposited under ATCC accession number PTA3356.

13. The method of claim 4, wherein the anti-VLA-1 antibody or antigen binding fragment thereof comprises an antibody or antigen-binding fragment thereof produced by cell line haAQC2 which is deposited under ATCC accession number PTA3274.

14. The method of claim 4, wherein the anti-VLA-1 antibody or antigen binding fragment thereof comprises an antibody or antigen-binding fragment thereof that has a glutamine at amino acid position 298 as set forth in SEQ ID NO:5.

15. The method of claim 1, wherein the subject is a human.

16. A method of treating a subject with rheumatoid arthritis comprising administering to the subject a composition comprising an anti-VLA-1 antibody or antigen binding fragment thereof, and a pharmaceutically acceptable carrier, wherein the antibody or antigen-binding fragment thereof comprises a light chain and a heavy chain selected from one of the following light chain and heavy chain pairs:

(i) a light chain of an anti-VLA-1 antibody, or antigen-binding fragment thereof, which has the sequence of SEQ ID NO:3,
and a heavy chain of an anti-VLA-1 antibody, or antigen-binding fragment thereof, which has the sequence of SEQ ID NO:4;

(ii) a light chain of an anti-VLA-1 antibody, or antigen-binding fragment thereof, whose light chain variable domain has the sequence of SEQ ID NO:49,
and a heavy chain of an anti-VLA-1 antibody, or antigen-binding fragment thereof, whose heavy chain variable domain has the sequence of SEQ ID NO:42;

(iii) a light chain of an anti-VLA-1 antibody, or antigen-binding fragment thereof, whose light chain variable domain has the sequence of SEQ ID NO:51,
and a heavy chain of an anti-VLA-1 antibody, or antigen-binding fragment thereof, whose heavy chain variable domain has the sequence of SEQ ID NO:44;

(iv) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:42;

(v) a light chain of an anti-VLA-1 antibody, or antigen-binding fragment thereof, whose light chain variable domain has the sequence of SEQ ID NO:58,
and a heavy chain of an anti-VLA-1 antibody, or antigen-binding fragment thereof, whose heavy chain variable domain has the sequence of SEQ ID NO:68;

(vi) a light chain of an anti-VLA-1 antibody, or antigen-binding fragment thereof, whose light chain variable domain has the sequence of SEQ ID NO:70,
and a heavy chain of an anti-VLA-1 antibody, or antigen-binding fragment thereof, whose heavy chain variable domain has the sequence of SEQ ID NO:68;

(vii) a light chain of an anti-VLA-1 antibody, or antigen-binding fragment thereof, whose light chain variable domain has the sequence of SEQ ID NO:66,
and a heavy chain of an anti-VLA-1 antibody, or antigen-binding fragment thereof, whose heavy chain variable domain has the sequence of SEQ ID NO:42;

(viii) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:68;

(ix) a light chain of an anti-VLA-1 antibody, or antigen-binding fragment thereof, whose light chain variable domain has the sequence of SEQ ID NO:47, and a heavy chain of an anti-VLA-1 antibody, or antigen-binding fragment thereof, whose heavy chain variable domain has the sequence of SEQ ID NO:68;

(x) a light chain of an antibody produced by hybridoma mAQC2 (ATCC accession number PTA3273), and a heavy chain of an antibody produced by hybridoma mAQC2 (ATCC accession number PTA3273);

(xi) a light chain of an antibody produced by cell line hAQC2 (ATCC accession number PTA3275), and a heavy chain of an antibody produced by cell line hAQC2 (ATCC accession number PTA3275);

(xii) a light chain of an antibody produced by cell line haAQC2 (ATCC accession number PTA3274), and a heavy chain of an antibody produced by cell line haAQC2 (ATCC accession number PTA3274);

(xiii) a light chain of an antibody produced by cell line hsAQC2 (ATCC accession number PTA3356), and a heavy chain of an antibody produced by cell line hsAQC2 (ATCC accession number PTA3356); or (xiv) a light chain of an anti-VLA-1 antibody, or antigen-binding fragment thereof, whose light chain variable domain has the sequence of SEQ ID NO:66, and a heavy chain of an anti-VLA-1 antibody, or antigen-binding fragment thereof, whose heavy chain variable domain has the sequence of SEQ ID NO:68.

17. The method of claim 16, wherein the subject is a human.

* * * * *

SEQUENCE LISTING

<160> NUMBER OF SEQ ID NOS: 70

<210> SEQ ID NO 1
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 1

Gln Ile Val Leu Thr Gln Phe Pro Ala Leu Met Ser Ala Ser Pro Gly
 1               5                  10                  15

Glu Lys Val Thr Met Thr Cys Ser Ala Ser Ser Val Asn His Met
                20                  25                  30

Phe Trp Tyr Gln Gln Lys Pro Lys Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105

<210> SEQ ID NO 2
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 2

Asp Val Lys Val Val Glu Ser Gly Gly Gly Leu Val Lys Pro Gly Gly
 1               5                  10                  15

Ser Leu Lys Leu Ala Cys Ala Ala Ser Gly Phe Ser Phe Ser Arg Tyr
                20                  25                  30

Thr Met Ser Trp Val Arg Gln Ile Pro Glu Lys Arg Leu Glu Trp Val
            35                  40                  45

Ala Thr Ile Ser Gly Gly Gly His Thr Tyr Tyr Leu Asp Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
            100                 105                 110

Thr Val Thr Val Ser Ser
        115

<210> SEQ ID NO 3
<211> LENGTH: 213
<212> TYPE: PRT
<213> ORGANISM: Artificial Sequence
<220> FEATURE:
<223> OTHER INFORMATION: Synthetically generated peptide

<400> SEQUENCE: 3

Gln Ile Gln Leu Thr Gln Ser Pro Ser Ser Leu Ser Ala Ser Val Gly

```
                1               5                  10                 15
Asp Arg Val Thr Ile Thr Cys Ser Ala Ser Ser Ser Val Asn His Met
                20                  25                  30

Phe Trp Tyr Gln Gln Lys Pro Gly Lys Ala Pro Lys Pro Trp Ile Tyr
                35                  40                  45

Leu Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                    85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 4
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Thr Met Ser Trp Val Arg Gln Ala Pro Gly Lys Gly Leu Glu Trp Val
            35                  40                  45

Ala Thr Ile Ser Gly Gly His Thr Tyr Tyr Leu Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                    85                  90                  95

Arg Gly Phe Gly Asp Gly Gly Tyr Phe Asp Val Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 5
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Gly Gly His Thr Tyr Tyr Leu Asp Ser Val Lys
            50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Thr
            85                  90                  95

Arg Gly Phe Gly Asp Gly Tyr Phe Asp Val Trp Gly Gln Gly Thr
        100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
            435                 440                 445
```

<210> SEQ ID NO 6
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 6

Glu Val Gln Leu Val Glu Ser Gly Gly Gly Leu Val Gln Pro Gly Gly

```
            1               5                  10                 15
        Ser Leu Arg Leu Ser Cys Ala Ala Ser Gly Phe Thr Phe Ser Arg Tyr
                    20                  25                  30

Thr Met Ser Trp Val Arg Gln Ala Pro Gly Lys Gly Leu Glu Trp Val
                    35                  40                  45

Ala Thr Ile Ser Gly Gly His Thr Tyr Tyr Leu Asp Ser Val Lys
                    50              55                  60

Gly Arg Phe Thr Ile Ser Arg Asp Asn Ser Lys Asn Thr Leu Tyr Leu
         65                 70                  75                  80

Gln Met Asn Ser Leu Arg Ala Glu Asp Thr Ala Val Tyr Tyr Cys Thr
                        85                  90                  95

Arg Gly Phe Gly Asp Gly Gly Tyr Phe Asp Val Trp Gly Gln Gly Thr
                    100                 105                 110

Leu Val Thr Val Ser Ser Ala Ser Thr Lys Gly Pro Ser Val Phe Pro
                    115                 120                 125

Leu Ala Pro Ser Ser Lys Ser Thr Ser Gly Gly Thr Ala Ala Leu Gly
                    130                 135                 140

Cys Leu Val Lys Asp Tyr Phe Pro Glu Pro Val Thr Val Ser Trp Asn
        145                 150                 155                 160

Ser Gly Ala Leu Thr Ser Gly Val His Thr Phe Pro Ala Val Leu Gln
                        165                 170                 175

Ser Ser Gly Leu Tyr Ser Leu Ser Val Val Thr Val Pro Ser Ser
                    180                 185                 190

Ser Leu Gly Thr Gln Thr Tyr Ile Cys Asn Val Asn His Lys Pro Ser
                    195                 200                 205

Asn Thr Lys Val Asp Lys Lys Val Glu Pro Lys Ser Cys Asp Lys Thr
                    210                 215                 220

His Thr Cys Pro Pro Cys Pro Ala Pro Glu Ala Ala Gly Gly Pro Ser
        225                 230                 235                 240

Val Phe Leu Phe Pro Pro Lys Pro Lys Asp Thr Leu Met Ile Ser Arg
                        245                 250                 255

Thr Pro Glu Val Thr Cys Val Val Val Asp Val Ser His Glu Asp Pro
                    260                 265                 270

Glu Val Lys Phe Asn Trp Tyr Val Asp Gly Val Glu Val His Asn Ala
                    275                 280                 285

Lys Thr Lys Pro Arg Glu Glu Gln Tyr Asn Ser Thr Tyr Arg Val Val
                    290                 295                 300

Ser Val Leu Thr Val Leu His Gln Asp Trp Leu Asn Gly Lys Glu Tyr
        305                 310                 315                 320

Lys Cys Lys Val Ser Asn Lys Ala Leu Pro Ala Pro Ile Glu Lys Thr
                        325                 330                 335

Ile Ser Lys Ala Lys Gly Gln Pro Arg Glu Pro Gln Val Tyr Thr Leu
                    340                 345                 350

Pro Pro Ser Arg Asp Glu Leu Thr Lys Asn Gln Val Ser Leu Thr Cys
                    355                 360                 365

Leu Val Lys Gly Phe Tyr Pro Ser Asp Ile Ala Val Glu Trp Glu Ser
                    370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Lys Leu Thr Val Asp Lys Ser
                        405                 410                 415

Arg Trp Gln Gln Gly Asn Val Phe Ser Cys Ser Val Met His Glu Ala
                    420                 425                 430
```

-continued

Leu His Asn His Tyr Thr Gln Lys Ser Leu Ser Leu Ser Pro Gly
    435                 440                 445

<210> SEQ ID NO 7
<211> LENGTH: 26
<212> TYPE: DNA
<213> ORGANISM: Homo sapiens

<400> SEQUENCE: 7
caggatccgt cagccccaca tttcaa                                          26

<210> SEQ ID NO 8
<211> LENGTH: 26
<212> TYPE: DNA
<213> ORGANISM: Homo sapiens

<400> SEQUENCE: 8
tcctcgaggg cttgcagggc aaatat                                          26

<210> SEQ ID NO 9
<211> LENGTH: 26
<212> TYPE: DNA
<213> ORGANISM: Rattus sp.

<400> SEQUENCE: 9
caggatccgt cagtcctaca tttcaa                                          26

<210> SEQ ID NO 10
<211> LENGTH: 26
<212> TYPE: DNA
<213> ORGANISM: Rattus sp.

<400> SEQUENCE: 10
tcctcgagcg cttccaaagc gaatat                                          26

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
tgaggagacg gtgaccgtgg cccttggccc c                                    31

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aggtsmarct gcagsagtcw gg                                              22

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
actagtcgac atggatttwc aggtgcagat twtcagcttc                           40

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
actggatggt gggaagatgg a                                              21

<210> SEQ ID NO 15
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 15

Asp Val Lys Val Val Glu Ser Gly Gly
 1               5

<210> SEQ ID NO 16
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 16

Asp Val Lys Val Val Glu
 1               5

<210> SEQ ID NO 17
<211> LENGTH: 54
<212> TYPE: DNA
<213> ORGANISM: Artificial Sequence
<220> FEATURE:
<223> OTHER INFORMATION: Primer

<400> SEQUENCE: 17
gcaccaggtg cccactccga cgtcaaggtg gtggagtcag ggggaggctt agtg          54

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
ggaggcacca agctggagat ctaacgggct gatgctgc                            38

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
cataatgtcc aggggagaaa ttgttctcac ccag                                34

<210> SEQ ID NO 20
<211> LENGTH: 93
<212> TYPE: DNA
<213> ORGANISM: Artificial Sequence
<220> FEATURE:
<223> OTHER INFORMATION: Primer

<400> SEQUENCE: 20
ggtgcccact ccgacgtcca gctggtcgag tcaggggag gcttagtcca gcctggaggg    60
tccctgagac tctcctgtgc agcctctgga ttc    93

<210> SEQ ID NO 21
<211> LENGTH: 51
<212> TYPE: DNA
<213> ORGANISM: Artificial Sequence
<220> FEATURE:
<223> OTHER INFORMATION: Primer

<400> SEQUENCE: 21
atgtcttggg ttcgccaggc tccggggaag gggctggagt gggtcgcaac c    51

<210> SEQ ID NO 22
<211> LENGTH: 93
<212> TYPE: DNA
<213> ORGANISM: Artificial Sequence
<220> FEATURE:
<223> OTHER INFORMATION: Primer

<400> SEQUENCE: 22
ttcaccatct ccagagacaa ttccaagaac accctgtacc tgcagatgaa cagtctgagg    60
gccgaggaca cagccgtgta ttactgtaca aga    93

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tggggccaag gtaccctggt caccgtctcc tcaggtgag    39

<210> SEQ ID NO 24
<211> LENGTH: 51
<212> TYPE: DNA
<213> ORGANISM: Artificial Sequence
<220> FEATURE:
<223> OTHER INFORMATION: Primer

<400> SEQUENCE: 24
tcctgtgcag cctctggatt caccttcagt aggtatacta tgtcttgggt t    51

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
gcaccaggtg cgcactccga ggtccagctg gtcgagtca    39

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
gagtcagggg gaggcttaat ccagcctgga gggtccctg    39

-continued

<210> SEQ ID NO 27
<211> LENGTH: 81
<212> TYPE: DNA
<213> ORGANISM: Artificial Sequence
<220> FEATURE:
<223> OTHER INFORMATION: Primer

<400> SEQUENCE: 27
caaattgttc tcacccagtc tccatcctcc ctgtctgcgt ctgtagggga cagagtcacc    60
atcacatgca gtgccagctc a                                             81

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
ttctggtatc agcagaagcc cgggaaagcc cccaaaccct ggatt                   45

<210> SEQ ID NO 29
<211> LENGTH: 105
<212> TYPE: DNA
<213> ORGANISM: Artificial Sequence
<220> FEATURE:
<223> OTHER INFORMATION: Primer

<400> SEQUENCE: 29
gcttctggag tcccttcacg cttcagtggc agtgggtctg ggacagatta cactctcaca   60
atcagcagcc tgcaacctga agattttgcc acttattact gccag                  105

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
ggtggaggca ctaaggtgga gatctaacgg gct                                33

<210> SEQ ID NO 31
<211> LENGTH: 39
<212> TYPE: DNA
<213> ORGANISM: Artificial Sequence
<220> FEATURE:
<223> OTHER INFORMATION: Primer

<400> SEQUENCE: 31
cccgggaaag cgcccaaact cctgatttat ctcacatcc                          39

<210> SEQ ID NO 32
<211> LENGTH: 51
<212> TYPE: DNA
<213> ORGANISM: Artificial Sequence
<220> FEATURE:
<223> OTHER INFORMATION: Primer

<400> SEQUENCE: 32
gcctcagtca taatgtcccg gggacaaatt cagctcaccc agtctccatc c            51

<210> SEQ ID NO 33
<211> LENGTH: 51

-continued

<210> SEQ ID NO 33
<211> LENGTH: 51
<212> TYPE: DNA
<213> ORGANISM: Artificial Sequence
<220> FEATURE:
<223> OTHER INFORMATION: Primer

<400> SEQUENCE: 33
ggtaacccgt ggacgttcgg tcagggcact aaggtggaga tctaacgggc t        51

<210> SEQ ID NO 34
<211> LENGTH: 51
<212> TYPE: DNA
<213> ORGANISM: Artificial Sequence
<220> FEATURE:
<223> OTHER INFORMATION: Primer

<400> SEQUENCE: 34
gcctcagtca taatgtcccg gggacaaatt cagctcaccc agtctccatc c        51

<210> SEQ ID NO 35
<211> LENGTH: 51
<212> TYPE: DNA
<213> ORGANISM: Artificial Sequence
<220> FEATURE:
<223> OTHER INFORMATION: Primer

<400> SEQUENCE: 35
ggtaacccgt ggacgttcgg tcagggcact aaggtggaga tctaacgggc t        51

<210> SEQ ID NO 36
<211> LENGTH: 39
<212> TYPE: DNA
<213> ORGANISM: Artificial Sequence
<220> FEATURE:
<223> OTHER INFORMATION: Primer

<400> SEQUENCE: 36
gggaaagcac ccaaactctg gatctatctc acatccaac        39

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
aagcccggga aggcgcccaa acccctgatt tatctcacat ccaac        45

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
gtcataatgt cccggggaga tatccagctc acccagtct        39

<210> SEQ ID NO 39
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

```
<400> SEQUENCE: 39 gac gtc aag gtg gtg gag tca ggg gga ggc tta gtg aag cct gga ggg      48
Asp Val Lys Val Val Glu Ser Gly Gly Gly Leu Val Lys Pro Gly Gly
 1               5                  10                  15 tcc ctg aaa ctc gcc tgt gca gcc tct gga ttc agt ttc agt aga tat      96
Ser Leu Lys Leu Ala Cys Ala Ala Ser Gly Phe Ser Phe Ser Arg Tyr
            20                  25                  30 act atg tct tgg gtt cgc cag att ccg gag aag agg ctg gag tgg gtc     144
Thr Met Ser Trp Val Arg Gln Ile Pro Glu Lys Arg Leu Glu Trp Val
        35                  40                  45 gca acc att agt ggt ggt ggt cac acc tac tat cta gac agt gtg aag     192
Ala Thr Ile Ser Gly Gly Gly His Thr Tyr Tyr Leu Asp Ser Val Lys
 50                  55                  60 ggc cga ttc acc atc tcc aga gac aat gcc aag aac acc ctg tac ctg     240
Gly Arg Phe Thr Ile Ser Arg Asp Asn Ala Lys Asn Thr Leu Tyr Leu
 65                  70                  75                  80 caa atg agc agt ctg agg tct gag gac aca gcc atg tat tac tgt aca     288
Gln Met Ser Ser Leu Arg Ser Glu Asp Thr Ala Met Tyr Tyr Cys Thr
                85                  90                  95 aga ggt ttt gga gac ggg ggg tac ttc gat gtc tgg ggc caa ggg acc     336
Arg Gly Phe Gly Asp Gly Gly Tyr Phe Asp Val Trp Gly Gln Gly Thr
            100                 105                 110 acg gtc acc gtc tcc tca                                             354
Thr Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 40

Asp Val Lys Val Val Glu Ser Gly Gly Gly Leu Val Lys Pro Gly Gly
 1               5                  10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
            100                 105                 110

Thr Val Thr Val Ser Ser
        115

<210> SEQ ID NO 41
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 41
```

```
gac gtc cag ctg gtc gag tca ggg gga ggc tta gtc cag cct gga ggg       48
Asp Val Gln Leu Val Glu Ser Gly Gly Gly Leu Val Gln Pro Gly Gly
  1               5                  10                  15 tcc ctg aga ctc tcc tgt gca gcc tct gga ttc agt ttc agt aga tat       96
Ser Leu Arg Leu Ser Cys Ala Ala Ser Gly Phe Ser Phe Ser Arg Tyr
             20                  25                  30 act atg tct tgg gtt cgc cag gct ccg ggg aag ggg ctg gag tgg gtc      144
Thr Met Ser Trp Val Arg Gln Ala Pro Gly Lys Gly Leu Glu Trp Val
         35                  40                  45 gca acc att agt ggt ggt ggt cac acc tac tat cta gac agt gtg aag      192
Ala Thr Ile Ser Gly Gly Gly His Thr Tyr Tyr Leu Asp Ser Val Lys
     50                  55                  60 ggc cga ttc acc atc tcc aga gac aat tcc aag aac acc ctg tac ctg      240
Gly Arg Phe Thr Ile Ser Arg Asp Asn Ser Lys Asn Thr Leu Tyr Leu
 65                  70                  75                  80 cag atg aac agt ctg agg gcc gag gac aca gcc gtg tat tac tgt aca      288
Gln Met Asn Ser Leu Arg Ala Glu Asp Thr Ala Val Tyr Tyr Cys Thr
                 85                  90                  95 aga ggt ttt gga gac ggg ggg tac ttc gat gtc tgg ggc caa ggt acc      336
Arg Gly Phe Gly Asp Gly Gly Tyr Phe Asp Val Trp Gly Gln Gly Thr
                100                 105                 110 ctg gtc acc gtc tcc tca                                              354
Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 42

Asp Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Phe Ser Arg Tyr
             20                  25                  30

Thr Met Ser Trp Val Arg Gln Ala Pro Gly Lys Gly Leu Glu Trp Val
         35                  40                  45

Ala Thr Ile Ser Gly Gly Gly His Thr Tyr Tyr Leu Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Arg Gly Phe Gly Asp Gly Gly Tyr Phe Asp Val Trp Gly Gln Gly Thr
                100                 105                 110

Leu Val Thr Val Ser Ser
        115

<210> SEQ ID NO 43
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 43
```

| gag gtc cag ctg gtc gag tca ggg gga ggc tta atc cag cct gga ggg | 48 |
| Glu Val Gln Leu Val Glu Ser Gly Gly Gly Leu Ile Gln Pro Gly Gly | |
| 1               5                  10                 15       | |

| tcc ctg aga ctc tcc tgt gca gcc tct gga ttc acc ttc agt agg tat | 96 |
| Ser Leu Arg Leu Ser Cys Ala Ala Ser Gly Phe Thr Phe Ser Arg Tyr | |
|             20                 25                 30            | |

| act atg tct tgg gtt cgc cag gct ccg ggg aag ggg ctg gag tgg gtc | 144 |
| Thr Met Ser Trp Val Arg Gln Ala Pro Gly Lys Gly Leu Glu Trp Val | |
|         35                 40                 45                | |

| gca acc att agt ggt ggt ggt cac acc tac tat cta gac agt gtg aag | 192 |
| Ala Thr Ile Ser Gly Gly Gly His Thr Tyr Tyr Leu Asp Ser Val Lys | |
|     50                 55                 60                    | |

| ggc cga ttc acc atc tcc aga gac aat tcc aag aac acc ctg tac ctg | 240 |
| Gly Arg Phe Thr Ile Ser Arg Asp Asn Ser Lys Asn Thr Leu Tyr Leu | |
| 65                 70                 75                 80      | |

| cag atg aac agt ctg agg gcc gag gac aca gcc gtg tat tac tgt aca | 288 |
| Gln Met Asn Ser Leu Arg Ala Glu Asp Thr Ala Val Tyr Tyr Cys Thr | |
|             85                 90                 95            | |

| aga ggt ttt gga gac ggg ggg tac ttc gat gtc tgg ggc caa ggt acc | 336 |
| Arg Gly Phe Gly Asp Gly Gly Tyr Phe Asp Val Trp Gly Gln Gly Thr | |
|         100                105                110               | |

| ctg gtc acc gtc tcc tca gg | 356 |
| Leu Val Thr Val Ser Ser    | |
|     115                    | |

<210> SEQ ID NO 44
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 44

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 45
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 45

| gag gtc cag ctg gtc gag tca ggg gga ggc tta gtc cag cct gga ggg | 48 |

```
Glu Val Gln Leu Val Glu Ser Gly Gly Gly Leu Val Gln Pro Gly Gly
  1               5                  10                  15 tcc ctg aga ctc tcc tgt gca gcc tct gga ttc acc ttc agt agg tat      96
Ser Leu Arg Leu Ser Cys Ala Ala Ser Gly Phe Thr Phe Ser Arg Tyr
             20                  25                  30 act atg tct tgg gtt cgc cag gct ccg ggg aag ggg ctg gag tgg gtc     144
Thr Met Ser Trp Val Arg Gln Ala Pro Gly Lys Gly Leu Glu Trp Val
         35                  40                  45 gca acc att agt ggt ggt ggt cac acc tac tat cta gac agt gtg aag     192
Ala Thr Ile Ser Gly Gly Gly His Thr Tyr Tyr Leu Asp Ser Val Lys
     50                  55                  60 ggc cga ttc acc atc tcc aga gac aat tcc aag aac acc ctg tac ctg     240
Gly Arg Phe Thr Ile Ser Arg Asp Asn Ser Lys Asn Thr Leu Tyr Leu
 65              70                  75                  80 cag atg aac agt ctg agg gcc gag gac aca gcc gtg tat tac tgt aca     288
Gln Met Asn Ser Leu Arg Ala Glu Asp Thr Ala Val Tyr Tyr Cys Thr
             85                  90                  95 aga ggt ttt gga gac ggg ggg tac ttc gat gtc tgg ggc caa ggt acc     336
Arg Gly Phe Gly Asp Gly Gly Tyr Phe Asp Val Trp Gly Gln Gly Thr
            100                 105                 110 ctg gtc acc gtc tcc tca gg                                          356
Leu Val Thr Val Ser Ser
            115

<210> SEQ ID NO 46
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 46 caa att gtt ctc acc cag ttt cca gca ctc atg tct gcg tct cca ggg      48
Gln Ile Val Leu Thr Gln Phe Pro Ala Leu Met Ser Ala Ser Pro Gly
  1               5                  10                  15 gag aag gtc acc atg acc tgc agt gcc agc tca agt gta aat cac atg      96
Glu Lys Val Thr Met Thr Cys Ser Ala Ser Ser Ser Val Asn His Met
             20                  25                  30 ttc tgg tat cag cag aag cca aaa tcc tcc ccc aaa ccc tgg att tat     144
Phe Trp Tyr Gln Gln Lys Pro Lys Ser Ser Pro Lys Pro Trp Ile Tyr
         35                  40                  45 ctc aca tcc aac ctg gct tct gga gtc cct gct cgc ttc agt ggc agt     192
Leu Thr Ser Asn Leu Ala Ser Gly Val Pro Ala Arg Phe Ser Gly Ser
     50                  55                  60 ggg tct ggg acc tct tac tct ctc aca atc agc agc atg gag gct gaa     240
Gly Ser Gly Thr Ser Tyr Ser Leu Thr Ile Ser Ser Met Glu Ala Glu
 65              70                  75                  80 gat gct gcc act tat tac tgc cag cag tgg agt ggt aac ccg tgg acg     288
Asp Ala Ala Thr Tyr Tyr Cys Gln Gln Trp Ser Gly Asn Pro Trp Thr
             85                  90                  95 ttc ggt gga ggc acc aag ctg gag atc aaa                             318
Phe Gly Gly Gly Thr Lys Leu Glu Ile Lys
            100                 105

<210> SEQ ID NO 47
<211> LENGTH: 106
<212> TYPE: PRT
<213> ORGANISM: Artificial Sequence
<220> FEATURE:
<223> OTHER INFORMATION: Synthetically generated peptide
```

<400> SEQUENCE: 47

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn His Met
            20                  25                  30

Phe Trp Tyr Gln Gln Lys Pro Gly Lys Ala Pro Lys Leu Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 48
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 48

```
caa att gtt ctc acc cag tct cca tcc tcc ctg tct gcg tct gta ggg      48
Gln Ile Val Leu Thr Gln Ser Pro Ser Ser Leu Ser Ala Ser Val Gly
1               5                   10                  15 gac aga gtc acc atc aca tgc agt gcc agc tca agt gta aat cac atg      96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                85                  90                  95 ttc ggt gga ggc act aag gtg gag atc aaa                             318
Phe Gly Gly Gly Thr Lys Val Glu Ile Lys
            100                 105
```

<210> SEQ ID NO 49
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 49

Gln Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

```
Phe Trp Tyr Gln Gln Lys Pro Gly Lys Ala Pro Lys Pro Trp Ile Tyr
            35                  40                  45

Leu Thr Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gly Gly Thr Lys Val Glu Ile Lys
            100                 105

<210> SEQ ID NO 50
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 50 caa att gtt ctc acc cag tct cca tcc tcc ctg tct gcg tct gta ggg    48
Gln Ile Val Leu Thr Gln Ser Pro Ser Ser Leu Ser Ala Ser Val Gly
 1               5                  10                  15 gac aga gtc acc atc aca tgc agt gcc agc tca agt gta aat cac atg    96
Asp Arg Val Thr Ile Thr Cys Ser Ala Ser Ser Ser Val Asn His Met
             20                  25                  30 ttc tgg tat cag cag aag ccc ggg aaa gcg ccc aaa ctc ctg att tat   144
Phe Trp Tyr Gln Gln Lys Pro Gly Lys Ala Pro Lys Leu Leu Ile Tyr
         35                  40                  45 ctc aca tcc aac ctg gct tct gga gtc cct tca cgc ttc agt ggc agt   192
Leu Thr Ser Asn Leu Ala Ser Gly Val Pro Ser Arg Phe Ser Gly Ser
 50                  55                  60 ggg tct ggg aca gat tac act ctc aca atc agc agc ctg caa cct gaa   240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg   288
Asp Phe Ala Thr Tyr Tyr Cys Gln Gln Trp Ser Gly Asn Pro Trp Thr
                 85                  90                  95 ttc ggt gga ggc act aag gtg gag atc aaa                           318
Phe Gly Gly Gly Thr Lys Val Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 51

Gln Ile Val Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
             20                  25                  30

Phe Trp Tyr Gln Gln Lys Pro Gly Lys Ala Pro Lys Leu Leu Ile Tyr
         35                  40                  45

Leu Thr Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80
```

```
Asp Phe Ala Thr Tyr Tyr Cys Gln Gln Trp Ser Gly Asn Pro Trp Thr
                85                  90                  95

Phe Gly Gly Gly Thr Lys Val Glu Ile Lys
                100                 105

<210> SEQ ID NO 52
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 52 caa att cag ctc acc cag tct cca tcc tcc ctg tct gcg tct gta ggg       48
Gln Ile Gln Leu Thr Gln Ser Pro Ser Ser Leu Ser Ala Ser Val Gly
  1               5                  10                  15 gac aga gtc acc atc aca tgc agt gcc agc tca agt gta aat cac atg       96
Asp Arg Val Thr Ile Thr Cys Ser Ala Ser Ser Ser Val Asn His Met
                 20                  25                  30 ttc tgg tat cag cag aag ccc ggg aaa gcc ccc aaa ccc tgg att tat      144
Phe Trp Tyr Gln Gln Lys Pro Gly Lys Ala Pro Lys Pro Trp Ile Tyr
             35                  40                  45 ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
         50                  55                  60 ggg tct ggg aca gat tac act ctc aca atc agc agc ctg caa cct gaa      240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                 85                  90                  95 ttc ggt cag ggc act aag gtg gag atc aaa                              318
Phe Gly Gln Gly Thr Lys Val Glu Ile Lys
            100                 105

<210> SEQ ID NO 53
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 53 caa att cag ctc acc cag tct cca tcc tcc ctg tct gcg tct gta ggg       48
Gln Ile Gln Leu Thr Gln Ser Pro Ser Ser Leu Ser Ala Ser Val Gly
  1               5                  10                  15 gac aga gtc acc atc aca tgc agt gcc agc tca agt gta aat cac atg       96
Asp Arg Val Thr Ile Thr Cys Ser Ala Ser Ser Ser Val Asn His Met
                 20                  25                  30 ttc tgg tat cag cag aag ccc ggg aaa gcc ccc aaa ctc ctg att tat      144
Phe Trp Tyr Gln Gln Lys Pro Gly Lys Ala Pro Lys Leu Leu Ile Tyr
             35                  40                  45 ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
         50                  55                  60 ggg tct ggg aca gat tac act ctc aca atc agc agc ctg caa cct gaa      240
Gly Ser Gly Thr Asp Tyr Thr Leu Thr Ile Ser Ser Leu Gln Pro Glu
 65                  70                  75                  80
```

```
gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95 ttc ggt cag ggc act aag gtg gag atc aaa                              318
Phe Gly Gln Gly Thr Lys Val Glu Ile Lys
        100                 105
```

<210> SEQ ID NO 54
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 54

```
Gln Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
        100                 105
```

<210> SEQ ID NO 55
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 55

```
gaa att gtt ctc acc cag ttt cca gca ctc atg tct gcg tct cca ggg       48
Glu Ile Val Leu Thr Gln Phe Pro Ala Leu Met Ser Ala Ser Pro Gly
 1               5                  10                  15 gag aag gtc acc atg acc tgc agt gcc agc tca agt gta aat cac atg       96
Glu Lys Val Thr Met Thr Cys Ser Ala Ser Ser Ser Val Asn His Met
            20                  25                  30 ttc tgg tat cag cag aag cca aaa tcc tcc ccc aaa ccc tgg att tat      144
Phe Trp Tyr Gln Gln Lys Pro Lys Ser Ser Pro Lys Pro Trp Ile Tyr
        35                  40                  45 ctc aca tcc aac ctg gct tct gga gtc cct gct cgc ttc agt ggc agt      192
Leu Thr Ser Asn Leu Ala Ser Gly Val Pro Ala Arg Phe Ser Gly Ser
    50                  55                  60 ggg tct ggg acc tct tac tct ctc aca atc agc agc atg gag gct gaa      240
Gly Ser Gly Thr Ser Tyr Ser Leu Thr Ile Ser Ser Met Glu Ala Glu
65                  70                  75                  80 gat gct gcc act tat tac tgc cag cag tgg agt ggt aac ccg tgg acg      288
Asp Ala Ala Thr Tyr Tyr Cys Gln Gln Trp Ser Gly Asn Pro Trp Thr
                85                  90                  95 ttc ggt gga ggc acc aag ctg gag atc aaa                              318
Phe Gly Gly Gly Thr Lys Leu Glu Ile Lys
        100                 105
```

<210> SEQ ID NO 56
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 56

```
Glu Ile Val Leu Thr Gln Phe Pro Ala Leu Met Ser Ala Ser Pro Gly
 1               5                  10                  15

Glu Lys Val Thr Met Thr Cys Ser Ala Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105
```

<210> SEQ ID NO 57
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 57

```
gat atc cag ctc acc cag tct cca tcc tcc ctg tct gcg tct gta ggg     48
Asp Ile Gln Leu Thr Gln Ser Pro Ser Ser Leu Ser Ala Ser Val Gly
 1               5                  10                  15 gac aga gtc acc atc aca tgc agt gcc agc tca agt gta aat cac atg     96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat    144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt    192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa    240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg    288
Asp Phe Ala Thr Tyr Tyr Cys Gln Gln Trp Ser Gly Asn Pro Trp Thr
                85                  90                  95 ttc ggt cag ggc act aag gtg gag atc aaa                            318
Phe Gly Gln Gly Thr Lys Val Glu Ile Lys
            100                 105
```

<210> SEQ ID NO 58
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 59
<211> LENGTH: 192
<212> TYPE: PRT
<213> ORGANISM: Artificial Sequence
<220> FEATURE:
<223> OTHER INFORMATION: Rat and human chimeric I domain construct

<400> SEQUENCE: 59

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Asn
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
    50                  55                  60

Val Leu Val Ala Ala Asn Lys Ile Val Gln Arg Gly Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
    130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Thr Val Lys Ala Leu Gly Glu Arg Ile Phe
            180                 185                 190

<210> SEQ ID NO 60
<211> LENGTH: 192
<212> TYPE: PRT
<213> ORGANISM: Rattus sp.

<400> SEQUENCE: 60

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Met
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
    50                  55                  60

Val Leu Val Ala Ala Asn Lys Ile Gly Arg Gln Gly Gly Leu Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
    130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Ile Val Lys Ala Leu Gly Arg Ile Phe
            180                 185                 190

<210> SEQ ID NO 61
<211> LENGTH: 192
<212> TYPE: PRT
<213> ORGANISM: Homo sapiens

<400> SEQUENCE: 61

Thr Gln Leu Asp Ile Val Ile Val Leu Asp Gly Ser Asn Ser Ile Tyr
1               5                   10                  15

Pro Trp Asp Ser Val Thr Ala Phe Leu Asn Asp Leu Leu Lys Arg Met
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
    50                  55                  60

Val Leu Val Ala Ala Lys Lys Ile Val Gln Arg Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn His Arg Leu Lys Lys Val Ile Gln Asp
        115                 120                 125

Cys Glu Asp Glu Asn Ile Gln Arg Phe Ser Ile Ala Ile Leu Gly Ser
    130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Ile Ala Leu Val Thr Ile Val Lys Thr Leu Gly Glu Arg Ile Phe
            180                 185                 190

<210> SEQ ID NO 62

```
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 62

Gly Phe Gly Asp Gly Gly Tyr
1               5

<210> SEQ ID NO 63
<211> LENGTH: 214
<212> TYPE: PRT
<213> ORGANISM: Rattus sp.

<400> SEQUENCE: 63

Val Ser Pro Thr Phe Gln Val Val Asn Ser Phe Ala Pro Val Gln Glu
1               5                   10                  15

Cys Ser Thr Gln Leu Asp Ile Val Ile Val Leu Asp Gly Ser Asn Ser
                20                  25                  30

Ile Tyr Pro Trp Glu Ser Val Ile Ala Phe Leu Asn Asp Leu Leu Lys
            35                  40                  45

Arg Met Asp Ile Gly Pro Lys Gln Thr Gln Val Gly Ile Val Gln Tyr
    50                  55                  60

Gly Glu Asn Val Thr His Glu Phe Asn Leu Asn Lys Tyr Ser Ser Thr
65              70                  75                  80

Glu Glu Val Leu Val Ala Ala Lys Lys Ile Gly Arg Gln Gly Gly Leu
                85                  90                  95

Gln Thr Met Thr Ala Leu Gly Ile Asp Thr Ala Arg Lys Glu Ala Phe
                100                 105                 110

Thr Glu Ala Arg Gly Ala Arg Arg Gly Val Lys Lys Val Met Val Ile
            115                 120                 125

Val Thr Asp Gly Glu Ser His Asp Asn Tyr Arg Leu Lys Gln Val Ile
    130                 135                 140

Gln Asp Cys Glu Asp Glu Asn Ile Gln Arg Phe Ser Ile Ala Ile Leu
145                 150                 155                 160

Gly His Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Ala Leu Gly Glu Arg
    195                 200                 205

Ile Phe Ala Leu Glu Ala
    210

<210> SEQ ID NO 64
<211> LENGTH: 214
<212> TYPE: PRT
<213> ORGANISM: Homo sapiens

<400> SEQUENCE: 64

Val Ser Pro Thr Phe Gln Val Val Asn Ser Ile Ala Pro Val Gln Glu
1               5                   10                  15

Cys Ser Thr Gln Leu Asp Ile Val Ile Val Leu Asp Gly Ser Asn Ser
                20                  25                  30

Ile Tyr Pro Trp Asp Ser Val Thr Ala Phe Leu Asn Asp Leu Leu Lys
            35                  40                  45

Arg Met Asp Ile Gly Pro Lys Gln Thr Gln Val Gly Ile Val Gln Tyr
    50                  55                  60
```

```
Gly Glu Asn Val Thr His Glu Phe Asn Leu Asn Lys Tyr Ser Ser Thr
 65                  70                  75                  80

Glu Glu Val Leu Val Ala Ala Lys Lys Ile Val Gln Arg Gly Gly Arg
                 85                  90                  95

Gln Thr Met Thr Ala Leu Gly Thr Asp Thr Ala Arg Lys Glu Ala Phe
            100                 105                 110

Thr Glu Ala Arg Gly Ala Arg Arg Gly Val Lys Lys Val Met Val Ile
        115                 120                 125

Val Thr Asp Gly Glu Ser His Asp Asn His Arg Leu Lys Lys Val Ile
130                 135                 140

Gln Asp Cys Glu Asp Glu Asn Ile Gln Arg Phe Ser Ile Ala Ile Leu
145                 150                 155                 160

Gly Ser Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Thr Leu Gly Glu Arg
        195                 200                 205

Ile Phe Ala Leu Glu Ala
    210

<210> SEQ ID NO 65
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 65

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Tyr Leu
                 20                  25                  30

Asn Trp Tyr Gln Gln Lys Pro Gly Lys Ala Pro Lys Leu Leu Ile Tyr
             35                  40                  45

Ala Ala Ser Ser Leu Gln Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Leu Thr
                 85                  90                  95

Phe Gly Gly Gly Thr Lys Val Glu Ile Lys
            100                 105

<210> SEQ ID NO 66
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 66

Gln Ile Gln Leu Thr Gln Ser Pro Ser Ser Leu Ser Ala Ser Val Gly
  1               5                  10                  15

Asp Arg Val Thr Ile Thr Cys Ser Ala Ser Ser Ser Val Asn His Met
                 20                  25                  30

Phe Trp Tyr Gln Gln Lys Pro Gly Lys Ala Pro Lys Pro Trp Ile Tyr
             35                  40                  45
```

```
Leu Thr Ser Asn Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gln Gly Thr Lys Val Glu Ile Lys
             100                 105
```

<210> SEQ ID NO 67
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 67

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
         35                  40                  45

Ser Val Ile Tyr Ser Gly Gly Ser Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ser Ile Arg Phe Leu Glu Trp Ser Phe Asp Tyr Trp Gly Gln Gly Thr
             100                 105                 110

Leu Val Thr Val Ser Ser
         115
```

<210> SEQ ID NO 68
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 68

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
             20                  25                  30

Thr Met Ser Trp Val Arg Gln Ala Pro Gly Lys Gly Leu Glu Trp Val
         35                  40                  45

Ala Thr Ile Ser Gly Gly Gly His Thr Tyr Tyr Leu Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Arg Gly Phe Gly Asp Gly Gly Tyr Phe Asp Val Trp Gly Gln Gly Thr
             100                 105                 110

Leu Val Thr Val Ser Ser
         115
```

<210> SEQ ID NO 69
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 69

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 70
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 70

Gln Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105